US012466879B2

(12) United States Patent
Perlroth et al.

(10) Patent No.: US 12,466,879 B2
(45) Date of Patent: Nov. 11, 2025

(54) COMPLEMENT FACTOR D ANTAGONIST ANTIBODIES AND CONJUGATES THEREOF

(71) Applicant: KODIAK SCIENCES INC., Palo Alto, CA (US)

(72) Inventors: Daniel Victor Perlroth, Palo Alto, CA (US); Wah Yuen To, San Mateo, CA (US); Hong Liang, Hillsborough, CA (US); Rachel Marie DeVay Jacobson, Belmont, CA (US); Fernando Corrêa, Hayward, CA (US)

(73) Assignee: KODIAK SCIENCES INC., Palo Alto, CA (US)

( * ) Notice: Subject to any disclaimer, the term of this patent is extended or adjusted under 35 U.S.C. 154(b) by 66 days.

(21) Appl. No.: 18/165,233

(22) Filed: Feb. 6, 2023

(65) Prior Publication Data

US 2023/0382983 A1 Nov. 30, 2023

Related U.S. Application Data

(62) Division of application No. 15/952,092, filed on Apr. 12, 2018, now Pat. No. 11,584,790.

(60) Provisional application No. 62/485,718, filed on Apr. 14, 2017.

(51) Int. Cl.

| | |
|---|---|
| ***C07K 16/18*** | (2006.01) |
| ***A61K 47/68*** | (2017.01) |
| ***C07K 14/47*** | (2006.01) |
| ***C07K 16/40*** | (2006.01) |

(52) U.S. Cl.

CPC .......... *C07K 16/18* (2013.01); *A61K 47/6843* (2017.08); *A61K 47/6885* (2017.08); *C07K 16/40* (2013.01); *C07K 14/472* (2013.01); *C07K 2317/24* (2013.01); *C07K 2317/33* (2013.01); *C07K 2317/34* (2013.01); *C07K 2317/41* (2013.01); *C07K 2317/51* (2013.01); *C07K 2317/515* (2013.01); *C07K 2317/55* (2013.01); *C07K 2317/565* (2013.01); *C07K 2317/734* (2013.01); *C07K 2317/76* (2013.01); *C07K 2317/92* (2013.01); *C07K 2317/94* (2013.01); *C12Y 304/21046* (2013.01)

(58) Field of Classification Search

None

See application file for complete search history.

(56) References Cited

U.S. PATENT DOCUMENTS

| | | | |
|---|---|---|---|
| 4,485,045 | A | 11/1984 | Regen |
| 4,544,545 | A | 10/1985 | Ryan et al. |
| 4,634,664 | A | 1/1987 | Oestberg |
| 4,634,666 | A | 1/1987 | Engleman et al. |
| 4,683,195 | A | 7/1987 | Mullis et al. |
| 4,683,202 | A | 7/1987 | Mullis |
| 4,754,065 | A | 6/1988 | Levenson et al. |
| 4,777,127 | A | 10/1988 | Suni et al. |
| 4,800,159 | A | 1/1989 | Mullis et al. |
| 4,816,567 | A | 3/1989 | Cabilly et al. |
| 4,892,538 | A | 1/1990 | Aebischer et al. |
| 5,013,556 | A | 5/1991 | Woodle et al. |
| 5,047,335 | A | 9/1991 | Paulson et al. |
| 5,219,740 | A | 6/1993 | Dusty et al. |
| 5,225,539 | A | 7/1993 | Winter |
| 5,278,299 | A | 1/1994 | Wong et al. |
| 5,283,187 | A | 2/1994 | Aebischer et al. |
| 5,422,120 | A | 6/1995 | Kim et al. |
| 5,530,101 | A | 6/1996 | Queen et al. |
| 5,545,806 | A | 8/1996 | Lonberg et al. |
| 5,565,332 | A | 10/1996 | Hoogenboom et al. |
| 5,569,825 | A | 10/1996 | Lonberg et al. |
| 5,580,859 | A | 12/1996 | Felgner et al. |
| 5,585,089 | A | 12/1996 | Queen et al. |
| 5,624,821 | A | 4/1997 | Winter et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 5,663,425 | A | 9/1997 | Detroit et al. |
| 5,681,746 | A | 10/1997 | Bodner et al. |
| 5,733,743 | A | 3/1998 | Johnson et al. |
| 5,770,429 | A | 6/1998 | Lonberg et al. |
| 5,789,650 | A | 8/1998 | Lonberg et al. |
| 5,814,318 | A | 9/1998 | Lonberg et al. |
| 5,814,482 | A | 9/1998 | Dubensky, Jr. et al. |
| 5,834,597 | A | 11/1998 | Tso et al. |
| 5,837,242 | A | 11/1998 | Holliger et al. |
| 5,858,657 | A | 1/1999 | Winter et al. |

(Continued)

FOREIGN PATENT DOCUMENTS

| | | |
|---|---|---|
| CN | 106905431 | 6/2017 |
| EP | 0345242 | 12/1989 |
| EP | 0282160 | 5/1995 |
| EP | 0524968 | 6/1995 |
| WO | WO 90/07936 | 7/1990 |

(Continued)

OTHER PUBLICATIONS

Burgess et al., Journal of Cell Biology 111:2129-2138 (Year: 1990).*

(Continued)

*Primary Examiner* — Phuong Huynh

(74) *Attorney, Agent, or Firm* — KNOBBE, MARTENS, OLSON & BEAR, LLP

(57) ABSTRACT

The present invention provides antagonizing antibodies that bind to complement factor D (CFD), conjugates thereof, and methods of using same. The anti-CFD antibodies can be used therapeutically alone or in combination with other therapeutics to treat age related macular degeneration and other diseases.

22 Claims, 62 Drawing Sheets

Specification includes a Sequence Listing.

(56) References Cited

U.S. PATENT DOCUMENTS

| | | | | |
|---|---|---|---|---|
| 5,859,205 | A | 1/1999 | Adair et al. | |
| 5,871,907 | A | 2/1999 | Winter et al. | |
| 5,872,218 | A | 2/1999 | Wolf et al. | |
| 5,874,299 | A | 2/1999 | Lonberg et al. | |
| 5,877,218 | A | 3/1999 | Herzig et al. | |
| 5,877,397 | A | 3/1999 | Lonberg et al. | |
| 6,376,471 | B1 | 4/2002 | Lawrence, III et al. | |
| 6,407,213 | B1 | 6/2002 | Carter et al. | |
| 6,413,942 | B1 | 7/2002 | Felgner et al. | |
| 6,436,908 | B1 | 8/2002 | Koch et al. | |
| 6,624,821 | B1 | 9/2003 | Shin et al. | |
| 6,881,557 | B2 | 4/2005 | Foote | |
| 6,956,107 | B2 * | 10/2005 | Fung | C07K 16/40 435/328 |
| 7,521,541 | B2 | 4/2009 | Eigenbrot et al. | |
| 7,667,004 | B2 | 2/2010 | Zhong et al. | |
| 7,893,173 | B2 | 2/2011 | Matyjaszewski et al. | |
| 8,003,097 | B2 | 8/2011 | Schroeter et al. | |
| 8,008,453 | B2 | 8/2011 | Gegg et al. | |
| 8,067,002 | B2 | 11/2011 | An et al. | |
| 8,273,352 | B2 | 9/2012 | Huang et al. | |
| 8,455,622 | B2 | 6/2013 | McDonagh et al. | |
| 8,753,625 | B2 | 6/2014 | Fung et al. | |
| 8,765,432 | B2 | 7/2014 | Charles | |
| 8,846,021 | B2 | 9/2014 | Charles | |
| 8,969,526 | B2 | 3/2015 | Baehner et al. | |
| 9,840,553 | B2 | 12/2017 | Perlroth et al. | |
| 10,363,290 | B2 | 7/2019 | Perlroth et al. | |
| 10,407,510 | B2 | 9/2019 | Kelley et al. | |
| 10,702,608 | B2 | 7/2020 | Charles et al. | |
| 11,066,465 | B2 | 7/2021 | Perlroth et al. | |
| 11,071,771 | B2 | 7/2021 | Perlroth et al. | |
| 11,155,610 | B2 | 10/2021 | Perlroth et al. | |
| 11,584,790 | B2 * | 2/2023 | Perlroth | A61K 47/6843 |
| 11,590,235 | B2 | 2/2023 | Charles et al. | |
| 11,819,531 | B2 | 11/2023 | Charles et al. | |
| 11,912,784 | B2 | 2/2024 | Ehrlich et al. | |
| 12,071,476 | B2 | 8/2024 | Jacobson et al. | |
| 2003/0235536 | A1 | 12/2003 | Blumberg et al. | |
| 2005/0041080 | A1 | 2/2005 | Hall et al. | |
| 2006/0167230 | A1 | 7/2006 | Koga et al. | |
| 2008/0269318 | A1 | 10/2008 | Romano | |
| 2009/0060906 | A1 | 3/2009 | Barry et al. | |
| 2009/0249503 | A1 | 10/2009 | Rosendahl | |
| 2010/0166700 | A1 * | 7/2010 | Charles | A61P 25/00 530/391.1 |
| 2010/0291065 | A1 | 11/2010 | Kabanov et al. | |
| 2011/0165648 | A1 * | 7/2011 | Campagne | A61P 27/02 703/11 |
| 2012/0100166 | A1 | 4/2012 | Roschke et al. | |
| 2012/0213705 | A1 | 8/2012 | Dimasi et al. | |
| 2013/0045522 | A1 | 2/2013 | Charles et al. | |
| 2014/0024776 | A1 | 1/2014 | Charles et al. | |
| 2014/0065137 | A1 | 3/2014 | Huang et al. | |
| 2015/0004128 | A1 | 1/2015 | Charles et al. | |
| 2015/0050714 | A1 | 2/2015 | Charles | |
| 2015/0093390 | A1 | 4/2015 | Bansal | |
| 2015/0158952 | A1 | 6/2015 | Mao et al. | |
| 2015/0337053 | A1 | 11/2015 | McCarthy et al. | |
| 2015/0376271 | A1 * | 12/2015 | Perlroth | C07K 14/71 424/134.1 |
| 2016/0017052 | A1 * | 1/2016 | Kelley | A61P 27/10 435/69.6 |
| 2016/0287715 | A1 | 10/2016 | Charles et al. | |
| 2016/0369005 | A1 | 12/2016 | Lippincott et al. | |
| 2017/0007710 | A1 | 1/2017 | Charles et al. | |
| 2017/0143841 | A1 | 5/2017 | Charles et al. | |
| 2018/0319893 | A1 | 11/2018 | Stephen et al. | |
| 2019/0270806 | A1 | 9/2019 | Jacobson et al. | |
| 2019/0330335 | A1 | 10/2019 | Schwabe et al. | |
| 2020/0000930 | A1 | 1/2020 | Charles | |
| 2020/0171179 | A1 | 6/2020 | Charles et al. | |
| 2020/0262905 | A1 | 8/2020 | Perlroth et al. | |
| 2021/0107999 | A1 | 4/2021 | Ehrlich et al. | |
| 2021/0324063 | A1 | 10/2021 | Perlroth et al. | |
| 2021/0402015 | A1 | 12/2021 | Charles et al. | |
| 2022/0096643 | A1 | 3/2022 | Charles | |
| 2023/0173081 | A1 | 6/2023 | Charles et al. | |
| 2023/0250133 | A1 | 8/2023 | Zurbriggen et al. | |
| 2024/0084043 | A1 | 3/2024 | Ehrlich et al. | |
| 2024/0197810 | A1 | 6/2024 | Charles et al. | |
| 2024/0209076 | A1 | 6/2024 | Perlroth et al. | |
| 2024/0238427 | A1 | 7/2024 | Ehrlich et al. | |
| 2024/0293585 | A1 | 9/2024 | Charles et al. | |
| 2024/0368267 | A1 | 11/2024 | Jacobson et al. | |

FOREIGN PATENT DOCUMENTS

| | | | |
|---|---|---|---|
| WO | WO 90/11092 | 10/1990 | |
| WO | WO 91/00904 | 1/1991 | |
| WO | WO 91/02805 | 3/1991 | |
| WO | WO 91/10741 | 7/1991 | |
| WO | WO 91/14445 | 10/1991 | |
| WO | WO 91/17271 | 11/1991 | |
| WO | WO 92/01047 | 1/1992 | |
| WO | WO 93/03769 | 3/1993 | |
| WO | WO 93/10218 | 5/1993 | |
| WO | WO 93/11230 | 6/1993 | |
| WO | WO 93/12227 | 6/1993 | |
| WO | WO 93/19191 | 9/1993 | |
| WO | WO 93/25234 | 12/1993 | |
| WO | WO 93/25673 | 12/1993 | |
| WO | WO 93/25698 | 12/1993 | |
| WO | WO 94/03622 | 2/1994 | |
| WO | WO 94/12649 | 6/1994 | |
| WO | WO 94/16748 | 8/1994 | |
| WO | WO 94/23697 | 10/1994 | |
| WO | WO 94/28938 | 12/1994 | |
| WO | WO 95/00655 | 1/1995 | |
| WO | WO 95/07994 | 3/1995 | |
| WO | WO 95/11984 | 5/1995 | |
| WO | WO 95/13796 | 5/1995 | |
| WO | WO 95/30763 | 11/1995 | |
| WO | WO 96/17072 | 6/1996 | |
| WO | WO 97/14702 | 4/1997 | |
| WO | WO 97/14703 | 4/1997 | |
| WO | WO 97/42338 | 11/1997 | |
| WO | WO 99/42133 | 8/1999 | |
| WO | WO 00/09560 | 5/2000 | |
| WO | WO 2004/020405 | 3/2004 | |
| WO | WO 2007/100902 | 9/2007 | |
| WO | WO 2008/020827 | 2/2008 | |
| WO | WO 2008/055206 | 5/2008 | |
| WO | WO 2008/155134 | 12/2008 | |
| WO | WO 2009/052249 | 4/2009 | |
| WO | WO 2009/052439 | 6/2009 | |
| WO | WO 2009/134711 | 11/2009 | |
| WO | WO 2011/057014 | 5/2011 | |
| WO | WO 2011/075185 | 6/2011 | |
| WO | WO 2011/075736 | 6/2011 | |
| WO | WO 2011/101284 | 6/2011 | |
| WO | WO 2011/130694 | 10/2011 | |
| WO | WO 2012/145746 | 10/2012 | |
| WO | WO 2013/059137 | 4/2013 | |
| WO | WO 2013/093809 | 6/2013 | |
| WO | WO-2013093809 A1 * | 6/2013 | A61K 38/08 |
| WO | WO 2015/035342 | 3/2015 | |
| WO | WO 2015/168468 | 11/2015 | |
| WO | WO 2015/200905 | 12/2015 | |
| WO | WO 2016/061562 | 4/2016 | |
| WO | WO 2017/075173 | 5/2017 | |
| WO | WO 2017/117464 | 7/2017 | |
| WO | WO 2017/129064 | 8/2017 | |
| WO | WO 2018/191548 | 10/2018 | |
| WO | WO 2019/169341 | 9/2019 | |

OTHER PUBLICATIONS

Nilsen et al., Communications Biology 3(181): 1-11 (Year: 2020).*

Office Action for Australian Application No. AU 2022201163 in 4 pages, dated Apr. 26, 2024.

(56) References Cited

OTHER PUBLICATIONS

Office Action for Canadian Application No. CA 3,059,938 in 20 pages, dated Oct. 16, 2023.
U.S. Appl. No. 09/253,689, filed Feb. 20, 1999, Fung et al.
Anderson, W.F., "Human gene therapy," Science, May 8, 1992, vol. 256, No. 5058, pp. 808-813.
Binder, S et al., "Transplantation of the RPE in AMD", Progress in Retinal and Eye Research, 2007, vol. 26, pp. 516-554.
Boyd et al., "The effect of the removal of sialic acid, galactose and total carbohydrate on the functional activity of Campath-1H", Molecular Immunology, Dec. 1995, vol. 32, pp. 1311-1318.
Capel, P. J. A. et al., "Heterogeneity of human IgG Fc receptors", Immunomethods, Feb. 1994, vol. 4(1), pp. 25-34.
Capon, D. et al., "Designing CD4 immunoadhesins for AIDS therapy," Nature, 1989, vol. 337, pp. 525-531.
Chiou, H. et al., "In Vivo Gene Therapy via Receptor-Mediated DNA Delivery", in Gene Therapeutics: Methods and Applications of Direct Gene Transfer, J.A. Wolff, ed., 1994, in 14 pages.
Chothia, C. et al., "Canonical structures for the hypervariable regions of immunoglobulins," Journal of Molecular Biology, Aug. 20, 1987, vol. 196, Issue 4, pp. 901-917.
Chothia, C. et al., "Conformations of immunoglobulin hypervariable regions," Nature, Dec. 1989, vol. 342, pp. 877-883.
Connelly, S. et al., "In Vivo Gene Delivery and Expression of Physiological Levels of Functional Human Factor VIII in Mice", Human Gene Therapy, 1995, vol. 6, pp. 185-193.
Curiel, D. et al., "High-Efficiency Gene Transfer Mediated by Adenovirus Coupled to DNA-Polylysine Complexes", Human Gene Therapy, 1992, vol. 3(2), pp. 147-154.
Dayhoff, M.O. (ed.) Atlas of Protein Sequence and Structure, National Biomedical Research Foundation, Washington DC vol. 5, Suppl. 3, pp. 345-358. 1978.
De Haas et al., "Fc gamma receptors of phagocytes", Journal of Laboratory and Clinical Medicine, 126(4): dated Oct. 1995, pp. 330-341.
De Pascalis, R. et al., "Grafting of 'abbreviated' complementarity-determining regions containing specificity-determining residues essential for ligand contact to engineer a less immunogenic humanized monoclonal antibody," J. Immunol., vol. 169, No. 6, pp. 3076-3084, Sep. 15, 2002.
Edwards et al., "The Remarkable Flexibility of the Human Antibody Repertoire; Isolation of Over One Thousand Different Antibodies to a Single Protein, BLyS", J. Mol. Biol., vol. 334, pp. 103-118, 2003.
Eppstein et al., "Biological activity of liposome-encapsulated murine interferon gamma is mediated by a cell membrane receptor", Proc. Natl. Acad. Sci. USA, vol. 82: dated Jun. 1985 pp. 3688-3692.
Fares, F.A. et al., "Design of a long-acting follitropin agonist by fusing the C-terminal sequence of the chorionic gonadotropin beta subunit to the follitropin beta subunit," Proc Natl Acad Sci USA, vol. 89, No. 10, pp. 4304-4308, May 15, 1992.
Findeis et al., "Targeted delivery of DNA for gene therapy via receptors" Trends Biotechnol., 1993, 11: pp. 202-205.
Friedman, D.S. et al., "Prevalence of age-related macular degeneration in the United States," Arch. Ophthalmol., vol. 122, No. 4, pp. 564-572, Apr. 2004.
Greene, T. W. et al., "Protective Groups in Organic Synthesis," 3rd Edition, John Wiley and Sons, Inc., New York, (1999). In 52 pages which includes only the Title Page and Table of Contents.
Guyer et al., "Immunoglobulin Binding by Mouse Intestinal Epithelial Cell Receptors", The Journal of Immunology, 117(2): dated Aug. 1, 1976, pp. 587-893.
Hein J., 1990, Unified Approach to Alignment and Phylogenies pp. 626-645 Methods in Enzymology vol. 183, Academic Press, Inc., San Diego, CA.
Higgins, D.G. and Sharp, P.M., "Fast and sensitive multiple sequence alignments on a microcomputer" CABIOS 5: dated 1989, pp. 151-153.
Hinton et al., "Engineered human IgG antibodies with longer serum half-lives in primates", Journal of Biological Chemistry, 279(8): dated Feb. 20, 2004 in 5 pages.
Hsu et al., "Differential N-Glycan Patterns of Secreted and Intracellular IgG Produced in Trichoplusia ni Cells" Journey of Biol. Chem. vol. 272: dated 1997, pp. 9062-9070.
Huang, Y-S. et al., "Engineering a pharmacologically superior form of granulocyte-colony-stimulating factor by fusion with gelatin-like-protein polymer," European Journal of Pharmaceutics and Biopharmaceutics, vol. 74, Issue 3, pp. 435-441, Mar. 2010.
Hwang et al., "Hepatic uptake and degradation of unilamellar sphingomyelin/cholesterol liposomes: a kinetic study", Proceedings of the National Academy of Sciences of the United States of America, 77(7): dated Jul. 1980, pp. 4030-4034.
Iwahashi, M. et al., "CDR substitutions of a humanized monoclonal antibody (CC49): contributions of individual CDRs to antigen binding and immunogenicity," Mol. Immunol. 36: Issue 15-16, 1079-1091, 1999.
Jaffe, G. et al., "Intraocular drug delivery," CRC Press, Mar. 2006 (Table of Contents only).
Jefferis et al., "Glycosylation of Antibody Molecules: Structural and Functional Significance", Antibody Engineering, vol. 65: dated 1997, pp. 111-128.
Johnson et al., "Kabat Database and its applications: 30 years after the first variability plot", Nucleic Acids Research, 28(1): Jan. 1, 2000, pp. 214-218.
Joralemon et al., PEGylated Polymers for Medicine From Conjugation to Self-Assembled Systems, Chemical Communications, vol. 46, No. 9, pp. 1377, 2010.
Kabat, E.A. et al., "Sequences of proteins of immunological interest," in 10 pages, 1991 (Table of Contents only).
Kaplitt, "Long-term gene expression and phenotypic correction using adeno-associated virus vectors in the mammalian brain" Nature Genetics, 1994, 8:148.
Katschke, K. et al., "Inhibiting Alternative Pathway Complement Activation by Targeting the Factor D Exosite—Supplementary Material", The Journal of Biological Chemistry, Apr. 2012, vol. 287, No. 16, in 11 pages.
Katschke, K. et al., "Inhibiting Alternative Pathway Complement Activation by Targeting the Factor D Exosite", The Journal of Biological Chemistry, Apr. 2012, vol. 287, No. 16, pp. 12886-12892.
Kim et al., "Identifying amino acid residues that influence plasma clearance of murine IgG1 fragments by site-directed mutagenesis", European Journal of Immunology, 24(3): dated Mar. 1994.
Kim, J.K. et al., "Localization of the site of the murine IgG1 molecule that is involved in binding to the murine intestinal Fc receptor", European Journal of Immunology, Oct. 1994, vol. 24(10), pp. 2429-2434.
Kimura, "Retroviral Delivery of DNA into the Livers of Transgenic Mice Bearing Premalignant and Malignant Hepatocellular Carcinomas" Human Gene Therapy, 1994, 5(7): pp. 845-852.
Klein R, Klein BE, Jensen SC, Meuer SM. 1997. The five-year incidence and progression of age-related maculopathy: The Beaver Dam Eye Study. Ophthal. 104:7-21.
Kohler et al., "Continuous cultures of fused cells secreting antibody of predefined specificity", Nature, vol. 256: dated 1975, pp. 495-497.
Kunik et al., "Paratome: an online tool for systematic identification of antigen-binding regions in antibodies based on sequence or structure", Nucleic Acids Research, vol. 40: Jun. 6, 2012, W521-524.
Lazar et al., "Engineered antibody Fc variants with enhanced effector function", Proc Natl Acad Sci U S A, 103(11): dated Mar. 14, 2006 in 6 pages.
Lefranc et al., "IMGT unique numbering for immunoglobulin and T cell receptor variable domains and Ig superfamily V-like domains", Developmental and Comparative Immunology, vol. 27: dated 2003, pp. 55-77.
Lloyd et al., "Modeling the human immune response: performance of a 1011 human antibody repertoire against a broad panel of therapeutically relevant antigens", Protein Engineering Design & Selection, vol. 22, No. 3, pp. 159-168, 2009.
Maccallum, R. et al., Antibody-Antigen Interactions: Contact Analysis and Binding Site Topography, J. Mol Biol., vol. 262, pp. 732-745, (1996).

(56) References Cited

OTHER PUBLICATIONS

Makabe et al., "Thermodynamic Consequences of Mutations in Vernier Zone Residues of a Humanized Anti-human Epidermal Growth Factor Receptor Murine Antibody, 528", Journal of Biological Chemistry, vol. 283: dated Jan. 11, 2008, pp. 1156-1166.
Martin et al., "Modeling antibody hypervariable loops: A combined algorithm", Proc. Natl. Acad. Sci. USA, vol. 86: dated Dec. 1989, pp. 9268-9272.
Mccafferty et al., "Phage antibodies: filamentous phage displaying antibody variable domains", Nature, vol. 348: dated 1990, pp. 552-554.
Mcpherson, D. et al., "Production and Purification of a Recombinant Elastomeric Polypeptide, G-(VPGVG)19-VPGV, from *Escherichia coli*," Biotechnology Process, vol. 8, Issue 4, pp. 347-352, Jul./Aug. 1992.
Neuberger, M., "Generating high-avidity human Mabs in mice," Nature Biotechnology, vol. 14, pp. 826, 1996.
Östberg, L. et al., "Human X (mouse X human) hybridomas stably producing human antibodies," Hybridoma, vol. 2, No. 4, pp. 361-367, 1983.
Padlan, Eduardo A., "A possible procedure for reducing the immunogenicity of antibody variable domains while preserving their ligand-binding properties," Molecular Immunology, vol. 28, Issues 4-5, pp. 489-498, Apr.-May 1991.
Paul, "Fv Structure and Diversity in Three Dimensions," Fundamental Immunology, 1993, 3rd Edition, pp. 292-295.
Philip, "Efficient and sustained gene expression in primary T lymphocytes and primary and cultured tumor cells mediated by adeno-associated virus plasmid DNA complexed to cationic liposomes." Mol. Cell Biol., 1994, 14(4): pp. 2411-2418.
Piatesi, A. et al., "Immunological Optimization of a Generic Hydrophobic Pocket for High Affinity Hapten Binding and Diels-Alder Activity", ChemBio Chem, 2004, vol. 5, pp. 460-466.
Ravetch et al., "FC Receptors," 1991, Ann. Rev. Immunol., vol. 9:457-92.
RecName: Full=Complement factor D; EC=3.4.21.46; AltName: Full=Adipsin; AltName: Full=C3 convertase activator; AltName: Full=Properdin factor D; Flags: Precursor, Uniprot, Jul. 21, 1986 (Jul. 21, 1986), XP002614847, [retrieved on Jul. 21, 1986]. This appears to refer to a web page, which indicates that the page was last modified on Nov. 30, 2010. Contents of the web page may have been available at an earlier date.
Robinson, D.F, "Comparison of Labeled Trees with Valency Three," Journal of Combinational Theory 11: pp. 105-119 (1971).
Roitt, I.M., "Immunology—Second Edition", Gower Medical Publishing, 1989, p. 5.8, 5.9.
Rudikoff, S. et al., Single Amino Acid Substitution Altering Antigen-Binding Specificity, Proc Natl. Acad. Sci. USA, vol. 79, pp. 1979-1983, (1982).
Saitou, N., Nei, M., "The neighbor-joining method: a new method for reconstructing phylogenetic trees." Mol. Biol. Evol. vol. 4: dated 1987, pp. 406-425.
Samudrala et al., "Ab initio protein structure prediction using a combined hierarchical approach", Proteins, Structure, and Genetics Suppl, 37(S3): dated 1999, pp. 194-198.
Schellenberger, V. et al., "A recombinant polypeptide extends the in vivo half-life of peptides and proteins in a tunable manner," Nature Biotechnology, vol. 27, pp. 1186-1190, 2009.
Schlapschy, M. et al., "Fusion of a recombinant antibody fragment with a homo-amino-acid polymer: effects on biophysical properties and prolonged plasma half-life," Protein Eng Des Sel, vol. 20, Issue 6, pp. 273-284, Jun. 1, 2007.
Tamura, M. et al., "Structural correlates of an anticarcinoma antibody: Identification of specificity-determining residues (SDRs) and development of a minimally immunogenic antibody variant by retention of SDRs only," The Journal of Immunology, vol. 164, No. 3, pp. 1432-1441, Feb. 1, 2000.
Tonkinson, J. et al., "New Drugs: Antisense Oligodeoxynucleotides as Clinical Therapeutic Agents," Cancer Investigation, vol. 14, No. 1, pp. 54-65, 1996.
Umana et al., "Engineered glycoforms of an antineuroblastoma IgG1 with optimized antibody-dependent cellular cytotoxic activity." 1999, Nature Biotech. 17:176-180.
Vajdos, F. et al., "Comprehensive functional maps of the antigen-binding site of an anti-ErbB2 antibody obtained with shotgun scanning mutagenesis," Journal of Molecular Biology, vol. 320, Issue 2, pp. 415-428, Jul. 5, 2002.
Wagner, E. et al., "Transferrin-polycation conjugates as carriers for DNA uptake into cells," Proc. Natl. Acad. Sci. USA, vol. 87, No. 9, pp. 3410-3414, May 1, 1990.
Wilbur, W.J. and Lipman, D.J., "Rapid similarity searches of nucleic acid and protein data banks" 1983, Proc. Natl. Acad. Sci. USA 80: pp. 726-730.
Wittwer et al., "Glycosylation at Asn-184 inhibits the conversion of single-chain to two-chain tissue-type plasminogen activator by plasmin", Biochemistry, 29(17): dated May 1, 1990, pp. 4175-4180.
Woffendin, "Nonviral and viral delivery of a human immunodeficiency virus protective gene into primary human T cells" Proc. Natl. Acad. Sci., 1994, 91: pp. 11581-11585.
Wright et al., "Effect of glycosylation on antibody function: implications for genetic engineering", Trends Biotechnol, 15(1): dated Jan. 1997, pp. 26-32.
Wu et al., "Incorporation of Adenovirus into a Ligand-based DNA Carrier System Results in Retention of Original Receptor Specificity and Enhances Targeted Gene Expression" J. Biol. Chem., 1994, 269 (15): pp. 11542-11546.
Wu et al., "Receptor-mediated Gene Delivery and Expression in Vivo" J. Biol. Chem., 1988, 263.
Wu et al., "Receptor-mediated Gene Delivery in Vivo" J. Biol. Chem., 1991, 266, pp. 14338-14342.
Wu, "Targeting Genes: Delivery and Persistent Expression of a Foreign Gene Driven by Mammalian Regulatory Elements in Vivo" J. Biol. Chem., 1989, 264(29):16985-19687.
Wu, G.Y. et al., "Receptor-mediated in vitro gene transformation by a soluble DNA carrier system," Journal of Biological Chemistry, vol. 262, pp. 4429-4432, Apr. 5, 1987.
Wu, H et al., Humanization of a Murine Monoclonal Antibody by Simultaneous Optimization of Framework and CDR Residues, J. Mol. Biol., vol. 294, pp. 151-162, (1999).
Wyss et al., "The structural role of sugars in glycoproteins", Current Opin. Biotech. 1996, vol. 7, pp. 409-416.
Yeh, P. et al., "Design of yeast-secreted albumin derivatives for human therapy: biological and antiviral properties of a serum albumin-CD4 genetic conjugate," Proc Natl Acad Sci USA, vol. 89, No. 5, pp. 1904-1908, Mar. 1, 1992.
Zenke et al., "Receptor-mediated endocytosis of transferrin-polycation conjugates: an efficient way to introduce DNA into hematopoietic cells." Proc. Natl. Acad. Sci. USA, 1990, 87(10):3655-3659.
Office Action for Australian Application No. AU 2018250695 in 4 pages, dated Feb. 22, 2021.
Office Action for Australian Application No. AU 2018250695 in 5 pages, dated Nov. 19, 2021.
Office Action for Australian Application No. AU 2018250695 in 5 pages, dated Feb. 9, 2022.
Office Action for Canadian Application No. 3,059,938 dated Sep. 30, 2020.
Office Action for Canadian Application No. CA 3,059,938 in 4 pages, dated Sep. 27, 2021.
Office Action for Canadian Application No. CA 3,059,938 in 4 pages, dated Aug. 12, 2022.
Extended Search Report for European Application No. 18784891.6 in 15 pages, dated Jan. 21, 2021.
Office Action for European Application No. EP 18784891.6 in 6 pages, dated Jan. 2, 2023.
Invitation to Pay Additional Fees for PCT/US2018/027378 dated Aug. 1, 2018.
International Search Report and Written Opinion for PCT/US2018/027378 dated Sep. 27, 2018.
International Preliminary Report on Patentability for PCT/US2018/027378 dated Oct. 24, 2019.
Restriction Requirement for U.S. Appl. No. 15/952,092 dated Mar. 3, 2020.

(56) References Cited

OTHER PUBLICATIONS

Office Action for U.S. Appl. No. 15/952,092 dated Jun. 30, 2020.
Final Office Action for U.S. Appl. No. 15/952,092 dated Nov. 27, 2020.
Office Action for U.S. Appl. No. 15/952,092 in 29 pages, dated May 21, 2021.
Office Action for U.S. Appl. No. 15/952,092 in 17 pages, dated Sep. 13, 2021.
Notice of Allowance for U.S. Appl. No. 15/952,092 in 10 pages, dated Feb. 8, 2022.
Notice of Allowance for U.S. Appl. No. 15/952,092 in 9 pages, dated May 27, 2022.
Notice of Allowance for U.S. Appl. No. 15/952,092 in 9 pages, dated Oct. 17, 2022.
Notice of Allowance for U.S. Appl. No. 15/952,092 in 3 pages, dated Jan. 19, 2023.
Office Action for U.S. Appl. No. 15/820,325 dated Jul. 29, 2019.
File History of U.S. Appl. No. 15/952,092, filed Apr. 12, 2018.
File History of U.S. Appl. No. 15/394,500, filed Dec. 29, 2016.
File History of U.S. Appl. No. 13/959,563, filed Aug. 5, 2013.
File History of U.S. Appl. No. 14/456,875, filed Aug. 11, 2014.
File History of U.S. Appl. No. 16/424,265, filed Aug. 11, 2014.
File History of U.S. Appl. No. 12/281,071, filed Aug. 28, 2008.
File History of U.S. Appl. No. 14/265,174, filed Apr. 29, 2014.
File History of U.S. Appl. No. 15/182,278, filed Jun. 14, 2016.
File History of U.S. Appl. No. 13/515,913, filed Aug. 27, 2012.
File History of U.S. Appl. No. 13/516,173, filed Aug. 27, 2012.
File History of U.S. Appl. No. 15/099,234, filed Apr. 14, 2016.
File History of U.S. Appl. No. 13/901,483, filed May 23, 2013.
File History of U.S. Appl. No. 15/368,376, filed Dec. 2, 2016.
File History of U.S. Appl. No. 13/641,342, filed Dec. 2, 2016.
File History of U.S. Appl. No. 16/781,869, filed Mar. 2, 2016.
File History of U.S. Appl. No. 14/916,180, filed Mar. 2, 2016.
File History of U.S. Appl. No. 16/795,450, filed Jun. 29, 2015.
File History of U.S. Appl. No. 15/820,325, filed Nov. 21, 2017.
File History of U.S. Appl. No. 14/932,913, filed Nov. 4, 2015.
File History of U.S. Appl. No. 16/402,602, filed Nov. 4, 2015.
File History of U.S. Appl. No. 16/290,128, filed Mar. 1, 2019.
Office Action for Australian Application No. AU 2022201163 in 4 pages, dated Oct. 29, 2024.
Office Action for Canadian Application No. CA 3,059,938 in 3 pages, dated Dec. 30, 2024.

* cited by examiner

FIG. 1

ILGGREAEAHARPYMASVQLNGAHLCGGVLVAEQWVLSAAHCLEDAADGKVQVLLGAHS
LSQPEPSKRLYDVLRAVPHPDSQPDTIDHDLLLLQLSEKATLGPAVRPLPWQRVDRDVAP
GTLCDVAGWGIVNHAGRRPDSLQHVLLPVLDRATCNRRTHHDGAITERLMCAESNRRDS
CKGDSGGPLVCGGVLEGVVTSGSRVCGNRKKPGIYTRVASYAAWIDSVLA (SEQ ID NO: 1)

TFA

COMPOUND L

COMPOUND K

R3707

OG1802

OG1786

OG1550

OG1546

OG1546 OG1563

OG1784

OG1784

OG1405

OG1785

OG1786

OG1801

PC =

X=a) OR where R=H, methyl, ethyl, propyl, isopropyl, b) H, or c) any halide, including Br
n1, n2, n3, n4, n5, n6, n7, n8 and n9 are the same or different such that the sum of n1, n2, n3, n4, n5, n6, n6, n7, n8 and n9 is 2500 plus or minus 15%.

OG1802

Definitions:
PC =

X=a) OR where R=H, methyl, ethyl, propyl, isopropyl, b) H, or c) any halide, including Br n1, n2, n3, n4, n5, n6, n7, n8 and n9 are the same or different such that the sum of n1, n2, n3, n4, n5, n6, n6, n7, n8 and n9 is 2500 plus or minus 15%.

COMPOUND E

34I54I59D84S/54R101V

34I54I59D84S/54R101V

Single cycle kinetics of 34I54I59D84S/54R101V on cyno Factor D on a Protein A chip

| Ligand | Sample | ka (1/Ms) | kd (1/s) | KD (M) |
|---|---|---|---|---|
| OG1965 | cyCFD | 3.49E+07 | 9.78E-04 | 2.80E-11 |

Single cycle kinetics of 34I54I59D84S/54R101V; Biotinylated antibody on neutravidin chip 25 Degrees 37 Degrees

| | ka (1/Ms) | kd (1/s) | KD (M) |
|---|---|---|---|
| 25° | 1.40E+07 | 5.08E-05 | 3.64E-12 |
| 37° | 2.55E+07 | 2.41E-04 | 9.56E-12 |

25 Degrees Single Cycle Kinetics on a Protein A Chip

OG1965

OG1970

Kinetic Exclusion Assay data at 37 degrees and Biacore data at 25 degrees

| Molecule | Platform (°C) | $K_{on}$ (M) | $K_{off}$ (M) | $K_D$ (pM) |
|---|---|---|---|---|
| OG1965 | Biacore (25°) | $2.52x10^7$ | $6.30x10^{-5}$ | 2.50 |
| | KinExA (37°) | $3.06x10^7$ | $1.79x10^{-4}$ | 5.86 |
| OG1970 | Biacore (25°) | $2.16x10^7$ | $1.33x10^{-4}$ | 6.14 |
| | KinExA (37°) | $3.67x10^7$ | $2.96x10^{-4}$ | 8.07 |

| | Vmax (milliOD/min) | % control |
|---|---|---|
| OG1931 | 5.5885 | 179.8527 |
| OG1965 | 0.81 | 26.06794078 |
| OG1970 | 0.655 | 21.07963112 |

Factor B Cleavage Assay ELISA

FIG. 24A
Fab
Heavy Chain
Light Chain
Factor D

FIG. 26C
CFD : Fab Light Chain
CFD : Fab Heavy Chain
Residue Interactions < 6 Å
Total Number of Interactions

CFB binding inhibition assay

Complement activation on ARPE19 cells (immunofluorescence)

SEQUENCE LISTING

```
Sequence total quantity: 590
SEQ ID NO: 1           moltype = AA  length = 228
FEATURE                Location/Qualifiers
REGION                 1..228
                       note = Mature form of human complement factor D
source                 1..228
                       mol_type = protein
                       organism = synthetic construct
SEQUENCE: 1
ILGGREAEAH ARPYMASVQL NGAHLCGGVL VAEQWVLSAA HCLEDAADGK VQVLLGAHSL  60
SQPEPSKRLY DVLRAVPHPD SQPDTIDHDL LLLQLSEKAT LGPAVRPLPW QRVDRDVAPG  120
```

-continued

```
TLCDVAGWGI VNHAGRRPDS LQHVLLPVLD RATCNRRTHH DGAITERLMC AESNRRDSCK  180
GDSGGPLVCG GVLEGVVTSG SRVCGNRKKP GIYTRVASYA AWIDSVLA               228

SEQ ID NO: 2            moltype = AA  length = 120
FEATURE                 Location/Qualifiers
REGION                  1..120
                        note = mAb KCD002 heavy chain
source                  1..120
                        mol_type = protein
                        organism = synthetic construct
SEQUENCE: 2
EVKLVESEGG LVQPGSSMKL SCTASGFTFS DYYMAWVRQV PEKGLEWVGN INYDGSSTYY  60
LDSLKSRFII SRDSAKNILY LQMSSLKSED TATYFCARGE DFYLYAMDYW GQGTSVTVSS  120

SEQ ID NO: 3            moltype =   length =
SEQUENCE: 3
000

SEQ ID NO: 4            moltype = AA  length = 107
FEATURE                 Location/Qualifiers
REGION                  1..107
                        note = mAb KCD002 light chain
source                  1..107
                        mol_type = protein
                        organism = synthetic construct
SEQUENCE: 4
DIQMTQSPAS LSASVGETVT ITCRASENIH SYLAWYQQKQ GKSPQLIVYN TKTLAEGVPS  60
RFSGSGSGTQ FSLKINSLQP EDFGSYYCQH HYGIPPTFGG GTKLEIK                107

SEQ ID NO: 5            moltype = AA  length = 116
FEATURE                 Location/Qualifiers
REGION                  1..116
                        note = mAb KCD003 heavy chain
source                  1..116
                        mol_type = protein
                        organism = synthetic construct
SEQUENCE: 5
EVQLQQSRPE LVKPGASVKI FCKASGYTFT DYYMNWMRQR HGETLEWIGD INPNNGDPSY  60
NQKFKDKATL TVDKSSSTAS MELRSLTSDD SAVYYCAREG PSFAYWGQGT LVTVSA      116

SEQ ID NO: 6            moltype = AA  length = 112
FEATURE                 Location/Qualifiers
REGION                  1..112
                        note = mAb KCD003 light chain
source                  1..112
                        mol_type = protein
                        organism = synthetic construct
SEQUENCE: 6
DVLMTQTPLS LPVSLGEQAS ISCRSSQTIV HSNGDTYLEW YLQKPGQSPN LLIYKVSNRF  60
SGVPDRFSGS GSGTDFTLKI SRVEAEDLGV YYCFQGSHVP PTFGGGTKLE IK          112

SEQ ID NO: 7            moltype = AA  length = 116
FEATURE                 Location/Qualifiers
REGION                  1..116
                        note = mAb KCD005 heavy chain
source                  1..116
                        mol_type = protein
                        organism = synthetic construct
SEQUENCE: 7
EVQLQQSGPE LVKPGASVKI SCKASGYTFT DHYMNWVKQS HGKSLEWIGD INPNNGGTSC  60
NQKFKGKATL TVDKSSSTAY MELRSLTSGD SAVYYCTREG ASFAFWGQGT LVTVSA      116

SEQ ID NO: 8            moltype = AA  length = 112
FEATURE                 Location/Qualifiers
REGION                  1..112
                        note = mAb KCD005 light chain
source                  1..112
                        mol_type = protein
                        organism = synthetic construct
SEQUENCE: 8
DVLMTQTPLS LPVSLGDQAS ISCRSSQSIV HSNGDTYLEW YLQKPGQSPK LLIYKVSNRF  60
SGVPDRFSGS GSGTDFTLKI SRVEAEDLGV YYCFQGSHVP VTFGAGTKLE LK          112

SEQ ID NO: 9            moltype =   length =
SEQUENCE: 9
000

SEQ ID NO: 10           moltype =   length =
SEQUENCE: 10
```

-continued

```
000

SEQ ID NO: 11          moltype =   length =
SEQUENCE: 11
000

SEQ ID NO: 12          moltype =   length =
SEQUENCE: 12
000

SEQ ID NO: 13          moltype =   length =
SEQUENCE: 13
000

SEQ ID NO: 14          moltype =   length =
SEQUENCE: 14
000

SEQ ID NO: 15          moltype = AA  length = 116
FEATURE                Location/Qualifiers
REGION                 1..116
                       note = mAb KCD009 heavy chain
source                 1..116
                       mol_type = protein
                       organism = synthetic construct
SEQUENCE: 15
QIQLVQSGPE LKKPGETVKI SCKASGYIFR NYGMNWVKQG PGKGLKWMGW INTYTGEPTY  60
ADDFKGRFAF SLETSASTAY LQISNLKNED TATYFCVRDG PGFAYWGQGT LVTVSA      116

SEQ ID NO: 16          moltype = AA  length = 112
FEATURE                Location/Qualifiers
REGION                 1..112
                       note = mAb KCD009 light chain
source                 1..112
                       mol_type = protein
                       organism = synthetic construct
SEQUENCE: 16
DVLMTQTPLS LPVSLGDQAS ISCRSSLIIE HSDGNTYLEW YLQKPGQSPK LLIYKVSNRF  60
SGVPDRFSGS GSGTDFTLKI SRVEADDLGV YYCFQGSHVP VTFGAGTNLE LK          112

SEQ ID NO: 17          moltype = AA  length = 114
FEATURE                Location/Qualifiers
REGION                 1..114
                       note = mAb KCD010 heavy chain
source                 1..114
                       mol_type = protein
                       organism = synthetic construct
SEQUENCE: 17
EVLLQQSGPE LVKPGASVKI PCKASGYTFT DYDMDWVKQS HGKSLEWIGH INPNNGGTIY  60
NQKFKGKATL TVDKSSSTAY MELRSLTSED TAVYYCGTGD FAYWGHGTLV TVSA        114

SEQ ID NO: 18          moltype = AA  length = 108
FEATURE                Location/Qualifiers
REGION                 1..108
                       note = mAb KCD010 light chain
source                 1..108
                       mol_type = protein
                       organism = synthetic construct
SEQUENCE: 18
QIVLTQSPAI MSVSPGEKVT LTCSASSSVS SSYLYWYQKK PGSSPKLWIY STSNLASGVP  60
ARFSGSGSGT SYSLTISSME AEDAASYFCH QWSSYPPTFG AGTKLELK               108

SEQ ID NO: 19          moltype = AA  length = 114
FEATURE                Location/Qualifiers
REGION                 1..114
                       note = mAb KCD023 heavy chain
source                 1..114
                       mol_type = protein
                       organism = synthetic construct
SEQUENCE: 19
EVLLQQSGPE LVKPGASVKI PCKASGYTFT DYNIDWVKQS HGKSLEWIGD INPNNGGINY  60
NQKFKGKATL TVDKSSSTAY MELRSLTSED TAVYYCGTGD YAYWGQGTLV TVSA        114

SEQ ID NO: 20          moltype = AA  length = 108
FEATURE                Location/Qualifiers
REGION                 1..108
                       note = mAb KCD023 light chain
source                 1..108
                       mol_type = protein
```

```
                       organism = synthetic construct
SEQUENCE: 20
QIVLTQSPAF MSASPGEKVT LTCSASSSVS SSYLYWYQQK PGSSPKLWIY STSNLASGVP  60
GRFSGSGSGT SYSLTISSME AEDAASYFCH QWTSYPPTFG AGTKLELK              108

SEQ ID NO: 21          moltype = AA  length = 118
FEATURE                Location/Qualifiers
REGION                 1..118
                       note = mAb KCD036 heavy chain
source                 1..118
                       mol_type = protein
                       organism = synthetic construct
SEQUENCE: 21
EVQLQQSGPE LVKPGASMKI SCKASGYSFT GYTMTWVKQS HGKNLEWIGL INPYNGGTNY  60
NQKFKGKATF TVDKSSSTAY MELLSLTSED SAVYYCARRH YGSSWDYWGQ GTTLTVSS    118

SEQ ID NO: 22          moltype = AA  length = 107
FEATURE                Location/Qualifiers
REGION                 1..107
                       note = mAb KCD036 light chain
source                 1..107
                       mol_type = protein
                       organism = synthetic construct
SEQUENCE: 22
DIKLTQSPSS MYASLGERVT ITCKASQDIN TYLSWFQQKP GKSPKTLIYR ANRLVDGVPS  60
RFSGSGSGQD YSLTISSLEY EEMGIYYCLQ YDEFPYTFGG GTKLEIK               107

SEQ ID NO: 23          moltype = AA  length = 113
FEATURE                Location/Qualifiers
REGION                 1..113
                       note = mAb KCD040 heavy chain
source                 1..113
                       mol_type = protein
                       organism = synthetic construct
SEQUENCE: 23
EVQLQQSGAE LVKPGASVKL SCTASDFNIK DTYMHWVMQR PEQGLEWIGK IDPANGNTEF  60
DPKFQGKATI TADTSSNTAY LQLTSLTSED TAVYYCTRAM DYWGQGTSVT VSS         113

SEQ ID NO: 24          moltype = AA  length = 106
FEATURE                Location/Qualifiers
REGION                 1..106
                       note = mAb KCD040 light chain
source                 1..106
                       mol_type = protein
                       organism = synthetic construct
SEQUENCE: 24
QIVLTQSPAI MSASPGEKVT MTCSAGSSVS YMYWYQQKPG SSPRVLIYDT SNLASGVPVR  60
FSGSGSGTSY SLTISRMEAE DAATYYCQQW SNYPYTFGGG TKLEIK                106

SEQ ID NO: 25          moltype = AA  length = 113
FEATURE                Location/Qualifiers
REGION                 1..113
                       note = mAb KCD042 heavy chain
source                 1..113
                       mol_type = protein
                       organism = synthetic construct
SEQUENCE: 25
EVQLQQSGAE LVKPGASVRL SCTASGFNIK HTYIHWVSQR PEQGLEWIGK IDPANGNTKY  60
DPKFQGKATI TADTSSNTAY LQLSSLTSED TAVYYCVNAM EYWGQGTSVT VSS         113

SEQ ID NO: 26          moltype = AA  length = 106
FEATURE                Location/Qualifiers
REGION                 1..106
                       note = mAb KCD042 light chain
source                 1..106
                       mol_type = protein
                       organism = synthetic construct
SEQUENCE: 26
QSVLTQSPAI MSASPGEKVT MTCSANSSVS DMYWFQQRPG SSPRLLIYDT SNLASGVPVR  60
FSGSGSGTSY SLTISRMEAE DAATYYCQQW STYPWTFGGG TKLEIK                106

SEQ ID NO: 27          moltype = AA  length = 113
FEATURE                Location/Qualifiers
REGION                 1..113
                       note = mAb KCD044 heavy chain
source                 1..113
                       mol_type = protein
                       organism = synthetic construct
SEQUENCE: 27
```

-continued

```
EVQLQQSGAE LVKPGASVRL SCTASGFNIK HTYMHWVSQR PERGLEWIGK IDPANGNTKY  60
DPKFQGKATI TADTSSNTVY LQLSSLTSED TAVYYCLNAM EYWGQGTSVT VSS         113

SEQ ID NO: 28          moltype = AA  length = 106
FEATURE                Location/Qualifiers
REGION                 1..106
                       note = mAb KCD044 light chain
source                 1..106
                       mol_type = protein
                       organism = synthetic construct
SEQUENCE: 28
QSVLTQSPAI MSASPGEKVT MTCSANSSVS DMYWYQQRPG SSPRLLIYDT SNLASGVPVR  60
FSGSGSGTSY SLTISRMEAE DAATYYCQQW STYPWTFGGG TKLEIK                 106

SEQ ID NO: 29          moltype = AA  length = 113
FEATURE                Location/Qualifiers
REGION                 1..113
                       note = mAb KCD047 heavy chain
source                 1..113
                       mol_type = protein
                       organism = synthetic construct
SEQUENCE: 29
EVQLQQSGAE FVKPGASVRL SCTASGFNIK DTYMHWVKQR PEQGLEWIGR IDPANGYTKD  60
DPKFQGKATI TADTSSNTAY LQLSSLTSED TAVYYCASAM DYWGQGTSVT VSS         113

SEQ ID NO: 30          moltype = AA  length = 106
FEATURE                Location/Qualifiers
REGION                 1..106
                       note = mAb KCD047 light chain
source                 1..106
                       mol_type = protein
                       organism = synthetic construct
SEQUENCE: 30
QIVLTQSPAV MSASPGEKVA MTCSASSSVT YMYWYQQKPG SSPRLLIYDT SNLASGVPVR  60
FSGSGSGTSY SLTISRMEAE DAATYYCQQW STYPFPFGSG TKLEIK                 106

SEQ ID NO: 31          moltype = AA  length = 113
FEATURE                Location/Qualifiers
REGION                 1..113
                       note = mAb KCD048 heavy chain
source                 1..113
                       mol_type = protein
                       organism = synthetic construct
SEQUENCE: 31
EVQLQQSGAD LVKPGASVKL SCTASGFNIK ATYMHWVRQR PEKGLEWIGR IDPANGHTIY  60
DPQFQGKATI TSDTSSNTAY LQLNSLTSED TAVYYCAEAM DYWGQGTSVT VSS         113

SEQ ID NO: 32          moltype = AA  length = 106
FEATURE                Location/Qualifiers
REGION                 1..106
                       note = mAb KCD048 light chain
source                 1..106
                       mol_type = protein
                       organism = synthetic construct
SEQUENCE: 32
QIVLTQSPAI MSASPGEKVT LTCSATSSVS YMYWYQQKPG SSPRLLIYDT SNLASGVPVR  60
FSGSGSGTSY SLTISRMEAE DDATYYCQQW SNYPFTFGGG TKLEIK                 106

SEQ ID NO: 33          moltype = AA  length = 118
FEATURE                Location/Qualifiers
REGION                 1..118
                       note = mAb KCD070 heavy chain
source                 1..118
                       mol_type = protein
                       organism = synthetic construct
SEQUENCE: 33
EIQLQQTGPE LVKPGASVKI SCKASGYSFT DYIILWVKQS HGKSLEWIGN INPYYDYTSY  60
NLKFKGKATL TVDKSSSTAY MQLNSLTSED SAVYYCARSD GYYGGDYWGQ GTSVTVSS    118

SEQ ID NO: 34          moltype = AA  length = 107
FEATURE                Location/Qualifiers
REGION                 1..107
                       note = mAb KCD070 light chain
source                 1..107
                       mol_type = protein
                       organism = synthetic construct
SEQUENCE: 34
DIVMTQSHKF MSTSVGDRVS ITCKASQDVG TAVAWYQQKP GQSPKLLIYW ASTRHTGVPD  60
RFTGSGSGTD FTLTINNVQS EDLADYFCQQ YSSYPWTFGG GTTLEIK                107
```

```
SEQ ID NO: 35          moltype = AA  length = 118
FEATURE                Location/Qualifiers
REGION                 1..118
                       note = mAb KCD101 heavy chain
source                 1..118
                       mol_type = protein
                       organism = synthetic construct
SEQUENCE: 35
QVQLQQPGAE LVRPGTSVKL SCKASGYTFT SYWMHWVKQR PGQGLEWIGV IDPSDSYTNY  60
NQKFKGKATL TVDTSSSTAY MQLSSLTSED SAVYYCGRNG YDGSMDYWGQ GTSVTVSS    118

SEQ ID NO: 36          moltype = AA  length = 107
FEATURE                Location/Qualifiers
REGION                 1..107
                       note = mAb KCD101 light chain
source                 1..107
                       mol_type = protein
                       organism = synthetic construct
SEQUENCE: 36
DIQMTQTTSS LSASLGDRVT ISCRASQDIS NYLNWYQQKP DGTVKLLIYY PSRLHSGVPS  60
RFSGSGSGTD YSLTISNLEQ EDFATYFCQQ GNTLPYTFGG GTKLEIK                107

SEQ ID NO: 37          moltype = AA  length = 118
FEATURE                Location/Qualifiers
REGION                 1..118
                       note = mAb KCD102 heavy chain
source                 1..118
                       mol_type = protein
                       organism = synthetic construct
SEQUENCE: 37
QVQLQQPGAE LVRPGTSVKL SCKASGYTFT SYWMHWVKQR PGQGLEWIGV IDPSDSYTNY  60
NQKFKGKATL TVDTSSSTAY MQLSSLTSED SAVYYCARNG YDGSMDYWGQ GTSVTVSS    118

SEQ ID NO: 38          moltype = AA  length = 107
FEATURE                Location/Qualifiers
REGION                 1..107
                       note = mAb KCD102 light chain
source                 1..107
                       mol_type = protein
                       organism = synthetic construct
SEQUENCE: 38
EIQMTQTTSS LSASLGDRVT ISCRASQDIS NYLNWYQQKP DGTVKLLIYY PSRLHSGVPS  60
RFSGSGSGTD YSLTISNLEQ EDFATYFCQQ GNTLPYTFGG GTKLEIK                107

SEQ ID NO: 39          moltype = AA  length = 118
FEATURE                Location/Qualifiers
REGION                 1..118
                       note = mAb KCD103 heavy chain
source                 1..118
                       mol_type = protein
                       organism = synthetic construct
SEQUENCE: 39
QVQLQQPGAE LVRPGTSVKL SCKASGYTFT SYWMHWVKQR PGQGLEWIGV IDPSDSYTKY  60
NQKFKDKATL TVETSSSTAY MQLSSLTSED SAVYYCAGNG YDGSMDYWGQ GTSVTVSS    118

SEQ ID NO: 40          moltype = AA  length = 107
FEATURE                Location/Qualifiers
REGION                 1..107
                       note = mAb KCD103 light chain
source                 1..107
                       mol_type = protein
                       organism = synthetic construct
SEQUENCE: 40
DIQMTQTTSS LSASLGDRVT ISCRASQDIS NSLNWYQQKP DGTVKLLIYY TSRLHSRVPS  60
RFSGSGSGTD YSLTISNLDQ EDIATYFCQQ ANTLPYTFGG GTKLEIK                107

SEQ ID NO: 41          moltype = AA  length = 118
FEATURE                Location/Qualifiers
REGION                 1..118
                       note = mAb KCD104 heavy chain
source                 1..118
                       mol_type = protein
                       organism = synthetic construct
SEQUENCE: 41
QVQLQQPGAE LVRPGTSVKL SCKASGYTFT SYWMHWVKQR PGQGLEWIGV IDPSDSYTYY  60
NQKFKGKATL TVDTSSSTAY MQLSSLTSED SAVYYCARNG YDGAMDYWGQ GTSVTVSS    118

SEQ ID NO: 42          moltype = AA  length = 107
```

```
FEATURE                Location/Qualifiers
REGION                 1..107
                       note = mAb KCD104 light chain
source                 1..107
                       mol_type = protein
                       organism = synthetic construct
SEQUENCE: 42
EIQMTQTTSS LSASLGDRVT ISCRASQDIS NYLNWYQQKP DGTVKLLIYY PSRLHSGVPS  60
RFSGSGSGTD YSLTISNLEQ EDFATYFCQQ GNTLPYTFGG GTKLEIK                107

SEQ ID NO: 43          moltype = AA  length = 116
FEATURE                Location/Qualifiers
REGION                 1..116
                       note = mAb KCD118 heavy chain
source                 1..116
                       mol_type = protein
                       organism = synthetic construct
SEQUENCE: 43
EVQLQQSGPE LVKPGASVKI SCKAFGYTFT DYYKNWMRQR HGESLEWIGD INPNSGDANY  60
NQKFKGKATL TVDKSSSTAY MELRSLTSED SAVYYCAREG PSFAYWGHGT LVTVSA      116

SEQ ID NO: 44          moltype = AA  length = 112
FEATURE                Location/Qualifiers
REGION                 1..112
                       note = mAb KCD118 light chain
source                 1..112
                       mol_type = protein
                       organism = synthetic construct
SEQUENCE: 44
DVLMTQTPLS LPVSLGDQAS ISCRSSQTIV HSNGDTYLEW YLQKPGQSPN LLIYKVSNRF  60
SGVPDRFSGS GSGTDFTLKI SRVEAEDLGI YYCFQGSHVP PTFGGGTKLE IK          112

SEQ ID NO: 45          moltype = AA  length = 116
FEATURE                Location/Qualifiers
REGION                 1..116
                       note = mAb KCD119 heavy chain
source                 1..116
                       mol_type = protein
                       organism = synthetic construct
SEQUENCE: 45
EVQLQQSGPE LVKPGASVKI SCKASGYTFT DYYTNWMRQR HGESLEWIGD INPNTGDTSY  60
NQKFRVKATL TVDKSSGTAY MGLRSLTSED SAVYYCTREG PSFAYWGQGT LVTVSA      116

SEQ ID NO: 46          moltype = AA  length = 112
FEATURE                Location/Qualifiers
REGION                 1..112
                       note = mAb KCD119 light chain
source                 1..112
                       mol_type = protein
                       organism = synthetic construct
SEQUENCE: 46
DVLMTQTPLS LPVSLGDQAS ISCRSSQTIV HSNGDTYLEW YLQKPGQSPN LLIYKVSNRF  60
SGVPDRFSGS GSGTDFTLKI SRVEAEDLGV YYCFQGSHVP PTFGGGTTLE IK          112

SEQ ID NO: 47          moltype = AA  length = 116
FEATURE                Location/Qualifiers
REGION                 1..116
                       note = mAb KCD121 heavy chain
source                 1..116
                       mol_type = protein
                       organism = synthetic construct
SEQUENCE: 47
EVQLQQSGPE LVKPGASVKI SCKASGYTFT DYYKNWMRQR HGESLEWIGD INPNNGDTSY  60
NQKFRGKATL TVDKSSSTAF MELRSLTSED SAVYYCAREG PSFAYWGQGT LVTVSA      116

SEQ ID NO: 48          moltype = AA  length = 112
FEATURE                Location/Qualifiers
REGION                 1..112
                       note = mAb KCD121 light chain
source                 1..112
                       mol_type = protein
                       organism = synthetic construct
SEQUENCE: 48
DVLMTQTPLS LPVSLGDQAS ISCRSNQTIV HSNGDTYLEW YLQKPGQSPN LLIYKVSNRF  60
SGVPDRFSGS GSGTDFTLRI SRVEAEDLGV YYCFQGSHVP PTFGGGTKLE IK          112

SEQ ID NO: 49          moltype = AA  length = 116
FEATURE                Location/Qualifiers
REGION                 1..116
```

```
                         note = mAb KCD122 heavy chain
source                   1..116
                         mol_type = protein
                         organism = synthetic construct
SEQUENCE: 49
EVQLQQSGPE LVKPGASVKI SCKASGYTFT DYYKNWMRQR HGESLEWIGD INPNNGDANY  60
NQKFKGKATL TVDKSSSTAY MELRSLTSED SAVYFCAREG PSFAYWGHGT LVTVSA      116

SEQ ID NO: 50            moltype = AA  length = 112
FEATURE                  Location/Qualifiers
REGION                   1..112
                         note = mAb KCD122 light chain
source                   1..112
                         mol_type = protein
                         organism = synthetic construct
SEQUENCE: 50
DVLMTQTPLS LPVSLGDQAS ISCRSSQTIV HSNGDTYLEW YLQKPGQSPN LLIYKVSNRF  60
SGVPDRFSGS GSGTDFTLKI SRVEAEDLGV YYCFQGSHVP PTFGGGTKLE IK          112

SEQ ID NO: 51            moltype = AA  length = 116
FEATURE                  Location/Qualifiers
REGION                   1..116
                         note = mAb KCD123 heavy chain
source                   1..116
                         mol_type = protein
                         organism = synthetic construct
SEQUENCE: 51
EVHLQQSGPE LVKPGASVKI SCKASGYTFT DFYKNWMRQR HGESLEWIGD INPNNGGTNY  60
NQKFKGKATL TVDKSSSTAY MELRSLTSED SAVYYCAREG PSFAYWGQGT LVTVSA      116

SEQ ID NO: 52            moltype = AA  length = 112
FEATURE                  Location/Qualifiers
REGION                   1..112
                         note = mAb KCD123 light chain
source                   1..112
                         mol_type = protein
                         organism = synthetic construct
SEQUENCE: 52
DVLMTQTPLS LPVSLGDQAS ISCRSSQTIV HSNGDTYLEW YLQKPGQSPN LLIYKVSNRF  60
SGVPDRFSGS GSGTDFTLKI SRVEAEDLGV YYCFQGSHVP PTFGGGTKLE IK          112

SEQ ID NO: 53            moltype = AA  length = 116
FEATURE                  Location/Qualifiers
REGION                   1..116
                         note = mAb KCD124 heavy chain
source                   1..116
                         mol_type = protein
                         organism = synthetic construct
SEQUENCE: 53
EVQLQQSGPE LVKPGASVKI SCKASGYTFT DHYMNWVKQS HGKSLEWIGD INPNNGGTSY  60
NQKFKGKATL TVDKSSSTAY MELRSLTSGD SAVYYCTREG ASFAFWGQGT LVTVSA      116

SEQ ID NO: 54            moltype = AA  length = 112
FEATURE                  Location/Qualifiers
REGION                   1..112
                         note = mAb KCD124 light chain
source                   1..112
                         mol_type = protein
                         organism = synthetic construct
SEQUENCE: 54
DVLMTQTPLS LPVSLGDQAS ISCRSSQSIV HSNGDTYLEW YLQKPGQSPK LLIYKVSNRF  60
SGVPDRFSGS GSGTDFTLKI SRVEAEDLGV YYCFQGSHVP LTFGAGTKLE LK          112

SEQ ID NO: 55            moltype = AA  length = 122
FEATURE                  Location/Qualifiers
REGION                   1..122
                         note = mAb KCD131 heavy chain
source                   1..122
                         mol_type = protein
                         organism = synthetic construct
SEQUENCE: 55
QVQLQQSGPE LVKPGASVKI SCKASAYTFT DYYINWVKQR PGQGPEWIGW IFPGSNSTYS  60
NEKFEVKATL TVDESSSTAY MLLSSLTSED SAVYFCARLG YFGSSYHALD YWGQGTSVTV  120
SS                                                                 122

SEQ ID NO: 56            moltype = AA  length = 107
FEATURE                  Location/Qualifiers
REGION                   1..107
                         note = mAb KCD131 light chain
```

```
source                  1..107
                        mol_type = protein
                        organism = synthetic construct
SEQUENCE: 56
DIQMTQSPAS LSVSVGETVT ITCRASENIY SHLAWFQQKQ GKSPRLLVYS ATNLPDGVPS  60
RFSGSGSGTQ YSLKINILQS EDFGSYYCQH FWGTPWTFGG GTKLEIK               107

SEQ ID NO: 57           moltype = AA  length = 113
FEATURE                 Location/Qualifiers
REGION                  1..113
                        note = mAb KCD136 heavy chain
source                  1..113
                        mol_type = protein
                        organism = synthetic construct
SEQUENCE: 57
EVQLQQSVAE LVRPGASVKL SCSASGFNIK NTYMHWVNQR PEQGLEWIGR IDPANGITKY  60
APNFQGKATI TADTSSNTAY LQLSNLTSED TAIYYCTRAM DYWGQGTSVT VSS         113

SEQ ID NO: 58           moltype = AA  length = 106
FEATURE                 Location/Qualifiers
REGION                  1..106
                        note = mAb KCD136 light chain
source                  1..106
                        mol_type = protein
                        organism = synthetic construct
SEQUENCE: 58
QIVLTQSPAI MSASPGEKVT MTCSASSSVS YMYWYQQKPG SSPRLLIYDI SNLASGVPVR  60
FSGSGSGTSY SLTISRMEAE DAATYYCQQW DTYPWTFGGG TKLEIK                106

SEQ ID NO: 59           moltype = AA  length = 116
FEATURE                 Location/Qualifiers
REGION                  1..116
                        note = mAb KCD200 heavy chain
source                  1..116
                        mol_type = protein
                        organism = synthetic construct
SEQUENCE: 59
EVQLQQSGPE LVKPGASVKI SCKASGYTFT SYYKNWMRQR HGESLEWIGD INPNSGDTAY  60
NQKFKGKATL TVDRSSSTAY MELRSLTSED SAVYYCAREG PSFAYWGQGT LVTVSA      116

SEQ ID NO: 60           moltype = AA  length = 112
FEATURE                 Location/Qualifiers
REGION                  1..112
                        note = mAb KCD200 light chain
source                  1..112
                        mol_type = protein
                        organism = synthetic construct
SEQUENCE: 60
DVLMTQTPLS LPVSLGDQVS ISCRSSQTIV HSNGDTYLEW YLQKPGQSPN LLIYKVSNRF  60
SGVPDRFSGS GSGTDFTLKI SRVEAEDLGV YYCFQGSHVP PTFGGGTKLE IK          112

SEQ ID NO: 61           moltype = AA  length = 115
FEATURE                 Location/Qualifiers
REGION                  1..115
                        note = mAb KCD208 heavy chain
source                  1..115
                        mol_type = protein
                        organism = synthetic construct
SEQUENCE: 61
EVQLQQSVAE LVRPGASVKL SCTVSGFNIK NTYMHWVKQR PEQGLEWIGR IDPANGDTTY  60
APKFQGKATI TADTSSNSAY LHLSRLTSED TAIYYCSLYD YDGYWGQGTT LTVSS       115

SEQ ID NO: 62           moltype = AA  length = 108
FEATURE                 Location/Qualifiers
REGION                  1..108
                        note = mAb KCD208 light chain
source                  1..108
                        mol_type = protein
                        organism = synthetic construct
SEQUENCE: 62
EIVLTQSPAL MAASPGEKVT ITCSVSSSIS SSSLHWYRQK SGTSPKPWIY GTSHLASGVP  60
VRFSGSGSGT SYSLTISSME AEDAATYYCQ QWDTYPWTFG GGTKLEIK              108

SEQ ID NO: 63           moltype = AA  length = 115
FEATURE                 Location/Qualifiers
REGION                  1..115
                        note = mAb KCD214 heavy chain
source                  1..115
                        mol_type = protein
```

-continued

```
                       organism = synthetic construct
SEQUENCE: 63
EVQLQQSVAE FVRPGASVKL SCTASGFNIK NTYMHWVKQR PEQGLEWIGR IDPANGNTEY  60
APKFQGKATI TADTSSNTAY LQLSSLTSED TAIYYCALYD YDGYWGQGTT LTVSS       115

SEQ ID NO: 64          moltype = AA  length = 108
FEATURE                Location/Qualifiers
REGION                 1..108
                       note = mAb KCD214 light chain
source                 1..108
                       mol_type = protein
                       organism = synthetic construct
SEQUENCE: 64
EIVLTQSPAL MAASPGEKVT ITCRVSSSIS SSSLHWYQQK SGTSPKPWIY GTSNLASGVP  60
VRFSGSRSGT SYSLTISSME AEDAATYYCQ QWSDYPWTFG GGTKLEIK               108

SEQ ID NO: 65          moltype = AA  length = 119
FEATURE                Location/Qualifiers
REGION                 1..119
                       note = mAb KCD220 heavy chain
source                 1..119
                       mol_type = protein
                       organism = synthetic construct
SEQUENCE: 65
QVQLQQSGAE LMEPGASVKL SCKATGYTFT GYWIEWVKQR PGHGLEWIGE TLPGSDSNNY  60
NEKFKGKATF TADTSSNTAY MQLSSLTTED SAIYYCARDY SNYWYFDVWG TGTTVTVSS   119

SEQ ID NO: 66          moltype = AA  length = 106
FEATURE                Location/Qualifiers
REGION                 1..106
                       note = mAb KCD220 light chain
source                 1..106
                       mol_type = protein
                       organism = synthetic construct
SEQUENCE: 66
DIQMTQTTSS LSASLGDRVT ISCRASQDIS NYLNWYQQKP DGTVKLLIYY TSNLHSGVPS  60
RFSGSGSGTD YSLTISNLEQ EDIATYFCQQ DSKHRTFGGG TKLEIK                 106

SEQ ID NO: 67          moltype = AA  length = 119
FEATURE                Location/Qualifiers
REGION                 1..119
                       note = mAb KCD224 heavy chain
source                 1..119
                       mol_type = protein
                       organism = synthetic construct
SEQUENCE: 67
QVQLKESGPG LVAPSQSLSI TCTVSGFSLT SYGVDWIRQS PGKGLEWLGV IWGVGSTNYN  60
SALKSRLSIS KDNSKSQVFL KMNSLQTDDT AMYYCARSYD GSYWYFDVWG TGTTVTVSS   119

SEQ ID NO: 68          moltype = AA  length = 107
FEATURE                Location/Qualifiers
REGION                 1..107
                       note = mAb KCD224 light chain
source                 1..107
                       mol_type = protein
                       organism = synthetic construct
SEQUENCE: 68
DIQMTQTTSS LSASLGDRVT ISCRASQVIS NYLNWYQQKP DGTVKLLIYY TSRLHSGVPS  60
RFSGSGSGTD YSLTISNLEP EDIATYYCQQ YSKLPYTFGS GTKLEIK                107

SEQ ID NO: 69          moltype = AA  length = 116
FEATURE                Location/Qualifiers
REGION                 1..116
                       note = mAb 119_TAF heavy chain
source                 1..116
                       mol_type = protein
                       organism = synthetic construct
SEQUENCE: 69
EVQLVESGGG LVQPGGSLRL SCAASGYTFT DYYMNWVRQA PGKGLEWIGD INPNTGDTSY  60
NADFKRRFTF SLDTSKSTAY LQMNSLRAED TAVYYCTREG PSFAYWGQGT LVTVSS      116

SEQ ID NO: 70          moltype = AA  length = 112
FEATURE                Location/Qualifiers
REGION                 1..112
                       note = mAb 119_TAF light chain
source                 1..112
                       mol_type = protein
                       organism = synthetic construct
SEQUENCE: 70
```

-continued

```
DIQLTQSPSS LSASVGDRVT ITCRSSQTIV HSNGDTYLEW YQQKPGKAPN LLIYKVSNRF  60
SGVPSRFSGS GSGTDFTLTI SSLQPEDFAT YYCFQGSHVP PTFGQGTKVE IK          112

SEQ ID NO: 71          moltype = AA  length = 116
FEATURE                Location/Qualifiers
REGION                 1..116
                       note = mAb 119_TAF Germ heavy chain
source                 1..116
                       mol_type = protein
                       organism = synthetic construct
SEQUENCE: 71
EVQLVESGGG LVQPGGSLRL SCAASGYTFT DYYMSWVRQA PGKGLEWIGD INPNTGDTSY  60
NADSVKGRFT ISRDNSKNTL YLQMNSLRAE DTAVYYCTRE GPSFAYWGQG TLVTVS      116

SEQ ID NO: 72          moltype = AA  length = 112
FEATURE                Location/Qualifiers
REGION                 1..112
                       note = mAb 119_TAF Germ light chain
source                 1..112
                       mol_type = protein
                       organism = synthetic construct
SEQUENCE: 72
DIQMTQSPSS LSASVGDRVT ITCRSSQTIV HSNGDTYLEW YQQKPGKAPN LLIYKVSNRF  60
SGVPSRFSGS GSGTDFTLTI SSLQPEDFAT YYCFQGSHVP PTFGQGTKVE IK          112

SEQ ID NO: 73          moltype = AA  length = 107
FEATURE                Location/Qualifiers
REGION                 1..107
                       note = mAb 119_Human Germ heavy chain
source                 1..107
                       mol_type = protein
                       organism = synthetic construct
SEQUENCE: 73
EVKKPGASVK VSCKASGYTF TDYYMHWVRQ APGQGLEWIG DINPNTGDTS YNQKFQGRVT  60
STRDTSISTA YMELSRLRSD DTVVYYCTRE GPSFAYWGQG TLVTVSS                107

SEQ ID NO: 74          moltype = AA  length = 112
FEATURE                Location/Qualifiers
REGION                 1..112
                       note = mAb 119_Human Germ light chain
source                 1..112
                       mol_type = protein
                       organism = synthetic construct
SEQUENCE: 74
DVVMTQSPLS LPVTLGQPAS ISCRSSQTIV HSNGDTYLEW FQQRPGQSPN LLIYKVSNRF  60
SGVPDRFSGS GSGTDFTLKI SRVEAEDVGV YYCFQGSHVP PTFGGGTKVE IK          112

SEQ ID NO: 75          moltype = AA  length = 10
FEATURE                Location/Qualifiers
REGION                 1..10
                       note = KCD002 H1
source                 1..10
                       mol_type = protein
                       organism = synthetic construct
SEQUENCE: 75
GFTFSDYYMA                                                         10

SEQ ID NO: 76          moltype = AA  length = 16
FEATURE                Location/Qualifiers
REGION                 1..16
                       note = KCD002 H2
source                 1..16
                       mol_type = protein
                       organism = synthetic construct
SEQUENCE: 76
INYDGSSTYY LDSLKS                                                  16

SEQ ID NO: 77          moltype = AA  length = 13
FEATURE                Location/Qualifiers
REGION                 1..13
                       note = KCD002 H3
source                 1..13
                       mol_type = protein
                       organism = synthetic construct
SEQUENCE: 77
ARGEDFYLYA MDY                                                     13

SEQ ID NO: 78          moltype = AA  length = 11
FEATURE                Location/Qualifiers
```

-continued

```
REGION                1..11
                      note = KCD002 L1
source                1..11
                      mol_type = protein
                      organism = synthetic construct
SEQUENCE: 78
RASENIHSYL A                                                  11

SEQ ID NO: 79         moltype = AA  length = 7
FEATURE               Location/Qualifiers
REGION                1..7
                      note = KCD002 L2
source                1..7
                      mol_type = protein
                      organism = synthetic construct
SEQUENCE: 79
NTKTLAE                                                       7

SEQ ID NO: 80         moltype = AA  length = 9
FEATURE               Location/Qualifiers
REGION                1..9
                      note = KCD002 L3
source                1..9
                      mol_type = protein
                      organism = synthetic construct
SEQUENCE: 80
QHHYGIPPT                                                     9

SEQ ID NO: 81         moltype = AA  length = 10
FEATURE               Location/Qualifiers
REGION                1..10
                      note = KCD003 H1
source                1..10
                      mol_type = protein
                      organism = synthetic construct
SEQUENCE: 81
GYTFTDYYMN                                                    10

SEQ ID NO: 82         moltype = AA  length = 16
FEATURE               Location/Qualifiers
REGION                1..16
                      note = KCD003 H2
source                1..16
                      mol_type = protein
                      organism = synthetic construct
SEQUENCE: 82
INPNNGDPSY NQKFKD                                             16

SEQ ID NO: 83         moltype = AA  length = 9
FEATURE               Location/Qualifiers
REGION                1..9
                      note = KCD003 H3
source                1..9
                      mol_type = protein
                      organism = synthetic construct
SEQUENCE: 83
AREGPSFAY                                                     9

SEQ ID NO: 84         moltype = AA  length = 16
FEATURE               Location/Qualifiers
REGION                1..16
                      note = KCD003 L1
source                1..16
                      mol_type = protein
                      organism = synthetic construct
SEQUENCE: 84
RSSQTIVHSN GDTYLE                                             16

SEQ ID NO: 85         moltype = AA  length = 7
FEATURE               Location/Qualifiers
REGION                1..7
                      note = KCD003 L2
source                1..7
                      mol_type = protein
                      organism = synthetic construct
SEQUENCE: 85
KVSNRFS                                                       7

SEQ ID NO: 86         moltype = AA  length = 9
```

-continued

```
FEATURE                Location/Qualifiers
REGION                 1..9
                       note = KCD003 L3
source                 1..9
                       mol_type = protein
                       organism = synthetic construct
SEQUENCE: 86
FQGSHVPPT                                                                  9

SEQ ID NO: 87          moltype = AA  length = 10
FEATURE                Location/Qualifiers
REGION                 1..10
                       note = KCD005 H1
source                 1..10
                       mol_type = protein
                       organism = synthetic construct
SEQUENCE: 87
GYTFTDHYMN                                                                 10

SEQ ID NO: 88          moltype = AA  length = 16
FEATURE                Location/Qualifiers
REGION                 1..16
                       note = KCD005 H2
source                 1..16
                       mol_type = protein
                       organism = synthetic construct
SEQUENCE: 88
INPNNGGTSC NQKFKG                                                          16

SEQ ID NO: 89          moltype = AA  length = 9
FEATURE                Location/Qualifiers
REGION                 1..9
                       note = KCD005 H3
source                 1..9
                       mol_type = protein
                       organism = synthetic construct
SEQUENCE: 89
TREGASFAF                                                                  9

SEQ ID NO: 90          moltype = AA  length = 16
FEATURE                Location/Qualifiers
REGION                 1..16
                       note = KCD005 L1
source                 1..16
                       mol_type = protein
                       organism = synthetic construct
SEQUENCE: 90
RSSQSIVHSN GDTYLE                                                          16

SEQ ID NO: 91          moltype = AA  length = 7
FEATURE                Location/Qualifiers
REGION                 1..7
                       note = KCD005 L2
source                 1..7
                       mol_type = protein
                       organism = synthetic construct
SEQUENCE: 91
KVSNRFS                                                                    7

SEQ ID NO: 92          moltype = AA  length = 9
FEATURE                Location/Qualifiers
REGION                 1..9
                       note = KCD005 L3
source                 1..9
                       mol_type = protein
                       organism = synthetic construct
SEQUENCE: 92
FQGSHVPVT                                                                  9

SEQ ID NO: 93          moltype = AA  length = 10
FEATURE                Location/Qualifiers
REGION                 1..10
                       note = KCD009 H1
source                 1..10
                       mol_type = protein
                       organism = synthetic construct
SEQUENCE: 93
GYIFRNYGMN                                                                 10
```

-continued

```
SEQ ID NO: 94           moltype = AA  length = 16
FEATURE                 Location/Qualifiers
REGION                  1..16
                        note = KCD009 H2
source                  1..16
                        mol_type = protein
                        organism = synthetic construct
SEQUENCE: 94
INTYTGEPTY ADDFKG                                                   16

SEQ ID NO: 95           moltype = AA  length = 9
FEATURE                 Location/Qualifiers
REGION                  1..9
                        note = KCD009 H3
source                  1..9
                        mol_type = protein
                        organism = synthetic construct
SEQUENCE: 95
VRDGPGFAY                                                           9

SEQ ID NO: 96           moltype = AA  length = 16
FEATURE                 Location/Qualifiers
REGION                  1..16
                        note = KCD009 L1
source                  1..16
                        mol_type = protein
                        organism = synthetic construct
SEQUENCE: 96
RSSLIIEHSD GNTYLE                                                   16

SEQ ID NO: 97           moltype = AA  length = 7
FEATURE                 Location/Qualifiers
REGION                  1..7
                        note = KCD009 L2
source                  1..7
                        mol_type = protein
                        organism = synthetic construct
SEQUENCE: 97
KVSNRFS                                                             7

SEQ ID NO: 98           moltype = AA  length = 9
FEATURE                 Location/Qualifiers
REGION                  1..9
                        note = KCD009 L3
source                  1..9
                        mol_type = protein
                        organism = synthetic construct
SEQUENCE: 98
FQGSHVPVT                                                           9

SEQ ID NO: 99           moltype = AA  length = 10
FEATURE                 Location/Qualifiers
REGION                  1..10
                        note = KCD010 H1
source                  1..10
                        mol_type = protein
                        organism = synthetic construct
SEQUENCE: 99
GYTFTDYDMD                                                          10

SEQ ID NO: 100          moltype = AA  length = 16
FEATURE                 Location/Qualifiers
REGION                  1..16
                        note = KCD010 H2
source                  1..16
                        mol_type = protein
                        organism = synthetic construct
SEQUENCE: 100
INPNNGGTIY NQKFKG                                                   16

SEQ ID NO: 101          moltype = AA  length = 7
FEATURE                 Location/Qualifiers
REGION                  1..7
                        note = KCD010 H3
source                  1..7
                        mol_type = protein
                        organism = synthetic construct
SEQUENCE: 101
GTGDFAY                                                             7
```

-continued

```
SEQ ID NO: 102          moltype = AA  length = 12
FEATURE                 Location/Qualifiers
REGION                  1..12
                        note = KCD010 L1
source                  1..12
                        mol_type = protein
                        organism = synthetic construct
SEQUENCE: 102
SASSSVSSSY LY                                                        12

SEQ ID NO: 103          moltype = AA  length = 7
FEATURE                 Location/Qualifiers
REGION                  1..7
                        note = KCD010 L2
source                  1..7
                        mol_type = protein
                        organism = synthetic construct
SEQUENCE: 103
STSNLAS                                                              7

SEQ ID NO: 104          moltype = AA  length = 9
FEATURE                 Location/Qualifiers
REGION                  1..9
                        note = KCD010 L3
source                  1..9
                        mol_type = protein
                        organism = synthetic construct
SEQUENCE: 104
HQWSSYPPT                                                            9

SEQ ID NO: 105          moltype = AA  length = 10
FEATURE                 Location/Qualifiers
REGION                  1..10
                        note = KCD023 H1
source                  1..10
                        mol_type = protein
                        organism = synthetic construct
SEQUENCE: 105
GYTFTDYNID                                                           10

SEQ ID NO: 106          moltype = AA  length = 16
FEATURE                 Location/Qualifiers
REGION                  1..16
                        note = KCD023 H2
source                  1..16
                        mol_type = protein
                        organism = synthetic construct
SEQUENCE: 106
INPNNGGINY NQKFKG                                                    16

SEQ ID NO: 107          moltype = AA  length = 7
FEATURE                 Location/Qualifiers
REGION                  1..7
                        note = KCD023 H3
source                  1..7
                        mol_type = protein
                        organism = synthetic construct
SEQUENCE: 107
GTGDYAY                                                              7

SEQ ID NO: 108          moltype = AA  length = 12
FEATURE                 Location/Qualifiers
REGION                  1..12
                        note = KCD023 L1
source                  1..12
                        mol_type = protein
                        organism = synthetic construct
SEQUENCE: 108
SASSSVSSSY LY                                                        12

SEQ ID NO: 109          moltype = AA  length = 7
FEATURE                 Location/Qualifiers
REGION                  1..7
                        note = KCD023 L2
source                  1..7
                        mol_type = protein
                        organism = synthetic construct
SEQUENCE: 109
```

```
STSNLAS                                                 7

SEQ ID NO: 110          moltype = AA  length = 9
FEATURE                 Location/Qualifiers
REGION                  1..9
                        note = KCD023 L3
source                  1..9
                        mol_type = protein
                        organism = synthetic construct
SEQUENCE: 110
HQWTSYPPT                                               9

SEQ ID NO: 111          moltype = AA  length = 10
FEATURE                 Location/Qualifiers
REGION                  1..10
                        note = KCD036 H1
source                  1..10
                        mol_type = protein
                        organism = synthetic construct
SEQUENCE: 111
GYSFTGYTMT                                              10

SEQ ID NO: 112          moltype = AA  length = 16
FEATURE                 Location/Qualifiers
REGION                  1..16
                        note = KCD036 H2
source                  1..16
                        mol_type = protein
                        organism = synthetic construct
SEQUENCE: 112
INPYNGGTNY NQKFKG                                       16

SEQ ID NO: 113          moltype = AA  length = 11
FEATURE                 Location/Qualifiers
REGION                  1..11
                        note = KCD036 H3
source                  1..11
                        mol_type = protein
                        organism = synthetic construct
SEQUENCE: 113
ARRHYGSSWD Y                                            11

SEQ ID NO: 114          moltype = AA  length = 11
FEATURE                 Location/Qualifiers
REGION                  1..11
                        note = KCD036 L1
source                  1..11
                        mol_type = protein
                        organism = synthetic construct
SEQUENCE: 114
KASQDINTYL S                                            11

SEQ ID NO: 115          moltype = AA  length = 7
FEATURE                 Location/Qualifiers
REGION                  1..7
                        note = KCD036 L2
source                  1..7
                        mol_type = protein
                        organism = synthetic construct
SEQUENCE: 115
RANRLVD                                                 7

SEQ ID NO: 116          moltype = AA  length = 9
FEATURE                 Location/Qualifiers
REGION                  1..9
                        note = KCD036 L3
source                  1..9
                        mol_type = protein
                        organism = synthetic construct
SEQUENCE: 116
LQYDEFPYT                                               9

SEQ ID NO: 117          moltype = AA  length = 10
FEATURE                 Location/Qualifiers
REGION                  1..10
                        note = KCD040 H1
source                  1..10
                        mol_type = protein
                        organism = synthetic construct
```

-continued

```
SEQUENCE: 117
DFNIKDTYMH                                                  10

SEQ ID NO: 118          moltype = AA  length = 16
FEATURE                 Location/Qualifiers
REGION                  1..16
                        note = KCD040 H2
source                  1..16
                        mol_type = protein
                        organism = synthetic construct
SEQUENCE: 118
IDPANGNTEF DPKFQG                                           16

SEQ ID NO: 119          moltype = AA  length = 6
FEATURE                 Location/Qualifiers
REGION                  1..6
                        note = KCD040 H3
source                  1..6
                        mol_type = protein
                        organism = synthetic construct
SEQUENCE: 119
TRAMDY                                                      6

SEQ ID NO: 120          moltype = AA  length = 10
FEATURE                 Location/Qualifiers
REGION                  1..10
                        note = KCD040 L1
source                  1..10
                        mol_type = protein
                        organism = synthetic construct
SEQUENCE: 120
SAGSSVSYMY                                                  10

SEQ ID NO: 121          moltype = AA  length = 7
FEATURE                 Location/Qualifiers
REGION                  1..7
                        note = KCD040 L2
source                  1..7
                        mol_type = protein
                        organism = synthetic construct
SEQUENCE: 121
DTSNLAS                                                     7

SEQ ID NO: 122          moltype = AA  length = 9
FEATURE                 Location/Qualifiers
REGION                  1..9
                        note = KCD040 L3
source                  1..9
                        mol_type = protein
                        organism = synthetic construct
SEQUENCE: 122
QQWSNYPYT                                                   9

SEQ ID NO: 123          moltype = AA  length = 10
FEATURE                 Location/Qualifiers
REGION                  1..10
                        note = KCD042 H1
source                  1..10
                        mol_type = protein
                        organism = synthetic construct
SEQUENCE: 123
GFNIKHTYIH                                                  10

SEQ ID NO: 124          moltype = AA  length = 16
FEATURE                 Location/Qualifiers
REGION                  1..16
                        note = KCD042 H2
source                  1..16
                        mol_type = protein
                        organism = synthetic construct
SEQUENCE: 124
IDPANGNTKY DPKFQG                                           16

SEQ ID NO: 125          moltype = AA  length = 6
FEATURE                 Location/Qualifiers
REGION                  1..6
                        note = KCD042 H3
source                  1..6
                        mol_type = protein
```

```
                       organism = synthetic construct
SEQUENCE: 125
VNAMEY                                                        6

SEQ ID NO: 126         moltype = AA  length = 10
FEATURE                Location/Qualifiers
REGION                 1..10
                       note = KCD042 L1
source                 1..10
                       mol_type = protein
                       organism = synthetic construct
SEQUENCE: 126
SANSSVSDMY                                                    10

SEQ ID NO: 127         moltype = AA  length = 7
FEATURE                Location/Qualifiers
REGION                 1..7
                       note = KCD042 L2
source                 1..7
                       mol_type = protein
                       organism = synthetic construct
SEQUENCE: 127
DTSNLAS                                                       7

SEQ ID NO: 128         moltype = AA  length = 9
FEATURE                Location/Qualifiers
REGION                 1..9
                       note = KCD042 L3
source                 1..9
                       mol_type = protein
                       organism = synthetic construct
SEQUENCE: 128
QQWSTYPWT                                                     9

SEQ ID NO: 129         moltype = AA  length = 10
FEATURE                Location/Qualifiers
REGION                 1..10
                       note = KCD044 H1
source                 1..10
                       mol_type = protein
                       organism = synthetic construct
SEQUENCE: 129
GFNIKHTYMH                                                    10

SEQ ID NO: 130         moltype = AA  length = 16
FEATURE                Location/Qualifiers
REGION                 1..16
                       note = KCD044 H2
source                 1..16
                       mol_type = protein
                       organism = synthetic construct
SEQUENCE: 130
IDPANGNTKY DPKFQG                                             16

SEQ ID NO: 131         moltype = AA  length = 6
FEATURE                Location/Qualifiers
REGION                 1..6
                       note = KCD044 H3
source                 1..6
                       mol_type = protein
                       organism = synthetic construct
SEQUENCE: 131
LNAMEY                                                        6

SEQ ID NO: 132         moltype = AA  length = 10
FEATURE                Location/Qualifiers
REGION                 1..10
                       note = KCD044 L1
source                 1..10
                       mol_type = protein
                       organism = synthetic construct
SEQUENCE: 132
SANSSVSDMY                                                    10

SEQ ID NO: 133         moltype = AA  length = 7
FEATURE                Location/Qualifiers
REGION                 1..7
                       note = KCD044 L2
source                 1..7
```

```
                        mol_type = protein
                        organism = synthetic construct
SEQUENCE: 133
DTSNLAS                                                     7

SEQ ID NO: 134          moltype = AA  length = 9
FEATURE                 Location/Qualifiers
REGION                  1..9
                        note = KCD044 L3
source                  1..9
                        mol_type = protein
                        organism = synthetic construct
SEQUENCE: 134
QQWSTYPWT                                                   9

SEQ ID NO: 135          moltype = AA  length = 10
FEATURE                 Location/Qualifiers
REGION                  1..10
                        note = KCD047 H1
source                  1..10
                        mol_type = protein
                        organism = synthetic construct
SEQUENCE: 135
GFNIKDTYMH                                                  10

SEQ ID NO: 136          moltype = AA  length = 16
FEATURE                 Location/Qualifiers
REGION                  1..16
                        note = KCD047 H2
source                  1..16
                        mol_type = protein
                        organism = synthetic construct
SEQUENCE: 136
IDPANGYTKD DPKFQG                                           16

SEQ ID NO: 137          moltype = AA  length = 6
FEATURE                 Location/Qualifiers
REGION                  1..6
                        note = KCD047 H3
source                  1..6
                        mol_type = protein
                        organism = synthetic construct
SEQUENCE: 137
ASAMDY                                                      6

SEQ ID NO: 138          moltype = AA  length = 10
FEATURE                 Location/Qualifiers
REGION                  1..10
                        note = KCD047 L1
source                  1..10
                        mol_type = protein
                        organism = synthetic construct
SEQUENCE: 138
SASSSVTYMY                                                  10

SEQ ID NO: 139          moltype = AA  length = 7
FEATURE                 Location/Qualifiers
REGION                  1..7
                        note = KCD047 L2
source                  1..7
                        mol_type = protein
                        organism = synthetic construct
SEQUENCE: 139
DTSNLAS                                                     7

SEQ ID NO: 140          moltype = AA  length = 9
FEATURE                 Location/Qualifiers
REGION                  1..9
                        note = KCD047 L3
source                  1..9
                        mol_type = protein
                        organism = synthetic construct
SEQUENCE: 140
QQWSNYPFT                                                   9

SEQ ID NO: 141          moltype = AA  length = 10
FEATURE                 Location/Qualifiers
REGION                  1..10
                        note = KCD048 H1
```

```
source                  1..10
                        mol_type = protein
                        organism = synthetic construct
SEQUENCE: 141
GFNIKATYMH                                                  10

SEQ ID NO: 142          moltype = AA  length = 16
FEATURE                 Location/Qualifiers
REGION                  1..16
                        note = KCD048 H2
source                  1..16
                        mol_type = protein
                        organism = synthetic construct
SEQUENCE: 142
IDPANGHTIY DPQFQG                                           16

SEQ ID NO: 143          moltype = AA  length = 6
FEATURE                 Location/Qualifiers
REGION                  1..6
                        note = KCD048 H3
source                  1..6
                        mol_type = protein
                        organism = synthetic construct
SEQUENCE: 143
AEAMDY                                                      6

SEQ ID NO: 144          moltype = AA  length = 10
FEATURE                 Location/Qualifiers
REGION                  1..10
                        note = KCD048 L1
source                  1..10
                        mol_type = protein
                        organism = synthetic construct
SEQUENCE: 144
SATSSVSYMY                                                  10

SEQ ID NO: 145          moltype = AA  length = 7
FEATURE                 Location/Qualifiers
REGION                  1..7
                        note = KCD048 L2
source                  1..7
                        mol_type = protein
                        organism = synthetic construct
SEQUENCE: 145
DTSNLAS                                                     7

SEQ ID NO: 146          moltype = AA  length = 9
FEATURE                 Location/Qualifiers
REGION                  1..9
                        note = KCD048 L3
source                  1..9
                        mol_type = protein
                        organism = synthetic construct
SEQUENCE: 146
QQWSNYPFT                                                   9

SEQ ID NO: 147          moltype = AA  length = 10
FEATURE                 Location/Qualifiers
REGION                  1..10
                        note = KCD070 H1
source                  1..10
                        mol_type = protein
                        organism = synthetic construct
SEQUENCE: 147
GYSFTDYIIL                                                  10

SEQ ID NO: 148          moltype = AA  length = 16
FEATURE                 Location/Qualifiers
REGION                  1..16
                        note = KCD070 H2
source                  1..16
                        mol_type = protein
                        organism = synthetic construct
SEQUENCE: 148
INPYYDYTSY NLKFKG                                           16

SEQ ID NO: 149          moltype = AA  length = 11
FEATURE                 Location/Qualifiers
REGION                  1..11
```

-continued

```
                        note = KCD070 H3
source                  1..11
                        mol_type = protein
                        organism = synthetic construct
SEQUENCE: 149
ARSDGYYGGD Y                                                        11

SEQ ID NO: 150          moltype = AA  length = 11
FEATURE                 Location/Qualifiers
REGION                  1..11
                        note = KCD070 L1
source                  1..11
                        mol_type = protein
                        organism = synthetic construct
SEQUENCE: 150
KASQDVGTAV A                                                        11

SEQ ID NO: 151          moltype = AA  length = 7
FEATURE                 Location/Qualifiers
REGION                  1..7
                        note = KCD070 L2
source                  1..7
                        mol_type = protein
                        organism = synthetic construct
SEQUENCE: 151
WASTRHT                                                             7

SEQ ID NO: 152          moltype = AA  length = 9
FEATURE                 Location/Qualifiers
REGION                  1..9
                        note = KCD070 L3
source                  1..9
                        mol_type = protein
                        organism = synthetic construct
SEQUENCE: 152
QQYSSYPWT                                                           9

SEQ ID NO: 153          moltype = AA  length = 10
FEATURE                 Location/Qualifiers
REGION                  1..10
                        note = KCD101 H1
source                  1..10
                        mol_type = protein
                        organism = synthetic construct
SEQUENCE: 153
GYTFTSYWMH                                                          10

SEQ ID NO: 154          moltype = AA  length = 16
FEATURE                 Location/Qualifiers
REGION                  1..16
                        note = KCD101 H2
source                  1..16
                        mol_type = protein
                        organism = synthetic construct
SEQUENCE: 154
IDPSDSYTNY NQKFKG                                                   16

SEQ ID NO: 155          moltype = AA  length = 11
FEATURE                 Location/Qualifiers
REGION                  1..11
                        note = KCD101 H3
source                  1..11
                        mol_type = protein
                        organism = synthetic construct
SEQUENCE: 155
GRNGYDGSMD Y                                                        11

SEQ ID NO: 156          moltype = AA  length = 11
FEATURE                 Location/Qualifiers
REGION                  1..11
                        note = KCD101 L1
source                  1..11
                        mol_type = protein
                        organism = synthetic construct
SEQUENCE: 156
RASQDISNYL N                                                        11

SEQ ID NO: 157          moltype = AA  length = 7
FEATURE                 Location/Qualifiers
```

```
REGION                  1..7
                        note = KCD101 L2
source                  1..7
                        mol_type = protein
                        organism = synthetic construct
SEQUENCE: 157
YPSRLHS                                                                   7

SEQ ID NO: 158          moltype = AA  length = 9
FEATURE                 Location/Qualifiers
REGION                  1..9
                        note = KCD101 L3
source                  1..9
                        mol_type = protein
                        organism = synthetic construct
SEQUENCE: 158
QQGNTLPYT                                                                 9

SEQ ID NO: 159          moltype = AA  length = 10
FEATURE                 Location/Qualifiers
REGION                  1..10
                        note = KCD102 H1
source                  1..10
                        mol_type = protein
                        organism = synthetic construct
SEQUENCE: 159
GYTFTSYWMH                                                                10

SEQ ID NO: 160          moltype = AA  length = 16
FEATURE                 Location/Qualifiers
REGION                  1..16
                        note = KCD102 H2
source                  1..16
                        mol_type = protein
                        organism = synthetic construct
SEQUENCE: 160
IDPSDSYTNY NQKFKG                                                         16

SEQ ID NO: 161          moltype = AA  length = 11
FEATURE                 Location/Qualifiers
REGION                  1..11
                        note = KCD102 H3
source                  1..11
                        mol_type = protein
                        organism = synthetic construct
SEQUENCE: 161
ARNGYDGSMD Y                                                              11

SEQ ID NO: 162          moltype = AA  length = 11
FEATURE                 Location/Qualifiers
REGION                  1..11
                        note = KCD102 L1
source                  1..11
                        mol_type = protein
                        organism = synthetic construct
SEQUENCE: 162
RASQDISNYL N                                                              11

SEQ ID NO: 163          moltype = AA  length = 7
FEATURE                 Location/Qualifiers
REGION                  1..7
                        note = KCD102 L2
source                  1..7
                        mol_type = protein
                        organism = synthetic construct
SEQUENCE: 163
YPSRLHS                                                                   7

SEQ ID NO: 164          moltype = AA  length = 9
FEATURE                 Location/Qualifiers
REGION                  1..9
                        note = KCD102 L3
source                  1..9
                        mol_type = protein
                        organism = synthetic construct
SEQUENCE: 164
QQGNTLPYT                                                                 9

SEQ ID NO: 165          moltype = AA  length = 10
```

```
FEATURE                 Location/Qualifiers
REGION                  1..10
                        note = KCD103 H1
source                  1..10
                        mol_type = protein
                        organism = synthetic construct
SEQUENCE: 165
GYTFTSYWMH                                                                10

SEQ ID NO: 166          moltype = AA  length = 16
FEATURE                 Location/Qualifiers
REGION                  1..16
                        note = KCD103 H2
source                  1..16
                        mol_type = protein
                        organism = synthetic construct
SEQUENCE: 166
IDPSDSYTKY NQKFKD                                                         16

SEQ ID NO: 167          moltype = AA  length = 11
FEATURE                 Location/Qualifiers
REGION                  1..11
                        note = KCD103 H3
source                  1..11
                        mol_type = protein
                        organism = synthetic construct
SEQUENCE: 167
AGNGYDGSMD Y                                                              11

SEQ ID NO: 168          moltype = AA  length = 11
FEATURE                 Location/Qualifiers
REGION                  1..11
                        note = KCD103 L1
source                  1..11
                        mol_type = protein
                        organism = synthetic construct
SEQUENCE: 168
RASQDISNSL N                                                              11

SEQ ID NO: 169          moltype = AA  length = 7
FEATURE                 Location/Qualifiers
REGION                  1..7
                        note = KCD103 L2
source                  1..7
                        mol_type = protein
                        organism = synthetic construct
SEQUENCE: 169
YTSRLHS                                                                   7

SEQ ID NO: 170          moltype = AA  length = 9
FEATURE                 Location/Qualifiers
REGION                  1..9
                        note = KCD103 L3
source                  1..9
                        mol_type = protein
                        organism = synthetic construct
SEQUENCE: 170
QQANTLPYT                                                                 9

SEQ ID NO: 171          moltype = AA  length = 10
FEATURE                 Location/Qualifiers
REGION                  1..10
                        note = KCD104 H1
source                  1..10
                        mol_type = protein
                        organism = synthetic construct
SEQUENCE: 171
GYTFTSYWMH                                                                10

SEQ ID NO: 172          moltype = AA  length = 16
FEATURE                 Location/Qualifiers
REGION                  1..16
                        note = KCD104 H2
source                  1..16
                        mol_type = protein
                        organism = synthetic construct
SEQUENCE: 172
IDPSDSYTYY NQKFKG                                                         16
```

```
SEQ ID NO: 173          moltype = AA  length = 11
FEATURE                 Location/Qualifiers
REGION                  1..11
                        note = KCD104 H3
source                  1..11
                        mol_type = protein
                        organism = synthetic construct
SEQUENCE: 173
ARNGYDGAMD Y                                                      11

SEQ ID NO: 174          moltype = AA  length = 11
FEATURE                 Location/Qualifiers
REGION                  1..11
                        note = KCD104 L1
source                  1..11
                        mol_type = protein
                        organism = synthetic construct
SEQUENCE: 174
RASQDISNYL N                                                      11

SEQ ID NO: 175          moltype = AA  length = 7
FEATURE                 Location/Qualifiers
REGION                  1..7
                        note = KCD104 L2
source                  1..7
                        mol_type = protein
                        organism = synthetic construct
SEQUENCE: 175
YPSRLHS                                                           7

SEQ ID NO: 176          moltype = AA  length = 9
FEATURE                 Location/Qualifiers
REGION                  1..9
                        note = KCD104 L3
source                  1..9
                        mol_type = protein
                        organism = synthetic construct
SEQUENCE: 176
QQGNTLPYT                                                         9

SEQ ID NO: 177          moltype = AA  length = 10
FEATURE                 Location/Qualifiers
REGION                  1..10
                        note = KCD118 H1
source                  1..10
                        mol_type = protein
                        organism = synthetic construct
SEQUENCE: 177
GYTFTDYYKN                                                        10

SEQ ID NO: 178          moltype = AA  length = 16
FEATURE                 Location/Qualifiers
REGION                  1..16
                        note = KCD118 H2
source                  1..16
                        mol_type = protein
                        organism = synthetic construct
SEQUENCE: 178
INPNSGDANY NQKFKG                                                 16

SEQ ID NO: 179          moltype = AA  length = 9
FEATURE                 Location/Qualifiers
REGION                  1..9
                        note = KCD118 H3
source                  1..9
                        mol_type = protein
                        organism = synthetic construct
SEQUENCE: 179
AREGPSFAY                                                         9

SEQ ID NO: 180          moltype = AA  length = 16
FEATURE                 Location/Qualifiers
REGION                  1..16
                        note = KCD118 L1
source                  1..16
                        mol_type = protein
                        organism = synthetic construct
SEQUENCE: 180
RSSQTIVHSN GDTYLE                                                 16
```

```
SEQ ID NO: 181          moltype = AA  length = 7
FEATURE                 Location/Qualifiers
REGION                  1..7
                        note = KCD118 L2
source                  1..7
                        mol_type = protein
                        organism = synthetic construct
SEQUENCE: 181
KVSNRFS                                                     7

SEQ ID NO: 182          moltype = AA  length = 9
FEATURE                 Location/Qualifiers
REGION                  1..9
                        note = KCD118 L3
source                  1..9
                        mol_type = protein
                        organism = synthetic construct
SEQUENCE: 182
FQGSHVPPT                                                   9

SEQ ID NO: 183          moltype = AA  length = 446
FEATURE                 Location/Qualifiers
REGION                  1..446
                        note = Exemplary human IgG1 heavy chain
source                  1..446
                        mol_type = protein
                        organism = synthetic construct
SEQUENCE: 183
EVQLVESGGG LVQPGGSLRL SCAASGYTFT DYYINWVRQA PGKGLEWIGD INPITGDTDY  60
NADFKRRFTF SLDTSKSTAY LQMSSLRAED TAVYYCTREG PSFAYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PEAAGAPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SCSPGK                                  446

SEQ ID NO: 184          moltype = AA  length = 219
FEATURE                 Location/Qualifiers
REGION                  1..219
                        note = Exemplary human kappa light chain
source                  1..219
                        mol_type = protein
                        organism = synthetic construct
SEQUENCE: 184
DIQLTQSPSS LSASVGDRVT ITCRSSQTIV HSNGDTYLEW YQQKPGKAPN LLIRKVSNRF  60
SGVPSRFSGS GSGTDFTLTI SSLQPEDFAT YYCFQGSHVP VTFGQGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                    219

SEQ ID NO: 185          moltype = AA  length = 10
FEATURE                 Location/Qualifiers
REGION                  1..10
                        note = KCD119 H1
source                  1..10
                        mol_type = protein
                        organism = synthetic construct
SEQUENCE: 185
GYTFTDYYTN                                                  10

SEQ ID NO: 186          moltype = AA  length = 16
FEATURE                 Location/Qualifiers
REGION                  1..16
                        note = KCD119 H2
source                  1..16
                        mol_type = protein
                        organism = synthetic construct
SEQUENCE: 186
INPNTGDTSY NQKFRV                                           16

SEQ ID NO: 187          moltype = AA  length = 9
FEATURE                 Location/Qualifiers
REGION                  1..9
                        note = KCD119 H3
source                  1..9
                        mol_type = protein
                        organism = synthetic construct
SEQUENCE: 187
```

-continued

```
TREGPSFAY                                                          9

SEQ ID NO: 188          moltype = AA  length = 16
FEATURE                 Location/Qualifiers
REGION                  1..16
                        note = KCD119 L1
source                  1..16
                        mol_type = protein
                        organism = synthetic construct
SEQUENCE: 188
RSSQTIVHSN GDTYLE                                                  16

SEQ ID NO: 189          moltype = AA  length = 7
FEATURE                 Location/Qualifiers
REGION                  1..7
                        note = KCD119 L2
source                  1..7
                        mol_type = protein
                        organism = synthetic construct
SEQUENCE: 189
KVSNRFS                                                            7

SEQ ID NO: 190          moltype = AA  length = 9
FEATURE                 Location/Qualifiers
REGION                  1..9
                        note = KCD119 L3
source                  1..9
                        mol_type = protein
                        organism = synthetic construct
SEQUENCE: 190
FQGSHVPPT                                                          9

SEQ ID NO: 191          moltype = AA  length = 10
FEATURE                 Location/Qualifiers
REGION                  1..10
                        note = KCD121 H1
source                  1..10
                        mol_type = protein
                        organism = synthetic construct
SEQUENCE: 191
GYTFTDYYKN                                                         10

SEQ ID NO: 192          moltype = AA  length = 16
FEATURE                 Location/Qualifiers
REGION                  1..16
                        note = KCD121 H2
source                  1..16
                        mol_type = protein
                        organism = synthetic construct
SEQUENCE: 192
INPNNGDTSY NQKFRG                                                  16

SEQ ID NO: 193          moltype = AA  length = 9
FEATURE                 Location/Qualifiers
REGION                  1..9
                        note = KCD121 H3
source                  1..9
                        mol_type = protein
                        organism = synthetic construct
SEQUENCE: 193
AREGPSFAY                                                          9

SEQ ID NO: 194          moltype = AA  length = 16
FEATURE                 Location/Qualifiers
REGION                  1..16
                        note = KCD121 L1
source                  1..16
                        mol_type = protein
                        organism = synthetic construct
SEQUENCE: 194
RSNQTIVHSN GDTYLE                                                  16

SEQ ID NO: 195          moltype = AA  length = 7
FEATURE                 Location/Qualifiers
REGION                  1..7
                        note = KCD121 L2
source                  1..7
                        mol_type = protein
                        organism = synthetic construct
```

-continued

```
SEQUENCE: 195
KVSNRFS                                                                    7

SEQ ID NO: 196          moltype = AA  length = 9
FEATURE                 Location/Qualifiers
REGION                  1..9
                        note = KCD121 L3
source                  1..9
                        mol_type = protein
                        organism = synthetic construct
SEQUENCE: 196
FQGSHVPPT                                                                  9

SEQ ID NO: 197          moltype = AA  length = 10
FEATURE                 Location/Qualifiers
REGION                  1..10
                        note = KCD122 H1
source                  1..10
                        mol_type = protein
                        organism = synthetic construct
SEQUENCE: 197
GYTFTDYYKN                                                                 10

SEQ ID NO: 198          moltype = AA  length = 16
FEATURE                 Location/Qualifiers
REGION                  1..16
                        note = KCD122 H2
source                  1..16
                        mol_type = protein
                        organism = synthetic construct
SEQUENCE: 198
INPNNGDANY NQKFKG                                                          16

SEQ ID NO: 199          moltype = AA  length = 9
FEATURE                 Location/Qualifiers
REGION                  1..9
                        note = KCD122 H3
source                  1..9
                        mol_type = protein
                        organism = synthetic construct
SEQUENCE: 199
AREGPSFAY                                                                  9

SEQ ID NO: 200          moltype = AA  length = 16
FEATURE                 Location/Qualifiers
REGION                  1..16
                        note = KCD122 L1
source                  1..16
                        mol_type = protein
                        organism = synthetic construct
SEQUENCE: 200
RSSQTIVHSN GDTYLE                                                          16

SEQ ID NO: 201          moltype = AA  length = 7
FEATURE                 Location/Qualifiers
REGION                  1..7
                        note = KCD122 L2
source                  1..7
                        mol_type = protein
                        organism = synthetic construct
SEQUENCE: 201
KVSNRFS                                                                    7

SEQ ID NO: 202          moltype = AA  length = 9
FEATURE                 Location/Qualifiers
REGION                  1..9
                        note = KCD122 L3
source                  1..9
                        mol_type = protein
                        organism = synthetic construct
SEQUENCE: 202
FQGSHVPPT                                                                  9

SEQ ID NO: 203          moltype = AA  length = 10
FEATURE                 Location/Qualifiers
REGION                  1..10
                        note = KCD123 H1
source                  1..10
                        mol_type = protein
```

```
                        organism = synthetic construct
SEQUENCE: 203
GYTFTDFYKN                                                  10

SEQ ID NO: 204          moltype = AA  length = 16
FEATURE                 Location/Qualifiers
REGION                  1..16
                        note = KCD123 H2
source                  1..16
                        mol_type = protein
                        organism = synthetic construct
SEQUENCE: 204
INPNNGGTNY NQKFKG                                           16

SEQ ID NO: 205          moltype = AA  length = 9
FEATURE                 Location/Qualifiers
REGION                  1..9
                        note = KCD123 H3
source                  1..9
                        mol_type = protein
                        organism = synthetic construct
SEQUENCE: 205
AREGPSFAY                                                   9

SEQ ID NO: 206          moltype = AA  length = 16
FEATURE                 Location/Qualifiers
REGION                  1..16
                        note = KCD123 L1
source                  1..16
                        mol_type = protein
                        organism = synthetic construct
SEQUENCE: 206
RSSQTIVHSN GDTYLE                                           16

SEQ ID NO: 207          moltype = AA  length = 7
FEATURE                 Location/Qualifiers
REGION                  1..7
                        note = KCD123 L2
source                  1..7
                        mol_type = protein
                        organism = synthetic construct
SEQUENCE: 207
KVSNRFS                                                     7

SEQ ID NO: 208          moltype = AA  length = 9
FEATURE                 Location/Qualifiers
REGION                  1..9
                        note = KCD123 L3
source                  1..9
                        mol_type = protein
                        organism = synthetic construct
SEQUENCE: 208
FQGSHVPPT                                                   9

SEQ ID NO: 209          moltype = AA  length = 10
FEATURE                 Location/Qualifiers
REGION                  1..10
                        note = KCD124 H1
source                  1..10
                        mol_type = protein
                        organism = synthetic construct
SEQUENCE: 209
GYTFTDHYMN                                                  10

SEQ ID NO: 210          moltype = AA  length = 16
FEATURE                 Location/Qualifiers
REGION                  1..16
                        note = KCD124 H2
source                  1..16
                        mol_type = protein
                        organism = synthetic construct
SEQUENCE: 210
INPNNGGTSY NQKFKG                                           16

SEQ ID NO: 211          moltype = AA  length = 9
FEATURE                 Location/Qualifiers
REGION                  1..9
                        note = KCD124 H3
source                  1..9
```

```
                         mol_type = protein
                         organism = synthetic construct
SEQUENCE: 211
TREGASFAF                                                  9

SEQ ID NO: 212           moltype = AA  length = 16
FEATURE                  Location/Qualifiers
REGION                   1..16
                         note = KCD124 L1
source                   1..16
                         mol_type = protein
                         organism = synthetic construct
SEQUENCE: 212
RSSQSIVHSN GDTYLE                                          16

SEQ ID NO: 213           moltype = AA  length = 7
FEATURE                  Location/Qualifiers
REGION                   1..7
                         note = KCD124 L2
source                   1..7
                         mol_type = protein
                         organism = synthetic construct
SEQUENCE: 213
KVSNRFS                                                    7

SEQ ID NO: 214           moltype = AA  length = 9
FEATURE                  Location/Qualifiers
REGION                   1..9
                         note = KCD124 L3
source                   1..9
                         mol_type = protein
                         organism = synthetic construct
SEQUENCE: 214
FQGSHVPLT                                                  9

SEQ ID NO: 215           moltype = AA  length = 10
FEATURE                  Location/Qualifiers
REGION                   1..10
                         note = KCD131 H1
source                   1..10
                         mol_type = protein
                         organism = synthetic construct
SEQUENCE: 215
AYTFTDYYIN                                                 10

SEQ ID NO: 216           moltype = AA  length = 16
FEATURE                  Location/Qualifiers
REGION                   1..16
                         note = KCD131 H2
source                   1..16
                         mol_type = protein
                         organism = synthetic construct
SEQUENCE: 216
IFPGSNSTYS NEKFEV                                          16

SEQ ID NO: 217           moltype = AA  length = 15
FEATURE                  Location/Qualifiers
REGION                   1..15
                         note = KCD131 H3
source                   1..15
                         mol_type = protein
                         organism = synthetic construct
SEQUENCE: 217
ARLGYFGSSY HALDY                                           15

SEQ ID NO: 218           moltype = AA  length = 11
FEATURE                  Location/Qualifiers
REGION                   1..11
                         note = KCD131 L1
source                   1..11
                         mol_type = protein
                         organism = synthetic construct
SEQUENCE: 218
RASENIYSHL A                                               11

SEQ ID NO: 219           moltype = AA  length = 7
FEATURE                  Location/Qualifiers
REGION                   1..7
                         note = KCD131 L2
```

-continued

```
source                1..7
                      mol_type = protein
                      organism = synthetic construct
SEQUENCE: 219
SATNLPD                                                 7

SEQ ID NO: 220        moltype = AA  length = 9
FEATURE               Location/Qualifiers
REGION                1..9
                      note = KCD131 L3
source                1..9
                      mol_type = protein
                      organism = synthetic construct
SEQUENCE: 220
QHFWGTPWT                                               9

SEQ ID NO: 221        moltype = AA  length = 10
FEATURE               Location/Qualifiers
REGION                1..10
                      note = KCD136 H1
source                1..10
                      mol_type = protein
                      organism = synthetic construct
SEQUENCE: 221
GFNIKNTYMH                                              10

SEQ ID NO: 222        moltype = AA  length = 17
FEATURE               Location/Qualifiers
REGION                1..17
                      note = KCD136 H2
source                1..17
                      mol_type = protein
                      organism = synthetic construct
SEQUENCE: 222
RIDPANGITK YAPNFQG                                      17

SEQ ID NO: 223        moltype = AA  length = 6
FEATURE               Location/Qualifiers
REGION                1..6
                      note = KCD136 H3
source                1..6
                      mol_type = protein
                      organism = synthetic construct
SEQUENCE: 223
TRAMDY                                                  6

SEQ ID NO: 224        moltype = AA  length = 10
FEATURE               Location/Qualifiers
REGION                1..10
                      note = KCD136 L1
source                1..10
                      mol_type = protein
                      organism = synthetic construct
SEQUENCE: 224
SASSSVSYMY                                              10

SEQ ID NO: 225        moltype = AA  length = 7
FEATURE               Location/Qualifiers
REGION                1..7
                      note = KCD136 L2
source                1..7
                      mol_type = protein
                      organism = synthetic construct
SEQUENCE: 225
DISNLAS                                                 7

SEQ ID NO: 226        moltype = AA  length = 9
FEATURE               Location/Qualifiers
REGION                1..9
                      note = KCD136 L3
source                1..9
                      mol_type = protein
                      organism = synthetic construct
SEQUENCE: 226
QQWDTYPWT                                               9

SEQ ID NO: 227        moltype = AA  length = 10
FEATURE               Location/Qualifiers
REGION                1..10
```

-continued

```
                        note = KCD200 H1
source                  1..10
                        mol_type = protein
                        organism = synthetic construct
SEQUENCE: 227
GYTFTSYYKN                                                        10

SEQ ID NO: 228          moltype = AA  length = 16
FEATURE                 Location/Qualifiers
REGION                  1..16
                        note = KCD200 H2
source                  1..16
                        mol_type = protein
                        organism = synthetic construct
SEQUENCE: 228
INPNSGDTAY NQKFKG                                                 16

SEQ ID NO: 229          moltype = AA  length = 9
FEATURE                 Location/Qualifiers
REGION                  1..9
                        note = KCD200 H3
source                  1..9
                        mol_type = protein
                        organism = synthetic construct
SEQUENCE: 229
AREGPSFAY                                                         9

SEQ ID NO: 230          moltype = AA  length = 16
FEATURE                 Location/Qualifiers
REGION                  1..16
                        note = KCD200 L1
source                  1..16
                        mol_type = protein
                        organism = synthetic construct
SEQUENCE: 230
RSSQTIVHSN GDTYLE                                                 16

SEQ ID NO: 231          moltype = AA  length = 7
FEATURE                 Location/Qualifiers
REGION                  1..7
                        note = KCD200 L2
source                  1..7
                        mol_type = protein
                        organism = synthetic construct
SEQUENCE: 231
KVSNRFS                                                           7

SEQ ID NO: 232          moltype = AA  length = 9
FEATURE                 Location/Qualifiers
REGION                  1..9
                        note = KCD200 L3
source                  1..9
                        mol_type = protein
                        organism = synthetic construct
SEQUENCE: 232
FQGSHVPPT                                                         9

SEQ ID NO: 233          moltype = AA  length = 10
FEATURE                 Location/Qualifiers
REGION                  1..10
                        note = KCD208 H1
source                  1..10
                        mol_type = protein
                        organism = synthetic construct
SEQUENCE: 233
GFNIKNTYMH                                                        10

SEQ ID NO: 234          moltype = AA  length = 17
FEATURE                 Location/Qualifiers
REGION                  1..17
                        note = KCD208 H2
source                  1..17
                        mol_type = protein
                        organism = synthetic construct
SEQUENCE: 234
RIDPANGDTT YAPKFQG                                                17

SEQ ID NO: 235          moltype = AA  length = 8
FEATURE                 Location/Qualifiers
```

-continued

```
REGION              1..8
                    note = KCD208 H3
source              1..8
                    mol_type = protein
                    organism = synthetic construct
SEQUENCE: 235
SLYDYDGY                                                  8

SEQ ID NO: 236      moltype = AA  length = 12
FEATURE             Location/Qualifiers
REGION              1..12
                    note = KCD208 L1
source              1..12
                    mol_type = protein
                    organism = synthetic construct
SEQUENCE: 236
SVSSSISSSS LH                                             12

SEQ ID NO: 237      moltype = AA  length = 7
FEATURE             Location/Qualifiers
REGION              1..7
                    note = KCD208 L2
source              1..7
                    mol_type = protein
                    organism = synthetic construct
SEQUENCE: 237
GTSHLAS                                                   7

SEQ ID NO: 238      moltype = AA  length = 9
FEATURE             Location/Qualifiers
REGION              1..9
                    note = KCD208 L3
source              1..9
                    mol_type = protein
                    organism = synthetic construct
SEQUENCE: 238
QQWDTYPWT                                                 9

SEQ ID NO: 239      moltype = AA  length = 10
FEATURE             Location/Qualifiers
REGION              1..10
                    note = KCD214 H1
source              1..10
                    mol_type = protein
                    organism = synthetic construct
SEQUENCE: 239
GFNIKNTYMH                                                10

SEQ ID NO: 240      moltype = AA  length = 17
FEATURE             Location/Qualifiers
REGION              1..17
                    note = KCD214 H2
source              1..17
                    mol_type = protein
                    organism = synthetic construct
SEQUENCE: 240
RIDPANGDTT YAPKFQG                                        17

SEQ ID NO: 241      moltype = AA  length = 8
FEATURE             Location/Qualifiers
REGION              1..8
                    note = KCD214 H3
source              1..8
                    mol_type = protein
                    organism = synthetic construct
SEQUENCE: 241
ALYDYDGY                                                  8

SEQ ID NO: 242      moltype = AA  length = 12
FEATURE             Location/Qualifiers
REGION              1..12
                    note = KCD214 L1
source              1..12
                    mol_type = protein
                    organism = synthetic construct
SEQUENCE: 242
RVSSSISSSS LH                                             12

SEQ ID NO: 243      moltype = AA  length = 7
```

```
FEATURE                Location/Qualifiers
REGION                 1..7
                       note = KCD214 L2
source                 1..7
                       mol_type = protein
                       organism = synthetic construct
SEQUENCE: 243
GTSNLAS                                                                    7

SEQ ID NO: 244         moltype = AA  length = 9
FEATURE                Location/Qualifiers
REGION                 1..9
                       note = KCD214 L3
source                 1..9
                       mol_type = protein
                       organism = synthetic construct
SEQUENCE: 244
QQWSDYPWT                                                                  9

SEQ ID NO: 245         moltype = AA  length = 10
FEATURE                Location/Qualifiers
REGION                 1..10
                       note = KCD220 H1
source                 1..10
                       mol_type = protein
                       organism = synthetic construct
SEQUENCE: 245
GYTFTGYWIE                                                                 10

SEQ ID NO: 246         moltype = AA  length = 17
FEATURE                Location/Qualifiers
REGION                 1..17
                       note = KCD220 H2
source                 1..17
                       mol_type = protein
                       organism = synthetic construct
SEQUENCE: 246
ETLPGSDSNN YNEKFKG                                                         17

SEQ ID NO: 247         moltype = AA  length = 12
FEATURE                Location/Qualifiers
REGION                 1..12
                       note = KCD220 H3
source                 1..12
                       mol_type = protein
                       organism = synthetic construct
SEQUENCE: 247
ARDYSNYWYF DV                                                              12

SEQ ID NO: 248         moltype = AA  length = 11
FEATURE                Location/Qualifiers
REGION                 1..11
                       note = KCD220 L1
source                 1..11
                       mol_type = protein
                       organism = synthetic construct
SEQUENCE: 248
RASQDISNYL N                                                               11

SEQ ID NO: 249         moltype = AA  length = 7
FEATURE                Location/Qualifiers
REGION                 1..7
                       note = KCD220 L2
source                 1..7
                       mol_type = protein
                       organism = synthetic construct
SEQUENCE: 249
YTSNLHS                                                                    7

SEQ ID NO: 250         moltype = AA  length = 8
FEATURE                Location/Qualifiers
REGION                 1..8
                       note = KCD220 L3
source                 1..8
                       mol_type = protein
                       organism = synthetic construct
SEQUENCE: 250
QQDSKHRT                                                                   8
```

-continued

```
SEQ ID NO: 251          moltype = AA  length = 10
FEATURE                 Location/Qualifiers
REGION                  1..10
                        note = KCD224 H1
source                  1..10
                        mol_type = protein
                        organism = synthetic construct
SEQUENCE: 251
GFSLTSYGVD                                                          10

SEQ ID NO: 252          moltype = AA  length = 16
FEATURE                 Location/Qualifiers
REGION                  1..16
                        note = KCD224 H2
source                  1..16
                        mol_type = protein
                        organism = synthetic construct
SEQUENCE: 252
VIWGVGSTNY NSALKS                                                   16

SEQ ID NO: 253          moltype = AA  length = 13
FEATURE                 Location/Qualifiers
REGION                  1..13
                        note = KCD224 H3
source                  1..13
                        mol_type = protein
                        organism = synthetic construct
SEQUENCE: 253
ARSYDGSYWY FDV                                                      13

SEQ ID NO: 254          moltype = AA  length = 11
FEATURE                 Location/Qualifiers
REGION                  1..11
                        note = KCD224 L1
source                  1..11
                        mol_type = protein
                        organism = synthetic construct
SEQUENCE: 254
RASQVISNYL N                                                        11

SEQ ID NO: 255          moltype = AA  length = 7
FEATURE                 Location/Qualifiers
REGION                  1..7
                        note = KCD224 L2
source                  1..7
                        mol_type = protein
                        organism = synthetic construct
SEQUENCE: 255
YTSRLHS                                                             7

SEQ ID NO: 256          moltype = AA  length = 9
FEATURE                 Location/Qualifiers
REGION                  1..9
                        note = KCD224 L3
source                  1..9
                        mol_type = protein
                        organism = synthetic construct
SEQUENCE: 256
QQYSKLPYT                                                           9

SEQ ID NO: 257          moltype = DNA  length = 420
FEATURE                 Location/Qualifiers
misc_feature            1..420
                        note = mAb KCD002 heavy chain
source                  1..420
                        mol_type = other DNA
                        organism = synthetic construct
SEQUENCE: 257
atgtatcgaa tgcaacttct cagttgtatt gcgttgtctt tggctttggt cactaattct  60
gaggtgaaac ttgtagaatc tgaaggtggt cttgtccagc caggaagttc catgaaactg  120
agctgtaccg cttccgggtt tacgtttagt gattactata tggcctgggt gagacaagtg  180
cctgaaaagg gcctcgagtg ggtaggaaac attaactatg atgggtctag cacctattac  240
cttgatagtc ttaagtcacg attcattatt tcaagagact cagcaaagaa tatcctttat  300
ctgcagatgt cttctcttaa gagtgaggat acggccactt acttctgtgc gagaggtgaa  360
gatttctacc tttatgctat ggattactgg gggcaaggca ctagcgttac cgtctcctca  420

SEQ ID NO: 258          moltype = DNA  length = 380
FEATURE                 Location/Qualifiers
misc_feature            1..380
```

```
                        note = mAb KCD002 light chain
source                  1..380
                        mol_type = other DNA
                        organism = synthetic construct
SEQUENCE: 258
tgtaccgaat gcagctcttg tcctgcattg ctttgtctct cgctttggtc acgaactccg  60
atattcaaat gactcagagc cccgcatctc tctctgcttc cgtaggcgaa accgtaacaa  120
tcacttgtcg agctagtgaa aacatacact cctatctcgc ttggtaccaa cagaaacagg  180
gaaagtcacc acaacttatt gtgtataaca ccaagacgct ggccgagggt gtacctagtc  240
ggttttctgg atccggtagc ggtacacagt tttctttgaa aataaatagc cttcaacctg  300
aagattttgg atcctactat tgccagcatc actatgggat accaccgacg ttcggaggcg  360
gtacaaagct tgaaattaaa                                              380

SEQ ID NO: 259          moltype = DNA  length = 408
FEATURE                 Location/Qualifiers
misc_feature            1..408
                        note = mAb KCD003 heavy chain
source                  1..408
                        mol_type = other DNA
                        organism = synthetic construct
SEQUENCE: 259
atgtatagaa tgcaattgtt gtcctgtatc gctctgagcc ttgcccttgt cacgaatagc  60
gaagtccaac ttcagcagtc tcgccccgaa ctggtgaagc ctggggcgag tgtaaaaatt  120
ttttgcaaag catccggcta tacatttacg gactactaca tgaattggat gaggcagagg  180
cacggcgaga cccttgagtg gataggagac atcaacccga acaacgggga cccgtcatac  240
aatcagaagt tcaaagataa agcaactctt actgttgata aatcctcaag cactgcgagc  300
atggaactga ggagtcttac atccgacgat tccgctgttt actattgcgc cagggaaggt  360
ccttccttcg cttattgggg tcaggggaca ttggttaccg tctccgca                408

SEQ ID NO: 260          moltype = DNA  length = 396
FEATURE                 Location/Qualifiers
misc_feature            1..396
                        note = mAb KCD003 light chain
source                  1..396
                        mol_type = other DNA
                        organism = synthetic construct
SEQUENCE: 260
atgtatcgaa tgcagctctt gtcatgtata gccctttctc tggctctcgt tactaacagc  60
gatgtgttga tgacacaaac ccctctcagt ctgcccgttt cacttggcga acaggcgagt  120
attagctgcc gatcttccca aactatagtt cacagtaacg gagatacgta cctggagtgg  180
tacctgcaga aaccgggcca gtcacctaac ttgctcattt acaaagtctc aaatagattc  240
tccggagttc cagataggtt ttccggtagt ggttctggta cggacttcac tttgaagatt  300
agccgcgtcg aggcggagga ccttggggtc tactattgct tccaaggctc ccatgtgcct  360
cccacgtttg gaggaggcac taagcttgaa attaaa                            396

SEQ ID NO: 261          moltype = DNA  length = 408
FEATURE                 Location/Qualifiers
misc_feature            1..408
                        note = mAb KCD005 heavy chain
source                  1..408
                        mol_type = other DNA
                        organism = synthetic construct
SEQUENCE: 261
atgtatcgga tgcaactgtt gagttgcatt gcacttagtc tcgcactcgt gacgaacagc  60
gaggtacaac tgcaacagtc tggccctgaa ttggtaaaac ccggtgcctc tgttaaaatc  120
agctgtaaag cgtccggcta tacatttaca gaccactata tgaattgggt caagcaatct  180
catggaaaat cccttgaatg gataggagat ataaatccga ataacggagg cactagttgt  240
aaccagaagt ttaagggaaa agctactctg actgtggata aatcatcttc cactgcctat  300
atggagctta ggtctcttac tagcggggac tctgcggtct actactgcac ccgcgaaggg  360
gcatctttcg ctttctgggg tcagggaaca ctggttacag tctctgca                408

SEQ ID NO: 262          moltype = DNA  length = 396
FEATURE                 Location/Qualifiers
misc_feature            1..396
                        note = mAb KCD005 light chain
source                  1..396
                        mol_type = other DNA
                        organism = synthetic construct
SEQUENCE: 262
atgtatagaa tgcaattgtt gtcatgtatc gcgctctcac tcgcattggt tactaactct  60
gatgtgttga tgacgcagac tcccctgtct ctcccagtgt cacttggcga tcaggcttct  120
atatcctgcc gaagctccca gagcattgtc cacagtaacg gagacactta tctggaatgg  180
tacctccaaa agccgggcca gagtccaaaa cttttgatct ataaagtcag taatagattt  240
agtggggttc cagacaggtt ctcaggcagc ggctcaggca ccgacttcac tctgaagata  300
agccgggttg aagctgagga tctcggggtg tattactgtt tccaagggtc acatgtacca  360
gttacatttg gagcaggcac taagcttgaa attaaa                            396

SEQ ID NO: 263          moltype = AA  length = 408
FEATURE                 Location/Qualifiers
```

```
REGION                  1..408
                        note = mAb KCD009 heavy chain
source                  1..408
                        mol_type = protein
                        organism = synthetic construct
SEQUENCE: 263
ATGTACCGCA TGCAACTTCT TAGCTGTATT GCCCTCTCCC TTGCACTCGT TACCAATAGC  60
CAGATACAAC TGGTGCAAAG CGGGCCTGAG CTTAAGAAAC CAGGAGAAAC AGTCAAAATT  120
TCCTGCAAAG CGTCAGGCTA CATATTCAGG AACTACGGCA TGAATTGGGT GAAGCAAGGT  180
CCGGGCAAAG GCCTCAAATG GATGGGGTGG ATCAACACAT ACACGGGTGA GCCCACTTAC  240
GCAGACGACT TCAAGGGAAG ATTTGCATTT TCACTTGAAA CGTCAGCCAG TACAGCATAT  300
TTGCAGATTT CCAACCTTAA GAACGAGGAT ACAGCCACTT ATTTCTGTGT TAGGGATGGT  360
CCAGGTTTTG CGTACTGGGG GCAAGGAACT CTGGTGACTG TATCTGCA              408

SEQ ID NO: 264          moltype = DNA  length = 396
FEATURE                 Location/Qualifiers
misc_feature            1..396
                        note = mAb KCD009 light chain
source                  1..396
                        mol_type = other DNA
                        organism = synthetic construct
SEQUENCE: 264
atgtaccgaa tgcagctcct gtcttgcatc gcccttagcc tcgctcttgt aacaaattct  60
gatgtattga tgactcagac acctctgtcc cttcctgtct cactcggaga ccaagcctca  120
atttcttgta gatccagtct tataatagag cattctgatg gtaatactta tctggagtgg  180
tatcttcaga aacccggtca gtctccgaag ttgcttatct acaaggtctc caatcggttt  240
tctggagttc cggataggtt ttctggctca gggagcggga ccgattttac cttgaaaatt  300
tcacgggtgg aagcagatga cttgggtgtg tactattgtt ttcaggggag ccatgtcccg  360
gtgacgttcg gcgctgggac caagcttgaa attaaa                            396

SEQ ID NO: 265          moltype = DNA  length = 402
FEATURE                 Location/Qualifiers
misc_feature            1..402
                        note = mAb KCD010 heavy chain
source                  1..402
                        mol_type = other DNA
                        organism = synthetic construct
SEQUENCE: 265
atgtatcgaa tgcagctttt gtcctgtata gctttgtctt tggcccttgt gacaaattcc  60
gaggtcctgc ttcagcaatc aggccccgag ctggtcaagc caggagcatc tgtcaaaata  120
ccctgtaagg caagcggcta cacgtttacg gactacgata tggattgggt taagcaatca  180
cacggaaagt cattggagtg gataggccac atcaatccaa ataacggtgg cactatttat  240
aaccaaaagt tcaagggcaa agccaccctg accgtcgata agtcatcatc tactgcgtac  300
atggagttga ggtctctgac atcagaagat accgccgttt attactgtgg cactggggat  360
ttcgcatatt ggggacatgg aactctggtc acagtttcag ca                      402

SEQ ID NO: 266          moltype = DNA  length = 384
FEATURE                 Location/Qualifiers
misc_feature            1..384
                        note = mAb KCD010 light chain
source                  1..384
                        mol_type = other DNA
                        organism = synthetic construct
SEQUENCE: 266
atgtatagga tgcaactgtt gtcctgcatt gctctttctc ttgcacttgt aacaaactcc  60
caaatcgtac tcacccaatc cccagccata atgtccgtca gtccaggaga aaaagttacc  120
ttgacctgca gcgcgagttc aagcgtgtcc tcctcttatt tgtactggta ccagaagaag  180
ccgggtagct ctcctaaact ctggatctac tccaccagta acttggctag tggtgtccct  240
gcgagatttt cagggtctgg gagtgggaca tcctattccc tcacaataag ctcaatggaa  300
gctgaggatg cggcgagcta tttttgccat cagtggtcta gctacccacc tacatttggt  360
gctggaacga agcttgaaat taaa                                          384

SEQ ID NO: 267          moltype = DNA  length = 402
FEATURE                 Location/Qualifiers
misc_feature            1..402
                        note = mAb KCD023 heavy chain
source                  1..402
                        mol_type = other DNA
                        organism = synthetic construct
SEQUENCE: 267
atgtaccgaa tgcagttgct ctcatgtatt gctcttagcc tcgccctcgt gaccaatagt  60
gaagtcctcc ttcaacaaag tggccctgaa ctcgttaaac cgggggcctc tgtcaagata  120
ccttgtaaag cgagtggcta tacctttaca gactataata ttgactgggt taaacaatca  180
catggaaaga gcctggaatg gatcggtgat ataaatccca acaacggtgg aattaactac  240
aatcaaaaat ttaaagggaa agccactctt actgttgaca agagtagctc aacggcgtac  300
atggaactcc ggtctctcac ttcagaggac acagccgtat attattgcgg gacaggagac  360
tatgcctatt ggggacaggg cactctggtc acagtttcag ca                      402

SEQ ID NO: 268          moltype = DNA  length = 384
```

```
FEATURE                Location/Qualifiers
misc_feature           1..384
                       note = mAb KCD023 light chain
source                 1..384
                       mol_type = other DNA
                       organism = synthetic construct
SEQUENCE: 268
atgtatagaa tgcagctctt gagctgcatc gctctttcct tggccctcgt gacaaactct  60
cagatcgtat tgacccagag ccccgccttc atgagcgcca gtcctggcga gaaagttact  120
ctcacctgct ccgcttcaag tagtgtgtcc agtagttacc tgtactggta tcaacaaaaa  180
cccggaagta gtcctaagtt gtggatttac tccacttcta atcttgccag cggagtgcct  240
ggaaggttta gtgggagtgg cagcggaact tcctacagtc ttacaatctc cagcatggaa  300
gccgaggatg cggcgtccta cttctgccac cagtggacat cctatccccc taccttcgga  360
gccgggacca agcttgaaat taaa                                          384

SEQ ID NO: 269         moltype = DNA  length = 414
FEATURE                Location/Qualifiers
misc_feature           1..414
                       note = mAb KCD036 heavy chain
source                 1..414
                       mol_type = other DNA
                       organism = synthetic construct
SEQUENCE: 269
atgtatagaa tgcaacttct gagttgcata gcgttgagtc tcgccttggt tacgaactct  60
gaggtgcaac tgcaacaatc tgggccggag cttgtgaagc caggagcatc tatgaaaata  120
agttgcaagg catctggata ctcttttaca ggatacacta tgacatgggt aaagcaaagc  180
cacgggaaaa atcttgaatg gatcggcctc atcaatcctt acaatggtgg gaccaattac  240
aatcagaaat ttaaagggaa ggcgaccttt actgtcgaca aatcaagctc cactgcatat  300
atggaactct tgtcccttac gagcgaggac agcgcggtct attattgcgc caggcgacac  360
tacggaagct cttgggatta ctgggggcaa gggaccacac tgacagtttc atca        414

SEQ ID NO: 270         moltype = DNA  length = 381
FEATURE                Location/Qualifiers
misc_feature           1..381
                       note = mAb KCD036 light chain
source                 1..381
                       mol_type = other DNA
                       organism = synthetic construct
SEQUENCE: 270
atgtaccgaa tgcagttgtt gagttgtata gctctgtcac tcgcgcttgt aaccaattca  60
gacataaagt tgacccaaag tccgagttca atgtatgcct ctcttggtga aagggtaacg  120
ataacttgca aggcgtccca ggatataaac acgtatctta gttggtttca acagaaaccg  180
ggtaaaagtc ccaaaactct tatctaccga gctaataggt tggtagatgg ggtgccgtca  240
agattcagcg gttcaggctc aggccaggac tactctttga ccatcagctc acttgaatac  300
gaggagatgg gcatatacta ttgcctgcaa tacgacgagt tcccgtacac tttcggaggg  360
ggtacgaagc ttgaaattaa a                                             381

SEQ ID NO: 271         moltype = DNA  length = 399
FEATURE                Location/Qualifiers
misc_feature           1..399
                       note = mAb KCD040 heavy chain
source                 1..399
                       mol_type = other DNA
                       organism = synthetic construct
SEQUENCE: 271
atgtatagaa tgcagctcct ttcttgtatt gccctgagtt tggccttggt aactaatagt  60
gaggttcaac tccagcaaag tggcgcggag ctggtcaagc caggtgctag tgtaaaactt  120
tcatgcaccg cctccgactt caatatcaag gatacgtata tgcactgggt gatgcagcgg  180
ccagaacagg gtctggaatg gatcggtaaa atagacccgg cgaacggtaa cactgagttt  240
gaccctaaat ttcagggcaa ggcaaccatc acagctgaca cctccagtaa tacagcgtac  300
ctccagttga cctcactcac cagcgaggac accgcagtct attactgcac gcgagctatg  360
gactattggg gtcaagggac ttcagttaca gtgagctca                         399

SEQ ID NO: 272         moltype = DNA  length = 378
FEATURE                Location/Qualifiers
misc_feature           1..378
                       note = mAb KCD040 light chain
source                 1..378
                       mol_type = other DNA
                       organism = synthetic construct
SEQUENCE: 272
atgtaccgga tgcagttgtt gagctgtata gccctgagct tggcgcttgt cacaaactct  60
caaatcgtcc tcacgcaatc acctgcgatc atgtcagcta gtccggggga gaaagtcacg  120
atgacgtgct ctgccggatc ttccgtttct tatatgtatt ggtaccagca gaagccaggg  180
agttcccctc gcgtcttgat ttacgataca tctaatcttg ctagtggcgt cccggtccgg  240
ttctccgggt ccggcagcgg tacatcatat tctctgacga taagtaggat ggaggccgaa  300
gatgctgcaa catactattg ccagcagtgg agtaactatc cctacacttt tggcggaggc  360
actaagcttg aaattaaa                                                 378
```

-continued

```
SEQ ID NO: 273         moltype = DNA  length = 399
FEATURE                Location/Qualifiers
misc_feature           1..399
                       note = mAb KCD042 heavy chain
source                 1..399
                       mol_type = other DNA
                       organism = synthetic construct
SEQUENCE: 273
atgtaccgca tgcaattgct ttcttgtatt gctctgagtt tggcattggt aaccaactcc  60
gaggttcagc tccagcagtc aggtgcagaa cttgtcaaac cgggcgcgag tgtgcgcctc  120
tcttgtaccg cctcaggttt taacattaag catacatata ttcattgggt atcccagcgc  180
ccggaacaag gcttggagtg gatcgggaaa atagatcctg ccaatgggaa taccaaatac  240
gacccaaagt tccaggggaa ggccaccatt acggcagata cctcttctaa taccgcttat  300
ctccaactct catcacttac gtcagaagat accgcggttt attactgcgt taatgcaatg  360
gaatactggg gccaaggcac gtccgttaca gtatcttca                         399

SEQ ID NO: 274         moltype = DNA  length = 378
FEATURE                Location/Qualifiers
misc_feature           1..378
                       note = mAb KCD042 light chain
source                 1..378
                       mol_type = other DNA
                       organism = synthetic construct
SEQUENCE: 274
atgtatcgga tgcaattgct gtcttgtatc gcccttagcc tcgccctcgt cacgaacagc  60
cagtccgtgc tgacgcagag tccggcaatc atgtctgcga gtcccggtga gaaagtaacg  120
atgacttgct ccgctaatag ctccgtgagc gatatgtatt ggttccagca acggccagga  180
tcatccccgc gcttgttgat atacgacaca tctaatctgg cttccggtgt gccagttcga  240
ttctctgggt ctgggtccgg tacgtcatat agtctcacca ttagccggat ggaagcagaa  300
gatgcggcga cgtattattg ccagcaatgg agtacctatc catggacctt tgggggtgga  360
acgaagcttg aaattaaa                                                378

SEQ ID NO: 275         moltype = DNA  length = 399
FEATURE                Location/Qualifiers
misc_feature           1..399
                       note = mAb KCD044 heavy chain
source                 1..399
                       mol_type = other DNA
                       organism = synthetic construct
SEQUENCE: 275
atgtatcgaa tgcaactttt gagttgcata gcactgagtc ttgctctggt aacaaactcc  60
gaggttcagc ttcagcaatc aggtgcagaa ctggtaaagc ctggggcatc cgttagactt  120
agttgtaccg caagtggatt caacataaaa cacacctata tgcattgggt cagccagaga  180
cccgaaaggg gtcttgaatg gattggcaaa atagaccctg caaacgggaa tacgaaatat  240
gatccaaagt ttcagggtaa agcaactata acagccgata cgtcatccaa tacagtatac  300
ttgcaactta gcagccttac gtccgaagac accgctgtct actattgctt gaatgctatg  360
gaatactggg gacaggggac ttctgtaacc gtatcctca                         399

SEQ ID NO: 276         moltype = DNA  length = 378
FEATURE                Location/Qualifiers
misc_feature           1..378
                       note = mAb KCD044 light chain
source                 1..378
                       mol_type = other DNA
                       organism = synthetic construct
SEQUENCE: 276
atgtacagaa tgcaactcct gagttgcatc gcactgtctc tggcgctggt gacaaactca  60
cagtctgtcc tcacgcagag tcctgcgatt atgtccgcaa gcccagggga gaaggtaacg  120
atgacatgct ccgctaatag ctctgtgtct gatatgtatt ggtatcagca acgcccaggg  180
tctagtcccc ggctcctcat ttacgatacc agcaacctcg ctagtggcgt ccccgtgcga  240
ttttctggct ccgggtcagg gactagctac agcctcacta tctccagaat ggaagcggaa  300
gatgcagcga cgtattattg tcagcagtgg agcacatatc catggacctt tgggggtggg  360
actaagcttg aaattaaa                                                378

SEQ ID NO: 277         moltype = DNA  length = 399
FEATURE                Location/Qualifiers
misc_feature           1..399
                       note = mAb KCD047 heavy chain
source                 1..399
                       mol_type = other DNA
                       organism = synthetic construct
SEQUENCE: 277
atgtatcgaa tgcaactgct ttcatgtatt gcgctttcat tggctcttgt tactaactcc  60
gaagttcaac ttcagcagtc tggagctgag tttgtaaagc ccggtgcctc agtaaggctg  120
tcttgcaccg cttctgggtt caatatcaag gacacgtaca tgcactgggt caagcaaagg  180
ccagagcagg gattggaatg gattggtcgg atcgatcctg cgaatggtta caccaaggat  240
gacccgaagt tccaaggcaa agctacgata acggcagaca cgtcaagcaa tacggcgtat  300
cttcagctta gtagcttgac ttctgaagac actgccgttt attactgtgc ttccgcaatg  360
gactactggg gccaagggac ttccgtgact gtatcatca                         399
```

```
SEQ ID NO: 278          moltype = DNA  length = 378
FEATURE                 Location/Qualifiers
misc_feature            1..378
                        note = mAb KCD047 light chain
source                  1..378
                        mol_type = other DNA
                        organism = synthetic construct
SEQUENCE: 278
atgtatagaa tgcagttgct ctcctgtatc gctctctctc tggctttggt gactaacagt  60
cagatcgtgc tcactcaatc acccgccgtt atgtctgcgt ctccagggga gaaggtagcc  120
atgacctgct cagcaagtag cagcgtgacg tatatgtatt ggtatcagca aaaacctgga  180
agctccccca ggttgcttat atatgacact tctaatttgg cgagtggcgt acctgtacga  240
ttttctggca gcggttctgg cacaagttat agtctcacga ttagtcgcat ggaagccgaa  300
gacgccgcga cttactattg ccaacaatgg agcacatatc cattcccatt cggctccggc  360
acgaagcttg aaattaaa                                                378

SEQ ID NO: 279          moltype = DNA  length = 399
FEATURE                 Location/Qualifiers
misc_feature            1..399
                        note = mAb KCD048 heavy chain
source                  1..399
                        mol_type = other DNA
                        organism = synthetic construct
SEQUENCE: 279
atgtaccgaa tgcaacttct gagttgcatt gccttgtccc tggcacttgt gactaatagt  60
gaagtgcagc tccaacaaag tggcgctgat ctggtcaagc ctggtgcgag tgtgaaactt  120
agctgcacag cgagcgggtt caatatcaaa gcaacttaca tgcactgggt acggcagcga  180
ccggagaaag gcctcgaatg gataggccgc atcgaccccg ccaatggaca tacaatctat  240
gacccccagt ttcaggggaa ggctaccatt acgtccgata ctagtagcaa tacagcatac  300
ctccagttga actctctcac aagcgaggat acggcagtct actattgtgc ggaggcgatg  360
gattattggg gtcaaggtac atctgtgact gtttcctca                         399

SEQ ID NO: 280          moltype = DNA  length = 378
FEATURE                 Location/Qualifiers
misc_feature            1..378
                        note = mAb KCD048 light chain
source                  1..378
                        mol_type = other DNA
                        organism = synthetic construct
SEQUENCE: 280
atgtatcgga tgcagcttct ttcctgcatc gctcttagtc tcgccttggt tacaaattct  60
caaattgtgc tcactcagtc accagcgata atgtccgcct ctcccggtga aaaggtgact  120
ctgacatgca gcgctacatc cagcgtctca tacatgtact ggtatcagca gaagcctggt  180
tccagccctc ggctcctgat atacgacaca agtaacctgg cttccggcgt gccggtgagg  240
ttctctggaa gcgggagtgg cacctcttat tccttgacga tttccagaat ggaagcggag  300
gatgatgcga cctattattg tcaacaatgg agcaactatc cctttacttt tggcggtgga  360
acgaagcttg aaattaaa                                                378

SEQ ID NO: 281          moltype = DNA  length = 414
FEATURE                 Location/Qualifiers
misc_feature            1..414
                        note = mAb KCD070 heavy chain
source                  1..414
                        mol_type = other DNA
                        organism = synthetic construct
SEQUENCE: 281
atgtacagaa tgcaactcct ctcctgtata gctctgtccc tggccctcgt aactaattcc  60
gagatacagt tgcaacaaac tggaccagaa cttgtcaagc caggtgcatc tgtcaagata  120
agctgcaaag cctccggtta cagctttaca gactacatta tcctgtgggt gaaacagtca  180
catggtaaaa gtctggagtg gataggaaac ataaatcctt actacgatta taccagctat  240
aatctcaaat tcaaaggtaa agcgactctg actgtagaca aatccagctc taccgcctac  300
atgcagctta actcacttac ttctgaggac agtgccgtct actattgcgc ccgctccgac  360
ggctactacg gaggggatta ctggggtcag ggtacgagtg taacggtttc atca        414

SEQ ID NO: 282          moltype = DNA  length = 381
FEATURE                 Location/Qualifiers
misc_feature            1..381
                        note = mAb KCD070 light chain
source                  1..381
                        mol_type = other DNA
                        organism = synthetic construct
SEQUENCE: 282
atgtaccgaa tgcagcttct gagttgtatc gcgctgtcat tggccctggt cacgaactcc  60
gacatagtta tgacccagtc acacaaattt atgtccacgt cagtaggtga tcgcgtgagt  120
ataacgtgta aagcgagcca ggatgttggc accgccgtgg cgtggtatca acaaaagcct  180
ggccagtccc cgaagctcct catatattgg gccagtacga gacatacagg cgtgcctgac  240
cgattcactg ggagtggttc cggcacagac ttcaccctca cgataaataa tgttcagtct  300
gaagacctgg ctgattactt ctgtcagcaa tattcttctt acccttggac atttggcgga  360
```

```
ggcaccaagc ttgaaattaa a                                           381

SEQ ID NO: 283         moltype = DNA  length = 413
FEATURE                Location/Qualifiers
misc_feature           1..413
                       note = mAb KCD101 heavy chain
source                 1..413
                       mol_type = other DNA
                       organism = synthetic construct
SEQUENCE: 283
tgtacaggat gcaactcctg tcttgcattg cactaagtct tgcacttgtc actaactcac  60
aggtccaact gcagcagcct ggggctgagc tggtgaggcc tgggacttca gtgaagttgt  120
cctgcaaggc ttctggctac accttcacca gctactggat gcactgggta aagcagaggc  180
ctggacaagg ccttgagtgg atcggagtga ttgatccttc tgatagttat actaattaca  240
atcaaaagtt caagggcaag gccacattga ctgtagacac atcctccagc acagcctaca  300
tgcagctcag cagcctgaca tctgaggact ctgcggtcta ttactgtgga agaaatggtt  360
acgacgggtc tatggactac tggggtcaag gaacctcagt caccgtctcc tca         413

SEQ ID NO: 284         moltype = DNA  length = 372
FEATURE                Location/Qualifiers
misc_feature           1..372
                       note = mAb KCD101 light chain
source                 1..372
                       mol_type = other DNA
                       organism = synthetic construct
SEQUENCE: 284
atgtacagga tgcaactcct gtcttgcatt gcactaagtc ttgcacttgt cactaactca  60
gatatccaga tgacacagac tacatcctcc ctgtctgcct ctctgggaga cagagtcacc  120
atcagttgca gggcaagtca ggacattagc aattatttaa actggtatca gcagaaacca  180
gatggaactg ttaaactcct gatctactac ccatcaagat tacactcagg agtcccatca  240
aggttcagtg gcagtgggtc tggaacagat tattctctca ccattagcaa cctggagcaa  300
gaagattttg ccacttactt ttgccaacag ggtaatacgc ttccgtacac gttcggaggg  360
gggaccaagc tt                                                     372

SEQ ID NO: 285         moltype = DNA  length = 414
FEATURE                Location/Qualifiers
misc_feature           1..414
                       note = mAb KCD102 heavy chain
source                 1..414
                       mol_type = other DNA
                       organism = synthetic construct
SEQUENCE: 285
atgtacagga tgcaactcct gtcttgcatt gcactaagtc ttgcacttgt cactaactca  60
caggtccaac tgcagcagcc tggggctgag ctggtgaggc ctgggacttc agtgaagttg  120
tcctgcaagg cttctggcta caccttcacc agctactgga tgcactgggt aaagcagagg  180
cctggacaag gccttgagtg gatcggagtg attgatcctt ctgatagtta tactaactac  240
aatcaaaagt tcaagggcaa ggccacattg actgtagaca catcctccag cacagcctac  300
atgcagctca gcagcctgac atctgaggac tctgcggtct attactgtgc aagaaatggt  360
tacgacgggt ctatggacta ctggggtcaa ggaacctcag tcaccgtctc ctca        414

SEQ ID NO: 286         moltype = DNA  length = 372
FEATURE                Location/Qualifiers
misc_feature           1..372
                       note = mAb KCD102 light chain
source                 1..372
                       mol_type = other DNA
                       organism = synthetic construct
SEQUENCE: 286
atgtacagga tgcaactcct gtcttgcatt gcactaagtc ttgcacttgt cactaactca  60
gaaatccaga tgacacagac tacatcctcc ctgtctgcct ctctgggaga cagagtcacc  120
atcagttgca gggcaagtca ggacattagc aattatttaa actggtatca gcagaaacca  180
gatggaactg ttaaactcct gatctactac ccatcaagat tacactcagg agtcccatca  240
aggttcagtg gcagtgggtc tggaacagat tattctctca ccattagcaa cctggagcaa  300
gaagattttg ccacttactt ttgccaacag ggtaatacgc ttccgtacac gttcggaggg  360
gggaccaagc tt                                                     372

SEQ ID NO: 287         moltype = DNA  length = 414
FEATURE                Location/Qualifiers
misc_feature           1..414
                       note = mAb KCD103 heavy chain
source                 1..414
                       mol_type = other DNA
                       organism = synthetic construct
SEQUENCE: 287
atgtacagga tgcaactcct gtcttgcatt gcactaagtc ttgcacttgt cactaactca  60
caggtccaac tgcagcagcc tggggctgag ctggtgaggc ctgggacttc agtgaagttg  120
tcctgcaagg cttctggcta caccttcacc agctactgga tgcactgggt aaagcagagg  180
cctggacaag gccttgagtg gatcggagtg attgatcctt ctgatagtta tactaagtac  240
aatcaaaagt tcaaggacaa ggccacattg actgtagaga catcctccag cacagcctac  300
```

```
atgcagctca gcagcctgac atctgaggac tctgcggtct attactgtgc aggaaatggt  360
tacgacgggt ctatggacta ctggggtcaa ggaacctcag tcaccgtctc ctca        414

SEQ ID NO: 288         moltype = DNA  length = 372
FEATURE                Location/Qualifiers
misc_feature           1..372
                       note = mAb KCD103 light chain
source                 1..372
                       mol_type = other DNA
                       organism = synthetic construct
SEQUENCE: 288
atgtacagga tgcaactcct gtcttgcatt gcactaagtc ttgcacttgt cactaactca  60
gatatccaga tgacacagac tacatcctcc ctgtctgcct ctctgggaga cagagtcacc  120
atcagttgca gggcaagtca ggacattagc aattctttaa actggtatca gcagaaacca  180
gatggaactg ttaaactcct gatctactac acatcaagat tacactcacg agtcccatca  240
aggttcagtg gcagtgggtc tggaacagat tattctctca ccattagcaa cctggaccaa  300
gaagatattg ccacttactt ttgccaacag gctaatacgc ttccgtacac gttcggaggg  360
gggaccaagc tt                                                      372

SEQ ID NO: 289         moltype = DNA  length = 414
FEATURE                Location/Qualifiers
misc_feature           1..414
                       note = mAb KCD104 heavy chain
source                 1..414
                       mol_type = other DNA
                       organism = synthetic construct
SEQUENCE: 289
atgtacagga tgcaactcct gtcttgcatt gcactaagtc ttgcacttgt cactaactca  60
caggtccaac tgcagcagcc tggggctgag ctggtgaggc ctgggacttc agtgaagttg  120
tcctgcaagg cttctggcta caccttcacc agctactgga tgcactgggt aaagcagagg  180
cctggacaag gccttgagtg gatcggagtg attgatcctt ctgatagtta tacttactac  240
aatcaaaagt tcaagggcaa ggccacattg actgtagaca catcctccag cacagcctac  300
atgcagctca gcagcctgac atctgaggac tctgcggtct attactgtgc aagaaatggt  360
tacgacgggg ctatggacta ctggggtcaa ggaacctcag tcaccgtctc ctca        414

SEQ ID NO: 290         moltype = DNA  length = 372
FEATURE                Location/Qualifiers
misc_feature           1..372
                       note = mAb KCD104 light chain
source                 1..372
                       mol_type = other DNA
                       organism = synthetic construct
SEQUENCE: 290
atgtacagga tgcaactcct gtcttgcatt gcactaagtc ttgcacttgt cactaactca  60
gaaatccaga tgacacagac tacatcctcc ctgtctgcct ctctgggaga cagagtcacc  120
atcagttgca gggcaagtca ggacattagc aattatttaa actggtatca gcagaaacca  180
gatggaactg ttaaactcct gatctactac ccatcaagat tacactcagg agtcccatca  240
aggttcagtg gcagtgggtc tggaacagat tattctctca ccattagcaa cctggagcaa  300
gaagattttg ccacttactt ttgccaacag ggtaatacgc ttccgtacac gttcggaggg  360
gggaccaagc tt                                                      372

SEQ ID NO: 291         moltype = DNA  length = 408
FEATURE                Location/Qualifiers
misc_feature           1..408
                       note = mAb KCD118 heavy chain
source                 1..408
                       mol_type = other DNA
                       organism = synthetic construct
SEQUENCE: 291
atgtacagga tgcaactcct gtcttgcatt gcactaagtc ttgcacttgt cactaactca  60
gaggtccagc tgcaacagtc tggacctgaa ctggtgaagc ctggggcttc agtgaagata  120
tcctgtaagg cttttggata cacgttcact gactactaca agaactggat gaggcagaga  180
catggagaga gccttgagtg gattggagat attaatccta acagtggtga tgctaactac  240
aaccagaagt tcaagggcaa ggccacattg actgttgaca agtcctccag cacagcctac  300
atggagctcc gcagcctgac atctgaggac tctgcagtct attactgtgc aagagaggga  360
ccttcgtttg cttactgggg ccatgggact ctggtcactg tctctgca                408

SEQ ID NO: 292         moltype = DNA  length = 387
FEATURE                Location/Qualifiers
misc_feature           1..387
                       note = mAb KCD118 light chain
source                 1..387
                       mol_type = other DNA
                       organism = synthetic construct
SEQUENCE: 292
atgtacagga tgcaactcct gtcttgcatt gcactaagtc ttgcacttgt cactaactca  60
gatgttttga tgacccaaac tccactctcc ctgcctgtca gtcttggaga tcaagcctcc  120
atctcttgca gatctagtca gaccattgtt catagtaatg gagacaccta tttagaatgg  180
tacctgcaga aaccaggcca gtctccaaac ctcctgatct acaaagtttc caaccgattt  240
```

```
tctggggtcc cagacaggtt cagtggcagt ggatccggga cagatttcac actcaagatc  300
agcagagtgg aggctgagga tctgggaatt tattactgct ttcaaggttc acatgttcct  360
ccgacgttcg gtggaggcac caagctt                                      387

SEQ ID NO: 293         moltype = DNA  length = 408
FEATURE                Location/Qualifiers
misc_feature           1..408
                       note = mAb KCD119 heavy chain
source                 1..408
                       mol_type = other DNA
                       organism = synthetic construct
SEQUENCE: 293
atgtacagga tgcaactcct gtcttgcatt gcactaagtc ttgcacttgt cactaactca  60
gaggtccagc tgcaacagtc tggacctgaa ctggtgaagc ctggggcttc agtgaagata  120
tcctgtaagg cttctggata cactttcact gactactaca cgaactggat gaggcagaga  180
catggagaga gccttgagtg gattggagat attaatccta acactggtga tactagctac  240
aaccagaagt tcagggtcaa ggccacattg actgtagaca agtcctccgg cacagcctac  300
atggggctcc gcagcctgac atctgaggac tctgccgtct attactgtac aagagaggga  360
ccttcgtttg cttactgggg ccaagggact ctggtcactg tctctgca              408

SEQ ID NO: 294         moltype = DNA  length = 387
FEATURE                Location/Qualifiers
misc_feature           1..387
                       note = mAb KCD119 light chain
source                 1..387
                       mol_type = other DNA
                       organism = synthetic construct
SEQUENCE: 294
atgtacagga tgcaactcct gtcttgcatt gcactaagtc ttgcacttgt cactaactca  60
gatgttttga tgacccaaac tccactctcc ctgcctgtca gtcttggaga tcaagcctcc  120
atctcttgca gatctagtca gaccattgta catagtaatg gagacaccta tttagaatgg  180
tacctgcaga aaccaggcca gtctccaaac ctcctgatct ataaagtttc caaccgattt  240
tctggggtcc cagacaggtt cagtggcagt ggatccggga cagatttcac actcaagatc  300
agcagagtgg aggctgagga tctgggagtt tattactgct ttcaaggttc acatgttcct  360
ccgacgttcg gtggaggcac caagctt                                      387

SEQ ID NO: 295         moltype = DNA  length = 408
FEATURE                Location/Qualifiers
misc_feature           1..408
                       note = mAb KCD121 heavy chain
source                 1..408
                       mol_type = other DNA
                       organism = synthetic construct
SEQUENCE: 295
atgtacagga tgcaactcct gtcttgcatt gcactaagtc ttgcacttgt cactaactca  60
gaggtccagc tgcaacagtc tggacctgaa ctggtgaagc ctggggcttc agtgaagata  120
tcctgtaagg cttctggata cacgttcact gactactaca agaactggat gaggcagaga  180
catggagaga gccttgagtg gattggagat attaatccta acaatggtga tacttcctac  240
aaccagaagt tcaggggcaa ggccacattg actgtagaca agtcctccag cacagccttc  300
atggagctcc gcagcctgac atctgaggac tctgcagtct attactgtgc aagagaggga  360
ccttcctttg cttactgggg ccaagggact ctggtcactg tctctgca              408

SEQ ID NO: 296         moltype = DNA  length = 387
FEATURE                Location/Qualifiers
misc_feature           1..387
                       note = mAb KCD121 light chain
source                 1..387
                       mol_type = other DNA
                       organism = synthetic construct
SEQUENCE: 296
atgtacagga tgcaactcct gtcttgcatt gcactaagtc ttgcacttgt cactaactca  60
gatgttttga tgacccaaac tccactctcc ctgcctgtca gtcttggaga tcaagcctcc  120
atctcttgca gatctaatca gaccattgta catagtaatg gagacacgta tttagaatgg  180
tacctgcaga aaccaggcca gtctccaaac ctcctgatct acaaagtttc caaccgattt  240
tctggggtcc cagacaggtt cagtggcagt ggatccggga cagatttcac actcaggatc  300
agcagagtgg aggctgagga tctgggagtt tattactgct ttcaaggttc acatgttcct  360
ccgacgttcg gtggaggcac caagctt                                      387

SEQ ID NO: 297         moltype = DNA  length = 408
FEATURE                Location/Qualifiers
misc_feature           1..408
                       note = mAb KCD122 heavy chain
source                 1..408
                       mol_type = other DNA
                       organism = synthetic construct
SEQUENCE: 297
atgtacagga tgcaactcct gtcttgcatt gcactaagtc ttgcacttgt cactaactca  60
gaggtccagc tgcaacagtc tggacctgaa ctggtgaagc ctggggcttc agtgaagata  120
tcctgtaagg cttctggata cacgttcact gactactaca agaactggat gaggcagaga  180
```

```
catggagaga gccttgagtg gattggagat attaatccta acaatggtga tgctaactac  240
aaccagaagt tcaagggcaa ggccacattg actgttgaca agtcctccag cacagcctac  300
atggagctcc gcagcctgac atctgaggac tctgcagtct atttctgtgc aagagaggga  360
ccttcgtttg cttactgggg ccatgggact ctggtcactg tctctgca              408

SEQ ID NO: 298         moltype = DNA  length = 387
FEATURE                Location/Qualifiers
misc_feature           1..387
                       note = mAb KCD122 light chain
source                 1..387
                       mol_type = other DNA
                       organism = synthetic construct
SEQUENCE: 298
atgtacagga tgcaactcct gtcttgcatt gcactaagtc ttgcacttgt cactaactca  60
gatgttttga tgacccaaac tccactctcc ctgcctgtca gtcttggaga tcaagcctcc  120
atctcttgca gatctagtca gaccattgtt catagtaatg gagacaccta tttagaatgg  180
tacctgcaga aaccaggcca gtctccaaac ctcctgatct acaaagtttc caaccgattt  240
tctggggtcc cagacaggtt cagtggcagt ggatccggga cagatttcac actcaagatc  300
agcagagtgg aggctgagga tctgggagtt tattactgct ttcaaggttc acatgttcct  360
ccgacgttcg gtggaggcac caagctt                                     387

SEQ ID NO: 299         moltype = DNA  length = 408
FEATURE                Location/Qualifiers
misc_feature           1..408
                       note = mAb KCD123 heavy chain
source                 1..408
                       mol_type = other DNA
                       organism = synthetic construct
SEQUENCE: 299
atgtacagga tgcaactcct gtcttgcatt gcactaagtc ttgcacttgt cactaactca  60
gaggtccacc tgcaacagtc tggacctgaa ctggtgaagc ctggggcttc agtgaagata  120
tcctgtaagg cttctggata cacgttcact gacttctaca agaactggat gaggcagaga  180
catggagaga gccttgagtg gattggagat attaatccta acaatggtgg tactaactac  240
aaccagaagt tcaagggcaa ggccacattg actgtagaca agtcctccag cacagcctac  300
atggagctcc gcagcctgac atctgaggac tctgcagtct attactgtgc aagagaggga  360
ccttcgtttg cttactgggg ccaagggact ctggtcactg tctctgca              408

SEQ ID NO: 300         moltype = DNA  length = 387
FEATURE                Location/Qualifiers
misc_feature           1..387
                       note = mAb KCD123 light chain
source                 1..387
                       mol_type = other DNA
                       organism = synthetic construct
SEQUENCE: 300
atgtacagga tgcaactcct gtcttgcatt gcactaagtc ttgcacttgt cactaactca  60
gatgttttga tgacccaaac tccactctcc ctgcctgtca gtcttggaga tcaagcctcc  120
atctcttgca gatctagtca gaccattgtt catagtaatg gagacaccta tttagaatgg  180
tacctgcaga aaccaggcca gtctccaaac ctcctgatct acaaagtttc caaccgattt  240
tctggggtcc cagacaggtt cagtggcagt ggatccggga cagatttcac actcaagatc  300
agcagagtgg aggctgagga tctgggagtt tattactgct ttcaaggttc acatgttcct  360
ccgacgttcg gtggaggcac caagctt                                     387

SEQ ID NO: 301         moltype = DNA  length = 408
FEATURE                Location/Qualifiers
misc_feature           1..408
                       note = mAb KCD124 heavy chain
source                 1..408
                       mol_type = other DNA
                       organism = synthetic construct
SEQUENCE: 301
atgtacagga tgcaactcct gtcttgcatt gcactaagtc ttgcacttgt cactaactca  60
gaagtccagc tccaacagtc tggacctgag ctggtgaagc ctggggcttc agtgaagata  120
tcctgtaagg cttctggata cacattcact gaccactaca tgaactgggt gaaacagagc  180
catggaaaga gccttgagtg gattggagat attaatccta acaatggtgg tactagctac  240
aaccagaagt tcaagggcaa ggccacattg actgtagaca agtcctccag cacagcctac  300
atggagctcc gcagcctgac atctggggac tctgcagtct attactgtac aagagagggg  360
gcctcgtttg ctttctgggg ccaagggact ctggtcactg tctctgca              408

SEQ ID NO: 302         moltype = DNA  length = 387
FEATURE                Location/Qualifiers
misc_feature           1..387
                       note = mAb KCD124 light chain
source                 1..387
                       mol_type = other DNA
                       organism = synthetic construct
SEQUENCE: 302
atgtacagga tgcaactcct gtcttgcatt gcactaagtc ttgcacttgt cactaactca  60
gatgttttga tgacccaaac tccactctcc ctgcctgtca gtcttggaga tcaagcctcc  120
```

-continued

```
atctcttgca gatctagtca gagcattgta catagtaatg gagacaccta tttagagtgg  180
tacctgcaga agccaggcca gtctccaaag ctcctgatct acaaagtttc caaccgattt  240
tctggggtcc cagacaggtt cagtggcagt ggatcaggga cagatttcac actcaagatc  300
agcagagtgg aggctgagga tctgggagtt tattactgct ttcaaggttc acatgttccg  360
ctcacgttcg gtgctgggac caagctt                                     387

SEQ ID NO: 303         moltype = DNA  length = 426
FEATURE                Location/Qualifiers
misc_feature           1..426
                       note = mAb KCD131 heavy chain
source                 1..426
                       mol_type = other DNA
                       organism = synthetic construct
SEQUENCE: 303
atgtacagga tgcaactcct gtcttgcatt gcactaagtc ttgcacttgt cactaactca  60
caggtccagc tacagcagtc tggacctgag ctggtgaagc ctggggcttc agtgaagatc  120
tcctgcaagg cttctgccta caccttcact gactactata taaactgggt gaagcagagg  180
cctggacagg gacctgagtg gattggatgg atttttcctg gaagtaatag tacttattcc  240
aatgagaagt tcgaggtcaa ggccacactg actgtagacg aatcctccag cacagcctac  300
atgttgctca gcagcctgac ctctgaggac tctgcggtct atttctgtgc aagattggga  360
tacttcggta gtagttacca tgctttggac tactggggtc aaggcacctc agtcaccgtc  420
tcctca                                                            426

SEQ ID NO: 304         moltype = DNA  length = 372
FEATURE                Location/Qualifiers
misc_feature           1..372
                       note = mAb KCD131 light chain
source                 1..372
                       mol_type = other DNA
                       organism = synthetic construct
SEQUENCE: 304
atgtacagga tgcaactcct gtcttgcatt gcactaagtc ttgcacttgt cactaactca  60
gacatccaga tgactcagtc tccagcctcc ctatctgtat ctgtgggaga aactgtcacc  120
atcacatgtc gagcaagtga gaatatttac agtcatttag catggtttca gcagaaacag  180
ggaaaatctc ctcggctcct ggtctattct gcaacaaact taccagatgg tgtgccatca  240
agattcagtg gcagtggatc aggcacacag tattccctca agatcaacat cctgcagtct  300
gaagattttg ggagttatta ctgtcaacat tttggggta ctccgtggac gttcggtgga  360
ggcaccaagc tt                                                     372

SEQ ID NO: 305         moltype = DNA  length = 399
FEATURE                Location/Qualifiers
misc_feature           1..399
                       note = mAb KCD136 heavy chain
source                 1..399
                       mol_type = other DNA
                       organism = synthetic construct
SEQUENCE: 305
atgtacagga tgcaactcct gtcttgcatt gcactaagtc ttgcacttgt cactaactca  60
gaggttcagc tgcagcagtc tgtggcagag cttgtgaggc caggggcctc agtcaagttg  120
tcctgctcag cttctggctt caacattaaa aacacctata tgcactgggt gaaccagagg  180
cctgaacagg gcctggagtg gattggaagg attgatcctg cgaatggtat tactaaatat  240
gccccgaact tccagggcaa ggccactata actgcagaca catcttccaa cacagcctac  300
ctgcagctca gcaacctgac atctgaggac actgccatct attactgtac tagggctatg  360
gactactggg gtcaaggaac ctcagtcacc gtctcctca                        399

SEQ ID NO: 306         moltype = DNA  length = 369
FEATURE                Location/Qualifiers
misc_feature           1..369
                       note = mAb KCD136 light chain
source                 1..369
                       mol_type = other DNA
                       organism = synthetic construct
SEQUENCE: 306
atgtacagga tgcaactcct gtcttgcatt gcactaagtc ttgcacttgt cactaactca  60
caaattgttc tcacccagtc tccagcaatc atgtctgcat ctccagggga gaaggtcacc  120
atgacctgca gtgccagctc aagtgtaagt tacatgtact ggtaccagca gaagccagga  180
tcctccccca gactcctgat ttatgacata tccaacctgg cttctggagt ccctgttcgc  240
ttcagtggca gtgggtctgg gacctcttac tctctcacaa tcagccgaat ggaggctgaa  300
gatgctgcca cttattactg ccagcagtgg gatacttacc cgtggacgtt cggtggaggc  360
accaagctt                                                         369

SEQ ID NO: 307         moltype = DNA  length = 408
FEATURE                Location/Qualifiers
misc_feature           1..408
                       note = mAb KCD200 heavy chain
source                 1..408
                       mol_type = other DNA
                       organism = synthetic construct
SEQUENCE: 307
```

```
atgtacagga tgcaactcct gtcttgcatt gcactaagtc ttgcacttgt cactaactca  60
gaggtccagc tgcaacagtc tggacctgaa ctggtgaagc ctggggcttc agtgaagata  120
tcctgtaagg cttccggata cacgttcacc agctactaca agaactggat gaggcagaga  180
catggagaga gccttgagtg gattggagat attaatccta acagtggtga tactgcctac  240
aaccagaagt tcaagggcaa ggccacattg actgtagaca ggtcctccag cacagcctac  300
atggagctcc gcagcctgac atctgaggac tctgcagtct attactgtgc aagagaggga  360
ccttcgtttg cttactgggg ccaagggact ctggtcactg tctctgca              408

SEQ ID NO: 308          moltype = DNA  length = 387
FEATURE                 Location/Qualifiers
misc_feature            1..387
                        note = mAb KCD200 light chain
source                  1..387
                        mol_type = other DNA
                        organism = synthetic construct
SEQUENCE: 308
atgtacagga tgcaactcct gtcttgcatt gcactaagtc ttgcacttgt cactaactca  60
gatgttttga tgacccaaac tccactctcc ctgcctgtca gtcttggaga tcaagtctcc  120
atctcttgca gatctagtca gaccattgtt catagtaatg gagacaccta tttggaatgg  180
tacctgcaga aaccaggcca gtctccaaat ctcctgatct acaaagtttc caaccgtttt  240
tctggggtcc cagacaggtt cagtggcagt ggatccggga cagatttcac actcaagatc  300
agcagagtgg aggctgagga tctgggagtg tattactgct ttcaaggttc acatgttcct  360
ccgacgttcg gtggaggcac caagctt                                     387

SEQ ID NO: 309          moltype = DNA  length = 405
FEATURE                 Location/Qualifiers
misc_feature            1..405
                        note = mAb KCD208 heavy chain
source                  1..405
                        mol_type = other DNA
                        organism = synthetic construct
SEQUENCE: 309
atgtacagga tgcaactcct gtcttgcatt gcactaagtc ttgcacttgt cactaactca  60
gaggttcagc tgcagcagtc tgtggcagag cttgtgaggc caggggcctc agtcaagttg  120
tcctgcacag tttctggctt caacattaaa aacacctata tgcactgggt gaagcagagg  180
cctgaacagg gcctggagtg gattggaagg attgatcctg cgaatggtga tactacatat  240
gccccgaagt tccagggcaa ggccactata actgcagaca catcctccaa ctcagcctac  300
ctgcacctca gccgcctgac atctgaggac actgccatct attactgttc tctttatgat  360
tacgacggct actggggcca aggcaccact ctcacagtct cctca                 405

SEQ ID NO: 310          moltype = DNA  length = 375
FEATURE                 Location/Qualifiers
misc_feature            1..375
                        note = mAb KCD208 light chain
source                  1..375
                        mol_type = other DNA
                        organism = synthetic construct
SEQUENCE: 310
atgtacagga tgcaactcct gtcttgcatt gcactaagtc ttgcacttgt cactaactca  60
gaaattgtgc tcacccagtc tccagcactc atggctgcat ctccagggga gaaggtcacc  120
atcacctgca gtgtcagctc aagtataagt tccagctcct tacactggta ccggcagaag  180
tcaggaacct cccccaaacc ctggatttat ggcacatccc accttgcttc tggagtccct  240
gttcgcttca gtggcagtgg atctgggacc tcttattctc tcacaatcag cagcatggag  300
gctgaagatg ctgccactta ttactgtcaa cagtgggata cttacccgtg gacgttcggt  360
ggaggcacca agctt                                                  375

SEQ ID NO: 311          moltype = DNA  length = 405
FEATURE                 Location/Qualifiers
misc_feature            1..405
                        note = mAb KCD214 heavy chain
source                  1..405
                        mol_type = other DNA
                        organism = synthetic construct
SEQUENCE: 311
atgtacagga tgcaactcct gtcttgcatt gcactaagtc ttgcacttgt cactaactca  60
gaggttcagc tgcagcagtc tgtggcagag tttgtgaggc caggggcctc agtcaagttg  120
tcctgcacag cttctggctt caacattaaa aacacctata tgcactgggt gaagcagagg  180
cctgaacagg gcctggaatg gattggaagg attgatcctg cgaatggtaa tactgaatat  240
gccccgaagt tccagggcaa ggccactata actgcagaca catcctccaa cacagcctac  300
ctgcagctca gcagcctgac atctgaggac actgccatct attactgtgc tctttatgat  360
tacgacggct actggggcca aggcaccact ctcacagtct cctca                 405

SEQ ID NO: 312          moltype = DNA  length = 375
FEATURE                 Location/Qualifiers
misc_feature            1..375
                        note = mAb KCD214 light chain
source                  1..375
                        mol_type = other DNA
                        organism = synthetic construct
```

```
SEQUENCE: 312
atgtacagga tgcaactcct gtcttgcatt gcactaagtc ttgcacttgt cactaactca  60
gaaattgtgc tcacccagtc tccagcactc atggctgcat ctccagggga gaaggtcacc  120
atcacctgcc gtgtcagctc aagtataagt tccagcagct tacactggta ccagcaaaag  180
tcaggaacct cccccaaacc ctggatttat ggcacctcca accttgcttc tggagtccct  240
gttcgcttca gtggcagtag atctgggacc tcttattctc tcacaatcag cagcatggag  300
gctgaagatg ctgccactta ttactgtcaa cagtggagtg attacccgtg gacgttcggt  360
ggaggcacca agctt                                                   375

SEQ ID NO: 313         moltype = DNA  length = 417
FEATURE                Location/Qualifiers
misc_feature           1..417
                       note = mAb KCD220 heavy chain
source                 1..417
                       mol_type = other DNA
                       organism = synthetic construct
SEQUENCE: 313
atgtacagga tgcaactcct gtcttgcatt gcactaagtc ttgcacttgt cactaactca  60
caggttcagc tgcaacagtc tggagctgag ctgatggagc ctggggcctc agtgaagctt  120
tcctgcaagg ctactggcta cacattcact ggctactgga tagagtgggt aaagcagagg  180
cctggacatg gccttgagtg gattggagag actttacctg gaagtgatag taataattac  240
aatgagaagt tcaagggcaa ggccacattc actgcagata catcctccaa cacagcctac  300
atgcaactca gcagcctgac aactgaggac tctgccatct attactgtgc aagagactat  360
agtaactact ggtacttcga tgtctggggc acagggacca cggtcaccgt ctcctca     417

SEQ ID NO: 314         moltype = DNA  length = 369
FEATURE                Location/Qualifiers
misc_feature           1..369
                       note = mAb KCD220 light chain
source                 1..369
                       mol_type = other DNA
                       organism = synthetic construct
SEQUENCE: 314
atgtacagga tgcaactcct gtcttgcatt gcactaagtc ttgcacttgt cactaactca  60
gatatccaga tgacacagac tacatcctcc ctgtctgcct ctctgggaga cagagtcacc  120
attagttgca gggcaagtca ggacattagc aattatttaa actggtatca gcagaaacca  180
gatggaactg ttaaactcct gatctactac acatcaaact tacactcagg agtcccatca  240
aggttcagtg gcagtgggtc tgggacagat tattctctca ctattagtaa cctggaacaa  300
gaagatattg ccacttactt ttgccaacag gatagtaagc atcggacgtt cggtggaggc  360
accaagctt                                                          369

SEQ ID NO: 315         moltype = DNA  length = 417
FEATURE                Location/Qualifiers
misc_feature           1..417
                       note = mAb KCD224 heavy chain
source                 1..417
                       mol_type = other DNA
                       organism = synthetic construct
SEQUENCE: 315
atgtacagga tgcaactcct gtcttgcatt gcactaagtc ttgcacttgt cactaactca  60
caggtgcagc tgaaggagtc aggacctggc ctggtggcgc cctcacagag cctgtccatc  120
acatgcactg tctctgggtt ctcattaacc agctatggtg tagactggat tcgccagtct  180
ccaggaaagg gtctggagtg gctgggagta atatggggtg ttggaagcac aaattataat  240
tcagctctca aatccagact gagcatcagc aaggacaact ccaagagcca agttttctta  300
aaaatgaaca gtctgcaaac tgatgacaca gccatgtact actgtgcccg ctcctatgat  360
ggttcctact ggtacttcga tgtctggggc acagggacca cggtcaccgt ctcctca     417

SEQ ID NO: 316         moltype = DNA  length = 372
FEATURE                Location/Qualifiers
misc_feature           1..372
                       note = mAb KCD224 light chain
source                 1..372
                       mol_type = other DNA
                       organism = synthetic construct
SEQUENCE: 316
atgtacagga tgcaactcct gtcttgcatt gcactaagtc ttgcacttgt cactaactca  60
gatatccaga tgacacagac tacatcctcc ctgtctgcct ctctgggaga cagagtcacc  120
atcagttgca gggcaagtca ggttattagc aattatttaa actggtatca gcagaaacca  180
gatggaactg ttaaactcct gatctactac acatcaagat tacactcagg agtcccatca  240
aggttcagtg gcagtgggtc tgggacagat tattctctca ccatcagcaa cctggaacct  300
gaagatattg ccacttacta ttgtcagcag tatagtaaac ttccgtatac gttcggatcg  360
gggaccaagc tt                                                      372

SEQ ID NO: 317         moltype = DNA  length = 349
FEATURE                Location/Qualifiers
misc_feature           1..349
                       note = mAb 119_TAF heavy chain
source                 1..349
                       mol_type = other DNA
```

```
                        organism = synthetic construct
SEQUENCE: 317
gaggtgcagc tggtggaatc tggcggcgga ctggtgcagc ctggcggctc cctgagactg  60
tcttgcgccg cctccggcta caccttcacc gactactaca tgaactgggt gcgacaggcc  120
cctggcaagg gcctggaatg gatcggcgac atcaacccca acaccggcga caccagctac  180
aacgccgact tcaagcggcg gttcaccttc tccctggaca cctccaagtc caccgcctac  240
ctgcagatga actccctgcg ggccgaggac accgccgtgt actactgtac cagagagggc  300
ccctccttcg cctactgggg ccagggcaca ctggtgacag tgtcctccg             349

SEQ ID NO: 318          moltype = DNA  length = 337
FEATURE                 Location/Qualifiers
misc_feature            1..337
                        note = mAb 119_TAF light chain
source                  1..337
                        mol_type = other DNA
                        organism = synthetic construct
SEQUENCE: 318
gacatccagc tgacccagag cccctccagc ctgtccgcct ctgtgggcga cagagtgacc  60
atcacctgtc ggtcctccca gaccatcgtg cactccaacg gcgacaccta cctggaatgg  120
tatcagcaga agcccggcaa ggcccctaac ctgctgatct acaaggtgtc caaccggttc  180
tccggcgtgc cctccagatt ctccggctcc ggctctggca ccgacttcac cctgaccatc  240
tccagcctgc agcccgagga cttcgccacc tactactgtt ttcaaggctc ccacgtgcca  300
cccaccttcg gccagggcac caaggtggaa atcaagc                          337

SEQ ID NO: 319          moltype = DNA  length = 351
FEATURE                 Location/Qualifiers
misc_feature            1..351
                        note = mAb 119_TAF Germ heavy chain
source                  1..351
                        mol_type = other DNA
                        organism = synthetic construct
SEQUENCE: 319
gaggtgcagc tggtggaatc tggcggcgga ctggtgcagc ctggcggctc cctgagactg  60
tcttgcgccg cctccggcta caccttcacc gactactaca tgtcctgggt gcgacaggcc  120
cctggcaagg gcctggaatg gatcggcgac atcaacccca acaccggcga caccagctac  180
aacgccgact ccgtgaaggg ccggttcacc atctcccggg acaactccaa gaacaccctg  240
tacctgcaga tgaactccct gcgggccgag gacaccgccg tgtactactg taccagagag  300
ggcccctcct tcgcctactg gggccagggc acactggtga cagtgtcctc c          351

SEQ ID NO: 320          moltype = DNA  length = 336
FEATURE                 Location/Qualifiers
misc_feature            1..336
                        note = mAb 119_TAF Germ light chain
source                  1..336
                        mol_type = other DNA
                        organism = synthetic construct
SEQUENCE: 320
gacgtggtga tgacccagtc ccctctgtcc ctgcccgtga ccctgggcca gcctgcctcc  60
atctcctgcc ggtcctccca gaccatcgtg cactccaacg gcgacaccta cctggaatgg  120
ttccagcagc ggcctggcca gtcccctaac ctgctgatct acaaggtgtc caaccggttc  180
tccggcgtgc ccgacagatt ctccggctcc ggctctggca ccgacttcac cctgaagatc  240
tcccgggtgg aagccgagga cgtgggcgtg tactactgtt ttcaaggctc ccacgtgcca  300
cccaccttcg gcggaggcac caaggtggaa atcaag                           336

SEQ ID NO: 321          moltype = DNA  length = 348
FEATURE                 Location/Qualifiers
misc_feature            1..348
                        note = mAb 119_Human Germ heavy chain
source                  1..348
                        mol_type = other DNA
                        organism = synthetic construct
SEQUENCE: 321
caggtgcagc tggtgcagtc tggcgccgaa gtgaagaaac ctggcgcctc cgtgaaggtg  60
tcctgcaagg cctccggcta caccttcacc gactactaca tgcactgggt gcgacaggcc  120
ccaggccagg gcctggaatg gatcggcgac atcaacccca acaccggcga caccagctac  180
aaccagaaat tccagggcag agtgacctcc acccgggaca cctccatctc caccgcctac  240
atggaactgt cccggctgcg gagcgacgac accgtggtgt actactgtac cagagagggc  300
ccctccttcg cctactgggg ccagggcaca ctggtgacag tgtcctcc              348

SEQ ID NO: 322          moltype = DNA  length = 336
FEATURE                 Location/Qualifiers
misc_feature            1..336
                        note = mAb 119_Human Germ light chain
source                  1..336
                        mol_type = other DNA
                        organism = synthetic construct
SEQUENCE: 322
gacatccaga tgacccagag cccctccagc ctgtccgcct ccgtgggcga cagagtgacc  60
atcacctgtc ggtcctccca gaccatcgtg cactccaacg gcgacaccta cctggaatgg  120
```

```
tatcagcaga agcccggcaa ggcccctaac ctgctgatct acaaggtgtc caaccggttc  180
tccggcgtgc cctccagatt ctccggctcc ggctctggca ccgacttcac cctgaccatc  240
tccagcctgc agcccgagga cttcgccacc tactactgtt ttcaaggctc ccacgtgcca  300
cccaccttcg gccagggcac caaggtggaa atcaag                            336

SEQ ID NO: 323         moltype = AA  length = 13
FEATURE                Location/Qualifiers
REGION                 1..13
                       note = CDR1 light chain (lead)
VARIANT                2
                       note = Xaa = T, D, G, H, I, N, Q, R, V or W
VARIANT                3
                       note = Xaa = I, A or V
VARIANT                4
                       note = Xaa = V, A, D, E, F, I, K, L, Q, R, S, W or Y
VARIANT                6
                       note = Xaa = S, A, D, F, G, I, R, T, V or W
VARIANT                8
                       note = Xaa = G, E, F, or S
VARIANT                9
                       note = Xaa = D or E
VARIANT                10
                       note = Xaa = T, S or V
VARIANT                12
                       note = Xaa = L or I
source                 1..13
                       mol_type = protein
                       organism = synthetic construct
SEQUENCE: 323
QXXXHXNXXX YXE                                                     13

SEQ ID NO: 324         moltype =   length =
SEQUENCE: 324
000

SEQ ID NO: 325         moltype = AA  length = 9
FEATURE                Location/Qualifiers
REGION                 1..9
                       note = CDR3 light chain (lead)
VARIANT                1
                       note = Xaa = F or M
VARIANT                5
                       note = Xaa = H, A, E, F, G, L, N, Q, T, V, W or Y
VARIANT                6
                       note = Xaa = V, W, Q or N
VARIANT                8
                       note = Xaa = P or V
source                 1..9
                       mol_type = protein
                       organism = synthetic construct
SEQUENCE: 325
XQGSXXPXT                                                          9

SEQ ID NO: 326         moltype = AA  length = 9
FEATURE                Location/Qualifiers
REGION                 1..9
                       note = CDR1 heavy chain (lead)
VARIANT                3
                       note = Xaa = T, D, E, F, H, I, K, P, R, S, W or Y
VARIANT                6
                       note = Xaa = D, A, F, G, S, V or Y
VARIANT                7
                       note = Xaa = Y or F
VARIANT                8
                       note = Xaa = Y or P
VARIANT                9
                       note = Xaa = M, H or I
source                 1..9
                       mol_type = protein
                       organism = synthetic construct
SEQUENCE: 326
GYXFTXXXX                                                          9

SEQ ID NO: 327         moltype = AA  length = 14
FEATURE                Location/Qualifiers
REGION                 1..14
                       note = CDR2 heavy chain (lead)
VARIANT                5
                       note = Xaa =I, L or V
```

-continued

```
VARIANT                 6
                        note = Xaa = N, A or G
VARIANT                 7
                        note = Xaa = P or T
VARIANT                 8
                        note = Xaa = N, A, D, G, H, I, L, R, T,V, W or Y
VARIANT                 9
                        note = Xaa = T, I, K, L, Q, R, S or V
VARIANT                 10
                        note = Xaa = G or V
VARIANT                 11
                        note = Xaa = any amino acid
VARIANT                 12
                        note = Xaa = any amino acid except I
VARIANT                 13
                        note = Xaa = any amino acid except K or R
VARIANT                 14
                        note = Xaa = any amino acid except I or W
source                  1..14
                        mol_type = protein
                        organism = synthetic construct
SEQUENCE: 327
WIGDXXXXXX XXXX                                                     14

SEQ ID NO: 328          moltype = AA  length = 9
FEATURE                 Location/Qualifiers
REGION                  1..9
                        note = CDR3 heavy chain (lead)
VARIANT                 1
                        note = Xaa = T, A or Q
VARIANT                 6
                        note = Xaa = S or A
VARIANT                 8
                        note = Xaa = A or R
VARIANT                 9
                        note = Xaa = Y, A, H, F, V, Y or L
source                  1..9
                        mol_type = protein
                        organism = synthetic construct
SEQUENCE: 328
XREGPXFXX                                                           9

SEQ ID NO: 329          moltype = AA  length = 11
FEATURE                 Location/Qualifiers
REGION                  1..11
                        note = CDR1 light chain (lead)
VARIANT                 2
                        note = Xaa = T, D, G, H, I, N, Q, R, V or W
VARIANT                 3
                        note = Xaa = I, A or V
VARIANT                 4
                        note = Xaa = V, A, D, E, F, I, K, L, Q, R, S, W or Y
VARIANT                 6
                        note = Xaa = S, A, D, F, G, I, R, T, V or W
VARIANT                 8
                        note = Xaa = G, E, F or S
VARIANT                 9
                        note = Xaa = D or E
VARIANT                 10
                        note = Xaa = T, S or V
source                  1..11
                        mol_type = protein
                        organism = synthetic construct
SEQUENCE: 329
QXXXHXNXXX Y                                                        11

SEQ ID NO: 330          moltype =   length =
SEQUENCE: 330
000

SEQ ID NO: 331          moltype = AA  length = 9
FEATURE                 Location/Qualifiers
REGION                  1..9
                        note = CDR3 light chain (lead)
VARIANT                 1
                        note = Xaa = F or M
VARIANT                 5
                        note = Xaa = H, A, E, F, G, L, N, Q, T, V, W or Y
VARIANT                 6
```

```
                         note = Xaa = V, W, Q or N
VARIANT                  8
                         note = Xaa = P or V
source                   1..9
                         mol_type = protein
                         organism = synthetic construct
SEQUENCE: 331
XQGSXXPXT                                                    9

SEQ ID NO: 332           moltype =   length =
SEQUENCE: 332
000

SEQ ID NO: 333           moltype =   length =
SEQUENCE: 333
000

SEQ ID NO: 334           moltype = AA  length = 7
FEATURE                  Location/Qualifiers
REGION                   1..7
                         note = CDR3 heavy chain (lead)
VARIANT                  4
                         note = Xaa = S or A
VARIANT                  6
                         note = Xaa = A or R
VARIANT                  7
                         note = Xaa = Y, A, H, F, V, Y or L
source                   1..7
                         mol_type = protein
                         organism = synthetic construct
SEQUENCE: 334
EGPXFXX                                                      7

SEQ ID NO: 335           moltype = AA  length = 121
FEATURE                  Location/Qualifiers
REGION                   1..121
                         note = KCD001 heavy chain variable region AA sequence
source                   1..121
                         mol_type = protein
                         organism = synthetic construct
SEQUENCE: 335
EVQLQQSGPE LVKPGASVKI SCKASDNSFT GYYMHWVKQS HGNILDWIGY IDPYNGVSSY  60
NQKFKGKATL TVDKSSSTAY MEIRSLTSED SAVYYCASYY GSSPYWYFDV WGTGTTVTVS  120
S                                                            121

SEQ ID NO: 336           moltype = AA  length = 106
FEATURE                  Location/Qualifiers
REGION                   1..106
                         note = KCD001 light chain variable region AA sequence
source                   1..106
                         mol_type = protein
                         organism = synthetic construct
SEQUENCE: 336
QIVLSQSPAI LSASPGEKVT MTCRASSSVS YMHWYQQKPG SSPKPWIYAT SNLASGVPAR  60
FSGSGSGTSH FLTISRLEAE DAATYFCQQW SSNPYTFGGG TKLEIK                 106

SEQ ID NO: 337           moltype = AA  length = 120
FEATURE                  Location/Qualifiers
REGION                   1..120
                         note = KCD002 heavy chain variable region AA sequence
source                   1..120
                         mol_type = protein
                         organism = synthetic construct
SEQUENCE: 337
EVKLVESEGG LVQPGSSMKL SCTASGFTFS DYYMAWVRQV PEKGLEWVGN INYDGSSTYY  60
LDSLKSRFII SRDSAKNILY LQMSSLKSED TATYFCARGE DFYLYAMDYW GQGTSVTVSS  120

SEQ ID NO: 338           moltype = AA  length = 107
FEATURE                  Location/Qualifiers
REGION                   1..107
                         note = KCD002 light chain variable region AA sequence
source                   1..107
                         mol_type = protein
                         organism = synthetic construct
SEQUENCE: 338
DIQMTQSPAS LSASVGETVT ITCRASENIH SYLAWYQQKQ GKSPQLIVYN TKTLAEGVPS  60
RFSGSGSGTQ FSLKINSLQP EDFGSYYCQH HYGIPPTFGG GTKLEIK                107

SEQ ID NO: 339           moltype = AA  length = 116
```

-continued

```
FEATURE                Location/Qualifiers
REGION                 1..116
                       note = KCD003 heavy chain variable region AA sequence
source                 1..116
                       mol_type = protein
                       organism = synthetic construct
SEQUENCE: 339
EVQLQQSRPE LVKPGASVKI FCKASGYTFT DYYMNWMRQR HGETLEWIGD INPNNGDPSY  60
NQKFKDKATL TVDKSSSTAS MELRSLTSDD SAVYYCAREG PSFAYWGQGT LVTVSA      116

SEQ ID NO: 340         moltype = AA  length = 112
FEATURE                Location/Qualifiers
REGION                 1..112
                       note = KCD003 light chain variable region AA sequence
source                 1..112
                       mol_type = protein
                       organism = synthetic construct
SEQUENCE: 340
DVLMTQTPLS LPVSLGEQAS ISCRSSQTIV HSNGDTYLEW YLQKPGQSPN LLIYKVSNRF  60
SGVPDRFSGS GSGTDFTLKI SRVEAEDLGV YYCFQGSHVP PTFGGGTKLE IK          112

SEQ ID NO: 341         moltype = AA  length = 119
FEATURE                Location/Qualifiers
REGION                 1..119
                       note = KCD004 heavy chain variable region AA sequence
source                 1..119
                       mol_type = protein
                       organism = synthetic construct
SEQUENCE: 341
EVQLQQSGAE LVRPGSSVKM SCKTSGKTFT SHGINWVKQR PGQGLEWIGY IYIGNGYNEY  60
NEKFKGKATL TSDTSSSTAY MQLSSLTFED SAIYFCVRKA YGNYGFDDWG QGTTLTVSS   119

SEQ ID NO: 342         moltype = AA  length = 107
FEATURE                Location/Qualifiers
REGION                 1..107
                       note = KCD004 light chain variable region AA sequence
source                 1..107
                       mol_type = protein
                       organism = synthetic construct
SEQUENCE: 342
DIQMTQSPTS LSASLGESVS LTCRASQEIS GYLNWLQQKP DGSIKRLIYA ASTLDSGVPK  60
RFSGSRSGSD YSLTISSLES EDFADYYCLQ YANYPFTFGS GTKLEVK                107

SEQ ID NO: 343         moltype = AA  length = 116
FEATURE                Location/Qualifiers
REGION                 1..116
                       note = KCD005 heavy chain variable region AA sequence
source                 1..116
                       mol_type = protein
                       organism = synthetic construct
SEQUENCE: 343
EVQLQQSGPE LVKPGASVKI SCKASGYTFT DHYMNWVKQS HGKSLEWIGD INPNNGGTSC  60
NQKFKGKATL TVDKSSSTAY MELRSLTSGD SAVYYCTREG ASFAFWGQGT LVTVSA      116

SEQ ID NO: 344         moltype = AA  length = 112
FEATURE                Location/Qualifiers
REGION                 1..112
                       note = KCD005 light chain variable region AA sequence
source                 1..112
                       mol_type = protein
                       organism = synthetic construct
SEQUENCE: 344
DVLMTQTPLS LPVSLGDQAS ISCRSSQSIV HSNGDTYLEW YLQKPGQSPK LLIYKVSNRF  60
SGVPDRFSGS GSGTDFTLKI SRVEAEDLGV YYCFQGSHVP VTFGAGTKLE LK          112

SEQ ID NO: 345         moltype = AA  length = 113
FEATURE                Location/Qualifiers
REGION                 1..113
                       note = KCD006 heavy chain variable region AA sequence
source                 1..113
                       mol_type = protein
                       organism = synthetic construct
SEQUENCE: 345
EVQLQQSGAE LVKPGASVKL SCTASGFKIK DTYMHWVKER PEQGLEWIGR IDPANGNTKY  60
DPKFQGKATI TADTSSNTAY LQLSSLTSED TAVYYCANAM DYWGQGTSVT VSS         113

SEQ ID NO: 346         moltype = AA  length = 106
FEATURE                Location/Qualifiers
REGION                 1..106
```

```
                        note = KCD006 light chain variable region AA sequence
source                  1..106
                        mol_type = protein
                        organism = synthetic construct
SEQUENCE: 346
QIILTQSPAI MSASPGEKVT MTCSARSSVS NMYWYQQKPG SSPRLLIYDT SNLASGVPVR  60
FSGSGSGTSY SLTISRMEAE DAATYYCQQW SSYPWTFGGG TKLEIK                106

SEQ ID NO: 347          moltype = AA  length = 113
FEATURE                 Location/Qualifiers
REGION                  1..113
                        note = KCD007 heavy chain variable region AA sequence
source                  1..113
                        mol_type = protein
                        organism = synthetic construct
SEQUENCE: 347
EVQLQQSGAE LVKPGASVKL SCTASGFKIK DTYMHWVKER PEQGLEWIGR IDPANGNTKY  60
DPKFQGKATI TADTSSNTAY LQLSSLTSED TAVYYCANAM DYWGQGTSVT VSS        113

SEQ ID NO: 348          moltype = AA  length = 106
FEATURE                 Location/Qualifiers
REGION                  1..106
                        note = KCD007 light chain variable region AA sequence
source                  1..106
                        mol_type = protein
                        organism = synthetic construct
SEQUENCE: 348
QIILTQSPAI MSASPGERVT MTCSASSSVS NMYWYQQKPG SSPRLLIYDT SNLASGVPLR  60
FSGSGSGTSY SLTISRMEAE DAATYYCQQW SSYPWTFGGG TKLEIK                106

SEQ ID NO: 349          moltype = AA  length = 113
FEATURE                 Location/Qualifiers
REGION                  1..113
                        note = KCD008 heavy chain variable region AA sequence
source                  1..113
                        mol_type = protein
                        organism = synthetic construct
SEQUENCE: 349
EVQLQQSGPE LVKAGASVKM SCTASGFNIK DTYMHWVKQR PEQGLAWIGR IDPANGNIKY  60
DPKFQGKATI TADTSSNTAY LQLSSLTSDD TAVYYCTSAM DYWGQGTSVT VSS        113

SEQ ID NO: 350          moltype = AA  length = 106
FEATURE                 Location/Qualifiers
REGION                  1..106
                        note = KCD008 light chain variable region AA sequence
source                  1..106
                        mol_type = protein
                        organism = synthetic construct
SEQUENCE: 350
QIVLTQSPEI MSASPGEKVT MTCSARSSVS YMYWYQQKPG SSPRLLIYDT SNLASGVPVR  60
FSGSGSGTSY SLTISRMETE DAATYYCQQW STYPFTFGSG TKLEIK                106

SEQ ID NO: 351          moltype = AA  length = 116
FEATURE                 Location/Qualifiers
REGION                  1..116
                        note = KCD009 heavy chain variable region AA sequence
source                  1..116
                        mol_type = protein
                        organism = synthetic construct
SEQUENCE: 351
QIQLVQSGPE LKKPGETVKI SCKASGYIFR NYGMNWVKQG PGKGLKWMGW INTYTGEPTY  60
ADDFKGRFAF SLETSASTAY LQISNLKNED TATYFCVRDG PGFAYWGQGT LVTVSA     116

SEQ ID NO: 352          moltype = AA  length = 112
FEATURE                 Location/Qualifiers
REGION                  1..112
                        note = KCD009 light chain variable region AA sequence
source                  1..112
                        mol_type = protein
                        organism = synthetic construct
SEQUENCE: 352
DVLMTQTPLS LPVSLGDQAS ISCRSSLIIE HSDGNTYLEW YLQKPGQSPK LLIYKVSNRF  60
SGVPDRFSGS GSGTDFTLKI SRVEADDLGV YYCFQGSHVP VTFGAGTNLE LK         112

SEQ ID NO: 353          moltype = AA  length = 114
FEATURE                 Location/Qualifiers
REGION                  1..114
                        note = KCD010 heavy chain variable region AA sequence
source                  1..114
```

```
                        mol_type = protein
                        organism = synthetic construct
SEQUENCE: 353
EVLLQQSGPE LVKPGASVKI PCKASGYTFT DYDMDWVKQS HGKSLEWIGH INPNNGGTIY  60
NQKFKGKATL TVDKSSSTAY MELRSLTSED TAVYYCGTGD FAYWGHGTLV TVSA        114

SEQ ID NO: 354          moltype = AA  length = 108
FEATURE                 Location/Qualifiers
REGION                  1..108
                        note = KCD010 light chain variable region AA sequence
source                  1..108
                        mol_type = protein
                        organism = synthetic construct
SEQUENCE: 354
QIVLTQSPAI MSVSPGEKVT LTCSASSSVS SSYLYWYQKK PGSSPKLWIY STSNLASGVP  60
ARFSGSGSGT SYSLTISSME AEDAASYFCH QWSSYPPTFG AGTKLELK               108

SEQ ID NO: 355          moltype = AA  length = 117
FEATURE                 Location/Qualifiers
REGION                  1..117
                        note = KCD011 heavy chain variable region AA sequence
source                  1..117
                        mol_type = protein
                        organism = synthetic construct
SEQUENCE: 355
EVKLVESGGG LVQPGGSLKL SCAASGFTFS SNTMSWVRQT PEKRLEWVAY ITNGGGSTYY  60
PDTVKGRFTI SRDNARNTLY LQMSSLKSED TAMYYCARHD YYTMDYWGQG TSVTVSS     117

SEQ ID NO: 356          moltype = AA  length = 107
FEATURE                 Location/Qualifiers
REGION                  1..107
                        note = KCD011 light chain variable region AA sequence
source                  1..107
                        mol_type = protein
                        organism = synthetic construct
SEQUENCE: 356
DIQMTQSPSS LSASLGGKVT ITCKASQDIN KYIAWYQHKP GKGPRLLIHY TSTLQPGIPS  60
RFSGSGSGRD YSFSISNLEP EDIATYYCLQ YDNLLYTFGG GTKLEIK                107

SEQ ID NO: 357          moltype = AA  length = 113
FEATURE                 Location/Qualifiers
REGION                  1..113
                        note = KCD013 heavy chain variable region AA sequence
source                  1..113
                        mol_type = protein
                        organism = synthetic construct
SEQUENCE: 357
EVQLQQSGAE LVKPGASVKL SCTASGFKIK DTYMHWVKER PDQGLEWIGR IDPANGNTKY  60
DPKFQGKATI TADTSSNTAY LQLSSLTSED TAVYYCANAM DYWGQGTSVT VSS         113

SEQ ID NO: 358          moltype = AA  length = 106
FEATURE                 Location/Qualifiers
REGION                  1..106
                        note = KCD013 light chain variable region AA sequence
source                  1..106
                        mol_type = protein
                        organism = synthetic construct
SEQUENCE: 358
QIILTQSPAI MSASPGEKVT MTCSASSSVS NMYWYQQKPG SSPRLLIYDT SNLASGVPVR  60
FSGSGSGASY SLTISRMEAE DAATYYCQQW SSYPWTFGGG TKLEIK                 106

SEQ ID NO: 359          moltype = AA  length = 118
FEATURE                 Location/Qualifiers
REGION                  1..118
                        note = KCD014 heavy chain variable region AA sequence
source                  1..118
                        mol_type = protein
                        organism = synthetic construct
SEQUENCE: 359
EVKLVESGGG LVQPGGSLKL SCAASGFTFS SYIMSWVRQT PEKRLEWVAY ITNGGGNTYY  60
PDTIKGRFTI SRDNAKNTLY LQMSSLKSED TAMYYCARHG TGYAMDYWGQ GTSVTVSS    118

SEQ ID NO: 360          moltype = AA  length = 108
FEATURE                 Location/Qualifiers
REGION                  1..108
                        note = KCD014 light chain variable region AA sequence
source                  1..108
                        mol_type = protein
                        organism = synthetic construct
```

```
SEQUENCE: 360
EIVLTQSPTT MAASPGEKIT ITCSASSSIS SNYLHWYQQK PGFSPKLLIY RTSNLASGVP  60
ARFSGSGSGT SYSLTIGTME AEDVATYYCQ QGSSIPLTFG AGTKLELK              108

SEQ ID NO: 361         moltype = AA  length = 113
FEATURE                Location/Qualifiers
REGION                 1..113
                       note = KCD015 heavy chain variable region AA sequence
source                 1..113
                       mol_type = protein
                       organism = synthetic construct
SEQUENCE: 361
EVQLQQSGAE LVKPGASVKL SCTASGFNIK DTYMHWVKQR PEQGLEWIGR IDPANGYTEY  60
DPKFQGKATI TADTSSNTAY LQLSSLTSED SAAYYCTSAM EFWGQGTSVT VSS         113

SEQ ID NO: 362         moltype = AA  length = 106
FEATURE                Location/Qualifiers
REGION                 1..106
                       note = KCD015 light chain variable region AA sequence
source                 1..106
                       mol_type = protein
                       organism = synthetic construct
SEQUENCE: 362
QIVLTQSPAI LSASPGEKVT MTCSASSSVS YIYWYQQKPR SSPRLLIYDT SNLASGVPVR  60
FSGSGSGTSY SLTISRMEAE DAATYYCQQW SSYPFTFGGG TKLEVK                106

SEQ ID NO: 363         moltype = AA  length = 122
FEATURE                Location/Qualifiers
REGION                 1..122
                       note = KCD016 heavy chain variable region AA sequence
source                 1..122
                       mol_type = protein
                       organism = synthetic construct
SEQUENCE: 363
QVQLQQSGAE LAKPGASVKM SCKASGYTFT NFWMHWVKQR PGQGLEWIGF FNPSTAYTEY  60
NQKFKDKATL TADKSSSTAY LHLSSLTSED SAVYYCARRD YGSSYGWYFD VWGAGTTVTV  120
SS                                                                122

SEQ ID NO: 364         moltype = AA  length = 106
FEATURE                Location/Qualifiers
REGION                 1..106
                       note = KCD016 light chain variable region AA sequence
source                 1..106
                       mol_type = protein
                       organism = synthetic construct
SEQUENCE: 364
DIQMTQSPAS LSASVGETVT ITCRASGNIH NYLAWYQQKQ GKSPQLLVYN AKTLADGVPS  60
RFSGSGSGTQ YSLKINSLQP EDFGYYYCQH FWSTPTFGGG TKLEIK                106

SEQ ID NO: 365         moltype = AA  length = 122
FEATURE                Location/Qualifiers
REGION                 1..122
                       note = KCD017 heavy chain variable region AA sequence
source                 1..122
                       mol_type = protein
                       organism = synthetic construct
SEQUENCE: 365
DVQLQESGPD LVKPSQSLSL TCTVTDYSIT SGYSWHWIRQ FPGNKLEWLG YIHSSGNTNY  60
NPSLKSRFSI TRDTSKNQFF LQLNSVTSED TATYYCALHY YGSSFGWYFD VWGAGTTVTV  120
SS                                                                122

SEQ ID NO: 366         moltype = AA  length = 107
FEATURE                Location/Qualifiers
REGION                 1..107
                       note = KCD017 light chain variable region AA sequence
source                 1..107
                       mol_type = protein
                       organism = synthetic construct
SEQUENCE: 366
DIVMTQSHKF MSTSVGDRVY ITCKASQDVG TAVAWYQQTS GQSPKLLIYW ASTRHTGVPD  60
RFTGSGSGTD FTLTLSNVQS EDLADYFCQQ YTSYPLTFGA GTKLELK               107

SEQ ID NO: 367         moltype = AA  length = 119
FEATURE                Location/Qualifiers
REGION                 1..119
                       note = KCD018 heavy chain variable region AA sequence
source                 1..119
                       mol_type = protein
                       organism = synthetic construct
```

```
SEQUENCE: 367
QVQLQQSAAE LARPGASVKM SCKASGYTFT SYTVHWVKQR PGQGLEWIGY INPSSGFTDY  60
NQKFKDKTTL TADISSSTAY IQLSSLTSED SAVYYCARRG VNWSWFAYWG QGTLVTVSA   119

SEQ ID NO: 368         moltype = AA  length = 112
FEATURE                Location/Qualifiers
REGION                 1..112
                       note = KCD018 light chain variable region AA sequence
source                 1..112
                       mol_type = protein
                       organism = synthetic construct
SEQUENCE: 368
NIMMTQSPSS LAVSAGEKVT MSCKSSQSVL YSSNQKNYLA WYQQKPGQSP QLLIYWASTR  60
ESGVPERFTG SGSGTDFTLT ISSVQAEDLA VYYCHQYLSS WTFGGGTKLE IK          112

SEQ ID NO: 369         moltype = AA  length = 122
FEATURE                Location/Qualifiers
REGION                 1..122
                       note = KCD019 heavy chain variable region AA sequence
source                 1..122
                       mol_type = protein
                       organism = synthetic construct
SEQUENCE: 369
QVQLQQSGAE LARPGASVKM SCKASGYTFA TYTIHWVKQR PGQGLEWIGY LNLRNDYTHY  60
NQKFRDKAAL TADKSSSTAY MQLSSLTSED SAVYNCAFRL GNDRQGWYFD VWGAGTTVTV  120
SS                                                                 122

SEQ ID NO: 370         moltype = AA  length = 107
FEATURE                Location/Qualifiers
REGION                 1..107
                       note = KCD019 light chain variable region AA sequence
source                 1..107
                       mol_type = protein
                       organism = synthetic construct
SEQUENCE: 370
DIVMTQAHRF MSTSVGDRVI ISCKASQDVG TAVAWYQQTP GQSPKILIYW TSTRHTGVPD  60
RFTGSRSGTD FTLTISNVQS EDLADYFCQQ YTTYPLTFGG GTKLEIK                107

SEQ ID NO: 371         moltype = AA  length = 122
FEATURE                Location/Qualifiers
REGION                 1..122
                       note = KCD022 heavy chain variable region AA sequence
source                 1..122
                       mol_type = protein
                       organism = synthetic construct
SEQUENCE: 371
DVQLQESGPD LVKPSQSLSL TCTVTGYSIT SGYSWHWIRQ FPGNTLEWMG YIHYSGSTNY  60
NPSLESRISF TRDTSKNQFF LQLNSVTTED TATYYCALHF YGYNLGWYFD VWGAGTTVTV  120
SS                                                                 122

SEQ ID NO: 372         moltype = AA  length = 107
FEATURE                Location/Qualifiers
REGION                 1..107
                       note = KCD022 light chain variable region AA sequence
source                 1..107
                       mol_type = protein
                       organism = synthetic construct
SEQUENCE: 372
DIVMTQSHKF MSTSIGDRVI ITCKASQDVG TTVAWYQQRP GQSPKLLIYW ASTRHTAVPD  60
RFTGSGSGTD FTLTISNVQS EDLADYFCQQ YTSYPLTFGA GTQLELK                107

SEQ ID NO: 373         moltype = AA  length = 114
FEATURE                Location/Qualifiers
REGION                 1..114
                       note = KCD023 heavy chain variable region AA sequence
source                 1..114
                       mol_type = protein
                       organism = synthetic construct
SEQUENCE: 373
EVLLQQSGPE LVKPGASVKI PCKASGYTFT DYNIDWVKQS HGKSLEWIGD INPNNGGINY  60
NQKFKGKATL TVDKSSSTAY MELRSLTSED TAVYYCGTGD YAYWGQGTLV TVSA        114

SEQ ID NO: 374         moltype = AA  length = 108
FEATURE                Location/Qualifiers
REGION                 1..108
                       note = KCD023 light chain variable region AA sequence
source                 1..108
                       mol_type = protein
                       organism = synthetic construct
```

```
SEQUENCE: 374
QIVLTQSPAF MSASPGEKVT LTCSASSSVS SSYLYWYQQK PGSSPKLWIY STSNLASGVP  60
GRFSGSGSGT SYSLTISSME AEDAASYFCH QWTSYPPTFG AGTKLELK               108

SEQ ID NO: 375         moltype = AA  length = 117
FEATURE                Location/Qualifiers
REGION                 1..117
                       note = KCD030 heavy chain variable region AA sequence
source                 1..117
                       mol_type = protein
                       organism = synthetic construct
SEQUENCE: 375
QVQLQQSGAE LAKPGASVKM SCKASGYTFT NYWMHWVKQR PGQGLEWIGY INPSIGYTEY  60
NQKFKDKATL TADKSSSTAY MQLSSLTSED SAVFYCATFI YYAMDYWGQG TSVTVSS     117

SEQ ID NO: 376         moltype = AA  length = 107
FEATURE                Location/Qualifiers
REGION                 1..107
                       note = KCD030 light chain variable region AA sequence
source                 1..107
                       mol_type = protein
                       organism = synthetic construct
SEQUENCE: 376
DIQMNQSPSS LSASLGDTIT ITCHASQNIN VWLSWYQQKP GNIPKLLIYK ASNLHTGVPS  60
RFSGSGSGTG FTLTISSLQP EDIATYYCQQ GQSYPYTFGG GTKLEIK                107

SEQ ID NO: 377         moltype = AA  length = 118
FEATURE                Location/Qualifiers
REGION                 1..118
                       note = KCD033 heavy chain variable region AA sequence
source                 1..118
                       mol_type = protein
                       organism = synthetic construct
SEQUENCE: 377
EVQLQQSGPE LVKPGASMKI SCTASGYSFT GYTMTWVKQS HGKNLEWIGL INPYNGGTNY  60
NQKFKGKATL TVDKSSSIAY MELLSLTSED SAVYYCARRH YGSNWDYWGQ GTTLTVSS    118

SEQ ID NO: 378         moltype = AA  length = 107
FEATURE                Location/Qualifiers
REGION                 1..107
                       note = KCD033 light chain variable region AA sequence
source                 1..107
                       mol_type = protein
                       organism = synthetic construct
SEQUENCE: 378
DIKLTQSPSS IYTSLGERVT ITCKASQDIN TYLSWFQQRP GKSPKTLIYR ADRLVDGVPS  60
RVRGSGSGQD YSLTISSLEY EDMGIYYCLQ YDEFPYTFGG GTKLEIK                107

SEQ ID NO: 379         moltype = AA  length = 118
FEATURE                Location/Qualifiers
REGION                 1..118
                       note = KCD036 heavy chain variable region AA sequence
source                 1..118
                       mol_type = protein
                       organism = synthetic construct
SEQUENCE: 379
EVQLQQSGPE LVKPGASMKI SCKASGYSFT GYTMTWVKQS HGKNLEWIGL INPYNGGTNY  60
NQKFKGKATF TVDKSSSTAY MELLSLTSED SAVYYCARRH YGSSWDYWGQ GTTLTVSS    118

SEQ ID NO: 380         moltype = AA  length = 107
FEATURE                Location/Qualifiers
REGION                 1..107
                       note = KCD036 light chain variable region AA sequence
source                 1..107
                       mol_type = protein
                       organism = synthetic construct
SEQUENCE: 380
DIKLTQSPSS MYASLGERVT ITCKASQDIN TYLSWFQQKP GKSPKTLIYR ANRLVDGVPS  60
RFSGSGSGQD YSLTISSLEY EEMGIYYCLQ YDEFPYTFGG GTKLEIK                107

SEQ ID NO: 381         moltype = AA  length = 123
FEATURE                Location/Qualifiers
REGION                 1..123
                       note = KCD038 heavy chain variable region AA sequence
source                 1..123
                       mol_type = protein
                       organism = synthetic construct
SEQUENCE: 381
EVQLQQSGPE LVKPGTSMKI SCKASGYSFA DYTMNWVKQS HGKSLEWIGL INPYNGGTSY  60
```

```
NQKFMGKATL TVDKSSSTAY MELLSLTSED SAVYYCARWG TYSHNYDYAM DYWGQGTSVT  120
VSS                                                                123

SEQ ID NO: 382         moltype = AA  length = 113
FEATURE                Location/Qualifiers
REGION                 1..113
                       note = KCD038 light chain variable region AA sequence
source                 1..113
                       mol_type = protein
                       organism = synthetic construct
SEQUENCE: 382
DVVMTQTPLS LPVSLGDQAS ISCRSSQSLV HSNGNTYLYW YFQKPGQSPK FLIYKVSNRF  60
SGISDRFSGS GSGTDFTLKI SRVEAEDLGV YFCSQSTHVP PFTFGSGTKL EIK         113

SEQ ID NO: 383         moltype = AA  length = 123
FEATURE                Location/Qualifiers
REGION                 1..123
                       note = KCD039 heavy chain variable region AA sequence
source                 1..123
                       mol_type = protein
                       organism = synthetic construct
SEQUENCE: 383
EVQLQQSGPE MVKPGASMKI SCKASGYSFA DYTLNWVKQS HGKSLEWIGL INPYNGGTSY  60
NQKFMGKATL TVDKSSSTAY MELLSLTSED SAVYYCTRWG TYSHNYDYAM DYWGQGTSVT  120
VSS                                                                123

SEQ ID NO: 384         moltype = AA  length = 113
FEATURE                Location/Qualifiers
REGION                 1..113
                       note = KCD039 light chain variable region AA sequence
source                 1..113
                       mol_type = protein
                       organism = synthetic construct
SEQUENCE: 384
DVVMTQTPLS LSVSLGDQAS ISCRSSQSLV HSNGNTYLYW YLQKPGQSPK LLIYKVSNRF  60
SGITDRFSGS GSGTDFTLKI SRVEAEDLGV YFCSQSTHVP PFTFGSGTKL EIK         113

SEQ ID NO: 385         moltype = AA  length = 113
FEATURE                Location/Qualifiers
REGION                 1..113
                       note = KCD040 heavy chain variable region AA sequence
source                 1..113
                       mol_type = protein
                       organism = synthetic construct
SEQUENCE: 385
EVQLQQSGAE LVKPGASVKL SCTASDFNIK DTYMHWVMQR PEQGLEWIGK IDPANGNTEF  60
DPKFQGKATI TADTSSNTAY LQLTSLTSED TAVYYCTRAM DYWGQGTSVT VSS         113

SEQ ID NO: 386         moltype = AA  length = 106
FEATURE                Location/Qualifiers
REGION                 1..106
                       note = KCD040 light chain variable region AA sequence
source                 1..106
                       mol_type = protein
                       organism = synthetic construct
SEQUENCE: 386
QIVLTQSPAI MSASPGEKVT MTCSAGSSVS YMYWYQQKPG SSPRVLIYDT SNLASGVPVR  60
FSGSGSGTSY SLTISRMEAE DAATYYCQQW SNYPYTFGGG TKLEIK                 106

SEQ ID NO: 387         moltype = AA  length = 113
FEATURE                Location/Qualifiers
REGION                 1..113
                       note = KCD042 heavy chain variable region AA sequence
source                 1..113
                       mol_type = protein
                       organism = synthetic construct
SEQUENCE: 387
EVQLQQSGAE LVKPGASVRL SCTASGFNIK HTYIHWVSQR PEQGLEWIGK IDPANGNTKY  60
DPKFQGKATI TADTSSNTAY LQLSSLTSED TAVYYCVNAM EYWGQGTSVT VSS         113

SEQ ID NO: 388         moltype = AA  length = 106
FEATURE                Location/Qualifiers
REGION                 1..106
                       note = KCD042 light chain variable region AA sequence
source                 1..106
                       mol_type = protein
                       organism = synthetic construct
SEQUENCE: 388
QSVLTQSPAI MSASPGEKVT MTCSANSSVS DMYWFQQRPG SSPRLLIYDT SNLASGVPVR  60
```

```
FSGSGSGTSY SLTISRMEAE DAATYYCQQW STYPWTFGGG TKLEIK                 106

SEQ ID NO: 389         moltype = AA  length = 113
FEATURE                Location/Qualifiers
REGION                 1..113
                       note = KCD044 heavy chain variable region AA sequence
source                 1..113
                       mol_type = protein
                       organism = synthetic construct
SEQUENCE: 389
EVQLQQSGAE LVKPGASVRL SCTASGFNIK HTYMHWVSQR PERGLEWIGK IDPANGNTKY  60
DPKFQGKATI TADTSSNTVY LQLSSLTSED TAVYYCLNAM EYWGQGTSVT VSS         113

SEQ ID NO: 390         moltype = AA  length = 106
FEATURE                Location/Qualifiers
REGION                 1..106
                       note = KCD044 light chain variable region AA sequence
source                 1..106
                       mol_type = protein
                       organism = synthetic construct
SEQUENCE: 390
QSVLTQSPAI MSASPGEKVT MTCSANSSVS DMYWYQQRPG SSPRLLIYDT SNLASGVPVR  60
FSGSGSGTSY SLTISRMEAE DAATYYCQQW STYPWTFGGG TKLEIK                 106

SEQ ID NO: 391         moltype = AA  length = 113
FEATURE                Location/Qualifiers
REGION                 1..113
                       note = KCD047 heavy chain variable region AA sequence
source                 1..113
                       mol_type = protein
                       organism = synthetic construct
SEQUENCE: 391
EVQLQQSGAE FVKPGASVRL SCTASGFNIK DTYMHWVKQR PEQGLEWIGR IDPANGYTKD  60
DPKFQGKATI TADTSSNTAY LQLSSLTSED TAVYYCASAM DYWGQGTSVT VSS         113

SEQ ID NO: 392         moltype = AA  length = 106
FEATURE                Location/Qualifiers
REGION                 1..106
                       note = KCD047 light chain variable region AA sequence
source                 1..106
                       mol_type = protein
                       organism = synthetic construct
SEQUENCE: 392
QIVLTQSPAV MSASPGEKVA MTCSASSSVT YMYWYQQKPG SSPRLLIYDT SNLASGVPVR  60
FSGSGSGTSY SLTISRMEAE DAATYYCQQW STYPFPFGSG TKLEIK                 106

SEQ ID NO: 393         moltype = AA  length = 113
FEATURE                Location/Qualifiers
REGION                 1..113
                       note = KCD048 heavy chain variable region AA sequence
source                 1..113
                       mol_type = protein
                       organism = synthetic construct
SEQUENCE: 393
EVQLQQSGAD LVKPGASVKL SCTASGFNIK ATYMHWVRQR PEKGLEWIGR IDPANGHTIY  60
DPQFQGKATI TSDTSSNTAY LQLNSLTSED TAVYYCAEAM DYWGQGTSVT VSS         113

SEQ ID NO: 394         moltype = AA  length = 106
FEATURE                Location/Qualifiers
REGION                 1..106
                       note = KCD048 light chain variable region AA sequence
source                 1..106
                       mol_type = protein
                       organism = synthetic construct
SEQUENCE: 394
QIVLTQSPAI MSASPGEKVT LTCSATSSVS YMYWYQQKPG SSPRLLIYDT SNLASGVPVR  60
FSGSGSGTSY SLTISRMEAE DDATYYCQQW SNYPFTFGGG TKLEIK                 106

SEQ ID NO: 395         moltype = AA  length = 122
FEATURE                Location/Qualifiers
REGION                 1..122
                       note = KCD049 heavy chain variable region AA sequence
source                 1..122
                       mol_type = protein
                       organism = synthetic construct
SEQUENCE: 395
QVQLKESGPG LVAPSQSLSI TCTVSGFSLS SYGVQWVRQP PGQGLEWLVV IWRDGSITYN  60
SALKSRLSIS KDNSKSQVFL KMNSLQTDDT AMYYCGRTSH YGNYNYYVMD YWGQGTAVTV  120
SS                                                                 122
```

```
SEQ ID NO: 396          moltype = AA  length = 111
FEATURE                 Location/Qualifiers
REGION                  1..111
                        note = KCD049 light chain variable region AA sequence
source                  1..111
                        mol_type = protein
                        organism = synthetic construct
SEQUENCE: 396
DIVMTQSPAS LAVSLGQRAT ISCRASESVD KYGISFLNWF QQKPGQPPKL LIYAASNQGS  60
GVPARFSGSG SGTDFSLNIH PMEEDDPAMY FCQQGKEVPW TFGGGTKLEI K           111

SEQ ID NO: 397          moltype = AA  length = 122
FEATURE                 Location/Qualifiers
REGION                  1..122
                        note = KCD050 heavy chain variable region AA sequence
source                  1..122
                        mol_type = protein
                        organism = synthetic construct
SEQUENCE: 397
QVQLKESGPG LVAPSQSLSI TCTVSGFSLN SYGVQWVRQP PGQGLEWLVV IWRDGTITYN  60
SALKSRLSIN KDNSKSQVFL KMNSLQTDDT AMYYCGRTSH YGNFNYYVMD YWGQGTAVTV  120
SS                                                                122

SEQ ID NO: 398          moltype = AA  length = 111
FEATURE                 Location/Qualifiers
REGION                  1..111
                        note = KCD050 light chain variable region AA sequence
source                  1..111
                        mol_type = protein
                        organism = synthetic construct
SEQUENCE: 398
DIVMTQSPTS LAVSLGQRAT ISCRASESVD KYGISFLNWF QQKPGQPPRL LIYAASNQGS  60
GVPARFSGSG SGTDFSLNIH PMEEDDPAVY FCQQGKEFPW TFGGGTKLEI K           111

SEQ ID NO: 399          moltype = AA  length = 122
FEATURE                 Location/Qualifiers
REGION                  1..122
                        note = KCD052 heavy chain variable region AA sequence
source                  1..122
                        mol_type = protein
                        organism = synthetic construct
SEQUENCE: 399
QVQLKESGPG LVAPSQSLSI TCTVSGFSLN SYGVQWVRQP PGQGLEWLGV IWRDGSITYN  60
SALKSRLSIR KDNSKSQVFL KMNSLQTDDT AMYYCGRTSH YGNYNYYVMD YWGQGTAVTV  120
SS                                                                122

SEQ ID NO: 400          moltype = AA  length = 111
FEATURE                 Location/Qualifiers
REGION                  1..111
                        note = KCD052 light chain variable region AA sequence
source                  1..111
                        mol_type = protein
                        organism = synthetic construct
SEQUENCE: 400
DIVMTQSPAS LAVSLGQRAT ISCRASESVD KYGISFLNWF QQKPGQPPKL LIYAASNQGS  60
GVPARFSGSG SGTDFSLNIH PMEEDDPAIY FCQQGKEVPW TFGGGTKLEI K           111

SEQ ID NO: 401          moltype = AA  length = 117
FEATURE                 Location/Qualifiers
REGION                  1..117
                        note = KCD056 heavy chain variable region AA sequence
source                  1..117
                        mol_type = protein
                        organism = synthetic construct
SEQUENCE: 401
EVKLVESGGG LVQPGGSLKV SCAASGFTFS TYTMSWVRQT PEKRLEWVAY ITNGGGSTYY  60
PDTEKGRFTI SRDNAKNTLY LQMSSLKSED TAMYYCVRHD YYAMDYWGQG TSVTVSS     117

SEQ ID NO: 402          moltype = AA  length = 107
FEATURE                 Location/Qualifiers
REGION                  1..107
                        note = KCD056 light chain variable region AA sequence
source                  1..107
                        mol_type = protein
                        organism = synthetic construct
SEQUENCE: 402
DIQMTQSPSS LSASLGGKVT ITCKASQDIN KYIAWYQHKP GKGPRLLIHY TSTLQPGIPS  60
RFSGSGSGRD YSFSISNLEP EDIATYYCLQ YDNLLYTFGG GTTLEIK               107
```

```
SEQ ID NO: 403         moltype = AA  length = 117
FEATURE                Location/Qualifiers
REGION                 1..117
                       note = KCD057 heavy chain variable region AA sequence
source                 1..117
                       mol_type = protein
                       organism = synthetic construct
SEQUENCE: 403
EVKLVESGGG LVQPGGSLKL SCAASGFTFS NYIMSWVRQT PEKRLEWVAY ITNGGGATYY  60
PDTVKGQFTI SRDNAKNTLY LQMSSLKSED TAIYYCARHD FYALDFWGQG TSVTVSS     117

SEQ ID NO: 404         moltype = AA  length = 107
FEATURE                Location/Qualifiers
REGION                 1..107
                       note = KCD057 light chain variable region AA sequence
source                 1..107
                       mol_type = protein
                       organism = synthetic construct
SEQUENCE: 404
DIQMTQSPSS LSASLGGKVT ITCKASQDIN KYIAWYQHKP GKGPRLLIHY TSTLQPGIPS  60
RFSGSGSGRD YSFSISNLEP EDIATYYCLK YDNLLYTFGG GTKLEIK                107

SEQ ID NO: 405         moltype = AA  length = 117
FEATURE                Location/Qualifiers
REGION                 1..117
                       note = KCD058 heavy chain variable region AA sequence
source                 1..117
                       mol_type = protein
                       organism = synthetic construct
SEQUENCE: 405
EVKLVESGGD LVQPGGSLKL SCAASGFTFS RYIMSWVRLT PEKRLEWVAF ITNGGGNTYH  60
PDTVKGRFTI SRDNANNTLY LQMSSLKSED TAIYYCARHD YYALDYWGQG TSVTVSS     117

SEQ ID NO: 406         moltype = AA  length = 107
FEATURE                Location/Qualifiers
REGION                 1..107
                       note = KCD058 light chain variable region AA sequence
source                 1..107
                       mol_type = protein
                       organism = synthetic construct
SEQUENCE: 406
DIQMTQSPSS LSASLGGKVT ITCKASQDIN KYIAWYQHKP GKGPRLLIHY TSTLQPGIPS  60
RFSGSGSGRD YSFSISNLEP EDIATYYCLQ YDNLLYTFGG GTKLEIK                107

SEQ ID NO: 407         moltype = AA  length = 118
FEATURE                Location/Qualifiers
REGION                 1..118
                       note = KCD062 heavy chain variable region AA sequence
source                 1..118
                       mol_type = protein
                       organism = synthetic construct
SEQUENCE: 407
EVKLVESGGG LVQPGGSLKL SCAASGFTFS TYIMSWVRQT PEKRLEWVAY ITSGGSSTYY  60
PDTVKGRFTI SRDNAKSTLY LQMSSLKSED TAMYYCARHA HFYAMDYWGQ GTSVTVSS    118

SEQ ID NO: 408         moltype = AA  length = 107
FEATURE                Location/Qualifiers
REGION                 1..107
                       note = KCD062 light chain variable region AA sequence
source                 1..107
                       mol_type = protein
                       organism = synthetic construct
SEQUENCE: 408
DIQMTQSPSS LSASLGGKVT ITCKASQDIN KYIAWYQHKP GKGPRLLIHY TSTLQPGIPS  60
RFSGSGSGRD YSFSISNLEP EDIATYYCLQ YDNLLYTFGG GTKLEIK                107

SEQ ID NO: 409         moltype = AA  length = 118
FEATURE                Location/Qualifiers
REGION                 1..118
                       note = KCD063 heavy chain variable region AA sequence
source                 1..118
                       mol_type = protein
                       organism = synthetic construct
SEQUENCE: 409
EVKLVESGGG LVQPGGSLKL SCAASGFIFS SYIMSWVRQT PEKRLEWVAY ITNGGGSTYY  60
PDTVKGRLTI SRDNAKNTLY LQMSSLKSED TAMYYCVRHA HYYAMDYWGQ GTSVTVSS    118

SEQ ID NO: 410         moltype = AA  length = 107
```

```
FEATURE                Location/Qualifiers
REGION                 1..107
                       note = KCD063 light chain variable region AA sequence
source                 1..107
                       mol_type = protein
                       organism = synthetic construct
SEQUENCE: 410
DIQMTQSPSS LSASLGGKVT ITCKASQDIN KYITWYQHKP GKGPRLLIHY TSTLQPGIPS  60
RFSGSGSGRD YSFSISNLEP EDIATYYCLQ YDNLLYTFGG GTKLEIK                107

SEQ ID NO: 411         moltype = AA  length = 118
FEATURE                Location/Qualifiers
REGION                 1..118
                       note = KCD064 heavy chain variable region AA sequence
source                 1..118
                       mol_type = protein
                       organism = synthetic construct
SEQUENCE: 411
EVKLVESGGG LVQPGGSLKL SCAASGFTFS SYIMSWVRQT PEKRLGWVAY ITSGGGSTYY  60
PDTVKGRFTI SRDNAKNTLY LQMSSLKSED TAMYYCARHG TGYAMDYWGQ GTSVTVSS    118

SEQ ID NO: 412         moltype = AA  length = 107
FEATURE                Location/Qualifiers
REGION                 1..107
                       note = KCD064 light chain variable region AA sequence
source                 1..107
                       mol_type = protein
                       organism = synthetic construct
SEQUENCE: 412
DIQMTQSPSS LSASLGGKVT ITCKASQDIN KYIAWYQHKP GKGPRLLIHY TSTLQPGIPS  60
RFSGSGSGRD YSFSISNLEP EDIATYYCLQ YDNLLYTFGG GTELEIK                107

SEQ ID NO: 413         moltype = AA  length = 122
FEATURE                Location/Qualifiers
REGION                 1..122
                       note = KCD065 heavy chain variable region AA sequence
source                 1..122
                       mol_type = protein
                       organism = synthetic construct
SEQUENCE: 413
QVQLQQSGAE LARPGASVKM SCKASGYTFT TYTIHWVKQR PGQGLEWIGY INPSSDFTNY  60
NQNFADKATL TADRSSSTAY MQLSSLTSEE SAVYYCAIRL GYDRQGWYFD VWGAGTTVTV  120
SS                                                                 122

SEQ ID NO: 414         moltype = AA  length = 107
FEATURE                Location/Qualifiers
REGION                 1..107
                       note = KCD065 light chain variable region AA sequence
source                 1..107
                       mol_type = protein
                       organism = synthetic construct
SEQUENCE: 414
DIVMTQSHKF LSTSLGDRVS ITCKASQDVG SAVAWYQQKP GQSPDLLIYW TFTRHTGVPD  60
RFTGSRSGTD FTLTISNVQS GDLADYFCQQ YSNYPLTFGG GTKLEIK                107

SEQ ID NO: 415         moltype = AA  length = 117
FEATURE                Location/Qualifiers
REGION                 1..117
                       note = KCD066 heavy chain variable region AA sequence
source                 1..117
                       mol_type = protein
                       organism = synthetic construct
SEQUENCE: 415
QVQLQQSAAE LARPGASVKM SCKASGYTFT DYTMHWVKQR PGQGLEWIGY INPSGGYTDY  60
NQKFKDKTAL TADKSSSTAY MQLSSLTSED SAVYYCARRR DYWFAYWGQG TLVTVSA     117

SEQ ID NO: 416         moltype = AA  length = 112
FEATURE                Location/Qualifiers
REGION                 1..112
                       note = KCD066 light chain variable region AA sequence
source                 1..112
                       mol_type = protein
                       organism = synthetic construct
SEQUENCE: 416
DIVMSQSPSS LAVSVGEKVT MSCKSSQSLL YSGNQKNYLA WYQQKPGQSP KLLIYWASTR  60
ESGVPDRFTG SGSGTDFTLT ISSVKAEDLA VYYCHQYYSY LTFGAGTKLE LK          112

SEQ ID NO: 417         moltype = AA  length = 118
FEATURE                Location/Qualifiers
```

-continued

```
REGION                  1..118
                        note = KCD070 heavy chain variable region AA sequence
source                  1..118
                        mol_type = protein
                        organism = synthetic construct
SEQUENCE: 417
EIQLQQTGPE LVKPGASVKI SCKASGYSFT DYIILWVKQS HGKSLEWIGN INPYYDYTSY  60
NLKFKGKATL TVDKSSSTAY MQLNSLTSED SAVYYCARSD GYYGGDYWGQ GTSVTVSS    118

SEQ ID NO: 418          moltype = AA  length = 107
FEATURE                 Location/Qualifiers
REGION                  1..107
                        note = KCD070 light chain variable region AA sequence
source                  1..107
                        mol_type = protein
                        organism = synthetic construct
SEQUENCE: 418
DIVMTQSHKF MSTSVGDRVS ITCKASQDVG TAVAWYQQKP GQSPKLLIYW ASTRHTGVPD  60
RFTGSGSGTD FTLTINNVQS EDLADYFCQQ YSSYPWTFGG GTTLEIK                107

SEQ ID NO: 419          moltype = AA  length = 116
FEATURE                 Location/Qualifiers
REGION                  1..116
                        note = KCD075 heavy chain variable region AA sequence
source                  1..116
                        mol_type = protein
                        organism = synthetic construct
SEQUENCE: 419
QVQLLQPGAE LVRPGTSVKL SCKASGYTFS NYWINWVKQR PGQGLEWIGN IYPSDSSINY  60
NQKFKDKATL TVDKSSTTAY MQLSSPTSED SAVYYCTGTD WYFDVWGAGT TVTVSS      116

SEQ ID NO: 420          moltype = AA  length = 107
FEATURE                 Location/Qualifiers
REGION                  1..107
                        note = KCD075 light chain variable region AA sequence
source                  1..107
                        mol_type = protein
                        organism = synthetic construct
SEQUENCE: 420
DIQMTQTTSS LSASLGDRVT ISCSGGQGIS NYLNWYQQKP DGTFKLLIYY TSTLHSGVPS  60
RFSGSGSGTD YSLTISNLEP EDVATYYCQQ YSKLPYTFGG GTKLEIK                107

SEQ ID NO: 421          moltype = AA  length = 116
FEATURE                 Location/Qualifiers
REGION                  1..116
                        note = KCD077 heavy chain variable region AA sequence
source                  1..116
                        mol_type = protein
                        organism = synthetic construct
SEQUENCE: 421
EVQLQQSGAE LVRPGALVKL SCKASGFNIK DYYMHWVKQR PEQGLEWIGW IDPENGHTIY  60
DPRFQGKATI TADTSSNTAY LQLSSLTSED TAVYYCSRGL LGFAYWGQGT LVTVSA      116

SEQ ID NO: 422          moltype = AA  length = 109
FEATURE                 Location/Qualifiers
REGION                  1..109
                        note = KCD077 light chain variable region AA sequence
source                  1..109
                        mol_type = protein
                        organism = synthetic construct
SEQUENCE: 422
DIVMTQSQKF MSTSVGDRVS VTCKASQNVG TNVAWYQQKP GQSPKALIYT ASYRYSGVPD  60
RFTGSGSGTD FTLTISNVQS EDLAEYFCQQ YNSYPHMYTF GGGTKLEIK              109

SEQ ID NO: 423          moltype = AA  length = 118
FEATURE                 Location/Qualifiers
REGION                  1..118
                        note = KCD101 heavy chain variable region AA sequence
source                  1..118
                        mol_type = protein
                        organism = synthetic construct
SEQUENCE: 423
QVQLQQPGAE LVRPGTSVKL SCKASGYTFT SYWMHWVKQR PGQGLEWIGV IDPSDSYTNY  60
NQKFKGKATL TVDTSSSTAY MQLSSLTSED SAVYYCGRNG YDGSMDYWGQ GTSVTVSS    118

SEQ ID NO: 424          moltype = AA  length = 107
FEATURE                 Location/Qualifiers
REGION                  1..107
                        note = KCD101 light chain variable region AA sequence
```

```
source                  1..107
                        mol_type = protein
                        organism = synthetic construct
SEQUENCE: 424
DIQMTQTTSS LSASLGDRVT ISCRASQDIS NYLNWYQQKP DGTVKLLIYY PSRLHSGVPS  60
RFSGSGSGTD YSLTISNLEQ EDFATYFCQQ GNTLPYTFGG GTKLEIK               107

SEQ ID NO: 425          moltype = AA  length = 121
FEATURE                 Location/Qualifiers
REGION                  1..121
                        note = KCD110 heavy chain variable region AA sequence
source                  1..121
                        mol_type = protein
                        organism = synthetic construct
SEQUENCE: 425
EVQLQQSGPE LVKPGASVKI SCKASGYSFT GYYMHWVKQS HGNILDWIGY IDPDNGVSSK  60
NQKFTGKATV TADKSSSTAY MELRSLTSED SAVYYCAGYY GSSWYWYFDV WGTGTTVTVS  120
S                                                                 121

SEQ ID NO: 426          moltype = AA  length = 106
FEATURE                 Location/Qualifiers
REGION                  1..106
                        note = KCD110 light chain variable region AA sequence
source                  1..106
                        mol_type = protein
                        organism = synthetic construct
SEQUENCE: 426
QIVLSQSPAI LSASPGEKVT MTCRASSSVS YMHWYQQKPG SSPKPWIYAT SNLASGVPAR  60
FSGSGSGTSY SLTISRVEAE DAATYYCQQW SSNPYTFGGG TKLEIK                106

SEQ ID NO: 427          moltype = AA  length = 121
FEATURE                 Location/Qualifiers
REGION                  1..121
                        note = KCD111 heavy chain variable region AA sequence
source                  1..121
                        mol_type = protein
                        organism = synthetic construct
SEQUENCE: 427
EVQLQQSGPE LVKPGASVKI SCKASGYSFT DYYMHWVKQS HGNILDWIGY IDPYNGVSSY  60
NQKFKGKATL SVDQSSSTAY MELRSLTSED SAVYYCSSYY GSSPYWYFDV WGTGTRVTVS  120
S                                                                 121

SEQ ID NO: 428          moltype = AA  length = 106
FEATURE                 Location/Qualifiers
REGION                  1..106
                        note = KCD111 light chain variable region AA sequence
source                  1..106
                        mol_type = protein
                        organism = synthetic construct
SEQUENCE: 428
QIVLSQSPAI LSASPGEKVT MTCRASSSVS YMHWYQQKPG SSPKPWIYAT SNLASGVPTR  60
FSGSGSGTSY SLTISKLEAE DAATYYCQQW SSNPYTFGGG TKLEIK                106

SEQ ID NO: 429          moltype = AA  length = 122
FEATURE                 Location/Qualifiers
REGION                  1..122
                        note = KCD112 heavy chain variable region AA sequence
source                  1..122
                        mol_type = protein
                        organism = synthetic construct
SEQUENCE: 429
EVQLQQSGPE LVKPGASVKI SCKASGYSFT AYYMNWVKHS PEKSLEWIGD INPSTGGTTY  60
NQKFKARATL TVDKSSSTAY MQLKSLTSED SAVYYCATTY YSGNSYVGFA YWGQGTLVTV  120
SA                                                                122

SEQ ID NO: 430          moltype = AA  length = 107
FEATURE                 Location/Qualifiers
REGION                  1..107
                        note = KCD112 light chain variable region AA sequence
source                  1..107
                        mol_type = protein
                        organism = synthetic construct
SEQUENCE: 430
DIVMTQSHKF MSTSVGDRVS ITCKASQDVS TAVAWYQQKP GQSPKLLIFW TSTRHTGVPD  60
RFTGSGSGTD YTLTISSVQA EDLALYYCQQ HYTTPWTFGG GTKLEIK               107

SEQ ID NO: 431          moltype = AA  length = 122
FEATURE                 Location/Qualifiers
REGION                  1..122
```

```
                        note = KCD114 heavy chain variable region AA sequence
source                  1..122
                        mol_type = protein
                        organism = synthetic construct
SEQUENCE: 431
EVQLQQSGPE LVKPGASVKI SCKASGYSFT AYYMNWVKQS PEKSLEWIGD INPSTGGTTY  60
NQNFKAKATL TVDKSSSTAY MHLKSLTSED SAVYYCATTY YSGNSYVGFA YWGQGTLVTV  120
SA                                                                122

SEQ ID NO: 432          moltype = AA  length = 107
FEATURE                 Location/Qualifiers
REGION                  1..107
                        note = KCD114 light chain variable region AA sequence
source                  1..107
                        mol_type = protein
                        organism = synthetic construct
SEQUENCE: 432
DIVMTQSHKF MSTSVGDRVS ITCKASQDVS TAVAWYQQKP GQSPKLLIFW ASTRHTGVPD  60
RFTGSGSGTD YTLTISSVQA EDLALYYCQQ HYSTPWTFGG GTKLEIK               107

SEQ ID NO: 433          moltype = AA  length = 122
FEATURE                 Location/Qualifiers
REGION                  1..122
                        note = KCD115 heavy chain variable region AA sequence
source                  1..122
                        mol_type = protein
                        organism = synthetic construct
SEQUENCE: 433
EVQLQQSGPE LVKPGASVKI SCKASGYSFT GYYMNWVKQS PEKSLEWIGD INPSTGGTTY  60
NQKFKAKATL TVDKSSSTAY MQLKSLTSED SAVYYCATPY YYGSSYVGFA YWGQGTLVTV  120
SA                                                                122

SEQ ID NO: 434          moltype = AA  length = 107
FEATURE                 Location/Qualifiers
REGION                  1..107
                        note = KCD115 light chain variable region AA sequence
source                  1..107
                        mol_type = protein
                        organism = synthetic construct
SEQUENCE: 434
DIVMTQSHKF MSTSVGDRVS ITCKASQDVS TAVDWYQQKP GQSPKLLIYW ASTRHTGVPD  60
RFTGSGSGTD YTLTISSVQA EDLALYYCQQ HYSTPWTFGG GTKLEIK               107

SEQ ID NO: 435          moltype = AA  length = 116
FEATURE                 Location/Qualifiers
REGION                  1..116
                        note = KCD118 heavy chain variable region AA sequence
source                  1..116
                        mol_type = protein
                        organism = synthetic construct
SEQUENCE: 435
EVQLQQSGPE LVKPGASVKI SCKAFGYTFT DYYKNWMRQR HGESLEWIGD INPNSGDANY  60
NQKFKGKATL TVDKSSSTAY MELRSLTSED SAVYYCAREG PSFAYWGHGT LVTVSA      116

SEQ ID NO: 436          moltype = AA  length = 112
FEATURE                 Location/Qualifiers
REGION                  1..112
                        note = KCD118 light chain variable region AA sequence
source                  1..112
                        mol_type = protein
                        organism = synthetic construct
SEQUENCE: 436
DVLMTQTPLS LPVSLGDQAS ISCRSSQTIV HSNGDTYLEW YLQKPGQSPN LLIYKVSNRF  60
SGVPDRFSGS GSGTDFTLKI SRVEAEDLGI YYCFQGSHVP PTFGGGTKLE IK          112

SEQ ID NO: 437          moltype = AA  length = 116
FEATURE                 Location/Qualifiers
REGION                  1..116
                        note = KCD119 heavy chain variable region AA sequence
source                  1..116
                        mol_type = protein
                        organism = synthetic construct
SEQUENCE: 437
EVQLQQSGPE LVKPGASVKI SCKASGYTFT DYYTNWMRQR HGESLEWIGD INPNTGDTSY  60
NQKFRVKATL TVDKSSGTAY MGLRSLTSED SAVYYCTREG PSFAYWGQGT LVTVSA      116

SEQ ID NO: 438          moltype = AA  length = 112
FEATURE                 Location/Qualifiers
REGION                  1..112
```

```
                          note = KCD119 light chain variable region AA sequence
source                    1..112
                          mol_type = protein
                          organism = synthetic construct
SEQUENCE: 438
DVLMTQTPLS LPVSLGDQAS ISCRSSQTIV HSNGDTYLEW YLQKPGQSPN LLIYKVSNRF  60
SGVPDRFSGS GSGTDFTLKI SRVEAEDLGV YYCFQGSHVP PTFGGGTTLE IK          112

SEQ ID NO: 439            moltype = AA  length = 118
FEATURE                   Location/Qualifiers
REGION                    1..118
                          note = KCD102 heavy chain variable region AA sequence
source                    1..118
                          mol_type = protein
                          organism = synthetic construct
SEQUENCE: 439
QVQLQQPGAE LVRPGTSVKL SCKASGYTFT SYWMHWVKQR PGQGLEWIGV IDPSDSYTNY  60
NQKFKGKATL TVDTSSSTAY MQLSSLTSED SAVYYCARNG YDGSMDYWGQ GTSVTVSS    118

SEQ ID NO: 440            moltype = AA  length = 107
FEATURE                   Location/Qualifiers
REGION                    1..107
                          note = KCD102 light chain variable region AA sequence
source                    1..107
                          mol_type = protein
                          organism = synthetic construct
SEQUENCE: 440
EIQMTQTTSS LSASLGDRVT ISCRASQDIS NYLNWYQQKP DGTVKLLIYY PSRLHSGVPS  60
RFSGSGSGTD YSLTISNLEQ EDFATYFCQQ GNTLPYTFGG GTKLEIK                107

SEQ ID NO: 441            moltype = AA  length = 116
FEATURE                   Location/Qualifiers
REGION                    1..116
                          note = KCD121 heavy chain variable region AA sequence
source                    1..116
                          mol_type = protein
                          organism = synthetic construct
SEQUENCE: 441
EVQLQQSGPE LVKPGASVKI SCKASGYTFT DYYKNWMRQR HGESLEWIGD INPNNGDTSY  60
NQKFRGKATL TVDKSSSTAF MELRSLTSED SAVYYCAREG PSFAYWGQGT LVTVSA      116

SEQ ID NO: 442            moltype = AA  length = 112
FEATURE                   Location/Qualifiers
REGION                    1..112
                          note = KCD121 light chain variable region AA sequence
source                    1..112
                          mol_type = protein
                          organism = synthetic construct
SEQUENCE: 442
DVLMTQTPLS LPVSLGDQAS ISCRSNQTIV HSNGDTYLEW YLQKPGQSPN LLIYKVSNRF  60
SGVPDRFSGS GSGTDFTLRI SRVEAEDLGV YYCFQGSHVP PTFGGGTKLE IK          112

SEQ ID NO: 443            moltype = AA  length = 116
FEATURE                   Location/Qualifiers
REGION                    1..116
                          note = KCD122 heavy chain variable region AA sequence
source                    1..116
                          mol_type = protein
                          organism = synthetic construct
SEQUENCE: 443
EVQLQQSGPE LVKPGASVKI SCKASGYTFT DYYKNWMRQR HGESLEWIGD INPNNGDANY  60
NQKFKGKATL TVDKSSSTAY MELRSLTSED SAVYFCAREG PSFAYWGHGT LVTVSA      116

SEQ ID NO: 444            moltype = AA  length = 112
FEATURE                   Location/Qualifiers
REGION                    1..112
                          note = KCD122 light chain variable region AA sequence
source                    1..112
                          mol_type = protein
                          organism = synthetic construct
SEQUENCE: 444
DVLMTQTPLS LPVSLGDQAS ISCRSSQTIV HSNGDTYLEW YLQKPGQSPN LLIYKVSNRF  60
SGVPDRFSGS GSGTDFTLKI SRVEAEDLGV YYCFQGSHVP PTFGGGTKLE IK          112

SEQ ID NO: 445            moltype = AA  length = 116
FEATURE                   Location/Qualifiers
REGION                    1..116
                          note = KCD123 heavy chain variable region AA sequence
source                    1..116
```

```
                         mol_type = protein
                         organism = synthetic construct
SEQUENCE: 445
EVHLQQSGPE LVKPGASVKI SCKASGYTFT DFYKNWMRQR HGESLEWIGD INPNNGGTNY  60
NQKFKGKATL TVDKSSSTAY MELRSLTSED SAVYYCAREG PSFAYWGQGT LVTVSA      116

SEQ ID NO: 446           moltype = AA  length = 112
FEATURE                  Location/Qualifiers
REGION                   1..112
                         note = KCD123 light chain variable region AA sequence
source                   1..112
                         mol_type = protein
                         organism = synthetic construct
SEQUENCE: 446
DVLMTQTPLS LPVSLGDQAS ISCRSSQTIV HSNGDTYLEW YLQKPGQSPN LLIYKVSNRF  60
SGVPDRFSGS GSGTDFTLKI SRVEAEDLGV YYCFQGSHVP PTFGGGTKLE IK          112

SEQ ID NO: 447           moltype = AA  length = 116
FEATURE                  Location/Qualifiers
REGION                   1..116
                         note = KCD124 heavy chain variable region AA sequence
source                   1..116
                         mol_type = protein
                         organism = synthetic construct
SEQUENCE: 447
EVQLQQSGPE LVKPGASVKI SCKASGYTFT DHYMNWVKQS HGKSLEWIGD INPNNGGTSY  60
NQKFKGKATL TVDKSSSTAY MELRSLTSGD SAVYYCTREG ASFAFWGQGT LVTVSA      116

SEQ ID NO: 448           moltype = AA  length = 112
FEATURE                  Location/Qualifiers
REGION                   1..112
                         note = KCD124 light chain variable region AA sequence
source                   1..112
                         mol_type = protein
                         organism = synthetic construct
SEQUENCE: 448
DVLMTQTPLS LPVSLGDQAS ISCRSSQSIV HSNGDTYLEW YLQKPGQSPK LLIYKVSNRF  60
SGVPDRFSGS GSGTDFTLKI SRVEAEDLGV YYCFQGSHVP LTFGAGTKLE LK          112

SEQ ID NO: 449           moltype = AA  length = 119
FEATURE                  Location/Qualifiers
REGION                   1..119
                         note = KCD125 heavy chain variable region AA sequence
source                   1..119
                         mol_type = protein
                         organism = synthetic construct
SEQUENCE: 449
EVQLQQSGAE LVRPGSSVKM SCKTSGNTFT SYGINWVKQR PGQGLEWIGY IYIGTGYTEY  60
NEKFKGKATL TSDTSSSTAY MQLSSLTSED SAIYFCVRKA YGNYGFDYWG QGTTLTVSS   119

SEQ ID NO: 450           moltype = AA  length = 107
FEATURE                  Location/Qualifiers
REGION                   1..107
                         note = KCD125 light chain variable region AA sequence
source                   1..107
                         mol_type = protein
                         organism = synthetic construct
SEQUENCE: 450
DIQMTQSPSS LSASLGERVS LTCRASQEIS GYLSWLQQKP DGTIKRLIYA ASTLDSGVPK  60
RFSGSRSGSD YSLTISSLES EDFADYYCLQ YASYPFTFGS GTKLEIK                107

SEQ ID NO: 451           moltype = AA  length = 119
FEATURE                  Location/Qualifiers
REGION                   1..119
                         note = KCD126 heavy chain variable region AA sequence
source                   1..119
                         mol_type = protein
                         organism = synthetic construct
SEQUENCE: 451
EVQLQQSGAE LVRPGSSVKM SCKTSGKTFT SHGINWVKQR PGQGLEWIGY IYIGNGYNEY  60
NEKFKGKATL TSDTSSSTAY MQLSSLTFED SAIYFCVRKA YGNYGFDDWG QGTTLTVSS   119

SEQ ID NO: 452           moltype = AA  length = 107
FEATURE                  Location/Qualifiers
REGION                   1..107
                         note = KCD126 light chain variable region AA sequence
source                   1..107
                         mol_type = protein
                         organism = synthetic construct
```

-continued

```
SEQUENCE: 452
DIQMTQSPTS LSASLGESVS LTCRASQEIS GNLNWLQQKP DGSIKRLIYA ASTLDSGVPK  60
RFSGSRSGSD YSLTISSLES EDFADYYCLQ YANYPFTFGS GTKLEVK                107

SEQ ID NO: 453          moltype = AA  length = 123
FEATURE                 Location/Qualifiers
REGION                  1..123
                        note = KCD127 heavy chain variable region AA sequence
source                  1..123
                        mol_type = protein
                        organism = synthetic construct
SEQUENCE: 453
QVQLQQPGAE LVRPESSVKL SCKASGYTFT NFWMDWVKQR PGQGLEWIGN IYPSGSETHY  60
NQKFKDKATL TVDKSSTTAY MQLSSLTSED SAVYYCARSG YYGSRYLYYF DYWGQGTTLT  120
VSS                                                                123

SEQ ID NO: 454          moltype = AA  length = 107
FEATURE                 Location/Qualifiers
REGION                  1..107
                        note = KCD127 light chain variable region AA sequence
source                  1..107
                        mol_type = protein
                        organism = synthetic construct
SEQUENCE: 454
DIVMTQSHKF MSTSVGDRVS ITCKASQDVS TAVAWYQQKP GQSPKLLIYS ASYRSTGVPD  60
RFTGSGSGTD FTFTISSVQA EDLAVYYCQQ HYSTPYTFGG GTKLEIR                107

SEQ ID NO: 455          moltype = AA  length = 123
FEATURE                 Location/Qualifiers
REGION                  1..123
                        note = KCD128 heavy chain variable region AA sequence
source                  1..123
                        mol_type = protein
                        organism = synthetic construct
SEQUENCE: 455
QVQLQQPGAE LVRPESSVKL SCKASGYTFT SYWMDWVMQR PGQGLEWIGN IYPSGSETHY  60
NQKFKDKATL TVDKSSTTAY MQLSSLTFED SAVYYCARSG FIGSRYLYYF DYWGQGTTLT  120
VSS                                                                123

SEQ ID NO: 456          moltype = AA  length = 107
FEATURE                 Location/Qualifiers
REGION                  1..107
                        note = KCD128 light chain variable region AA sequence
source                  1..107
                        mol_type = protein
                        organism = synthetic construct
SEQUENCE: 456
DIVMTQSHKF MSTSVGDRVT ITCKASQDVS NAVAWYQLKP GQSPKLLIYS ASYRYTGVPD  60
RFTGSGSGTD FTFTISSVQA ADLAVYYCQQ HYITPYTFGG GTKLEIK                107

SEQ ID NO: 457          moltype = AA  length = 120
FEATURE                 Location/Qualifiers
REGION                  1..120
                        note = KCD129 heavy chain variable region AA sequence
source                  1..120
                        mol_type = protein
                        organism = synthetic construct
SEQUENCE: 457
EVQLVESGGG LVQPKGSLKL SCAASGFSFN TYAMNWVRQA PGKGLEWVAR IRSKSNNYAT  60
YYADSVKDRF TISRDDSESM VYLQMNNLKT EDTAMYYCVR HGYYWYFDVW GTGTTVTVSS  120

SEQ ID NO: 458          moltype = AA  length = 112
FEATURE                 Location/Qualifiers
REGION                  1..112
                        note = KCD129 light chain variable region AA sequence
source                  1..112
                        mol_type = protein
                        organism = synthetic construct
SEQUENCE: 458
DVLMTQTPLS LPVSLGDQAS ISCRSSQSIV HSDGNTYLEW YLQKPGQSPK LLIYRVSNRF  60
SGVPDRFSGS GSGTDFTLKI SRMEAEDLGV YYCFQGSHVP YTFGGGTKLE IK          112

SEQ ID NO: 459          moltype = AA  length = 118
FEATURE                 Location/Qualifiers
REGION                  1..118
                        note = KCD103 heavy chain variable region AA sequence
source                  1..118
                        mol_type = protein
                        organism = synthetic construct
```

-continued

```
SEQUENCE: 459
QVQLQQPGAE LVRPGTSVKL SCKASGYTFT SYWMHWVKQR PGQGLEWIGV IDPSDSYTKY  60
NQKFKDKATL TVETSSSTAY MQLSSLTSED SAVYYCAGNG YDGSMDYWGQ GTSVTVSS    118

SEQ ID NO: 460         moltype = AA  length = 107
FEATURE                Location/Qualifiers
REGION                 1..107
                       note = KCD103 light chain variable region AA sequence
source                 1..107
                       mol_type = protein
                       organism = synthetic construct
SEQUENCE: 460
DIQMTQTTSS LSASLGDRVT ISCRASQDIS NSLNWYQQKP DGTVKLLIYY TSRLHSRVPS  60
RFSGSGSGTD YSLTISNLDQ EDIATYFCQQ ANTLPYTFGG GTKLEIK                107

SEQ ID NO: 461         moltype = AA  length = 122
FEATURE                Location/Qualifiers
REGION                 1..122
                       note = KCD131 heavy chain variable region AA sequence
source                 1..122
                       mol_type = protein
                       organism = synthetic construct
SEQUENCE: 461
QVQLQQSGPE LVKPGASVKI SCKASAYTFT DYYINWVKQR PGQGPEWIGW IFPGSNSTYS  60
NEKFEVKATL TVDESSSTAY MLLSSLTSED SAVYFCARLG YFGSSYHALD YWGQGTSVTV  120
SS                                                                 122

SEQ ID NO: 462         moltype = AA  length = 107
FEATURE                Location/Qualifiers
REGION                 1..107
                       note = KCD131 light chain variable region AA sequence
source                 1..107
                       mol_type = protein
                       organism = synthetic construct
SEQUENCE: 462
DIQMTQSPAS LSVSVGETVT ITCRASENIY SHLAWFQQKQ GKSPRLLVYS ATNLPDGVPS  60
RFSGSGSGTQ YSLKINILQS EDFGSYYCQH FWGTPWTFGG GTKLEIK                107

SEQ ID NO: 463         moltype = AA  length = 121
FEATURE                Location/Qualifiers
REGION                 1..121
                       note = KCD132 heavy chain variable region AA sequence
source                 1..121
                       mol_type = protein
                       organism = synthetic construct
SEQUENCE: 463
QVQLQQSGPE LVKPGASVKI SCKASGYSFT DYYINWVKQR PGQGLEWIGW IFPGSGSTYY  60
NEKFKGKATL TVDKSSSTAY MLLSSLTSED SAVYFCARTG YYSNLYAVDY WGQGTSVTVS  120
S                                                                  121

SEQ ID NO: 464         moltype = AA  length = 107
FEATURE                Location/Qualifiers
REGION                 1..107
                       note = KCD132 light chain variable region AA sequence
source                 1..107
                       mol_type = protein
                       organism = synthetic construct
SEQUENCE: 464
DIQMTQSPAS LSVSVGETVT ITCRASENIY SNLAWYQQKQ GKSPQLLVYV ATNLADGVPS  60
RFSGSGSGTQ YSLKINSLQS EDFGNYYCQH FWGTPYTFGG GTKLEMR                107

SEQ ID NO: 465         moltype = AA  length = 121
FEATURE                Location/Qualifiers
REGION                 1..121
                       note = KCD133 heavy chain variable region AA sequence
source                 1..121
                       mol_type = protein
                       organism = synthetic construct
SEQUENCE: 465
EVQLVESGGG LLQPKGSLKL SCAASGFTFN TYAMNWVRQA PGKGLEWVAR IRSKSSNYAT  60
YYADSVKDRF TISRDDSQSM FYLEMNNLKT EDTAMYYCVR DRGYYYVMDY WGQGTSVTVS  120
S                                                                  121

SEQ ID NO: 466         moltype = AA  length = 111
FEATURE                Location/Qualifiers
REGION                 1..111
                       note = KCD133 light chain variable region AA sequence
source                 1..111
                       mol_type = protein
```

```
                         organism = synthetic construct
SEQUENCE: 466
DIVLTQSPAS LAVSLGQRAT ISCRASESVE YYGTSLMQWY QQKPGQPPKL LINAASNVES  60
GVPARFSGSG SGTDFSLNIH PVEEDDIAMY FCQQSRKVPW TFGGGTKLEI K           111

SEQ ID NO: 467           moltype = AA  length = 121
FEATURE                  Location/Qualifiers
REGION                   1..121
                         note = KCD134 heavy chain variable region AA sequence
source                   1..121
                         mol_type = protein
                         organism = synthetic construct
SEQUENCE: 467
EVQLQQSGPE MVKPGASVKM SCQASGYTFT DYYMNWVKQS HGETLEWIGD IYPHNGYTAY  60
NQKFKGKATL TVDKSSSTAY MELRSLTSED SAVYYCARGG QLRLPAWFAY WGQGTLVTVS  120
A                                                                  121

SEQ ID NO: 468           moltype = AA  length = 107
FEATURE                  Location/Qualifiers
REGION                   1..107
                         note = KCD134 light chain variable region AA sequence
source                   1..107
                         mol_type = protein
                         organism = synthetic construct
SEQUENCE: 468
ETTVTQSPAS LSMAIGEKVT IRCITSTDID DDMNWYQQKP GEPPKLLISE GNSLRPGVPS  60
RFSSSGYGTD FVFTIEDMFS EDVADYHCLQ SDNLPYTFGG GTKLEIK                107

SEQ ID NO: 469           moltype = AA  length = 117
FEATURE                  Location/Qualifiers
REGION                   1..117
                         note = KCD135 heavy chain variable region AA sequence
source                   1..117
                         mol_type = protein
                         organism = synthetic construct
SEQUENCE: 469
EVQLQQSGPE LVKPGASVRM SCKASGYIFT DYSIHWVKQS HGKSLEWIGY INPNNGGTSY  60
NQKFKGKATL TVNKSSTTAY MELRSLTSED SAVYFCARDT TIVGDYWGQG TTLTVSS     117

SEQ ID NO: 470           moltype = AA  length = 107
FEATURE                  Location/Qualifiers
REGION                   1..107
                         note = KCD135 light chain variable region AA sequence
source                   1..107
                         mol_type = protein
                         organism = synthetic construct
SEQUENCE: 470
DIVMTQSQKF MSTSVGDRVS VTCKASQHVG TNVVWYQQKP GQSPKALIYS ASYRYSGVPD  60
RFSGSGSGTD FTLTISNVQS EDLAEYFCQQ FNSYPLTFGG GTKLEIK                107

SEQ ID NO: 471           moltype = AA  length = 113
FEATURE                  Location/Qualifiers
REGION                   1..113
                         note = KCD136 heavy chain variable region AA sequence
source                   1..113
                         mol_type = protein
                         organism = synthetic construct
SEQUENCE: 471
EVQLQQSVAE LVRPGASVKL SCSASGFNIK NTYMHWVNQR PEQGLEWIGR IDPANGITKY  60
APNFQGKATI TADTSSNTAY LQLSNLTSED TAIYYCTRAM DYWGQGTSVT VSS         113

SEQ ID NO: 472           moltype = AA  length = 106
FEATURE                  Location/Qualifiers
REGION                   1..106
                         note = KCD136 light chain variable region AA sequence
source                   1..106
                         mol_type = protein
                         organism = synthetic construct
SEQUENCE: 472
QIVLTQSPAI MSASPGEKVT MTCSASSSVS YMYWYQQKPG SSPRLLIYDI SNLASGVPVR  60
FSGSGSGTSY SLTISRMEAE DAATYYCQQW DTYPWTFGGG TKLEIK                 106

SEQ ID NO: 473           moltype = AA  length = 122
FEATURE                  Location/Qualifiers
REGION                   1..122
                         note = KCD137 heavy chain variable region AA sequence
source                   1..122
                         mol_type = protein
                         organism = synthetic construct
```

```
SEQUENCE: 473
EVQLVESGGD LVKPGGSLKL SCAASGFTFS GYGMSWVRQI PDKRLEWVAI SSRDNSFTYY  60
PDSVKGRFTI SRDNAKNTLY LQMSSLKSED TALYFCTRHP YLPTGGYVMD YWGQGTSVTV  120
SS                                                                122

SEQ ID NO: 474         moltype = AA  length = 107
FEATURE                Location/Qualifiers
REGION                 1..107
                       note = KCD137 light chain variable region AA sequence
source                 1..107
                       mol_type = protein
                       organism = synthetic construct
SEQUENCE: 474
DIVMTQSHKF MSTSVGDRVS ITCKASQDVG TAVAWYQQRP GQSPKLLIYW ASTRHTGVPD  60
RFTGSGSGTD FTLTVSNVQS EDLADYFCQQ YTSYPLTFGA GTKLELK               107

SEQ ID NO: 475         moltype = AA  length = 119
FEATURE                Location/Qualifiers
REGION                 1..119
                       note = KCD139 heavy chain variable region AA sequence
source                 1..119
                       mol_type = protein
                       organism = synthetic construct
SEQUENCE: 475
EVQLQQSGAE LVRPGSSVKM SCKTSGYTFT SYGINWVKQR PGQGLEWIGY IYIANGYTEN  60
NEKFKGKAKL TSDISSSTAY MQLSSLTSED SAIYFCARRF DYAGALDYWG QGTSVTVSS   119

SEQ ID NO: 476         moltype = AA  length = 111
FEATURE                Location/Qualifiers
REGION                 1..111
                       note = KCD139 light chain variable region AA sequence
source                 1..111
                       mol_type = protein
                       organism = synthetic construct
SEQUENCE: 476
DIVLTQSPAS LAVSLGQRAT ISCRASESVD SYGNSFMHWY QQKPGQPPKL LIHRASNLES  60
GIPARFSGSG SRTDFTLTIN PVEADDVAIY YCQQTNDDPY TFGGGTNLEI K           111

SEQ ID NO: 477         moltype = AA  length = 118
FEATURE                Location/Qualifiers
REGION                 1..118
                       note = KCD104 heavy chain variable region AA sequence
source                 1..118
                       mol_type = protein
                       organism = synthetic construct
SEQUENCE: 477
QVQLQQPGAE LVRPGTSVKL SCKASGYTFT SYWMHWVKQR PGQGLEWIGV IDPSDSYTYY  60
NQKFKGKATL TVDTSSSTAY MQLSSLTSED SAVYYCARNG YDGAMDYWGQ GTSVTVSS    118

SEQ ID NO: 478         moltype = AA  length = 107
FEATURE                Location/Qualifiers
REGION                 1..107
                       note = KCD104 light chain variable region AA sequence
source                 1..107
                       mol_type = protein
                       organism = synthetic construct
SEQUENCE: 478
EIQMTQTTSS LSASLGDRVT ISCRASQDIS NYLNWYQQKP DGTVKLLIYY PSRLHSGVPS  60
RFSGSGSGTD YSLTISNLEQ EDFATYFCQQ GNTLPYTFGG GTKLEIK               107

SEQ ID NO: 479         moltype = AA  length = 116
FEATURE                Location/Qualifiers
REGION                 1..116
                       note = KCD200 heavy chain variable region AA sequence
source                 1..116
                       mol_type = protein
                       organism = synthetic construct
SEQUENCE: 479
EVQLQQSGPE LVKPGASVKI SCKASGYTFT SYYKNWMRQR HGESLEWIGD INPNSGDTAY  60
NQKFKGKATL TVDRSSSTAY MELRSLTSED SAVYYCAREG PSFAYWGQGT LVTVSA      116

SEQ ID NO: 480         moltype = AA  length = 112
FEATURE                Location/Qualifiers
REGION                 1..112
                       note = KCD200 light chain variable region AA sequence
source                 1..112
                       mol_type = protein
                       organism = synthetic construct
SEQUENCE: 480
```

```
DVLMTQTPLS LPVSLGDQVS ISCRSSQTIV HSNGDTYLEW YLQKPGQSPN LLIYKVSNRF  60
SGVPDRFSGS GSGTDFTLKI SRVEAEDLGV YYCFQGSHVP PTFGGGTKLE IK          112

SEQ ID NO: 481          moltype = AA  length = 119
FEATURE                 Location/Qualifiers
REGION                  1..119
                        note = KCD210 heavy chain variable region AA sequence
source                  1..119
                        mol_type = protein
                        organism = synthetic construct
SEQUENCE: 481
EVQLQQSGPV LVKPGASVTM SCKASGYTFT EYYMNWVKQS HGKSLDWIGV INPYSGGTSY  60
KQKFKDKATL TVDKSSSTAY MELNGLTSED SAVYFCVRGG LRRNYFDYWG QGTTLTVSS   119

SEQ ID NO: 482          moltype = AA  length = 108
FEATURE                 Location/Qualifiers
REGION                  1..108
                        note = KCD210 light chain variable region AA sequence
source                  1..108
                        mol_type = protein
                        organism = synthetic construct
SEQUENCE: 482
EIVLTQSPAL MTASPGEKVT ITCSVSSSIS STNLHWYQQK SGTSPKPWIF GTSNLASGVP  60
VRFSGSGSGT SYSLTISNME AEDAATYYCQ QWNSYPFTFG TGTKLEIK              108

SEQ ID NO: 483          moltype = AA  length = 121
FEATURE                 Location/Qualifiers
REGION                  1..121
                        note = KCD212 heavy chain variable region AA sequence
source                  1..121
                        mol_type = protein
                        organism = synthetic construct
SEQUENCE: 483
EVHLVESGGD LVKPGGSLKL SCAASGFTFS RYGMSWVRQT PDKRLEWVAT ISSAGSYTYY  60
PDSVKGRFTI SRDNAKNTLF LQMSSLKSED TAMYYCARPL NYYGTSSFDY WGQGTTLTVS  120
S                                                                 121

SEQ ID NO: 484          moltype = AA  length = 108
FEATURE                 Location/Qualifiers
REGION                  1..108
                        note = KCD212 light chain variable region AA sequence
source                  1..108
                        mol_type = protein
                        organism = synthetic construct
SEQUENCE: 484
QIVLTQSPAI MSASPGEKVT MTCRASSSVS STYLHWYQQK PGSSPKLWIY STSNLASGVP  60
PRFSGSGSGT SYSLTISSVE AEDAATYYCQ QYDSSPNTFG AGTKLELK              108

SEQ ID NO: 485          moltype = AA  length = 115
FEATURE                 Location/Qualifiers
REGION                  1..115
                        note = KCD214 heavy chain variable region AA sequence
source                  1..115
                        mol_type = protein
                        organism = synthetic construct
SEQUENCE: 485
EVQLQQSVAE FVRPGASVKL SCTASGFNIK NTYMHWVKQR PEQGLEWIGR IDPANGNTEY  60
APKFQGKATI TADTSSNTAY LQLSSLTSED TAIYYCALYD YDGYWGQGTT LTVSS       115

SEQ ID NO: 486          moltype = AA  length = 108
FEATURE                 Location/Qualifiers
REGION                  1..108
                        note = KCD214 light chain variable region AA sequence
source                  1..108
                        mol_type = protein
                        organism = synthetic construct
SEQUENCE: 486
EIVLTQSPAL MAASPGEKVT ITCRVSSSIS SSSLHWYQQK SGTSPKPWIY GTSNLASGVP  60
VRFSGSRSGT SYSLTISSME AEDAATYYCQ QWSDYPWTFG GGTKLEIK              108

SEQ ID NO: 487          moltype = AA  length = 122
FEATURE                 Location/Qualifiers
REGION                  1..122
                        note = KCD216 heavy chain variable region AA sequence
source                  1..122
                        mol_type = protein
                        organism = synthetic construct
SEQUENCE: 487
QVHLQQSGPE LVKPGASVKI SCKASGYTFI DYYINWVKQR PGQGLEWIGW IFPGSDSTYY  60
```

-continued

```
NEKFKGKATL TVDKSSSTAY MLLSSLTSED SAVYFCARYG YYGSSFYAMD YWGQGTSVTV  120
SS                                                                 122

SEQ ID NO: 488          moltype = AA  length = 107
FEATURE                 Location/Qualifiers
REGION                  1..107
                        note = KCD216 light chain variable region AA sequence
source                  1..107
                        mol_type = protein
                        organism = synthetic construct
SEQUENCE: 488
DIQMTQSPAS LSVSVGETVT ITCRASENIY SNLAWYQQKQ GKSPQLLVYA ATNLADGVPS  60
RFSGSGSGTQ YSLKINSLQS EDFGSYYCQH FWGTPPTFGG GSKLEIK                107

SEQ ID NO: 489          moltype = AA  length = 118
FEATURE                 Location/Qualifiers
REGION                  1..118
                        note = KCD217 heavy chain variable region AA sequence
source                  1..118
                        mol_type = protein
                        organism = synthetic construct
SEQUENCE: 489
QVQVQQPGAE FVKTGASVKL SCKTSGYTFI DYWIHWVKQR PGHGLEWIGR IDPNTGGSKY  60
YEKFKRKATL TVDKPSRTVY MQLSSLTSED SAVYYCTREY DYGWFGYWGQ GTLVTVSE    118

SEQ ID NO: 490          moltype = AA  length = 107
FEATURE                 Location/Qualifiers
REGION                  1..107
                        note = KCD217 light chain variable region AA sequence
source                  1..107
                        mol_type = protein
                        organism = synthetic construct
SEQUENCE: 490
DIQMTQSPAS LSASVGETVT ITCGASENIY GALNWYQRKQ GKSPQLLIYG ATNLADGMSS  60
RFSGSGSGRQ YSLKISSLHP DDVATYYCQN VLSTPWTFGG GTKLEIK                107

SEQ ID NO: 491          moltype = AA  length = 122
FEATURE                 Location/Qualifiers
REGION                  1..122
                        note = KCD219 heavy chain variable region AA sequence
source                  1..122
                        mol_type = protein
                        organism = synthetic construct
SEQUENCE: 491
QVQLQQSGPE LVKPGASVKI SCKASGYTFT DYYINWVKQR PGQGLEWIGW IFPGSGSTYY  60
NEKFKGKATL TVDKSSSTAY MLLSSLPSED SAVYFCARYG YYGSSFYAMD YWGQGTSVTV  120
SS                                                                 122

SEQ ID NO: 492          moltype = AA  length = 107
FEATURE                 Location/Qualifiers
REGION                  1..107
                        note = KCD219 light chain variable region AA sequence
source                  1..107
                        mol_type = protein
                        organism = synthetic construct
SEQUENCE: 492
DIQMTQSPAS LSVSVGETVT ITCRASENIY SNLAWYQQKQ GKSPQLLVYA ATNLADGVPS  60
RFSGSGSGTQ YSLKINSLQS EDFGSYYCQH FWGSPPTFGG GTKLEIK                107

SEQ ID NO: 493          moltype = AA  length = 119
FEATURE                 Location/Qualifiers
REGION                  1..119
                        note = KCD220 heavy chain variable region AA sequence
source                  1..119
                        mol_type = protein
                        organism = synthetic construct
SEQUENCE: 493
QVQLQQSGAE LMEPGASVKL SCKATGYTFT GYWIEWVKQR PGHGLEWIGE TLPGSDSNNY  60
NEKFKGKATF TADTSSNTAY MQLSSLTTED SAIYYCARDY SNYWYFDVWG TGTTVTVSS   119

SEQ ID NO: 494          moltype = AA  length = 106
FEATURE                 Location/Qualifiers
REGION                  1..106
                        note = KCD220 light chain variable region AA sequence
source                  1..106
                        mol_type = protein
                        organism = synthetic construct
SEQUENCE: 494
DIQMTQTTSS LSASLGDRVT ISCRASQDIS NYLNWYQQKP DGTVKLLIYY TSNLHSGVPS  60
```

-continued

```
RFSGSGSGTD YSLTISNLEQ EDIATYFCQQ DSKHRTFGGG TKLEIK                106

SEQ ID NO: 495         moltype = AA  length = 119
FEATURE                Location/Qualifiers
REGION                 1..119
                       note = KCD224 heavy chain variable region AA sequence
source                 1..119
                       mol_type = protein
                       organism = synthetic construct
SEQUENCE: 495
QVQLKESGPG LVAPSQSLSI TCTVSGFSLT SYGVDWIRQS PGKGLEWLGV IWGVGSTNYN  60
SALKSRLSIS KDNSKSQVFL KMNSLQTDDT AMYYCARSYD GSYWYFDVWG TGTTVTVSS   119

SEQ ID NO: 496         moltype = AA  length = 107
FEATURE                Location/Qualifiers
REGION                 1..107
                       note = KCD224 light chain variable region AA sequence
source                 1..107
                       mol_type = protein
                       organism = synthetic construct
SEQUENCE: 496
DIQMTQTTSS LSASLGDRVT ISCRASQVIS NYLNWYQQKP DGTVKLLIYY TSRLHSGVPS  60
RFSGSGSGTD YSLTISNLEP EDIATYYCQQ YSKLPYTFGS GTKLEIK                107

SEQ ID NO: 497         moltype = AA  length = 122
FEATURE                Location/Qualifiers
REGION                 1..122
                       note = KCD225 heavy chain variable region AA sequence
source                 1..122
                       mol_type = protein
                       organism = synthetic construct
SEQUENCE: 497
QVQLQQSGPE LVKPGASVKI SCKASGYTFT DYYINWMKQR PGQGLEWIGW IFPGSDSTYY  60
NEKFKGKATL TVDKSSSTAY MLLSSLTSED SAVYFCARLG YYSHSYYAMD YWGQGTSVTV  120
SS                                                                 122

SEQ ID NO: 498         moltype = AA  length = 107
FEATURE                Location/Qualifiers
REGION                 1..107
                       note = KCD225 light chain variable region AA sequence
source                 1..107
                       mol_type = protein
                       organism = synthetic construct
SEQUENCE: 498
DIQMTQSPAS LSVSTGETVT ITCRASENIY SNLAWFQQKQ GKSPQLLVYA ATNLADGVPS  60
RFSGSGSGTQ YSLKITSLQS EDFGSYYCQH FWGTPLTFGA GTKLDLK                107

SEQ ID NO: 499         moltype = AA  length = 120
FEATURE                Location/Qualifiers
REGION                 1..120
                       note = KCD229 heavy chain variable region AA sequence
source                 1..120
                       mol_type = protein
                       organism = synthetic construct
SEQUENCE: 499
EVQLVESGGG LVQPKGSLKL SCAASGFSFN TYAMNWVRQA PGKGLEWVAR IRSKSNNYAT  60
YYADSVKDRF TIFRDDSESM LYLQMNNLKT EDTAMYYCVR HGYYWYFDVW GTGTTVTVSS  120

SEQ ID NO: 500         moltype = AA  length = 112
FEATURE                Location/Qualifiers
REGION                 1..112
                       note = KCD229 light chain variable region AA sequence
source                 1..112
                       mol_type = protein
                       organism = synthetic construct
SEQUENCE: 500
DVLMTQNPLS LPVSLGDQAS ISCRSSQSIV HSNGNTYLEW YLQKPGQSPN LLIYNVFNRF  60
SGVPDRFSGS GSGTDFTLKI SRVEAEDLGV YYCFQGSHVP YTFGSGTKLE IK          112

SEQ ID NO: 501         moltype = AA  length = 118
FEATURE                Location/Qualifiers
REGION                 1..118
                       note = KCD230 heavy chain variable region AA sequence
source                 1..118
                       mol_type = protein
                       organism = synthetic construct
SEQUENCE: 501
QVQLQQPGTE LVKPGASVKL PCKASGYTFT SYWMQWVKQR PGQGLEWIGE IDPSDTYINY  60
NQKFKGKATL TVDTSSTTAY MQLSSLTSED SAVYYCARYT TIMASDYWGQ GTTLTVSS    118
```

```
SEQ ID NO: 502         moltype = AA  length = 107
FEATURE                Location/Qualifiers
REGION                 1..107
                       note = KCD230 light chain variable region AA sequence
source                 1..107
                       mol_type = protein
                       organism = synthetic construct
SEQUENCE: 502
DIQMTQTTSS LSVSLGDRVT ISCRASQDIT NYLNWYQQKP DGTVKLLIYF TSRLHSGVPS  60
RFSGSGSGTD YSLTISNLEP EDIATYYCQQ YSKLPWTFGG GTKLEIK                107

SEQ ID NO: 503         moltype = AA  length = 120
FEATURE                Location/Qualifiers
REGION                 1..120
                       note = KCD232 heavy chain variable region AA sequence
source                 1..120
                       mol_type = protein
                       organism = synthetic construct
SEQUENCE: 503
EVQLVESGGG LVQPKGSLKL SCAASGFSFN TYAMNWVRQA PGKGLEWVAR IRSKSNNYAT  60
YYADSVKDRF TISRDDSESM VYLQMNNLKT EDTAMYYCVR HGYYWYFDVW GTGTTVTVSS  120

SEQ ID NO: 504         moltype = AA  length = 112
FEATURE                Location/Qualifiers
REGION                 1..112
                       note = KCD232 light chain variable region AA sequence
source                 1..112
                       mol_type = protein
                       organism = synthetic construct
SEQUENCE: 504
DVLMTQTPLS LPVSLGDQAS ISCRSSQSIV HSDGNTYLEW YLQKPGQSPK LLIYRVSNRF  60
SGVPDRFSGS GSGTDFTLKI SRMEAEDLGV YYCFQGSHVP YTFGGGTKLE IK          112

SEQ ID NO: 505         moltype = AA  length = 119
FEATURE                Location/Qualifiers
REGION                 1..119
                       note = KCD205 heavy chain variable region AA sequence
source                 1..119
                       mol_type = protein
                       organism = synthetic construct
SEQUENCE: 505
EVQLQQSGAE LVRPGSSVKM SCKTSGNTFT SHGINWVKQR PGQGLEWIGY IYIGNGYNEY  60
NEKFKGKATL TSDTSSSTAY MQLSSLTSED SAIYFCVRKA YGNYGFDDWG QGTTLTVSS   119

SEQ ID NO: 506         moltype = AA  length = 107
FEATURE                Location/Qualifiers
REGION                 1..107
                       note = KCD205 light chain variable region AA sequence
source                 1..107
                       mol_type = protein
                       organism = synthetic construct
SEQUENCE: 506
DIQMTQSPSS LSASLGERVS LTCRASQEIS GYLSWLQQKP DGTIKRLIYA ASTLDSGVPK  60
RFSGSSSGSD YSLTISSLES DDFADYYCLQ YASYPFTFGS GTKLEIK                107

SEQ ID NO: 507         moltype = AA  length = 120
FEATURE                Location/Qualifiers
REGION                 1..120
                       note = KCD207 heavy chain variable region AA sequence
source                 1..120
                       mol_type = protein
                       organism = synthetic construct
SEQUENCE: 507
AVQLVESGGG LVQPKGSLKL SCAASGFSFN TYAMNWVRQA PGKGLEWVAR IRSKSNNYAT  60
YYADSVKDRF TLSRDDSESM LYLQMNNLKT EDTAMYYCVR QGFYWYFDVW GTGTTVTVSS  120

SEQ ID NO: 508         moltype = AA  length = 112
FEATURE                Location/Qualifiers
REGION                 1..112
                       note = KCD207 light chain variable region AA sequence
source                 1..112
                       mol_type = protein
                       organism = synthetic construct
SEQUENCE: 508
DVLMTQTPLS LPVSLGDQAS ISCRSSQTIV HSNGNTYLEW YLQKSGQSPK LLIYNVSNRF  60
SGVPDRFRGS GSGTDFTLKI SRVEAEDLGV YYCFQGSHVP YTFGSGTKLE IK          112

SEQ ID NO: 509         moltype = AA  length = 115
```

-continued

```
FEATURE                Location/Qualifiers
REGION                 1..115
                       note = KCD208 heavy chain variable region AA sequence
source                 1..115
                       mol_type = protein
                       organism = synthetic construct
SEQUENCE: 509
EVQLQQSVAE LVRPGASVKL SCTVSGFNIK NTYMHWVKQR PEQGLEWIGR IDPANGDTTY  60
APKFQGKATI TADTSSNSAY LHLSRLTSED TAIYYCSLYD YDGYWGQGTT LTVSS       115

SEQ ID NO: 510         moltype = AA  length = 108
FEATURE                Location/Qualifiers
REGION                 1..108
                       note = KCD208 light chain variable region AA sequence
source                 1..108
                       mol_type = protein
                       organism = synthetic construct
SEQUENCE: 510
EIVLTQSPAL MAASPGEKVT ITCSVSSSIS SSSLHWYRQK SGTSPKPWIY GTSHLASGVP  60
VRFSGSGSGT SYSLTISSME AEDAATYYCQ QWDTYPWTFG GGTKLEIK               108

SEQ ID NO: 511         moltype = DNA  length = 29
FEATURE                Location/Qualifiers
misc_feature           1..29
                       note = Primer RDJ121
source                 1..29
                       mol_type = other DNA
                       organism = synthetic construct
SEQUENCE: 511
gatcgaattc ggaggtgcag ctggtggaa                                    29

SEQ ID NO: 512         moltype = DNA  length = 22
FEATURE                Location/Qualifiers
misc_feature           1..22
                       note = Primer RDJ122
source                 1..22
                       mol_type = other DNA
                       organism = synthetic construct
SEQUENCE: 512
gatcggagga cactgtcacc ag                                           22

SEQ ID NO: 513         moltype = AA  length = 116
FEATURE                Location/Qualifiers
REGION                 1..116
                       note = KCD119 TAF heavy chain
source                 1..116
                       mol_type = protein
                       organism = synthetic construct
SEQUENCE: 513
EVQLVESGGG LVQPGGSLRL SCAASGYTFT DYYMNWVRQA PGKGLEWIGD INPNTGDTSY  60
NADFKRRFTF SLDTSKSTAY LQMNSLRAED TAVYYCTREG PSFAYWGQGT LVTVSS      116

SEQ ID NO: 514         moltype = AA  length = 116
FEATURE                Location/Qualifiers
REGION                 1..116
                       note = 54V heavy chain
source                 1..116
                       mol_type = protein
                       organism = synthetic construct
SEQUENCE: 514
EVQLVESGGG LVQPGGSLRL SCAASGYTFT DYYMNWVRQA PGKGLEWIGD INPVTGDTSY  60
NADFKRRFTF SLDTSKSTAY LQMNSLRAED TAVYYCTREG PSFAYWGQGT LVTVSS      116

SEQ ID NO: 515         moltype = AA  length = 116
FEATURE                Location/Qualifiers
REGION                 1..116
                       note = 54I heavy chain
source                 1..116
                       mol_type = protein
                       organism = synthetic construct
SEQUENCE: 515
EVQLVESGGG LVQPGGSLRL SCAASGYTFT DYYMNWVRQA PGKGLEWIGD INPITGDTSY  60
NADFKRRFTF SLDTSKSTAY LQMNSLRAED TAVYYCTREG PSFAYWGQGT LVTVSS      116

SEQ ID NO: 516         moltype = AA  length = 116
FEATURE                Location/Qualifiers
REGION                 1..116
                       note = 54V59D heavy chain
source                 1..116
```

```
                        mol_type = protein
                        organism = synthetic construct
SEQUENCE: 516
EVQLVESGGG LVQPGGSLRL SCAASGYTFT DYYMNWVRQA PGKGLEWIGD INPVTGDTDY  60
NADFKRRFTF SLDTSKSTAY LQMNSLRAED TAVYYCTREG PSFAYWGQGT LVTVSS      116

SEQ ID NO: 517          moltype = AA  length = 116
FEATURE                 Location/Qualifiers
REGION                  1..116
                        note = 54I59D heavy chain
source                  1..116
                        mol_type = protein
                        organism = synthetic construct
SEQUENCE: 517
EVQLVESGGG LVQPGGSLRL SCAASGYTFT DYYMNWVRQA PGKGLEWIGD INPITGDTDY  60
NADFKRRFTF SLDTSKSTAY LQMNSLRAED TAVYYCTREG PSFAYWGQGT LVTVSS      116

SEQ ID NO: 518          moltype = AA  length = 116
FEATURE                 Location/Qualifiers
REGION                  1..116
                        note = 34I54I59D heavy chain
source                  1..116
                        mol_type = protein
                        organism = synthetic construct
SEQUENCE: 518
EVQLVESGGG LVQPGGSLRL SCAASGYTFT DYYINWVRQA PGKGLEWIGD INPITGDTDY  60
NADFKRRFTF SLDTSKSTAY LQMNSLRAED TAVYYCTREG PSFAYWGQGT LVTVSS      116

SEQ ID NO: 519          moltype = AA  length = 116
FEATURE                 Location/Qualifiers
REGION                  1..116
                        note = 31S34I54I59D heavy chain
source                  1..116
                        mol_type = protein
                        organism = synthetic construct
SEQUENCE: 519
EVQLVESGGG LVQPGGSLRL SCAASGYTFT SYYINWVRQA PGKGLEWIGD INPITGDTDY  60
NADFKRRFTF SLDTSKSTAY LQMNSLRAED TAVYYCTREG PSFAYWGQGT LVTVSS      116

SEQ ID NO: 520          moltype = AA  length = 116
FEATURE                 Location/Qualifiers
REGION                  1..116
                        note = 34I54I59D84S heavy chain
source                  1..116
                        mol_type = protein
                        organism = synthetic construct
SEQUENCE: 520
EVQLVESGGG LVQPGGSLRL SCAASGYTFT DYYINWVRQA PGKGLEWIGD INPITGDTDY  60
NADFKRRFTF SLDTSKSTAY LQMSSLRAED TAVYYCTREG PSFAYWGQGT LVTVSS      116

SEQ ID NO: 521          moltype = AA  length = 116
FEATURE                 Location/Qualifiers
REGION                  1..116
                        note = 31S34I54I59D84S heavy chain
source                  1..116
                        mol_type = protein
                        organism = synthetic construct
SEQUENCE: 521
EVQLVESGGG LVQPGGSLRL SCAASGYTFT SYYINWVRQA PGKGLEWIGD INPITGDTDY  60
NADFKRRFTF SLDTSKSTAY LQMSSLRAED TAVYYCTREG PSFAYWGQGT LVTVSS      116

SEQ ID NO: 522          moltype = AA  length = 112
FEATURE                 Location/Qualifiers
REGION                  1..112
                        note = KCD119 TAF light chain
source                  1..112
                        mol_type = protein
                        organism = synthetic construct
SEQUENCE: 522
DIQLTQSPSS LSASVGDRVT ITCRSSQTIV HSNGDTYLEW YQQKPGKAPN LLIYKVSNRF  60
SGVPSRFSGS GSGTDFTLTI SSLQPEDFAT YYCFQGSHVP PTFGQGTKVE IK          112

SEQ ID NO: 523          moltype = AA  length = 112
FEATURE                 Location/Qualifiers
REGION                  1..112
                        note = 54R light chain
source                  1..112
                        mol_type = protein
                        organism = synthetic construct
```

```
SEQUENCE: 523
DIQLTQSPSS LSASVGDRVT ITCRSSQTIV HSNGDTYLEW YQQKPGKAPN LLIRKVSNRF  60
SGVPSRFSGS GSGTDFTLTI SSLQPEDFAT YYCFQGSHVP PTFGQGTKVE IK          112

SEQ ID NO: 524         moltype = AA  length = 112
FEATURE                Location/Qualifiers
REGION                 1..112
                       note = 101V light chain
source                 1..112
                       mol_type = protein
                       organism = synthetic construct
SEQUENCE: 524
DIQLTQSPSS LSASVGDRVT ITCRSSQTIV HSNGDTYLEW YQQKPGKAPN LLIYKVSNRF  60
SGVPSRFSGS GSGTDFTLTI SSLQPEDFAT YYCFQGSHVP VTFGQGTKVE IK          112

SEQ ID NO: 525         moltype = AA  length = 112
FEATURE                Location/Qualifiers
REGION                 1..112
                       note = 54R101V light chain
source                 1..112
                       mol_type = protein
                       organism = synthetic construct
SEQUENCE: 525
DIQLTQSPSS LSASVGDRVT ITCRSSQTIV HSNGDTYLEW YQQKPGKAPN LLIRKVSNRF  60
SGVPSRFSGS GSGTDFTLTI SSLQPEDFAT YYCFQGSHVP VTFGQGTKVE IK          112

SEQ ID NO: 526         moltype = AA  length = 112
FEATURE                Location/Qualifiers
REGION                 1..112
                       note = 54G101V light chain
source                 1..112
                       mol_type = protein
                       organism = synthetic construct
SEQUENCE: 526
DIQLTQSPSS LSASVGDRVT ITCRSSQTIV HSNGDTYLEW YQQKPGKAPN LLIGKVSNRF  60
SGVPSRFSGS GSGTDFTLTI SSLQPEDFAT YYCFQGSHVP VTFGQGTKVE IK          112

SEQ ID NO: 527         moltype = DNA  length = 348
FEATURE                Location/Qualifiers
misc_feature           1..348
                       note = KCD119 Taf heavy chain
source                 1..348
                       mol_type = other DNA
                       organism = synthetic construct
SEQUENCE: 527
gaggtgcagc tggtggaatc tggcggcgga ctggtgcagc ctggcggctc cctgagactg  60
tcttgcgccg cctccggcta caccttcacc gactactaca tgaactgggt gcgacaggcc  120
cctggcaagg gcctggaatg gatcggcgac atcaacccca acaccggcga caccagctac  180
aacgccgact tcaagcggcg gttcaccttc tccctggaca cctccaagtc caccgcctac  240
ctgcagatga actccctgcg ggccgaggac accgccgtgt actactgtac cagagagggc  300
ccctccttcg cctactgggg ccagggcaca ctggtgacag tgtcctcc              348

SEQ ID NO: 528         moltype = DNA  length = 348
FEATURE                Location/Qualifiers
misc_feature           1..348
                       note = 54V heavy chain
source                 1..348
                       mol_type = other DNA
                       organism = synthetic construct
SEQUENCE: 528
gaggtgcagc tggtggaatc tggcggcgga ctggtgcagc ctggcggctc cctgagactg  60
tcttgcgccg cctccggcta caccttcacc gactactaca tgaactgggt gcgacaggcc  120
cctggcaagg gcctggaatg gatcggcgac atcaaccccg tcaccggcga caccagctac  180
aacgccgact tcaagcggcg gttcaccttc tccctggaca cctccaagtc caccgcctac  240
ctgcagatga actccctgcg ggccgaggac accgccgtgt actactgtac cagagagggc  300
ccctccttcg cctactgggg ccagggcaca ctggtgacag tgtcctcc              348

SEQ ID NO: 529         moltype = DNA  length = 348
FEATURE                Location/Qualifiers
misc_feature           1..348
                       note = 54I heavy chain
source                 1..348
                       mol_type = other DNA
                       organism = synthetic construct
SEQUENCE: 529
gaggtgcagc tggtggaatc tggcggcgga ctggtgcagc ctggcggctc cctgagactg  60
tcttgcgccg cctccggcta caccttcacc gactactaca tgaactgggt gcgacaggcc  120
cctggcaagg gcctggaatg gatcggcgac atcaacccca tcaccggcga caccagctac  180
aacgccgact tcaagcggcg gttcaccttc tccctggaca cctccaagtc caccgcctac  240
```

```
ctgcagatga actccctgcg ggccgaggac accgccgtgt actactgtac cagagagggc  300
ccctccttcg cctactgggg ccagggcaca ctggtgacag tgtcctcc              348

SEQ ID NO: 530         moltype = DNA  length = 348
FEATURE                Location/Qualifiers
misc_feature           1..348
                       note = 54V59D heavy chain
source                 1..348
                       mol_type = other DNA
                       organism = synthetic construct
SEQUENCE: 530
gaggtgcagc tggtggaatc tggcggcgga ctggtgcagc ctggcggctc cctgagactg  60
tcttgcgccg cctccggcta caccttcacc gactactaca tgaactgggt gcgacaggcc  120
cctggcaagg gcctggaatg gatcggcgac atcaaccccg tcaccggcga caccgactac  180
aacgccgact tcaagcggcg gttcaccttc tccctggaca cctccaagtc caccgcctac  240
ctgcagatga actccctgcg ggccgaggac accgccgtgt actactgtac cagagagggc  300
ccctccttcg cctactgggg ccagggcaca ctggtgacag tgtcctcc              348

SEQ ID NO: 531         moltype = DNA  length = 348
FEATURE                Location/Qualifiers
misc_feature           1..348
                       note = 54I59D heavy chain
source                 1..348
                       mol_type = other DNA
                       organism = synthetic construct
SEQUENCE: 531
gaggtgcagc tggtggaatc tggcggcgga ctggtgcagc ctggcggctc cctgagactg  60
tcttgcgccg cctccggcta caccttcacc gactactaca tgaactgggt gcgacaggcc  120
cctggcaagg gcctggaatg gatcggcgac atcaacccca tcaccggcga caccgactac  180
aacgccgact tcaagcggcg gttcaccttc tccctggaca cctccaagtc caccgcctac  240
ctgcagatga actccctgcg ggccgaggac accgccgtgt actactgtac cagagagggc  300
ccctccttcg cctactgggg ccagggcaca ctggtgacag tgtcctcc              348

SEQ ID NO: 532         moltype = DNA  length = 348
FEATURE                Location/Qualifiers
misc_feature           1..348
                       note = 34I54I59D heavy chain
source                 1..348
                       mol_type = other DNA
                       organism = synthetic construct
SEQUENCE: 532
gaggtgcagc tggtggaatc tggcggcgga ctggtgcagc ctggcggctc cctgagactg  60
tcttgcgccg cctccggcta caccttcacc gactactaca tcaactgggt gcgacaggcc  120
cctggcaagg gcctggaatg gatcggcgac atcaacccca tcaccggcga caccgactac  180
aacgccgact tcaagcggcg gttcaccttc tccctggaca cctccaagtc caccgcctac  240
ctgcagatga actccctgcg ggccgaggac accgccgtgt actactgtac cagagagggc  300
ccctccttcg cctactgggg ccagggcaca ctggtgacag tgtcctcc              348

SEQ ID NO: 533         moltype = DNA  length = 348
FEATURE                Location/Qualifiers
misc_feature           1..348
                       note = 31S34I54I59D heavy chain
source                 1..348
                       mol_type = other DNA
                       organism = synthetic construct
SEQUENCE: 533
gaggtgcagc tggtggaatc tggcggcgga ctggtgcagc ctggcggctc cctgagactg  60
tcttgcgccg cctccggcta caccttcacc agctactaca tcaactgggt gcgacaggcc  120
cctggcaagg gcctggaatg gatcggcgac atcaacccca tcaccggcga caccgactac  180
aacgccgact tcaagcggcg gttcaccttc tccctggaca cctccaagtc caccgcctac  240
ctgcagatga actccctgcg ggccgaggac accgccgtgt actactgtac cagagagggc  300
ccctccttcg cctactgggg ccagggcaca ctggtgacag tgtcctcc              348

SEQ ID NO: 534         moltype = DNA  length = 348
FEATURE                Location/Qualifiers
misc_feature           1..348
                       note = 34I54I59D84S heavy chain
source                 1..348
                       mol_type = other DNA
                       organism = synthetic construct
SEQUENCE: 534
gaggtgcagc tggtggaatc tggcggcgga ctggtgcagc ctggcggctc cctgagactg  60
tcttgcgccg cctccggcta caccttcacc gactactaca tcaactgggt gcgacaggcc  120
cctggcaagg gcctggaatg gatcggcgac atcaacccca tcaccggcga caccgactac  180
aacgccgact tcaagcggcg gttcaccttc tccctggaca cctccaagtc caccgcctac  240
ctgcagatga gctccctgcg ggccgaggac accgccgtgt actactgtac cagagagggc  300
ccctccttcg cctactgggg ccagggcaca ctggtgacag tgtcctcc              348

SEQ ID NO: 535         moltype = DNA  length = 348
```

```
FEATURE                 Location/Qualifiers
misc_feature            1..348
                        note = 31S34I54I59D84S heavy chain
source                  1..348
                        mol_type = other DNA
                        organism = synthetic construct
SEQUENCE: 535
gaggtgcagc tggtggaatc tggcggcgga ctggtgcagc ctggcggctc cctgagactg  60
tcttgcgccg cctccggcta caccttcacc agctactaca tcaactgggt gcgacaggcc  120
cctggcaagg gcctggaatg gatcggcgac atcaacccca tcaccggcga caccgactac  180
aacgccgact tcaagcggcg gttcaccttc tccctggaca cctccaagtc caccgcctac  240
ctgcagatga gctccctgcg ggccgaggac accgccgtgt actactgtac cagagagggc  300
ccctccttcg cctactgggg ccagggcaca ctggtgacag tgtcctcc              348

SEQ ID NO: 536          moltype = DNA  length = 336
FEATURE                 Location/Qualifiers
misc_feature            1..336
                        note = KCD119 Taf light chain
source                  1..336
                        mol_type = other DNA
                        organism = synthetic construct
SEQUENCE: 536
gacatccagc tgacccagag cccctccagc ctgtccgcct ctgtgggcga cagagtgacc  60
atcacctgtc ggtcctccca gaccatcgtg cactccaacg gcgacaccta cctggaatgg  120
tatcagcaga agcccggcaa ggcccctaac ctgctgatct acaaggtgtc caaccggttc  180
tccggcgtgc cctccagatt ctccggctcc ggctctggca ccgacttcac cctgaccatc  240
tccagcctgc agcccgagga cttcgccacc tactactgtt ttcaaggctc ccacgtgcca  300
cccaccttcg gccagggcac caaggtggaa atcaag                            336

SEQ ID NO: 537          moltype = DNA  length = 335
FEATURE                 Location/Qualifiers
misc_feature            1..335
                        note = 54R light chain
source                  1..335
                        mol_type = other DNA
                        organism = synthetic construct
SEQUENCE: 537
gacatccagc tgacccagag cccctccagc ctgtccgcct ctgtgggcga cagagtgacc  60
atcacctgtc ggtcctccca gaccatcgtg cactccaacg gcgacaccta cctggaatgg  120
tatcagcaga agcccggcaa ggcccctaac ctgctgatcc gcaaggtgtc caaccggttc  180
tccggcgtgc cctccagatt ctccggctcc ggctctggca ccgacttcac cctgaccatc  240
tccagcctgc agcccgagga cttcgccacc tactactgtt ttcaaggctc ccacgtgcca  300
cccaccttcg gccagggcac caaggtggaa atcaa                             335

SEQ ID NO: 538          moltype = DNA  length = 336
FEATURE                 Location/Qualifiers
misc_feature            1..336
                        note = 101V light chain
source                  1..336
                        mol_type = other DNA
                        organism = synthetic construct
SEQUENCE: 538
gacatccagc tgacccagag cccctccagc ctgtccgcct ctgtgggcga cagagtgacc  60
atcacctgtc ggtcctccca gaccatcgtg cactccaacg gcgacaccta cctggaatgg  120
tatcagcaga agcccggcaa ggcccctaac ctgctgatct acaaggtgtc caaccggttc  180
tccggcgtgc cctccagatt ctccggctcc ggctctggca ccgacttcac cctgaccatc  240
tccagcctgc agcccgagga cttcgccacc tactactgtt ttcaaggctc ccacgtgcca  300
gtcaccttcg gccagggcac caaggtggaa atcaag                            336

SEQ ID NO: 539          moltype = DNA  length = 336
FEATURE                 Location/Qualifiers
misc_feature            1..336
                        note = 54R101V light chain
source                  1..336
                        mol_type = other DNA
                        organism = synthetic construct
SEQUENCE: 539
gacatccagc tgacccagag cccctccagc ctgtccgcct ctgtgggcga cagagtgacc  60
atcacctgtc ggtcctccca gaccatcgtg cactccaacg gcgacaccta cctggaatgg  120
tatcagcaga agcccggcaa ggcccctaac ctgctgatcc gcaaggtgtc caaccggttc  180
tccggcgtgc cctccagatt ctccggctcc ggctctggca ccgacttcac cctgaccatc  240
tccagcctgc agcccgagga cttcgccacc tactactgtt ttcaaggctc ccacgtgcca  300
gtcaccttcg gccagggcac caaggtggaa atcaag                            336

SEQ ID NO: 540          moltype = DNA  length = 336
FEATURE                 Location/Qualifiers
misc_feature            1..336
                        note = 54G101V light chain
source                  1..336
```

```
                         mol_type = other DNA
                         organism = synthetic construct
SEQUENCE: 540
gacatccagc tgacccagag cccctccagc ctgtccgcct ctgtgggcga cagagtgacc  60
atcacctgtc ggtcctccca gaccatcgtg cactccaacg gcgacaccta cctggaatgg  120
tatcagcaga agcccggcaa ggcccctaac ctgctgatcg gaaaggtgtc caaccggttc  180
tccggcgtgc cctccagatt ctccggctcc ggctctggca ccgacttcac cctgaccatc  240
tccagcctgc agcccgagga cttcgccacc tactactgtt ttcaaggctc ccacgtgcca  300
gtcaccttcg gccagggcac caaggtggaa atcaag                            336

SEQ ID NO: 541           moltype =   length =
SEQUENCE: 541
000

SEQ ID NO: 542           moltype = AA  length = 8
FEATURE                  Location/Qualifiers
REGION                   1..8
                         note = HCDR2
source                   1..8
                         mol_type = protein
                         organism = synthetic construct
SEQUENCE: 542
INPITGDT                                                            8

SEQ ID NO: 543           moltype = AA  length = 7
FEATURE                  Location/Qualifiers
REGION                   1..7
                         note = HCDR3
source                   1..7
                         mol_type = protein
                         organism = synthetic construct
SEQUENCE: 543
EGPSFAY                                                             7

SEQ ID NO: 544           moltype = AA  length = 10
FEATURE                  Location/Qualifiers
REGION                   1..10
                         note = LCDR1
source                   1..10
                         mol_type = protein
                         organism = synthetic construct
SEQUENCE: 544
QTIVHSNGDT                                                          10

SEQ ID NO: 545           moltype =   length =
SEQUENCE: 545
000

SEQ ID NO: 546           moltype = AA  length = 9
FEATURE                  Location/Qualifiers
REGION                   1..9
                         note = LCDR3
source                   1..9
                         mol_type = protein
                         organism = synthetic construct
SEQUENCE: 546
FQGSHVPVT                                                           9

SEQ ID NO: 547           moltype = AA  length = 49
FEATURE                  Location/Qualifiers
REGION                   1..49
                         note = KCD119 heavy chain
source                   1..49
                         mol_type = protein
                         organism = synthetic construct
SEQUENCE: 547
DTQPLGICQY WQPGPLISSG VPRFSGSGSG TFTLISEDYY CQPTFGGTK               49

SEQ ID NO: 548           moltype = AA  length = 112
FEATURE                  Location/Qualifiers
REGION                   1..112
                         note = KCD119
source                   1..112
                         mol_type = protein
                         organism = synthetic construct
SEQUENCE: 548
DVLMTQTPLS LPVSLGDQAS ISCRSSQTIV HSNGDTYLEW YLQKPGQSPN LLIYKVSNRF  60
SGVPDRFSGS GSGTDFTLKI SRVEAEDLGI YYCFQGSHVP PTFGGTKLE IK           112
```

-continued

```
SEQ ID NO: 549         moltype = AA  length = 112
FEATURE                Location/Qualifiers
REGION                 1..112
                       note = KCD200
source                 1..112
                       mol_type = protein
                       organism = synthetic construct
SEQUENCE: 549
DVLMTQTPLS LPVSLGDQVS ISCRSSQTIV HSNGDTYLEW YLQKPGQSPN LLIYKVSNRF  60
SGVPDRFSGS GSGTDFTLKI SRVEAEDLGV YYCFQGSHVP PTFGGGTKLE IK          112

SEQ ID NO: 550         moltype = AA  length = 112
FEATURE                Location/Qualifiers
REGION                 1..112
                       note = KCD118
source                 1..112
                       mol_type = protein
                       organism = synthetic construct
SEQUENCE: 550
DVLMTQTPLS LPVSLGDQAS ISCRSSQTIV HSNGDTYLEW YLQKPGQSPN LLIYKVSNRF  60
SGVPDRFSGS GSGTDFTLKI SRVEAEDLGI YYCFQGSHVP PTFGGGTKLE IK          112

SEQ ID NO: 551         moltype = AA  length = 112
FEATURE                Location/Qualifiers
REGION                 1..112
                       note = KCD120
source                 1..112
                       mol_type = protein
                       organism = synthetic construct
SEQUENCE: 551
DVLMTQTPLS LPVSLGDQVS ISCRSSQTIV HSNGDTYLEW YLQKPGQSPN LLIYKVSNRF  60
SGVPDRFSGS GSGTDFTLKI SRVEAEDLGV YYCFQGSHVP PTFGGGTKLE IK          112

SEQ ID NO: 552         moltype = AA  length = 112
FEATURE                Location/Qualifiers
REGION                 1..112
                       note = KCD121
source                 1..112
                       mol_type = protein
                       organism = synthetic construct
SEQUENCE: 552
DVLMTQTPLS LPVSLGDQAS ISCRSNQTIV HSNGDTYLEW YLQKPGQSPN LLIYKVSNRF  60
SGVPDRFSGS GSGTDFTLRI SRVEAEDLGV YYCFQGSHVP PTFGGGTKLE IK          112

SEQ ID NO: 553         moltype = AA  length = 112
FEATURE                Location/Qualifiers
REGION                 1..112
                       note = KCD122
source                 1..112
                       mol_type = protein
                       organism = synthetic construct
SEQUENCE: 553
DVLMTQTPLS LPVSLGDQAS ISCRSSQTIV HSNGDTYLEW YLQKPGQSPN LLIYKVSNRF  60
SGVPDRFSGS GSGTDFTLKI SRVEAEDLGV YYCFQGSHVP PTFGGGTKLE IK          112

SEQ ID NO: 554         moltype = AA  length = 112
FEATURE                Location/Qualifiers
REGION                 1..112
                       note = KCD123
source                 1..112
                       mol_type = protein
                       organism = synthetic construct
SEQUENCE: 554
DVLMTQTPLS LPVSLGDQAS ISCRSSQTIV HSNGDTYLEW YLQKPGQSPN LLIYKVSNRF  60
SGVPDRFSGS GSGTDFTLKI SRVEAEDLGV YYCFQGSHVP PTFGGGTKLE IK          112

SEQ ID NO: 555         moltype = AA  length = 112
FEATURE                Location/Qualifiers
REGION                 1..112
                       note = KCD124
source                 1..112
                       mol_type = protein
                       organism = synthetic construct
SEQUENCE: 555
DVLMTQTPLS LPVSLGDQAS ISCRSSQSIV HSNGDTYLEW YLQKPGQSPK LLIYKVSNRF  60
SGVPDRFSGS GSGTDFTLKI SRVEAEDLGV YYCFQGSHVP LTFGAGTKLE LK          112

SEQ ID NO: 556         moltype = AA  length = 109
FEATURE                Location/Qualifiers
```

-continued

```
REGION                  1..109
                        note = KCD003
source                  1..109
                        mol_type = protein
                        organism = synthetic construct
SEQUENCE: 556
DVLMTQTPLS LPVSLGEQAS ISCRSSQTIV HSNGDTYLEW YLQKPGQSPN LLIYKVSNRF  60
SGVPDRFSGS GSGTDFTLKI SRVEAEDLGV YYCFQGSHVP PTFGGGTKL             109

SEQ ID NO: 557          moltype = AA  length = 109
FEATURE                 Location/Qualifiers
REGION                  1..109
                        note = KCD005
source                  1..109
                        mol_type = protein
                        organism = synthetic construct
SEQUENCE: 557
DVLMTQTPLS LPVSLGDQAS ISCRSSQSIV HSNGDTYLEW YLQKPGQSPK LLIYKVSNRF  60
SGVPDRFSGS GSGTDFTLKI SRVEAEDLGV YYCFQGSHVP VTFGAGTKL             109

SEQ ID NO: 558          moltype = AA  length = 112
FEATURE                 Location/Qualifiers
REGION                  1..112
                        note = IGKV2-30
source                  1..112
                        mol_type = protein
                        organism = synthetic construct
SEQUENCE: 558
DVVMTQSPLS LPVTLGQPAS ISCRSSQSLV HSDGNTYLNW FQQRPGQSPR RLIYKVSNRD  60
SGVPDRFSGS GSGTDFTLKI SRVEAEDVGV YYCMQGTHWP LTFGGGTKVE IK          112

SEQ ID NO: 559          moltype = AA  length = 110
FEATURE                 Location/Qualifiers
REGION                  1..110
                        note = Mouse Germline
source                  1..110
                        mol_type = protein
                        organism = synthetic construct
SEQUENCE: 559
DVVMTQTPLS LPVSLGDQAS ISCRSSQSIV HSNGNTYLEW YLQKPGQSPK LLIYKVSNRL  60
SGVPDRFSGS GSGTFTLKIS RVEAEDLGVY YCFQGSHVPP TFGGGTKLEI            110

SEQ ID NO: 560          moltype = AA  length = 107
FEATURE                 Location/Qualifiers
REGION                  1..107
                        note = IGKVD1-39
source                  1..107
                        mol_type = protein
                        organism = synthetic construct
SEQUENCE: 560
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPWTFGQ GTKVEIK               107

SEQ ID NO: 561          moltype = AA  length = 107
FEATURE                 Location/Qualifiers
REGION                  1..107
                        note = TAF
source                  1..107
                        mol_type = protein
                        organism = synthetic construct
SEQUENCE: 561
DIQLTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIK               107

SEQ ID NO: 562          moltype = AA  length = 116
FEATURE                 Location/Qualifiers
REGION                  1..116
                        note = KCD119 light chain
source                  1..116
                        mol_type = protein
                        organism = synthetic construct
SEQUENCE: 562
EVQLQQSGPE LVKPGASVKI SCKASGYTFT DYYMNWMRQR HGESLEWIGD INPNNGDTSY  60
NQKFKGKATL TVDKSSSTAY MELRSLTSED SAVYYCAREG PSFAYWGQGT LVTVSA      116

SEQ ID NO: 563          moltype = AA  length = 116
FEATURE                 Location/Qualifiers
REGION                  1..116
                        note = KCD119
```

```
source                  1..116
                        mol_type = protein
                        organism = synthetic construct
SEQUENCE: 563
EVQLQQSGPE LVKPGASVKI SCKASGYTFT DYYTNWMRQR HGESLEWIGD INPNTGDTSY  60
NQKFRVKATL TVDKSSGTAY MGLRSLTSED SAVYYCTREG PSFAYWGQGT LVTVSA      116

SEQ ID NO: 564          moltype = AA  length = 116
FEATURE                 Location/Qualifiers
REGION                  1..116
                        note = KCD200
source                  1..116
                        mol_type = protein
                        organism = synthetic construct
SEQUENCE: 564
EVQLQQSGPE LVKPGASVKI SCKASGYTFT SYYKNWMRQR HGESLEWIGD INPNSGDTAY  60
NQKFKGKATL TVDRSSSTAY MELRSLTSED SAVYYCAREG PSFAYWGQGT LVTVSA      116

SEQ ID NO: 565          moltype = AA  length = 116
FEATURE                 Location/Qualifiers
REGION                  1..116
                        note = KCD118
source                  1..116
                        mol_type = protein
                        organism = synthetic construct
SEQUENCE: 565
EVQLQQSGPE LVKPGASVKI SCKAFGYTFT DYYKNWMRQR HGESLEWIGD INPNSGDANY  60
NQKFKGKATL TVDKSSSTAY MELRSLTSED SAVYYCAREG PSFAYWGHGT LVTVSA      116

SEQ ID NO: 566          moltype = AA  length = 116
FEATURE                 Location/Qualifiers
REGION                  1..116
                        note = KCD120
source                  1..116
                        mol_type = protein
                        organism = synthetic construct
SEQUENCE: 566
EVQLQQSGPE LVKPGASVKI SCKASGYTFT SYYKNWMRQR HGESLEWIGD INPNSGDTAY  60
NQKFKGKATL TVDRSSSTAY MELRSLTSED SAVYYCAREG PSFAYWGQGT LVTVSA      116

SEQ ID NO: 567          moltype = AA  length = 116
FEATURE                 Location/Qualifiers
REGION                  1..116
                        note = KCD121
source                  1..116
                        mol_type = protein
                        organism = synthetic construct
SEQUENCE: 567
EVQLQQSGPE LVKPGASVKI SCKASGYTFT DYYKNWMRQR HGESLEWIGD INPNNGDTSY  60
NQKFRGKATL TVDKSSSTAF MELRSLTSED SAVYYCAREG PSFAYWGQGT LVTVSA      116

SEQ ID NO: 568          moltype = AA  length = 116
FEATURE                 Location/Qualifiers
REGION                  1..116
                        note = KCD122
source                  1..116
                        mol_type = protein
                        organism = synthetic construct
SEQUENCE: 568
EVQLQQSGPE LVKPGASVKI SCKASGYTFT DYYKNWMRQR HGESLEWIGD INPNNGDANY  60
NQKFKGKATL TVDKSSSTAY MELRSLTSED SAVYFCAREG PSFAYWGHGT LVTVSA      116

SEQ ID NO: 569          moltype = AA  length = 116
FEATURE                 Location/Qualifiers
REGION                  1..116
                        note = KCD123
source                  1..116
                        mol_type = protein
                        organism = synthetic construct
SEQUENCE: 569
EVHLQQSGPE LVKPGASVKI SCKASGYTFT DFYKNWMRQR HGESLEWIGD INPNNGGTNY  60
NQKFKGKATL TVDKSSSTAY MELRSLTSED SAVYYCAREG PSFAYWGQGT LVTVSA      116

SEQ ID NO: 570          moltype = AA  length = 116
FEATURE                 Location/Qualifiers
REGION                  1..116
                        note = KCD124
source                  1..116
                        mol_type = protein
```

```
                         organism = synthetic construct
SEQUENCE: 570
EVQLQQSGPE LVKPGASVKI SCKASGYTFT DHYMNWVKQS HGKSLEWIGD INPNNGGTSY  60
NQKFKGKATL TVDKSSSTAY MELRSLTSGD SAVYYCTREG ASFAFWGQGT LVTVSA      116

SEQ ID NO: 571           moltype = AA  length = 116
FEATURE                  Location/Qualifiers
REGION                   1..116
                         note = KCD003
source                   1..116
                         mol_type = protein
                         organism = synthetic construct
SEQUENCE: 571
EVQLQQSRPE LVKPGASVKI FCKASGYTFT DYYMNWMRQR HGETLEWIGD INPNNGDPSY  60
NQKFKDKATL TVDKSSSTAS MELRSLTSDD SAVYYCAREG PSFAYWGQGT LVTVSA      116

SEQ ID NO: 572           moltype = AA  length = 116
FEATURE                  Location/Qualifiers
REGION                   1..116
                         note = KCD005
source                   1..116
                         mol_type = protein
                         organism = synthetic construct
SEQUENCE: 572
EVQLQQSGPE LVKPGASVKI SCKASGYTFT DHYMNWVKQS HGKSLEWIGD INPNNGGTSC  60
NQKFKGKATL TVDKSSSTAY MELRSLTSGD SAVYYCTREG ASFAFWGQGT LVTVSA      116

SEQ ID NO: 573           moltype = AA  length = 115
FEATURE                  Location/Qualifiers
REGION                   1..115
                         note = IGHV3-66
source                   1..115
                         mol_type = protein
                         organism = synthetic construct
SEQUENCE: 573
EVQLVESGGG LVQPGGSLRL SCAASGFTVS SNYMSWVRQA PGKGLEWVSV IYSGGSTYYA  60
DADSVKGRFT ISRDNSKNTL YLQMNSLRAE DTAVYYCARD AFDVWGQGTM VTVSS       115

SEQ ID NO: 574           moltype = AA  length = 113
FEATURE                  Location/Qualifiers
REGION                   1..113
                         note = IGHV1-2
source                   1..113
                         mol_type = protein
                         organism = synthetic construct
SEQUENCE: 574
QVQLVQSGAE VKKPGASVKV SCKASGYTFT GYYMHWVRQA PGQGLEWMGW INPNSGGTNY  60
AQKFQGRVTM TRDTSISTAY MELRSLRSDD TAVYYCARYF DYWGQGTLVT VSS         113

SEQ ID NO: 575           moltype = AA  length = 113
FEATURE                  Location/Qualifiers
REGION                   1..113
                         note = Mouse Germline
source                   1..113
                         mol_type = protein
                         organism = synthetic construct
SEQUENCE: 575
EVQLQQSGPE LVKPGASVKI SCKASGYTFT DYYMNWVKQS HGKSLEWIGD INPNNGGTSY  60
NQKFKGKATL TVDKSSSTAY MELRSLTSED SAVYYCARWF AYWGQGTLVT VSA         113

SEQ ID NO: 576           moltype = AA  length = 123
FEATURE                  Location/Qualifiers
REGION                   1..123
                         note = TAF
source                   1..123
                         mol_type = protein
                         organism = synthetic construct
SEQUENCE: 576
EVQLVESGGG LVQPGGSLRL SCAASGYDFT HYGMNWVRQA PGKGLEWVGW INTYTGEPTY  60
AADFKRRFTF SLDTSKSTAY LQMNSLRAED TAVYYCAKYP YYYGTSHWYF DVWGQGTLVT  120
VSS                                                                123

SEQ ID NO: 577           moltype = AA  length = 10
FEATURE                  Location/Qualifiers
REGION                   1..10
                         note = CDR sequence
source                   1..10
                         mol_type = protein
                         organism = synthetic construct
```

```
SEQUENCE: 577
GYTFTDYYIN                                                  10

SEQ ID NO: 578          moltype = AA  length = 16
FEATURE                 Location/Qualifiers
REGION                  1..16
                        note = CDR sequence
source                  1..16
                        mol_type = protein
                        organism = synthetic construct
SEQUENCE: 578
INPITGDTDY NADFKR                                           16

SEQ ID NO: 579          moltype = AA  length = 9
FEATURE                 Location/Qualifiers
REGION                  1..9
                        note = CDR sequence
source                  1..9
                        mol_type = protein
                        organism = synthetic construct
SEQUENCE: 579
TREGPSFAY                                                   9

SEQ ID NO: 580          moltype = AA  length = 16
FEATURE                 Location/Qualifiers
REGION                  1..16
                        note = CDR sequence
source                  1..16
                        mol_type = protein
                        organism = synthetic construct
SEQUENCE: 580
RSSQTIVHSN GDTYLE                                           16

SEQ ID NO: 581          moltype = AA  length = 11
FEATURE                 Location/Qualifiers
REGION                  1..11
                        note = CDR sequence
source                  1..11
                        mol_type = protein
                        organism = synthetic construct
SEQUENCE: 581
LLIRKVSNRF S                                                11

SEQ ID NO: 582          moltype = AA  length = 9
FEATURE                 Location/Qualifiers
REGION                  1..9
                        note = CDR sequence
source                  1..9
                        mol_type = protein
                        organism = synthetic construct
SEQUENCE: 582
FQGSHVPVT                                                   9

SEQ ID NO: 583          moltype = AA  length = 113
FEATURE                 Location/Qualifiers
REGION                  1..113
                        note = IGHV3-66*01; IGHJ3*01
source                  1..113
                        mol_type = protein
                        organism = synthetic construct
SEQUENCE: 583
EVQLVESGGG LVQPGGSLRL SCAASGFTVS SNYMSWVRQA PGKGLEWVSV IYSGGSTYYA  60
DSVKGRFTIS RDNSKNTLYL QMNSLRAEDT AVYYCARDAF DVWGQGTMVT VSS         113

SEQ ID NO: 584          moltype = AA  length = 110
FEATURE                 Location/Qualifiers
REGION                  1..110
                        note = IGKV2-30*02; IGKJ1*01
source                  1..110
                        mol_type = protein
                        organism = synthetic construct
SEQUENCE: 584
DVVMTQSPLS LPVTLGQPAS ISCRSSQSLV HSDGNTYLNW FQQRPGQSPR RLIYKVSNRD  60
SGVPDRFSGS GSGTDFTLKI SRVEAEDVGV YYCMQGTHWP FGQGTKVEIK             110

SEQ ID NO: 585          moltype = AA  length = 113
FEATURE                 Location/Qualifiers
REGION                  1..113
                        note = IGHV1-2*02; IGHJ4*01
```

-continued

```
source                  1..113
                        mol_type = protein
                        organism = synthetic construct
SEQUENCE: 585
QVQLVQSGAE VKKPGASVKV SCKASGYTFT GYYMHWVRQA PGQGLEWMGW INPNSGGTNY  60
AQKFQGRVTM TRDTSISTAY MELSRLRSDD TAVYYCARYF DYWGQGTLVT VSS         113

SEQ ID NO: 586          moltype = AA  length = 110
FEATURE                 Location/Qualifiers
source                  1..110
                        mol_type = protein
                        organism = Mus musculus
SEQUENCE: 586
DVVMTQTPLS LPVSLGDQAS ISCRSSQSIV HSNGNTYLEW YLQKPGQSPK LLIYKVSNRL  60
SGVPDRFSGS GSGTFTLKIS RVEAEDLGVY YCFQGSHVPP TFGGGTKLEI             110

SEQ ID NO: 587          moltype = AA  length = 113
FEATURE                 Location/Qualifiers
source                  1..113
                        mol_type = protein
                        organism = Mus musculus
SEQUENCE: 587
EVQLQQSGPE LVKPGASVKI SCKASGYTFT DYYMNWVKQS HGKSLEWIGD INPNNGGTSY  60
NQKFKGKATL TVDKSSSTAY MELRSLTSED SAVYYCARWF AYWGQGTLVT VSA         113

SEQ ID NO: 588          moltype = AA  length = 107
FEATURE                 Location/Qualifiers
REGION                  1..107
                        note = IGKV1D-39; IGKJ1*01
source                  1..107
                        mol_type = protein
                        organism = synthetic construct
SEQUENCE: 588
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPWTFGQ GTKVEIK                107

SEQ ID NO: 589          moltype = AA  length = 123
FEATURE                 Location/Qualifiers
REGION                  1..123
                        note = TAF HC
source                  1..123
                        mol_type = protein
                        organism = synthetic construct
SEQUENCE: 589
EVQLVESGGG LVQPGGSLRL SCAASGYDFT HYGMNWVRQA PGKGLEWVGW INTYTGEPTY  60
AADFKRRFTF SLDTSKSTAY LQMNSLRAED TAVYYCAKYP YYYGTSHWYF DVWGQGTLVT  120
VSS                                                                123

SEQ ID NO: 590          moltype = AA  length = 112
FEATURE                 Location/Qualifiers
REGION                  1..112
                        note = TAF LC
source                  1..112
                        mol_type = protein
                        organism = synthetic construct
SEQUENCE: 590
DIQMTQSPSS LSASVGDRVT ITCRSSQTIV HSNGDTYLEW YQQKPGKAPN LLIYKVSNRF  60
SGVPSRFSGS GSGTDFTLTI SSLQPEDFAT YYCFQGSHVP PTFGQGTKVE IK          112
```

COMPLEMENT FACTOR D ANTAGONIST ANTIBODIES AND CONJUGATES THEREOF

CROSS REFERENCE TO RELATED APPLICATION

This application is a divisional application of U.S. application Ser. No. 15/952,092, filed Apr. 12, 2018, now U.S. Pat. No. 11,584,790, issued Feb. 21, 2023, which claims the benefit of U.S. Provisional Application No. 62/485,718, filed on Apr. 14, 2017. The entirety of each of these related applications is hereby incorporated by reference.

SEQUENCE LISTING AND ELECTRONIC TABLE

The present application is being filed along with a Sequence Listing XML in electronic format. The Sequence Listing XML is provided as a file entitled KDIAK001D1.xml, created Jan. 12, 2023, which is 805,069 bytes in size. The information in the electronic format of the Sequence Listing XML is incorporated herein by reference in its entirety. The present application is being filed along with a Table in electronic format. The Table is provided as a file entitled CTKDK001A.txt, created and last saved on Apr. 12, 2018, which is 819,316 bytes in size. The information in the electronic format of the Table is incorporated herein by reference in its entirety.

LENGTHY TABLES

The patent contains a lengthy table section. A copy of the table is available in electronic form from the USPTO web site (https://seqdata.uspto.gov/?pageRequest=docDetail&DocID=US00000000B0). An electronic copy of the table will also be available from the USPTO upon request and payment of the fee set forth in 37 CFR 1.19(b)(3).

BIOLOGICAL SAMPLE DEPOSIT STATEMENT

In some embodiments, anti-CFD antagonistic antibodies and conjugates thereof are provided, which were deposited in the American Type Culture Collection (ATCC), in accordance with the Budapest Treaty, under the numbers PTA-123800 and PTA-123801, on Jan. 31, 2017.

These deposits were made under the provisions of the Budapest Treaty on the International Recognition of the Deposit of Microorganisms for the Purposes of Patent Procedure and the Regulations thereunder (Budapest Treaty). This assures maintenance of the deposit for 30 years from date of deposit. The deposit will be made available by the ATCC under the terms of the Budapest Treaty, and subject to an agreement between Applicant and the ATCC, which assures permanent and unrestricted availability of the deposit to the public upon issuance of the pertinent U.S. patent or upon laying open to the public of any U.S. or foreign patent application, whichever comes first, and assures availability of the deposit to one determined by the U.S. Commissioner of Patents and Trademarks to be entitled thereto according to 35 U.S.C. § 122 and the Commissioner's Rules pursuant thereto (including 37 C.F.R. § 1.14). Availability of the deposited biological material is not to be construed as a license to practice the invention in contravention of the rights granted under the authority of any Government in accordance with its Patent Laws.

FIELD

The present invention relates generally to constructs, including conjugates thereof, that bind complement factor D (CFD).

BACKGROUND

Age related macular degeneration (AMD) is a leading cause of vision loss and blindness in the elderly. About ten million Americans are afflicted with AMD. The prevalence of AMD in the population increases steadily with age: at 40 years of age only about 2% of the population is affected by AMD but by the age of 80 it is about 25%. Friedman D S et al. 2004. Prevalence of age-related macular degeneration in the United States. Arch Ophthalmol. 122:564-572.

AMD is a progressive disease that evolves over time through various stages eventually resulting in severe central vision loss. One of the hallmarks of AMD are extracellular deposits called drusen. Drusen are subretinal deposits of oxidized lipids and proteins that appear beneath the retinal pigment epithelium (RPE). Also often seen in early AMD are visible clumps of pigment in the macula. As AMD progresses, drusen become larger and pigment changes in the macula become more pronounced. Subsequently, some 10 to 15% of patients will develop subretinal choroidal neovascularization (CNV), typically called wet AMD. CNV is characterized by the presence of new immature blood vessels which grow towards the outer retina from the choroid. These immature blood vessels leak fluid below and in the retina, causing vision loss and blindness. Other patients will develop non-neovascular or dry AMD.

Advanced cases of dry AMD are characterized by sharply demarcated uni- or multi-focal regions of dysfunctional macula, termed geographic atrophy (GA). Over time, GA patches enlarge and involve the RPE and corresponding neurosensory retina and the choriocapillary layer of the choroid. These changes to the eye are progressive and irreversible, resulting in permanent loss visual function. GA occurs bilaterally in over 50% of patients. Binder S, Stanzel B V, Krebs I, Glittenberg C. 2007. Transplantation of the RPE in AMD. Prog Retn Eye Res. 26:516-554. GA accounts for some 20-25% of patients with severe visual loss secondary to AMD (i.e. legal blindness related to AMD). Klein R, Klein B E, Jensen S C, Meuer S M. 1997. The five-year incidence and progression of age-related maculopathy: The Beaver Dam Eye Study. Ophthal. 104:7-21. Forms of dry AMD less severe than GA are responsible for a much larger percentage of moderate visual function loss.

SUMMARY

In some embodiments, an isolated antagonist antibody is provided that specifically binds to complement factor D (CFD) and directly inhibits a proteolytic activity of CFD.

In some embodiments, an isolated antagonist antibody is provided that specifically binds to complement factor D (CFD), inhibits a proteolytic activity of CFD, and inhibits CFD binding to C3bB complex.

In some embodiments, an isolated antagonist antibody is provided that specifically binds to complement factor D (CFD), wherein the antibody does not bind a human CFD mutant comprising mutations R157A and R207A.

In some embodiments, an isolated antagonist antibody is provided that binds an epitope on human CFD, wherein the epitope excludes positions R157 and R207.

In some embodiments, an isolated antagonistic antibody is provided. The antibody comprises a heavy chain amino acid variable region that comprises SEQ ID NO 183; and a light chain amino acid variable region that comprises SEQ ID NO. 184.

In some embodiments, an isolated antagonist antibody is provided that comprises: a heavy chain variable region (VH) comprising a VH complementarity determining region one (CDR1), VH CDR2, and VH CDR3 of the VH having an amino acid sequence selected group the group consisting of SEQ ID NO: 541, SEQ ID NO: 542; and SEQ ID NO: 543; and a light chain variable region (VL) comprising a VL CDR1, VL CDR2, and VL CDR3 of the VL having an amino acid sequence selected from the group consisting of SEQ ID NO: 544; SEQ ID NO: 545; and SEQ ID NO: 546.

In some embodiments, an isolated antagonist antibody that specifically binds to CFD is provided that comprises a heavy chain variable region (VH); and a light chain variable region (VL), wherein the antibody comprises the following mutations: L234A, L235A, and G237A.

In some embodiments, an isolated antagonist antibody is provided. The antibody binds an epitope on human CFD that is the same as or overlaps with the epitope recognized by an antibody comprising the amino acid sequences shown in SEQ ID NO: 61 and SEQ ID NO: 62. In some embodiments, an isolated antagonist antibody is provided. The antibody binds an epitope on human CFD that is the same as or overlaps with the epitope recognized by an antibody comprising the amino acid sequences shown in SEQ ID NO: 45 and SEQ ID NO: 46.

In some embodiments, an isolated antagonist antibody that binds to CFD is provided. The antibody comprises: a heavy chain comprising the amino acid sequence shown in SEQ ID NO: 183, with or without the C-terminal lysine; and a light chain comprising the amino acid sequence shown in SEQ ID NO: 184.

In some embodiments, an isolated antagonist antibody that binds to CFD is provided. The antibody comprises a VH comprising the amino acid sequence shown in SEQ ID NO: 520, or a sequence that is at least 90% identical thereto, having amino acid substitutions in residues that are not within a CDR of SEQ ID NO: 520 and 525.

In some embodiments, an isolated antagonistic antibody that binds to CFD is provided. The antibody comprises a $CDR_H1$ that is the $CDR_H1$ in SEQ ID NO: 520; a $CDR_H2$ that is the $CDR_H2$ in SEQ ID NO: 520; a $CDR_H3$ that is the $CDR_H3$ in SEQ ID NO: 520; a $CDR_L1$ that is the $CDR_L1$ in SEQ ID NO: 525; a $CDR_L2$ that is the $CDR_L2$ in SEQ ID NO: 525; a $CDR_L3$ that is the $CDR_L3$ in SEQ ID NO: 525; at least one of the following mutations (EU numbering): L234A, L235A, and G237A; and at least one of the following mutations (EU numbering): Q347C or L443C.

In some embodiments, an isolated antagonist antibody that specifically binds to complement factor D (CFD) is provided. The antibody is configured to provide a reduced complement reaction, wherein the antibody specifically binds to complement factor D (CFD), and wherein the antibody at least inhibits a proteolytic activity of CFD or inhibits CFD binding to C3bB complex.

In some embodiments, a conjugate is provided that comprises: a) any of the isolated antagonistic antibodies provided herein; and b) a polymer, wherein the polymer is covalently attached to the antibody.

In some embodiments, a conjugate is provided that comprises: a) an isolated antagonist antibody that specifically binds to complement factor D (CFD); and b) a phosphorylcholine containing polymer, wherein the polymer is covalently bonded to the antibody.

In some embodiments, a conjugate is provided that comprises: a) an isolated antagonist antibody that specifically binds to complement factor D (CFD); and b) a polymer comprising a zwitterionic monomer, wherein the zwitterionic monomer is selected from the group consisting of HEMA-phosphorylcholine, PEG, biocompatible fatty acids and derivatives thereof, Hydroxy Alkyl Starch (HAS), Hydroxy Ethyl Starch (HES), Poly Ethylene Glycol (PEG), Poly ($Gly_x$-$Ser_y$) (HAP), Hyaluronic acid (HA), Heparosan polymers (HEP), Fleximers, Dextran, Poly-sialic acids (PSA), Fc domains, Transferrin, 25 Albumin, Elastin like (ELP) peptides, XTEN polymers, PAS polymers, PA polymers, Albumin binding peptides, CTP peptides, and FcRn binding peptides.

In some embodiments, a conjugate comprising an anti-CFD antibody and a polymer that is capable of blocking at least 80% of an interaction between CFD and C3bB is provided.

In some embodiments, a conjugate comprising (1) an anti-CFD antibody and (2) a phosphorylcholine containing polymer is provided. The polymer is covalently bonded to the antibody at a cysteine outside a variable region of the antibody wherein said cysteine has been added via recombinant DNA technology.

In some embodiments of the conjugate, the conjugate the polymer has 9 arms; and the polymer has a molecular weight of between about 600,000 to about 900,000 Da.

In some embodiments of the conjugate, the conjugate has the following structure:

Formula (17)

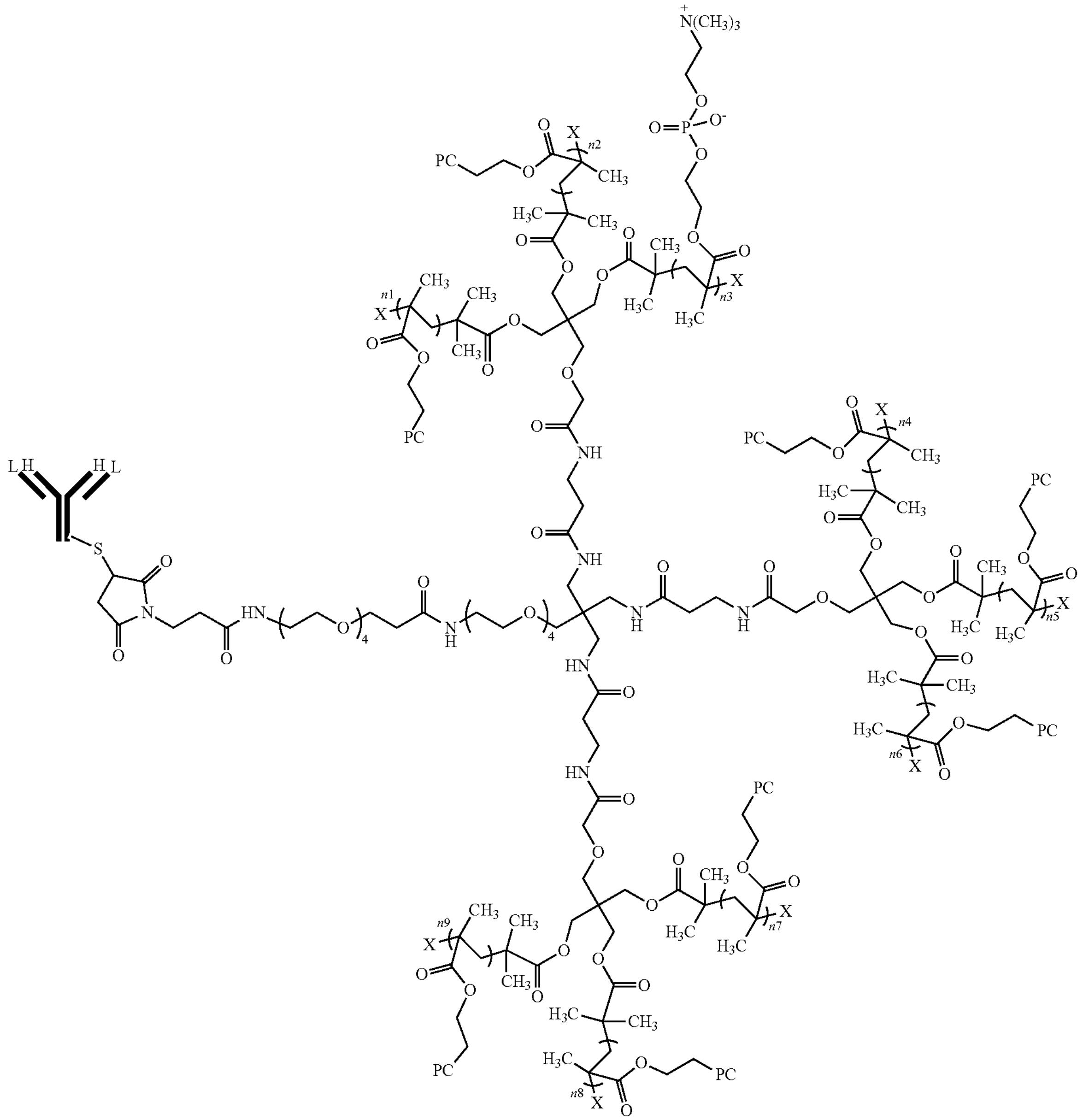

wherein:

each heavy chain of the antibody is denoted by the letter H, and each light chain of the anti-CFD antibody is denoted by the letter L;

the polymer is bonded to the antibody through the sulfhydryl of C443 (EU numbering), which bond is depicted on one of the heavy chains;

PC is

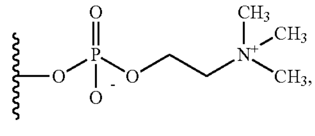 [SMILES: *OP(=O)(O)OCC[N+](C)(C)C]

where the curvy line indicates the point of attachment to the rest of the polymer, where X=a) OR where R=H, methyl, ethyl, propyl, isopropyl, b) H, or c) any halide, including Br; and n1, n2, n3, n4, n5, n6, n7, n8 and n9 are the same or different such that the sum of n1, n2, n3, n4, n5, n6, n6, n7, n8 and n9 is 2500 plus or minus 15%.

In some embodiments, an isolated cell line is provided that produces an isolated antagonistic antibody provided herein.

In some embodiments, an isolated nucleic acid is provided that encodes an isolated antagonistic antibody as provided herein.

In some embodiments, a recombinant expression vector is provided that comprises the nucleic acid.

In some embodiments, a host cell is provided that comprises the expression vector.

In some embodiments, a method of producing a CFD antagonist antibody is provided. The method comprises: culturing a cell line that recombinantly produces an isolated antagonistic antibody of as provided herein under conditions wherein the antibody is produced; and recovering the antibody.

In some embodiments, a method of producing a CFD antagonist antibody is provided. The method comprises: culturing a cell line comprising nucleic acid encoding an antibody comprising a heavy chain comprising the amino acid sequence shown in SEQ ID NO: 520 and a light chain comprising the amino acid sequence shown in SEQ ID NO: 525 under conditions wherein the antibody is produced; and recovering the antibody.

In some embodiments, a pharmaceutical composition is provided. The composition comprises an isolated antagonistic antibody as provided herein and/or a conjugate as provided herein, and a pharmaceutically acceptable carrier.

In some embodiments, a method for the treatment or prophylaxis of a disease in a patient in need thereof is provided. The method comprises administering to the patient an isolated antagonist antibody as provided herein, and/or a conjugate as provided herein.

In some embodiments, a method for the treatment or prophylaxis of a disease in a patient in need thereof is provided. The method comprises: identifying a patient having hyperactive CFD activity; and administering to the patient an isolated antagonist antibody as provided herein and/or a conjugate as provided herein.

In some embodiments, a method for the treatment or prophylaxis of a disease in a patient in need thereof is provided. The method comprises administering to the patient a conjugate as provided herein, and/or a composition as provided herein.

In some embodiments, an isolated antagonist antibody is provided. The antibody binds an epitope on human CFD that is the same as or overlaps with the epitope recognized by an antibody comprising the amino acid sequences shown in SEQ ID NO: 520 and SEQ ID NO: 525.

In some embodiments, an isolated antagonist antibody that binds to CFD is provided. The antibody does not increase an enzymatic activity of CFD when bound thereto.

In some embodiments, an isolated antagonist antibody is provided. The antibody competes for binding to human CFD with an antibody comprising the amino acid sequences shown in SEQ ID NO: 520 and SEQ ID NO: 525.

In some embodiments, an isolated antagonist antibody that binds to CFD is provided. The antibody does not maintain an enzymatic activity of CFD when bound thereto.

In some embodiments, an isolated antagonist antibody that specifically binds to complement factor D (CFD) is provided. When bound, the antibody is within 3A of residue 209 of SEQ ID NO: 1 of CFD.

In some embodiments, an isolated antagonist antibody that specifically binds to complement factor D (CFD) is provided. When bound, the antibody is within 3A of residue 156 of SEQ ID NO: 1 of CFD.

In some embodiments, an isolated antagonist antibody that specifically binds to complement factor D (CFD) is provided. The antibody binds to one or more of residues 156 or 209 of SEQ ID NO: 1 of CFD.

In some embodiments, an isolated antagonist antibody that specifically binds to complement factor D (CFD) is provided. The antibody binds to both of residues 156 and 209 of SEQ ID NO: 1 of CFD.

In some embodiments, an isolated antagonist antibody that specifically binds to complement factor D (CFD) is provided. The antibody, when bound to CFD, is not within 6 angstroms of at least one of 117, 118, and 156 of SEQ ID NO: 1.

In some embodiments, an isolated antagonist antibody that specifically binds to complement factor D (CFD) is provided. The antibody binds to CFD as described in Tables: 1.1, 0.1A, 0.1B, 0.1D, and/or 11.3.

In some embodiments, a crystalized CFD-antibody complex is provided, wherein the antibody comprises any one or more of the CDRs within SEQ ID NO:s 183 or 520 and 184 or 525.

BRIEF DESCRIPTION OF THE DRAWINGS

FIG. 1 Depicts a sequence of CFD.

FIG. 2I shows the synthesis of OG1786 from OG1785.

DETAILED DESCRIPTION

Figure 2A:
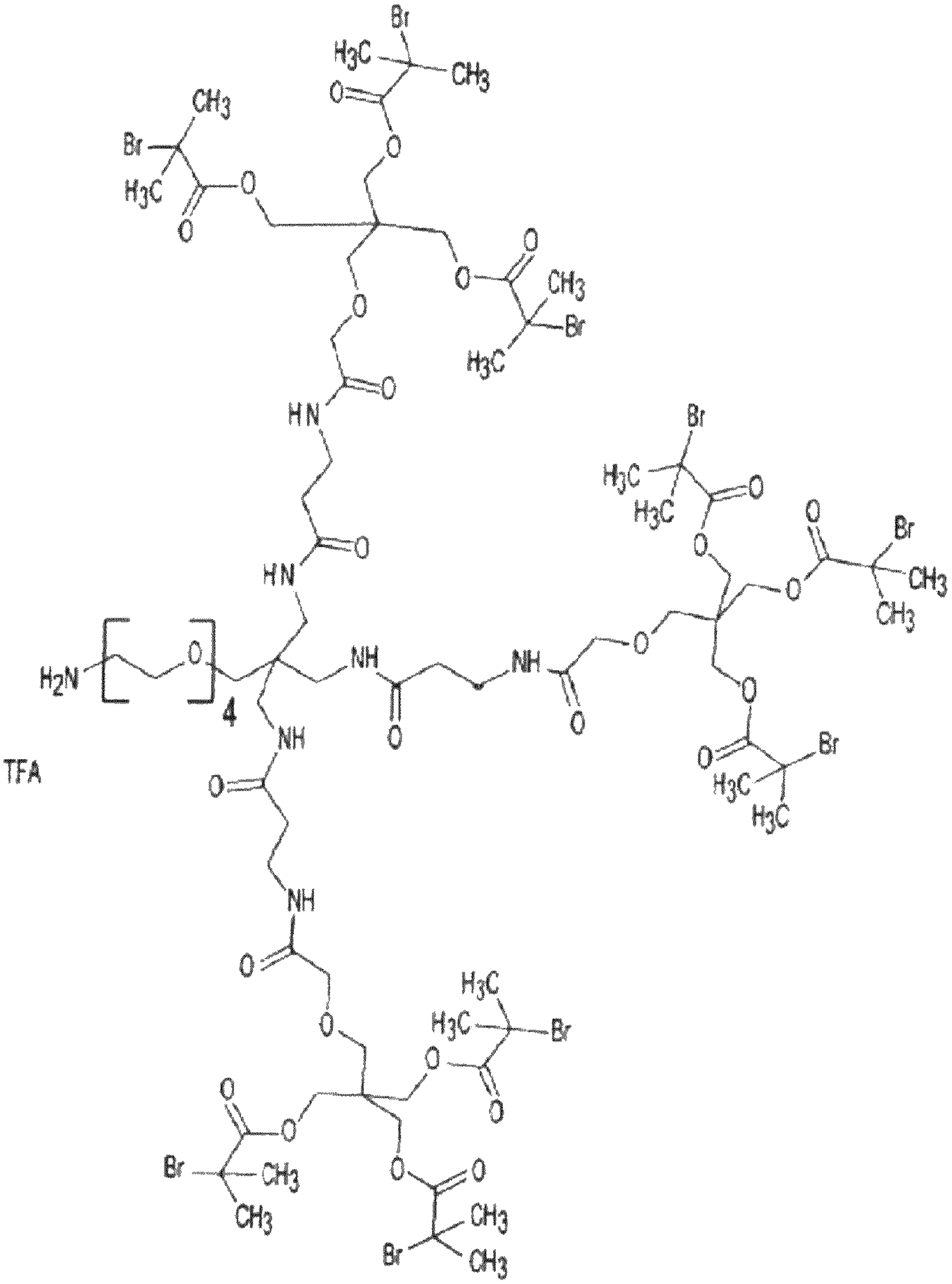
FIG. 2A shows Compound L.

Although progress had been made toward treatment of wet AMD, presently, there is no corresponding treatment for dry AMD or GA. There are also no available treatments to halt GA patch enlargement or slow vision loss. Because of the rapidly aging population and that dry AMD remains an untreated source of morbidity, there is a need for treatments for dry AMD.

There is also a need for dry AMD therapeutics and therapy regimes which will lead to good patient compliance. Currently, Roche's lampalizumab is in phase III clinical trials for treatment of GA. Lampalizumab is administered by intravitreal injection. While phase II results indicate some positive efficacy, efficacy was only seen for the monthly dosage of lampalizumab. In the study, bimonthly injections of lampalizumab were found to be no better than sham injections.

From the view point of both patients and treating physicians, intravitreal injections are not trivial. Many patients experience pain and discomfort from the injection and patient compliance is a serious issue. Common side effects of intravitreal injections include conjunctival hemorrhage, eye pain, vitreous floaters, increased intraocular pressure, and intraocular inflammation. Intravitreal injections are associated with relatively rare serious adverse events, including endophthalmitis, retinal detachment and traumatic cataracts.

There is, thus, also a need in the art for therapies that can be effectively administered less frequently, e.g., less than once a month.

Disclosed herein are antibodies that specifically bind to complement factor D (CFD), and conjugates thereof. Methods of making anti-CFD antibodies, anti-CFD antibody conjugates, compositions comprising these antibodies and/or antibody conjugates, and methods of using these antibodies and/or antibody conjugates as a medicament are also provided. Anti-CFD antibodies and anti-CFD antibody conjugates provided herein can be used in the prevention and/or treatment of age related macular degeneration and/or other diseases.

OG1965 is a high affinity antagonistic humanized antibody against complement factor D (CFD). In some embodiments, it can be covalently conjugated to a high molecular weight biopolymer to result in OG1970, for intravitreal injection for the treatment of intermediate dry AMD and Geographic Atrophy (GA), as well as other indications. OG1970 is expected to have a longer resident half-life in the eye for potent efficacy and superior dosing intervals.

In some embodiments, the estimated Q12w or Q16w dosing interval of OG1970 can allow treatment of broad set of patients with increasingly earlier and less advanced forms of dry AMD Various embodiments provided herein can employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

The following terms, unless otherwise indicated, shall be understood to have the following meanings: the term "isolated molecule" as referring to a molecule (where the molecule is, for example, a polypeptide, a polynucleotide, or an antibody) that by virtue of its origin or source of derivation (1) is not associated with naturally associated components that accompany it in its native state, (2) is substantially free of other molecules from the same source, e.g., species, cell from which it is expressed, library, etc., (3) is expressed by a cell from a different species, or (4) does not occur in nature. Thus, a molecule that is chemically synthesized, or expressed in a cellular system different from the system from which it naturally originates, will be "isolated" from its naturally associated components. A molecule also may be rendered substantially free of naturally associated components by isolation, using purification techniques well known in the art. Molecule 8purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

As used herein, the term "CFD," "complement factor D," "factor D," or "FD," as used interchangeably herein, refers to any form of CFD and variants thereof that retain at least part of the activity of CFD. Unless indicated differently, such as by specific reference to human CFD, CFD includes all mammalian species of native sequence CFD, e.g., human, canine, feline, equine, and bovine. One exemplary human CFD is found as UniProt Accession Number P00746, which displayed sequence is further processed into a mature form, as shown in (SEQ ID NO: 1).

Anti-CFD antibodies or other biologics described herein are typically provided in isolated form. This means that an antibody is typically at least 50% w/w pure of interfering proteins and other contaminants arising from its production or purification but does not exclude the possibility that the antibody is combined with a pharmaceutically acceptable excipient intended to facilitate its use. Sometimes antibodies are at least 60, 70, 80, 90, 95 or 99% w/w pure of interfering proteins and contaminants from production or purification. Often an antibody (or antibody conjugate) is the predominant macromolecular species remaining after its purification. In some embodiments, no other protein material is present in at meaningful (functioning) level and/or detectable level.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also, unless otherwise specified, any antigen binding portion thereof that competes with the intact antibody for specific binding, fusion proteins comprising an antigen binding portion, and any other modified configuration of the immunoglobulin molecule that comprises an antigen recognition site. Antigen binding portions include, for example, Fab, Fab', $F(ab')_2$, Fd, Fv, domain antibodies (dAbs, e.g., shark and camelid antibodies), fragments including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$ and $IgA_2$. The heavy-chain constant regions that correspond to the different classes of immunoglobulins are called alpha, delta, epsilon, gamma, and mu, respectively. The subunit structures and three-dimensional configurations of different classes of immunoglobulins are well known.

A "variable region" of an antibody refers to the variable region of the antibody light chain or the variable region of the antibody heavy chain, either alone or in combination. As known in the art, the variable regions of the heavy and light chains each consist of four framework regions (FRs) connected by three complementarity determining regions (CDRs) also known as hypervariable regions, and contribute to the formation of the antigen binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canoninical class as the subject variable region (Chothia and Lesk, J Mol Biol 196(4): 901-917, 1987).

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. In certain embodiments, various methods of analysis can be employed to identify or approximate the CDR regions. Examples of such methods include, but are not limited to, the Kabat definition, the Chothia definition, the IMGT approach (Lefranc et al., 2003) Dev Comp Immunol. 27:55-77), computational programs such as Paratome (Kunik et al., 2012, Nucl Acids Res. W521-4), the AbM definition, and the conformational definition.

The Kabat definition is a standard for numbering the residues in an antibody and is typically used to identify CDR regions. See, e.g., Johnson & Wu, 2000, Nucleic Acids Res., 28: 214-8. The Chothia definition is similar to the Kabat definition, but the Chothia definition takes into account positions of certain structural loop regions. See, e.g., Chothia et al., 1986, J. Mol. Biol., 196: 901-17; Chothia et al., 1989, Nature, 342: 877-83. The AbM definition uses an integrated suite of computer programs produced by Oxford Molecular Group that model antibody structure. See, e.g., Martin et al., 1989, Proc Natl Acad Sci (USA), 86:9268-9272; "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., 1999, "Ab Initio Protein Structure Prediction Using a Combined Hierarchical Approach," in PROTEINS, Structure, Function and Genetics Suppl., 3:194-198. The contact definition is based on an analysis of the available complex crystal structures. See, e.g., MacCallum et al., 1996, J. Mol. Biol., 5:732-45. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, IMGT, Paratome, AbM, and/or conformational definitions, or a combination of any of the foregoing.

As known in the art, a "constant region" of an antibody refers to the constant region of the antibody light chain or the constant region of the antibody heavy chain, either alone or in combination.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example. As used herein, "humanized" antibody refers to forms of non-human (e.g. murine) antibodies that are chimeric immunoglobulins, immunoglobulin chains, or fragments thereof (such as Fv, Fab, Fab', F(ab')2 or other antigen-binding subsequences of antibodies) that contain minimal sequence derived from non-human immunoglobulin. Preferably, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. The humanized antibody may comprise residues that are found neither in the recipient antibody nor in the imported CDR or framework sequences, but are included to further refine and optimize antibody performance.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen binding residues. A human antibody can be modified to provide altered (including superior) binding.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody. The term "epitope" refers to that portion of a molecule capable of being recognized by and bound by an antibody at one or more of the antibody's antigen-binding regions. Epitopes often consist of a surface grouping of molecules such as amino acids or sugar side chains and have specific three-dimensional structural characteristics as well as specific charge characteristics. In some embodiments, the epitope can be a protein epitope. Protein epitopes can be linear or conformational. In a linear epitope, all of the points of interaction between the protein and the interacting molecule (such as an antibody) occur linearly along the primary amino acid sequence of the protein. A "nonlinear epitope" or "conformational epitope" comprises noncontiguous polypeptides (or amino acids) within the antigenic protein to which an antibody specific to the epitope binds. The term "antigenic epitope" as used herein, is defined as a portion of an antigen to which an antibody can specifically bind as determined by any method well known in the art, for example, by conventional immunoassays. Once a desired epitope on an antigen is determined, it is possible to generate antibodies to that epitope, e.g., using the techniques described in the present specification. Alternatively, during the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another for binding to CFD, e.g., the antibodies compete for binding to the antigen.

The term "compete," as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

As used herein, an antibody "interacts with" CFD when the equilibrium dissociation constant is equal to or less than 20 nM, preferably less than about 6 nM, more preferably less than about 1 nM, most preferably less than about 0.2 nM, as measured by the methods disclosed herein in Example 8.

A CFD antagonist antibody encompasses antibodies that block, antagonize, suppress or reduce (to any degree including significantly) a CFD biological activity such as, e.g., substrate (including but not limited to, synthetic peptides or Factor B pre-bound to C3b) binding and/or cleavage, C3bB (a complex of factor B, magnesium ions, and complement component 3b) binding, and/or downstream pathways mediated by CFD signaling, such as elicitation of a cellular response to CFD activation. For purpose of the present invention, it will be explicitly understood that the term "CFD antagonist antibody" encompasses all the previously identified terms, titles, and functional states and characteristics whereby the CFD itself, a CFD biological activity (including but not limited to its ability to mediate any aspect of interaction with the C3bB, and downregulation of the alternative complement cascade), or the consequences of the biological activity, are substantially nullified, decreased, or neutralized in any meaningful degree. In some embodiments, a CFD antagonist antibody binds CFD and substantially blocks CFD catalysis. Examples of CFD antagonist antibodies are provided herein.

An antibody that "preferentially binds" or "specifically binds" (used interchangeably herein) to an epitope is a term well understood in the art, and methods to determine such specific or preferential binding are also well known in the art. A molecule is said to exhibit "specific binding" or "preferential binding" if it reacts or associates more frequently, and/or more rapidly, and/or with greater duration and/or with greater affinity with a particular cell or substance than it does with alternative cells or substances. An antibody "specifically binds" or "preferentially binds" to a target if it binds with greater affinity, and/or avidity, and/or more readily, and/or with greater duration than it binds to other substances. For example, an antibody that specifically or preferentially binds to a CFD epitope is an antibody that binds this epitope with greater affinity, and/or avidity, and/or more readily, and/or with greater duration than it binds to other CFD epitopes or non-CFD epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant domains, CH2 and CH3. As is known in the art, an Fc region can be present in dimer or monomeric form.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976, J. Immunol., 117:587; and Kim et al., 1994, J. Immunol., 24:249).

A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g. B cell receptor), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

As used herein, "treatment" is an approach for obtaining beneficial or desired clinical results.

As used herein, "CFD related disorders" include, for example, inflammatory disorders and disorders of the Complement cascade in patients. Inflammatory disorders include eye inflammatory disorders such as dry and wet age-related macular degeneration (including geographic strophy GA), glaucoma, diabetic retinopathy, corneal disease (e.g. chemical insults, acute bacterial infection, pseudophakic bullous keratopathy, HSV-1 keratitis, and herpes Zoster scleritis), and uveitis. Inflammatory disorders also include sepsis, systemic inflammatory response syndrome (SIRS), ischemia/reperfusion injury (I/R injury), psoriasis, myasthenia gravis, system lupus erythematosus (SLE), paroxysmal nocturnal hemoglobinuria (PNH), hereditary angioedema, multiple sclerosis, trauma, burn injury, capillary leak syndrome, obesity, diabetes, Alzheimer's dementia, stroke, schizophrenia, epilepsy, asthma, allergy, acute respiratory distress syndrome (ARDS), atypical hemolytic uremic syndrome (aHUS), hemolytic uremic syndrome (HUS), cystic fibrosis, myocardial infarction, lupus nephritides, Crohn's disease, rheumatoid arthritis, atherosclerosis, transplant rejection, prevention of fetal loss, biomaterial reactions (e.g. in hemodialysis, inplants), C3 glomerulonephritis, abdominal aortic aneurysm, and vasculitis.

Benefits can also be obtained from applying the methods and compositions provided herein to slowing the rate of deposition of drusen, decreasing the rate of atrophy and/or thinning of the RPE or conversely the rate of hypertrophy/hyperpigmentation of the RPE, decreasing the rate of formation of new abnormal blood vessels or rate of growth of existing abnormal blood vessels and magnitude of associated leakage of fluid and/or blood, slowing or reversing the deterioration in visual function loss as well as other symptoms resulting from dry and/or wet AMD, decreasing the frequency of administration and or dose of other medications required to treat dry and/or wet AMD, and in general slowing the progression of dry and/or wet AMD, curing dry and/or wet AMD.

As used herein, "Ameliorating" means a lessening or improvement of one or more symptoms as compared to not administering an CFD antibody. "Ameliorating" also includes shortening or reduction in duration of a symptom.

As used herein, "Antagonistic antibody" denotes an antibody that blocks one or more function or activity of the molecule that the antibody binds to.

As used herein, an "effective dosage" or "effective amount" of drug, compound, or pharmaceutical composition is an amount sufficient to effect any one or more beneficial or desired results. In more specific aspects, an effective amount prevents, alleviates or ameliorates symptoms of disease, and/or prolongs the survival of the subject being treated. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing one or more symptoms of a disease such as, for example, AMD including, for example without limitation, dry AMD and wet AMD, decreasing the dose of other medications required to treat the disease, enhancing the effect of another medication, and/or delaying the progression of AMD in patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

Anti-CFD antibodies are administered in an effective regime meaning a dosage, route of administration and frequency of administration that delays the onset, reduces the severity, inhibits further deterioration, and/or ameliorates at least one sign or symptom of a disorder. If a patient is already suffering from a disorder, the regime can be referred to as a therapeutically effective regime. If the patient is at elevated risk of the disorder relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

The "biological half-life" of a substance is a pharmacokinetic parameter which specifies the time required for one half of the substance to be removed from an organism following introduction of the substance into the organism.

The term "preventing" or "prevent" refers to (a) keeping a disorder from occurring (b) delaying the onset of a disorder or onset of symptoms of a disorder, and/or (c) slowing the progression of an existing condition. Unless denoted otherwise, "preventing" does not require the absolute prohibition of the event from occurring.

An "individual" or a "subject" is a mammal or bird, more preferably, a human. Mammals also include, but are not limited to, farm animals (e.g., cows, pigs, horses, chickens, etc.), sport animals, pets, primates, horses, dogs, cats, mice and rats.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, various types of wetting agents, detergents such as polysorbate 20 to prevent aggregation, and sugars such as sucrose as cryoprotectant. Preferred diluents for aerosol or parenteral administration are phosphate buffered saline (PBS) or normal (0.9%) saline. Compositions comprising such carriers are formulated by well-known conventional methods (see, for example, Remington's Pharmaceutical Sciences, 18th edition, A. Gennaro, ed., Mack Publishing Co., Easton, P A, 1990; and Remington, The Science and Practice of Pharmacy 20th Ed. Mack Publishing, 2000).

The term "$k_{on}$", as used herein, refers to the rate constant for association of an antibody (or bioconjugate) to an antigen. Specifically, the rate constants ($k_{on}$ and $k_{off}$) and equilibrium dissociation constants are measured using full-length antibodies and/or Fab antibody fragments (i.e. univalent) and CFD.

The term "$k_{off}$", as used herein, refers to the rate constant for dissociation of an antibody (or bioconjugate) from the antibody/antigen complex.

The term "$K_D$", as used herein, refers to the equilibrium dissociation constant of an antibody-antigen (or bioconjugate-antigen) interaction.

Reference to "about" a value or parameter herein includes (and describes) embodiments that are directed to that value or parameter per se. For example, description referring to "about X" includes description of "X." Numeric ranges are inclusive of the numbers defining the range.

The term "patient" includes human and other subjects (including mammals) that receive either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention for a variable region or EU numbering for a constant region. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage. Sequence identities of other sequences can be determined by aligning sequences using algorithms, such as BESTFIT, FASTA, and TFASTA in the Wisconsin Genetics Software Package Release 7.0, Genetics Computer Group, 575 Science Dr., Madison, WI, using default gap parameters, or by inspection, and the best alignment (i.e., resulting in the highest percentage of sequence similarity over a comparison window). Percentage of sequence identity is calculated by comparing two optimally aligned sequences over a window of comparison, determining the number of positions at which the identical residues occurs in both sequences to yield the number of matched positions, dividing the number of matched positions by the total number of positions in the window of comparison (i.e., the window size), and multiplying the result by 100 to yield the percentage of sequence identity.

The term "antibody-dependent cellular cytotoxicity", or ADCC, is a mechanism for inducing cell death that depends upon the interaction of antibody-coated target cells (i.e., cells with bound antibody) with immune cells possessing lytic activity (also referred to as effector cells). Such effector cells include natural killer cells, monocytes/macrophages and neutrophils. ADCC is triggered by interactions between the Fc region of an antibody bound to a cell and Fcγ receptors, particularly FcγRI and FcγRIII, on immune effector cells such as neutrophils, macrophages and natural killer cells. The target cell is eliminated by phagocytosis or lysis, depending on the type of mediating effector cell. Death of the antibody-coated target cell occurs as a result of effector cell activity.

A humanized antibody is a genetically engineered antibody in which the CDRs from a non-human "donor" antibody are grafted into a human "acceptor" antibody sequences (see, e.g., Queen, U.S. Pat. Nos. 5,530,101 and 5,585,089; Winter, U.S. Pat. No. 5,225,539, Carter, U.S. Pat. No. 6,407,213, Adair, U.S. Pat. No. 5,859,205 6,881,557, Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85, 90, 95 or 100% of corresponding residues defined by Kabat are identical.

Although humanized antibodies often incorporate all six CDRs (preferably as defined by Kabat) from a mouse antibody, they can also be made with less than all CDRs (e.g., at least 3, 4, or 5 CDRs from a mouse antibody) (e.g., Pascalis et al, J. Immunol. 169:3076, 2002; Vajdos et al., Journal of Molecular Biology, 320: 415-428, 2002; Iwahashi et al., Mol. Immunol. 36: 1079-1091, 1999; Tamura et al, Journal of Immunology, 164: 1432-1441, 2000).

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions. A human antibody can be isolated from a human, or otherwise result from expression of human immunoglobulin genes (e.g., in a transgenic mouse, in vitro or by phage display). Methods for producing human antibodies include the trioma method of Oestberg et al., Hybridoma 2:361-367 (1983); Oestberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. Nos. 5,877,397, 5,874,299, 5,814,318, 5,789,650, 5,770,429, 5,661,016, 5,633,425, 5,625,126, 5,569,825, 5,545,806, Nature 148, 1547-1553 (1994), Nature Biotechnology 14, 826 (1996), Kucherlapati, WO 91/10741 (1991) and phage display methods (see, e.g. Dower et al., WO 91/17271 and McCafferty et al., WO 92/01047, U.S. Pat. Nos. 5,877,218, 5,871,907, 5,858,657, 5,837,242, 5,733,743 and 5,565,332.

A "polymer" is a molecule composed of many repeating subunits. The subunits, also sometimes referred to as "monomers" can be the same or different. There are both natural and synthetic polymers. DNA, protein and complex carbohydrates are examples of natural polymers. Poly-styrene and poly-acrylamide are examples of synthetic polymers. A polymer composed of repeating units of a single monomer is called a homopolymer. A polymer composed of two or more monomers is called a copolymer or sometimes a heteropolymer. A copolymer in which certain monomer types are clustered together are sometimes called block copolymers. Polymers can be linear or branched. When the polymer is branched, polymer chains having a common origin are sometimes referred to as a polymer arm(s).

An "initiator" is a compound capable of serving as a substrate on which one or more polymerizations can take place using monomers or comonomers as described herein. The polymerization can be a conventional free radical polymerization or preferably a controlled/"living" radical polymerization, such as Atom Transfer Radical Polymerization (ATRP), Reversible Addition-Fragmentation-Termination (RAFT) polymerization or nitroxide mediated polymerization (NMP). The polymerization can be a "pseudo" controlled polymerization, such as degenerative transfer. Initiators suitable for ATRP contain one or more labile bonds which can be homolytically cleaved to form an initiator fragment, I, being a radical capable of initiating a radical polymerization, and a radical scavenger, I', which reacts with the radical of the growing polymer chain to reversibly terminate the polymerization. The radical scavenger I' is typically a halogen, but can also be an organic moiety, such as a nitrile. In some embodiments of the present invention, the initiator contains one or more 2-bromoisobutyrate groups as sites for polymerization via ATRP.

A "chemical linker" refers to a chemical moiety that links two groups together, such as a half-life extending moiety and a protein. The linker can be cleavable or non-cleavable. Cleavable linkers can be hydrolysable, enzymatically cleavable, pH sensitive, photolabile, or disulfide linkers, among others. Other linkers include homobifunctional and heterobifunctional linkers. A "linking group" is a functional group capable of forming a covalent linkage consisting of one or more bonds to a bioactive agent. Non-limiting examples include those illustrated in Table 1 of WO2013059137 (incorporated by reference).

The term "reactive group" refers to a group that is capable of reacting with another chemical group to form a covalent bond, i.e. is covalently reactive under suitable reaction conditions, and generally represents a point of attachment for another substance. The reactive group is a moiety, such as maleimide or succinimidyl ester, is capable of chemically reacting with a functional group on a different moiety to form a covalent linkage. Reactive groups generally include nucleophiles, electrophiles and photoactivatable groups.

As used herein, "phosphorylcholine," also denoted as "PC," refers to the following:

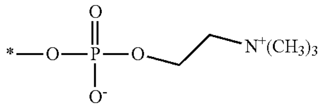

where * denotes the point of attachment. The phosphorylcholine is a zwitterionic group and includes salts (such as inner salts), and protonated and deprotonated forms thereof.

As used herein, "phosphorylcholine containing polymer" is a polymer that contains phosphorylcholine. "Zwitterion containing polymer" refers to a polymer that contains a zwitterion.

Poly(acryloyloxyethyl phosphorylcholine) containing polymer refers to a polymer containing 2-(acryloyloxy) ethyl-2-(trimethylammonium)ethyl phosphate as monomer.

Poly(methacryloyloxyethyl phosphorylcholine) containing polymer refers to a polymer containing 2-(methacryloyloxy)ethyl-2-(trimethylammonium)ethyl phosphate as monomer.

As used herein, "molecular weight" in the context of the polymer can be expressed as either a number average molecular weight, or a weight average molecular weight or a peak molecular weight. Unless otherwise indicated, all references to molecular weight herein refer to the peak molecular weight. These molecular weight determinations, number average (Mn), weight average (Mw) and peak (Mp), can be measured using size exclusion chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number average molecular weight, or the use of light scattering techniques, ultracentrifugation or viscometry to determine weight average molecular weight. In a preferred embodiment of the present invention, the molecular weight is measured by SEC-MALS (size exclusion chromatography-multi angle light scattering). The polymeric reagents of the invention are typically polydisperse (i.e., number average molecular weight and weight average molecular weight of the polymers are not equal). The Poly Dispersity Index (PDI) provides a measure for the dispersity of polymers in a mixture. PDI is given by the formula Mw/Mn. In this regard a homogenous protein will have a PDI of 1.0 (Mn is the same as Mw). Typically, the PDI for polymers will be above 1.0. Polymers in accordance with the present invention preferably have relatively low polydispersity (PDI) values of, for example, less than about 1.5, as judged, for example, by SEC-MALS. In other embodiments, the polydispersities (PDI) are more preferably in the range of about 1.4 to about 1.2, still more preferably less than about 1.15, and still more preferably less than about 1.10, yet still more preferably less than about 1.05, and most preferably less than about 1.03.

As used herein, "protected," "protected form," "protecting group" and "protective group" refer to the presence of a group (i.e., the protecting group) that prevents or blocks reaction of a particular chemically reactive functional group in a molecule under certain reaction conditions. Protecting groups vary depending upon the type of chemically reactive group being protected as well as the reaction conditions to be employed and the presence of additional reactive or protecting groups in the molecule, if any. Suitable protecting groups include those such as found in the treatise by Greene et al., "Protective Groups In Organic Synthesis," 3rd Edition, John Wiley and Sons, Inc., New York, 1999.

As used herein, "alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6 carbons.

The term "lower" referred to above and hereinafter in connection with organic radicals or compounds respectively defines a compound or radical which can be branched or unbranched with up to and including 7, preferably up to and including 4 and (as unbranched) one or two carbon atoms.

As used herein, "alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of $-(CH_2)_n$, where n is 1, 2, 3, 4, 5 or 6. Alkylene groups include, but are not limited to, methylene, ethylene, propylene, isopropylene, butylene, isobutylene, sec-butylene, pentylene and hexylene.

Substituents for the alkyl, alkenyl, alkylene, heteroalkyl, heteroalkylene, heteroalkenyl, alkynyl, cycloalkyl, heterocycloalkyl, cycloalkenyl, and heterocycloalkenyl radicals can be one or more of a variety of groups selected from, but not limited to: —OR', =O, =NR', =N—OR', —NR'R", —SR', -halogen, —SiR'R"R"', —OC(O)R', —C(O)R', $-CO_2R'$, —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR', —S(O)R', —S(O)$_2$R', —S(O)$_2$NR'R", $-NRSO_2R'$, —CN and $-NO_2$ in a number ranging from 1 to (2m'+1), where m' is the total number of carbon atoms in such radical. Each of R', R", R"' and R"" independently refers to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl.

As used herein, "alkoxy" refers to alkyl group attached to an oxygen atom and forms radical —O—R, wherein R is alkyl. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described herein. For example, the alkoxy groups can be substituted with halogens to form a "halo-alkoxy" group.

As used herein, "carboxyalkyl" means an alkyl group (as defined herein) substituted with a carboxy group. The term "carboxycycloalkyl" means an cycloalkyl group (as defined herein) substituted with a carboxy group. The term alkoxyalkyl means an alkyl group (as defined herein) substituted with an alkoxy group. The term "carboxy" employed herein refers to carboxylic acids and their esters.

As used herein, "haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, fluoromethyl, 1,2,3,4,5-pentafluoro-phenyl, etc. The term "perfluoro"

defines a compound or radical which has all available hydrogens that are replaced with fluorine. For example, perfluorophenyl refers to 1,2,3,4,5-pentafluorophenyl, perfluoromethyl refers to 1,1,1-trifluoromethyl, and perfluoromethoxy refers to 1,1,1-trifluoromethoxy. Haloalkyl can also be referred to as halo-substitute alkyl, such as fluoro-substituted alkyl.

As used herein, "cytokine" in the context of this invention is a member of a group of protein signaling molecules that may participate in cell-cell communication in immune and inflammatory responses. Cytokines are typically small, water-soluble glycoproteins that have a mass of about 8-35 kDa.

As used herein, "cycloalkyl" refers to a saturated mono- or multi-cyclic aliphatic ring system that contains from about 3 to 12, from 3 to 10, from 3 to 7, or from 3 to 6 carbon atoms. When cycloalkyl group is composed of two or more rings, the rings may be joined together with a fused ring or a spiro ring structure. When cycloalkyl group is composed of three or more rings, the rings may also join together forming a bridged ring structure. Monocyclic rings include, for example, cyclopropyl, cyclobutyl, cyclopentyl, cyclohexyl, and cyclooctyl. Bicyclic and polycyclic rings include, for example, bicyclo[1.1.1]pentane, bicyclco[2.1.1]heptane, norbornane, decahydronaphthalene and adamantane. For example, $C_{3-8}$ cycloalkyl includes cyclopropyl, cyclobutyl, cyclopentyl, cyclohexyl, cyclooctyl, and norbornane.

As used herein, "endocyclic" refers to an atom or group of atoms which comprise part of a cyclic ring structure.

As used herein, "exocyclic" refers to an atom or group of atoms which are attached but do not define the cyclic ring structure.

As used herein, "cyclic alkyl ether" refers to a 4 or 5 member cyclic alkyl group having 3 or 4 endocyclic carbon atoms and 1 endocyclic oxygen or sulfur atom (e.g., oxetane, thietane, tetrahydrofuran, tetrahydrothiophene); or a 6 to 7 member cyclic alkyl group having 1 or 2 endocyclic oxygen or sulfur atoms (e.g., tetrahydropyran, 1,3-dioxane, 1,4-dioxane, tetrahydrothiopyran, 1,3-dithiane, 1,4-dithiane, 1,4-oxathiane).

As used herein, "alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can also have from 2 to 3, 2 to 4, 2 to 5, 3 to 4, 3 to 5, 3 to 6, 4 to 5, 4 to 6 and 5 to 6 carbons.

As used herein, "alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene.

As used herein, "alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can also have from 2 to 3, 2 to 4, 2 to 5, 3 to 4, 3 to 5, 3 to 6, 4 to 5, 4 to 6 and 5 to 6 carbons.

As used herein, "alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, butynylene, sec-butynylene, pentynylene and hexynylene.

As used herein, "cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

As used herein, "heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and $—S(O)_2—$. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

As used herein, "heterocycloalkylene" refers to a heterocyclalkyl group, as defined above, linking at least two other groups. The two moieties linked to the heterocycloalkylene can be linked to the same atom or different atoms of the heterocycloalkylene.

As used herein, "aryl" refers to a monocyclic or multicyclic (e.g., fused bicyclic, tricyclic or greater) aromatic ring assembly containing 6 to 16 carbon atoms. For example, aryl may be phenyl, benzyl or naphthyl, preferably phenyl. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phenyl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

As used herein, "arylene" refers to an aryl group, as defined above, linking at least two other groups. The two moieties linked to the arylene are linked to different atoms of the arylene. Arylene groups include, but are not limited to, phenylene.

As used herein, "arylene-oxy" refers to an arylene group, as defined above, where one of the moieties linked to the arylene is linked through an oxygen atom. Arylene-oxy groups include, but are not limited to, phenylene-oxy.

Similarly, substituents for the aryl and heteroaryl groups are varied and are selected from: -halogen, —OR', —OC(O)R', —NR'R", —SR', —R', —CN, $—NO_2$, $—CO_2R'$, —CONR'R", —C(O)R', —OC(O)NR'R", —NR"C(O)R', $—NR"C(O)_2R'$, —NR'—C(O)NR"R'", $—NH—C(NH_2)=NH$, $—NR'C(NH_2)=NH$, $—NH—C(NH_2)=NR'$, —S(O)R', $—S(O)_2R'$, $—S(O)_2NR'R"$, $—N_3$, $—CH(Ph)_2$, perfluoro(C1-$C_4$)alkoxy, and perfluoro(C1-$C_4$)alkyl, in a number ranging from zero to the total number of open valences on the aromatic ring system; and where R', R" and R'" are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

Two of the substituents on adjacent atoms of the aryl or heteroaryl ring may optionally be replaced with a substituent of the formula $-T-C(O)—(CH_2)_q—U—$, wherein T and U are independently —NH—, —O—, $—CH_2—$ or a single bond, and q is an integer of from 0 to 2. Alternatively, two of the substituents on adjacent atoms of the aryl or heteroaryl ring may optionally be replaced with a substituent of the formula $-A-(CH_2)_r—B—$, wherein A and B are independently $—CH_2—$, —O—, —NH—, —S—, —S(O)—, $—S(O)_2—$, $—S(O)_2NR'—$ or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula $—(CH_2)_s—X—(CH_2)_t—$, where s and t are independently integers of from 0 to 3, and X is —O—, —NR'—, —S—, —S(O)—, $—S(O)_2—$, or $—S(O)_2NR'—$. The substituent R' in —NR'— and $—S(O)_2NR'—$ is selected from hydrogen or unsubstituted ($C_1$-$C_6$)alkyl.

As used herein, "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

The term "heteroalkyl" refers to an alkyl group having from 1 to 3 heteroatoms such as N, O and S. Additional heteroatoms can also be useful, including, but not limited to, B, Al, Si and P. The heteroatoms can also be oxidized, such as, but not limited to, —S(O)— and $—S(O)_2—$. For example, heteroalkyl can include ethers, thioethers, alkyl-amines and alkyl-thiols.

The term "heteroalkylene" refers to a heteroalkyl group, as defined above, linking at least two other groups. The two moieties linked to the heteroalkylene can be linked to the same atom or different atoms of the heteroalkylene.

As used herein, "electrophile" refers to an ion or atom or collection of atoms, which may be ionic, having an electrophilic center, i.e., a center that is electron seeking, capable of reacting with a nucleophile. An electrophile (or electrophilic reagent) is a reagent that forms a bond to its reaction partner (the nucleophile) by accepting both bonding electrons from that reaction partner.

As used herein, "nucleophile" refers to an ion or atom or collection of atoms, which may be ionic, having a nucleophilic center, i.e., a center that is seeking an electrophilic center or capable of reacting with an electrophile. A nucleophile (or nucleophilic reagent) is a reagent that forms a bond to its reaction partner (the electrophile) by donating both bonding electrons. A "nucleophilic group" refers to a nucleophile after it has reacted with a reactive group. Non limiting examples include amino, hydroxyl, alkoxy, haloalkoxy and the like.

As used herein, "maleimido" refers to a pyrrole-2,5-dione-1-yl group having the structure:

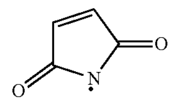

which upon reaction with a sulfhydryl (e.g., a thio alkyl) forms an —S-maleimido group having the structure

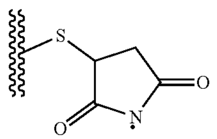

where "•" indicates the point of attachment for the maleimido group and

""

vindicates the point of attachment of the sulfur atom the thiol to the remainder of the original sulfhydryl bearing group.

For the purpose of this disclosure, "naturally occurring amino acids" found in proteins and polypeptides are L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and or L-valine. "Non-naturally occurring amino acids" found in proteins are any amino acid other than those recited as naturally occurring amino acids. Non-naturally occurring amino acids include, without limitation, the D isomers of the naturally occurring amino acids, and mixtures of D and L isomers of the naturally occurring amino acids. Other amino acids, such as 4-hydroxyproline, desmosine, isodesmosine, 5-hydroxylysine, epsilon-N-methyllysine, 3-methylhistidine, although found in naturally occurring proteins, are considered to be non-naturally occurring amino acids found in proteins for the purpose of this disclosure as they are generally introduced by means other than ribosomal translation of mRNA.

As used herein, "linear" in reference to the geometry, architecture or overall structure of a polymer, refers to polymer having a single polymer arm.

As used herein, "branched," in reference to the geometry, architecture or overall structure of a polymer, refers to a polymer having 2 or more polymer "arms" extending from a core structure contained within an initiator. The initiator may be employed in an atom transfer radical polymerization (ATRP) reaction. A branched polymer may possess 2 polymer chains (arms), 3 polymer arms, 4 polymer arms, 5 polymer arms, 6 polymer arms, 7 polymer arms, 8 polymer arms, 9 polymer arms or more. Each polymer arm extends from a polymer initiation site. Each polymer initiation site is capable of being a site for the growth of a polymer chain by the addition of monomers. For example and not by way of limitation, using ATRP, the site of polymer initiation on an initiator is typically an organic halide undergoing a reversible redox process catalyzed by a transition metal compound such as cuprous halide. Preferably, the halide is a bromine.

As used herein, "pharmaceutically acceptable excipient" refer to an excipient that can be included in the compositions of the invention and that causes no significant adverse toxicological effect on the patient and is approved or approvable by the FDA for therapeutic use, particularly in humans. Non-limiting examples of pharmaceutically acceptable excipients include water, NaCl, normal saline solutions, lactated Ringer's, normal sucrose, normal glucose and the like.

Figure 2B:
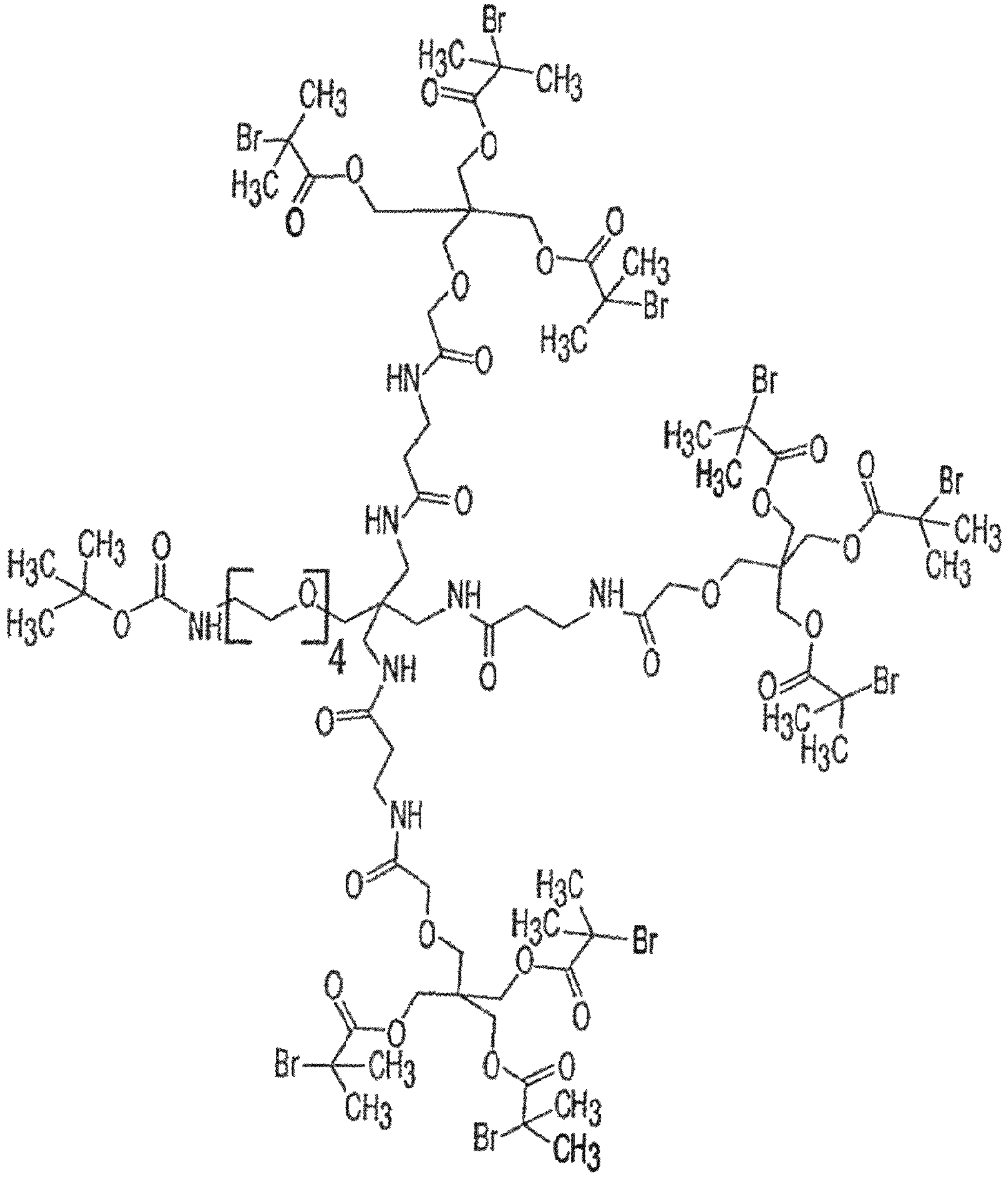
FIG. 2B shows Compound K.
Figure 2C:
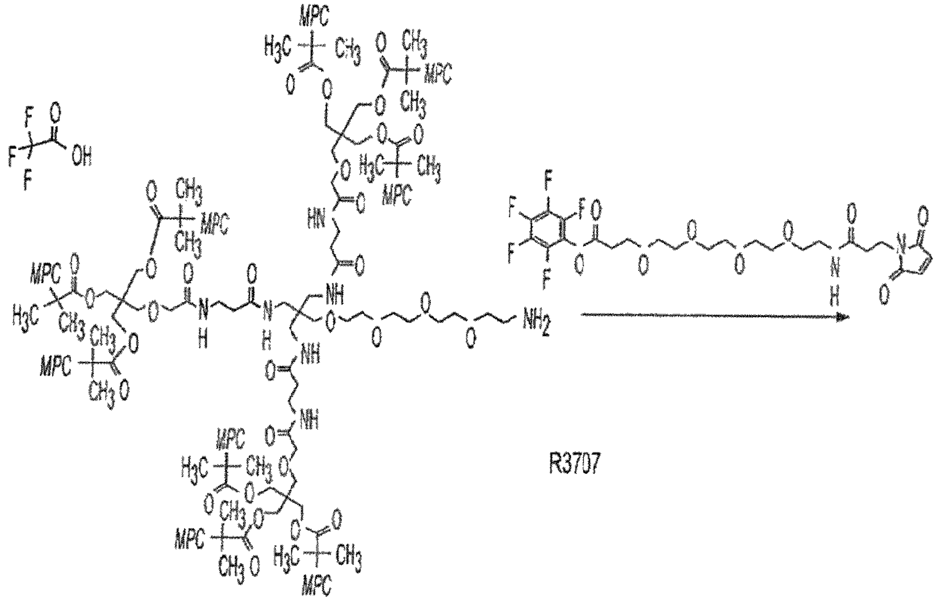
FIG. 2C shows the synthesis of OG1802 from R3707.
Figure 2C:
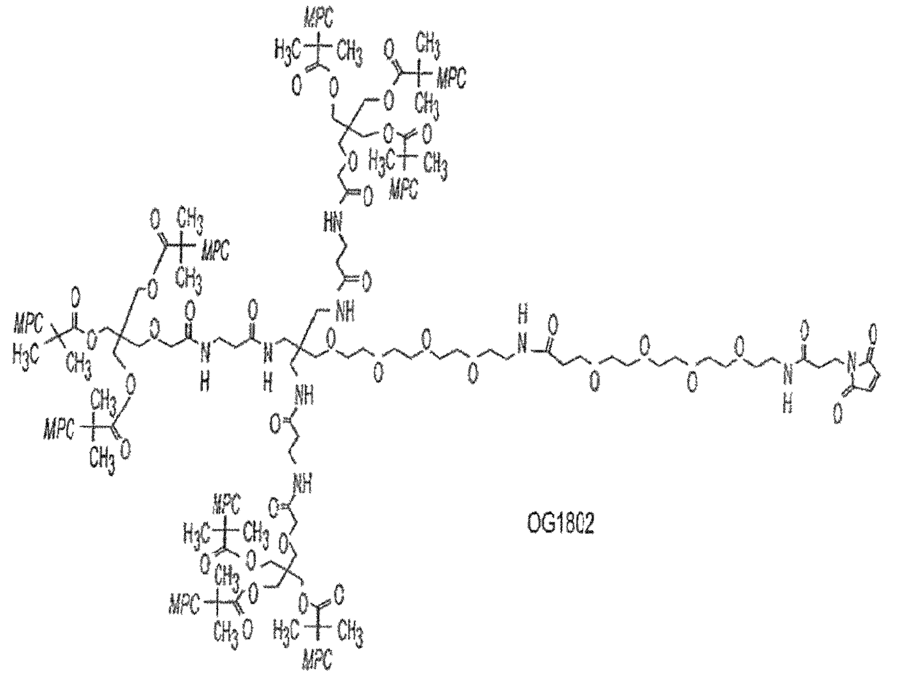
Figure 2D:
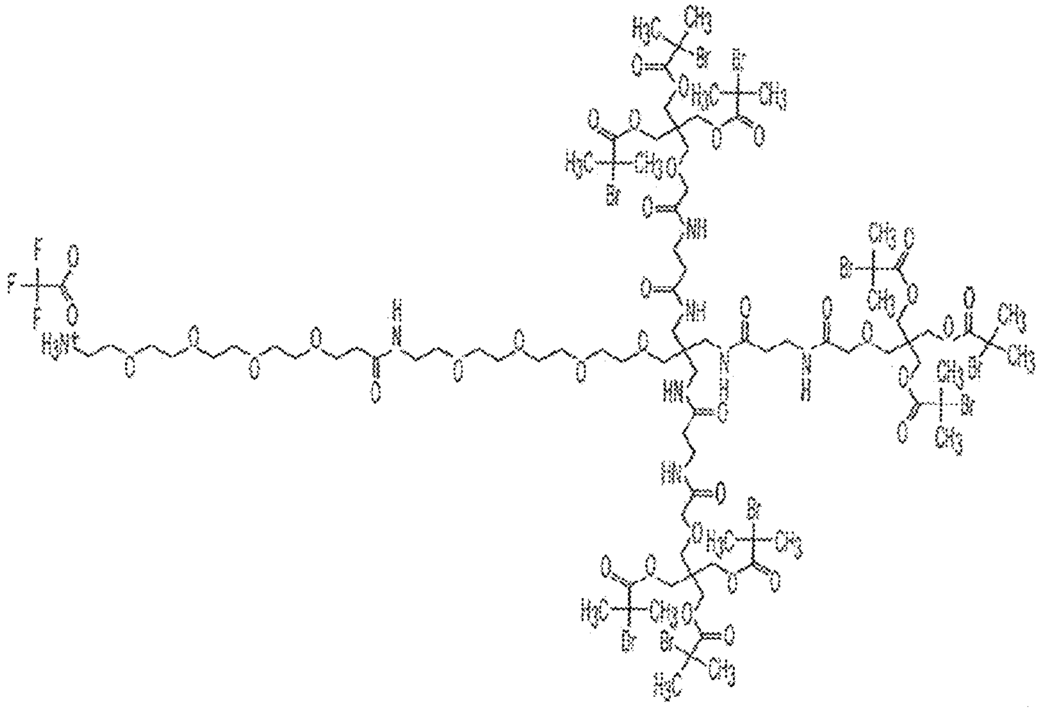
FIG. 2D shows OG1786.

As used herein, "OG1786" is a 9-arm initiator used for polymer synthesis with the structure shown in FIG. 2D, which depicts that salt form of OG1786 with trifluororacetic acid. OG1786 may be used in accordance with the present invention as other salts or as the free base.

Figure 2E:
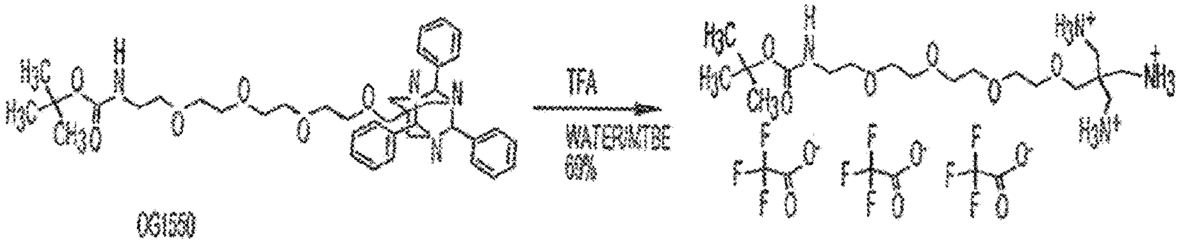
FIG. 2E shows the synthesis of OG1546 from OG1550.

As used herein, "OG1801" is an approximately (+/−15%) 750 kDa polymer (either by Mn or Mp) made using OG1786 as an initiator for ATRP synthesis using the monomer HEMA-PC. The structure of OG1801 is shown in FIG. 2J.

Figure 2F:
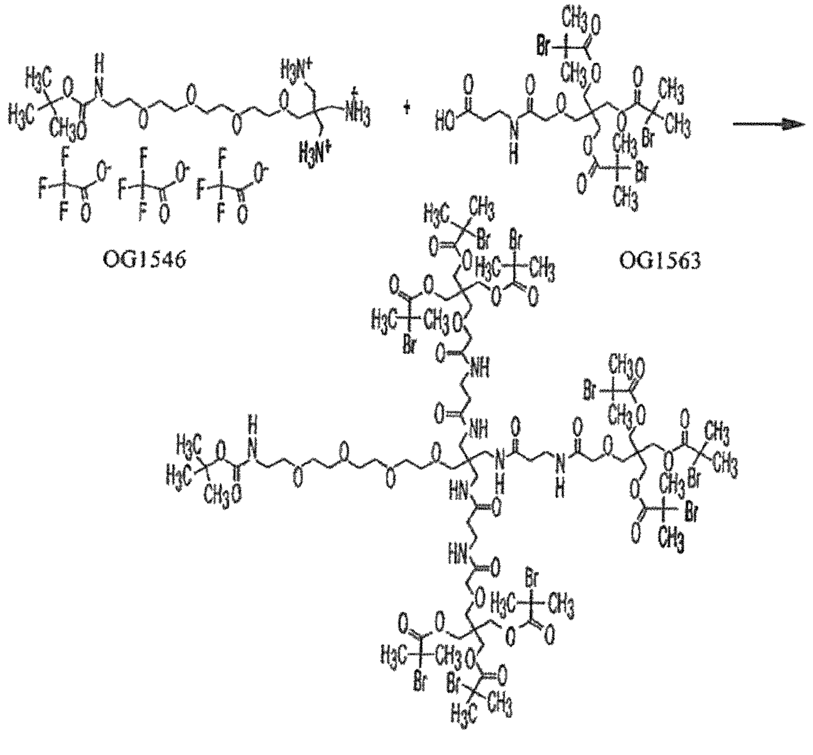
FIG. 2F shows the synthesis of OG1784 from OG1546 and OG1563.
Figure 2G:
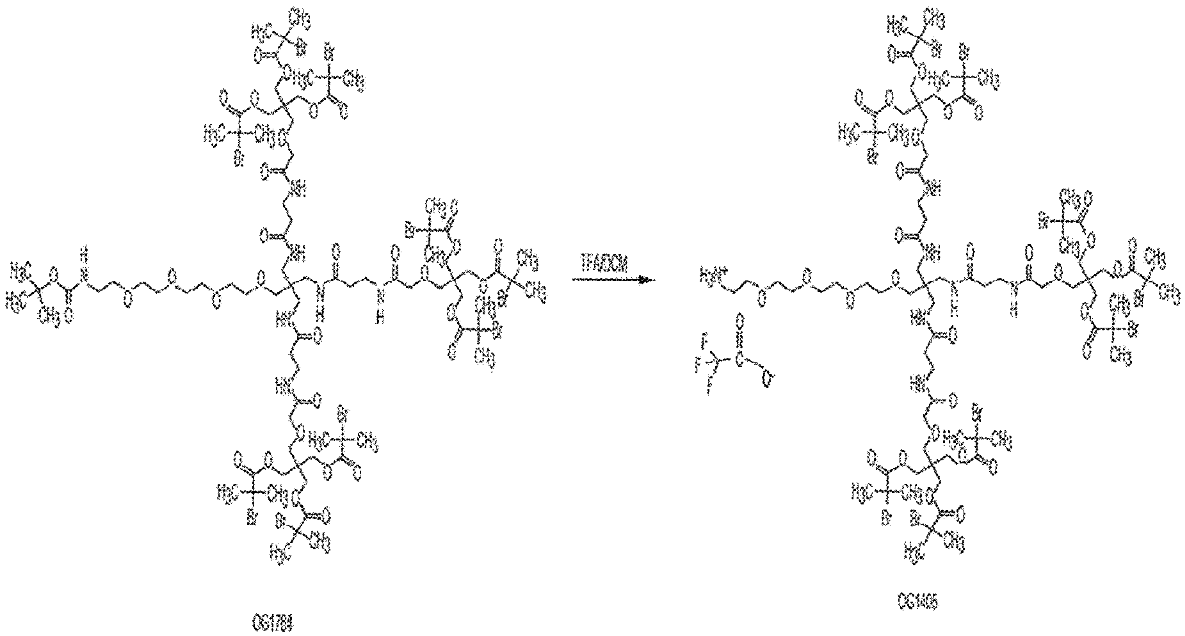
FIG. 2G shows the synthesis of OG1405 from OG1784.
Figure 2H:
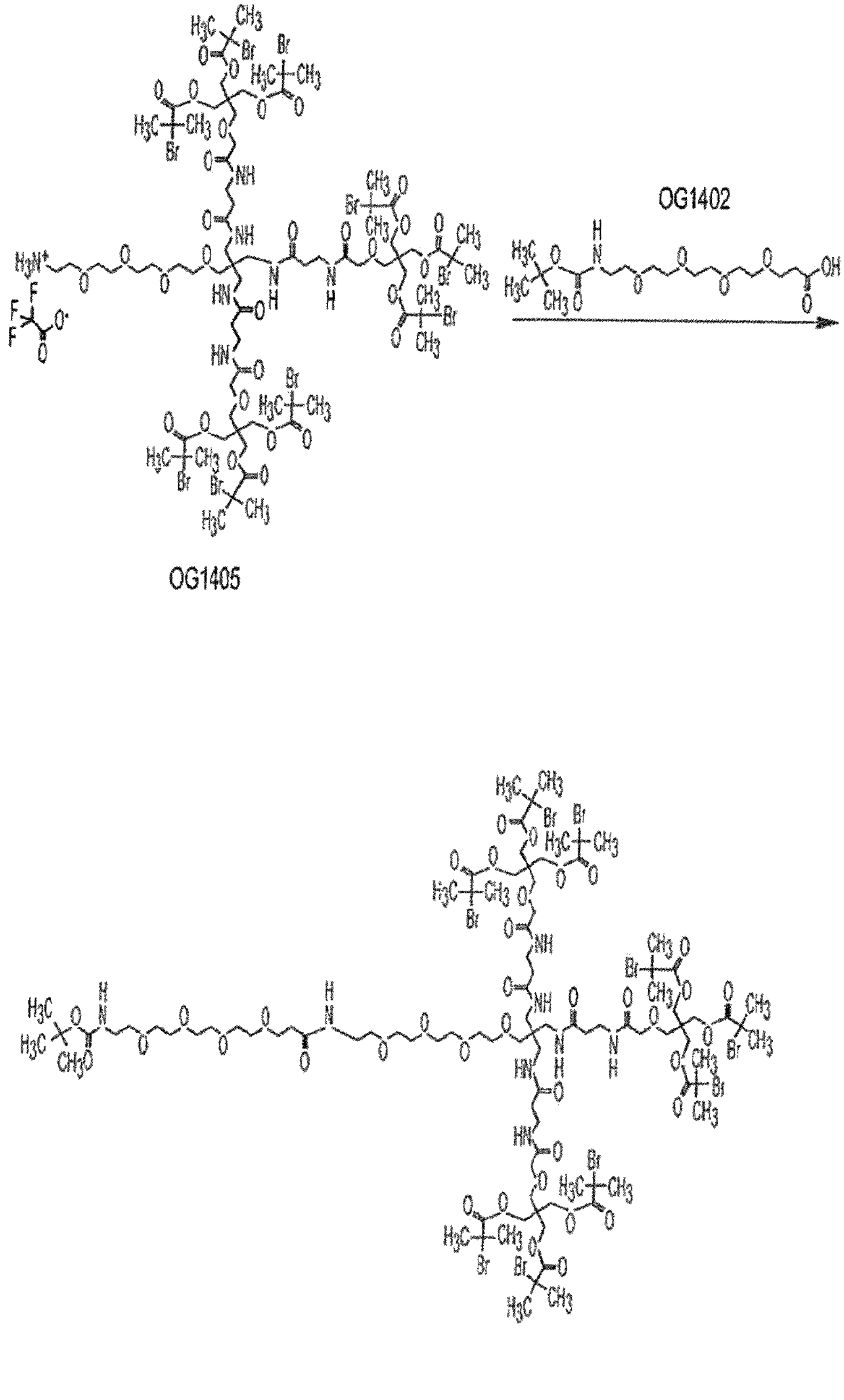
FIG. 2H shows the synthesis of OG1785 from OG1405.
Figure 2J:
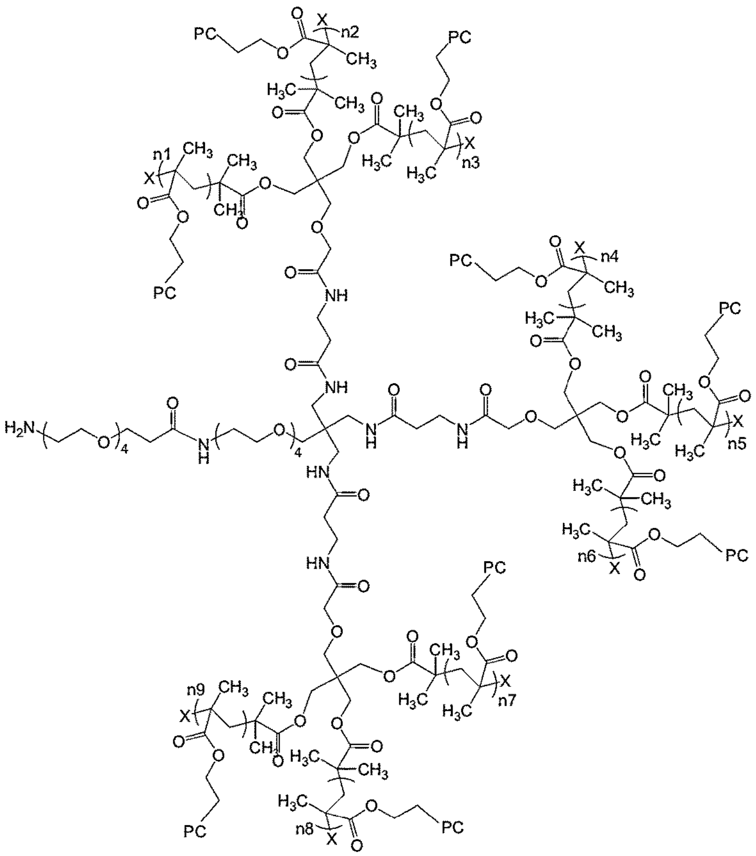
FIG. 2J shows OG1801.
Figure 2J:
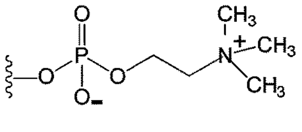
Figure 2K:
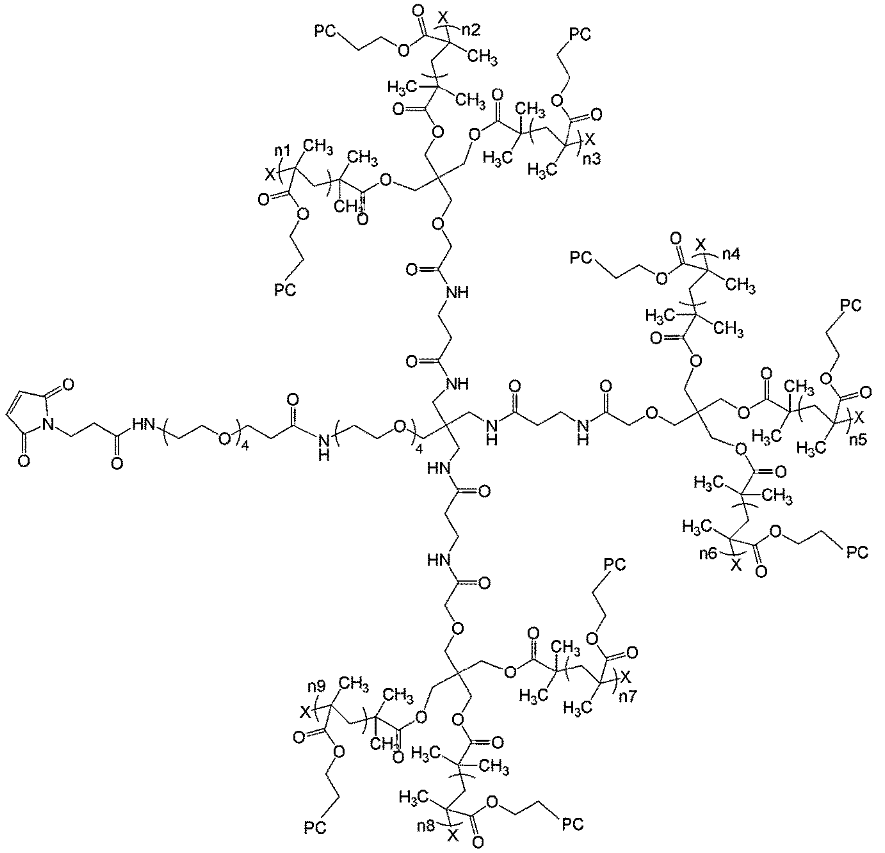
FIG. 2K shows OG1802.
Figure 2K:
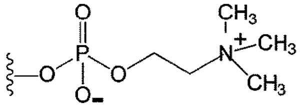

As used herein, "OG1802" is OG1801 with a maleimide functionality added, and it has the structure shown in FIG. 2K, wherein each of $n_1$, $n_2$, $n_3$, $n_4$, $n_5$, $n_6$, $n_7$, $n_8$ and $n_9$ is an integer (positive) (from 0 up to about 3000) such that the total molecular weight of the polymer is (Mw) 750,000±15% Daltons.

By "directly inhibit", "direct inhibitor", or other similar phrase in regard to the proteolytic activity of CFD, it is meant that the antibody reduces the enzymatic activity of CFD itself, rather than reducing a downstream activity of CFD or by some other mechanism of action. Thus, for example, an antibody that reduces CFD proteolytic activity indirectly, by altering an activity or function of CFD that occurs as a result of (e.g., downstream of) the proteolytic activity, would not "directly inhibit" proteolytic activity. Similarly, an antibody that binds to CFD and does not reduce the proteolytic activity of CFD, would not "directly inhibit" the proteolytic activity, even if it also blocked other aspects (for example, preventing a substrate from accessing the enzymatic binding location of CFD or from leaving the enzymatic location of CFD. A direct inhibitor of proteolytic activity of CFD will decrease the enzymatic activity of CFD. While not expressly stated, all disclosure in the present specification that is directed to inhibiting proteolytic activity of CFD, contemplates both the direct inhibition of CFD and the indirect inhibition of CFD, unless stated otherwise (e.g., through data or a statement). Thus, each disclosure provides support for both forms of inhibition, unless expressly stated otherwise (this does not apply for the claims.) The term "directly inhibits" proteolytic processing excludes the mechanism of action by which lampalizumab functions, as lampalizumab allows CFD to maintain proteolytic processing, even while bound to CFD. While lampalizumab may "block" some activity of CFD by preventing the binding of CFD to its substrate, lampalizumab does not appear to actually reduce or prevent CFD enzymatic activity itself. In some embodiments, this can be assayed for by using a small peptide substrate, for example, N-carbobenzyloxy-Lys-ThioBenzyl ester. Lampalizumab will not block CFD processing of N-carbobenzyloxy-Lys-ThioBenzyl ester, while various embodiments provided herein can reduce CFD processing of N-carbobenzyloxy-Lys-ThioBenzyl ester, thereby serving as direct inhibitors of proteolytic processing by CFD.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

The phrase "a" or "an" entity refers to one or more of that entity; for example, a compound refers to one or more compounds or at least one compound. As such, the terms "a" (or "an"), "one or more", and "at least one" can be used interchangeably herein.

As used herein, "about" means variation one might see in measurements taken among different instruments, samples, and sample preparations.

Multi-angle light scattering (MALS) is a technique of analyzing macromolecules where the laser light impinges on the molecule, the oscillating electric field of the light induces an oscillating dipole within it. This oscillating dipole will re-radiate light and can be measured using a MALS detector such as Wyatt miniDawn TREOS. The intensity of the radiated light depends on the magnitude of the dipole induced in the macromolecule which in turn is proportional to the polarizability of the macromolecule, the larger the induced dipole, and hence, the greater the intensity of the scattered light. Therefore, in order to analyze the scattering from a solution of such macromolecules, one should know their polarizability relative to the surrounding medium (e.g., the solvent). This may be determined from a measurement of the change, $\Delta n$, of the solution's refractive index n with the molecular concentration change, $\Delta c$, by measuring the dn/dc ($=\Delta n/\Delta c$) value using a Wyatt Optilab T-rEX differential refractometer. Two molar weight parameters that MALS determination employ are number average molecular weight (Mn) and weight average molecular weight (Mw) where the polydispersity index (PDI) equals Mw divided by Mn. SEC also allows another average molecular weight determination of the peak molecular weight Mp which is defined as the molecular weight of the highest peak at the SEC.

The PDI is used as a measure of the broadness of a molecular weight distribution of a polymer and bioconjugate which is derived from conjugation of a discrete protein to a polydisperse biopolymer (e.g., OG1802). For a protein sample, its polydispersity is close to 1.0 due to the fact that it is a product of translation where every protein molecule in a solution is expected to have almost the same length and molar mass. In contrast, due to the polydisperse nature of the biopolymer where the various length of polymer chains are synthesized during the polymerization process, it is very important to determine the PDI of the sample as one of its quality attribute for narrow distribution of molecular weight.

Size exclusion chromatography (SEC) is a chromatography technique in which molecules in solution are separated by their size. Typically an aqueous solution is applied to transport the sample through the column which is packed with resins of various pore sizes. The resin is expected to be inert to the analyte when passing through the column and the analytes separate from each other based on their unique size and the pore size characteristics of the selected column.

Coupling the SEC with MALS or SEC/MALS provides accurate distribution of molar mass and size (root mean square radius) as opposed to relying on a set of SEC calibration standards. This type of arrangement has many advantages over traditional column calibration methods. Since the light scattering and concentration are measured for each eluting fraction, the molar mass and size can be determined independently of the elution position. This is particularly relevant for species with non-globular shaped macromolecules such as the biopolymers (OG1802) or bioconjugates; such species typically do not elute in a manner that might be described by a set of column calibration standards.

In some embodiments, a SEC/MALS analysis includes a Waters HPLC system with Alliance 2695 solvent delivery module and Waters 2996 Photodiole Array Detector equipped with a Shodex SEC-HPLC column (7.8×300 mm). This is connected online with a Wyatt miniDawn TREOS and Wyatt Optilab T-rEX differential refractometer. The Empower software from Waters can be used to control the Waters HPLC system and the ASTRA V 6.1.7.16 software from Wyatt can be used to acquire the MALS data from the Wyatt miniDawn TREOS, dn/dc data from the T-rEX detector and the mass recovery data using the A280 absorbance signal from the Waters 2996 Photodiole Array detector. SEC can be carried out at 1 ml/min in 1×PBS pH 7.4, upon sample injection, the MALS and RI signals can be analyzed by the ASTRA software for determination of absolute molar mass (Mp, Mw, Mn) and polydisperse index (PDI). In addition, the calculation also involves the input dn/dc values for polymer and protein as 0.142 and 0.183, respectively. For OG1970 bioconjugates dn/dc value, the dn/dc is calculated based on the weighted MW of the polymer and the protein to be about 0.148 using the formula below:

$$\text{Conjugate } dn/dc = 0.142\times[MW\text{polymer}/(MW\text{polymer}+MW\text{protein})]+0.183\times[MW\text{protein}/(MW\text{polymer}+MW\text{protein})]$$

Where MWpolymer for OG1802 measured by SEC-MALS is about 800 kDa and the MWprotein for OG1965 measured by SEC-MALS is about 145 kDa, the expected total molecular weight of OG1970 bioconjugate measured by SEC-MALS is about 1000 kDa Exemplary methods and materials are described herein, although methods and materials similar or equivalent to those described herein can also be used in the practice or testing of the present invention. The materials, methods, and examples are illustrative only and not intended to be limiting.

CFD Antagonist Antibodies and Conjugates Thereof

Provided herein are anti-CFD antibodies that block, suppress or reduce (including significantly reduces) CFD biological activity, including downstream events mediated by CFD. In some embodiments, a CFD antagonist antibody can exhibit any one or more of the following characteristics: (a) bind to CFD and block downstream signaling events; (b) block C3bB (a complex of factor B, magnesium ions, and complement component 3b) binding to CFD; (c) directly inhibit proteolytic activity of CFD; and (d) block the alternative complement cascade. In some embodiments, the CFD antagonist antibody will have one or more of the CDR sequences provided herein.

In some embodiments, the isolated antagonist antibody specifically binds to complement factor D (CFD). In some embodiments, the isolated antagonist antibody specifically inhibits a proteolytic activity of CFD. In some embodiments, the isolated antagonist antibody specifically inhibits CFD binding to C3bB complex. In some embodiments, the isolated antagonist antibody specifically binds to complement factor D (CFD) and specifically inhibits a proteolytic activity of CFD. In some embodiments, the isolated antagonist antibody directly inhibits the proteolytic activity of CFD.

In some embodiments, the isolated antagonist antibody specifically binds to complement factor D (CFD) and specifically inhibits CFD binding to C3bB complex. In some embodiments, the isolated antagonist antibody specifically inhibits a proteolytic activity of CFD and specifically inhibits CFD binding to C3bB complex. In some embodiments, the isolated antagonist antibody specifically binds to complement factor D (CFD), specifically inhibits a proteolytic activity of CFD and specifically inhibits CFD binding to C3bB complex.

In some embodiments, the isolated antagonist antibody specifically binds to complement factor D (CFD) but does not bind a human CFD mutant comprising mutations R157A and R207A. In some embodiments, the isolated antagonist antibody binds an epitope on human CFD, wherein the epitope excludes positions R157 and R207. In some embodiments, the isolated antagonist antibody does not bind a human CFD mutant comprising the mutations R157A and R207A. In some embodiments, the isolated antagonist antibody binds a human CFD mutant comprising mutations R157A and R207A.

In some embodiments, the antibody preferably reacts with CFD in a manner that inhibits CFD signaling function. In some embodiments, the CFD antagonist antibody specifically binds primate CFD.

In some embodiments, the isolated antagonist anti-CFD antibody blocks the alternative complement cascade. In some embodiments, the isolated antagonist anti-CFD antibody blocks C3bB binding to CFD. In some embodiments, the isolated antagonist anti-CFD antibody blocks the alternative complement cascade by blocking C3bB binding to CFD.

The antibodies useful in the present invention can encompass monoclonal antibodies, polyclonal antibodies, antibody fragments (e.g., Fab, Fab', $F(ab')_2$, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). In some embodiments, the CFD antagonist antibody is a monoclonal antibody. In some embodiments, the antibody is a human or humanized antibody.

In some embodiments, the antibody comprises a heavy chain amino acid variable region that comprises SEQ ID NO: 520 and a light chain amino acid variable region that comprises SEQ ID NO. 184. In some embodiments, an isolated antagonist antibody comprises a heavy chain variable region (VH) comprising a VH complementarity determining region one (CDR1), VH CDR2, and VH CDR3 of the VH having an amino acid sequence of SEQ ID NO: 520, and a light chain variable region (VL) comprising a VL CDR1, VL CDR2, and VL CDR3 of the VL having an amino acid sequence of SEQ ID NO: 525.

In some embodiments, an isolated antagonist anti-CFD antibody is provided. The antibody comprises a heavy chain constant domain comprising one or more mutations to reduce effector function. In some embodiments, the one or more mutations reduce effector functions of the antibody related to the complement cascade, for example, a reduced activation of the complement cascade. In some embodiments, the reduction in effector function is at least about 50%.

In some embodiments, an isolated antagonist antibody that specifically binds to CFD comprising a heavy chain variable region (VH) and a light chain variable region (VL), wherein the antibody comprises the mutations L234A, L235A, and G237A (based on EU numbering) is provided. In some embodiments, the isolated antagonist antibody comprises the mutations L234A, L235A, and G237A. In some embodiments, the isolated antagonist antibody with mutations has minimized binding to FC gamma receptors or C1q. In some embodiments, the isolated antagonist antibody with mutations L234A, L235A, and G237A has minimized binding to FC gamma receptors or C1q. In some embodiments, an isolated antagonist anti-CFD antibody is provided, wherein the mutation(s) is located at one or more of the following amino acid positions (EU numbering): E233, L234, L235, G236, G237, A327, A330, and P331. In some embodiments, an isolated antagonist anti-CFD antibody is provided, wherein the mutation (s) is selected from the group consisting of E233P, L234V, L234A, L235A, G237A, A327G, A330S, and P331S.

In some embodiments, an isolated antagonist anti-CFD antibody is provided. The heavy chain constant domain further comprises a cysteine residue introduced by recombinant DNA technology. In some embodiments, the cysteine residue is selected from the group consisting of Q347C and L443C (EU numbering). In some embodiments, the cysteine residue is L443C (EU numbering).

In some embodiments, the isolated antagonist antibody specifically binds to complement factor D (CFD). The antibody is configured to provide a reduced complement reaction. The antibody specifically binds to complement factor D (CFD), and the antibody at least inhibits a proteolytic activity of CFD or inhibits CFD binding to C3bB complex. In some embodiments, the antibody comprises all three of the following mutations (EU numbering) L234A, L235A, and G237A, and the antibody comprises L443C (EU numbering). In some embodiments, the antibody is a human IgG1, and a heavy chain constant domain of the antibody comprises one or more mutations that reduce an immune-mediated effector function.

In some embodiments, an isolated antagonist antibody is provided that binds an epitope on human CFD that is the same as or overlaps with the epitope recognized by an antibody comprising the amino acid sequences in SEQ ID NO: 61 and SEQ ID NO: 62. In some embodiments, an isolated antagonist antibody is provided that binds an epitope on human CFD that is the same as or overlaps with the epitope recognized by an antibody comprising the amino acid sequences in SEQ ID NO: 45 and SEQ ID NO: 46.

In some embodiments, an isolated antagonist antibody is provided that binds an epitope on human CFD that is the same as or overlaps with the epitope recognized by an antibody comprising the amino acid sequences in SEQ ID NO: 520 and SEQ ID NO: 525. In some embodiments, an isolated antagonist antibody is provided that binds an epitope on human CFD that is the same as or overlaps with the epitope recognized by an antibody comprising the amino acid sequences in any one or more of Tables: 1.1, 0.1A, 0.1B, 0.1D, and/or 11.3. In some embodiments, the isolated antibody is one that comprises the amino acid sequences of the heavy and/or light chain sequences within deposited material PTA-123800 and/or PTA-123801. In some embodiments, the antibody is one that competes for binding with an antibody that comprises the heavy and/or light chain sequences within PTA-123800 (light chain) and/or PTA-123801 (heavy chain). In some embodiments, the antibody is one that is encoded by a nucleic acid sequence that hybridizes to the plasmid sequences provided in PTA-123800 (light chain) and/or PTA-123801 (heavy chain) under moderate to stringent conditions.

In some embodiments, an isolated antagonist antibody that binds to CFD is provided. In some embodiments, the isolated antagonist antibody that binds to CFD comprises a heavy chain comprising the amino acid sequence shown in SEQ ID NO: 183, with or without the C-terminal lysine and a light chain comprising the amino acid sequence shown in SEQ ID NO: 184.

In some embodiments, an isolated antagonist antibody that binds to CFD is provided. The antibody comprises a VH comprising the amino acid sequence shown in SEQ ID NO: 520, or a sequence that is at least 90% identical thereto, having amino acid substitutions in residues that are not within a CDR. In some embodiments, the antibody comprises one or more of: HCDR1: DYY (SEQ ID NO: 541), HCDR2: INPITGDT (SEQ ID NO: 542), HCDR3: EGPSFAY (SEQ ID NO: 543); LCDR1: QTIVHSNGDT (SEQ ID NO: 544), LCDR2: KVS (SEQ ID NO: 545), LCDR3: FQGSHVPVT (SEQ ID NO: 546), for example, 1, 2, 3, 4, 5, or all 6 CDRs. In some embodiments, the antibody includes HCDR3.

In some embodiments, an antibody that binds to CFD is provided, wherein the antibody comprises a CDRH1 that is the CDRH1 in SEQ ID NO: 520, a CDRH2 that is the CDRH2 in SEQ ID NO: 520, a CDRH3 that is the CDRH3 in SEQ ID NO: 520, a CDRL1 that is the CDRL1 in SEQ ID NO: 525, a CDRL2 that is the CDRL2 in SEQ ID NO: 525, a CDRL3 that is the CDRL3 in SEQ ID NO: 525, at least one of the following mutations: L234A, L235A, and G237A based on EU numbering, or L233A, L234 A, and G236A in SEQ ID NO 183, and at least one of the following mutations: Q347C or L443C based on EU numbering, or Q346C or L442C in SEQ ID NO 183.

In some embodiments, an isolated antagonist anti-CFD antibody is provided. The heavy chain variable region of the antibody comprises three complementarity determining regions (CDRs) comprising the amino acid sequences shown in SEQ ID NO: 541, 542, and 543. In some embodiments, an isolated antagonist anti-CFD antibody is provided, wherein the light chain variable region of the antibody comprises three complementarity determining regions (CDRs) comprising the amino acid sequences shown in SEQ ID NO: 544, 545, and 546.

In some embodiments, an isolated antagonist anti-CFD antibody comprises a heavy chain variable region (VH) that comprises three CDRs comprising the amino acid sequences shown in SEQ ID NO: 541, SEQ ID NO: 542, and SEQ ID NO: 543, and the light chain variable region (VL) of the antibody comprises three CDRs comprising the amino acid sequences shown in SEQ ID NO: 544, SEQ ID NO: 545, and SEQ ID NO: 546.

In some embodiments, an isolated antagonist anti-CFD antibody is provided. The VH comprises the amino acid sequences shown in SEQ ID NO: 520 and the light chain variable region of the antibody comprises three CDRs comprising the amino acid sequences shown in SEQ ID NO: 544, SEQ ID NO: 545, and SEQ ID NO: 546.

In some embodiments, an isolated antagonist anti-CFD antibody is provided, wherein the antibody comprises a VL comprising the amino acid sequence shown in SEQ ID NO: 525, or a variant thereof with one amino acid substitution in amino acids that are not within a CDR. In some embodiments, an isolated antagonist anti-CFD antibody is provided, wherein the antibody comprises a VH comprising the amino acid sequence shown in SEQ ID NO: 520, or a variant thereof with several amino acid substitutions in amino acids that are not within a CDR.

In some embodiments, an isolated antagonist antibody is provided, wherein the antibody comprises a heavy chain comprising the amino acid sequence shown in SEQ ID NO: 183, with a C-terminal lysine, and a light chain comprising the amino acid sequence shown in SEQ ID NO: 184. In some embodiments, an isolated antagonist antibody is provided, wherein the antibody comprises a heavy chain comprising the amino acid sequence shown in SEQ ID NO: 183, without a C-terminal lysine, and a light chain comprising the amino acid sequence shown in SEQ ID NO: 184.

The CFD antagonist antibodies may be made by any method known in the art. General techniques for production of human and mouse antibodies are known in the art and/or are described herein.

CFD antagonist antibodies can be identified or characterized using methods known in the art, whereby reduction, amelioration, or neutralization of CFD biological activity is detected and/or measured. In some embodiments, an CFD antagonist antibody is identified by incubating a candidate agent with CFD and monitoring binding and/or attendant reduction or neutralization of a biological activity of CFD. The binding assay may be performed with, e.g., purified CFD polypeptide(s), or with cells naturally expressing (e.g., various strains), or transfected to express, CFD polypeptide (s). In one embodiment, the binding assay is a competitive binding assay, where the ability of a candidate antibody to compete with a known CFD antagonist antibody for CFD binding is evaluated. The assay may be performed in various formats, including the ELISA format. In some embodiments, an CFD antagonist antibody is identified by incubating a candidate antibody with CFD and monitoring binding.

Following initial identification, the activity of a candidate CFD antagonist antibody can be further confirmed and refined by bioassays, known to test the targeted biological activities. In some embodiments, an in vitro cell assay is used to further characterize a candidate CFD antagonist antibody. For example, a direct functional assay based on human alternative complement-mediated rabbit red blood cell lysis assay (hemolysis assay) can be used to characterize a candidate anti-CFD antibody. In this assay, human serum complement components are activated, triggering the alternative complement cascade and resulting in lysis of rabbit blood cells. Anti-CFD antibodies that block the enzyme active site may block the alternative complement cascade, thus preventing lysis of the red blood cells. Greater than 50% inhibition of red blood cell lysis is the standard measure for successful antibody-mediated blockade of the alternative complement cascade.

A candidate anti-CFD antibody can be evaluated for its ability to affect the proteolytic activity of human CFD for the synthetic substrate Z-L-Lys-SBzl hydrochloride. Alternatively, bioassays can be used to screen candidates directly.

The CFD antagonist antibodies of the invention exhibit one or more of the following characteristics: (a) bind to CFD and block downstream signaling events; (b) block C3bB (a complex of factor B, magnesium ions, and complement component 3b) binding to CFD; (c) block C3bB cleavage by CFD; (d) block the alternative complement cascade; and e) directly inhibit CFD proteolytic activity. In some embodiments, the CFD antagonist antibodies have two or more of these features. In some embodiments, the CFD antagonist antibodies have three or more of these features. In some embodiments, the CFD antagonist antibodies have four or more of these features. In some embodiments, the antibodies have all five characteristics. In some embodiments, the CFD antagonist antibodies of the invention can inhibit the ability of human serum to lyse rabbit red blood cells in a hemolytic assay. In preferred embodiments, CFD antagonist antibodies of the invention can inhibit the proteolytic activity of CFD. In some embodiments, CFD antagonist antibodies of the invention can directly inhibit the proteolytic activity of CFD. In some embodiments, CFD antagonist antibodies of the invention can increase the proteolytic activity of CFD. In some embodiments, CFD antagonist antibodies are provided which have little to no direct effect on the proteolytic activity of CFD.

CFD antagonist antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, New York, 1999. In an additional example, epitope mapping can be used to determine the sequence to which an CFD antagonist antibody binds. CFD antagonist antibody Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with an CFD antagonist antibody. In another example, the epitope to which the CFD antagonist antibody binds can be determined in a systematic screening by using overlapping peptides derived from the CFD sequence and determining binding by the CFD antagonist antibody. According to the gene fragment expression assays, the open reading frame encoding CFD is fragmented either randomly or by specific genetic constructions and the reactivity of the expressed fragments of CFD with the antibody to be tested is determined. The gene fragments may, for example, be produced by PCR and then transcribed and translated into protein in vitro, in the presence of radioactive amino acids. The binding of the antibody to the radioactively labeled CFD fragments is then determined by immunoprecipitation and gel electrophoresis. Certain epitopes can also be identified by using large libraries of random peptide sequences displayed on the surface of phage particles (phage libraries) or yeast (yeast display). Alternatively, a defined library of overlapping peptide fragments can be tested for binding to the test antibody in simple binding assays. In an additional example, mutagenesis of an antigen, domain swapping experiments and alanine scanning mutagenesis can be performed to identify residues required, sufficient, and/or necessary for epitope binding. For example, alanine scanning mutagenesis experiments can be performed using a mutant CFD in which various residues of the CFD polypeptide have been replaced with alanine. By assessing binding of the antibody to the mutant CFD, the importance of the particular CFD residues to antibody binding can be assessed.

In some embodiments, the antibody binds to one or more of residues R157 and R207 on CFD, and does not increase the activity of CFD in the proteolytic processing of a small peptide substrate N-carbobenzyloxy-Lys-ThioBenzyl.

In some embodiments, the antibody binds to CFD with an interaction involving one or more of R157, K209, D150, T153, R156, R157, and D161 (of SEQ ID NO: 1) at 3 angstroms or less. In some embodiments, the antibody binds to CFD with an interaction involving one or more of R157, T158, H159, D161, R207, K208, K209, D116, P119, D150, R151, A152, T153, N155, R156, G162, 1164, or E166 (of SEQ ID NO: 1) at 5 angstroms or less. In some embodiments, the antibody binds to CFD with an interaction involving one or more of R157, T158, H159, D161, N206, R207, K208, K209, D116, P119, D150, R151, A152, T153, N155, R156, R157, T158, or D161, G162, A163, 1164, T165, E166 (of SEQ ID NO: 1) at 6 angstroms or less.

In some embodiments, the antibody binds to CFD with an interaction involving one or more of 157, 209, 150, 153, 156, 157, and 161 (of SEQ ID NO: 1) at 3 angstroms or less. In some embodiments, the antibody binds to CFD with an interaction involving one or more of 157, 158, 159, 161, 207, 208, 209; 116, 119, 150, 151, 152, 153, 155, 156, 162, 164, or 166 (of SEQ ID NO: 1) at 5 angstroms or less. In some embodiments, the antibody binds to CFD with an interaction involving one or more of 157-159, 161; 206-209; 116, 119, 150-153, 155-158; or 161-166 (of SEQ ID NO: 1) at 6 angstroms or less.

In some embodiments, the antibody binds to CFD at R157, K209, D150, T153, R156, R157, and D161 (of SEQ ID NO: 1). In some embodiments, the antibody binds to CFD at one or more of R157, T158, H159, D161, R207, K208, K209, D116, P119, D150, R151, A152, T153, N155, R156, G162, 1164, or E166 (of SEQ ID NO: 1). In some embodiments, the antibody binds to CFD at one or more of R157, T158, H159, D161, N206, R207, K208, K209, D116, P119, D150, R151, A152, T153, N155, R156, R157, T158, or D161, G162, A163, 1164, T165, E166 (of SEQ ID NO: 1).

In some embodiments, the antibody binds to CFD and is no more than 3 angstroms from one or more of 157, 209, 150, 153, 156, 157, and 161 (of SEQ ID NO: 1). In some embodiments, the antibody is no more than this distance from 2, 3, 4, 5, 6, or 7 of these residues. In some embodiments, the antibody binds to CFD and is no more than 5 angstroms from one or more of 157, 158, 159, 161, 207, 208, 209, 116, 119, 150, 151, 152, 153, 155, 156, 162, 164, or 166 (of SEQ ID NO: 1). In some embodiments, the antibody is no more than this distance from 2, 3, 4, 5, 6, 7, 8, 9, 10, 11, 12, 13, 14, 15, 16, 17, or 18 of these residues. In some embodiments, the antibody binds to CFD and is no more than 6 angstroms from one or more of 157-159, 161; 206-209; 116, 119, 150-153, 155-158; or 161-166 (of SEQ ID NO: 1). In some embodiments, the antibody is no more than this distance from 2, 3, 4, 5, 6, 7, 8, 9, 10, 11, 12, 13, 14, 15, 16, 17, 18, 19, 20, 21, 22, 23, or 24 of these residues.

In some embodiments, the antibody interacts with CFD at 2, 3, 4, 5, 6 or 7 of 157, 209, 150, 153, 156, 157, and 161 (of SEQ ID NO: 1) at 3 angstroms or less. In some embodiments, the antibody interacts with CFD at 2, 3, 4, 5, 6, 7, 8, 9, 10, 11, 12, 13, 14, 15, 16, 17, or 18 of 157, 158, 159, 161, 207, 208, 209; 116, 119, 150, 151, 152, 153, 155, 156, 162, 164, or 166 (of SEQ ID NO: 1) at 5 angstroms or less.

In some embodiments, the antibody interacts with CFD at one or more of 157, 158, 159, 161, 206, 207, 208, 209, 116, 119, 150, 151, 152, 153, 155, 156, 162, 163, 164, 165, or 166 of SEQ ID NO: 1. In some embodiments, the antibody interacts with CFD 2, 3, 4, 5, 6, 7, 8, 9, 10, 11, 12, 13, 14, 15, 16, 17, 18, 19, 20 or more of 157, 158, 159, 161, 206, 207, 208, 209, 116, 119, 150, 151, 152, 153, 155, 156, 162, 163, 164, 165, or 166 of SEQ ID NO: 1.

In some embodiments, an isolated antagonist antibody that specifically binds to complement factor D (CFD) is provided. When bound, the antibody is within 3 angstroms of residue 209 of SEQ ID NO: 1 of CFD.

In some embodiments, an isolated antagonist antibody that specifically binds to complement factor D (CFD) is provided. When bound, the antibody is within 3A of residue 156 of SEQ ID NO: 1 of CFD.

In some embodiments, an isolated antagonist antibody that specifically binds to complement factor D (CFD) is provided. The antibody binds to one or more of residues 156 or 209 of SEQ ID NO: 1 of CFD. In some embodiments, an isolated antagonist antibody that specifically binds to complement factor D (CFD) is provided. The antibody binds to both of residues 156 and 209 of SEQ ID NO: 1 of CFD. In some embodiments, an isolated antagonist antibody that specifically binds to complement factor D (CFD) is provided. The antibody, when bound to CFD, is not within 6 angstroms of at least one of 117, 118, and 156. In some embodiments, an isolated antagonist antibody that specifically binds to complement factor D (CFD) is provided. The antibody binds to CFD as described in any one or more of Tables: 1.1, 0.1A, 0.1B, 0.1D, and/or 11.3 (e.g., binds in the same manner as the designated antibodies in the noted tables).

In some embodiments, the antibody has the same or similar paratope as the antibody in the crystal structure provided herewith (in CTKDK001A.txt). In some embodiments, the paratope is the same as that shown in FIGS. 24A-26C (or the residues designated therein. In some embodiments, the paratope allows for an interaction with one or more of the residues designated in Table 38.1. In some embodiments, the paratope allows for an interaction with one or more of the residues designated in Table 38.2. In some embodiments, the paratope allows for an interaction with one or more of the residues designated in Table 38.3.

In some embodiments, any antibody with the same paratope as KCD119 can be used in any of the method provided herein. In some embodiments, the paratope of the antibody includes one or more of: N52, D50, E99, and 5103 on one chain (e.g., heavy chain) and E39, and D35 on the other chain (e.g., light chain). In some embodiments, 1, 2, 3, or 4 of the residues on the heavy chain are part of the paratope. In some embodiments, 1 or 2 of the residues on the light chain are part of the paratope. In some embodiments, 1, 2, 3, 4, 5, or 6 of N52, D50, E99, and S103 on the heavy chain and E39, and D35 on the light chain are the paratope. In some embodiments, this is the paratope of KCD119, involving SEQ ID NOs: 183 and 184 for the antibody. In some embodiments, the antibody's paratope includes residues positions 52, 50, 99, and 103 on the heavy chain and 39 and 35 on the light chain. In some embodiments, 1, 2, 3, 4, 5, or 6 of the paratope residues are maintained, while the rest of the heavy and/or light chain can be 80, 85, 90, 95, 98, 99, or 100 identical to, a starting sequence, e.g., SEQ ID NOs; 183/184 or 520/525. In some embodiments, the paratope includes one or more of the antibody residues in tables 38.1, 38.2, and 38.3.

In some embodiments, a crystalized CFD-antibody complex is provided. The antibody within the crystal comprises any one or more of the CDRs within SEQ ID NO:s 183 and 184, or any of the CDRs within any of Tables: 1.1, 0.1A, 0.1B, 0.1D, 11.3.

In some embodiments, the antibody is any antibody that binds to a same residues as any of the antibodies provided in Tables: 1.1, 0.1A, 0.1B, 0.1D, and/or 11.3. This can be identified through alanine scanning or other scanning mutagenesis studies. This can also be identified through solved crystal structures, in which residues that are less than 8, for example less than 5, angstroms from one another can be characterized as binding to one another. Thus, for any crystal structure produced, when a residue in the CDR of the antibody is less than 5 Angstroms from a particular residue on CFD, then that antibody can be characterized as binding to said residue. Antibodies that bind to the same residues as those antibodies provided herein are contemplated for all of the various embodiments provided herein, as appropriate (e.g., compositions, methods, etc.)

Yet another method which can be used to characterize a CFD antagonist antibody is to use competition assays with other antibodies known to bind to the same antigen, i.e., various fragments of CFD, to determine if the CFD antagonist antibody binds to the same epitope as other antibodies. Competition assays are well known to those of skill in the art, including in an ELISA format, and SPR (Surface Plasmon Resonance) biosensor.

In some embodiments, an isolated antagonist anti-CFD antibody is provided, wherein the antibody binds human CFD with an affinity of between about 0.01 pM to about 100 pM. In some embodiments, an isolated antagonist anti-CFD antibody is provided, wherein the antibody binds human CFD with an affinity of between about 0.1 pM to about 20 pM. In some embodiments, an isolated antagonist anti-CFD antibody is provided, wherein the antibody binds human CFD with an affinity of about 0.01, 0.05, 0.1, 0.5, 1, 5, 10, 15, 20, 25, 30, 35, 40, 45, 50, 55, 60, 65, 70, 75, 80, 85, 90, 95 or 100 pM.

The binding affinity ($K_D$) of an CFD antagonist antibody to CFD can be about 0.001 to about 200 nM. In some embodiments, the binding affinity is any of about 200 nM, about 100 nM, about 50 nM, about 10 nM, about 1 nM, about 500 pM, about 100 pM, about 60 pM, about 50 pM, about 20 pM, about 15 pM, about 10 pM, about 5 pM, about 2 pM, or about 1 pM. In some embodiments, the binding affinity is less than any of about 250 nM, about 200 nM, about 100 nM, about 50 nM, about 10 nM, about 1 nM, about 500 pM, about 100 pM, about 50 pM, about 20 pM, about 10 pM, about 5 pM, about 2 pM, about 1 pM, about 0.5 pM, about 0.1 pM, about 0.05 pM, about 0.01 pM, about 0.005 pM, or about 0.001 pM.

In some embodiments, an isolated antagonist anti-CFD antibody is provided, wherein the antibody binds human CFD with a koff that is at least 5.0E-03 at 37 degrees. In some embodiments the koff is 5E-04. In some embodiments, an isolated antagonist anti-CFD antibody is provided, wherein the antibody binds human CFD with a koff that is better than 5.0E-04 at 37 degrees.

In some embodiments, binding affinity can be defined in terms of one or more of association constant ($k_a$), dissociation constant ($k_d$), and analyte concentration that achieves half-maximum binding capacity (KD). In some embodiments, $k_a$ can range from about 0.50E+05 to about 5.00E+08. In some embodiments, $k_d$ can range from about 0.50E-06 to about 5.00E-03. In some embodiments, $K_D$ can range from about 0.50E-12 to about 0.50E-07.

In some embodiments, a pharmaceutical composition comprising any of the antibodies disclosed herein is provided. In some embodiments, a pharmaceutical composition comprising any of the conjugates disclosed herein is provided. In some embodiments, the pharmaceutical composition comprises one or more pharmaceutically acceptable carriers. In some embodiments, the pharmaceutical composition is a liquid. In some embodiments, the pharmaceutical composition has an endotoxin level less than about 0.2 EU/ml. In some embodiments, the pharmaceutical composition is a liquid and has an endotoxin level less than about 0.2 EU/ml. In some embodiments, the pharmaceutical composition is a liquid and has an endotoxin level less than about 2.0, 1, 0.5, 0.2 EU/ml. In some embodiments, for example in intravitreal injection, the endotoxin limit is 0.01-0.02 EU/injection/eye.

Some embodiments provide any of the following, or compositions (including pharmaceutical compositions) comprising an antibody having a partial light chain sequence and a partial heavy chain sequence as found in Tables 1.1, 0.1A, and 11.3, or variants thereof. In Table 0.1A, the underlined sequences are some embodiments of CDR sequences as provided herein. In some embodiments, a composition as disclosed herein comprises an antibody having a partial or complete light chain sequence and a partial or complete heavy chain sequence from any of the options provided in Tables 1.1, 0.1A, and 11.3 and SEQ ID NO:s 184 and 183, or variants thereof. In some embodiments, the antibody (or binding fragment thereof) can include any one or more of the CDRs provided in Tables: 1.1, 0.1A, 0.1B, 0.1D, 11.3. In some embodiments, the antibody (or binding fragment thereof) can include any three or more of the CDRs provided in Tables: 1.1, 0.1A, 0.1B, 0.1D, 11.3. In some embodiments, the antibody (or binding fragment thereof) can include any all six of the CDRs provided in Tables 1.1, 0.1A, 0.1B, 0.1D, 11.3. CDR sequences for various constructs are also found in Tables 1.1, 0.1A, 0.1B, 0.1D, 11.3, and Table 1C depicts the nucleic acid sequences for a variety of the identified antibodies in the other tables.

TABLE 0.1A

Variable Regions Sequences of anti-CFD Antagonist monoclonal Antibodies (CDRs are underlined).

| mAb | Heavy Chain | Light Chain |
|---|---|---|
| KCD002 | EVKLVESEGGLVQPGSSMKLSCTASGFTFSDYYMAWVRQVPEKGLEWVGNINYDGSSTYYLDSLKSRFIISRDSAKNILYLQMSSLKSEDTATYFCARGEDFYLYAMDYWGQGTSVTVSS (SEQ ID NO: 2) | DIQMTQSPASLSASVGETVTITCRASENIHSYLAWYQQKQGKSPQLIVYNTKTLAEGVPSRFSGSGSGTQFSLKINSLQPEDEGSYYCQHHYGIPPTFGGGTKLEIK (SEQ ID NO: 4) |
| KCD003 | EVQLQQSRPELVKPGASVKIECKASGYTFTDYYMNWMRQRHGETLEWIGDINPNNGDPSYNQKFKDKATLTVDKSSSTASMELRSLTSDDSAVYYCAREGPSFAYWGQGTLVTVSA (SEQ ID NO: 5) | DVLMTQTPLSLPVSLGEQASISCRSSQTIVHSNGDTYLEWYLQKPGQSPNLLIYKVSNRFSGVPDRFSGSGSGTDFTLKISRVEAEDLGVYYCFQGSHVPPTFGGGTKLEIK (SEQ ID NO: 6) |
| KCD005 | EVQLQQSGPELVKPGASVKISCKASGYTFTDHYMNWVKQSHGKSLEWIGDINPNNGGTSCNQKFKGKATLTVDKSSSTAYMELRSLTSGDSAVYYCTREGASFAFWGQGTLVTVSA (SEQ ID NO: 7) | DVLMTQTPLSLPVSLGDQASISCRSSQSIVHSNGDTYLEWYLQKPGQSPKLLIYKVSNRFSGVPDRFSGSGSGTDFTLKISRVEAEDLGVYYCFQGSHVPVTFGAGTKLELK (SEQ ID NO: 8) |
| KCD009 | QIQLVQSGPELKKPGETVKISCKASGYIFRNYGMNWVKQGPGKGLKWMGWINTYTGEPTYADDFKGRFAFSLETSASTAYLQISNLKNEDTATYFCVRDGPGFAYWGQGTLVTVSA (SEQ ID NO: 15) | DVLMTQTPLSLPVSLGDQASISCRSSLIIEHSDGNTYLEWYLQKPGQSPKLLIYKVSNRFSGVPDRFSGSGSGTDFTLKISRVEADDLGVYYCFQGSHVPVTFGAGTNLELK (SEQ ID NO: 16) |
| KCD010 | EVLLQQSGPELVKPGASVKIPCKASGYTFTDYDMDWVKQSHGKSLEWIGHINPNNGGTIYNQKFKGKATLTVDKSSSTAYMELRSLTSEDTAVYYCGTGDFAYWGHGTLVTVSA (SEQ ID NO: 17) | QIVLTQSPAIMSVSPGEKVTLTCSASSSVSSSYLYWYQKKPGSSPKLWIYSTSNLASGVPARFSGSGSGTSYSLTISSMEAEDAASYFCHQWSSYPPTFGAGTKLELK (SEQ ID NO: 18) |
| KCD023 | EVLLQQSGPELVKPGASVKIPCKASGYTFTDYNIDWVKQSHGKSLEWIGDINPNNGGINYNQKFKGKATLTVDKSSSTAYMELRSLTSEDTAVYYCGTGDYAYWGQGTLVTVSA (SEQ ID NO: 19) | QIVLTQSPAFMSASPGEKVTLTCSASSSVSSSYLYWYQQKPGSSPKLWIYSTSNLASGVPGRFSGSGSGTSYSLTISSMEAEDAASYFCHQWTSYPPTFGAGTKLELK (SEQ ID NO: 20) |
| KCD036 | EVQLQQSGPELVKPGASMKISCKASGYSFTGYTMTWVKQSHGKNLEWIGLINPYNGGTNYNQKFKGKATFTVDKSSSTAYMELLSLTSEDSAVYYCARRHYGSSWDYWGQGTTLTVSS (SEQ ID NO: 21) | DIKLTQSPSSMYASLGERVTITCKASQDINTYLSWFQQKPGKSPKTLIYRANRLVDGVPSRFSGSGSGQDYSLTISSLEYEEMGIYYCLQYDEFPYTFGGGTKLEIK (SEQ ID NO: 22) |
| KCD040 | EVQLQQSGAELVKPGASVKLSCTASDFNIKDTYMHWVMQRPEQGLEWIGKIDPANGNTEFDPKFQGKATITADTSSNTAYLQLTSLTSEDTAVYYCTRAMDYWGQGTSVTVSS (SEQ ID NO: 23) | QIVLTQSPAIMSASPGEKVTMTCSAGSSVSYMYWYQQKPGSSPRVLIYDTSNLASGVPVRFSGSGSGTSYSLTISRMEAEDAATYYCQQWSNYPYTFGGGTKLEIK (SEQ ID NO: 24) |
| KCD042 | EVQLQQSGAELVKPGASVRLSCTASGFNIKHTYIHWVSQRPEQGLEWIGKIDPANGNTKYDPKFQGKATITADTSSNTAYLQLSSLTSEDTAVYYCVNAMEYWGQGTSVTVSS (SEQ ID NO: 25) | QSVLTQSPAIMSASPGEKVTMTCSANSSVSDMYWFQQRPGSSPRLLIYDTSNLASGVPVRFSGSGSGTSYSLTISRMEAEDAATYYCQQWSTYPWTFGGGTKLEIK (SEQ ID NO: 26) |
| KCD044 | EVQLQQSGAELVKPGASVRLSCTASGFNIKHTYMHWVSQRPERGLEWIGKIDPANGNTKYDPKFQGKATITADTSSNTVYLQLSSLTSEDTAVYYCLNAMEYWGQGTSVTVSS (SEQ ID NO: 27) | QSVLTQSPAIMSASPGEKVTMTCSANSSVSDMYWYQQRPGSSPRLLIYDTSNLASGVPVRFSGSGSGTSYSLTISRMEAEDAATYYCQQWSTYPWTFGGGTKLEIK (SEQ ID NO: 28) |
| KCD047 | EVQLQQSGAEFVKPGASVRLSCTASGFNIKDTYMHWVKQRPEQGLEWIGRIDPANGYTKDDPKFQGKATITADTSSNTAYLQLSSLTSEDTAVYYCASAMDYWGQGTSVTVSS (SEQ ID NO: 29) | QIVLTQSPAVMSASPGEKVAMTCSASSSVTYMYWYQQKPGSSPRLLIYDTSNLASGVPVRFSGSGSGTSYSLTISRMEAEDAATYYCQQWSTYPFPFGSGTKLEIK (SEQ ID NO: 30) |
| KCD048 | EVQLQQSGADLVKPGASVKLSCTASGFNIKATYMHWVRQRPEKGLEWIGRIDPANGHTIYDPQFQGKATITSDTSSNTAYLQLNSLTSEDTAVYYCAEAMDYWGQGTSVTVSS (SEQ ID NO: 31) | QIVLTQSPAIMSASPGEKVTLTCSATSSVSYMYWYQQKPGSSPRLLIYDTSNLASGVPVRFSGSGSGTSYSLTISRMEAEDDATYYCQQWSNYPFTFGGGTKLEIK (SEQ ID NO: 32) |
| KCD070 | EIQLQQTGPELVKPGASVKISCKASGYSFTDYIILWVKQSHGKSLEWIGNINPYYDYTSYNLKFKGKATLTVDKSSSTAYMQLNSLTSEDSAVYYCARSDGYYGGDYWGQGTSVTVSS (SEQ ID NO: 33) | DIVMTQSHKFMSTSVGDRVSITCKASQDVGTAVAWYQQKPGQSPKLLIYWASTRHTGVPDRFTGSGSGTDFTLTINNVQSEDLADYFCQQYSSYPWTFGGGTTLEIK (SEQ ID NO: 34) |
| KCD101 | QVQLQQPGAELVRPGTSVKLSCKASGYTFTSYWMHWVKQRPGQGLEWIGVIDPSDSYTNYNQKFKGKATLTVDTSSSTAYMQLSSLTSEDSAVYYCGRNGYDGSMDYWGQGTSVTVSS (SEQ ID NO: 35) | DIQMTQTTSSLSASLGDRVTISCRASQDISNYLNWYQQKPDGTVKLLIYYPSRLHSGVPSRFSGSGSGTDYSLTISNLEQEDFATYFCQQGNTLPYTFGGGTKLEIK (SEQ ID NO: 36) |

TABLE 0.1A-continued

Variable Regions Sequences of anti-CFD Antagonist monoclonal Antibodies (CDRs are underlined).

| mAb | Heavy Chain | Light Chain |
|---|---|---|
| KCD102 | QVQLQQPGAELVRPGTSVKLSCKASGYTFTSYWMHWVKQRPGQGLEWIGVIDPSDSYTNYNQKFKGKATLTVDTSSSTAYMQLSSLTSEDSAVYYCARNGYDGSMDYWGQGTSVTVSS (SEQ ID NO: 37) | EIQMTQTTSSLSASLGDRVTISCRASQDISNYLNWYQQKPDGTVKLLIYYPSRLHSGVPSRFSGSGSGTDYSLTISNLEQEDFATYFCQQGNTLPYTFGGGTKLEIK (SEQ ID NO: 38) |
| KCD103 | QVQLQQPGAELVRPGTSVKLSCKASGYTFTSYWMHWVKQRPGQGLEWIGVIDPSDSYTKYNQKFKDKATLTVETSSSTAYMQLSSLTSEDSAVYYCAGNGYDGSMDYWGQGTSVTVSS (SEQ ID NO: 39) | DIQMTQTTSSLSASLGDRVTISCRASQDISNSLNWYQQKPDGTVKLLIYYTSRLHSRVPSRFSGSGSGTDYSLTISNLDQEDIATYFCQQANTLPYTFGGGTKLEIK (SEQ ID NO: 40) |
| KCD104 | QVQLQQPGAELVRPGTSVKLSCKASGYTFTSYWMHWVKQRPGQGLEWIGVIDPSDSYTYYNQKFKGKATLTVDTSSSTAYMQLSSLTSEDSAVYYCARNGYDGAMDYWGQGTSVTVSS (SEQ ID NO: 41) | EIQMTQTTSSLSASLGDRVTISCRASQDISNYLNWYQQKPDGTVKLLIYYPSRLHSGVPSRFSGSGSGTDYSLTISNLEQEDFATYFCQQGNTLPYTFGGGTKLEIK (SEQ ID NO: 42) |
| KCD118 | EVQLQQSGPELVKPGASVKISCKAFGYTFTDYYKNWMRQRHGESLEWIGDINPNSGDANYNQKFKGKATLTVDKSSSTAYMELRSLTSEDSAVYYCAREGPSFAYWGHGTLVTVSA (SEQ ID NO: 43) | DVLMTQTPLSLPVSLGDQASISCRSSQTIVHSNGDTYLEWYLQKPGQSPNLLIYKVSNRFSGVPDRFSGSGSGTDFTLKISRVEAEDLGIYYCFQGSHVPPTFGGGTKLEIK (SEQ ID NO: 44) |
| KCD119 | EVQLQQSGPELVKPGASVKISCKASGYTFTDYYTNWMRQRHGESLEWIGDINPNTGDTSYNQKFRVKATLTVDKSSGTAYMGLRSLTSEDSAVYYCTREGPSFAYWGQGTLVTVSA (SEQ ID NO: 45) | DVLMTQTPLSLPVSLGDQASISCRSSQTIVHSNGDTYLEWYLQKPGQSPNLLIYKVSNRFSGVPDRFSGSGSGTDFTLKISRVEAEDLGVYYCFQGSHVPPTFGGGTTLEIK (SEQ ID NO: 46) |
| KCD121 | EVQLQQSGPELVKPGASVKISCKASGYTFTDYYKNWMRQRHGESLEWIGDINPNNGDTSYNQKFRGKATLTVDKSSSTAFMELRSLTSEDSAVYYCAREGPSFAYWGQGTLVTVSA (SEQ ID NO: 47) | DVLMTQTPLSLPVSLGDQASISCRSNQTIVHSNGDTYLEWYLQKPGQSPNLLIYKVSNRFSGVPDRFSGSGSGTDFTLRISRVEAEDLGVYYCFQGSHVPPTFGGGTKLEIK (SEQ ID NO: 48) |
| KCD122 | EVQLQQSGPELVKPGASVKISCKASGYTFTDYYKNWMRQRHGESLEWIGDINPNNGDANYNQKFKGKATLTVDKSSSTAYMELRSLTSEDSAVYFCAREGPSFAYWGHGTLVTVSA (SEQ ID NO: 49) | DVLMTQTPLSLPVSLGDQASISCRSSQTIVHSNGDTYLEWYLQKPGQSPNLLIYKVSNRFSGVPDRFSGSGSGTDFTLKISRVEAEDLGVYYCFQGSHVPPTFGGGTKLEIK (SEQ ID NO: 50) |
| KCD123 | EVHLQQSGPELVKPGASVKISCKASGYTFTDFYKNWMRQRHGESLEWIGDINPNNGGTNYNQKFKGKATLTVDKSSSTAYMELRSLTSEDSAVYYCAREGPSFAYWGQGTLVTVSA (SEQ ID NO: 51) | DVLMTQTPLSLPVSLGDQASISCRSSQTIVHSNGDTYLEWYLQKPGQSPNLLIYKVSNRFSGVPDRFSGSGSGTDFTLKISRVEAEDLGVYYCFQGSHVPPTFGGGTKLEIK (SEQ ID NO: 52) |
| KCD124 | EVQLQQSGPELVKPGASVKISCKASGYTFTDHYMNWVKQSHGKSLEWIGDINPNNGGTSYNQKFKGKATLTVDKSSSTAYMELRSLTSGDSAVYYCTREGASFAFWGQGTLVTVSA (SEQ ID NO: 53) | DVLMTQTPLSLPVSLGDQASISCRSSQSIVHSNGDTYLEWYLQKPGQSPKLLIYKVSNRFSGVPDRFSGSGSGTDFTLKISRVEAEDLGVYYCFQGSHVPLTFGAGTKLELK (SEQ ID NO: 54) |
| KCD131 | QVQLQQSGPELVKPGASVKISCKASAYTFTDYYINWVKQRPGQGPEWIGWIFPGSNSTYSNEKFEVKATLTVDESSSTAYMLLSSLTSEDSAVYFCARLGYFGSSYHALDYWGQGTSVTVSS (SEQ ID NO: 55) | DIQMTQSPASLSVSVGETVTITCRASENIYSHLAWFQQKQGKSPRLLVYSATNLPDGVPSRFSGSGSGTQYSLKINILQSEDEGSYYCQHFWGTPWTFGGGTKLEIK (SEQ ID NO: 56) |
| KCD136 | EVQLQQSVAELVRPGASVKLSCSASGFNIKNTYMHWVNQRPEQGLEWIGRIDPANGITKYAPNFQGKATITADTSSNTAYLQLSNLTSEDTAIYYCTRAMDYWGQGTSVTVSS (SEQ ID NO: 57) | QIVLTQSPAIMSASPGEKVTMTCSASSSVSYMYWYQQKPGSSPRLLIYDISNLASGVPVRFSGSGSGTSYSLTISRMEAEDAATYYCQQWDTYPWTFGGGTKLEIK (SEQ ID NO: 58) |
| KCD200 | EVQLQQSGPELVKPGASVKISCKASGYTFTSYYKNWMRQRHGESLEWIGDINPNSGDTAYNQKFKGKATLTVDRSSSTAYMELRSLTSEDSAVYYCAREGPSFAYWGQGTLVTVSA (SEQ ID NO: 59) | DVLMTQTPLSLPVSLGDQVSISCRSSQTIVHSNGDTYLEWYLQKPGQSPNLLIYKVSNRFSGVPDRFSGSGSGTDFTLKISRVEAEDLGVYYCFQGSHVPPTFGGGTKLEIK (SEQ ID NO: 60) |
| KCD208 | EVQLQQSVAELVRPGASVKLSCTVSGFNIKNTYMHWVKQRPEQGLEWIGRIDPANGDTTYAPKFQGKATITADTSSNSAYLHLSRLTSEDTAIYYCSLYDYDGYWGQGTTLTVSS (SEQ ID NO: 61) | EIVLTQSPALMAASPGEKVTITCSVSSSISSSSLHWYRQKSGTSPKPWIYGTSHLASGVPVRFSGSGSGTSYSLTISSMEAEDAATYYCQQWDTYPWTFGGGTKLEIK (SEQ ID NO: 62) |
| KCD214 | EVQLQQSVAEFVRPGASVKLSCTASGFNIKNTYMHWVKQRPEQGLEWIGRIDPANGNTEYAPKFQGKATITADTSSNTAYLQLSSLTSEDTAIYYCALYDYDGYWGQGTTLTVSS (SEQ ID NO: 63) | EIVLTQSPALMAASPGEKVTITCRVSSSISSSSLHWYQQKSGTSPKPWIYGTSNLASGVPVRFSGSRSGTSYSLTISSMEAEDAATYYCQQWSDYPWTFGGGTKLEIK (SEQ ID NO: 64) |

TABLE 0.1A-continued

Variable Regions Sequences of anti-CFD Antagonist monoclonal Antibodies (CDRs are underlined).

| mAb | Heavy Chain | Light Chain |
|---|---|---|
| KCD220 | QVQLQQSGAELMEPGASVKLSCKATGYTFTGYWIEWVKQRPGHGLEWIGETLPGSDSNNYNEKFKGKATFTADTSSNTAYMQLSSLTTEDSAIYYCARDYSNYWYFDVWGTGTTVTVSS (SEQ ID NO: 65) | DIQMTQTTSSLSASLGDRVTISCRASQDISNYLNWYQQKPDGTVKLLIYYTSNLHSGVPSRFSGSGSGTDYSLTISNLEQEDIATYFCQQDSKHRTFGGGTKLEIK (SEQ ID NO: 66) |
| KCD224 | QVQLKESGPGLVAPSQSLSITCTVSGFSLTSYGVDWIRQSPGKGLEWLGVIWGVGSTNYNSALKSRLSISKDNSKSQVFLKMNSLQTDDTAMYYCARSYDGSYWYFDVWGTGTTVTVSS (SEQ ID NO: 67) | DIQMTQTTSSLSASLGDRVTISCRASQVISNYLNWYQQKPDGTVKLLIYYTSRLHSGVPSRFSGSGSGTDYSLTISNLEPEDIATYYCQQYSKLPYTFGSGTKLEIK (SEQ ID NO: 68) |
| 119_TAF | EVQLVESGGGLVQPGGSLRLSCAASGYTFTDYYMNWVRQAPGKGLEWIGDINPNTGDTSYNADFKRRFTFSLDTSKSTAYLQMNSLRAEDTAVYYCTREGPSFAYWGQGTLVTVSS (SEQ ID NO: 69) | DIQLTQSPSSLSASVGDRVTITCRSSQTIVHSNGDTYLEWYQQKPGKAPNLLIYKVSNRFSGVPSRFSGSGSGTDFTLTISSLQPEDFATYYCFQGSHVPPTFGQGTKVEIK (SEQ ID NO: 70) |
| 119_TAF Germ | EVQLVESGGGLVQPGGSLRLSCAASGYTFTDYYMSWVRQAPGKGLEWIGDINPNTGDTSYNADSVKGRFTISRDNSKNTLYLQMNSLRAEDTAVYYCTREGPSFAYWGQGTLVTVSS (SEQ ID NO: 71) | DIQMTQSPSSLSASVGDRVTITCRSSQTIVHSNGDTYLEWYQQKPGKAPNLLIYKVSNRFSGVPSRFSGSGSGTDFTLTISSLQPEDFATYYCFQGSHVPPTFGQGTKVEIK (SEQ ID NO: 72) |
| 119_Human Germ | EVKKPGASVKVSCKASGYTFTDYYMHWVRQAPGQGLEWIGDINPNTGDTSYNQKFQGRVTSTRDTSISTAYMELSRLRSDDTVVYYCTREGPSFAYWGQGTLVTVSS (SEQ ID NO: 73) | DVVMTQSPLSLPVTLGQPASISCRSSQTIVHSNGDTYLEWFQQRPGQSPNLLIYKVSNRFSGVPDRFSGSGSGTDFTLKISRVEAEDVGVYYCFQGSHVPPTFGGGTKVEIK (SEQ ID NO: 74) |

TABLE 0.1B

CDRs of anti-CFD Antagonist monoclonal Antibodies based on a broad CDR definition

| | H1 | H2 | H3 | L1 | L2 | L3 |
|---|---|---|---|---|---|---|
| KCD002 | GFTFSDYYMA (SEQ ID NO: 75) | INYDGSSTYYLDSLKS (SEQ ID NO: 76) | ARGEDFYLYAMDY (SEQ ID NO: 77) | RASENIHSYLA (SEQ ID NO: 78) | NTKTLAE (SEQ ID NO: 79) | QHHYGIPPT (SEQ ID NO: 80) |
| KCD003 | GYTFTDYYMN (SEQ ID NO: 81) | INPNNGDPSYNQKFKD (SEQ ID NO: 82) | AREGPSFAY (SEQ ID NO: 83) | RSSQTIVHSNGDTYLE (SEQ ID NO: 84) | KVSNRFS (SEQ ID NO: 85) | FQGSHVPPT (SEQ ID NO: 86) |
| KCD005 | GYTFTDHYMN (SEQ ID NO: 87) | INPNNGGTSCNQKFKG (SEQ ID NO: 88) | TREGASFAF (SEQ ID NO: 89) | RSSQSIVHSNGDTYLE (SEQ ID NO: 90) | KVSNRFS (SEQ ID NO: 91) | FQGSHVPVT (SEQ ID NO: 92) |
| KCD009 | GYIFRNYGMN (SEQ ID NO: 93) | INTYTGEPTYADDFKG (SEQ ID NO: 94) | VRDGPGFAY (SEQ ID NO: 95) | RSSLIIEHSDGNTYLE (SEQ ID NO: 96) | KVSNRFS (SEQ ID NO: 97) | FQGSHVPVT (SEQ ID NO: 98) |
| KCD010 | GYTFTDYDMD (SEQ ID NO: 99) | INPNNGGTIYNQKFKG (SEQ ID NO: 100) | GTGDFAY (SEQ ID NO: 101) | SASSSVSSSYLY (SEQ ID NO: 102) | STSNLAS (SEQ ID NO: 103) | HQWSSYPPT (SEQ ID NO: 104) |
| KCD023 | GYTFTDYNID (SEQ ID NO: 105) | INPNNGGINYNQKFKG (SEQ ID NO: 106) | GTGDYAY (SEQ ID NO: 107) | SASSSVSSSYLY (SEQ ID NO: 108) | STSNLAS (SEQ ID NO: 109) | HQWTSYPPT (SEQ ID NO: 110) |
| KCD036 | GYSFTGYTMT (SEQ ID NO: 111) | INPYNGGTNYNQKFKG (SEQ ID NO: 112) | ARRHYGSSWDY (SEQ ID NO: 113) | KASQDINTYLS (SEQ ID NO: 114) | RANRLVD (SEQ ID NO: 115) | LQYDEFPYT (SEQ ID NO: 116) |
| KCD040 | DFNIKDTYMH (SEQ ID NO: 117) | IDPANGNTEFDPKFQG (SEQ ID NO: 118) | TRAMDY (SEQ ID NO: 119) | SAGSSVSYMY (SEQ ID NO: 120) | DTSNLAS (SEQ ID NO: 121) | QQWSNYPYT (SEQ ID NO: 122) |
| KCD042 | GFNIKHTYIH (SEQ ID NO: 123) | IDPANGNTKYDPKFQG (SEQ ID NO: 124) | VNAMEY (SEQ ID NO: 125) | SANSSVSDMY (SEQ ID NO: 126) | DTSNLAS (SEQ ID NO: 127) | QQWSTYPWT (SEQ ID NO: 128) |
| KCD044 | GFNIKHTYMH (SEQ ID NO: 129) | IDPANGNTKYDPKFQG (SEQ ID NO: 130) | LNAMEY(SEQ ID NO: 131) | SANSSVSDMY (SEQ ID NO: 132) | DTSNLAS (SEQ ID NO: 133) | QQWSTYPWT (SEQ ID NO: 134) |

TABLE 0.1B-continued

CDRs of anti-CFD Antagonist monoclonal Antibodies based on a broad CDR definition

| | H1 | H2 | H3 | L1 | L2 | L3 |
|---|---|---|---|---|---|---|
| KCD047 | GFNIKDTYMH (SEQ ID NO: 135) | IDPANGYTKD DPKFQG (SEQ ID NO: 136) | ASAMDY (SEQ ID NO: 137) | SASSSVTYMY (SEQ ID NO: 138) | DTSNLAS (SEQ ID NO: 139) | QQWSNYPFT (SEQ ID NO: 140) |
| KCD048 | GFNIKATYMH (SEQ ID NO: 141) | IDPANGHTIY DPQFQG (SEQ ID NO: 142) | AEAMDY (SEQ ID NO: 143) | SATSSVSYMY (SEQ ID NO: 144) | DTSNLAS (SEQ ID NO: 145) | QQWSNYPFT (SEQ ID NO: 146) |
| KCD070 | GYSFTDYIIL (SEQ ID NO: 147) | INPYYDYTSY NLKFKG (SEQ ID NO: 148) | ARSDGYYGG DY (SEQ ID NO: 149) | KASQDVGTA VA (SEQ ID NO: 150) | WASTRHT (SEQ ID NO: 151) | QQYSSYPWT (SEQ ID NO: 152) |
| KCD101 | GYTFTSYWM H (SEQ ID NO: 153) | IDPSDSYTNY NQKFKG (SEQ ID NO: 154) | GRNGYDGSM DY (SEQ ID NO: 155) | RASQDISNYL N (SEQ ID NO: 156) | YPSRLHS (SEQ ID NO: 157) | QQGNTLPYT (SEQ ID NO: 158) |
| KCD102 | GYTFTSYWM H (SEQ ID NO: 159) | IDPSDSYTNY NQKFKG (SEQ ID NO: 160) | ARNGYDGSM DY (SEQ ID NO: 161) | RASQDISNYL N (SEQ ID NO: 162) | YPSRLHS (SEQ ID NO: 163) | QQGNTLPYT (SEQ ID NO: 164) |
| KCD103 | GYTFTSYWM H (SEQ ID NO: 165) | IDPSDSYTKY NQKFKD (SEQ ID NO: 166) | AGNGYDGSM DY (SEQ ID NO: 167) | RASQDISNSL N (SEQ ID NO: 168) | YTSRLHS (SEQ ID NO: 169) | QQANTLPYT (SEQ ID NO: 170) |
| KCD104 | GYTFTSYWM H (SEQ ID NO: 171) | IDPSDSYTYY NQKFKG (SEQ ID NO: 172) | ARNGYDGAM DY (SEQ ID NO: 173) | RASQDISNYL N (SEQ ID NO: 174) | YPSRLHS (SEQ ID NO: 175) | QQGNTLPYT (SEQ ID NO: 176) |
| KCD118 | GYTFTDYYKN (SEQ ID NO: 177) | INPNSGDANY NQKFKG(SEQ ID NO: 178) | AREGPSFAY (SEQ ID NO: 179) | RSSQTIVHSN GDTYLE (SEQ ID NO: 180) | KVSNRFS (SEQ ID NO: 181) | FQGSHVPPT (SEQ ID NO: 182) |
| KCD119 | GYTFTDYYTN (SEQ ID NO: 185) | INPNTGDTSY NQKFRV (SEQ ID NO: 186) | TREGPSFAY (SEQ ID NO: 187) | RSSQTIVHSN GDTYLE (SEQ ID NO: 188) | KVSNRFS (SEQ ID NO: 189) | FQGSHVPPT (SEQ ID NO: 190) |
| KCD121 | GYTFTDYYKN (SEQ ID NO: 191) | INPNNGDTSY NQKFRG (SEQ ID NO: 192) | AREGPSFAY (SEQ ID NO: 193) | RSNQTIVHSN GDTYLE (SEQ ID NO: 194) | KVSNRFS (SEQ ID NO: 195) | FQGSHVPPT (SEQ ID NO: 196) |
| KCD122 | GYTFTDYYKN (SEQ ID NO: 197) | INPNNGDANY NQKFKG (SEQ ID NO: 198) | AREGPSFAY (SEQ ID NO: 199) | RSSQTIVHSN GDTYLE (SEQ ID NO: 200) | KVSNRFS (SEQ ID NO: 201) | FQGSHVPPT (SEQ ID NO: 202) |
| KCD123 | GYTFTDFYKN (SEQ ID NO: 203) | INPNNGGTNY NQKFKG (SEQ ID NO: 204) | AREGPSFAY (SEQ ID NO: 205) | RSSQTIVHSN GDTYLE (SEQ ID NO: 206) | KVSNRFS (SEQ ID NO: 207) | FQGSHVPPT (SEQ ID NO: 208) |
| KCD124 | GYTFTDHYM N (SEQ ID NO: 209) | INPNNGGTSY NQKFKG (SEQ ID NO: 210) | TREGASFAF (SEQ ID NO: 211) | RSSQSIVHSN GDTYLE (SEQ ID NO: 212) | KVSNRFS (SEQ ID NO: 213) | FQGSHVPLT (SEQ ID NO: 214) |
| KCD131 | AYTFTDYYIN (SEQ ID NO: 215) | IFPGSNSTYSN EKFEV (SEQ ID NO: 216) | ARLGYFGSSY HALDY(SEQ ID NO: 217) | RASENIYSHL A (SEQ ID NO: 218) | SATNLPD (SEQ ID NO: 219) | QHFWGTPWT (SEQ ID NO: 220) |
| KCD136 | GFNIKNTYMH (SEQ ID NO: 221) | RIDPANGITK YAPNFQG (SEQ ID NO: 222) | TRAMDY (SEQ ID NO: 223) | SASSSVSYMY (SEQ ID NO: 224) | DISNLAS (SEQ ID NO: 225) | QQWDTYPWT (SEQ ID NO: 226) |
| KCD200 | GYTFTSYYKN (SEQ ID NO: 227) | INPNSGDTAY NQKFKG (SEQ ID NO: 228) | AREGPSFAY (SEQ ID NO: 229) | RSSQTIVHSN GDTYLE (SEQ ID NO: 230) | KVSNRFS (SEQ ID NO: 231) | FQGSHVPPT (SEQ ID NO: 232) |
| KCD208 | GFNIKNTYMH (SEQ ID NO: 233) | RIDPANGDTT YAPKFQG (SEQ ID NO: 234) | SLYDYDGY (SEQ ID NO: 235) | SVSSSISSSL H (SEQ ID NO: 236) | GTSHLAS (SEQ ID NO: 237) | QQWDTYPWT (SEQ ID NO: 238) |
| KCD214 | GFNIKNTYMH (SEQ ID NO: 239) | RIDPANGDTT YAPKFQG (SEQ ID NO: 240) | ALYDYDGY (SEQ ID NO: 241) | RVSSSISSSL H (SEQ ID NO: 242) | GTSNLAS (SEQ ID NO: 243) | QQWSDYPWT (SEQ ID NO: 244) |

TABLE 0.1B-continued

CDRs of anti-CFD Antagonist monoclonal Antibodies based on a broad CDR definition

| | H1 | H2 | H3 | L1 | L2 | L3 |
|---|---|---|---|---|---|---|
| KCD220 | GYTFTGYWIE (SEQ ID NO: 245) | ETLPGSDSNN YNEKFKG (SEQ ID NO: 246) | ARDYSNYWY FDV (SEQ ID NO: 247) | RASQDISNYL N (SEQ ID NO: 248) | YTSNLHS (SEQ ID NO: 249) | QQDSKHRT (SEQ ID NO: 250) |
| KCD224 | GFSLTSYGVD (SEQ ID NO: 251) | VIWGVGSTNY NSALKS(SEQ ID NO: 252) | ARSYDGSYW YFDV (SEQ ID NO: 253) | RASQVISNYL N (SEQ ID NO: 254) | YTSRLHS (SEQ ID NO: 255) | QQYSKLPYT (SEQ ID NO: 256) |

TABLE 0.1C

Nucleotide sequences of variable domains of anti-CFD Antagonist monoclonal Antibodies

| mAb | Heavy Chain | Light Chain |
|---|---|---|
| KCD002 | ATGTATCGAATGCAACTTCTCAGTTGTATT<br>GCGTTGTCTTTGGCTTTGGTCACTAATTCT<br>GAGGTGAAACTTGTAGAATCTGAAGGTGGT<br>CTTGTCCAGCCAGGAAGTTCCATGAAACTG<br>AGCTGTACCGCTTCCGGGTTTACGTTTAGT<br>GATTACTATATGGCCTGGGTGAGACAAGTG<br>CCTGAAAAGGGCCTCGAGTGGGTAGGAAA<br>CATTAACTATGATGGGTCTAGCACCTATTA<br>CCTTGATAGTCTTAAGTCACGATTCATTATT<br>TCAAGAGACTCAGCAAAGAATATCCTTTAT<br>CTGCAGATGTCTTCTCTTAAGAGTGAGGAT<br>ACGGCCACTTACTTCTGTGCGAGAGGTGAA<br>GATTTCTACCTTTATGCTATGGATTACTGG<br>GGGCAAGGCACTAGCGTTACCGTCTCCTCA<br>(SEQ ID NO: 257) | ATGTACCGAATGCAGCTCTTGTCCTGCATT<br>GCTTTGTCTCTCGCTTTGGTCACGAACTCC<br>GATATTCAAATGACTCAGAGCCCCGCATCT<br>CTCTCTGCTTCCGTAGGCGAAACCGTAACA<br>ATCACTTGTCGAGCTAGTGAAAACATACAC<br>TCCTATCTCGCTTGGTACCAACAGAAACAG<br>GGAAAGTCACCACAACTTATTGTGTATAAC<br>ACCAAGACGCTGGCCGAGGGTGTACCTAGT<br>CGGTTTTCTGGATCCGGTAGCGGTACACAG<br>TTTTCTTTGAAAATAAATAGCCTTCAACCTG<br>AAGATTTTGGATCCTACTATTGCCAGCATC<br>ACTATGGGATACCACCGACGTTCGGAGGCG<br>GTACAAAGCTTGAAATTAAA<br>(SEQ ID NO: 258) |
| KCD003 | ATGTATAGAATGCAATTGTTGTCCTGTATC<br>GCTCTGAGCCTTGCCCTTGTCACGAATAGC<br>GAAGTCCAACTTCAGCAGTCTCGCCCCGAA<br>CTGGTGAAGCCTGGGGCGAGTGTAAAAATT<br>TTTTGCAAAGCATCCGGCTATACATTTACG<br>GACTACTACATGAATTGGATGAGGCAGAGG<br>CACGGCGAGACCCTTGAGTGGATAGGAGA<br>CATCAACCCGAACAACGGGGACCCGTCATA<br>CAATCAGAAGTTCAAAGATAAAGCAACTCT<br>TACTGTTGATAAATCCTCAAGCACTGCGAG<br>CATGGAACTGAGGAGTCTTACATCCGACGA<br>TTCCGCTGTTTACTATTGCGCCAGGGAAGG<br>TCCTTCCTTCGCTTATTGGGGTCAGGGGAC<br>ATTGGTTACCGTCTCCGCA<br>(SEQ ID NO: 259) | ATGTATCGAATGCAGCTCTTGTCATGTATA<br>GCCCTTTCTCTGGCTCTCGTTACTAACAGC<br>GATGTGTTGATGACACAAACCCCTCTCAGT<br>CTGCCCGTTTCACTTGGCGAACAGGCGAGT<br>ATTAGCTGCCGATCTTCCCAAACTATAGTT<br>CACAGTAACGGAGATACGTACCTGGAGTGG<br>TACCTGCAGAAACCGGGCCAGTCACCTAAC<br>TTGCTCATTTACAAAGTCTCAAATAGATTCT<br>CCGGAGTTCCAGATAGGTTTTCCGGTAGTG<br>GTTCTGGTACGGACTTCACTTTGAAGATTA<br>GCCGCGTCGAGGCGGAGGACCTTGGGGTC<br>TACTATTGCTTCCAAGGCTCCCATGTGCCT<br>CCCACGTTTGGAGGAGGCACTAAGCTTGAA<br>ATTAAA (SEQ ID NO: 260) |
| KCD005 | ATGTATCGGATGCAACTGTTGAGTTGCATT<br>GCACTTAGTCTCGCACTCGTGACGAACAGC<br>GAGGTACAACTGCAACAGTCTGGCCCTGAA<br>TTGGTAAAACCCGGTGCCTCTGTTAAAATC<br>AGCTGTAAAGCGTCCGGCTATACATTTACA<br>GACCACTATATGAATTGGGTCAAGCAATCT<br>CATGGAAAATCCCTTGAATGGATAGGAGAT<br>ATAAATCCGAATAACGGAGGCACTAGTTGT<br>AACCAGAAGTTTAAGGGAAAAGCTACTCTG<br>ACTGTGGATAAATCATCTTCCACTGCCTAT<br>ATGGAGCTTAGGTCTCTTACTAGCGGGGAC<br>TCTGCGGTCTACTACTGCACCCGCGAAGGG<br>GCATCTTTCGCTTTCTGGGGTCAGGGAACA<br>CTGGTTACAGTCTCTGCA<br>(SEQ ID NO: 261) | ATGTATAGAATGCAATTGTTGTCATGTATC<br>GCGCTCTCACTCGCATTGGTTACTAACTCT<br>GATGTGTTGATGACGCAGACTCCCCTGTCT<br>CTCCCAGTGTCACTTGGCGATCAGGCTTCT<br>ATATCCTGCCGAAGCTCCCAGAGCATTGTC<br>CACAGTAACGGAGACACTTATCTGGAATGG<br>TACCTCCAAAAGCCGGGCCAGAGTCCAAAA<br>CTTTTGATCTATAAAGTCAGTAATAGATTTA<br>GTGGGGTTCCAGACAGGTTCTCAGGCAGC<br>GGCTCAGGCACCGACTTCACTCTGAAGATA<br>AGCCGGGTTGAAGCTGAGGATCTCGGGGT<br>GTATTACTGTTTCCAAGGGTCACATGTACC<br>AGTTACATTTGGAGCAGGCACTAAGCTTGA<br>AATTAAA (SEQ ID NO: 262) |
| KCD009 | ATGTACCGCATGCAACTTCTTAGCTGTATT<br>GCCCTCTCCCTTGCACTCGTTACCAATAGC<br>CAGATACAACTGGTGCAAAGCGGGCCTGA<br>GCTTAAGAAACCAGGAGAAACAGTCAAAAT<br>TTCCTGCAAAGCGTCAGGCTACATATTCAG<br>GAACTACGGCATGAATTGGGTGAAGCAAG<br>GTCCGGGCAAAGGCCTCAAATGGATGGGG | ATGTACCGAATGCAGCTCCTGTCTTGCATC<br>GCCCTTAGCCTCGCTCTTGTAACAAATTCT<br>GATGTATTGATGACTCAGACACCTCTGTCC<br>CTTCCTGTCTCACTCGGAGACCAAGCCTCA<br>ATTTCTTGTAGATCCAGTCTTATAATAGAG<br>CATTCTGATGGTAATACTTATCTGGAGTGG<br>TATCTTCAGAAACCCGGTCAGTCTCCGAAG |

TABLE 0.1C-continued

Nucleotide sequences of variable domains of anti-CFD Antagonist monoclonal Antibodies

| mAb | Heavy Chain | Light Chain |
|---|---|---|
| | TGGATCAACACATACACGGGTGAGCCCACT<br>TACGCAGACGACTTCAAGGGAAGATTTGCA<br>TTTTCACTTGAAACGTCAGCCAGTACAGCA<br>TATTTGCAGATTTCCAACCTTAAGAACGAG<br>GATACAGCCACTTATTTCTGTGTTAGGGAT<br>GGTCCAGGTTTTGCGTACTGGGGCCAAGG<br>AACTCTGGTGACTGTATCTGCA<br>(SEQ ID NO: 263) | TTGCTTATCTACAAGGTCTCCAATCGGTTTT<br>CTGGAGTTCCGGATAGGTTTTCTGGCTCAG<br>GGAGCGGGACCGATTTTACCTTGAAAATTT<br>CACGGGTGGAAGCAGATGACTTGGGTGTG<br>TACTATTGTTTTCAGGGGAGCCATGTCCCG<br>GTGACGTTCGGCGCTGGGACCAAGCTTGAA<br>ATTAAA (SEQ ID NO: 264) |
| KCD010 | ATGTATCGAATGCAGCTTTTGTCCTGTATA<br>GCTTTGTCTTTGGCCCTTGTGACAAATTCC<br>GAGGTCCTGCTTCAGCAATCAGGCCCCGAG<br>CTGGTCAAGCCAGGAGCATCTGTCAAAATA<br>CCCTGTAAGGCAAGCGGCTACACGTTTACG<br>GACTACGATATGGATTGGGTTAAGCAATCA<br>CACGGAAAGTCATTGGAGTGGATAGGCCAC<br>ATCAATCCAAATAACGGTGGCACTATTTAT<br>AACCAAAAGTTCAAGGGCAAAGCCACCCTG<br>ACCGTCGATAAGTCATCATCTACTGCGTAC<br>ATGGAGTTGAGGTCTCTGACATCAGAAGAT<br>ACCGCCGTTTATTACTGTGGCACTGGGGAT<br>TTCGCATATTGGGGACATGGAACTCTGGTC<br>ACAGTTTCAGCA (SEQ ID NO: 265) | ATGTATAGGATGCAACTGTTGTCCTGCATT<br>GCTCTTTCTCTTGCACTTGTAACAAACTCCC<br>AAATCGTACTCACCCAATCCCCAGCCATAA<br>TGTCCGTCAGTCCAGGAGAAAAGTTACCT<br>TGACCTGCAGCGCGAGTTCAAGCGTGTCCT<br>CCTCTTATTTGTACTGGTACCAGAAGAAGC<br>CGGGTAGCTCTCCTAAACTCTGGATCTACT<br>CCACCAGTAACTTGGCTAGTGGTGTCCCTG<br>CGAGATTTTCAGGGTCTGGGAGTGGGACAT<br>CCTATTCCCTCACAATAAGCTCAATGGAAG<br>CTGAGGATGCGGCGAGCTATTTTTGCCATC<br>AGTGGTCTAGCTACCCACCTACATTTGGTG<br>CTGGAACGAAGCTTGAAATTAAA<br>(SEQ ID NO: 266) |
| KCD023 | ATGTACCGAATGCAGTTGCTCTCATGTATT<br>GCTCTTAGCCTCGCCCTCGTGACCAATAGT<br>GAAGTCCTCCTTCAACAAAGTGGCCCTGAA<br>CTCGTTAAACCGGGGGCCTCTGTCAAGATA<br>CCTTGTAAAGCGAGTGGCTATACCTTTACA<br>GACTATAATATTGACTGGGTTAAACAATCA<br>CATGGAAAGAGCCTGGAATGGATCGGTGAT<br>ATAAATCCCAACAACGGTGGAATTAACTAC<br>AATCAAAAATTTAAAGGGAAAGCCACTCTT<br>ACTGTTGACAAGAGTAGCTCAACGGCGTAC<br>ATGGAACTCCGGTCTCTCACTTCAGAGGAC<br>ACAGCCGTATATTATTGCGGGACAGGAGAC<br>TATGCCTATTGGGGACAGGGCACTCTGGTC<br>ACAGTTTCAGCA (SEQ ID NO: 267) | ATGTATAGAATGCAGCTCTTGAGCTGCATC<br>GCTCTTTCCTTGGCCCTCGTGACAAACTCT<br>CAGATCGTATTGACCCAGAGCCCCGCCTTC<br>ATGAGCGCCAGTCCTGGCGAGAAAGTTACT<br>CTCACCTGCTCCGCTTCAAGTAGTGTGTCC<br>AGTAGTTACCTGTACTGGTATCAACAAAAA<br>CCCGGAAGTAGTCCTAAGTTGTGGATTTAC<br>TCCACTTCTAATCTTGCCAGCGGAGTGCCT<br>GGAAGGTTTAGTGGGAGTGGCAGCGGAAC<br>TTCCTACAGTCTTACAATCTCCAGCATGGA<br>AGCCGAGGATGCGGCGTCCTACTTCTGCCA<br>CCAGTGGACATCCTATCCCCCTACCTTCGG<br>AGCCGGGACCAAGCTTGAAATTAAA<br>(SEQ ID NO: 268) |
| KCD036 | ATGTATAGAATGCAACTTCTGAGTTGCATA<br>GCGTTGAGTCTCGCCTTGGTTACGAACTCT<br>GAGGTGCAACTGCAACAATCTGGGCCGGA<br>GCTTGTGAAGCCAGGAGCATCTATGAAAAT<br>AAGTTGCAAGGCATCTGGATACTCTTTTAC<br>AGGATACACTATGACATGGGTAAAGCAAAG<br>CCACGGGAAAAATCTTGAATGGATCGGCCT<br>CATCAATCCTTACAATGGTGGGACCAATTA<br>CAATCAGAAATTTAAAGGGAAGGCGACCTT<br>TACTGTCGACAAATCAAGCTCCACTGCATA<br>TATGGAACTCTTGTCCCTTACGAGCGAGGA<br>CAGCGCGGTCTATTATTGCGCCAGGCGACA<br>CTACGGAAGCTCTTGGGATTACTGGGGGCA<br>AGGGACCACACTGACAGTTTCATCA (SEQ<br>ID NO: 269) | ATGTACCGAATGCAGTTGTTGAGTTGTATA<br>GCTCTGTCACTCGCGCTTGTAACCAATTCA<br>GACATAAAGTTGACCCAAAGTCCGAGTTCA<br>ATGTATGCCTCTCTTGGTGAAAGGGTAACG<br>ATAACTTGCAAGGCGTCCCAGGATATAAAC<br>ACGTATCTTAGTTGGTTTCAACAGAAACCG<br>GGTAAAAGTCCCAAAACTCTTATCTACCGA<br>GCTAATAGGTTGGTAGATGGGGTGCCGTCA<br>AGATTCAGCGGTTCAGGCTCAGGCCAGGAC<br>TACTCTTTGACCATCAGCTCACTTGAATAC<br>GAGGAGATGGGCATATACTATTGCCTGCAA<br>TACGACGAGTTCCCGTACACTTTCGGAGGG<br>GGTACGAAGCTTGAAATTAAA<br>(SEQ ID NO: 270) |
| KCD040 | ATGTATAGAATGCAGCTCCTTTCTTGTATT<br>GCCCTGAGTTTGGCCTTGGTAACTAATAGT<br>GAGGTTCAACTCCAGCAAAGTGGCGCGGA<br>GCTGGTCAAGCCAGGTGCTAGTGTAAAACT<br>TTCATGCACCGCCTCCGACTTCAATATCAA<br>GGATACGTATATGCACTGGGTGATGCAGCG<br>GCCAGAACAGGGTCTGGAATGGATCGGTA<br>AAATAGACCCGGCGAACGGTAACACTGAGT<br>TTGACCCTAAATTTCAGGGCAAGGCAACCA<br>TCACAGCTGACACCTCCAGTAATACAGCGT<br>ACCTCCAGTTGACCTCACTCACCAGCGAGG<br>ACACCGCAGTCTATTACTGCACGCGAGCTA<br>TGGACTATTGGGGTCAAGGGACTTCAGTTA<br>CAGTGAGCTCA (SEQ ID NO: 271) | ATGTACCGGATGCAGTTGTTGAGCTGTATA<br>GCCCTGAGCTTGGCGCTTGTCACAAACTCT<br>CAAATCGTCCTCACGCAATCACCTGCGATC<br>ATGTCAGCTAGTCCGGGGGAGAAAGTCAC<br>GATGACGTGCTCTGCCGGATCTTCCGTTTC<br>TTATATGTATTGGTACCAGCAGAAGCCAGG<br>GAGTTCCCCTCGCGTCTTGATTTACGATAC<br>ATCTAATCTTGCTAGTGGCGTCCCGGTCCG<br>GTTCTCCGGGTCCGGCAGCGGTACATCATA<br>TTCTCTGACGATAAGTAGGATGGAGGCCGA<br>AGATGCTGCAACATACTATTGCCAGCAGTG<br>GAGTAACTATCCCTACACTTTTGGCGGAGG<br>CACTAAGCTTGAAATTAAA<br>(SEQ ID NO: 272) |
| KCD042 | ATGTACCGCATGCAATTGCTTTCTTGTATT<br>GCTCTGAGTTTGGCATTGGTAACCAACTCC<br>GAGGTTCAGCTCCAGCAGTCAGGTGCAGAA<br>CTTGTCAAACCGGGCGCGAGTGTGCGCCTC<br>TCTTGTACCGCCTCAGGTTTTAACATTAAG | ATGTATCGGATGCAATTGCTGTCTTGTATC<br>GCCCTTAGCCTCGCCCTCGTCACGAACAGC<br>CAGTCCGTGCTGACGCAGAGTCCGGCAATC<br>ATGTCTGCGAGTCCCGGTGAGAAAGTAACG<br>ATGACTTGCTCCGCTAATAGCTCCGTGAGC |

TABLE 0.1C-continued

Nucleotide sequences of variable domains of anti-CFD Antagonist monoclonal Antibodies

| mAb | Heavy Chain | Light Chain |
|---|---|---|
| | CATACATATATTCATTGGGTATCCCAGCGC | GATATGTATTGGTTCCAGCAACGGCCAGGA |
| | CCGGAACAAGGCTTGGAGTGGATCGGGAA | TCATCCCCGCGCTTGTTGATATACGACACA |
| | AATAGATCCTGCCAATGGGAATACCAAATA | TCTAATCTGGCTTCCGGTGTGCCAGTTCGA |
| | CGACCCAAAGTTCCAGGGGAAGGCCACCAT | TTCTCTGGGTCTGGGTCCGGTACGTCATAT |
| | TACGGCAGATACCTCTTCTAATACCGCTTA | AGTCTCACCATTAGCCGGATGGAAGCAGAA |
| | TCTCCAACTCTCATCACTTACGTCAGAAGA | GATGCGGCGACGTATTATTGCCAGCAATGG |
| | TACCGCGGTTTATTACTGCGTTAATGCAAT | AGTACCTATCCATGGACCTTTGGGGGTGGA |
| | GGAATACTGGGGCCAAGGCACGTCCGTTAC | ACGAAGCTTGAAATTAAA |
| | AGTATCTTCA (SEQ ID NO: 273) | (SEQ ID NO: 274) |
| KCD044 | ATGTATCGAATGCAACTTTTGAGTTGCATA | ATGTACAGAATGCAACTCCTGAGTTGCATC |
| | GCACTGAGTCTTGCTCTGGTAACAAACTCC | GCACTGTCTCTGGCGCTGGTGACAAACTCA |
| | GAGGTTCAGCTTCAGCAATCAGGTGCAGAA | CAGTCTGTCCTCACGCAGAGTCCTGCGATT |
| | CTGGTAAAGCCTGGGGCATCCGTTAGACTT | ATGTCCGCAAGCCCAGGGGAGAAGGTAAC |
| | AGTTGTACCGCAAGTGGATTCAACATAAAA | GATGACATGCTCCGCTAATAGCTCTGTGTC |
| | CACACCTATATGCATTGGGTCAGCCAGAGA | TGATATGTATTGGTATCAGCAACGCCCAGG |
| | CCCGAAAGGGGTCTTGAATGGATTGGCAAA | GTCTAGTCCCCGGCTCCTCATTTACGATAC |
| | ATAGACCCTGCAAACGGGAATACGAAATAT | CAGCAACCTCGCTAGTGGCGTCCCCGTGCG |
| | GATCCAAAGTTTCAGGGTAAAGCAACTATA | ATTTTCTGGCTCCGGGTCAGGGACTAGCTA |
| | ACAGCCGATACGTCATCCAATACAGTATAC | CAGCCTCACTATCTCCAGAATGGAAGCGGA |
| | TTGCAACTTAGCAGCCTTACGTCCGAAGAC | AGATGCAGCGACGTATTATTGTCAGCAGTG |
| | ACCGCTGTCTACTATTGCTTGAATGCTATG | GAGCACATATCCATGGACCTTTGGGGGTGG |
| | GAATACTGGGGACAGGGGACTTCTGTAACC | GACTAAGCTTGAAATTAAA |
| | GTATCCTCA (SEQ ID NO: 275) | (SEQ ID NO: 276) |
| KCD047 | ATGTATCGAATGCAACTGCTTTCATGTATT | ATGTATAGAATGCAGTTGCTCTCCTGTATC |
| | GCGCTTTCATTGGCTCTTGTTACTAACTCC | GCTCTCTCTCTGGCTTTGGTGACTAACAGT |
| | GAAGTTCAACTTCAGCAGTCTGGAGCTGAG | CAGATCGTGCTCACTCAATCACCCGCCGTT |
| | TTTGTAAAGCCCGGTGCCTCAGTAAGGCTG | ATGTCTGCGTCTCCAGGGGAGAAGGTAGCC |
| | TCTTGCACCGCTTCTGGGTTCAATATCAAG | ATGACCTGCTCAGCAAGTAGCAGCGTGACG |
| | GACACGTACATGCACTGGGTCAAGCAAAGG | TATATGTATTGGTATCAGCAAAAACCTGGA |
| | CCAGAGCAGGGATTGGAATGGATTGGTCG | AGCTCCCCCAGGTTGCTTATATATGACACT |
| | GATCGATCCTGCGAATGGTTACACCAAGGA | TCTAATTTGGCGAGTGGCGTACCTGTACGA |
| | TGACCCGAAGTTCCAAGGCAAAGCTACGAT | TTTTCTGGCAGCGGTTCTGGCACAAGTTAT |
| | AACGGCAGACACGTCAAGCAATACGGCGTA | AGTCTCACGATTAGTCGCATGGAAGCCGAA |
| | TCTTCAGCTTAGTAGCTTGACTTCTGAAGA | GACGCCGCGACTTACTATTGCCAACAATGG |
| | CACTGCCGTTTATTACTGTGCTTCCGCAAT | AGCACATATCCATTCCCATTCGGCTCCGGC |
| | GGACTACTGGGGCCAAGGGACTTCCGTGA | ACGAAGCTTGAAATTAAA |
| | CTGTATCATCA (SEQ ID NO: 277) | (SEQ ID NO: 278) |
| KCD048 | ATGTACCGAATGCAACTTCTGAGTTGCATT | ATGTATCGGATGCAGCTTCTTTCCTGCATC |
| | GCCTTGTCCCTGGCACTTGTGACTAATAGT | GCTCTTAGTCTCGCCTTGGTTACAAATTCT |
| | GAAGTGCAGCTCCAACAAAGTGGCGCTGAT | CAAATTGTGCTCACTCAGTCACCAGCGATA |
| | CTGGTCAAGCCTGGTGCGAGTGTGAAACTT | ATGTCCGCCTCTCCCGGTGAAAAGGTGACT |
| | AGCTGCACAGCGAGCGGGTTCAATATCAAA | CTGACATGCAGCGCTACATCCAGCGTCTCA |
| | GCAACTTACATGCACTGGGTACGGCAGCGA | TACATGTACTGGTATCAGCAGAAGCCTGGT |
| | CCGGAGAAAGGCCTCGAATGGATAGGCCG | TCCAGCCCTCGGCTCCTGATATACGACACA |
| | CATCGACCCCGCCAATGGACATACAATCTA | AGTAACCTGGCTTCCGGCGTGCCGGTGAG |
| | TGACCCCCAGTTTCAGGGGAAGGCTACCAT | GTTCTCTGGAAGCGGGAGTGGCACCTCTTA |
| | TACGTCCGATACTAGTAGCAATACAGCATA | TTCCTTGACGATTTCCAGAATGGAAGCGGA |
| | CCTCCAGTTGAACTCTCTCACAAGCGAGGA | GGATGATGCGACCTATTATTGTCAACAATG |
| | TACGGCAGTCTACTATTGTGCGGAGGCGAT | GAGCAACTATCCCTTTACTTTTGGCGGTGG |
| | GGATTATTGGGGTCAAGGTACATCTGTGAC | AACGAAGCTTGAAATTAAA |
| | TGTTTCCTCA (SEQ ID NO: 279) | (SEQ ID NO: 280) |
| KCD070 | ATGTACAGAATGCAACTCCTCTCCTGTATA | ATGTACCGAATGCAGCTTCTGAGTTGTATC |
| | GCTCTGTCCCTGGCCCTCGTAACTAATTCC | GCGCTGTCATTGGCCCTGGTCACGAACTCC |
| | GAGATACAGTTGCAACAAACTGGACCAGAA | GACATAGTTATGACCCAGTCACACAAATTT |
| | CTTGTCAAGCCAGGTGCATCTGTCAAGATA | ATGTCCACGTCAGTAGGTGATCGCGTGAGT |
| | AGCTGCAAAGCCTCCGGTTACAGCTTTACA | ATAACGTGTAAAGCGAGCCAGGATGTTGGC |
| | GACTACATTATCCTGTGGGTGAAACAGTCA | ACCGCCGTGGCGTGGTATCAACAAAAGCCT |
| | CATGGTAAAAGTCTGGAGTGGATAGGAAAC | GGCCAGTCCCCGAAGCTCCTCATATATTGG |
| | ATAAATCCTTACTACGATTATACCAGCTATA | GCCAGTACGAGACATACAGGCGTGCCTGAC |
| | ATCTCAAATTCAAAGGTAAAGCGACTCTGA | CGATTCACTGGGAGTGGTTCCGGCACAGAC |
| | CTGTAGACAAATCCAGCTCTACCGCCTACA | TTCACCCTCACGATAAATAATGTTCAGTCT |
| | TGCAGCTTAACTCACTTACTTCTGAGGACA | GAAGACCTGGCTGATTACTTCTGTCAGCAA |
| | GTGCCGTCTACTATTGCGCCCGCTCCGACG | TATTCTTCTTACCCTTGGACATTTGGCGGA |
| | GCTACTACGGAGGGGATTACTGGGGTCAG | GGCACCAAGCTTGAAATTAAA |
| | GGTACGAGTGTAACGGTTTCATCA | (SEQ ID NO: 282) |
| | (SEQ ID NO: 281) | |
| KCD101 | ATGTACAGGATGCAACTCCTGTCTTGCATT | ATGTACAGGATGCAACTCCTGTCTTGCATT |
| | GCACTAAGTCTTGCACTTGTCACTAACTCA | GCACTAAGTCTTGCACTTGTCACTAACTCA |
| | CAGGTCCAACTGCAGCAGCCTGGGGCTGA | GATATCCAGATGACACAGACTACATCCTCC |
| | GCTGGTGAGGCCTGGGACTTCAGTGAAGTT | CTGTCTGCCTCTCTGGGAGACAGAGTCACC |

TABLE 0.1C-continued

Nucleotide sequences of variable domains of anti-CFD Antagonist monoclonal Antibodies

| mAb | Heavy Chain | Light Chain |
|---|---|---|
| | GTCCTGCAAGGCTTCTGGCTACACCTTCAC CAGCTACTGGATGCACTGGGTAAAGCAGAG GCCTGGACAAGGCCTTGAGTGGATCGGAG TGATTGATCCTTCTGATAGTTATACTAATTA CAATCAAAAGTTCAAGGGCAAGGCCACATT GACTGTAGACACATCCTCCAGCACAGCCTA CATGCAGCTCAGCAGCCTGACATCTGAGGA CTCTGCGGTCTATTACTGTGGAAGAAATGG TTACGACGGGTCTATGGACTACTGGGGTCA AGGAACCTCAGTCACCGTCTCCTCA (SEQ ID NO: 283) | ATCAGTTGCAGGGCAAGTCAGGACATTAGC AATTATTTAAACTGGTATCAGCAGAAACCA GATGGAACTGTTAAACTCCTGATCTACTAC CCATCAAGATTACACTCAGGAGTCCCATCA AGGTTCAGTGGCAGTGGGTCTGGAACAGAT TATTCTCTCACCATTAGCAACCTGGAGCAA GAAGATTTTGCCACTTACTTTTGCCAACAG GGTAATACGCTTCCGTACACGTTCGGAGGG GGGACCAAGCTT (SEQ ID NO: 284) |
| KCD102 | ATGTACAGGATGCAACTCCTGTCTTGCATT GCACTAAGTCTTGCACTTGTCACTAACTCA CAGGTCCAACTGCAGCAGCCTGGGGCTGA GCTGGTGAGGCCTGGGACTTCAGTGAAGTT GTCCTGCAAGGCTTCTGGCTACACCTTCAC CAGCTACTGGATGCACTGGGTAAAGCAGAG GCCTGGACAAGGCCTTGAGTGGATCGGAG TGATTGATCCTTCTGATAGTTATACTAACTA CAATCAAAAGTTCAAGGGCAAGGCCACATT GACTGTAGACACATCCTCCAGCACAGCCTA CATGCAGCTCAGCAGCCTGACATCTGAGGA CTCTGCGGTCTATTACTGTGCAAGAAATGG TTACGACGGGTCTATGGACTACTGGGGTCA AGGAACCTCAGTCACCGTCTCCTCA (SEQ ID NO: 285) | ATGTACAGGATGCAACTCCTGTCTTGCATT GCACTAAGTCTTGCACTTGTCACTAACTCA GAAATCCAGATGACACAGACTACATCCTCC CTGTCTGCCTCTCTGGGAGACAGAGTCACC ATCAGTTGCAGGGCAAGTCAGGACATTAGC AATTATTTAAACTGGTATCAGCAGAAACCA GATGGAACTGTTAAACTCCTGATCTACTAC CCATCAAGATTACACTCAGGAGTCCCATCA AGGTTCAGTGGCAGTGGGTCTGGAACAGAT TATTCTCTCACCATTAGCAACCTGGAGCAA GAAGATTTTGCCACTTACTTTTGCCAACAG GGTAATACGCTTCCGTACACGTTCGGAGGG GGGACCAAGCTT (SEQ ID NO: 286) |
| KCD103 | ATGTACAGGATGCAACTCCTGTCTTGCATT GCACTAAGTCTTGCACTTGTCACTAACTCA CAGGTCCAACTGCAGCAGCCTGGGGCTGA GCTGGTGAGGCCTGGGACTTCAGTGAAGTT GTCCTGCAAGGCTTCTGGCTACACCTTCAC CAGCTACTGGATGCACTGGGTAAAGCAGAG GCCTGGACAAGGCCTTGAGTGGATCGGAG TGATTGATCCTTCTGATAGTTATACTAAGTA CAATCAAAAGTTCAAGGACAAGGCCACATT GACTGTAGAGACATCCTCCAGCACAGCCTA CATGCAGCTCAGCAGCCTGACATCTGAGGA CTCTGCGGTCTATTACTGTGCAGGAAATGG TTACGACGGGTCTATGGACTACTGGGGTCA AGGAACCTCAGTCACCGTCTCCTCA (SEQ ID NO: 287) | ATGTACAGGATGCAACTCCTGTCTTGCATT GCACTAAGTCTTGCACTTGTCACTAACTCA GATATCCAGATGACACAGACTACATCCTCC CTGTCTGCCTCTCTGGGAGACAGAGTCACC ATCAGTTGCAGGGCAAGTCAGGACATTAGC AATTCTTTAAACTGGTATCAGCAGAAACCA GATGGAACTGTTAAACTCCTGATCTACTAC ACATCAAGATTACACTCACGAGTCCCATCA AGGTTCAGTGGCAGTGGGTCTGGAACAGAT TATTCTCTCACCATTAGCAACCTGGACCAA GAAGATATTGCCACTTACTTTTGCCAACAG GCTAATACGCTTCCGTACACGTTCGGAGGG GGGACCAAGCTT (SEQ ID NO: 288) |
| KCD104 | ATGTACAGGATGCAACTCCTGTCTTGCATT GCACTAAGTCTTGCACTTGTCACTAACTCA CAGGTCCAACTGCAGCAGCCTGGGGCTGA GCTGGTGAGGCCTGGGACTTCAGTGAAGTT GTCCTGCAAGGCTTCTGGCTACACCTTCAC CAGCTACTGGATGCACTGGGTAAAGCAGAG GCCTGGACAAGGCCTTGAGTGGATCGGAG TGATTGATCCTTCTGATAGTTATACTTACTA CAATCAAAAGTTCAAGGGCAAGGCCACATT GACTGTAGACACATCCTCCAGCACAGCCTA CATGCAGCTCAGCAGCCTGACATCTGAGGA CTCTGCGGTCTATTACTGTGCAAGAAATGG TTACGACGGGGCTATGGACTACTGGGGTCA AGGAACCTCAGTCACCGTCTCCTCA (SEQ ID NO: 289) | ATGTACAGGATGCAACTCCTGTCTTGCATT GCACTAAGTCTTGCACTTGTCACTAACTCA GAAATCCAGATGACACAGACTACATCCTCC CTGTCTGCCTCTCTGGGAGACAGAGTCACC ATCAGTTGCAGGGCAAGTCAGGACATTAGC AATTATTTAAACTGGTATCAGCAGAAACCA GATGGAACTGTTAAACTCCTGATCTACTAC CCATCAAGATTACACTCAGGAGTCCCATCA AGGTTCAGTGGCAGTGGGTCTGGAACAGAT TATTCTCTCACCATTAGCAACCTGGAGCAA GAAGATTTTGCCACTTACTTTTGCCAACAG GGTAATACGCTTCCGTACACGTTCGGAGGG GGGACCAAGCTT (SEQ ID NO: 290) |
| KCD118 | ATGTACAGGATGCAACTCCTGTCTTGCATT GCACTAAGTCTTGCACTTGTCACTAACTCA GAGGTCCAGCTGCAACAGTCTGGACCTGAA CTGGTGAAGCCTGGGGCTTCAGTGAAGATA TCCTGTAAGGCTTTTGGATACACGTTCACT GACTACTACAAGAACTGGATGAGGCAGAGA CATGGAGAGAGCCTTGAGTGGATTGGAGAT ATTAATCCTAACAGTGGTGATGCTAACTAC AACCAGAAGTTCAAGGGCAAGGCCACATTG ACTGTTGACAAGTCCTCCAGCACAGCCTAC ATGGAGCTCCGCAGCCTGACATCTGAGGAC TCTGCAGTCTATTACTGTGCAAGAGAGGGA CCTTCGTTTGCTTACTGGGGCCATGGGACT CTGGTCACTGTCTCTGCA (SEQ ID NO: 291) | ATGTACAGGATGCAACTCCTGTCTTGCATT GCACTAAGTCTTGCACTTGTCACTAACTCA GATGTTTTGATGACCCAAACTCCACTCTCC CTGCCTGTCAGTCTTGGAGATCAAGCCTCC ATCTCTTGCAGATCTAGTCAGACCATTGTT CATAGTAATGGAGACACCTATTTAGAATGG TACCTGCAGAAACCAGGCCAGTCTCCAAAC CTCCTGATCTACAAAGTTTCCAACCGATTTT CTGGGGTCCCAGACAGGTTCAGTGGCAGT GGATCCGGGACAGATTTCACACTCAAGATC AGCAGAGTGGAGGCTGAGGATCTGGGAAT TTATTACTGCTTTCAAGGTTCACATGTTCCT CCGACGTTCGGTGGAGGCACCAAGCTT (SEQ ID NO: 292) |

TABLE 0.1C-continued

Nucleotide sequences of variable domains of anti-CFD Antagonist monoclonal Antibodies

| mAb | Heavy Chain | Light Chain |
|---|---|---|
| KCD119 | ATGTACAGGATGCAACTCCTGTCTTGCATT<br>GCACTAAGTCTTGCACTTGTCACTAACTCA<br>GAGGTCCAGCTGCAACAGTCTGGACCTGAA<br>CTGGTGAAGCCTGGGGCTTCAGTGAAGATA<br>TCCTGTAAGGCTTCTGGATACACTTTCACT<br>GACTACTACACGAACTGGATGAGGCAGAGA<br>CATGGAGAGAGCCTTGAGTGGATTGGAGAT<br>ATTAATCCTAACACTGGTGATACTAGCTAC<br>AACCAGAAGTTCAGGGTCAAGGCCACATTG<br>ACTGTAGACAAGTCCTCCGGCACAGCCTAC<br>ATGGGGCTCCGCAGCCTGACATCTGAGGAC<br>TCTGCCGTCTATTACTGTACAAGAGAGGGA<br>CCTTCGTTTGCTTACTGGGGCCAAGGGACT<br>CTGGTCACTGTCTCTGCA<br>(SEQ ID NO: 293) | ATGTACAGGATGCAACTCCTGTCTTGCATT<br>GCACTAAGTCTTGCACTTGTCACTAACTCA<br>GATGTTTTGATGACCCAAACTCCACTCTCC<br>CTGCCTGTCAGTCTTGGAGATCAAGCCTCC<br>ATCTCTTGCAGATCTAGTCAGACCATTGTA<br>CATAGTAATGGAGACACCTATTTAGAATGG<br>TACCTGCAGAAACCAGGCCAGTCTCCAAAC<br>CTCCTGATCTATAAAGTTTCCAACCGATTTT<br>CTGGGGTCCCAGACAGGTTCAGTGGCAGT<br>GGATCCGGGACAGATTTCACACTCAAGATC<br>AGCAGAGTGGAGGCTGAGGATCTGGGAGT<br>TTATTACTGCTTTCAAGGTTCACATGTTCCT<br>CCGACGTTCGGTGGAGGCACCAAGCTT<br>(SEQ ID NO: 294) |
| KCD121 | ATGTACAGGATGCAACTCCTGTCTTGCATT<br>GCACTAAGTCTTGCACTTGTCACTAACTCA<br>GAGGTCCAGCTGCAACAGTCTGGACCTGAA<br>CTGGTGAAGCCTGGGGCTTCAGTGAAGATA<br>TCCTGTAAGGCTTCTGGATACACGTTCACT<br>GACTACTACAAGAACTGGATGAGGCAGAGA<br>CATGGAGAGAGCCTTGAGTGGATTGGAGAT<br>ATTAATCCTAACAATGGTGATACTTCCTAC<br>AACCAGAAGTTCAGGGGCAAGGCCACATTG<br>ACTGTAGACAAGTCCTCCAGCACAGCCTTC<br>ATGGAGCTCCGCAGCCTGACATCTGAGGAC<br>TCTGCAGTCTATTACTGTGCAAGAGAGGGA<br>CCTTCCTTTGCTTACTGGGGCCAAGGGACT<br>CTGGTCACTGTCTCTGCA<br>(SEQ ID NO: 295) | ATGTACAGGATGCAACTCCTGTCTTGCATT<br>GCACTAAGTCTTGCACTTGTCACTAACTCA<br>GATGTTTTGATGACCCAAACTCCACTCTCC<br>CTGCCTGTCAGTCTTGGAGATCAAGCCTCC<br>ATCTCTTGCAGATCTAATCAGACCATTGTA<br>CATAGTAATGGAGACACGTATTTAGAATGG<br>TACCTGCAGAAACCAGGCCAGTCTCCAAAC<br>CTCCTGATCTACAAAGTTTCCAACCGATTTT<br>CTGGGGTCCCAGACAGGTTCAGTGGCAGT<br>GGATCCGGGACAGATTTCACACTCAGGATC<br>AGCAGAGTGGAGGCTGAGGATCTGGGAGT<br>TTATTACTGCTTTCAAGGTTCACATGTTCCT<br>CCGACGTTCGGTGGAGGCACCAAGCTT<br>(SEQ ID NO: 296) |
| KCD122 | ATGTACAGGATGCAACTCCTGTCTTGCATT<br>GCACTAAGTCTTGCACTTGTCACTAACTCA<br>GAGGTCCAGCTGCAACAGTCTGGACCTGAA<br>CTGGTGAAGCCTGGGGCTTCAGTGAAGATA<br>TCCTGTAAGGCTTCTGGATACACGTTCACT<br>GACTACTACAAGAACTGGATGAGGCAGAGA<br>CATGGAGAGAGCCTTGAGTGGATTGGAGAT<br>ATTAATCCTAACAATGGTGATGCTAACTAC<br>AACCAGAAGTTCAAGGGCAAGGCCACATTG<br>ACTGTTGACAAGTCCTCCAGCACAGCCTAC<br>ATGGAGCTCCGCAGCCTGACATCTGAGGAC<br>TCTGCAGTCTATTTCTGTGCAAGAGAGGGA<br>CCTTCGTTTGCTTACTGGGGCCATGGGACT<br>CTGGTCACTGTCTCTGCA<br>(SEQ ID NO: 297) | ATGTACAGGATGCAACTCCTGTCTTGCATT<br>GCACTAAGTCTTGCACTTGTCACTAACTCA<br>GATGTTTTGATGACCCAAACTCCACTCTCC<br>CTGCCTGTCAGTCTTGGAGATCAAGCCTCC<br>ATCTCTTGCAGATCTAGTCAGACCATTGTT<br>CATAGTAATGGAGACACCTATTTAGAATGG<br>TACCTGCAGAAACCAGGCCAGTCTCCAAAC<br>CTCCTGATCTACAAAGTTTCCAACCGATTTT<br>CTGGGGTCCCAGACAGGTTCAGTGGCAGT<br>GGATCCGGGACAGATTTCACACTCAAGATC<br>AGCAGAGTGGAGGCTGAGGATCTGGGAGT<br>TTATTACTGCTTTCAAGGTTCACATGTTCCT<br>CCGACGTTCGGTGGAGGCACCAAGCTT<br>(SEQ ID NO: 298) |
| KCD123 | ATGTACAGGATGCAACTCCTGTCTTGCATT<br>GCACTAAGTCTTGCACTTGTCACTAACTCA<br>GAGGTCCACCTGCAACAGTCTGGACCTGAA<br>CTGGTGAAGCCTGGGGCTTCAGTGAAGATA<br>TCCTGTAAGGCTTCTGGATACACGTTCACT<br>GACTTCTACAAGAACTGGATGAGGCAGAGA<br>CATGGAGAGAGCCTTGAGTGGATTGGAGAT<br>ATTAATCCTAACAATGGTGGTACTAACTAC<br>AACCAGAAGTTCAAGGGCAAGGCCACATTG<br>ACTGTAGACAAGTCCTCCAGCACAGCCTAC<br>ATGGAGCTCCGCAGCCTGACATCTGAGGAC<br>TCTGCAGTCTATTACTGTGCAAGAGAGGGA<br>CCTTCGTTTGCTTACTGGGGCCAAGGGACT<br>CTGGTCACTGTCTCTGCA<br>(SEQ ID NO: 299) | ATGTACAGGATGCAACTCCTGTCTTGCATT<br>GCACTAAGTCTTGCACTTGTCACTAACTCA<br>GATGTTTTGATGACCCAAACTCCACTCTCC<br>CTGCCTGTCAGTCTTGGAGATCAAGCCTCC<br>ATCTCTTGCAGATCTAGTCAGACCATTGTT<br>CATAGTAATGGAGACACCTATTTAGAATGG<br>TACCTGCAGAAACCAGGCCAGTCTCCAAAC<br>CTCCTGATCTACAAAGTTTCCAACCGATTTT<br>CTGGGGTCCCAGACAGGTTCAGTGGCAGT<br>GGATCCGGGACAGATTTCACACTCAAGATC<br>AGCAGAGTGGAGGCTGAGGATCTGGGAGT<br>TTATTACTGCTTTCAAGGTTCACATGTTCCT<br>CCGACGTTCGGTGGAGGCACCAAGCTT<br>(SEQ ID NO: 300) |
| KCD124 | ATGTACAGGATGCAACTCCTGTCTTGCATT<br>GCACTAAGTCTTGCACTTGTCACTAACTCA<br>GAAGTCCAGCTCCAACAGTCTGGACCTGAG<br>CTGGTGAAGCCTGGGGCTTCAGTGAAGATA<br>TCCTGTAAGGCTTCTGGATACACATTCACT<br>GACCACTACATGAACTGGGTGAAACAGAGC<br>CATGGAAAGAGCCTTGAGTGGATTGGAGAT<br>ATTAATCCTAACAATGGTGGTACTAGCTAC<br>AACCAGAAGTTCAAGGGCAAGGCCACATTG<br>ACTGTAGACAAGTCCTCCAGCACAGCCTAC | ATGTACAGGATGCAACTCCTGTCTTGCATT<br>GCACTAAGTCTTGCACTTGTCACTAACTCA<br>GATGTTTTGATGACCCAAACTCCACTCTCC<br>CTGCCTGTCAGTCTTGGAGATCAAGCCTCC<br>ATCTCTTGCAGATCTAGTCAGAGCATTGTA<br>CATAGTAATGGAGACACCTATTTAGAGTGG<br>TACCTGCAGAAGCCAGGCCAGTCTCCAAAG<br>CTCCTGATCTACAAAGTTTCCAACCGATTTT<br>CTGGGGTCCCAGACAGGTTCAGTGGCAGT<br>GGATCAGGGACAGATTTCACACTCAAGATC |

TABLE 0.1C-continued

Nucleotide sequences of variable domains of anti-CFD Antagonist monoclonal Antibodies

| mAb | Heavy Chain | Light Chain |
| --- | --- | --- |
| | ATGGAGCTCCGCAGCCTGACATCTGGGGAC<br>TCTGCAGTCTATTACTGTACAAGAGAGGGG<br>GCCTCGTTTGCTTTCTGGGGCCAAGGGACT<br>CTGGTCACTGTCTCTGCA<br>(SEQ ID NO: 301) | AGCAGAGTGGAGGCTGAGGATCTGGGAGT<br>TTATTACTGCTTTCAAGGTTCACATGTTCCG<br>CTCACGTTCGGTGCTGGGACCAAGCTT<br>(SEQ ID NO: 302) |
| KCD131 | ATGTACAGGATGCAACTCCTGTCTTGCATT<br>GCACTAAGTCTTGCACTTGTCACTAACTCA<br>CAGGTCCAGCTACAGCAGTCTGGACCTGAG<br>CTGGTGAAGCCTGGGGCTTCAGTGAAGATC<br>TCCTGCAAGGCTTCTGCCTACACCTTCACT<br>GACTACTATATAAACTGGGTGAAGCAGAGG<br>CCTGGACAGGGACCTGAGTGGATTGGATG<br>GATTTTTCCTGGAAGTAATAGTACTTATTCC<br>AATGAGAAGTTCGAGGTCAAGGCCACACTG<br>ACTGTAGACGAATCCTCCAGCACAGCCTAC<br>ATGTTGCTCAGCAGCCTGACCTCTGAGGAC<br>TCTGCGGTCTATTTCTGTGCAAGATTGGGA<br>TACTTCGGTAGTAGTTACCATGCTTTGGAC<br>TACTGGGGTCAAGGCACCTCAGTCACCGTC<br>TCCTCA (SEQ ID NO: 303) | ATGTACAGGATGCAACTCCTGTCTTGCATT<br>GCACTAAGTCTTGCACTTGTCACTAACTCA<br>GACATCCAGATGACTCAGTCTCCAGCCTCC<br>CTATCTGTATCTGTGGGAGAAACTGTCACC<br>ATCACATGTCGAGCAAGTGAGAATATTTAC<br>AGTCATTTAGCATGGTTTCAGCAGAAACAG<br>GGAAAATCTCCTCGGCTCCTGGTCTATTCT<br>GCAACAAACTTACCAGATGGTGTGCCATCA<br>AGATTCAGTGGCAGTGGATCAGGCACACAG<br>TATTCCCTCAAGATCAACATCCTGCAGTCT<br>GAAGATTTTGGGAGTTATTACTGTCAACAT<br>TTTTGGGGTACTCCGTGGACGTTCGGTGGA<br>GGCACCAAGCTT (SEQ ID NO: 304) |
| KCD136 | ATGTACAGGATGCAACTCCTGTCTTGCATT<br>GCACTAAGTCTTGCACTTGTCACTAACTCA<br>GAGGTTCAGCTGCAGCAGTCTGTGGCAGA<br>GCTTGTGAGGCCAGGGGCCTCAGTCAAGTT<br>GTCCTGCTCAGCTTCTGGCTTCAACATTAA<br>AAACACCTATATGCACTGGGTGAACCAGAG<br>GCCTGAACAGGGCCTGGAGTGGATTGGAA<br>GGATTGATCCTGCGAATGGTATTACTAAAT<br>ATGCCCCGAACTTCCAGGGCAAGGCCACTA<br>TAACTGCAGACACATCTTCCAACACAGCCT<br>ACCTGCAGCTCAGCAACCTGACATCTGAGG<br>ACACTGCCATCTATTACTGTACTAGGGCTA<br>TGGACTACTGGGGTCAAGGAACCTCAGTCA<br>CCGTCTCCTCA (SEQ ID NO: 305) | ATGTACAGGATGCAACTCCTGTCTTGCATT<br>GCACTAAGTCTTGCACTTGTCACTAACTCA<br>CAAATTGTTCTCACCCAGTCTCCAGCAATC<br>ATGTCTGCATCTCCAGGGGAGAAGGTCACC<br>ATGACCTGCAGTGCCAGCTCAAGTGTAAGT<br>TACATGTACTGGTACCAGCAGAAGCCAGGA<br>TCCTCCCCCAGACTCCTGATTTATGACATA<br>TCCAACCTGGCTTCTGGAGTCCCTGTTCGC<br>TTCAGTGGCAGTGGGTCTGGGACCTCTTAC<br>TCTCTCACAATCAGCCGAATGGAGGCTGAA<br>GATGCTGCCACTTATTACTGCCAGCAGTGG<br>GATACTTACCCGTGGACGTTCGGTGGAGGC<br>ACCAAGCTT (SEQ ID NO: 306) |
| KCD200 | ATGTACAGGATGCAACTCCTGTCTTGCATT<br>GCACTAAGTCTTGCACTTGTCACTAACTCA<br>GAGGTCCAGCTGCAACAGTCTGGACCTGAA<br>CTGGTGAAGCCTGGGGCTTCAGTGAAGATA<br>TCCTGTAAGGCTTCCGGATACACGTTCACC<br>AGCTACTACAAGAACTGGATGAGGCAGAGA<br>CATGGAGAGAGCCTTGAGTGGATTGGAGAT<br>ATTAATCCTAACAGTGGTGATACTGCCTAC<br>AACCAGAAGTTCAAGGGCAAGGCCACATTG<br>ACTGTAGACAGGTCCTCCAGCACAGCCTAC<br>ATGGAGCTCCGCAGCCTGACATCTGAGGAC<br>TCTGCAGTCTATTACTGTGCAAGAGAGGGA<br>CCTTCGTTTGCTTACTGGGGCCAAGGGACT<br>CTGGTCACTGTCTCTGCA<br>(SEQ ID NO: 307) | ATGTACAGGATGCAACTCCTGTCTTGCATT<br>GCACTAAGTCTTGCACTTGTCACTAACTCA<br>GATGTTTTGATGACCCAAACTCCACTCTCC<br>CTGCCTGTCAGTCTTGGAGATCAAGTCTCC<br>ATCTCTTGCAGATCTAGTCAGACCATTGTT<br>CATAGTAATGGAGACACCTATTTGGAATGG<br>TACCTGCAGAAACCAGGCCAGTCTCCAAAT<br>CTCCTGATCTACAAAGTTTCCAACCGTTTTT<br>CTGGGGTCCCAGACAGGTTCAGTGGCAGT<br>GGATCCGGGACAGATTTCACACTCAAGATC<br>AGCAGAGTGGAGGCTGAGGATCTGGGAGT<br>GTATTACTGCTTTCAAGGTTCACATGTTCCT<br>CCGACGTTCGGTGGAGGCACCAAGCTT<br>(SEQ ID NO: 308) |
| KCD208 | ATGTACAGGATGCAACTCCTGTCTTGCATT<br>GCACTAAGTCTTGCACTTGTCACTAACTCA<br>GAGGTTCAGCTGCAGCAGTCTGTGGCAGA<br>GCTTGTGAGGCCAGGGGCCTCAGTCAAGTT<br>GTCCTGCACAGTTTCTGGCTTCAACATTAA<br>AAACACCTATATGCACTGGGTGAAGCAGAG<br>GCCTGAACAGGGCCTGGAGTGGATTGGAA<br>GGATTGATCCTGCGAATGGTGATACTACAT<br>ATGCCCCGAAGTTCCAGGGCAAGGCCACTA<br>TAACTGCAGACACATCCTCCAACTCAGCCT<br>ACCTGCACCTCAGCCGCCTGACATCTGAGG<br>ACACTGCCATCTATTACTGTTCTCTTTATGA<br>TTACGACGGCTACTGGGGCCAAGGCACCAC<br>TCTCACAGTCTCCTCA<br>(SEQ ID NO: 309) | ATGTACAGGATGCAACTCCTGTCTTGCATT<br>GCACTAAGTCTTGCACTTGTCACTAACTCA<br>GAAATTGTGCTCACCCAGTCTCCAGCACTC<br>ATGGCTGCATCTCCAGGGGAGAAGGTCACC<br>ATCACCTGCAGTGTCAGCTCAAGTATAAGT<br>TCCAGCTCCTTACACTGGTACCGGCAGAAG<br>TCAGGAACCTCCCCCAAACCCTGGATTTAT<br>GGCACATCCCACCTTGCTTCTGGAGTCCCT<br>GTTCGCTTCAGTGGCAGTGGATCTGGGACC<br>TCTTATTCTCTCACAATCAGCAGCATGGAG<br>GCTGAAGATGCTGCCACTTATTACTGTCAA<br>CAGTGGGATACTTACCCGTGGACGTTCGGT<br>GGAGGCACCAAGCTT<br>(SEQ ID NO: 310) |
| KCD214 | ATGTACAGGATGCAACTCCTGTCTTGCATT<br>GCACTAAGTCTTGCACTTGTCACTAACTCA<br>GAGGTTCAGCTGCAGCAGTCTGTGGCAGA<br>GTTTGTGAGGCCAGGGGCCTCAGTCAAGTT<br>GTCCTGCACAGCTTCTGGCTTCAACATTAA<br>AAACACCTATATGCACTGGGTGAAGCAGAG | ATGTACAGGATGCAACTCCTGTCTTGCATT<br>GCACTAAGTCTTGCACTTGTCACTAACTCA<br>GAAATTGTGCTCACCCAGTCTCCAGCACTC<br>ATGGCTGCATCTCCAGGGGAGAAGGTCACC<br>ATCACCTGCCGTGTCAGCTCAAGTATAAGT<br>TCCAGCAGCTTACACTGGTACCAGCAAAAG |

TABLE 0.1C-continued

Nucleotide sequences of variable domains of anti-CFD Antagonist monoclonal Antibodies

| mAb | Heavy Chain | Light Chain |
|---|---|---|
| | GCCTGAACAGGGCCTGGAATGGATTGGAA<br>GGATTGATCCTGCGAATGGTAATACTGAAT<br>ATGCCCCGAAGTTCCAGGGCAAGGCCACTA<br>TAACTGCAGACACATCCTCCAACACAGCCT<br>ACCTGCAGCTCAGCAGCCTGACATCTGAGG<br>ACACTGCCATCTATTACTGTGCTCTTTATGA<br>TTACGACGGCTACTGGGGCCAAGGCACCAC<br>TCTCACAGTCTCCTCA<br>(SEQ ID NO: 311) | TCAGGAACCTCCCCCAAACCCTGGATTTAT<br>GGCACCTCCAACCTTGCTTCTGGAGTCCCT<br>GTTCGCTTCAGTGGCAGTAGATCTGGGACC<br>TCTTATTCTCTCACAATCAGCAGCATGGAG<br>GCTGAAGATGCTGCCACTTATTACTGTCAA<br>CAGTGGAGTGATTACCCGTGGACGTTCGGT<br>GGAGGCACCAAGCTT<br>(SEQ ID NO: 312) |
| KCD220 | ATGTACAGGATGCAACTCCTGTCTTGCATT<br>GCACTAAGTCTTGCACTTGTCACTAACTCA<br>CAGGTTCAGCTGCAACAGTCTGGAGCTGAG<br>CTGATGGAGCCTGGGGCCTCAGTGAAGCTT<br>TCCTGCAAGGCTACTGGCTACACATTCACT<br>GGCTACTGGATAGAGTGGGTAAAGCAGAG<br>GCCTGGACATGGCCTTGAGTGGATTGGAGA<br>GACTTTACCTGGAAGTGATAGTAATAATTA<br>CAATGAGAAGTTCAAGGGCAAGGCCACATT<br>CACTGCAGATACATCCTCCAACACAGCCTA<br>CATGCAACTCAGCAGCCTGACAACTGAGGA<br>CTCTGCCATCTATTACTGTGCAAGAGACTA<br>TAGTAACTACTGGTACTTCGATGTCTGGGG<br>CACAGGGACCACGGTCACCGTCTCCTCA<br>(SEQ ID NO: 313) | ATGTACAGGATGCAACTCCTGTCTTGCATT<br>GCACTAAGTCTTGCACTTGTCACTAACTCA<br>GATATCCAGATGACACAGACTACATCCTCC<br>CTGTCTGCCTCTCTGGGAGACAGAGTCACC<br>ATTAGTTGCAGGGCAAGTCAGGACATTAGC<br>AATTATTTAAACTGGTATCAGCAGAAACCA<br>GATGGAACTGTTAAACTCCTGATCTACTAC<br>ACATCAAACTTACACTCAGGAGTCCCATCA<br>AGGTTCAGTGGCAGTGGGTCTGGGACAGA<br>TTATTCTCTCACTATTAGTAACCTGGAACAA<br>GAAGATATTGCCACTTACTTTTGCCAACAG<br>GATAGTAAGCATCGGACGTTCGGTGGAGG<br>CACCAAGCTT (SEQ ID NO: 314) |
| KCD224 | ATGTACAGGATGCAACTCCTGTCTTGCATT<br>GCACTAAGTCTTGCACTTGTCACTAACTCA<br>CAGGTGCAGCTGAAGGAGTCAGGACCTGG<br>CCTGGTGGCGCCCTCACAGAGCCTGTCCAT<br>CACATGCACTGTCTCTGGGTTCTCATTAAC<br>CAGCTATGGTGTAGACTGGATTCGCCAGTC<br>TCCAGGAAAGGGTCTGGAGTGGCTGGGAG<br>TAATATGGGGTGTTGGAAGCACAAATTATA<br>ATTCAGCTCTCAAATCCAGACTGAGCATCA<br>GCAAGGACAACTCCAAGAGCCAAGTTTTCT<br>TAAAAATGAACAGTCTGCAAACTGATGACA<br>CAGCCATGTACTACTGTGCCCGCTCCTATG<br>ATGGTTCCTACTGGTACTTCGATGTCTGGG<br>GCACAGGGACCACGGTCACCGTCTCCTCA<br>(SEQ ID NO: 315) | ATGTACAGGATGCAACTCCTGTCTTGCATT<br>GCACTAAGTCTTGCACTTGTCACTAACTCA<br>GATATCCAGATGACACAGACTACATCCTCC<br>CTGTCTGCCTCTCTGGGAGACAGAGTCACC<br>ATCAGTTGCAGGGCAAGTCAGGTTATTAGC<br>AATTATTTAAACTGGTATCAGCAGAAACCA<br>GATGGAACTGTTAAACTCCTGATCTACTAC<br>ACATCAAGATTACACTCAGGAGTCCCATCA<br>AGGTTCAGTGGCAGTGGGTCTGGGACAGA<br>TTATTCTCTCACCATCAGCAACCTGGAACC<br>TGAAGATATTGCCACTTACTATTGTCAGCA<br>GTATAGTAAACTTCCGTATACGTTCGGATC<br>GGGGACCAAGCTT (SEQ ID NO: 316) |
| 119_TAF | GAGGTGCAGCTGGTGGAATCTGGCGGCGG<br>ACTGGTGCAGCCTGGCGGCTCCCTGAGACT<br>GTCTTGCGCCGCCTCCGGCTACACCTTCAC<br>CGACTACTACATGAACTGGGTGCGACAGGC<br>CCCTGGCAAGGGCCTGGAATGGATCGGCG<br>ACATCAACCCCAACACCGGCGACACCAGCT<br>ACAACGCCGACTTCAAGCGCGGTTCACCT<br>TCTCCCTGGACACCTCCAAGTCCACCGCCT<br>ACCTGCAGATGAACTCCCTGCGGGCCGAG<br>GACACCGCCGTGTACTACTGTACCAGAGAG<br>GGCCCCTCCTTCGCCTACTGGGGCCAGGGC<br>ACACTGGTGACAGTGTCCTCCG<br>(SEQ ID NO: 317) | GACATCCAGCTGACCCAGAGCCCCTCCAGC<br>CTGTCCGCCTCTGTGGGCGACAGAGTGACC<br>ATCACCTGTCGGTCCTCCCAGACCATCGTG<br>CACTCCAACGGCGACACCTACCTGGAATGG<br>TATCAGCAGAAGCCCGGCAAGGCCCCTAAC<br>CTGCTGATCTACAAGGTGTCCAACCGGTTC<br>TCCGGCGTGCCCTCCAGATTCTCCGGCTCC<br>GGCTCTGGCACCGACTTCACCCTGACCATC<br>TCCAGCCTGCAGCCCGAGGACTTCGCCACC<br>TACTACTGTTTTCAAGGCTCCCACGTGCCA<br>CCCACCTTCGGCCAGGGCACCAAGGTGGA<br>AATCAAGC (SEQ ID NO: 318) |
| 119_TAF Germ | GAGGTGCAGCTGGTGGAATCTGGCGGCGG<br>ACTGGTGCAGCCTGGCGGCTCCCTGAGACT<br>GTCTTGCGCCGCCTCCGGCTACACCTTCAC<br>CGACTACTACATGTCCTGGGTGCGACAGGC<br>CCCTGGCAAGGGCCTGGAATGGATCGGCG<br>ACATCAACCCCAACACCGGCGACACCAGCT<br>ACAACGCCGACTCCGTGAAGGGCCGGTTCA<br>CCATCTCCCGGGACAACTCCAAGAACACCC<br>TGTACCTGCAGATGAACTCCCTGCGGGCCG<br>AGGACACCGCCGTGTACTACTGTACCAGAG<br>AGGGCCCCTCCTTCGCCTACTGGGGCCAGG<br>GCACACTGGTGACAGTGTCCTCC<br>(SEQ ID NO: 319) | GACGTGGTGATGACCCAGTCCCCTCTGTCC<br>CTGCCCGTGACCCTGGGCCAGCCTGCCTCC<br>ATCTCCTGCCGGTCCTCCCAGACCATCGTG<br>CACTCCAACGGCGACACCTACCTGGAATGG<br>TTCCAGCAGCGGCCTGGCCAGTCCCCTAAC<br>CTGCTGATCTACAAGGTGTCCAACCGGTTC<br>TCCGGCGTGCCCGACAGATTCTCCGGCTCC<br>GGCTCTGGCACCGACTTCACCCTGAAGATC<br>TCCCGGGTGGAAGCCGAGGACGTGGGCGT<br>GTACTACTGTTTTCAAGGCTCCCACGTGCC<br>ACCCACCTTCGGCGGAGGCACCAAGGTGG<br>AAATCAAG (SEQ ID NO: 320) |
| 119_Human Germ | CAGGTGCAGCTGGTGCAGTCTGGCGCCGA<br>AGTGAAGAAACCTGGCGCCTCCGTGAAGGT<br>GTCCTGCAAGGCCTCCGGCTACACCTTCAC<br>CGACTACTACATGCACTGGGTGCGACAGGC<br>CCCAGGCCAGGGCCTGGAATGGATCGGCG | GACATCCAGATGACCCAGAGCCCCTCCAGC<br>CTGTCCGCCTCCGTGGGCGACAGAGTGACC<br>ATCACCTGTCGGTCCTCCCAGACCATCGTG<br>CACTCCAACGGCGACACCTACCTGGAATGG<br>TATCAGCAGAAGCCCGGCAAGGCCCCTAAC |

TABLE 0.1C-continued

| Nucleotide sequences of variable domains of anti-CFD Antagonist monoclonal Antibodies | | |
|---|---|---|
| mAb | Heavy Chain | Light Chain |
| | ACATCAACCCCAACACCGGCGACACCAGCT ACAACCAGAAATTCCAGGGCAGAGTGACCT CCACCCGGGACACCTCCATCTCCACCGCCT ACATGGAACTGTCCCGGCTGCGGAGCGAC GACACCGTGGTGTACTACTGTACCAGAGAG GGCCCCTCCTTCGCCTACTGGGGCCAGGGC ACACTGGTGACAGTGTCCTCC (SEQ ID NO: 321) | CTGCTGATCTACAAGGTGTCCAACCGGTTC TCCGGCGTGCCCTCCAGATTCTCCGGCTCC GGCTCTGGCACCGACTTCACCCTGACCATC TCCAGCCTGCAGCCCGAGGACTTCGCCACC TACTACTGTTTTCAAGGCTCCCACGTGCCA CCCACCTTCGGCCAGGGCACCAAGGTGGA AATCAAG (SEQ ID NO: 322) |

In some embodiments, a composition as disclosed herein comprises an antibody having a partial or complete light chain sequence and a partial or complete heavy chain sequence from any of the options provided in Table 0.1D, or variants thereof. In Table 0.1D, the underlined sequences are some embodiments of CDR sequences.

TABLE 0.1D

| Variable Regions Sequences of Variant Humanized CFD Antagonist Antibodies based on a CDR definition | | | |
|---|---|---|---|
| | CDR1 | CDR2 | CDR3 |
| Table with CDR sequences | | | |
| Light chain | $QX_1X_2X_3HX_4NX_5X_6X_7YX_8E$, wherein $X_1$ is T, D, G, H, I, N, Q, R, V, or W; $X_2$ is I, A, or V; $X_3$ is V, A, D, E, F, I, K, L, Q, R, S, W, or Y; $X_4$ is S, A, D, F, G, I, R, T, V, or W; $X_5$ is G, E, F, or S; $X_6$ is D or E; $X_7$ is T, S, or V; $X_8$ is L or I (SEQ ID NO: 323) | $X_1X_2LX_3X_4KX_5X_6X_7RX_8$; wherein $X_1$ is N, D, E, R, S, V, or Y; $X_2$ is L or I; $X_3$ is I or T; $X_4$ is Y, D, E, F, G, L, R, S, T, or V; $X_5$ is V, A, or I; $X_6$ is S, A, F, G, K, L, Q, R, T, or Y; $X_7$ is N, E, G, H, I, L, Q, R, T, or Y; $X_8$ is F, E, G, I, L, R or W (SEQ ID NO: 324) | $X_1QGSX_2X_3PX_4T$, wherein $X_1$ is F or M; $X_2$ is H, A, E, F, G, L, N, Q, T, V, W, or Y; $X_3$ is V, W, Q or N; and $X_4$ is P or V (SEQ ID NO: 325) |
| Heavy chain | $GYX_1FTX_2X_3X_4X_5$, wherein $X_1$ is T, D, E, F, H, I, K, P, R, S, W, or Y; $X_2$ is D, A, F, G, S, V, or Y; $X_3$ is Y or F; $X_4$ is Y or P; $X_5$ is M, H, or I (SEQ ID NO: 326) | $WIGDX_1X_2X_3X_4X_5X_6X_7X_8X_9,X_{10}$, wherein $X_1$ is I, L, OR V; $X_2$ is N, A, or G; $X_3$ is P, or T; $X_4$ is N, A, D, G, H, I, L, R, T, V, W, OR Y; $X_5$ is T, I, K, L, Q, R, S, or V $X_6$ is G or V; $X_7$ is any amino acid; $X_8$ is any amino acid except I; $X_9$ is any amino acid except K or R; $X_{10}$ is any amino acid except I or W. (SEQ ID NO: 327) | $X_1REGPX_2FX_3X_4$, wherein $X_1$ is T, A, or Q; $X_2$ is S or A; $X_3$ is A or R; and $X_4$ is Y, A, H, F, V, Y, or L (SEQ ID NO: 328) |
| CDRs (streamlined CDR defined sequence): | | | |
| Light Chain | $QX_1X_2X_3HX_4NX_5X_6X_7Y$, wherein $X_1$ is T, D, G, H, I, N, Q, R, V, or W; $X_2$ is I, A, or V; $X_3$ is V, A, D, E, F, I, K, L, Q, R, S, W, or Y; $X_4$ is S, A, D, F, G, I, R, T, V, or W; $X_5$ is G, E, F, or S; $X_6$ is D or E; $X_7$ is T, S, or V (SEQ ID NO: 329) | $KX_1X_2$; wherein $X_1$ is V, A, or I; $X_2$ is S, A, F, G, K, L, Q, R, T, or Y (SEQ ID NO: 330) | $X_1QGSX_2X_3PX_4T$, wherein $X_1$ is F or M; $X_2$ is H, A, E, F, G, L, N, Q, T, V, W, or Y; $X_3$ is V, W, Q or N; and $X_4$ is P or V (SEQ ID NO: 331) |
| Heavy Chain | $X_1X_2X_3$, wherein $X_1$ is D, A, F, G, S, V, or Y; $X_2$ is Y or F; $X_3$ is Y or P (SEQ ID NO: 332) | $X_1X_2X_3X_4X_5X_6X_7X_8$, wherein $X_1$ is I, L, OR V; $X_2$ is N, A, or G; $X_3$ is P, or T; $X_4$ is N, A, D, G, H, I, L, R, T, V, W, OR Y; $X_5$ is T, I, K, L, Q, R, S, or V $X_6$ is G or V; $X_7$ is any amino acid; $X_8$ is any amino acid except I (SEQ ID NO: 333) | $EGPX_1FX_2X_3$, wherein $X_1$ is S or A; $X_2$ is A or R; and $X_3$ is Y, A, H, F, V, Y, or L (SEQ ID NO: 334) |

In some embodiments, a composition as disclosed herein comprises an antibody having a partial or complete light chain CDR sequence and a partial or complete heavy chain CDR sequence from any of the options provided in Tables 1.1, 0.1A, 0.1B, 0.1D, 11.3, or variants thereof. Tables 1.1, 0.1A, 0.1B, 0.1D, 11.3 provides examples of CDR sequences of variant CFD antagonist antibodies provided herein.

In some embodiments, CDR portions of CFD antagonist antibodies are also provided. Determination of CDR regions is well within the skill of the art. It is understood that in some embodiments, CDRs can be a combination of the IMGT and Paratome CDRs (also termed "combined CDRs" or "extended CDRs"). Determination of CDRs is well within the skill of the art. In some embodiments, the CDRs are the IMGT CDRs. In other embodiments, the CDRs are the Paratome CDRs. In other embodiments, the CDRs are the extended, AbM, conformational, Kabat, or Chothia CDRs. In embodiments with more than one CDR, the CDRs may be any of IMGT, Paratome, extended, Kabat, Chothia, AbM, conformational CDRs, or combinations thereof. In some embodiments, other CDR definitions may also be used. In some embodiments, only residues that are in common between 2, 3, 4, 5, 6, or 7 of the above definitions are used (resulting in a shorter sequence). In some embodiments, any residue in any of 2, 3, 4, 5, 6, or 7 of the above definitions can be used (resulting in a longer sequence).

In some embodiments, a CFD antagonist antibody comprises three CDRs of any one of the heavy chain variable regions shown in Tables 1.1, 0.1A, 0.1B, 0.1D, or 11.3. In some embodiments, the antibody comprises three CDRs of any one of the light chain variable regions shown in Tables 1.1, 0.1A, 0.1B, 0.1D, or 11.3. In some embodiments, the antibody comprises three CDRs of any one of the heavy chain variable regions shown in Tables 1.1, 0.1A, 0.1B, 0.1D, or 11.3, and three CDRs of any one of the light chain variable regions shown in Tables 1.1, 0.1A, 0.1B, 0.1D, or 11.3.

In some embodiments, the antibody used for binding to CFD can be one that includes one or more of the sequences in Tables: 1.1, 0.1A, 0.1B, 0.1D, and/or 11.3. In some embodiments, the antibody used for binding to CFD can be one that includes three or more of the sequences in Tables: 1.1, 0.1A, 0.1B, 0.1D, and/or 11.3. In some embodiments, the antibody used for binding to CFD can be one that includes six of the sequences in any one of Tables: 1.1, 0.1A, 0.1B, 0.1D, and/or 11.3. In some embodiments, the antibody that binds to CFD can be one that competes for binding with an antibody that includes 6 of the specified CDRs in any one of Tables: 1.1, 0.1A, 0.1B, 0.1D, 11.3.

To express the anti-CFD antibodies of the present invention, DNA fragments encoding VH and VL regions described can first be obtained. Various modifications, e.g. mutations, deletions, and/or additions can also be introduced into the DNA sequences using standard methods known to those of skill in the art. For example, mutagenesis can be carried out using standard methods, such as PCR-mediated mutagenesis, in which the mutated nucleotides are incorporated into the PCR primers such that the PCR product contains the desired mutations or site-directed mutagenesis.

The invention encompasses modifications to the variable regions shown in Tables: 1.1, 0.1A, and 11.3. For example, the invention includes antibodies comprising functionally equivalent variable regions and CDRs which do not significantly affect their properties as well as variants which have enhanced or decreased activity and/or affinity. For example, the amino acid sequence may be mutated to obtain an antibody with the desired binding affinity to CFD. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but framework alterations are also contemplated. Conservative substitutions are shown in Table 0.4 under the heading of "conservative substitutions." If such substitutions result in a change in biological activity, then more substantial changes, denominated "exemplary substitutions" in Table 0.4, or as further described below in reference to amino acid classes, may be introduced and the products screened.

TABLE 0.4

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a j-sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

The antibodies may also be modified, e.g. in the variable domains of the heavy and/or light chains, e.g., to alter a binding property of the antibody. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. For example, a mutation may be made in one or more of the CDR regions to increase or decrease the $K_D$ of the antibody for CFD, to increase or decrease $k_{off}$, or to alter the binding specificity of the antibody. Techniques in site-directed mutagenesis are well-known in the art. See, e.g., Sambrook et al. and Ausubel et al., supra.

According to an aspect of the present invention, the IgG domain of a CFD antagonist antibody can be IgG1, IgG2, IgG3 or IgG4. According to another aspect of the invention, the IgG domain can be a composite in which a constant regions is formed from more than one of the above isotypes (e.g., $CH_1$ region from IgG2 or IgG4, hinge, $CH_2$ and $CH_3$ regions from IgG1). In choosing an isotype, it is known in the art that human isotopes IgG1 and IgG3 have complement-mediated cytotoxicity whereas human isotypes IgG2 and IgG4 have poor or no complement-mediated cytotoxicity. In some embodiments the CFD antagonist antibody isotype is IgG1. An exemplary human IgG1 heavy chain has the sequence (SEQ ID NO: 183):

```
                                        (SEQ ID NO: 183)
EVQLVESGGGLVQPGGSLRLSCAASGYTFTDYYINWVRQAPGKGLEWI

GDINPITGDTDYNADFKRRFTFSLDTSKSTAYLQMSSLRAEDTAVYYC

TREGPSFAYWGQGTLVTVSSASTKGPSVFPLAPSSKSTSGGTAALGCL

VKDYFPEPVTVSWNSGALTSGVHTFPAVLQSSGLYSLSSVVTVPSSSL

GTQTYICNVNHKPSNTKVDKKVEPKSCDKTHTCPPCPAPEAAGAPSVF

LFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTIS

KAKGQPREPQVYTLPPSREEMTKNQVSLTCLVKGFYPSDIAVEWESNG
```

-continued

```
QPENNYKTTPPVLDSDGSFFLYSKLTVDKSRWQQGNVFSCSVMHEALH

NHYTQKSLSCSPGK
```

The light chain constant region can be either human lambda or kappa. In some embodiments, the CFD antagonist antibody has a human kappa light chain constant region.

An exemplary human kappa light chain has the sequence (SEQ ID NO: 184):

```
                                        (SEQ ID NO: 184)
DIQLTQSPSSLSASVGDRVTITCRSSQTIVHSNGDTYLEWYQQKPGKA

PNLLIRKVSNRFSGVPSRFSGSGSGTDFTLTISSLQPEDFATYYCFQG

SHVPVTFGQGTKVEIKRTVAAPSVFIFPPSDEQLKSGTASVVCLLNNF

YPREAKVQWKVDNALQSGNSQESVTEQDSKDSTYSLSSTLTLSKADYE

KHKVYACEVTHQGLSSPVTKSFNRGEC
```

Human constant regions show allotypic variation and isoallotypic variation between different individuals, that is, the constant regions can differ in different individuals at one or more polymorphic positions. Isoallotypes differ from allotypes in that sera recognizing an isoallotype binds to a non-polymorphic region of a one or more other isotypes. Reference to a human constant region includes a constant region with any natural allotype or any permutation of residues occupying polymorphic positions in natural allotypes or up to 3, 5 or 10 substitutions for reducing or increasing effector function as described below.

One or several amino acids at the amino or carboxy terminus of the light and/or heavy chains such as the C-terminal lysine of the heavy chain, may be missing or derivatized in a proportion or all of the molecules.

Substitutions can be made in the constant regions to reduce or increase effector function such as complement-mediated cytotoxicity (CDC), antibody-dependent cell-mediated cytotoxicity (ADCC) (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004).

In some embodiments, the CFD antagonist antibodies provided herein include one more substitutions that reduce complement mediated cytotoxicity. Reduction in complement mediated cytotoxicity can be accomplished with or without reduction in Fc receptor binding depending on the nature of the mutation(s). Antibodies with reduced complement mediated cytotoxicity but little or no reduction in Fc receptor allow a desired effect of Fc-mediated phagocytosis of iC3b without activating complement, which may contribute to side effects. Exemplary mutations known to reduce complement-mediated cytotoxicity in human constant regions include mutations at positions 241, 264, 265, 270, 296, 297, 322, 329 and 331 by EU numbering. Mutations in positions 318, 320, and 322 have been reported to reduce complement activation in mouse antibodies. Alanine is a preferred residue to occupy these positions in a mutated constant region. Some exemplary human mutations that have been used include F241A, V264A, D265A, V296A, N297A, K322A, and P331S in human IgG3 and D270A or E, N297Q, K322A, P329A, and P331S in human IgG1 (EU numbering).

Here, as elsewhere, the EU numbering scheme is used for numbering amino acids in the constant region of an antibody. When a residue in a variable region is referenced herein (unless designated otherwise) the residue numbering is according to the variable domain (or, if designated, the SEQ ID NO). Substitution at any or all of positions 234, 235, 236 and/or 237 reduce affinity for Fcγ receptors, particularly FcγRI receptor and also reduces complement binding and activation (see, e.g., U.S. Pat. No. 6,624,821 WO/2009/052439). An alanine substitution at positions 234, 235 and 237 reduces effector functions, particularly in the context of human IgG1. Optionally, positions 234, 236 and/or 237 in human IgG2 are substituted with alanine and position 235 with glutamine. (See, e.g., U.S. Pat. No. 5,624,821) to reduce Fc receptor binding. Exemplary substitutions for increasing half-life include a Gln at position 250 and/or a Leu at position 428. In accordance with an aspect of the present invention, where the anti-CFD antibody presented has a human IgG1 isotype, it is preferred that the antibody has at least one mutation in the constant region. Preferably, the mutation reduces complement fixation or activation by the constant region. In particularly preferred aspects of the present invention, the antibody has one or more mutations at positions E233, L234, L235, G236, G237, A327, A330 and P331 by EU numbering. Still more preferably, the mutations constitute one or more of the following E233P, L234V, L234A, L235A, G237A, A327G, A330S and P331S by EU numbering. In the most preferred embodiments the human IgG1 has the following mutations L234A, L235A and G237A by EU numbering.

Conjugates

The half-life of CFD antagonist antibodies can be extended by attachment of a "half-life extending moieties" or "half-life extending groups," which terms are herein used interchangeably to refer to one or more chemical groups attached to one or more amino acid site chain functionalities such as —SH, —OH, —COOH, —CONH2, —NH2, or one or more N- and/or O-glycan structures and that can increase in vivo circulatory half-life of proteins/peptides when conjugated to these proteins/peptides. Examples of half-life extending moieties include polymers described herein, particularly those of zwitterionic monomers, such as HEMA-phosphorylcholine, PEG, biocompatible fatty acids and derivatives thereof, Hydroxy Alkyl Starch (HAS) e.g. Hydroxy Ethyl Starch (HES), Poly Ethylene Glycol (PEG), Poly ($Gly_x$-$Ser_y$) (HAP), Hyaluronic acid (HA), Heparosan polymers (HEP), Fleximers, Dextran, Poly-sialic acids (PSA), Fc domains, Transferrin, 25 Albumin, Elastin like (ELP) peptides, XTEN polymers, PAS polymers, PA polymers, Albumin binding peptides, CTP peptides, FcRn binding peptides and any combination thereof.

In some embodiments, the antibody is conjugated with a phosphorylcholine containing polymer. In some embodiments, the antibody is conjugated with a poly(acryloyloxyethyl phosphorylcholine) containing polymer, such as a polymer of acrylic acid containing at least one acryloyloxyethyl phosphorylcholine monomer such as 2-methacryloyloxyethyl phosphorylcholine (i.e., 2-methacryloyl-2'-trimethylammonium ethyl phosphate).

In some embodiments, the antibody is conjugated with a water-soluble polymer, which refers to a polymer that is soluble in water. A solution of a water-soluble polymer may transmit at least about 75%, more preferably at least about 95% of light, transmitted by the same solution after filtering. On a weight basis, a water-soluble polymer or segment thereof may be at least about 35%, at least about 50%, about 70%, about 85%, about 95% or 100% (by weight of dry polymer) soluble in water.

In one embodiment a half-life extending moiety can be conjugated to a CFD antagonist antibody via free amino groups of the protein using N-hydroxysuccinimide (NHS) esters. Reagents targeting conjugation to amine groups can randomly react to ϵ-amine group of lysines, α-amine group of N-terminal amino acids, and δ-amine group of histidines.

However, CFD antagonist antibodies of the present invention have many amine groups available for polymer conjugation. Conjugation of polymers to free amino groups, thus, might negatively impact the ability of the antibody to bind to the epitope.

In another embodiment, a half-life extending moiety is coupled to one or more free SH groups using any appropriate thiol-reactive chemistry including, without limitation, maleimide chemistry, or the coupling of polymer hydrazides or polymer amines to carbohydrate moieties of the CFD antagonist antibody after prior oxidation. The use of maleimide coupling is a particularly preferred embodiment of the present invention. Coupling preferably occurs at cysteines naturally present or introduced via genetic engineering.

In some embodiments, polymers are covalently attached to cysteine residues introduced into CFD antagonist antibodies by site directed mutagenesis. In some embodiments, the cysteine residues in the Fc portion of the CFD antagonist antibody can be used. In some embodiments, sites to introduce cysteine residues into an Fc region are provided in WO 2013/093809, U.S. Pat. No. 7,521,541, WO 2008/020827, U.S. Pat. Nos. 8,008,453, 8,455,622 and US2012/0213705, incorporated herein by reference for all purposes. In some embodiments, cysteine mutations are Q347C and L443C referring to the human IgG heavy chain by the EU index of Kabat. In some embodiments, the cysteine added by directed mutagenesis for subsequent polymer attachment is L443C. In some embodiments, the stoichiometry of CFD antagonist antibody to polymer is 1:1; in other words, a conjugate consists essentially of molecules each comprising one molecule of CFD antagonist antibody conjugated to one molecule of polymer. In some embodiments, coupling can occur at one or more lysines.

In some embodiments, a conjugate comprises an isolated antagonist antibody that specifically binds to complement factor D (CFD) conjugated to a polymer. In some embodiments, the polymer comprises a zwitterionic monomer. In some embodiments, the zwitterionic monomer, without limitations, is HEMA-phosphorylcholine, PEG, biocompatible fatty acids and derivatives thereof, Hydroxy Alkyl Starch (HAS) e.g. Hydroxy Ethyl Starch (HES), Poly Ethylene Glycol (PEG), Poly (Glyx-Sery) (HAP), Hyaluronic acid (HA), Heparosan polymers (HEP), Fleximers, Dextran, Poly-sialic acids (PSA), Fc domains, Transferrin, 25 Albumin, Elastin like (ELP) peptides, XTEN polymers, PAS polymers, PA polymers, Albumin binding peptides, CTP peptides, or FcRn binding peptides. In some embodiments, the polymer comprising a zwitterionic monomer is a half-life extending moiety.

In some embodiments, the CFD antagonist antibody can have a half-life extending moiety attached. In some embodiments, the half-life extending moiety is a zwitterionic polymer but PEG or other half-life extenders discussed below can alternatively be used. In some embodiments, the zwitterionic polymer is formed of monomers having a phosphorylcholine group. In some embodiments, the monomer is 2-(acryloyloxyethyl)-2'-(trimethylammoniumethyl) phosphate. In some embodiments, the monomer is 2-(methacryloyloxyethyl)-2'-(trimethylammoniumethyl) phosphate (HEMA-PC).

In some embodiments, the polymer conjugated to the CFD antagonist antibody has at least 2 or 3 or more arms. Some polymers have 2, 3, 4, 5, 6, 7, 8, 9, 10, 11 or 12 arms. In some embodiments, the polymer has 3, 6 or 9 arms. In some embodiments, the polymer has 9 arms. In some embodiments, the polymer peak molecular weight is between 300,000 and 1,750,000 Da. In some embodiments, the polymer has a peak molecular weight between 500,000 and 1,000,000 Da. In some embodiments, the polymer has a peak molecular weight between 600,000 to 800,000 Da.

In some embodiments, a conjugate of antagonistic anti-CFD antibody and a polymer is provided. In some embodiments, the polymer has a peak molecular weight between 300,000 and 1,750,000 Daltons as measured by size exclusion chromatography-multi angle light scattering (hereinafter "SEC-MALS"). In some embodiments, the polymer has a peak molecular weight between 500,000 and 1,000,000 Daltons as measured by SEC-MALS. In some embodiments, the polymer has a peak molecular weight between 600,000 to 800,000 Daltons as measured by SEC-MALS.

In some embodiments, a half-life extending moiety may be conjugated to a naturally occurring cysteine residue of a CFD antagonist antibody provided herein. In some embodiments, the half-life extending moiety is conjugated added to a cysteine that is added via site directed mutagenesis. In some embodiments, the cysteine is added by using recombinant DNA technology to add the peptide SGGGC or CAA to the C-terminus of either the light or heavy chain. In some embodiments, the peptide is added to the heavy chain. In some embodiments, the cysteine residue introduced via recombinant DNA technology is selected from the group consisting of (EU numbering) Q347C and L443C.

In accordance with another aspect of the present invention, a pharmaceutical composition is presented having a CFD antagonist antibody and a pharmaceutically acceptable excipient.

CFD antagonist antibodies of the present invention can be produced by recombinant expression including (i) the production of recombinant DNA by genetic engineering, (ii) introducing recombinant DNA into prokaryotic or eukaryotic cells by, for example and without limitation, transfection, electroporation or microinjection, (iii) cultivating the transformed cells, (iv) expressing anti-CFD antibodies, e.g. constitutively or on induction, and (v) isolating the anti-CFD antibody, e.g. from the culture medium or by harvesting the transformed cells, in order to (vi) obtain purified anti-CFD antibody.

In some embodiments, a conjugate comprising an anti-CFD antibody and a polymer is provided. The antibody is any one of the antibodies disclosed herein. In some embodiments, the antibody is an IgG. In some embodiments, the antibody is IgA, IgE, IgD or IgM. In some embodiments, the polymer is covalently bonded to a sulfhydryl group. In some embodiments, the polymer is covalently bonded to a sulfhydryl group from a cysteine residue. In some embodiments, the polymer is covalently bonded to a sulfhydryl group from a cysteine residue on the heavy chain. In some embodiments, the polymer is covalently bonded to a sulfhydryl group from a cysteine residue on the heavy chain of the IgG. In some embodiments, the antibody comprises a cysteine residue at position 347 or 443 (EU numbering). In some embodiments, the polymer is covalently bonded to a sulfhydryl group from a cysteine residue at position 347 or 443 (EU numbering).

CFD antagonist antibodies can be produced by expression in a suitable prokaryotic or eukaryotic host system characterized by producing a pharmacologically acceptable anti-CFD antibody molecule. Examples of eukaryotic cells are mammalian cells, such as CHO, COS, HEK 293, BHK, SK-Hip, and HepG2. Other suitable expression systems are prokaryotic (e.g., *E. coli* with pET/BL21 expression system), yeast (*Saccharomyces cerevisiae* and/or *Pichia pastoris* systems), and insect cells. In some embodiments, an isolated cell line that produces any of the antibodies disclosed herein is provided. In some embodiments, the isolated cell line is selected, without limitations, from one or more of CHO, k1SV, XCeed, CHOK1SV, GS-KO.

In some embodiments, an isolated nucleic acid encoding any of the antibodies disclosed herein is provided. In some embodiments, a recombinant expression vector comprising the isolated nucleic acid is provided. In some embodiments, a host cell comprises the expression vector.

A wide variety of vectors can be used for the preparation of the CFD antagonist antibodies and may be selected from eukaryotic and prokaryotic expression vectors. Examples of vectors for prokaryotic expression include plasmids such as, and without limitation, preset, pet, and pad, wherein the promoters used in prokaryotic expression vectors include one or more of, and without limitation, lac, trc, trp, recA, or araBAD. Examples of vectors for eukaryotic expression include, without limitation: (i) for expression in yeast, vectors such as, and without limitation, pAO, pPIC, pYES, or pMET, using promoters such as, and without limitation, AOX1, GAP, GAL1, or AUG1; (ii) for expression in insect cells, vectors such as and without limitation, pMT, pAc5, pIB, pMIB, or pBAC, using promoters such as and without limitation PH, p10, MT, Ac5, OpIE2, gp64, or polh, and (iii) for expression in mammalian cells, vectors such as, and without limitation, pSVL, pCMV, pRc/RSV, pcDNA3, or pBPV, and vectors derived from, in one aspect, viral systems such as and without limitation vaccinia virus, adeno-associated viruses, herpes viruses, or retroviruses, using promoters such as and without limitation CMV, SV40, EF-1, UbC, RSV, ADV, BPV, and beta-actin.

In some embodiments, a method of producing a CFD antagonist antibody is provided. In some embodiments, the method comprises culturing a cell line that recombinantly produces any of the antibodies disclosed herein under conditions wherein the antibody is produced and recovered. In some embodiments, a method of producing a CFD antagonist antibody is provided. In some embodiments, the method comprises culturing a cell line comprising nucleic acid encoding an antibody comprising a heavy chain comprising the amino acid sequence shown in SEQ ID NO: 520 and a light chain comprising the amino acid sequence shown in SEQ ID NO: 525 under conditions wherein the antibody is produced and recovered. In some embodiments, the heavy and light chains of the antibody are encoded on separate vectors. In some embodiments, the heavy and light chains of the antibody are encoded on the same vector.

In accordance with another aspect of the present invention, provided are methods for synthesizing a zwitterionic polymer-CFD antagonist antibody conjugate, the conjugate having one or more functional agents and one or more polymer arms wherein each of the polymer arms has one or more monomer units wherein at least one of the units has a zwitterion. For example, such a method can have the steps of:

a. providing an initiator having one or more sites for monomer polymerization and a first linker having an amine group wherein the initiator is a trifluoro acetic acid salt;

b. providing one or more monomers suitable for polymerization wherein at least one of the monomers is zwitterionic;

c. reacting the monomers with the initiator to form one or more polymer arms each corresponding to the sites for monomer polymerization to provide an initiator-polymer conjugate having the first linker with the amine group;

d. providing a second linker having at least second and third reactive groups;

e. coupling one of the second and third reactive groups of the second linker to the amine group of the first linker of the initiator-polymer conjugate to provide a linker-initiator-polymer conjugate having one or more reactive groups that were not used in the coupling step; and f. coupling one or more functional agents to one or more of the unreacted reactive groups of the linker-initiator-polymer moiety to provide the polymer-functional agent conjugate.

In some embodiments, a conjugate comprising an isolated antagonist antibody that specifically binds to CFD and a phosphorylcholine-containing polymer is provided. In some embodiments, the polymer is covalently bonded to the antibody. In some embodiments, the polymer is non-covalently bonded to the antibody.

In some embodiments, a conjugate comprising an anti-CFD antibody and a polymer that is capable of blocking of an interaction between CFD and C3bB is provided. In some embodiments, the conjugate comprising an anti-CFD antibody and a polymer is capable of blocking at least 80% of an interaction between CFD and C3bB. In some embodiments, the conjugate comprises an anti-CFD antibody and a polymer that is capable of blocking about 80% to about 100% of an interaction between CFD and C3bB. In some embodiments, the conjugate comprising an anti-CFD antibody and a polymer is capable of blocking about 80, 85, 90, 91, 92, 93, 94, 95, 96, 97, 98, 99 or 100% of an interaction between CFD and C3bB.

In some embodiments, a conjugate comprising an anti-CFD antibody and a phosphorylcholine containing polymer is provided. The polymer is covalently bonded to the antibody outside a variable region of the antibody. In some embodiments, a conjugate comprising an anti-CFD antibody and a phosphorylcholine containing polymer is provided. The polymer is covalently bonded to the antibody at a cysteine outside a variable region of the antibody. In some embodiments, a conjugate comprising an anti-CFD antibody and a phosphorylcholine containing polymer is provided, wherein the polymer is covalently bonded to the antibody at a cysteine outside a variable region of the antibody wherein said cysteine has been added via recombinant DNA technology. In some embodiments of the conjugate, the polymer comprises 2(methacryloyloxy)ethyl (2-(trimethylammonio) ethyl) phosphate (MPC) monomers.

In accordance with another aspect of the present invention, a method is provided where the conjugation group (e.g. maleimide) is added after polymer synthesis. This is sometimes referred to as a "snap-on strategy" or "universal polymer strategy". See, e.g., U.S. patent application Ser. No. 14/916,180 (published as U.S. Patent Application Publication No. 20160199501), hereby incorporated by reference in its entirety. In some embodiments, a single initiator moiety can be used for large scale polymer synthesis. Thus, conditions can be developed for scaled up optimal polymer synthesis. Such polymers can then be adapted to various types of functional agents by "snapping-on" various types of linkers. For example, if it is desired to conjugate a larger functional agent to a polymer of the instant invention such as an antibody of even a Fab fragment, a longer linker sequence can be snapped on to the polymer. In contrast, smaller functional agents may call for relatively shorter linker sequences.

In some embodiments of the methods, the initiator has about 1, 2, 3, 4, 5, 6, 7, 8, 9, 10, 11, or 12 sites for polymer initiation. In some embodiments, the initiator has about 3, about 6, or about 9 sites for polymer initiation.

In accordance with another aspect of the present invention, a second linker has second, third, fourth, fifth, and sixth reactive groups. More preferably, a second linker has just second and third reactive groups.

In accordance with an aspect of the present invention, each polymer arm has from about 20 to about 2000 monomer units. Preferably, each arm has from about 100 to 500 monomer units or from about 500 to 1000 monomer units or from about 1000 to 1500 monomer units or from about 1500 to 2000 monomer units.

In accordance with an aspect of the present invention, the peak molecular weight of the polymer-functional agent conjugate is about 100,000 to 1,500,000 Da. Preferably, the peak molecular weight of the polymer-functional agent conjugate is about 200,000 to about 300,000 Da, about 400,000 to about 600,000 Da or about 650,000 to about 850,000 Da.

In accordance with another aspect of the present invention, the first linker is preferably alkyl, substituted alkyl, alkylene, alkoxy, carboxyalkyl, haloalkyl, cycloalkyl, cyclic alkyl ether, alkenyl, alkenylene, alkynyl, alkynylene, cycloalkylene, heterocycloalkyl, heterocycloalkylene, aryl, arylene, arylene-oxy, heteroaryl, amino, amido or any combination thereof. More preferably, the first linker has the formula:

Formula (1)

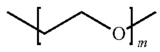

wherein m is 1 to 10. In some embodiments, the first linker has the above formula (Formula (1)) and m is 4.

In some embodiments, the initiator preferably includes a structure selected from group consisting of Formula (2)

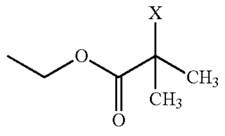

Formula (3)

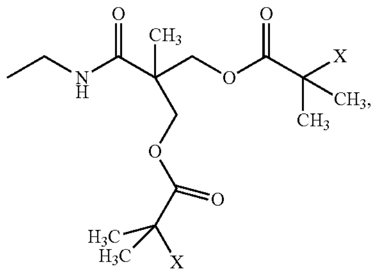

and

-continued

Formula (4)

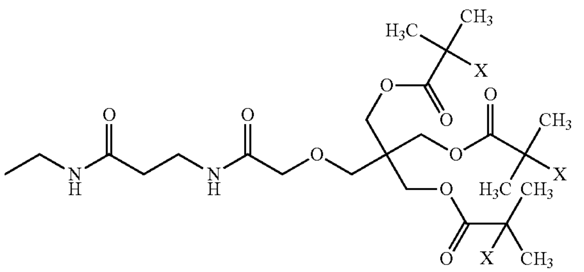

wherein X is selected from the group consisting of NCS, F, Cl, Br and I. More preferably, X in Formula (2), Formula (3) and/or Formula (4) is Br.

In some embodiments, the monomer is selected from the group consisting of

Formula (5)

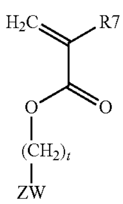

Formula (6)

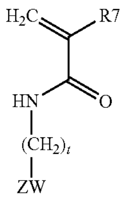

Formula (7)

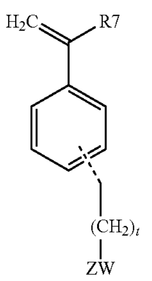

-continued

Formula (8)

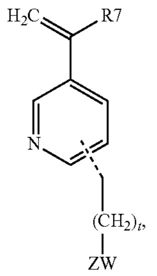

and

Formula (9)

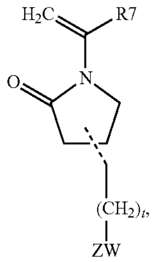

wherein R7 is H or $C_{1-6}$ alkyl and t is 1 to 6.

More preferably, the monomer is selected from the group consisting of 2-(methacryloyloxyethyl)-2'-(trimethylammoniumethyl) phosphate (HEMA-PC) and 2-(acryloyloxyethyl)-2'-(trimethylammoniumethyl) phosphate.

Most preferably, the monomer is 2-(methacryloyloxyethyl)-2'-(trimethylammoniumethyl) phosphate.

The second linker moiety preferably comprises an activated ester having the structure Formula (10)

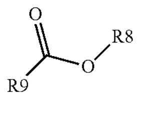

wherein R8 is selected from the group consisting of

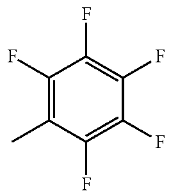

and

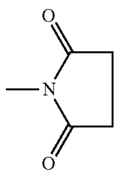

and R9 is

Formula (11)

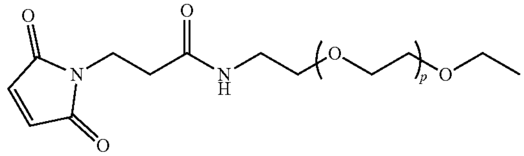

wherein p is 1 to 12.

In more preferred embodiments of the present invention, the polymer has 9 arms, m is 2-4, R9 is Formula (11)

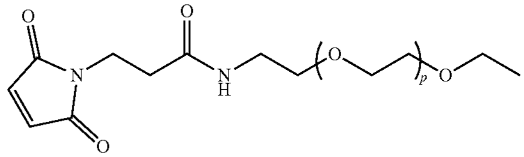

wherein p is 4 to 15. Still more preferably, m is 4 and p is 12.

In some embodiments, the radically polymerizable monomer is

Formula (12)

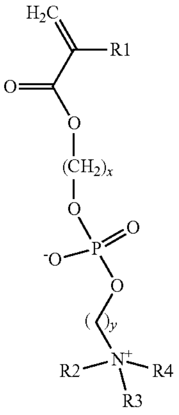

wherein R1 is H or C1-6 alkyl, R2, R3, R4 are the same or different and are H or C1-4alkyl and X and Y are the same or different and are integers from 1-6. In some embodiments, R1, R2, R3 and R4 are each methyl and X and Y are each 2 in Formula (12).

In some embodiments, the radically polymerizable monomer is

Formula (13)

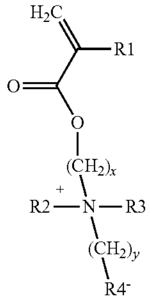

wherein R1 is H or C1-6alkyl, R2 and R3 are the same or different and are H or C1-4alkyl, R4 is PO4-, SO3- or CO2- and X and Y are the same or different and are integers from 1-6. In some embodiments, R1, R2 and R3 are methyl, R4 is PO4- and X and Y are each 2 in Formula (13).

In some embodiments, the monomer is

Formula (14)

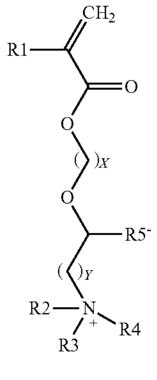

wherein R1 is H or C1-6alkyl, R2, R3 and R4 are the same or different and are H or C1-4alkyl, R5 is PO4-, SO3- or CO2- and X and Y are the same or different and are integers from 1-6. In some embodiments, R1, R2, R3 and R4 are methyl, R5 is PO4- and X and Y are 2 in Formula (14).

When a polymer is the to be conjugated via a cysteine (or other specified residue), the polymer can be linked directly or indirectly to the residue (e.g., with an intervening initiator, and or spacer or the like).

In some embodiments, the phosphorylcholine containing polymer comprises 2-(methacryloyloxyethyl)-2'-(trimethylammonium)ethyl phosphate (MPC) monomers as set forth below:

Formula (15)

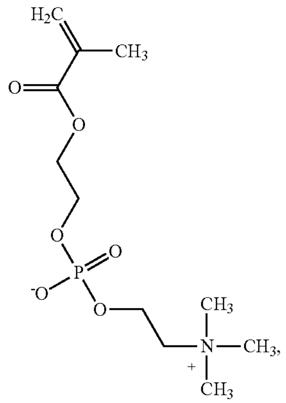

such that the polymer comprises the following repeating units:

Formula (16)

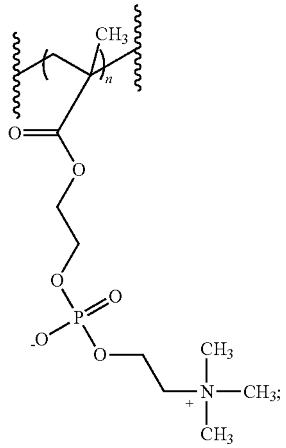

where n is an integer from 1 to 3000 and the wavy lines indicate the points of attachment between monomer units in the polymer.

In some embodiments, the polymer has three or more arms, or is synthesized with an initiator comprising 3 or more polymer initiation sites. In some embodiments, the polymer has 2, 3, 4, 5, 6, 7, 8, 9, 10, 11 or 12 arms, or is synthesized with an initiator comprising 2, 3, 4, 5, 6, 7, 8, 9, 10, 11, or 12 polymer initiation sites. More preferably, the polymer has 3, 6, or 9 arms, or is synthesized with an initiator comprising 3, 6, or 9 polymer initiation sites. In some embodiments, the polymer has 9 arms, or is synthesized with an initiator comprising 9 polymer initiation sites.

In some embodiments, the polymer that is added has a molecular weight between about 300,000 and about 1,750,000 Da (SEC-MALs). In some embodiments, the polymer has a molecular weight between about 500,000 and about 1,000,000 Da. In some embodiments, the polymer has a molecular weight of between about 600,000 to about 900,000 Da. In some embodiments, the polymer has a molecular weight of between about 750,000 to about 850,000 Da. In some embodiments, the polymer has a molecular weight of between about 800,000 to about 850,000 Da. In some embodiments, the polymer has a molecular weight of between about 750,000 to about 800,000 Da.

In some embodiments, any of the antibodies described herein can be further conjugated to a polymer to form a bioconjugate. The molecular weight of the bioconjugate (in total, SEC-MALs) can be between about 350,000 and 2,000,000 Daltons, for example, between about 450,000 and 1,900,000 Daltons, between about 550,000 and 1,800,000 Daltons, between about 650,000 and 1,700,000 Daltons, between about 750,000 and 1,600,000 Daltons, between about 850,000 and 1,500,000 Daltons, between about 900,000 and 1,400,000 Daltons, between about 950,000 and 1,300,000 Daltons, between about 900,000 and 1,000,000 Daltons, between about 1,000,000 and 1,300,000 Daltons, between about 850,000 and 1,300,000 Daltons, between about 850,000 and 1,000,000 Daltons, and between about 1,000,000 and 1,200,000 Daltons. In some embodiments, the bioconjugate has a molecular weight between about 350,000 and 1,900,000 Daltons.

In some embodiments, the antibody conjugate is purified. In some embodiments, the polymer in aspect of the antibody conjugate is polydisperse, i.e. the polymer PDI is not 1.0. In some embodiments, the PDI is less than 1.5. In some embodiments, the PDI is less than 1.4. In some embodiments, the PDI is less than 1.3. In some embodiments the PDI is less than 1.2. In some embodiments the PDI is less than 1.1. In some embodiments, the conjugate PDI is equal to or less than 1.5.

In some embodiments, the antibody conjugate has an anti-CFD immunoglobulin G (IgG) bonded to a polymer, which polymer comprises MPC monomers, wherein the sequence of the anti-CFD heavy chain is SEQ ID NO. 183, and the sequence of the anti-CFD light chain is SEQ ID NO. 184, and wherein the antibody is bonded only at C442 of SEQ ID NO 183 to the polymer. In some embodiments, the polymer has 9 arms and has a molecular weight of between about 600,000 to about 1,000,000 Da.

In some embodiments, the antibody conjugate has an anti-CFD immunoglobulin G (IgG) bonded to a polymer, which polymer comprises MPC monomers, wherein the sequence of the anti-CFD heavy chain comprises SEQ ID NO. 183, and the sequence of the anti-CFD light chain comprises SEQ ID NO. 184, and wherein the antibody is bonded only at C443 (EU numbering, or 442C in SEQ ID NO 183) to the polymer. In some embodiments, the polymer has 9 arms and has a molecular weight of between about 600,000 to about 1,000,000 Da. In some embodiments, the conjugate comprises a polymer that has 9 arms and the polymer has a molecular weight of between about 600,000 to about 900,000 Da.

In some embodiments, the antibody conjugate has the following structure:

Formula (17)

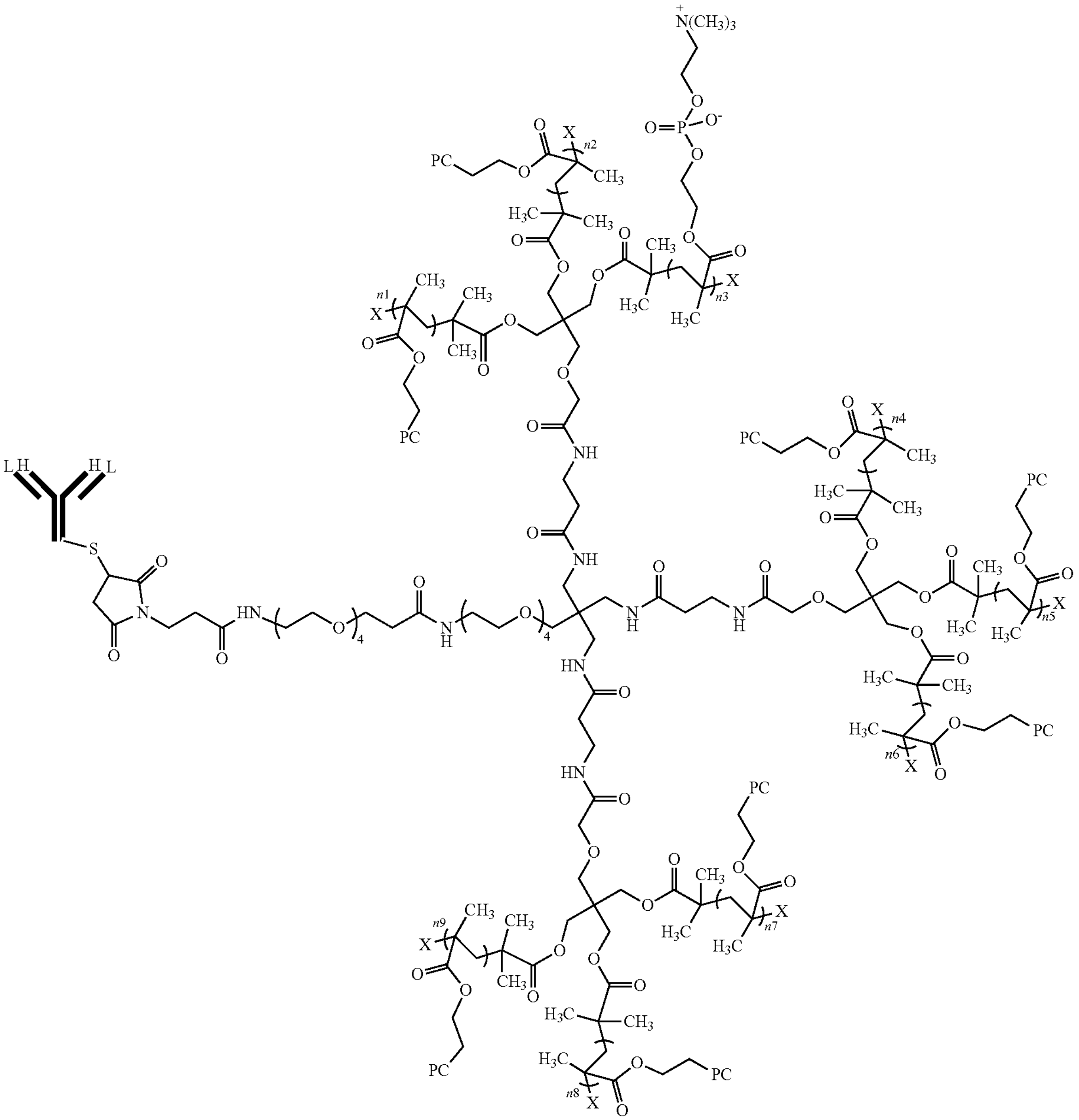

wherein: each heavy chain of the anti-CFD antibody is denoted by the letter H, and each light chain of the anti-CFD antibody is denoted by the letter L;

the polymer is bonded to the anti-CFD antibody through the sulfhydryl of C443 (EU numbering, or 442C in SEQ TD NO: 183), which bond is depicted on one of the heavy chains; PC is,

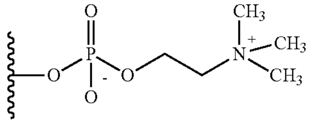

where the curvy line indicates the point of attachment to the rest of the polymer; wherein X=a) OR where R=H, Methyl, ethyl, propyl, isopropyl, b) H, or c) any halide, including Br; and n1, n2, n3, n4, n5, n6, n7, n8 and n9 are the same or different such that the sum of n1, n2, n3, n4, n5, n6, n6, n7, n8 and n9 is 2500 plus or minus 10%. In some embodiments, n1, n2, n3, n4, n5, n6, n7, n8 and n9 are the same or different and are integers from 0 to 3000. In some embodiments, n1, n2, n3, n4, n5, n6, n7, n8 and n9 are the same or different and are integers from 0 to 500. In some embodiments, X=OR, where R is a sugar, an aminoalkyl, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, —CO—O—$R_7$, carbonyl —CCO—$R_7$, —CO—$NR_8R_9$, —$(CH_2)_n$—$COOR_7$, —CO—$(CH)_n$—$COOR_7$, —$(CH_2)_n$—$NR_8R_9$, ester, alkoxycarbonyl, aryloxycarbonyl, wherein n is an integer from 1 to 6, wherein each $R_7$, $R_8$ and $R_9$ is separately selected from the group consisting of a hydrogen atom, halogen atom, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, a 5-membered ring, and a 6-membered ring.

In some embodiments, the antibody conjugate has the following structure:

Formula (17)

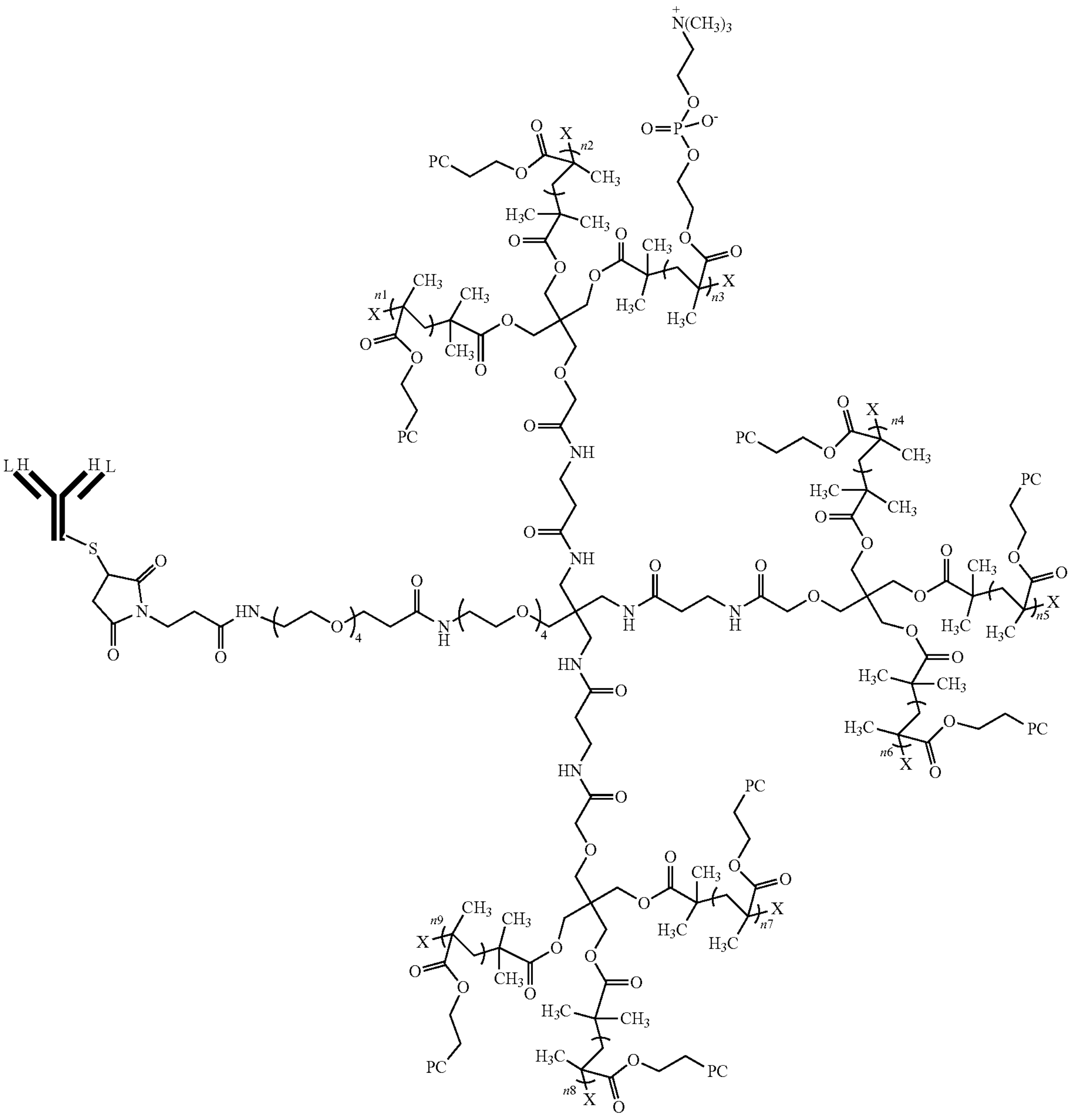

wherein:

each heavy chain of the antibody is denoted by the letter H, and each light chain of the anti-CFD antibody is denoted by the letter L;

the polymer is bonded to the antibody through the sulfhydryl of C443 (EU numbering), which bond is depicted on one of the heavy chains;

PC is

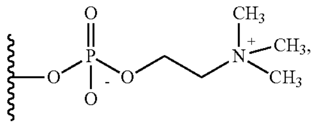

where the curvy line indicates the point of attachment to the rest of the polymer, where X=a) OR where R=H, methyl, ethyl, propyl, isopropyl, b) H, or c) any halide, including Br; and n1, n2, n3, n4, n5, n6, n7, n8 and n9 are the same or different such that the sum of n1, n2, n3, n4, n5, n6, n6, n7, n8 and n9 is 2500 plus or minus 15%. In some embodiments, the sum of n1, n2, n3, n4, n5, n6, n6, n7, n8 and n9 is about 1500 to about 3500 plus or minus about 10% to about 20%.

In some embodiments, the antibody conjugate is present in a liquid formulation. In some embodiments, the antibody conjugate is combined with a pharmaceutically acceptable carrier.

In some embodiments, an anti-CFD antibody is presented. The anti-CFD antibody heavy chain has at least the following CDR sequences: $CDR_H1$: SEQ ID NO: 541, $CDR_H2$: SEQ ID NO: 542, and $CDR_H3$: SEQ ID NO: 543. In some embodiments, the anti-CFD light chain has at least the following CDRs: $CDR_L1$: SEQ ID NO: 544, $CDR_L2$: SEQ ID NO: 545 and $CDR_L3$: SEQ ID NO: 546. In some embodiments, the anti-CFD antibody heavy chain has at least the following CDR sequences: $CDR_H1$: SEQ ID NO: 326, $CDR_H2$: SEQ ID NO: 327, and $CDR_H3$: SEQ ID NO: 328. In some embodiments, the anti-CFD light chain has at least the following CDRs: $CDR_L1$: SEQ ID NO: 323, $CDR_L2$: SEQ ID NO: 324 and $CDR_L3$: SEQ ID NO: 325. In some embodiments, the anti-CFD antibody heavy chain has at least the following CDR sequences: $CDR_H1$: SEQ ID NO: 332, $CDR_H2$: SEQ ID NO: 333, and $CDR_H3$: SEQ ID NO: 334. In some embodiments, the anti-CFD light chain has at least the following CDRs: $CDR_L1$: SEQ ID NO: 329, $CDR_L2$: SEQ ID NO: 330 and $CDR_L3$: SEQ ID NO: 331.

In some embodiments, the anti-CFD antibody heavy chain has at least the following CDR sequences: HCDR1: SEQ ID NO: 577: GYTFTDYYIN, HCDR2: SEQ ID NO: 578: INPITGDTDYNADFKR, and HCDR3: SEQ ID NO: 579: TREGPSFAY. In some embodiments, the anti-CFD light chain has at least the following CDRs: LCDR1: SEQ ID NO: 580: RSSQTIVHSNGDTYLE, LCDR2: SEQ ID NO: 581: LLIRKVSNRFS, and LCDR3: SEQ ID NO: 582: FQGSHVPVT. In some embodiments, the anti-CFD antibody has at least the following CDR sequences: HCDR1: SEQ ID NO: 577: GYTFTDYYIN, HCDR2: SEQ ID NO: 578: INPITGDTDYNADFKR, HCDR3: SEQ ID NO: 579: TREGPSFAY, LCDR1: SEQ ID NO: 580: RSSQTIVHSNGDTYLE, LCDR2: SEQ ID NO: 581: LLIRKVSNRFS, and LCDR3: SEQ ID NO: 582: FQGSHVPVT.

In some embodiments, the isotype of the anti-CFD antibody heavy chain, is IgG1 and has a $CH_1$, hinge, $CH_2$ and $CH_3$ domains. In some embodiments the light chain isotype is kappa.

In some embodiments, the IgG1 domain of the anti-CFD antibody has one or more mutations to modulate effector function, such as ADCC, ADCP, and CDC. In some embodiments, the IgG1 mutations reduce effector function. In some embodiments the amino acids to use for effector function mutations include (EU numbering) E233X, L234X, L235X, G236X, G237X, G236X, D270X, K322X, A327X, P329X, A330X, A330X, P331X, and P331X, in which X is any natural or non-natural amino acid. In some embodiments, the mutations include one or more of the following: E233P, L234V, L234A, L235A, G237A, A327G, A330S and P331S (EU numbering). In some embodiments, the anti-CFD heavy chain has the following mutations (EU numbering): L234A, L235A and G237A. In some embodiments, the number of effector function mutations relative to a natural human IgG1 sequence is no more than 10. In some embodiments the number of effector function mutations relative to a natural human IgG1 sequence is no more than 5, 4, 3, 2 or 1. In some embodiments, the antibody has decreased Fc gamma binding and/or complement C1q binding, such that the antibody's ability to result in an effector function is decreased. This can be especially advantageous for ophthalmic indications/disorders.

In some embodiments, the anti-CFD antibody comprises one or more of the following amino acid mutations: L234A, L235A, G237A, and L443C (EU numbering, or 233A, 234A, 236A, and 442C in SEQ ID NO: 183).

In some embodiments, the anti-CFD antibody is or is part of a human immunoglobulin G (IgG1).

In some embodiments, the CFD antibody comprises a heavy chain constant domain that comprises one or more mutations that reduce an immune-mediated effector function.

In some embodiments an anti-CFD antibody is provided. The anti-CFD antibody comprises a heavy chain that comprises a $CDR_H1$ comprising the sequence of any one of SEQ ID NOs: 541, 326, 332, or 577, a $CDR_H2$ comprising the sequence of any one of SEQ ID NOs: 542, 327, 333, or 578, a $CDR_H3$ comprising the sequence of any one of SEQ ID NOs: 543, 328, 334, or 579 a $CDR_L1$ comprising the sequence of any one of SEQ ID NOs: 544, 323, 329, or 580, a $CDR_L2$ comprising the sequence of any one of SEQ ID NOs: 545, 324, 330, or 581, and a $CDR_L3$ comprising the sequence of any one of SEQ ID NOs: 546, 325, 331, or 582.

Alternatively, the IgG domain can be IgG2, IgG3 or IgG4 or a composite in which a constant regions is formed from more than one of these isotypes (e.g., CH1 region from IgG2 or IgG4, hinge, CH2 and CH3 regions from IgG1). Such domains can contain mutations to reduce and/or modulate effector function at one or more of the EU position mentioned for IgG1. Human IgG2 and IgG4 have reduced effector functions relative to human IgG1 and IgG3.

In some embodiments, the anti-CFD heavy chain has a cysteine residue added as a mutation by recombinant DNA technology which can be used to conjugate a half-life extending moiety. In some embodiments, the mutation is Q347C (EU numbering, or 346C in SEQ ID NO 183)) and/or L443C (EU numbering, or 442C in SEQ ID NO: 183). In some embodiments, the mutation is L443C (EU numbering, or 442C in SEQ ID NO: 183). In some embodiments, the stoichiometry of antibody to polymer is 1:1; in other words, a conjugate has one molecule of antibody conjugated to one molecule of polymer.

The half-life of the anti-CFD antibodies can be extended by attachment of a "half-life ("half life") extending moieties" or "half-life ("half life") extending groups". Half-life extending moieties include peptides and proteins which can be expressed in frame with the biological drug of issue (or conjugated chemically depending on the situation) and various polymers which can be attached or conjugated to one or more amino acid side chain or end functionalities such as —SH, —OH, —COOH, —CONH2, —NH2, or one or more N- and/or O-glycan structures. Half-life extending moieties generally act to increase the in vivo circulatory half-life of biologic drugs.

Examples of peptide/protein half-life extending moieties include Fc fusion (Capon D J, Chamow S M, Mordenti J, et al. Designing CD4 immunoadhesions for AIDS therapy. Nature. 1989. 337:525-31), human serum albumin (HAS) fusion (Yeh P, Landais D, Lemaitre M, et al. Design of yeast-secreted albumin derivatives for human therapy: biological and antiviral properties of a serum albumin-CD4 genetic conjugate. Proc Natl Acad Sci USA. 1992. 89:1904-08), carboxy terminal peptide (CTP) fusion (Fares F A, Suganuma N. Nishimori K, et al. Design of a long-acting follitropin agonist by fusing the C-terminal sequence of the chorionic gonadotropin beta subunit to the follitropin beta subunit. Proc Natl Acad Sci USA. 1992. 89:4304-08), genetic fusion of non-exact repeat peptide sequence (XTEN) fusion (Schellenberger V, Wang C W, Geething N C, et al. A recombinant polypeptide extends the in vivo half-life of peptides and proteins in a tunable manner. Nat Biotechnol. 2009. 27:1186-90), elastin like peptide (ELPylation) (MCpherson D T, Morrow C, Minehan D S, et al. Production and purification of a recombinant elastomeric polypeptide, G(VPGVG19-VPGV, from *Escherichia coli*. Biotechnol Prog. 1992. 8:347-52), human transferrin fusion (Prior C P, Lai C-H, Sadehghi H et al. Modified transferrin fusion proteins. Patent WO2004/020405. 2004), proline-alanine-serine (PASylation) (Skerra A, Theobald I, Schlapsky M. Biological active proteins having increased in vivo and/or vitro stability. Patent WO2008/155134 A1. 2008), homo-amino acid polymer (HAPylation) (Schlapschy M, Theobald I, Mack H, et al. Fusion of a recombinant antibody fragment with a homo-amino acid polymer: effects on biophysical properties and prolonged plasma half-life. Protein Eng Des Sel. 2007. 20:273-84) and gelatin like protein (GLK) fusion (Huang Y-S, Wen X-F, Zaro J L, et al. Engineering a pharmacologically superior form of granulocyte-colony-stimulating-factor by fusion with gelatin-like protein polymer. Eur J. Pharm Biopharm. 2010. 72:435-41).

Examples of polymer half-life extending moieties include polyethylene glycol (PEG), branched PEG, PolyPEG® (Warwick Effect Polymers; Coventry, UK), polysialic acid (PSA), starch, hydroxylethyl starch (HES), hydroxyalkyl starch (HAS), carbohydrate, polysaccharides, pullulane, chitosan, hyaluronic acid, chondroitin sulfate, dermatan sulfate, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anyhydride, polystyrene-co-maleic acid anhydride, poly(1-hydroxymethyethylene hydroxymethylformal) (PHF), a zwitterionic polymer, a phosphorylcholine containing polymer and a polymer comprising MPC, Poly ($Gly_x$-$Ser_y$), Hyaluronic acid (HA), Heparosan polymers (HEP), Fleximers, Dextran, and Poly-sialic acids (PSA).

In one embodiment a half-life extending moiety can be conjugated to an antibody via free amino groups of the protein using N-hydroxysuccinimide (NHS) esters. Reagents targeting conjugation to amine groups can randomly react to ε-amine group of lysines, α-amine group of N-terminal amino acids, and δ-amine group of histidines.

However, the anti-CFD antibodies disclosed herein can have many amine groups available for polymer conjugation. Conjugation of polymers to free amino groups, thus, might negatively impact the ability of the antibody proteins to bind to CFD.

In some embodiments, a half-life extending moiety is coupled to one or more free SH groups using any appropriate thiol-reactive chemistry including, without limitation, maleimide chemistry, or the coupling of polymer hydrazides or polymer amines to carbohydrate moieties of the antibody after prior oxidation. In some embodiments maleimide coupling is used In some embodiments, coupling occurs at cysteines naturally present or introduced via genetic engineering.

In some embodiments, conjugates of antibody and high MW polymers serving as half-life extenders are provided. In some embodiments, a conjugate comprises an antibody that is coupled to a zwitterionic polymer wherein the polymer is formed from one or more monomer units and wherein at least one monomer unit has a zwitterionic group is provided. In some embodiments, the zwitterionic group is phosphorylcholine.

In some embodiments, one of the monomer units is HEMA-PC. In some embodiments, a polymer is synthesized from a single monomer which is HEMA-PC.

In some embodiments, some antibody conjugates have 2, 3, or more polymer arms wherein the monomer is HEMA-PC. In some embodiments, the conjugates have 2, 3, 4, 5, 6, 7, 8, 9, 10, 11, or 12 polymer arms wherein the monomer is HEMA-PC. In some embodiments, the conjugates have 3, 6 or 9 arms. In some embodiments, the conjugate has 9 arms.

In some embodiments, polymer-antibody conjugates have a polymer portion with a molecular weight of between 100,000 and 1,500,000 Da. In some embodiments, the conjugate has a polymer portion with a molecular weight between 500,000 and 1,000,000 Da. In some embodiments, the conjugate has a polymer portion with a molecular weight between 600,000 to 800,000 Da. In some embodiments, the conjugate has a polymer portion with a molecular weight between 600,000 and 850,000 Da and has 9 arms. When a molecular weight is given for an antibody conjugated to a polymer, the molecular weight will be the addition of the molecular weight of the protein, including any carbohydrate moieties associated therewith, and the molecular weight of the polymer.

In some embodiments, an anti-CFD antibody has a HEMA-PC polymer which has a molecular weight measured by Mw of between about 100 kDa and 1650 kDa is provided. In some embodiments, the molecular weight of the polymer as measured by Mw is between about 500 kDa and 1000 kDa. In some embodiments, the molecular weight of the polymer as measured by Mw is between about 600 kDa to about 900 kDa. In some embodiments, the polymer molecular weight as measured by Mw is 750 or 800 kDa plus or minus 15%.

In some embodiments, the polymer is made from an initiator suitable for ATRP having one or more polymer initiation sites. In some embodiments, the polymer initiation site has a 2-bromoisobutyrate site. In some embodiments, the initiator has 3 or more polymer initiation sites. In some embodiments, the initiator has 3, 4, 5, 6, 7, 8, 9, 10, 11 or 12 polymer initiation sites. In some embodiments, the initiator has 3, 6 or 9 polymer initiation sites. In some embodiments, the initiator has 9 polymer initiation sites. In some embodiments, the initiator is OG1786.

The anti-CFD antibodies can be produced by recombinant expression including (i) the production of recombinant DNA by genetic engineering, (ii) introducing recombinant DNA into prokaryotic or eukaryotic cells by, for example and without limitation, transfection, electroporation or microinjection, (iii) cultivating the transformed cells, (iv) expressing antibody, e.g. constitutively or on induction, and (v) isolating the antibody, e.g. from the culture medium or by harvesting the transformed cells, in order to (vi) obtain purified antibody.

The anti-CFD antibodies can be produced by expression in a suitable prokaryotic or eukaryotic host system characterized by producing a pharmacologically acceptable antibody molecule. Examples of eukaryotic cells are mammalian cells, such as CHO, COS, HEK 293, BHK, SK-Hip, and HepG2. Other suitable expression systems are prokaryotic (e.g., *E. coli* with pET/BL21 expression system), yeast (*Saccharomyces cerevisiae* and/or *Pichia pastoris* systems), and insect cells.

A wide variety of vectors can be used for the preparation of the antibodies disclosed herein and are selected from eukaryotic and prokaryotic expression vectors. Examples of vectors for prokaryotic expression include plasmids such as, and without limitation, preset, pet, and pad, wherein the promoters used in prokaryotic expression vectors include one or more of, and without limitation, lac, trc, trp, recA, or araBAD. Examples of vectors for eukaryotic expression include: (i) for expression in yeast, vectors such as, and without limitation, pAO, pPIC, pYES, or pMET, using promoters such as, and without limitation, AOX1, GAP, GAL1, or AUG1; (ii) for expression in insect cells, vectors such as and without limitation, pMT, pAc5, pIB, pMIB, or pBAC, using promoters such as and without limitation PH, p10, MT, Ac5, OpIE2, gp64, or polh, and (iii) for expression in mammalian cells, vectors such as, and without limitation, pSVL, pCMV, pRc/RSV, pcDNA3, or pBPV, and vectors derived from, in one aspect, viral systems such as and without limitation vaccinia virus, adeno-associated viruses, herpes viruses, or retroviruses, using promoters such as and without limitation CMV, SV40, EF-1, UbC, RSV, ADV, BPV, and beta-actin.

Method of Conjugating Proteins to Polymers

In some embodiments, a method is presented of preparing a therapeutic protein-half life extending moiety conjugate having the step of conjugating a therapeutic protein which has a cysteine residue added via recombinant DNA technology to a half-life extending moiety having a sulfhydryl specific reacting group selected from the group consisting of maleimide, vinylsulfones, orthopyridyl-disulfides, and iodoacetamides to provide the therapeutic protein-half life extending moiety conjugate.

Figure 17:
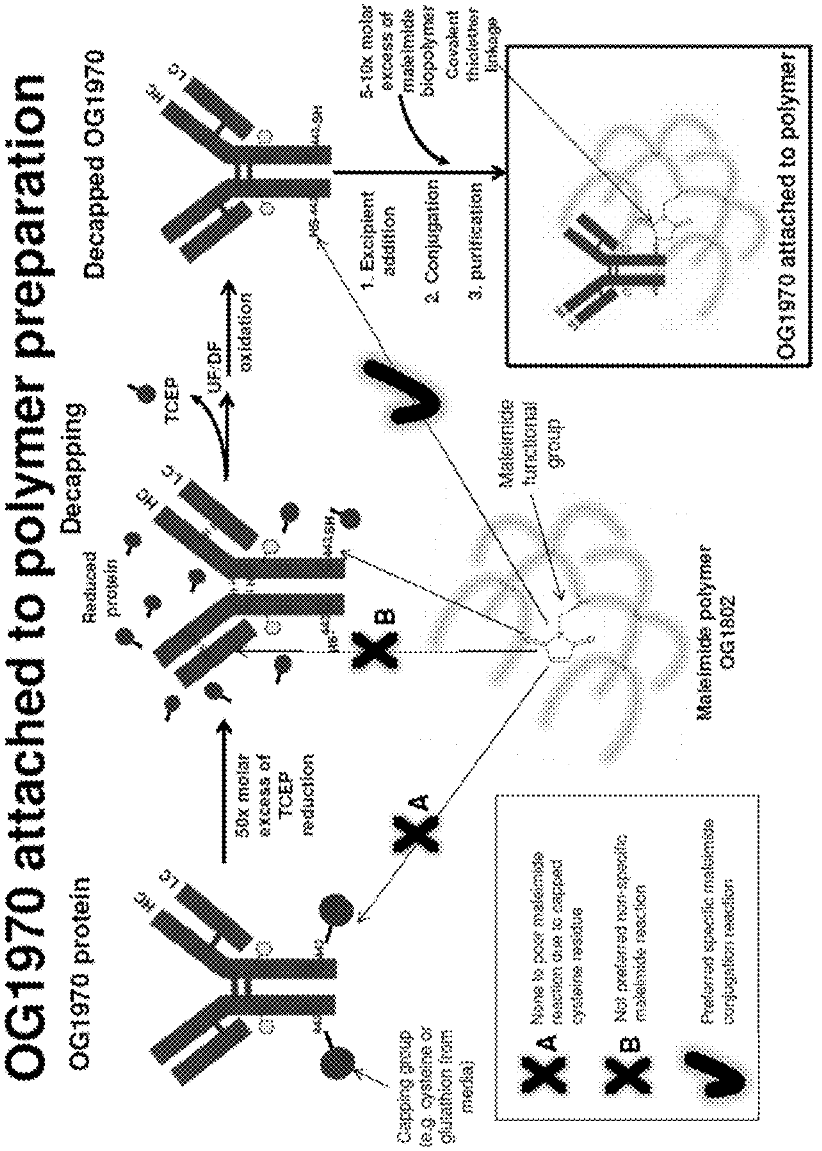
FIG. 17 depicts some embodiments of a method for preparing an antibody conjugate.

In some embodiments a method of preparing the antibody conjugate is provided. As shown in FIG. 17, the method comprises reducing the protein with a 30× molar excess of the TCEP reducing agent (FIG. 17). After reduction, the antibody is oxidized to produce a decapped antibody where the inter- and intra-light and heavy chain disulfide bonds naturally occurring in the antibody are formed, but the engineered Cysteine on the heavy chain position L443C (EU numbering, or 442C in SEQ ID NO: 183) remains to be decapped (FIG. 17). The antibody is then conjugated by adding an excipient and adding 2-10× molar excess of a maleimide biopolymer. (FIG. 17). The biopolymer links to the antibody through a covalent thiolether linkage (FIG. 17). After conjugation, the antibody conjugate is purified with both unconjugated antibody and polymer removed (FIG. 17).

The protein and process described above can be varied as well. Thus, in some embodiments, a process for preparing a conjugated protein (which need not be an antibody or an anti-CFD antibody) is provided. The process includes reducing one or more cysteines in a protein to form a decapped protein in a solution. After reducing the one or more cysteines the decapped protein is reoxidized to restore at least one disulfide linkage in the reduced protein while ensuring that an engineered cysteine residue in the protein remains in a free thiol form to form a reoxidized decapped protein in the solution. At least one excipient is then added to the solution. The excipient reduces a polymer induced protein precipitation. After the excipient is added, a polymer is added to the solution, which is conjugated to the reoxidized decapped protein at the engineered cysteine residue to form a conjugated protein.

In some embodiments, the molar excess of the reducing agent can be altered to any amount that functions. In some embodiments 10, 20, 30, 40, 50, 60, 70, 80, 90× molar excess of the reducing agent (which need not be TCEP in all embodiments) can be employed. In some embodiments, any antibody (therapeutic or otherwise) can be employed. In some embodiments, 1, 2, 3, 4, 5, 6, 7, 8, 9, 10, 11, 12, 13, 14, 15× molar excess of a maleimide biopolymer can be employed. In some embodiments, there is an excess of decapped protein to polymer. In some embodiments, the amount of the reduced protein is less than the amount of the polymer. In some embodiments, the amount of the reduced protein is 90%, 80%, 70%, 60%, 50%, 40%, 30%, 20%, 10%, 5%, 4%, 3%, 2%, 1% of the amount of the polymer. In some embodiments, 10-15 times as much polymer is used as protein. In some embodiments the amount of the reduced antibody is greater than the amount of the polymer. In some embodiments the amount of the polymer is greater than the amount of the reduced antibody.

In some embodiments, the purification step is optional.

In some embodiments, the method of making an antibody conjugate comprises conjugating an anti-CFD antibody to a phosphorylcholine containing polymer. In some embodiments the method comprises the steps of conjugating an anti-CFD antibody to a phosphorylcholine containing polymer. The anti-CFD antibody comprises an amino residue added via recombinant DNA technology. In some embodiments, the added amino acid residue is a cysteine residue. In some embodiments, the cysteine residue is added outside a variable region of the antibody. The cysteine residue can be added to either the heavy chain or light chain of the antibody.

In some embodiments, the polymer comprises or consists of a phosphorylcholine containing polymer. In some embodiments, the phosphorylcholine containing polymer comprises a sulfhydryl specific reacting group selected from the group consisting of a maleimide, a vinylsulfone, an orthopyridyl-disulfide, and an iodoacetamide. In some embodiments, the sulfhydryl specific reacting group on the phosphorylcholine containing polymer reacts with the cysteine residue on the anti-CFD antibody to make the antibody conjugate.

In some embodiments, the protein to be conjugated can be an antibody, an antibody protein fusion, or a binding fragment thereof. In some embodiments, the protein is not an antibody but is an enzyme, a ligand, a receptor, or other protein or mutants or variants thereof. In some embodiments, the native protein contains at least one disulfide bond and at least one non-native cysteine.

In some embodiments, the excipient can be an acid or a base. In some embodiments, the excipient is a detergent, a sugar, or a charged amino acid. In some embodiments, the excipient assists in keeping the protein in solution during the conjugation to the polymer. In some embodiments, the excipient is added to the solution containing the protein, prior to the addition of the polymer to the solution that contains the protein.

In some embodiments, the reaction occurs under aqueous conditions between about pH 5 to about pH 9. In some embodiments, the reaction occurs between 6.0 and 8.5, between 6.5 and 8.0 or between 7.0 and 7.5.

In some embodiments, the polymer is conjugated to the protein at 2-37 degrees Celsius. In some embodiments, the conjugation occurs at 0-40 degrees Celsius, 5-35 degrees Celsius, 10-30 degrees Celsius, and 15-25 degrees Celsius.

In some embodiments, the conjugated proteins described herein can be contacted to an ion exchange medium or hydrophobic interaction chromatography or affinity chromatography medium for purification (to remove the conjugated from the unconjugated). In some embodiments, the ion exchange medium, hydrophobic interaction chromatography, and/or affinity chromatography medium separates the conjugated protein from the unconjugated free polymer and from the unconjugated reoxidized decapped protein.

In some embodiments, the processes described herein and outlined in FIG. 17 involves an excipient that is capable of facilitating and/or maintaining a solubility system. In some embodiments, the process allows the solution to maintain the solubility of the two components meant to interact. This can include the solubility of the protein and the polymer and then the end conjugate as well. In some embodiments, without the excipient approach, the issue can be that while the protein it is soluble, when the biopolymer is added, the solubility of the solution (e.g., protein) drops and it crashes/precipitates out of solution. Of course, when the protein crashes out, it is not available to conjugate efficiently with the biopolymer. Thus, an excipient can be employed to maintain the solubility of the protein in the presence of the biopolymer so the two can couple to form the protein conjugate (or as depicted in FIG. 17, an antibody conjugate). This also allows for the solubility of the conjugate to be maintained.

In some embodiments, the polymers disclosed herein can comprise one or more of the following: a zwitterion, a phosphorylcholine, or a PEG linker bridging a center of a polymer branching point to the maleimide functional group. In some embodiments, any of the polymers provided herein can be added to a protein via the methods provided herein.

In some embodiments, any of the proteins provided herein can be conjugated to any of the polymers provided herein via one or more of the methods provided herein.

In some embodiments, the process(es) provided herein allow(s) for larger scale processing to make and purify protein and/or antibody conjugates. In some embodiments, the volume employed is at least 1 liter, for example 1, 10, 100, 1,000, 5,000, 10,000, liters or more. In some embodiments, the amount of the antibody conjugate produced and/or purified can be 0.1, 1, 10, 100, 1000, or more grams.

In some embodiments, the therapeutic protein may be any of the anti-CFD antibodies described herein having a cysteine residue added via recombinant DNA technology. In some embodiments, the anti-CFD antibody heavy chain has the following CDRs: HCDR1: DYY (SEQ ID NO: 541), HCDR2: INPITGDT (SEQ ID NO: 542), HCDR3: EGPSFAY (SEQ ID NO: 543); LCDR1: QTIVHSNGDT (SEQ ID NO: 544), LCDR2: KVS (SEQ ID NO: 545), LCDR3: FQGSHVPVT (SEQ ID NO: 546), for example, 1, 2, 3, 4, 5, or all 6 CDRs. In some embodiments, the antibody includes HCDR3.

In some embodiments, the anti-CFD antibody is IgG1. In some embodiments, the heavy chain has one or more mutations to modulate effector function. In some embodiments, the mutations are to one or more of the following amino acid positions (EU numbering): E233, L234, L235, G236, G237, A327, A330, and P331. In some embodiments, the mutations are selected from the group consisting of: E233P, L234V, L234A, L235A, G237A, A327G, A330S and P331S (EU numbering). In some embodiments, the mutations are (EU numbering) L234A, L235A and G237A.

In some embodiments, the cysteine residue added to the therapeutic protein via recombinant DNA technology should not be involved in Cys-Cys disulfide bond pairing. In this regard, therapeutic proteins may be dimeric. So for example, an intact anti-CFD antibody has two light chains and two heavy chains. If a Cys residue is introduced into the heavy chain for instance, the intact antibody will have two such introduced cysteines at identical positions and the possibility exists that these cysteine residues will form intra-chain disulfide bonds. If the introduced cysteine residues form Cys-Cys disulfide bonds or have a propensity to do so, that introduced Cys residue will not be useful for conjugation. It is known in the art how to avoid positions in the heavy and light chains that will give rise to intra-chain disulfide pairing. See, e.g., U.S. Patent Application No. 2015/0158952.

In some embodiments, the cysteine residue introduced via recombinant DNA technology is selected from the group consisting of (EU numbering) Q347C and L443C. In some embodiments, the cysteine residue is L443C (EU numbering, or 442C in SEQ ID NO: 183). In some embodiments, the heavy chain the antibody has the amino acid sequence set forth in SEQ ID NO. 1 and the light chain has the amino acid sequence of SEQ ID NO. 2.

In some embodiments, the sulfhydral specific reacting group is maleimide.

In some embodiments, the half-life extending moiety is selected from the group consisting of polyethylene glycol (PEG), branched PEG, PolyPEG® (Warwick Effect Polymers; Coventry, UK), polysialic acid (PSA), starch, hydroxylethyl starch (HES), hydroxyalkyl starch (HAS), carbohydrate, polysaccharides, pullulane, chitosan, hyaluronic acid, chondroitin sulfate, dermatan sulfate, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anyhydride, polystyrene-co-maleic acid anhydride, poly(1-hydroxymethyethylene hydroxymethylformal) (PHF), a zwitterionic polymer, a phosphorylcholine containing polymer and a polymer comprising 2-methacryloyloxy-2'-ethyltrimethylammoniumphosphate (MPC).

In some embodiments, the half-life extending moiety is a zwitterionic polymer. In some embodiments, the zwitterion is phosphorylcholine, i.e. a phosphorylcholine containing polymer. In some embodiments, the polymer is composed of MPC units.

In some embodiments, the MPC polymer has three or more arms. In some embodiments, the MPC polymer has 2, 3, 4, 5, 6, 7, 8, 9, 10, 11 or 12 arms. In some embodiments, the MPC polymer has 3, 6, or 9 arms. In some embodiments, the MPC polymer has 9 arms. In some embodiments, the polymer is synthesized with an initiator comprising 2, 3, 4, 5, 6, 7, 8, 9, 10, 11, 12, or more polymer initiation sites In some embodiments, the MPC polymer has a molecular weight between about 300,000 and 1,750,000 Da. In some embodiments, the MPC polymer has a molecular weight between about 500,000 and 1,000,000 Da or between about 600,000 to 900,000 Da.

In some embodiments, the method of preparing a therapeutic protein-half life extending moiety conjugate has an additional step of contacting the therapeutic protein with a thiol reductant under conditions that produce a reduced cysteine sulfhydryl group. As discussed above, it is preferable that the cysteine residue added via recombinant DNA technology are unpaired, i.e. are not involved in Cys-Cys intra chain disulfide bonds or are not substantially involved in such bonding. However, Cys residues which are not involved in such Cys-Cys disulfide bonding and are free for conjugation are known to react with with free cysteine in the culture media to form disulfide adducts. See, e.g., WO 2009/052249. A cysteine so derivatized will not be available for conjugation. To free the newly added cysteine from the disulfide adduct, the protein after purification is treated with a reducing agent, e.g., dithiothreitol. However, such treatment with a reducing agent will reduce all of the cysteine residues in the therapeutic protein, including native cysteines many of which are involved in inter and intra chain Cys-Cys disulfides bonds. The native Cys-Cys disulfides are generally crucial to protein stability and activity and they should be reformed. In some embodiments, all native (e.g., inter and intra) Cys-Cys disulfides are reformed.

To reform native inter and intra-chain disulfide residues, after reduction to remove the cysteine disulfide adducts, the therapeutic protein is exposed to oxidizing conditions and/or oxidizing agents for a prescribed period of time, e.g., overnight. In some embodiments, ambient air exposure overnight can be used to achieve reformation of the native disulfide bonds. In some embodiments, an oxidizing agent is employed to restore the native disulfides. In some embodiments, the oxidizing agent is selected from the group consisting of aqueous CuSO4 and dehydroascorbic acid (DHAA). In some embodiments, the oxidizing agent is DHAA. In some embodiments, the range of DHAA used is in the range of 5-30 equivalents. In some embodiments, the range is 10-30 equivalents. In some embodiments, the range is 15 equivalents.

In some embodiments, the thiol reductant is selected from the group consisting of: Tris[2-carboxyehtyl]phosphine hydrochloride (TCEP), dithiothreitol (DTT), dithioerythritol (DTE), sodium borohydride ($NaBH_4$), sodium cyanoborohydride (NaCNBH3), β-mercaptoethanol (BME), cysteine hydrochloride and cysteine. In some embodiments, the thiol reductant is TCEP.

In some embodiments, the thiol reductant concentration is between 1 and 100 fold molar excess relative to the therapeutic protein concentration. In some embodiments, the thiol reductant concentration is between 20 to 50 fold molar excess relative to the therapeutic protein concentration. In some embodiments, the thiol reductant is removed following incubation with the therapeutic protein prior to oxidation of the therapeutic protein.

In some embodiments, the method for conjugating a therapeutic protein to a half-life extending moiety has a further step of purifying the therapeutic protein conjugate after conjugation. In some embodiments, the therapeutic protein conjugate is purified using a technique selected from the group consisting of ion exchange chromatography, hydrophobic interaction chromatography, size exclusion chromatography, and affinity chromatography or combinations thereof.

In some embodiments, the therapeutic protein conjugate retains at least 20% biological activity relative to unconjugated therapeutic protein. In some embodiments, the therapeutic protein conjugate retains at least 50% biological activity relative to unconjugated therapeutic protein. In some embodiments, the therapeutic protein conjugate retains at least 90% biological activity relative to native therapeutic protein.

In some embodiments, the therapeutic protein conjugate has an increased half-life relative to unconjugated therapeutic protein. In some embodiments, the therapeutic protein conjugate has at least a 1.5 fold increase in half-life relative to unconjugated therapeutic protein. In some embodiments, the therapeutic protein conjugate has at least a 1.5, 2, 2.5, 3, 3.5, 4, 4.5 or 5 fold increase in half-life relative to unconjugated therapeutic protein.

In some embodiments, the zwitterionic polymer of the method of conjugating a therapeutic protein to a half-life extending moiety is a radically polymerizable monomer having a zwitterionc group and the method has a further step of polymerizing the free radically polymerizable zwitterionic monomer in a polymerization medium to provide a polymer, the medium comprising: the radically polymerizable zwitterionic monomer; a transition metal catalyst $M_t^{(q-1)+}$ wherein $M_t$ is a transition metal, q is a higher oxidation state of the metal and q−1 is a lower oxidation state of the metal, wherein the metal catalyst is supplied as a salt of the form $Mt^{(q-1)+}X'_{(q-1)}$ wherein X' is a counterion or group or the transition metal catalyst is supplied in situ by providing the inactive metal salt at its higher oxidation state $M_t^{q+}X'_q$ together with a reducing agent that is capable of reducing the transition metal from the oxidized inactive state to the reduced active state; a ligand; and an initiator.

To function as an ATRP transition metal catalyst, the transition metal should have at least two readily accessible oxidation states separated by one electron, a higher oxidation state and a lower oxidation state. In ATRP, a reversible redox reaction results in the transition metal catalyst cycling between the higher oxidation state and the lower oxidation state while the polymer chains cycle between having propagating chain ends and dormant chain ends. See, e.g., U.S. Pat. No. 7,893,173.

In some embodiments, the radically polymerizable zwitterionic monomer is selected from the group consisting of Formula (18)

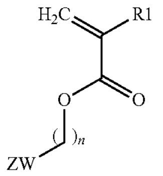

Formula (19)

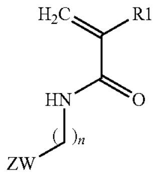

Formula (20)

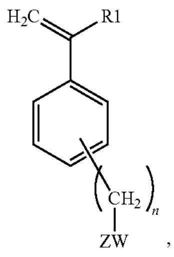

, and

-continued

Formula (21)

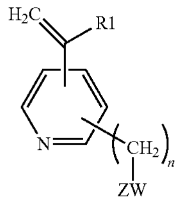

wherein R1 is H or C1-6 alkyl, ZW is a zwitterion and n is an integer from 1-6.

In some embodiments, the radically polymerizable monomer is

Formula (12)

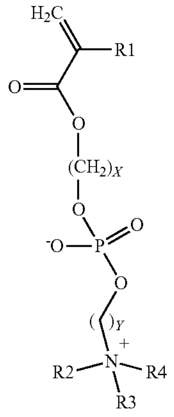

wherein R1 is H or C1-6 alkyl, R2, R3, R4 are the same or different and are H or C1-4alkyl and X and Y are the same or different and are integers from 1-6. In some embodiments, R1, R2, R3 and R4 are each methyl and X and Y are each 2 in Formula (12).

In some embodiments, the radically polymerizable monomer is

Formula (13)

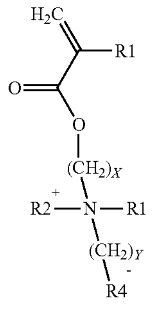

wherein R1 is H or C1-6alkyl, R2 and R3 are the same or different and are H or C1-4alkyl, R4 is PO4-, SO3- or CO2- and X and Y are the same or different and are integers from 1-6. In some embodiments, R1, R2 and R3 are methyl, R4 is PO4- and X and Y are each 2 in Formula (13).

In some embodiments, the monomer is

Formula (14)

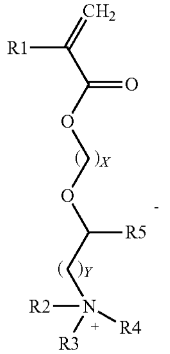

wherein R1 is H or C1-6alkyl, R2, R3 and R4 are the same or different and are H or C1-4alkyl, R5 is PO4-, SO3- or CO2- and X and Y are the same or different and are integers from 1-6. In some embodiments, R1, R2, R3 and R4 are methyl, R5 is PO4- and X and Y are 2 in Formula (14).

In some embodiments, the transition metal Mt is selected from the group consisting of Cu, Fe, Ru, Cr, Mo, W, Mn, Rh, Re, Co, V, Zn, Au, and Ag. In some embodiments, the metal catalyst is supplied as a salt of the form $Mt^{(q-1)+}X'_{(q-1)}$. $M_t^{(q-1)+}$ is selected from the group consisting of $Cu^{1+}$, $Fe^{2+}$, $Ru^{2+}$, $Cr^{2+}$, $Mo^{2+}$, $W^{2+}$, $Mn^{3+}$, $Rh^{3+}$, $Re^{2+}$, $Co^{+}$, $V^{2+}$, $Zn^{+}$, $Au^{+}$, and $Ag^{+}$ and X' is selected from the group consisting of halogen, $C_{1-6}$ alkoxy, $(SO_4)_{1/2}$, $(PO_4)_{1/3}$, $(R7PO_4)_{1/2}$, $(R7_2PO_4)$, triflate, hexaluorophosphate, methanesulfonate, arylsulfonate, CN and $R7CO_2$, where R7 is H or a straight or branched $C_{1-6}$ alkyl group which may be substituted from 1 to 5 times with a halogen. In some embodiments, $M_t^{(q-1)+}$ is $Cu^{1+}$ and X' is Br.

In some embodiments, $M_t^{(q-1)+}$ is supplied in situ. In some embodiments, $M_t^{q+}X_q$ is $CuBr_2$. In some embodiments, the reducing agent is an inorganic compound. In some embodiments, the reducing agent is selected from the group consisting of a sulfur compound of a low oxidation level, sodium hydrogen sulfite, an inorganic salt comprising a metal ion, a metal, hydrazine hydrate and derivatives of such compounds. In some embodiments, the reducing agent is a metal. In some embodiments, the reducing agent is $Cu^0$.

In some embodiments, the reducing agent is an organic compound. In some embodiments, the organic compound is selected from the group consisting of alkylthiols, mercaptoethanol, or carbonyl compounds that can be easily enolized, ascorbic acid, acetyl acetonate, camphosulfonic acid, hydroxy acetone, reducing sugars, monosaccharides, glucose, aldehydes, and derivatives of such organic compounds.

In some embodiments, the ligand is selected from the group consisting of 2,2'-bipyridine, 4,4'-Di-5-nonyl-2,2'-bipyridine, 4,4-dinonyl-2,2'-dipyridyl, 4,4',4"-tris(5-nonyl)-2,2':6',2"-terpyridine, N,N,N',N',N"-Pentamethyldiethylenetriamine, 1,1,4,7,10,10-Hexamethyltriethylenetetramine, Tris(2-dimethylaminoethyl)amine, N,N-bis(2-pyridylmethyl)octadecylamine, N,N,N',N'-tetra[(2-pyridal)methyl] ethylenediamine, tris[(2-pyridyl)methyl]amine, tris(2-aminoethyl)amine, tris(2-bis(3-butoxy-3-oxopropyl) aminoethyl)amine, tris(2-bis(3-(2-ethylhexoxy)-3-oxopropyl)aminoethyl)amine and Tris(2-bis(3-dodecoxy-3-oxopropyl)aminoethyl)amine. In some embodiments, the ligand is 2,2'-bipyridine.

In some embodiments the initiator has the structure:

Formula (22)

$$R1—R2—(R3)_s$$

wherein R1 is a nucleophilic reactive group, R2 comprises a linker, and R3 comprises a polymer synthesis initiator moiety having the structure Formula (23)

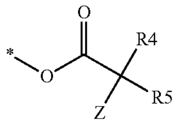

wherein R4 and R5 and are the same or different and are selected from the group consisting of alkyl, substituted alkyl, alkylene, alkoxy, carboxyalkyl, haloalkyl, cycloalkyl, cyclic alkyl ether, alkenyl, alkenylene, alkynyl, alkynylene, cycloalkylene, heterocycloalkyl, heterocycloalkylene, aryl, arylene, arylene-oxy, heteroaryl, amino, amido or any combination thereof; Z is a halogen or CN; and s is an integer between 1 and 20.

In some embodiments, Z in Formula (23) is Br and R4 and R5 are each methyl. In some embodiments, R1 in Formula (22) is selected from the group consisting of $NH_2$—, OH—, and SH—.

In some embodiments R2 in Formula (22) is alkyl, substituted alkyl, alkylene, alkoxy, carboxyalkyl, haloalkyl, cycloalkyl, cyclic alkyl ether, alkenyl, alkenylene, alkynyl, alkynylene, cycloalkylene, heterocycloalkyl, heterocycloalkylene, aryl, arylene, arylene-oxy, heteroaryl, amino, amido or any combination thereof. In some embodiments, R2 in Formula (22) is Formula (24)

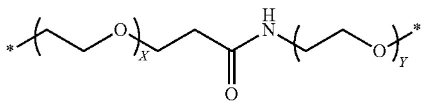

wherein X and Y are the same or different and are integers from 1-20. In some embodiments, X and Y are each 4.

In some embodiments, R3 in Formula (22) is

Formula (25)

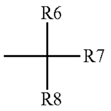

wherein R6, R7 and R8 are the same or different and are selected from the group consisting of Formula (26)

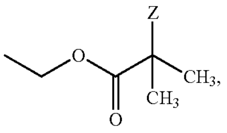

Formula (27)

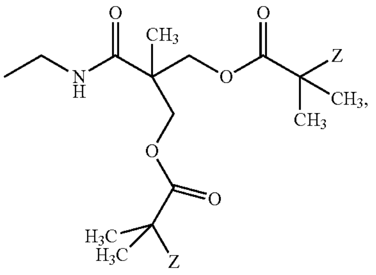

and

Formula (28)

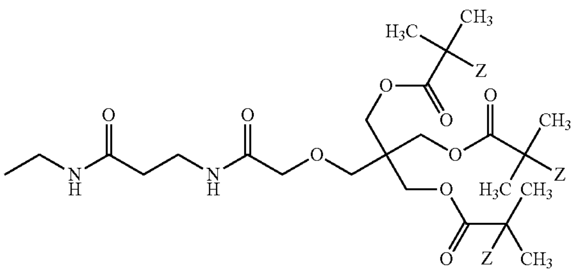

wherein Z is NCS, F, Cl, Br or I. In some embodiments, Z in Formula (26), Formula (27) and/or Formula (28) is Br and R6, R7 and R8 in Formula (25) are each Formula (29)

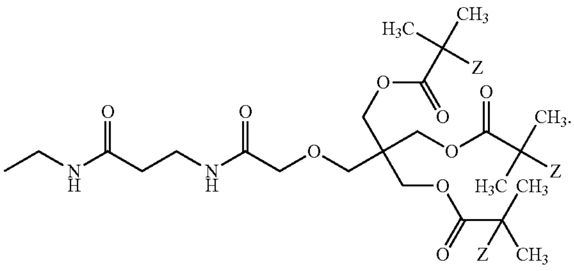

In some embodiments, the initiator has the structure:

of a CFD antagonist antibody. See, e.g., PCT Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. In some embodiments, no more than one to five conservative amino acid substitutions are made within the framework region or constant region. In other embodiments, no more than one to three conservative amino acid substitutions are made within the framework region or constant region. According to the invention, a single antibody may have mutations in any one or more of the CDRs or framework regions of the variable domain or in the constant region.

Modifications also include glycosylated and nonglycosylated polypeptides, as well as polypeptides with other post-translational modifications, such as, for example, glycosylation with different sugars, acetylation, and Formula (30)

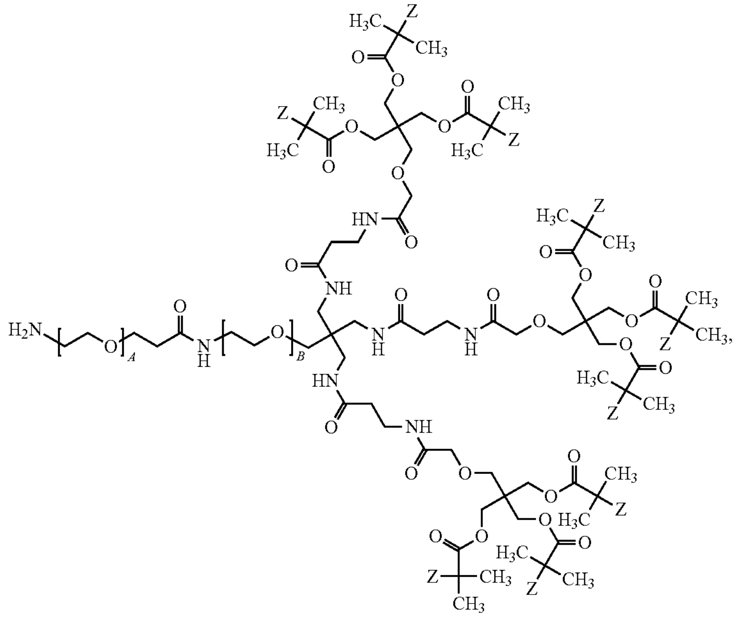

wherein A and B are the same or different and are integers from 2 to 12 and Z is any halide, for example Br. In some embodiments, A and B are each 4 in Formula (30).

In some embodiments, the method further has the step of reacting the polymer with a maleimide reagent to provide a polymer having a terminal maleimide. In some embodiments, the maleimide compound is Formula (31)

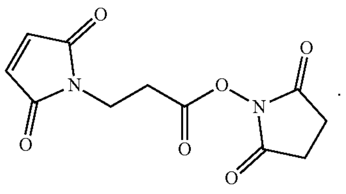

A modification or mutation may also be made in a framework region or constant region to increase the half-life phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Jefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, antibodies produced by CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., 1999, Nature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Polynucleotides, Vectors, and Host Cells

The invention also provides polynucleotides encoding any of the antibodies, including antibody fragments and modified antibodies described herein, such as, e.g., antibodies having impaired effector function. In another aspect, the invention provides a method of making any of the polynucleotides described herein. Polynucleotides can be made and expressed by procedures known in the art. Accordingly, the invention provides polynucleotides or compositions, including pharmaceutical compositions, comprising polynucleotides, encoding any of the CFD antagonists antibodies provided herein.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a fragment thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a fragment thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the MegAlign® program in the Lasergene® suite of bioinformatics software (DNASTAR®, Inc., Madison, WI), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J., 1990, Unified Approach to Alignment and Phylogenes pp. 626-645 Methods in Enzymology vol. 183, Academic Press, Inc., San Diego, CA; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, CA; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors are further provided. Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to CFD is effected by an immunoassay or FACS. A cell overexpressing the antibody or protein of interest can be identified.

An expression vector can be used to direct expression of a CFD antagonist antibody. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventricle, or pericardium.

Targeted delivery of therapeutic compositions containing an expression vector, or subgenomic polynucleotides can also be used. Receptor-mediated DNA delivery techniques are described in, for example, Findeis et al., Trends Biotechnol., 1993, 11:202; Chiou et al., Gene Therapeutics: Methods And Applications Of Direct Gene Transfer, J. A. Wolff, ed., 1994; Wu et al., J. Biol. Chem., 1988, 263:621; Wu et al., J. Biol. Chem., 1994, 269:542; Zenke et al., Proc. Natl. Acad. Sci. USA, 1990, 87:3655; Wu et al., J. Biol. Chem., 1991, 266:338. Therapeutic compositions containing a polynucleotide are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy, 1994, 1:51; Kimura, Human Gene Therapy, 1994, 5:845; Connelly, Human Gene Therapy, 1995, 1:185; and Kaplitt, Nature Genetics, 1994, 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther., 1992, 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther., 1992, 3:147); ligand-linked DNA (see, e.g., Wu, J. Biol. Chem., 1989, 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell Biol., 1994, 14:2411, and in Woffendin, Proc. Natl. Acad. Sci., 1994, 91:1581.

Compositions

The invention also provides pharmaceutical compositions comprising an effective amount of a CFD antagonist antibody conjugate described herein. Examples of such compositions, as well as how to formulate, are also described herein. In some embodiments, the composition comprises one or more CFD antagonist antibodies and/or antibody conjugates. In other embodiments, the CFD antagonist antibody recognizes human CFD. In other embodiments, the CFD antagonist antibody is a human antibody. In other embodiments, the CFD antagonist antibody is a humanized antibody. In some embodiments, the CFD antagonist antibody comprises a constant region that does not trigger an unwanted or undesirable immune response, such as antibody-mediated lysis or ADCC. In other embodiments, the CFD antagonist comprises one or more CDR(s) of the antibody (such as one, two, three, four, five, or, in some embodiments, all six CDRs).

It is understood that the compositions can comprise more than one CFD antagonist antibody (e.g., a mixture of CFD antibodies that recognize different epitopes of CFD). Other exemplary compositions comprise more than one CFD antagonist antibody that recognize the same epitope(s), or different species of CFD antagonist antibodies that bind to different epitopes of CFD. In some embodiments, the compositions comprise a mixture of CFD antagonist antibodies that recognize different variants of CFD.

The composition used in the present invention can further comprise pharmaceutically acceptable carriers, excipients, or stabilizers (Remington: The Science and practice of Pharmacy 20th Ed., 2000, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as Polysorbate, PLURONICS™ or polyethylene glycol (PEG). Pharmaceutically acceptable excipients are further described herein.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerin and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets. Pharmaceutical compositions can be substantially isotonic, implying an osmolality of about 250-350 mOsm/kg water.

The pharmaceutical compositions may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents or antioxidants. They may also contain therapeutically active agents in addition to the substance of the present invention. The pharmaceutical compositions of the invention may be employed in combination with one or more pharmaceutically acceptable excipients. Such excipients may include, but are not limited to, saline, buffered saline (such as phosphate buffered saline), dextrose, liposomes, water, glycerol, ethanol and combinations thereof.

The CFD antagonist antibodies, CFD antagonist antibody conjugates, and pharmaceutical compositions of the invention can be employed alone or in conjunction with other compounds, such as therapeutic compounds or molecules, e.g. anti-inflammatory drugs, analgesics or antibiotics. Such administration with other compounds may be simultaneous, separate or sequential. The components may be prepared in the form of a kit which may comprise instructions as appropriate.

Methods for Preventing or Treating Ophthalmic Disorders

In some embodiments, the antibodies and the antibody conjugates are useful in various applications including, but are not limited to, therapeutic treatment methods.

In some embodiments, the CFD antagonist antibodies can be used to treat (and/or effect prophylaxis) complement mediated disorders via appropriate administration of an effective regime of the antibody. In general, complement mediated disorders are those associated with or characterized by excessive, unregulated or under regulated complement activation. Complement mediated disorders include: complement activation during cardiopulmonary bypass operations; complement activation due to ischemia-reperfusion following acute myocardial infarction, aneurysm, stroke, hemorrhagic shock, crush injury, multiple organ failure, hypobolemic shock and intestinal ischemia. These disorders can also include disease in which there is an inflammatory event or condition such as severe burns, endotoxemia, septic shock, adult respiratory distress syndrome, hemodialysis; anaphylactic shock, severe asthma, angioedema, Crohn's disease, sickle cell anemia, poststreptococcal glomerulonephritis and pancreatitis. The disorder may be the result of an adverse drug reaction, drug allergy, IL-2 induced vascular leakage syndrome or radiographic contrast media allergy. It also includes autoimmune disease such as systemic lupus erythematosus, myasthenia gravis, rheumatoid arthritis, Alzheimer's disease and multiple sclerosis. Complement activation is also associated with transplant rejection. There is a strong correlation shown between complement activation and ocular diseases such as age-related macular degeneration, including dry AMD and wet AMD, diabetic retinopathy and other ischemia-related retinopathies, choroidal neovascularization (CNV), uveitis, diabetic macular edema, pathological myopia, von Hippel-Lindau disease, histoplasmosis of the eye, Central Retinal Vein Occlusion (CRVO), corneal neovascularization, and retinal neovascularization. In particularly preferred aspects of the present invention, a method is presented for treating or effecting prophylaxis of dry AMD by administering an effective regime of an anti-CFD antibody presented in accordance with the present invention.

In some embodiments, a method for treating ocular disease, such as for example AMD is provided. In some embodiments, the method of treating AMD in a subject comprises administering to the subject in need thereof an effective amount of a composition (e.g., pharmaceutical composition) comprising any of the anti-CFD antibodies as described herein. As used herein, AMD includes dry AMD and wet AMD. In some embodiments, provided is a method of treating AMD in a subject, comprising administering to the subject in need thereof an effective amount of a composition comprising CFD antagonist antibodies or the CFD antagonist antibody conjugates as described herein.

In some embodiments, the methods described herein further comprise a step of treating a subject with one or more additional form(s) of therapy. In some embodiments, the additional form of therapy is an additional AMD therapy including, but not limited to, VISUDYNE®, laser photocoagulation or intravitreal injection of, e.g., LUCENTIS®, MACUGEN®, EYLEA®, OZURDEX®, ILUVIEN®, TRIESENCE®, or TRIVARIS®.

With respect to all methods described herein, reference to CFD antagonist antibodies also includes compositions comprising one or more additional agents. These compositions may further comprise suitable excipients, such as pharmaceutically acceptable excipients including buffers, which are well known in the art. The present invention can be used alone or in combination with other methods of treatment.

In some embodiments, a method for the treatment or prophylaxis of a disease in a patient in need thereof is provided. In some embodiments, the method comprises administering to the patient any of the isolated antagonist antibodies disclosed herein. In some embodiments, the method comprises administering to the patient any of the conjugates disclosed herein. In some embodiments, the method comprises administering to the patient any of the compositions disclosed herein. In some embodiments, the method comprises identifying a patient having hyperactive CFD activity and administering to the patient any of the isolated antagonist antibodies disclosed herein. In some embodiments, the method comprises identifying a patient having hyperactive CFD activity and administering to the patient any of the conjugates disclosed herein. In some embodiments, the method comprises identifying a patient having hyperactive CFD activity and administering to the patient any of the compositions disclosed herein.

In some embodiments, the patient has a mutation in a complement pathway. In some embodiments, the disease is an ocular disorder. In some embodiments, the ocular disorder is dry age related macular degeneration (dry AMD). In some embodiments, the disorder is selected from the group consisting of Wet AMD, Dry AMD, geographic atrophy. In some embodiments, the disease is maternally inherited diabetes and deafness (MIDD).

In some embodiments, the isolated antibody, conjugate, composition or a combination thereof is administered no more frequently than once a month. In some embodiments, the isolated antibody, conjugate, composition or a combination thereof is administered no more frequently than once every two months. In some embodiments, the isolated antibody, conjugate, composition or a combination thereof is administered no more frequently than once every three months. In some embodiments, the isolated antibody, conjugate, composition or a combination thereof is administered with a frequency between once a year and once every two months. In some embodiments, the treatment can be a single application of the antibody. In some embodiments, the treatment can be as many applications of the antibody as needed or desired for an outcome.

In some embodiments, the subject has one or more risk factors selected from the group of cigarette smoking, exposure to hydroquinone (HQ), hypertension, atherosclerosis, high cholesterol, obesity, and fat intake.

In some embodiments, the antibody binds an epitope on human CFD that is the same as or overlaps with the epitope recognized by an antibody comprising the amino acid sequences shown in SEQ ID NO: 520 and SEQ ID NO: 525. In some embodiments, the antibody is one that prevents or reduces an ability of an antibody to bind to CFD, as shown through a competition assay with any one of the antibodies in Tables: 1.1, 01A, 0.1B, 0.1D, and/or 11.3. In some embodiments, the antibody binds to CFD and does not increase an enzymatic activity of CFD when bound thereto. In some embodiments, the antibody does not maintain an enzymatic activity of CFD when bound thereto. For example, the enzymatic activity of CFD decreases for all CFD substrates, including smaller substrates. In some embodiments, the antibody binds to the binding area and/or proteolytic site of CFD and decreases CFD's activity to proteolytically process a small molecule substrate, such as N-carbobenzyloxy-Lys-ThioBenzyl ester.

The CFD antagonist antibody can be administered to a subject via any suitable route. It should be apparent to a person skilled in the art that the examples described herein are not intended to be limiting but to be illustrative of the techniques available. Accordingly, in some embodiments, the CFD antagonist antibody is administered to a subject in accord with known methods, such as intravenous administration, e.g., as a bolus or by continuous infusion over a period of time, by intramuscular, intraperitoneal, intracerebrospinal, transdermal, subcutaneous, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, CFD antagonist antibody can be aerosolized using a fluorocarbon formulation and a metered dose inhaler, or inhaled as a lyophilized and milled powder.

In some embodiments, the CFD antagonist antibodies, CFD antagonist antibody conjugates, and pharmaceutical compositions disclosed herein are used for prophylaxis or treatment of an ocular disease or condition. So used, the conjugates are typically formulated for and administered by ocular, intraocular, and/or intravitreal injection, and/or juxtascleral injection, and/or subtenon injection, and/or suprachoroidal injection and/or topical administration in the form of eye drops and/or ointment. Such CFD antagonist antibodies, CFD antagonist antibody conjugates, and compositions can be delivered by a variety of methods, e.g. intravitreally as a device and/or a depot that allows for slow release of the compound into the vitreous, including those described in references such as Intraocular Drug Delivery, Jaffe, Jaffe, Ashton, and Pearson, editors, Taylor & Francis (March 2006). In one example, a device may be in the form of a minimum and/or a matrix and/or a passive diffusion system and/or encapsulated cells that release the compound for a prolonged period of time (Intraocular Drug Delivery, Jaffe, Jaffe, Ashton, and Pearson, editors, Taylor & Francis (March 2006). In therapy or as a prophylactic, the active agent may be administered to an individual as an injectable composition, for example as a sterile aqueous dispersion, preferably isotonic or substantially isotonic.

Formulations for ocular, intraocular or intravitreal administration can be prepared by methods and using ingredients known in the art. Proper penetration into the eye is desirable for efficient treatment. Unlike diseases of the front of the eye, where drugs can be delivered topically, retinal diseases merit a more site-specific approach. Eye drops and ointments rarely penetrate the back of the eye, and the blood-ocular barrier hinders penetration of systemically administered drugs into ocular tissue. In some embodiments, the method of choice for drug delivery to treat retinal disease, such as AMD and CNV, is direct intravitreal injection. In some embodiments, intravitreal injections are repeated at intervals which depend on the patient's condition, and the properties and half-life of the drug delivered.

For administration to mammals, and particularly humans, it is expected that the dosage of the active agent is from 0.01 mg/kg body weight, to typically around 1 mg/kg, for systemic administrations. For ocular diseases that require local administration (for example, intravitreal, supracoroidal, peri-ocular etc), dosage is typically 0.1 mg/eye/dose to 10 mg/eye/dose or more. In some embodiments, the dosage is 100 ul/dose/eye. In some embodiments, a needle can be used to administer the dosage. The needle can be, for example, a 30 gauge ½ inch needle or a ½ inch needle that is 27 G or 29 G. The physician can determine the actual dosage most suitable for an individual which depends on factors including the age, weight, sex and response of the individual, the disease or disorder being treated and the age and condition of the individual being treated. The above dosages are exemplary of the average case. There can, of course, be instances where higher or lower dosages are merited.

This dosage may be repeated as often as appropriate (e.g., weekly, fortnightly, monthly, quarterly). If side effects develop the amount and/or frequency of the dosage can be reduced, in accordance with normal clinical practice. In one embodiment, the pharmaceutical composition may be administered once every one to thirty days.

The CFD antagonist antibodies of the present invention may be employed in accordance with the instant invention by expression of such polypeptides in vivo in a patient, i.e., gene therapy. There are two major approaches to getting the nucleic acid (optionally contained in a vector) into the patient's cells: in vivo and ex vivo. For in vivo delivery the nucleic acid is injected directly into the patient, usually at the sites where the therapeutic protein is required, i.e., where biological activity of the therapeutic protein is needed. For ex vivo treatment, the patient's cells are removed, the nucleic acid is introduced into these isolated cells, and the modified cells are administered to the patient either directly or, for example, encapsulated within porous membranes that are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or transferred in vivo in the cells of the intended host. Techniques suitable for the transfer of nucleic acid into mammalian cells in vitro include the use of liposomes, electroporation, microinjection, transduction, cell fusion, DEAE-dextran, the calcium phosphate precipitation method, etc. Transduction involves the association of a replication-defective, recombinant viral (preferably retroviral) particle with a cellular receptor, followed by introduction of the nucleic acids contained by the particle into the cell. A commonly used vector for ex vivo delivery of the gene is a retrovirus.

The currently preferred in vivo nucleic acid transfer techniques include transfection with viral or non-viral vectors (such as adenovirus, lentivirus, Herpes simplex I virus, or adeno-associated virus (AAV)) and lipid-based systems (useful lipids for lipid-mediated transfer of the gene are, for example, DOTMA, DOPE, and DC-Chol; see, e.g., Tonkinison et al., Cancer Investigation, 14(1): 54-65 (1996)). The most preferred vectors for use in gene therapy are viruses, most preferably adenoviruses, AAV, lentiviruses, or retroviruses. A viral vector such as a retroviral vector includes at least one transcriptional promoter/enhancer or locus-defining element(s), or other elements that control gene expression by other means such as alternate splicing, nuclear RNA export, or post-translational modification of messenger. In addition, a viral vector such as a retroviral vector includes a nucleic acid molecule that, when transcribed in the presence of a gene encoding the therapeutic protein, is operably linked thereto and acts as a translation initiation sequence. Such vector constructs also include a packaging signal, long terminal repeats (LTRs) or portions thereof, and positive and negative strand primer binding sites appropriate to the virus used (if these are not already present in the viral vector). In addition, such vector typically includes a signal sequence for secretion of the PRO polypeptide from a host cell in which it is placed. Preferably the signal sequence for this purpose is a mammalian signal sequence, most preferably the native signal sequence for the therapeutic protein. Optionally, the vector construct may also include a signal that directs polyadenylation, as well as one or more restriction sites and a translation termination sequence. By way of example, such vectors will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

In some situations, it is desirable to provide the nucleic acid source with an agent that targets the target cells, such as an antibody specific for a cell-surface membrane protein or the target cell, a ligand for a receptor on the target cell, etc. Where liposomes are employed, proteins that bind to a cell-surface membrane protein associated with endocytosis may be used for targeting and/or to facilitate uptake, e.g., capsid proteins or fragments thereof tropic for a particular cell type, antibodies for proteins that undergo internalization in cycling, and proteins that target intracellular localization and enhance intracellular half-life. The technique of receptor-mediated endocytosis is described, for example, by Wu et al., J. Biol. Chem., 262: 4429-4432 (1987); and Wagner et al., Proc. Natl. Acad. Sci. USA, 87: 3410-3414(1990). For a review of the currently known gene marking and gene therapy protocols, see, Anderson et al., Science, 256: 808-813 (1992). See also WO 93/25673 and the references cited therein.

Suitable gene therapy and methods for making retroviral particles and structural proteins can be found in, e.g., U.S. Pat. No. 5,681,746.

In accordance some aspects, a method for treatment or prophylaxis of an ocular disease in a mammal is presented in which a nucleic acid molecule that encodes an CFD antagonist antibody is administered.

In some embodiments, the composition can be used as a complement pathway inhibitor, and can comprise administering the composition to an animal, a mammal, or a human, for treating a ocular disease, disorder, or condition involving complement pathway activation. The animal or subject may be an animal in need of a particular treatment, such as an animal having been diagnosed with a particular disorder, e.g., one relating to complement. Antibodies directed against Factor D are useful for inhibiting the alternative complement pathway and thus inhibiting complement pathway related disorders or conditions. In some embodiments, the composition can be used for the treatment of AMD, diabetic retinopathy, and/or choroidal neovascularization.

Formulations

Therapeutic formulations of the CFD antagonist antibodies and CFD antagonist antibody conjugates used in accordance with the present invention are prepared for storage by mixing an antibody having the desired degree of purity with optional pharmaceutically acceptable carriers, excipients or stabilizers (Remington, The Science and Practice of Pharmacy 20th Ed. Mack Publishing, 2000), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the CFD antagonist antibody and/or CFD antagonist antibody conjugate are prepared by methods known in the art, such as described in Epstein, et al., Proc. Natl. Acad. Sci. USA 82:3688 (1985); Hwang, et al., Proc. Natl Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 20th Ed. Mack Publishing (2000).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes. Therapeutic CFD antagonist antibody and/or antibody conjugate compositions are generally placed into a container having a sterile access port, for example, an intravenous solution bag or vial having a stopper pierceable by a hypodermic injection needle. In some embodiments, the antibody and/or antibody conjugate compositions are placed into a syringe to provide a prefilled syringe.

In some embodiments, the composition is a pyrogen-free composition which is substantially free of endotoxins and/or related pyrogenic substances. Endotoxins include toxins that are confined inside a microorganism and are released only when the microorganisms are broken down or die. Pyrogenic substances also include fever-inducing, thermostable substances from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. For systemic injection such as IV or IP, the Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight, as can be the case with proteins of interest (e.g., antibodies), even trace amounts of harmful and dangerous endotoxin must be removed. In some embodiments, the endotoxin and pyrogen levels in the composition are less than 10 EU/mg, or less than 5 EU/mg, or less than 1 EU/mg, or less than 0.1 EU/mg, or less than 0.01 EU/mg, or less than 0.001 EU/mg. In some embodiments, the compositions or methods provided herein allow for 0.1 EU/eye/injection. In some embodiments, the compositions or methods provided herein allow for 0.05 EU/eye/injection. In some embodiments, the compositions or methods provided herein allow for 0.02 EU/eye/injection. In some embodiments, the compositions or methods provided herein allow for 0.01 EU/eye/injection.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from about 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as Polysorbate or polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.01%, and 5% surface-active agent, and can be between 0.01 and 0.02% or 0.1 and 2.5% (polysorbate 20 or 80). It will be appreciated that other ingredients may be added, for example mannitol or other pharmaceutically acceptable vehicles, if necessary.

Suitable emulsions may be prepared using commercially available fat emulsions, such as INTRALIPID™, LIPOSYN™, INFONUTROL™, LIPOFUNDIN™ and LIPIPHYSAN™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 m, particularly 0.1 and 0.5 m, and have a pH in the range of 5.5 to 8.0.

The emulsion compositions can be those prepared by mixing an CFD antagonist antibody with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Kits

The invention also provides kits comprising any or all of the antibodies described herein. Kits of the invention include one or more containers comprising an CFD antagonist antibody or conjugate described herein and instructions for use in accordance with any of the methods of the invention described herein. Generally, these instructions comprise a description of administration of the CFD antagonist antibody or conjugate for the above described therapeutic treatments. In some embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In some embodiments, the antibody is a human antibody. In some embodiments, the antibody is a humanized antibody. In some embodiments, the antibody is a monoclonal antibody. The instructions relating to the use of an CFD antagonist antibody or conjugate generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as prefilled syringe, an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an CFD antagonist antibody or conjugate. The container may further comprise a second pharmaceutically active agent.

Kits may optionally provide additional components such as buffers and interpretive information. In some embodiments, the kits can include an additional syringe and needle used for back fill of the dosing syringe. Normally, the kit comprises a container and a label or package insert(s) on or associated with the container.

The following numbered arrangements are also provided:

1. An isolated antagonist antibody that specifically binds to complement factor D (CFD) and directly inhibits a proteolytic activity of CFD.

2. An isolated antagonist antibody that specifically binds to complement factor D (CFD), inhibits a proteolytic activity of CFD, and inhibits CFD binding to C3bB complex.

3. An isolated antagonist antibody that specifically binds to complement factor D (CFD), wherein the antibody does not bind a human CFD mutant comprising mutations R157A and R207A.

4. An isolated antagonist antibody that binds an epitope on human CFD, wherein the epitope excludes positions R157 and R207.

5. An isolated antagonistic antibody comprising:
- a heavy chain amino acid variable region that comprises SEQ ID NO: 183; and
- a light chain amino acid variable region that comprises SEQ ID NO: 184.

6. An isolated antagonist antibody comprising:
- a heavy chain variable region (VH) comprising a VH complementarity determining region one (CDR1), VH CDR2, and VH CDR3 of the VH having an amino acid sequence selected group the group consisting of SEQ ID NO: 541, SEQ ID NO: 542; and SEQ ID NO: 543; and
- a light chain variable region (VL) comprising a VL CDR1, VL CDR2, and VL CDR3 of the VL having an amino acid sequence selected from the group consisting of SEQ ID NO: 544; SEQ ID NO: 545; and SEQ ID NO: 546.

7. The isolated antagonist antibody of arrangement 4, wherein the antibody comprises the following mutations based on EU numbering: L234A, L235A, and G237A.

8. An isolated antagonist antibody that specifically binds to CFD comprising:
- a heavy chain variable region (VH); and
- a light chain variable region (VL), wherein the antibody comprises the following mutations: L234A, L235A, and G237A.

9. The isolated antagonist antibody of arrangement 7, wherein the antibody has minimized binding to FC gamma receptors or C1q.

10. An isolated antagonist antibody that binds an epitope on human CFD that is the same as or overlaps with the epitope recognized by an antibody comprising the amino acid sequences shown in SEQ ID NO: 61 and SEQ ID NO: 62.

11. An isolated antagonist antibody that binds to CFD, wherein the antibody comprises:
- a heavy chain comprising the amino acid sequence shown in SEQ ID NO: 183, with or without the C-terminal lysine; and
- a light chain comprising the amino acid sequence shown in SEQ ID NO: 184.

12. An isolated antagonist antibody that binds to CFD, wherein the antibody comprises a VH comprising the amino acid sequence shown in SEQ ID NO: 520, or a sequence that is at least 90% identical thereto, having amino acid substitutions in residues that are not within a CDR of SEQ ID NOs: 520 or 525.

13. An isolated antagonistic antibody that binds to CFD, the antibody comprising:
- a $CDR_H1$ that is the $CDR_H1$ in SEQ ID NO: 520;
- a $CDR_H2$ that is the $CDR_H2$ in SEQ ID NO: 520;
- a $CDR_H3$ that is the $CDR_H3$ in SEQ ID NO: 520;
- a $CDR_L1$ that is the $CDR_L1$ in SEQ ID NO: 525;
- a $CDR_L2$ that is the $CDR_L2$ in SEQ ID NO: 525;
- a $CDR_L3$ that is the $CDR_L3$ in SEQ ID NO: 525;
- at least one of the following mutations (EU numbering): L234A, L235A, and G237A; and
- at least one of the following mutations (EU numbering): Q347C or L443C.

14. The isolated antagonist antibody of any one of arrangements 1 to 12, wherein the antibody does not bind a human CFD mutant comprising the mutations R157A and R207A.

15. The isolated antagonist antibody of any one of arrangements 1 to 12, wherein the antibody binds a human CFD mutant comprising mutations R157A and R207A.

16. The isolated antagonist antibody of any one of arrangements 1 to 15, wherein the antibody blocks the alternative complement cascade.

17. The isolated antagonist antibody of any one of arrangements 1 to 16, wherein the antibody blocks C3bB binding to CFD.

18. The isolated antagonist antibody of any one of arrangements 1 to 17, wherein the antibody binds human CFD with an affinity of between about 0.1 pM to about 20 pM.

19. The isolated antagonist antibody of any one of arrangements 1 to 18, wherein the antibody binds human CFD with a koff at 37 degrees that is at least 5E-04.

20. The isolated antagonist antibody of any one of arrangements 1 to 19, wherein the heavy chain variable region of the antibody comprises three complementarity determining regions (CDRs) comprising the amino acid sequences shown in SEQ ID NO: 520.

21. The isolated antagonist antibody of any one of arrangements 1 to 20, wherein the light chain variable region of the antibody comprises three complementarity determining regions (CDRs) comprising the amino acid sequences shown in SEQ ID NO: 525.

22. The isolated antagonist antibody of any one of arrangements 1 to 21, wherein the heavy chain variable region (VH) of the antibody comprises three CDRs comprising the amino acid sequences shown in SEQ ID NO: 541, SEQ ID NO: 542, and SEQ ID NO: 543, and the light chain variable region (VL) of the antibody comprises three CDRs comprising the amino acid sequences shown in SEQ ID NO: 544, SEQ ID NO: 545, and SEQ ID NO: 546.

23. The isolated antagonist antibody of arrangement 22, wherein the VH comprises the amino acid sequences shown in SEQ ID NO: 520, and the light chain variable region of the antibody comprises three CDRs comprising the amino acid sequences shown in SEQ ID NO: 544, SEQ ID NO: 545 and SEQ ID NO: 546

24. The isolated antagonist antibody of arrangement 23, wherein the antibody comprises a VL comprising the amino acid sequence shown in SEQ ID NO: 525, or a variant thereof with one or several amino acid substitutions in amino acids that are not within a CDR.

25. The isolated antagonist antibody of any one of arrangements 1 to 24, wherein the antibody comprises a heavy chain comprising the amino acid sequence shown in SEQ ID NO: 183, with or without the C-terminal lysine, and a light chain comprising the amino acid sequence shown in SEQ ID NO: 184.

26. The isolated antagonist antibody of any one of arrangements 1 to 25, wherein the antibody comprises a heavy chain constant domain comprising one or more mutations to reduce an effector function.

27. The isolated antagonist antibody of any one of arrangements 1 to 26, wherein the antibody comprises a heavy chain constant domain comprising one or more mutations to reduce an effector function related to a complement cascade.

28. The isolated antagonist antibody of arrangement 27, wherein the mutation(s) is located at one or more of the following amino acid positions (EU numbering): E233, L234, L235, G236, G237, A327, A330, and P331.

29. The isolated antagonist antibody of arrangement 28, wherein the mutation(s) is selected from the group consisting of E233P, L234V, L234A, L235A, G237A, A327G, A330S, and P331S.

30. The isolated antagonist antibody of arrangement 29, wherein the heavy chain constant domain further comprises a cysteine residue introduced by recombinant DNA technology.

31. The isolated antagonist antibody of arrangement 30, wherein the cysteine residue is selected from the group consisting of Q347C and L443C (EU numbering).

32. The isolated antagonist antibody of arrangement 31, wherein the cysteine residue is L443C (EU numbering).

33. An isolated antagonist antibody that specifically binds to complement factor D (CFD), wherein the antibody is configured to provide a reduced complement reaction, wherein the antibody specifically binds to complement factor D (CFD), and wherein the antibody at least inhibits a proteolytic activity of CFD or inhibits CFD binding to C3bB complex.

34. The isolated antagonistic antibody of any one of arrangements 1 to 33, wherein the antibody comprises all three of the following mutations (EU numbering) L234A, L235A, and G237A, and wherein the antibody comprises L443C (EU numbering).

35. The isolated antagonistic antibody of any one of arrangements 1 to 34, wherein the antibody is a human IgG1, and wherein a heavy chain constant domain comprises one or more mutations that reduce an immune-mediated effector function.

36. A conjugate comprising:

(a) any of the isolated antagonistic antibodies from arrangements 1 to 35; and
(b) a polymer, wherein the polymer is covalently attached to the antibody.

37. A conjugate comprising:

(a) an isolated antagonist antibody that specifically binds to complement factor D (CFD); and
(b) a phosphorylcholine containing polymer, wherein the polymer is covalently bonded to the antibody.

38. A conjugate comprising:

(a) an isolated antagonist antibody that specifically binds to complement factor D (CFD); and
(b) a polymer comprising a zwitterionic monomer, wherein the zwitterionic monomer is selected from the group consisting of HEMA-phosphorylcholine, PEG, biocompatible fatty acids and derivatives thereof, Hydroxy Alkyl Starch (HAS), Hydroxy Ethyl Starch (HES), Poly Ethylene Glycol (PEG), Poly ($Gly_x$-$Ser_y$) (HAP), Hyaluronic acid (HA), Heparosan polymers (HEP), Fleximers, Dextran, Poly-sialic acids (PSA), Fc domains, Transferrin, 25 Albumin, Elastin like (ELP) peptides, XTEN polymers, PAS polymers, PA polymers, Albumin binding peptides, CTP peptides, and FcRn binding peptides.

39. A conjugate comprising an anti-CFD antibody and a polymer that is capable of blocking at least 80% of an interaction between CFD and C3bB.

40. A conjugate comprising (1) an anti-CFD antibody and (2) a phosphorylcholine containing polymer, wherein the polymer is covalently bonded to the antibody at a cysteine outside a variable region of the antibody wherein said cysteine has been added via recombinant DNA technology.

41. The conjugate of any one of arrangements 36 to 40, wherein the polymer comprises 2(methacryloyloxy)ethyl (2-(trimethylammonio)ethyl) phosphate (MPC) monomers.

42. The conjugate of any one of arrangements 36 to 41, wherein the polymer has a peak molecular weight between 300,000 and 1,750,000 Daltons as measured by size exclusion chromatography-multi angle light scattering (hereinafter "SEC-MALS").

43. The conjugate of any one of arrangements 36 to 42, wherein the polymer has a peak molecular weight between 500,000 and 1,000,000 Daltons as measured by SEC-MALS.

44. The conjugate of arrangement 43, wherein the polymer has a peak molecular weight between 600,000 to 800,000 Daltons as measured by SEC-MALS.

45. The conjugate of any one of arrangements 36 to 44, wherein the polymer has 2 or more arms.

46. The conjugate of any one of arrangements 36 to 45, wherein the polymer has 2, 3, 4, 5, 6, 7, 8, 9, 10, 11 or 12 arms.

47. The conjugate of arrangement 46, wherein the polymer has 9 arms.

48. The conjugate of any one of arrangements 36 to 47, wherein the antibody is the antibody of any one of arrangements 1-32.

49. The conjugate of any one of arrangements 36 to 48, wherein the antibody is an IgG.

50. The conjugate of arrangement 49, wherein the polymer is covalently bonded to a sulfhydryl group from a cysteine residue on the heavy chain the IgG.

51. The conjugate of any one of arrangements 36 to 50, wherein the antibody comprises a cysteine residue at position 347 or 443 (EU numbering).

52. The conjugate of arrangement 51, wherein the polymer is covalently bonded to a sulfhydryl group from a cysteine residue at position 347 or 443 (EU numbering).

53. The conjugate of any one of arrangements 36 to 52, wherein the antibody is further conjugated to a polymer to form a bioconjugate, and wherein the bioconjugate has a molecular weight between about 350,000 and 1,900,000 Daltons.

54. The conjugate any one of arrangements 36 to 53, wherein the PolyDispersity Index (PDI) is equal to or less than 1.5.

55. The conjugate of any one of arrangements 36 to 54, wherein the polymer has 9 arms; and
the polymer has a molecular weight of between about 600,000 to about 900,000 Da.

56. The conjugate of any one of arrangements 36 to 55, which has the following structure:
Formula (17)
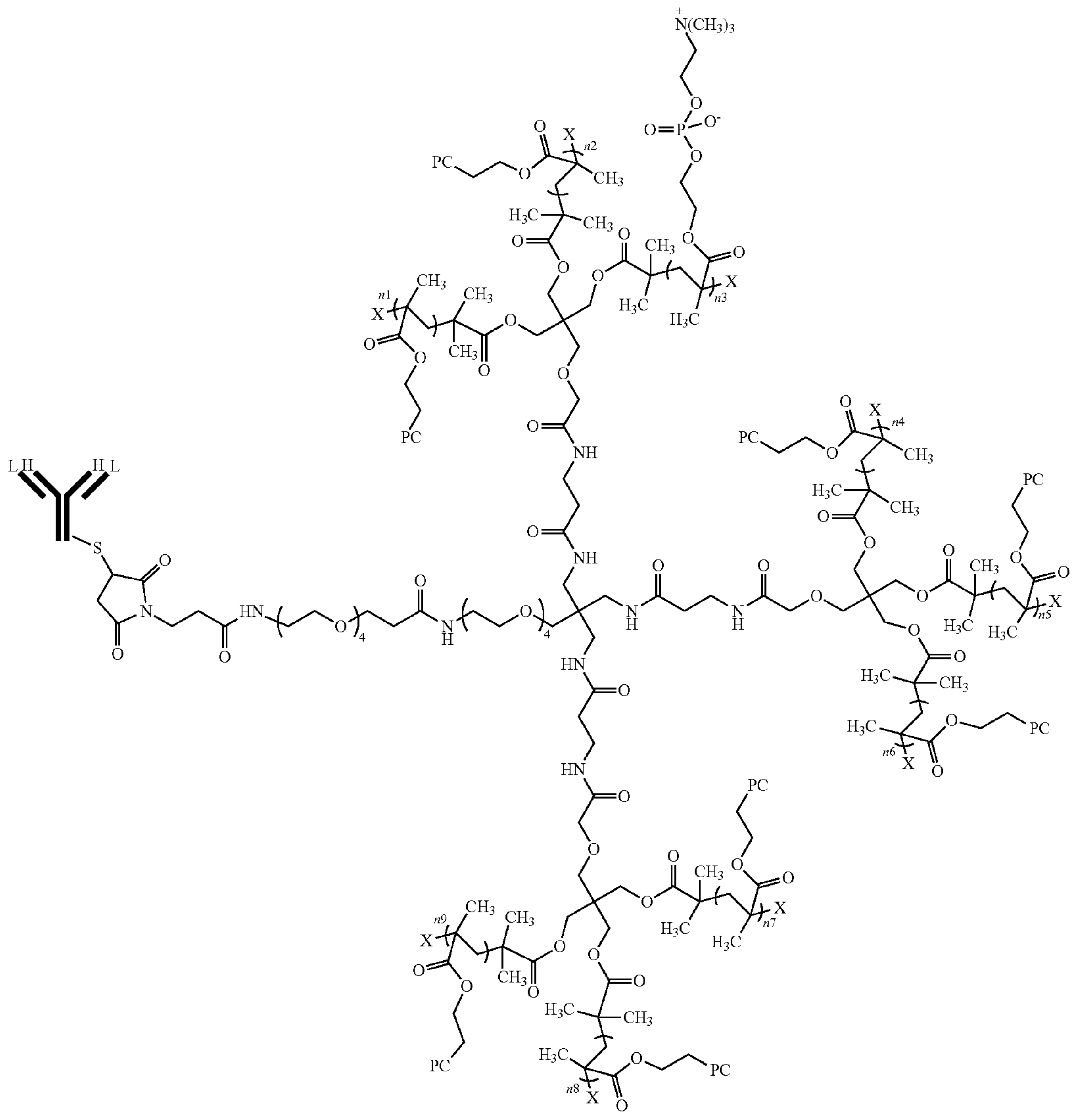
wherein:
each heavy chain of the antibody is denoted by the letter H, and each light chain of the anti-CFD antibody is denoted by the letter L;
the polymer is bonded to the antibody through the sulfhydryl of C443 (EU numbering), which bond is depicted on one of the heavy chains;
PC is
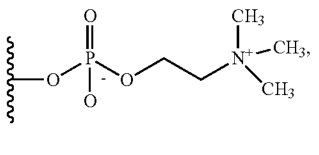 [SMILES: *OP(=O)(O)OCC[N+](C)(C)C]

where the curvy line indicates the point of attachment to the rest of the polymer, where X=a) OR where R=H, methyl, ethyl, propyl, isopropyl, b) H, or c) any halide, including Br; and n1, n2, n3, n4, n5, n6, n7, n8 and n9 are the same or different such that the sum of n1, n2, n3, n4, n5, n6, n6, n7, n8 and n9 is 2500 plus or minus 15%.

57. An isolated cell line that produces an isolated antagonistic antibody of any one of arrangements 1 to 35.

58. The isolated cell line of arrangement 57, wherein the cell line is selected from the group consisting of CHO, k1SV, XCeed, CHOK1SV, and GS-KO.

59. An isolated nucleic acid encoding an isolated antagonistic antibody of any one of arrangements 1 to 35.

60. A recombinant expression vector comprising the nucleic acid of arrangement 59.

61. A host cell comprising the expression vector of arrangement 60.

62. A method of producing a CFD antagonist antibody, the method comprising: culturing a cell line that recombinantly produces an isolated antagonistic antibody of any one of arrangements 1 to 35 under conditions wherein the antibody is produced; and recovering the antibody.

63. A method of producing a CFD antagonist antibody, the method comprising:

culturing a cell line comprising nucleic acid encoding an antibody comprising a heavy chain comprising the amino acid sequence shown in SEQ ID NO: 520 and a light chain comprising the amino acid sequence shown in SEQ ID NO: 525 under conditions wherein the antibody is produced; and recovering the antibody.

64. The method of arrangement 63, wherein the heavy and light chains of the antibody are encoded on separate vectors.

65. The method of arrangement 64, wherein the heavy and light chains of the antibody are encoded on the same vector.

66. A pharmaceutical composition comprising an isolated antagonistic antibody of any one of arrangements 1 to 35 and/or a conjugate of any one of arrangements 36-56, and a pharmaceutically acceptable carrier.

67. The pharmaceutical composition of arrangement 66, wherein the composition is a liquid and has an endotoxin level less than about 0.2 EU/ml.

68. A pharmaceutical composition comprising an isolated antagonistic antibody of any one of arrangements 1 to 35 and a pharmaceutically acceptable carrier.

69. The pharmaceutical composition of arrangement 68, wherein the composition is a liquid and has an endotoxin level less than about 2.0, 1, 0.5, 0.2 EU/ml.

70. A method for the treatment or prophylaxis of a disease in a patient in need thereof, said method comprising administering to the patient an isolated antagonist antibody of any one of arrangements 1 to 35, and/or a conjugate of arrangements 36 to 56.

71. A method for the treatment or prophylaxis of a disease in a patient in need thereof, said method comprising:

identifying a patient having hyperactive CFD activity; and administering to the patient an isolated antagonist antibody of any one of arrangements 1 to 35 and/or a conjugate of arrangements 36 to 56.

72. The method of arrangement 71, wherein the patient has a mutation in a complement pathway.

73. A method for the treatment or prophylaxis of a disease in a patient in need thereof, said method comprising administering to the patient a conjugate of any one of arrangements 36 to 56, and/or a composition of arrangements 66 to 69.

74. The method of any one of arrangements 70 to 73, wherein the disease is an ocular disorder.

75. The method of arrangement 74, wherein the ocular disorder is dry age related macular degeneration (dry AMD).

76. The method of arrangement 74, wherein the ocular disorder is selected from the group consisting of Wet AMD, Dry AMD, geographic atrophy, Maternally-inherited diabetes and deafness (MIDD).

77. The method of any one of arrangements 70 to 76, wherein the isolated antibody or the conjugate is administered no more frequently than once a month.

78. The method of any one of arrangements 70 to 76, wherein the isolated antibody or the conjugate is administered no more frequently than once every two months.

79. The method of any one of arrangements 70 to 76, wherein the isolated antibody or the conjugate is administered no more frequently than once every three months.

80. The method of any one of arrangements 70 to 76, wherein the isolated antibody or the conjugate is administered with a frequency between once a year and once every two months.

81. The method of any one of arrangements 70 to 76, wherein the subject has one or more risk factors selected from the group of cigarette smoking, exposure to hydroquinone (HQ), hypertension, atherosclerosis, high cholesterol, obesity, and fat intake.

82. An isolated antagonist antibody, wherein the antibody binds an epitope on human CFD that is the same as or overlaps with the epitope recognized by an antibody comprising the amino acid sequences shown in SEQ ID NO: 520 and SEQ ID NO: 525.

83. An isolated antagonist antibody that binds to CFD, wherein the antibody does not increase an enzymatic activity of CFD when bound thereto.

84. An isolated antagonist antibody, wherein the antibody competes for binding to human CFD with an antibody comprising the amino acid sequences shown in SEQ ID NO: 520 and SEQ ID NO: 525.

85. An isolated antagonist antibody that binds to CFD, wherein the antibody does not maintain an enzymatic activity of CFD when bound thereto.

86. An isolated antagonist antibody that specifically binds to complement factor D (CFD), wherein when bound, the antibody is within 3A of residue 209 of SEQ ID NO: 1 of CFD.

87. An isolated antagonist antibody that specifically binds to complement factor D (CFD), wherein when bound, the antibody is within 3A of residue 156 of SEQ ID NO: 1 of CFD.

88. An isolated antagonist antibody that specifically binds to complement factor D (CFD), wherein the antibody binds to one or more of residues 156 or 209 of SEQ ID NO: 1 of CFD.

89. An isolated antagonist antibody that specifically binds to complement factor D (CFD), wherein the antibody binds to both of residues 156 and 209 of SEQ ID NO: 1 of CFD.

90. An isolated antagonist antibody that specifically binds to complement factor D (CFD), wherein the antibody, when bound to CFD, is not within 6 angstroms of at least one of 117, 118, and 156 of SEQ ID NO: 1.

91. An isolated antagonist antibody that specifically binds to complement factor D (CFD), wherein the antibody binds to CFD as described in Tables: 1.1, 0.1A, 0.1B, 0.1D, and/or 11.3.

92. A crystalized CFD-antibody complex, wherein the antibody comprises any one or more of the CDRs within SEQ ID NO:s 183 and 184.

93. An isolated antagonist antibody that binds an epitope on human CFD that is the same as or overlaps with the epitope recognized by an antibody comprising the amino acid sequences shown in SEQ ID NO: 45 and SEQ ID NO: 46.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1—Initial Antibody Generation and Screening

Antibodies against human Complement Factor D (CFD) was generated and screened for binding by AbCellera Biologics. Briefly, rodents were immunized with CFD purified from human serum, and single antibody-secreting cells were enriched and isolated into nanoliter-volume chambers and used in bead-based binding assays to identify antibodies against CFD with diverse epitope binding.

414 cells expressing antibodies exhibiting diverse binding phenotypes were selected for sequencing to recover the heavy and light chain sequences. 146 unique pairs of heavy and light chains were identified.

TABLE 1.1

Heavy and Light Chain Variable Sequences of 88 mouse anti-CFD antibodies with CDRs underlined.

| ID | Heavy Chain Variable Region AA Sequence | ID | Light Chain Variable Region AA Sequence |
|---|---|---|---|
| FKCD001 | EVQLQQSGPELVKPGASVKISCKASDNSFTGYYMHWVKQSHGNILDWIGYIDPYNGVSSYNQKFKGKATLTVDKSSSTAYMEIRSLTSEDSAVYYCASYYGSSPYWYFDVWGTGTTVTVSS (SEQ ID NO: 335) | KCD001 | QIVLSQSPAILSASPGEKVTMTCRASSSVSYMHWYQQKPGSSPKPWIYATSNLASGVPARFSGSGSGTSHFLTISRLEAEDAATYFCQQWSSNPYTFGGGTKLEIK (SEQ ID NO: 336) |
| KCD002 | EVKLVESEGGLVQPGSSMKLSCTASGFTFSDYYMAWVRQVPEKGLEWVGNINYDGSSTYYLDSLKSRFIISRDSAKNILYLQMSSLKSEDTATYFCARGEDFYLYAMDYWGQGTSVTVSS (SEQ ID NO: 337) | KCD002 | DIQMTQSPASLSASVGETVTITCRASENIHSYLAWYQQKQGKSPQLIVYNTKTLAEGVPSRFSGSGSGTQFSLKINSLQPEDFGSYYCQHHYGIPPTFGGGTKLEIK (SEQ ID NO: 338) |
| KCD003 | EVQLQQSRPELVKPGASVKIFCKASGYTFTDYYMNWMRQRHGETLEWIGDINPNNGDPSYNQKFKDKATLTVDKSSSTASMELRSLTSDDSAVYYCAREGPSFAYWGQGTLVTVSA (SEQ ID NO: 339) | KCD003 | DVLMTQTPLSLPVSLGEQASISCRSSQTIVHSNGDTYLEWYLQKPGQSPNLLIYKVSNRFSGVPDRFSGSGSGTDFTLKISRVEAEDLGVYYCFQGSHVPPTFGGGTKLEIK (SEQ ID NO: 340) |
| KCD004 | EVQLQQSGAELVRPGSSVKMSCKTSGKTFTSHGINWVKQRPGQGLEWIGYIYIGNGYNEYNEKFKGKATLTSDTSSSTAYMQLSSLTFEDSAIYFCVRKAYGNYGFDDWGQGTTLTVSS (SEQ ID NO: 341) | KCD004 | DIQMTQSPTSLSASLGESVSLTCRASQEISGYLNWLQQKPDGSIKRLIYAASTLDSGVPKRFSGSRSGSDYSLTISSLESEDFADYYCLQYANYPFTFGSGTKLEVK (SEQ ID NO: 342) |
| KCD005 | EVQLQQSGPELVKPGASVKISCKASGYTFTDHYMNWVKQSHGKSLEWIGDINPNNGGTSCNQKFKGKATLTVDKSSSTAYMELRSLTSGDSAVYYCTREGASFAFWGQGTLVTVSA (SEQ ID NO: 343) | KCD005 | DVLMTQTPLSLPVSLGDQASISCRSSQSIVHSNGDTYLEWYLQKPGQSPKLLIYKVSNRFSGVPDRFSGSGSGTDFTLKISRVEAEDLGVYYCFQGSHVPVTFGAGTKLELK (SEQ ID NO: 344) |
| KCD006 | EVQLQQSGAELVKPGASVKLSCTASGFKIKDTYMHWVKERPEQGLEWIGRIDPANGNTKYDPKFQGKATITADTSSNTAYLQLSSLTSEDTAVYYCANAMDYWGQGTSVTVSS (SEQ ID NO: 345) | KCD006 | QIILTQSPAIMSASPGEKVTMTCSARSSVSNMYWYQQKPGSSPRLLIYDTSNLASGVPVRFSGSGSGTSYSLTISRMEAEDAATYYCQQWSSYPWTFGGGTKLEIK (SEQ ID NO: 346) |
| KCD007 | EVQLQQSGAELVKPGASVKLSCTASGFKIKDTYMHWVKERPEQGLEWIGRIDPANGNTKYDPKFQGKATITADTSSNTAYLQLSSLTSEDTAVYYCANAMDYWGQGTSVTVSS (SEQ ID NO: 347) | KCD007 | QIILTQSPAIMSASPGERVTMTCSASSSVSNMYWYQQKPGSSPRLLIYDTSNLASGVPLRFSGSGSGTSYSLTISRMEAEDAATYYCQQWSSYPWTFGGGTKLEIK (SEQ ID NO: 348) |

TABLE 1.1-continued

Heavy and Light Chain Variable Sequences of 88 mouse anti-CFD antibodies with CDRs underlined.

| ID | Heavy Chain Variable Region AA Sequence | ID | Light Chain Variable Region AA Sequence |
|---|---|---|---|
| KCD008 | EVQLQQSGPELVKAGASVKMSCTASGFNIKDTYMHWVKQRPEQGLAWIGRIDPANGNIKYDPKFQGKATITADTSSNTAYLQLSSLTSDDTAVYYCTSAMDYWGQGTSVTVSS (SEQ ID NO: 349) | KCD008 | QIVLTQSPEIMSASPGEKVTMTCSARSSVSYMYWYQQKPGSSPRLLIYDTSNLASGVPVRFSGSGSGTSYSLTISRMETEDAATYYCQQWSTYPFTFGSGTKLEIK (SEQ ID NO: 350) |
| KCD009 | QIQLVQSGPELKKPGETVKISCKASGYIFRNYGMNWVKQGPGKGLKWMGWINTYTGEPTYADDFKGRFAFSLETSASTAYLQISNLKNEDTATYFCVRDGPGFAYWGQGTLVTVSA (SEQ ID NO: 351) | KCD009 | DVLMTQTPLSLPVSLGDQASISCRSSLIIEHSDGNTYLEWYLQKPGQSPKLLIYKVSNRFSGVPDRFSGSGSGTDFTLKISRVEADDLGVYYCFQGSHVPVTFGAGTNLELK (SEQ ID NO: 352) |
| KCD010 | EVLLQQSGPELVKPGASVKIPCKASGYTFTDYDMDWVKQSHGKSLEWIGHINPNNGGTIYNQKFKGKATLTVDKSSSTAYMELRSLTSEDTAVYYCGTGDFAYWGHGTLVTVSA (SEQ ID NO: 353) | KCD010 | QIVLTQSPAIMSVSPGEKVTLTCSASSSVSSSYLYWYQKKPGSSPKLWIYSTSNLASGVPARFSGSGSGTSYSLTISSMEAEDAASYFCHQWSSYPPTFGAGTKLELK (SEQ ID NO: 354) |
| KCD011 | EVKLVESGGGLVQPGGSLKLSCAASGFTFSSNTMSWVRQTPEKRLEWVAYITNGGGSTYYPDTVKGRFTISRDNARNTLYLQMSSLKSEDTAMYYCARHDYYTMDYWGQGTSVTVSS (SEQ ID NO: 355) | KCD011 | DIQMTQSPSSLSASLGGKVTITCKASQDINKYIAWYQHKPGKGPRLLIHYTSTLQPGIPSRFSGSGSGRDYSFSISNLEPEDIATYYCLQYDNLLYTFGGGTKLEIK (SEQ ID NO: 356) |
| KCD013 | EVQLQQSGAELVKPGASVKLSCTASGFKIKDTYMHWVKERPDQGLEWIGRIDPANGNTKYDPKFQGKATITADTSSNTAYLQLSSLTSEDTAVYYCANAMDYWGQGTSVTVSS (SEQ ID NO: 357) | KCD013 | QIILTQSPAIMSASPGEKVTMTCSASSSVSNMYWYQQKPGSSPRLLIYDTSNLASGVPVRFSGSGSGASYSLTISRMEAEDAATYYCQQWSSYPWTFGGGTKLEIK (SEQ ID NO: 358) |
| KCD014 | EVKLVESGGGLVQPGGSLKLSCAASGFTFSSYIMSWVRQTPEKRLEWVAYITNGGGNTYYPDTIKGRFTISRDNAKNTLYLQMSSLKSEDTAMYYCARHGTGYAMDYWGQGTSVTVSS (SEQ ID NO: 359) | KCD014 | EIVLTQSPTTMAASPGEKITITCSASSSISSNYLHWYQQKPGFSPKLLIYRTSNLASGVPARFSGSGSGTSYSLTIGTMEAEDVATYYCQQGSSIPLTFGAGTKLELK (SEQ ID NO: 360) |
| KCD015 | EVQLQQSGAELVKPGASVKLSCTASGFNIKDTYMHWVKQRPEQGLEWIGRIDPANGYTEYDPKFQGKATITADTSSNTAYLQLSSLTSEDSAAYYCTSAMEFWGQGTSVTVSS (SEQ ID NO: 361) | KCD015 | QIVLTQSPAILSASPGEKVTMTCSASSSVSYIYWYQQKPRSSPRLLIYDTSNLASGVPVRFSGSGSGTSYSLTISRMEAEDAATYYCQQWSSYPFTFGGGTKLEVK (SEQ ID NO: 362) |
| KCD016 | QVQLQQSGAELAKPGASVKMSCKASGYTFTNFWMHWVKQRPGQGLEWIGFFNPSTAYTEYNQKFKDKATLTADKSSSTAYLHLSSLTSEDSAVYYCARRDYGSSYGWYFDVWGAGTTVTVSS (SEQ ID NO: 363) | KCD016 | DIQMTQSPASLSASVGETVTITCRASGNIHNYLAWYQQKQGKSPQLLVYNAKTLADGVPSRFSGSGSGTQYSLKINSLQPEDFGYYYCQHFWSTPTFGGGTKLEIK (SEQ ID NO: 364) |
| KCD017 | DVQLQESGPDLVKPSQSLSLTCTVTDYSITSGYSWHWIRQFPGNKLEWLGYIHSSGNTNYNPSLKSRFSITRDTSKNQFFLQLNSVTSEDTATYYCALHYYGSSFGWYFDVWGAGTTVTVSS (SEQ ID NO: 365) | KCD017 | DIVMTQSHKFMSTSVGDRVYITCKASQDVGTAVAWYQQTSGQSPKLLIYWASTRHTGVPDRFTGSGSGTDFTLTLSNVQSEDLADYFCQQYTSYPLTFGAGTKLELK (SEQ ID NO: 366) |
| KCD018 | QVQLQQSAAELARPGASVKMSCKASGYTFTSYTVHWVKQRPGQGLEWIGYINPSSGFTDYNQKFKDKTTLTADISSSTAYIQLSSLTSEDSAVYYCARRGVNWSWFAYWGQGTLVTVSA (SEQ ID NO: 367) | KCD018 | NIMMTQSPSSLAVSAGEKVTMSCKSSQSVLYSSNQKNYLAWYQQKPGQSPQLLIYWASTRESGVPERFTGSGSGTDFTLTISSVQAEDLAVYYCHQYLSSWTFGGGTKLEIK (SEQ ID NO: 368) |

TABLE 1.1-continued

Heavy and Light Chain Variable Sequences of 88 mouse anti-CFD antibodies with CDRs underlined.

| ID | Heavy Chain Variable Region AA Sequence | ID | Light Chain Variable Region AA Sequence |
|---|---|---|---|
| KCD019 | QVQLQQSGAELARPGASVKMSCKASGYTFATYTIHWVKQRPGQGLEWIGYLNLRNDYTHYNQKFRDKAALTADKSSSTAYMQLSSLTSEDSAVYNCAFRLGNDRQGWYFDVWGAGTTVTVSS (SEQ ID NO: 369) | KCD019 | DIVMTQAHRFMSTSVGDRVHSCKASQDVGTAVAWYQQTPGQSPKILIYWTSTRHTGVPDRFTGSRSGTDFTLTISNVQSEDLADYFCQQYTTYPLTFGGGTKLEIK (SEQ ID NO: 370) |
| KCD022 | DVQLQESGPDLVKPSQSLSLTCTVTGYSITSGYSWHWIRQFPGNTLEWMGYIHYSGSTNYNPSLESRISFTRDTSKNQFFLQLNSVTTEDTATYYCALHFYGYNLGWYFDVWGAGTTVTVSS (SEQ ID NO: 371) | KCD022 | DIVMTQSHKFMSTSIGDRVIITCKASQDVGTTVAWYQQRPGQSPKLLIYWASTRHTAVPDRFTGSGSGTDFTLTISNVQSEDLADYFCQQYTSYPLTFGAGTQLELK (SEQ ID NO: 372) |
| KCD023 | EVLLQQSGPELVKPGASVKIPCKASGYTFTDYNIDWVKQSHGKSLEWIGDINPNNGGINYNQKFKGKATLTVDKSSSTAYMELRSLTSEDTAVYYCGTGDYAYWGQGTLVTVSA (SEQ ID NO: 373) | KCD023 | QIVLTQSPAFMSASPGEKVTLTCSASSSVSSSYLYWYQQKPGSSPKLWIYSTSNLASGVPGRFSGSGSGTSYSLTISSMEAEDAASYFCHQWTSYPPTFGAGTKLELK (SEQ ID NO: 374) |
| KCD030 | QVQLQQSGAELAKPGASVKMSCKASGYTFTNYWMHWVKQRPGQGLEWIGYINPSIGYTEYNQKFKDKATLTADKSSSTAYMQLSSLTSEDSAVFYCATFIYYAMDYWGQGTSVTVSS (SEQ ID NO: 375) | KCD030 | DIQMNQSPSSLSASLGDTITITCHASQNINVWLSWYQQKPGNIPKLLIYKASNLHTGVPSRFSGSGSGTGFTLTISSLQPEDIATYYCQQGQSYPYTFGGGTKLEIK (SEQ ID NO: 376) |
| KCD033 | EVQLQQSGPELVKPGASMKISCTASGYSFTGYTMTWVKQSHGKNLEWIGLINPYNGGTNYNQKFKGKATLTVDKSSSIAYMELLSLTSEDSAVYYCARRHYGSNWDYWGQGTTLTVSS (SEQ ID NO: 377) | KCD033 | DIKLTQSPSSIYTSLGERVTITCKASQDINTYLSWFQQRPGKSPKTLIYRADRLVDGVPSRVRGSGSGQDYSLTISSLEYEDMGIYYCLQYDEFPYTFGGGTKLEIK (SEQ ID NO: 378) |
| KCD036 | EVQLQQSGPELVKPGASMKISCKASGYSFTGYTMTWVKQSHGKNLEWIGLINPYNGGTNYNQKFKGKATFTVDKSSSTAYMELLSLTSEDSAVYYCARRHYGSSWDYWGQGTTLTVSS (SEQ ID NO: 379) | KCD036 | DIKLTQSPSSMYASLGERVTITCKASQDINTYLSWFQQKPGKSPKTLIYRANRLVDGVPSRFSGSGSGQDYSLTISSLEYEEMGIYYCLQYDEFPYTFGGGTKLEIK (SEQ ID NO: 380) |
| KCD038 | EVQLQQSGPELVKPGTSMKISCKASGYSFADYTMNWVKQSHGKSLEWIGLINPYNGGTSYNQKFMGKATLTVDKSSSTAYMELLSLTSEDSAVYYCARWGTYSHNYDYAMDYWGQGTSVTVSS (SEQ ID NO: 381) | KCD038 | DVVMTQTPLSLPVSLGDQASISCRSSQSLVHSNGNTYLYWYFQKPGQSPKFLIYKVSNRFSGISDRFSGSGSGTDFTLKISRVEAEDLGVYFCSQSTHVPPFTFGSGTKLEIK (SEQ ID NO: 382) |
| KCD039 | EVQLQQSGPEMVKPGASMKISCKASGYSFADYTLNWVKQSHGKSLEWIGLINPYNGGTSYNQKFMGKATLTVDKSSSTAYMELLSLTSEDSAVYYCTRWGTYSHNYDYAMDYWGQGTSVTVSS (SEQ ID NO: 383) | KCD039 | DVVMTQTPLSLSVSLGDQASISCRSSQSLVHSNGNTYLYWYLQKPGQSPKLLIYKVSNRFSGITDRFSGSGSGTDFTLKISRVEAEDLGVYFCSQSTHVPPFTFGSGTKLEIK (SEQ ID NO: 384) |
| KCD040 | EVQLQQSGAELVKPGASVKLSCTASDFNIKDTYMHWVMQRPEQGLEWIGKIDPANGNTEFDPKFQGKATITADTSSNTAYLQLTSLTSEDTAVYYCTRAMDYWGQGTSVTVSS (SEQ ID NO: 385) | KCD040 | QIVLTQSPAIMSASPGEKVTMTCSAGSSVSYMYWYQQKPGSSPRVLIYDTSNLASGVPVRFSGSGSGTSYSLTISRMEAEDAATYYCQQWSNYPYTFGGGTKLEIK (SEQ ID NO: 386) |
| KCD042 | EVQLQQSGAELVKPGASVRLSCTASGFNIKHTYIHWVSQRPEQGLEWIGKIDPANGNTKYDPKFQGKATITADTSSNTAYLQLSSLTSEDTAVYYCVNAMEYWGQGTSVTVSS (SEQ ID NO: 387) | KCD042 | QSVLTQSPAIMSASPGEKVTMTCSANSSVSDMYWFQQRPGSSPRLLIYDTSNLASGVPVRFSGSGSGTSYSLTISRMEAEDAATYYCQQWSTYPWTFGGGTKLEIK (SEQ ID NO: 388) |

TABLE 1.1-continued

Heavy and Light Chain Variable Sequences of 88 mouse anti-CFD antibodies with CDRs underlined.

| ID | Heavy Chain Variable Region AA Sequence | ID | Light Chain Variable Region AA Sequence |
|---|---|---|---|
| KCD044 | EVQLQQSGAELVKPGASVRLSCTASGFNIKHTYMHWVSQRPERGLEWIGKIDPANGNTKYDPKFQGKATITADTSSNTVYLQLSSLTSEDTAVYYCLNAMEYWGQGTSVTVSS (SEQ ID NO: 389) | KCD044 | QSVLTQSPAIMSASPGEKVTMTCSANSSVSDMYWYQQRPGSSPRLLIYDTSNLASGVPVRFSGSGSGTSYSLTISRMEAEDAATYYCQQWSTYPWTFGGGTKLEIK (SEQ ID NO: 390) |
| KCD047 | EVQLQQSGAEFVKPGASVRLSCTASGFNIKDTYMHWVKQRPEQGLEWIGRIDPANGYTKDDPKFQGKATITADTSSNTAYLQLSSLTSEDTAVYYCASAMDYWGQGTSVTVSS (SEQ ID NO: 391) | KCD047 | QIVLTQSPAVMSASPGEKVAMTCSASSSVTYMYWYQQKPGSSPRLLIYDTSNLASGVPVRFSGSGSGTSYSLTISRMEAEDAATYYCQQWSTYPFTPGSGTKLEIK (SEQ ID NO: 392) |
| KCD048 | EVQLQQSGADLVKPGASVKLSCTASGFNIKATYMHWVRQRPEKGLEWIGRIDPANGHTIYDPQFQGKATITSDTSSNTAYLQLNSLTSEDTAVYYCAEAMDYWGQGTSVTVSS (SEQ ID NO: 393) | KCD048 | QIVLTQSPAIMSASPGEKVTLTCSATSSVSYMYWYQQKPGSSPRLLIYDTSNLASGVPVRFSGSGSGTSYSLTISRMEAEDDATYYCQQWSNYPFTFGGGTKLEIK (SEQ ID NO: 394) |
| KCD049 | QVQLKESGPGLVAPSQSLSITCTVSGFSLSSYGVQWVRQPPGQGLEWLVVIWRDGSITYNSALKSRLSISKDNSKSQVFLKMNSLQTDDTAMYYCGRTSHYGNYNYYVMDYWGQGTAVTVSS (SEQ ID NO: 395) | KCD049 | DIVMTQSPASLAVSLGQRATISCRASESVDKYGISFLNWFQQKPGQPPKLLIYAASNQGSGVPARFSGSGSGTDFSLNIHPMEEDDPAMYFCQQGKEVPWTFGGGTKLEIK (SEQ ID NO: 396) |
| KCD050 | QVQLKESGPGLVAPSQSLSITCTVSGFSLNSYGVQWVRQPPGQGLEWLVVIWRDGTITYNSALKSRLSINKDNSKSQVFLKMNSLQTDDTAMYYCGRTSHYGNFNYYVMDYWGQGTAVTVSS (SEQ ID NO: 397) | KCD050 | DIVMTQSPTSLAVSLGQRATISCRASESVDKYGISFLNWFQQKPGQPPRLLIYAASNQGSGVPARFSGSGSGTDFSLNIHPMEEDDPAVYFCQQGKEFPWTFGGGTKLEIK (SEQ ID NO: 398) |
| KCD052 | QVQLKESGPGLVAPSQSLSITCTVSGFSLNSYGVQWVRQPPGQGLEWLGVIWRDGSITYNSALKSRLSIRKDNSKSQVFLKMNSLQTDDTAMYYCGRTSHYGNYNYYVMDYWGQGTAVTVSS (SEQ ID NO: 399) | KCD052 | DIVMTQSPASLAVSLGQRATISCRASESVDKYGISFLNWFQQKPGQPPKLLIYAASNQGSGVPARFSGSGSGTDFSLNIHPMEEDDPAIYFCQQGKEVPWTFGGGTKLEIK (SEQ ID NO: 400) |
| KCD056 | EVKLVESGGGLVQPGGSLKVSCAASGFTFSTYTMSWVRQTPEKRLEWVAYITNGGGSTYYPDTEKGRFTISRDNAKNTLYLQMSSLKSEDTAMYYCVRHDYYAMDYWGQGTSVTVSS (SEQ ID NO: 401) | KCD056 | DIQMTQSPSSLSASLGGKVTITCKASQDINKYIAWYQHKPGKGPRLLIHYTSTLQPGIPSRFSGSGSGRDYSFSISNLEPEDIATYYCLQYDNLLYTFGGGTTLEIK (SEQ ID NO: 402) |
| KCD057 | EVKLVESGGGLVQPGGSLKLSCAASGFTFSNYIMSWVRQTPEKRLEWVAYITNGGGATYYPDTVKGQFTISRDNAKNTLYLQMSSLKSEDTAIYYCARHDFYALDFWGQGTSVTVSS (SEQ ID NO: 403) | KCD057 | DIQMTQSPSSLSASLGGKVTITCKASQDINKYIAWYQHKPGKGPRLLIHYTSTLQPGIPSRFSGSGSGRDYSFSISNLEPEDIATYYCLKYDNLLYTFGGGTKLEIK (SEQ ID NO: 404) |
| KCD058 | EVKLVESGGDLVQPGGSLKLSCAASGFTFSRYIMSWVRLTPEKRLEWVAFITNGGGNTYHPDTVKGRFTISRDNANNTLYLQMSSLKSEDTAIYYCARHDYYALDYWGQGTSVTVSS (SEQ ID NO: 405) | KCD058 | DIQMTQSPSSLSASLGGKVTITCKASQDINKYIAWYQHKPGKGPRLLIHYTSTLQPGIPSRFSGSGSGRDYSFSISNLEPEDIATYYCLQYDNLLYTFGGGTKLEIK (SEQ ID NO: 406) |
| KCD062 | EVKLVESGGGLVQPGGSLKLSCAASGFTFSTYIMSWVRQTPEKRLEWVAYITSGGSSTYYPDTVKGRFTISRDNAKSTLYLQMSSLKSEDTAMYYCARHAHFYAMDYWGQGTSVTVSS (SEQ ID NO: 407) | KCD062 | DIQMTQSPSSLSASLGGKVTITCKASQDINKYIAWYQHKPGKGPRLLIHYTSTLQPGIPSRFSGSGSGRDYSFSISNLEPEDIATYYCLQYDNLLYTFGGGTKLEIK (SEQ ID NO: 408) |
| KCD063 | EVKLVESGGGLVQPGGSLKLSCAASGFIFSSYIMSWVRQTPEKRLEWVAYITNGGGSTYYPDTVKGRLT | KCD063 | DIQMTQSPSSLSASLGGKVTITCKASQDINKYITWYQHKPGKGPRLLIHYTSTLQPGIPSRFSGSGSGRDYS |

TABLE 1.1-continued

Heavy and Light Chain Variable Sequences of 88 mouse anti-CFD antibodies with CDRs underlined.

| ID | Heavy Chain Variable Region AA Sequence | ID | Light Chain Variable Region AA Sequence |
|---|---|---|---|
| | ISRDNAKNTLYLQMSSLKSEDTAMYYCVRHAHYYAMDYWGQGTSVTVSS (SEQ ID NO: 409) | | FSISNLEPEDIATYYCLQYDNLLYTFGGGTKLEIK (SEQ ID NO: 410) |
| KCD064 | EVKLVESGGGLVQPGGSLKLSCAASGFTFSSYIMSWVRQTPEKRLGWVAYITSGGGSTYYPDTVKGRFTISRDNAKNTLYLQMSSLKSEDTAMYYCARHGTGYAMDYWGQGTSVTVSS (SEQ ID NO: 411) | KCD064 | DIQMTQSPSSLSASLGGKVTITCKASQDINKYIAWYQHKPGKGPRLLIHYTSTLQPGIPSRFSGSGSGRDYSFSISNLEPEDIATYYCLQYDNLLYTFGGGTELEIK (SEQ ID NO: 412) |
| KCD065 | QVQLQQSGAELARPGASVKMSCKASGYTFTTYTIHWVKQRPGQGLEWIGYINPSSDFTNYNQNFADKATLTADRSSSTAYMQLSSLTSEESAVYYCAIRLGYDRQGWYFDVWGAGTTVTVSS (SEQ ID NO: 413) | KCD065 | DIVMTQSHKFLSTSLGDRVSITCKASQDVGSAVAWYQQKPGQSPDLLIYWTFTRHTGVPDRFTGSRSGTDFTLTISNVQSGDLADYFCQQYSNYPLTFGGGTKLEIK (SEQ ID NO: 414) |
| KCD066 | QVQLQQSAAELARPGASVKMSCKASGYTFTDYTMHWVKQRPGQGLEWIGYINPSGGYTDYNQKFKDKTALTADKSSSTAYMQLSSLTSEDSAVYYCARRRDYWFAYWGQGTLVTVSA (SEQ ID NO: 415) | KCD066 | DIVMSQSPSSLAVSVGEKVTMSCKSSQSLLYSGNQKNYLAWYQQKPGQSPKLLIYWASTRESGVPDRFTGSGSGTDFTLTISSVKAEDLAVYYCHQYYSYLTFGAGTKLELK (SEQ ID NO: 416) |
| KCD070 | EIQLQQTGPELVKPGASVKISCKASGYSFTDYIILWVKQSHGKSLEWIGNINPYYDYTSYNLKFKGKATLTVDKSSSTAYMQLNSLTSEDSAVYYCARSDGYYGGDYWGQGTSVTVSS (SEQ ID NO: 417) | KCD070 | DIVMTQSHKFMSTSVGDRVSITCKASQDVGTAVAWYQQKPGQSPKLLIYWASTRHTGVPDRFTGSGSGTDFTLTINNVQSEDLADYFCQQYSSYPWTFGGGTTLEIK (SEQ ID NO: 418) |
| KCD075 | QVQLLQPGAELVRPGTSVKLSCKASGYTFSNYWINWVKQRPGQGLEWIGNIYPSDSSINYNQKFKDKATLTVDKSSTTAYMQLSSPTSEDSAVYYCTGTDWYFDVWGAGTTVTVSS (SEQ ID NO: 419) | KCD075 | DIQMTQTTSSLSASLGDRVTISCSGGQGISNYLNWYQQKPDGTFKLLIYYTSTLHSGVPSRFSGSGSGTDYSLTISNLEPEDVATYYCQQYSKLPYTFGGGTKLEIK (SEQ ID NO: 420) |
| KCD077 | EVQLQQSGAELVRPGALVKLSCKASGFNIKDYYMHWVKQRPEQGLEWIGWIDPENGHTIYDPRFQGKATITADTSSNTAYLQLSSLTSEDTAVYYCSRGLLGFAYWGQGTLVTVSA (SEQ ID NO: 421) | KCD077 | DIVMTQSQKFMSTSVGDRVSVTCKASQNVGTNVAWYQQKPGQSPKALIYTASYRYSGVPDRFTGSGSGTDFTLTISNVQSEDLAEYFCQQYNSYPHMYTFGGGTKLEIK (SEQ ID NO: 422) |
| KCD101 | QVQLQQPGAELVRPGTSVKLSCKASGYTFTSYWMHWVKQRPGQGLEWIGVIDPSDSYTNYNQKFKGKATLTVDTSSSTAYMQLSSLTSEDSAVYYCGRNGYDGSMDYWGQGTSVTVSS (SEQ ID NO: 423) | KCD101 | DIQMTQTTSSLSASLGDRVTISCRASQDISNYLNWYQQKPDGTVKLLIYYPSRLHSGVPSRFSGSGSGTDYSLTISNLEQEDFATYFCQQGNTLPYTFGGGTKLEIK (SEQ ID NO: 424) |
| KCD102 | QVQLQQPGAELVRPGTSVKLSCKASGYTFTSYWMHWVKQRPGQGLEWIGVIDPSDSYTNYNQKFKGKATLTVDTSSSTAYMQLSSLTSEDSAVYYCARNGYDGSMDYWGQGTSVTVSS (SEQ ID NO: 439) | KCD102 | EIQMTQTTSSLSASLGDRVTISCRASQDISNYLNWYQQKPDGTVKLLIYYPSRLHSGVPSRFSGSGSGTDYSLTISNLEQEDFATYFCQQGNTLPYTFGGGTKLEIK (SEQ ID NO: 440) |
| KCD103 | QVQLQQPGAELVRPGTSVKLSCKASGYTFTSYWMHWVKQRPGQGLEWIGVIDPSDSYTKYNQKFKDKATLTVETSSSTAYMQLSSLTSEDSAVYYCAGNGYDGSMDYWGQGTSVTVSS (SEQ ID NO: 459) | KCD103 | DIQMTQTTSSLSASLGDRVTISCRASQDISNSLNWYQQKPDGTVKLLIYYTSRLHSRVPSRFSGSGSGTDYSLTISNLDQEDIATYFCQQANTLPYTFGGGTKLEIK (SEQ ID NO: 460) |
| KCD104 | QVQLQQPGAELVRPGTSVKLSCKASGYTFTSYWMHWVKQRPGQGLEWIGVIDPSDSYTYYNQKFKGKATLTVDTSSSTAYMQLSSLTSEDSAVYYCARNGYDGAMDYWGQGTSVTVSS (SEQ ID NO: 477) | KCD104 | EIQMTQTTSSLSASLGDRVTISCRASQDISNYLNWYQQKPDGTVKLLIYYPSRLHSGVPSRFSGSGSGTDYSLTISNLEQEDFATYFCQQGNTLPYTFGGGTKLEIK (SEQ ID NO: 478) |

TABLE 1.1-continued

Heavy and Light Chain Variable Sequences of 88 mouse anti-CFD antibodies with CDRs underlined.

| ID | Heavy Chain Variable Region AA Sequence | ID | Light Chain Variable Region AA Sequence |
|---|---|---|---|
| KCD110 | EVQLQQSGPELVKPGASVKISCKASGYSFTGYYMHWVKQSHGNILDWIGYIDPDNGVSSKNQKFTGKATVTADKSSSTAYMELRSLTSEDSAVYYCAGYYGSSWYWYFDVWGTGTTVTVSS (SEQ ID NO: 425) | KCD110 | QIVLSQSPAILSASPGEKVTMTCRASSSVSYMHWYQQKPGSSPKPWIYATSNLASGVPARFSGSGSGTSYSLTISRVEAEDAATYYCQQWSSNPYTFGGGTKLEIK (SEQ ID NO: 426) |
| KCD111 | EVQLQQSGPELVKPGASVKISCKASGYSFTDYYMHWVKQSHGNILDWIGYIDPYNGVSSYNQKFKGKATLSVDQSSSTAYMELRSLTSEDSAVYYCSSYYGSSPYWYFDVWGTGTRVTVSS (SEQ ID NO: 427) | KCD111 | QIVLSQSPAILSASPGEKVTMTCRASSSVSYMHWYQQKPGSSPKPWIYATSNLASGVPTRFSGSGSGTSYSLTISKLEAEDAATYYCQQWSSNPYTFGGGTKLEIK (SEQ ID NO: 428) |
| KCD112 | EVQLQQSGPELVKPGASVKISCKASGYSFTAYYMNWVKHSPEKSLEWIGDINPSTGGTTYNQKFKARATLTVDKSSSTAYMQLKSLTSEDSAVYYCATTYYSGNSYVGFAYWGQGTLVTVSA (SEQ ID NO: 429) | KCD112 | DIVMTQSHKFMSTSVGDRVSITCKASQDVSTAVAWYQQKPGQSPKLLIFWTSTRHTGVPDRFTGSGSGTDYTLTISSVQAEDLALYYCQQHYTTPWTFGGGTKLEIK (SEQ ID NO: 430) |
| KCD114 | EVQLQQSGPELVKPGASVKISCKASGYSFTAYYMNWVKQSPEKSLEWIGDINPSTGGTTYNQNFKAKATLTVDKSSSTAYMHLKSLTSEDSAVYYCATTYYSGNSYVGFAYWGQGTLVTVSA (SEQ ID NO: 431) | KCD114 | DIVMTQSHKFMSTSVGDRVSITCKASQDVSTAVAWYQQKPGQSPKLLIFWASTRHTGVPDRFTGSGSGTDYTLTISSVQAEDLALYYCQQHYSTPWTFGGGTKLEIK (SEQ ID NO: 432) |
| KCD115 | EVQLQQSGPELVKPGASVKISCKASGYSFTGYYMNWVKQSPEKSLEWIGDINPSTGGTTYNQKFKAKATLTVDKSSSTAYMQLKSLTSEDSAVYYCATPYYYGSSYVGFAYWGQGTLVTVSA (SEQ ID NO: 433) | KCD115 | DIVMTQSHKFMSTSVGDRVSITCKASQDVSTAVDWYQQKPGQSPKLLIYWASTRHTGVPDRFTGSGSGTDYTLTISSVQAEDLALYYCQQHYSTPWTFGGGTKLEIK (SEQ ID NO: 434) |
| KCD118 | EVQLQQSGPELVKPGASVKISCKAFGYTFTDYYKNWMRQRHGESLEWIGDINPNSGDANYNQKFKGKATLTVDKSSSTAYMELRSLTSEDSAVYYCAREGPSFAYWGHGTLVTVSA (SEQ ID NO: 435) | KCD118 | DVLMTQTPLSLPVSLGDQASISCRSSQTIVHSNGDTYLEWYLQKPGQSPNLLIYKVSNRFSGVPDRFSGSGSGTDFTLKISRVEAEDLGIYYCGSHVPPTFGGGTKLEIK (SEQ ID NO: 436) |
| KCD119 | EVQLQQSGPELVKPGASVKISCKASGYTFTDYYTNWMRQRHGESLEWIGDINPNTGDTSYNQKFRVKATLTVDKSSGTAYMGLRSLTSEDSAVYYCTREGPSFAYWGQGTLVTVSA (SEQ ID NO: 437) | KCD119 | DVLMTQTPLSLPVSLGDQASISCRSSQTIVHSNGDTYLEWYLQKPGQSPNLLIYKVSNRFSGVPDRFSGSGSGTDFTLKISRVEAEDLGVYYCFQGSHVPPTFGGGTTLEIK (SEQ ID NO: 438) |
| KCD121 | EVQLQQSGPELVKPGASVKISCKASGYTFTDYYKNWMRQRHGESLEWIGDINPNNGDTSYNQKFRGKATLTVDKSSSTAFMELRSLTSEDSAVYYCAREGPSFAYWGQGTLVTVSA (SEQ ID NO: 441) | KCD121 | DVLMTQTPLSLPVSLGDQASISCRSNQTIVHSNGDTYLEWYLQKPGQSPNLLIYKVSNRFSGVPDRFSGSGSGTDFTLRISRVEAEDLGVYYCFQGSHVPPTFGGGTKLEIK (SEQ ID NO: 442) |
| KCD122 | EVQLQQSGPELVKPGASVKISCKASGYTFTDYYKNWMRQRHGESLEWIGDINPNNGDANYNQKFKGKATLTVDKSSSTAYMELRSLTSEDSAVYFCAREGPSFAYWGHGTLVTVSA (SEQ ID NO: 443) | KCD122 | DVLMTQTPLSLPVSLGDQASISCRSSQTIVHSNGDTYLEWYLQKPGQSPNLLIYKVSNRFSGVPDRFSGSGSGTDFTLKISRVEAEDLGVYYCFQGSHVPPTFGGGTKLEIK (SEQ ID NO: 444) |
| KCD123 | EVHLQQSGPELVKPGASVKISCKASGYTFTDFYKNWMRQRHGESLEWIGDINPNNGGTNYNQKFKGKATLTVDKSSSTAYMELRSLTSEDSAVYYCAREGPSFAYWGQGTLVTVSA (SEQ ID NO: 445) | KCD123 | DVLMTQTPLSLPVSLGDQASISCRSSQTIVHSNGDTYLEWYLQKPGQSPNLLIYKVSNRFSGVPDRFSGSGSGTDFTLKISRVEAEDLGVYYCFQGSHVPPTFGGGTKLEIK (SEQ ID NO: 446) |
| KCD124 | EVQLQQSGPELVKPGASVKISCKASGYTFTDHYMNWVKQSHGKSLEWIGDINPNNGGTSYNQKFKGKA | KCD124 | DVLMTQTPLSLPVSLGDQASISCRSSQSIVHSNGDTYLEWYLQKPGQSPKLLIYKVSNRFSGVPDRFSGSG |

TABLE 1.1-continued

Heavy and Light Chain Variable Sequences of 88 mouse anti-CFD antibodies with CDRs underlined.

| ID | Heavy Chain Variable Region AA Sequence | ID | Light Chain Variable Region AA Sequence |
|---|---|---|---|
| | TLTVDKSSSTAYMELRSLTSGDSA VVYYCTREGASFAFWGQGTLVTVS A (SEQ ID NO: 447) | | SGTDFTLKISRVEAEDLGVYYCF QGSHVPLTFGAGTKLELK (SEQ ID NO: 448) |
| KCD125 | EVQLQQSGAELVRPGSSVKMSCK TSGNTFTSYGINWVKQRPGQGLE WIGYIYIGTGYTEYNEKFKGKATL TSDTSSSTAYMQLSSLTSEDSAIY FCVRKAYGNYGFDYWGQGTTLT VSS (SEQ ID NO: 449) | KCD125 | DIQMTQSPSSLSASLGERVSLTCR ASQEISGYLSWLQQKPDGTIKRLI YAASTLDSGVPKRFSGSRSGSDYS LTISSLESEDFADYYCLQYASYPF TFGSGTKLEIK (SEQ ID NO: 450) |
| KCD126 | EVQLQQSGAELVRPGSSVKMSCK TSGKTFTSHGINWVKQRPGQGLE WIGYIYIGNGYNEYNEKFKGKAT LTSDTSSSTAYMQLSSLTFEDSAI YFCVRKAYGNYGFDDWGQGTTL TVSS (SEQ ID NO: 451) | KCD126 | DIQMTQSPTSLSASLGESVSLTCR ASQEISGNLNWLQQKPDGSIKRLI YAASTLDSGVPKRFSGSRSGSDYS LTISSLESEDFADYYCLQYANYPF TFGSGTKLEVK (SEQ ID NO: 452) |
| KCD127 | QVQLQQPGAELVRPESSVKLSCK ASGYTFTNFWMDWVKQRPGQGL EWIGNIYPSGSETHYNQKFKDKA TLTVDKSSTTAYMQLSSLTSEDSA VYYCARSGYYGSRYLYYFDYWGQ GTTLTVSS (SEQ ID NO: 453) | KCD127 | DIVMTQSHKFMSTSVGDRVSITC KASQDVSTAVAWYQQKPGQSPKL LIYSASYRSTGVPDRFTGSGSGTD FTFTISSVQAEDLAVYYCQQHYST PYTFGGGTKLEIR (SEQ ID NO: 454) |
| KCD128 | QVQLQQPGAELVRPESSVKLSCK ASGYTFTSYWMDWVMQRPGQGL EWIGNIYPSGSETHYNQKFKDKA TLTVDKSSTTAYMQLSSLTFEDSA VYYCARSGFIGSRYLYYFDYWGQ GTTLTVSS (SEQ ID NO: 455) | KCD128 | DIVMTQSHKFMSTSVGDRVTITC KASQDVSNAVAWYQLKPGQSPKL LIYSASYRYTGVPDRFTGSGSGTD FTFTISSVQAADLAVYYCQQHYIT PYTFGGGTKLEIK (SEQ ID NO: 456) |
| KCD129 | EVQLVESGGGLVQPKGSLKLSCA ASGFSFNTYAMNWVRQAPGKGL EWVARIRSKSNNYATYYADSVKD RFTISRDDSESMVYLQMNNLKTE DTAMYYCVRHGYYWYFDVWGTG TTVTVSS (SEQ ID NO: 457) | KCD129 | DVLMTQTPLSLPVSLGDQASISCR SSQSIVHSDGNTYLEWYLQKPGQ SPKLLIYRVSNRFSGVPDRFSGSG SGTDFTLKISRMEAEDLGVYYCF QGSHVPYTFGGGTKLEIK (SEQ ID NO: 458) |
| KCD131 | QVQLQQSGPELVKPGASVKISCK ASAYTFTDYYINWVKQRPGQGPE WIGWIFPGSNSTYSNEKFEVKAT LTVDESSSTAYMLLSSLTSEDSAV YFCARLGYFGSSYHALDYWGQG TSVTVSS (SEQ ID NO: 461) | KCD131 | DIQMTQSPASLSVSVGETVTITCR ASENIYSHLAWFQQKQGKSPRLL VYSATNLPDGVPSRFSGSGSGTQ YSLKINILQSEDFGSYYCQHFWG TPWTFGGGTKLEIK (SEQ ID NO: 462) |
| KCD132 | QVQLQQSGPELVKPGASVKISCK ASGYSFTDYYINWVKQRPGQGLE WIGWIFPGSGSTYYNEKFKGKAT LTVDKSSSTAYMLLSSLTSEDSAV YFCARTGYYSNLYAVDYWGQGTS VTVSS (SEQ ID NO: 463) | KCD132 | DIQMTQSPASLSVSVGETVTITCR ASENIYSNLAWYQQKQGKSPQLL VYVATNLADGVPSRFSGSGSGTQ YSLKINSLQSEDFGNYYCQHFWG TPYTFGGGTKLEMR (SEQ ID NO: 464) |
| KCD133 | EVQLVESGGGLLQPKGSLKLSCA ASGFTFNTYAMNWVRQAPGKGL EWVARIRSKSSNYATYYADSVKD RFTISRDDSQSMFYLEMNNLKTE DTAMYYCVRDRGYYYVMDYWGQ GTSVTVSS (SEQ ID NO: 465) | KCD133 | DIVLTQSPASLAVSLGQRATISCR ASESVEYYGTSLMQWYQQKPGQ PPKLLINAASNVESGVPARFSGSG SGTDFSLNIHPVEEDDIAMYFCQ QSRKVPWTFGGGTKLEIK (SEQ ID NO: 466) |
| KCD134 | EVQLQQSGPEMVKPGASVKMSC QASGYTFTDYYMNWVKQSHGET LEWIGDIYPHNGYTAYNQKFKGK ATLTVDKSSSTAYMELRSLTSEDS AVYYCARGGQLRLPAWFAYWGQ GTLVTVSA (SEQ ID NO: 467) | KCD134 | ETTVTQSPASLSMAIGEKVTIRCI TSTDIDDDMNWYQQKPGEPPKL LISEGNSLRPGVPSRFSSSGYGTD FVFTIEDMFSEDVADYHCLQSDN LPYTFGGGTKLEIK (SEQ ID NO: 468) |
| KCD135 | EVQLQQSGPELVKPGASVRMSCK ASGYIFTDYSIHWVKQSHGKSLE WIGYINPNNGGTSYNQKFKGKAT LTVNKSSTTAYMELRSLTSEDSAV YFCARDTTIVGDYWGQGTTLTVS S (SEQ ID NO: 469) | KCD135 | DIVMTQSQKFMSTSVGDRVSVTC KASQHVGTNVVWYQQKPGQSPK ALIYSASYRYSGVPDRFSGSGSGT DFTLTISNVQSEDLAEYFCQQFN SYPLTFGGGTKLEIK (SEQ ID NO: 470) |

TABLE 1.1-continued

Heavy and Light Chain Variable Sequences of 88 mouse anti-CFD antibodies with CDRs underlined.

| ID | Heavy Chain Variable Region AA Sequence | ID | Light Chain Variable Region AA Sequence |
|---|---|---|---|
| KCD136 | EVQLQQSVAELVRPGASVKLSCSASGFNIKNTYMHWVNQRPEQGLEWIGRIDPANGITKYAPNFQGKATITADTSSNTAYLQLSNLTSEDTAIYYCTRAMDYWGQGTSVTVSS (SEQ ID NO: 471) | KCD136 | QIVLTQSPAIMSASPGEKVTMTCSASSSVSYMYWYQQKPGSSPRLLIYDISNLASGVPVRFSGSGSGTSYSLTISRMEAEDAATYYCQQWDTYPWTFGGGTKLEIK (SEQ ID NO: 472) |
| KCD137 | EVQLVESGGDLVKPGGSLKLSCAASGFTFSGYGMSWVRQIPDKRLEWVAISSRDNSFTYYPDSVKGRFTISRDNAKNTLYLQMSSLKSEDTALYFCTRHPYLPTGGYVMDYWGQGTSVTVSS (SEQ ID NO: 473) | KCD137 | DIVMTQSHKFMSTSVGDRVSITCKASQDVGTAVAWYQQRPGQSPKLLIYWASTRHTGVPDRFTGSGSGTDFTLTVSNVQSEDLADYFCQQYTSYPLTFGAGTKLELK (SEQ ID NO: 474) |
| KCD139 | EVQLQQSGAELVRPGSSVKMSCKTSGYTFTSYGINWVKQRPGQGLEWIGYIYIANGYTENNEKFKGKAKLTSDISSSTAYMQLSSLTSEDSAIYFCARRFDYAGALDYWGQGTSVTVSS (SEQ ID NO: 475) | KCD139 | DIVLTQSPASLAVSLGQRATISCRASESVDSYGNSFMHWYQQKPGQPPKLLIHRASNLESGIPARFSGSGSRTDFTLTINPVEADDVAIYYCQQTNDDPYTFGGGTNLEIK (SEQ ID NO: 476) |
| KCD200 | EVQLQQSGPELVKPGASVKISCKASGYTFTSYYKNWMRQRHGESLEWIGDINPNSGDTAYNQKFKGKATLTVDRSSSTAYMELRSLTSEDSAVYYCAREGPSFAYWGQGTLVTVSA (SEQ ID NO: 479) | KCD200 | DVLMTQTPLSLPVSLGDQVSISCRSSQTIVHSNGDTYLEWYLQKPGQSPNLLIYKVSNRFSGVPDRFSGSGSGTDFTLKISRVEAEDLGVYYCFQGSHVPPTFGGGTKLEIK (SEQ ID NO: 480) |
| KCD205 | EVQLQQSGAELVRPGSSVKMSCKTSGNTFTSHGINWVKQRPGQGLEWIGYIYIGNGYNEYNEKFKGKATLTSDTSSSTAYMQLSSLTSEDSAIYFCVRKAYGNYGFDDWGQGTTLTVSS (SEQ ID NO: 505) | KCD205 | DIQMTQSPSSLSASLGERVSLTCRASQEISGYLSWLQQKPDGTIKRLIYAASTLDSGVPKRFSGSSSGSDYSLTISSLESDDFADYYCLQYASYPFTFGSGTKLEIK (SEQ ID NO: 506) |
| KCD207 | AVQLVESGGGLVQPKGSLKLSCAASGFSFNTYAMNWVRQAPGKGLEWVARIRSKSNNYATYYADSVKDRFTLSRDDSESMLYLQMNNLKTEDTAMYYCVRQGFYWYFDVWGTGTTVTVSS (SEQ ID NO: 507) | KCD207 | DVLMTQTPLSLPVSLGDQASISCRSSQTIVHSNGNTYLEWYLQKSGQSPKLLIYNVSNRFSGVPDRFRGSGSGTDFTLKISRVEAEDLGVYYCFQGSHVPYTFGSGTKLEIK (SEQ ID NO: 508) |
| KCD208 | EVQLQQSVAELVRPGASVKLSCTVSGFNIKNTYMHWVKQRPEQGLEWIGRIDPANGDTTYAPKFQGKATITADTSSNSAYLHLSRLTSEDTAIYYCSLYDYDGYWGQGTTLTVSS (SEQ ID NO: 509) | KCD208 | EIVLTQSPALMAASPGEKVTITCSVSSSISSSSLHWYRQKSGTSPKPWIYGTSHLASGVPVRFSGSGSGTSYSLTISSMEAEDAATYYCQQWDTYPWTFGGGTKLEIK (SEQ ID NO: 510) |
| KCD210 | EVQLQQSGPVLVKPGASVTMSCKASGYTFTEYYMNWVKQSHGKSLDWIGVINPYSGGTSYKQKFKDKATLTVDKSSSTAYMELNGLTSEDSAVYFCVRGGLRRNYFDYWGQGTTLTVSS (SEQ ID NO: 481) | KCD210 | EIVLTQSPALMTASPGEKVTITCSVSSSISSTNLHWYQQKSGTSPKPWIFGTSNLASGVPVRFSGSGSGTSYSLTISNMEAEDAATYYCQQWNSYPFTFGTGTKLEIK (SEQ ID NO: 482) |
| KCD212 | EVHLVESGGDLVKPGGSLKLSCAASGFTFSRYGMSWVRQTPDKRLEWVATISSAGSYTYYPDSVKGRFTISRDNAKNTLFLQMSSLKSEDTAMYYCARPLNYYGTSSFDYWGQGTTLTVSS (SEQ ID NO: 483) | KCD212 | QIVLTQSPAIMSASPGEKVTMTCRASSSVSSTYLHWYQQKPGSSPKLWIYSTSNLASGVPPRFSGSGSGTSYSLTISSVEAEDAATYYCQQYDSSPNTFGAGTKLELK (SEQ ID NO: 484) |
| KCD214 | EVQLQQSVAEFVRPGASVKLSCTASGFNIKNTYMHWVKQRPEQGLEWIGRIDPANGNTEYAPKFQGKATITADTSSNTAYLQLSSLTSEDTAIYYCALYDYDGYWGQGTTLTVSS (SEQ ID NO: 485) | KCD214 | EIVLTQSPALMAASPGEKVTITCRVSSSISSSSLHWYQQKSGTSPKPWIYGTSNLASGVPVRFSGSRSGTSYSLTISSMEAEDAATYYCQQWSDYPWTFGGGTKLEIK (SEQ ID NO: 486) |

TABLE 1.1-continued

Heavy and Light Chain Variable Sequences of 88 mouse anti-CFD antibodies with CDRs underlined.

| ID | Heavy Chain Variable Region AA Sequence | ID | Light Chain Variable Region AA Sequence |
|---|---|---|---|
| KCD216 | QVHLQQSGPELVKPGASVKISCKASGYTFIDYYINWVKQRPGQGLEWIGWIFPGSDSTYYNEKFKGKATLTVDKSSSTAYMLLSSLTSEDSAVYFCARYGYYGSSFYAMDYWGQGTSVTVSS (SEQ ID NO: 487) | KCD216 | DIQMTQSPASLSVSVGETVTITCRASENIYSNLAWYQQKQGKSPQLLVYAATNLADGVPSRFSGSGSGTQYSLKINSLQSEDFGSYYCQHFWGTPPTFGGGSKLEIK (SEQ ID NO: 488) |
| KCD217 | QVQVQQPGAEFVKTGASVKLSCKTSGYTFIDYWIHWVKQRPGHGLEWIGRIDPNTGGSKYYEKFKRKATLTVDKPSRTVYMQLSSLTSEDSAVYYCTREYDYGWFGYWGQGTLVTVSE (SEQ ID NO: 489) | KCD217 | DIQMTQSPASLSASVGETVTITCGASENIYGALNWYQRKQGKSPQLLIYGATNLADGMSSRFSGSGSGRQYSLKISSLHPDDVATYYCQNVLSTPWTFGGGTKLEIK (SEQ ID NO: 490) |
| KCD219 | QVQLQQSGPELVKPGASVKISCKASGYTFTDYYINWVKQRPGQGLEWIGWIFPGSGSTYYNEKFKGKATLTVDKSSSTAYMLLSSLPSEDSAVYFCARYGYYGSSFYAMDYWGQGTSVTVSS (SEQ ID NO: 491) | KCD219 | DIQMTQSPASLSVSVGETVTITCRASENIYSNLAWYQQKQGKSPQLLVYAATNLADGVPSRFSGSGSGTQYSLKINSLQSEDFGSYYCQHFWGSPPTFGGGTKLEIK (SEQ ID NO: 492) |
| KCD220 | QVQLQQSGAELMEPGASVKLSCKATGYTFTGYWIEWVKQRPGHGLEWIGETLPGSDSNNYNEKFKGKATFTADTSSNTAYMQLSSLTTEDSAIYYCARDYSNYWYFDVWGTGTTVTVSS (SEQ ID NO: 493) | KCD220 | DIQMTQTTSSLSASLGDRVTISCRASQDISNYLNWYQQKPDGTVKLLIYYTSNLHSGVPSRFSGSGSGTDYSLTISNLEQEDIATYFCQQDSKHRTFGGGTKLEIK (SEQ ID NO: 494) |
| KCD224 | QVQLKESGPGLVAPSQSLSITCTVSGFSLTSYGVDWIRQSPGKGLEWLGVIWGVGSTNYNSALKSRLSISKDNSKSQVFLKMNSLQTDDTAMYYCARSYDGSYWYFDVWGTGTTVTVSS (SEQ ID NO: 495) | KCD224 | DIQMTQTTSSLSASLGDRVTISCRASQVISNYLNWYQQKPDGTVKLLIYYTSRLHSGVPSRFSGSGSGTDYSLTISNLEPEDIATYYCQQYSKLPYTFGSGTKLEIK (SEQ ID NO: 496) |
| KCD225 | QVQLQQSGPELVKPGASVKISCKASGYTFTDYYINWMKQRPGQGLEWIGWIFPGSDSTYYNEKFKGKATLTVDKSSSTAYMLLSSLTSEDSAVYFCARLGYYSHSYYAMDYWGQGTSVTVSS (SEQ ID NO: 497) | KCD225 | DIQMTQSPASLSVSTGETVTITCRASENIYSNLAWFQQKQGKSPQLLVYAATNLADGVPSRFSGSGSGTQYSLKITSLQSEDFGSYYCQHFWGTPLTFGAGTKLDLK (SEQ ID NO: 498) |
| KCD229 | EVQLVESGGGLVQPKGSLKLSCAASGFSFNTYAMNWVRQAPGKGLEWVARIRSKSNNYATYYADSVKDRFTIFRDDSESMLYLQMNNLKTEDTAMYYCVRHGYYWYFDVWGTGTTVTVSS (SEQ ID NO: 499) | KCD229 | DVLMTQNPLSLPVSLGDQASISCRSSQSIVHSNGNTYLEWYLQKPGQSPNLLIYNVFNRFSGVPDRFSGSGSGTDFTLKISRVEAEDLGVYYCFQGSHVPYTFGSGTKLEIK (SEQ ID NO: 500) |
| KCD230 | QVQLQQPGTELVKPGASVKLPCKASGYTFTSYWMQWVKQRPGQGLEWIGEIDPSDTYINYNQKFKGKATLTVDTSSTTAYMQLSSLTSEDSAVYYCARYTTIMASDYWGQGTTLTVSS (SEQ ID NO: 501) | KCD230 | DIQMTQTTSSLSVSLGDRVTISCRASQDITNYLNWYQQKPDGTVKLLIYFTSRLHSGVPSRFSGSGSGTDYSLTISNLEPEDIATYYCQQYSKLPWTFGGGTKLEIK (SEQ ID NO: 502) |
| KCD232 | EVQLVESGGGLVQPKGSLKLSCAASGFSFNTYAMNWVRQAPGKGLEWVARIRSKSNNYATYYADSVKDRFTISRDDSESMVYLQMNNLKTEDTAMYYCVRHGYYWYFDVWGTGTTVTVSS (SEQ ID NO: 503) | KCD232 | DVLMTQTPLSLPVSLGDQASISCRSSQSIVHSDGNTYLEWYLQKPGQSPKLLIYRVSNRFSGVPDRFSGSGSGTDFTLKISRMEAEDLGVYYCFQGSHVPYTFGGGTKLEIK (SEQ ID NO: 504) |

Example 2—Binding of Chimeric Anti-CFD Antibodies to Human and Cynomolgus CFD 100 out of the 146 unique anti-CFD mouse antibodies sequences were chosen to be recombinantly expressed in Expi293 cells and purified using mAb select for further validation. The antibodies were selected based on the robustness of the sequencing data, distance from germline sequences, and to maximize immunoglobin heavy chain CDR3 diversity. 91 antibodies were successfully expressed and evaluated further.

A kinetic screen of all of 91 antibodies binding to serum purified CFD was performed by Wasatch Microfluidics on a MX96 SPR machine, by injecting CFD at varying concentrations over an array of 96 amine coupled antibodies. Binding kinetics and affinity of the antibodies were also determined for CFD-Mutant 1, recombinant human CFD, and recombinant Cyno-CFD. Data of the kinetic screen are shown in Table 2.1 and Table 2.2. 88 out of 91 anti-CFD mouse antibodies tested showed binding to human CFD. Variable domain sequences of these 88 mouse antibodies with confirmed binding to human CFD are listed in table 1.1.

TABLE 2.1

Binding affinities of recombinantly expressed anti-CFD antibodies to human CFD.

| | ka | kd | Rmax | KD | | ka | kd | Rmax | KD |
|---|---|---|---|---|---|---|---|---|---|
| KCDKCD000 | 6.94E+05 | 1.75E−04 | 201.8 | 2.52E−10 | KCD004 | 4.44E+05 | 1.57E−04 | 97.1 | 3.53E−10 |
| KCD009 | 3.12E+05 | 1.74E−03 | 51.96 | 5.57E−09 | KCD014 | 3.77E+05 | 8.21E−03 | 8.28 | 2.18E−08 |
| KCD019 | 1.90E+05 | 1.37E−03 | 52.6 | 7.24E−09 | KCD033 | 2.38E+05 | 2.60E−03 | 101.34 | 1.09E−08 |
| KCD040 | 2.21E+05 | 4.27E−04 | 384.58 | 1.93E−09 | KCD047 | 2.94E+05 | 1.29E−03 | 324.83 | 4.37E−09 |
| KCD056 | 2.17E+05 | 1.30E−02 | 84.43 | 6.02E−08 | KCD062 | 2.19E+05 | 5.26E−03 | 90.54 | 2.40E−08 |
| KCD066 | 2.42E+05 | 6.97E−04 | 23.43 | 2.88E−09 | KCD075 | 2.65E+05 | 9.94E−04 | 309.99 | 3.75E−09 |
| KCD103 | 3.30E+05 | 1.44E−03 | 179.72 | 4.37E−09 | KCD110 | 2.41E+05 | 8.93E−04 | 121.2 | 3.71E−09 |
| KCD115 | 2.18E+05 | 2.77E−03 | 74.25 | 1.27E−08 | KCD122 | 3.59E+05 | 5.16E−04 | 174.65 | 1.44E−09 |
| KCD126 | 4.35E+05 | 1.48E−04 | 62.33 | 3.40E−10 | KCD131 | 3.46E+05 | 4.85E−05 | 164.28 | 1.40E−10 |
| KCD136 | 3.62E+05 | 1.61E−03 | 194.38 | 4.46E−09 | KCD205 | 2.76E+05 | 8.23E−04 | 138.87 | 2.98E−09 |
| KCD212 | 5.93E+05 | 2.78E−04 | 52.41 | 4.69E−10 | KCD219 | 1.94E+05 | 8.33E−04 | 242.08 | 4.30E−09 |
| KCD225 | 3.19E+05 | 2.77E−03 | 118.29 | 8.67E−09 | KCD48-2 | 2.90E+05 | 5.78E−04 | 300.35 | 1.99E−09 |
| KCD001 | 4.25E+05 | 9.56E−05 | 124.66 | 2.25E−10 | KCD005 | 5.37E+05 | 7.48E−04 | 109.08 | 1.39E−09 |
| KCD010 | 6.01E+05 | 1.84E−03 | 154.28 | 3.05E−09 | KCD015 | 2.90E+05 | 1.80E−03 | 422.7 | 6.23E−09 |
| KCD022 | 1.27E+05 | 7.21E−03 | 103.5 | 5.68E−08 | KCD036 | 1.56E+05 | 3.98E−03 | 69.76 | 2.55E−08 |
| KCD042 | 6.85E+05 | 9.81E−04 | 72.1 | 1.43E−09 | KCD048 | 3.01E+05 | 5.62E−04 | 297.54 | 1.87E−09 |
| KCD057 | 3.94E+05 | 1.07E−03 | 66.47 | 2.71E−09 | KCD063 | 1.49E+05 | 4.97E−03 | 43.25 | 3.33E−08 |
| KCD068 | 0.00E+00*** | 0.00E+00*** | 0.00E+00*** | 0.00E+00*** | KCD077 | 2.88E+05 | 4.87E−03 | 116.48 | 1.69E−08 |
| KCD104 | 4.81E+05 | 7.60E−04 | 211.38 | 1.58E−09 | KCD111 | 2.96E+05 | 1.95E−03 | 260.3 | 6.58E−09 |
| KCD118 | 5.71E+05 | 4.32E−04 | 95.9 | 7.57E−10 | KCD123 | 2.85E+05 | 7.87E−04 | 134.7 | 2.77E−09 |
| KCD128 | 1.19E+05 | 1.68E−03 | 79.94 | 1.40E−08 | KCD132 | 1.77E+05 | 4.63E−04 | 277.7 | 2.61E−09 |
| KCD137 | 1.34E+05 | 6.74E−05 | 140.51 | 5.04E−10 | KCD207 | 1.85E+05 | 1.44E−04 | 53.42 | 7.81E−10 |
| KCD214 | 1.46E+05 | 2.27E−04 | 224 | 1.56E−09 | KCD220 | 4.69E+05 | 2.51E−05 | 161.1 | 5.35E−11 |
| KCD229 | 1.39E+05 | 1.70E−04 | 48.61 | 1.22E−09 | OG1931 | 2.93E+05 | 1.46E−04 | 406.9 | 4.97E−10 |
| KCD002 | 1.26E+06 | 1.67E−04 | 92.4 | 1.32E−10 | KCD006 | 4.00E+05 | 2.52E−03 | 181 | 6.30E−09 |
| KCD011 | 1.95E+05 | 1.51E−02 | 84.2 | 7.75E−08 | KCD017 | 1.73E+05 | 1.35E−03 | 146.58 | 7.85E−09 |
| KCD023 | 5.24E+05 | 2.77E−03 | 234.44 | 5.29E−09 | KCD038 | 2.02E+05 | 7.53E−03 | 80.56 | 3.72E−08 |
| KCD044 | 6.13E+05 | 1.61E−03 | 58.32 | 2.62E−09 | KCD050 | 2.49E+05 | 4.88E−04 | 107.09 | 1.96E−09 |
| KCD058 | 2.07E+05 | 2.05E−03 | 48.32 | 9.91E−09 | KCD064 | 2.21E+05 | 4.49E−03 | 87.19 | 2.03E−08 |
| KCD070 | 7.03E+05 | 2.69E−03 | 67.47 | 3.83E−09 | KCD101 | 3.46E+05 | 1.31E−03 | 321.4 | 3.78E−09 |
| KCD107 | 0.00E+00*** | 0.00E+00*** | 0.00E+00*** | 0.00E+00*** | KCD112 | 2.08E+05 | 1.67E−03 | 142.45 | 8.05E−09 |
| KCD119 | 4.88E+05 | 1.83E−04 | 148.79 | 3.75E−10 | KCD124 | 4.26E+05 | 1.84E−03 | 111.24 | 4.32E−09 |
| KCD129 | 1.47E+05 | 4.26E−04 | 30.07 | 2.90E−09 | KCD133 | 3.41E+05 | 3.92E−03 | 94.19 | 1.15E−08 |
| KCD138 | 0.00E+00*** | 0.00E+00*** | 0.00E+00*** | 0.00E+00*** | KCD208 | 1.86E+05 | 4.73E−04 | 213.44 | 2.55E−09 |
| KCD215 | 0.00E+00*** | 0.00E+00*** | 0.00E+00*** | 0.00E+00*** | KCD221 | 0.00E+00*** | 0.00E+00*** | 0.00E+00*** | 0.00E+00*** |
| KCD230 | 3.55E+05 | 8.80E−04 | 231.63 | 2.48E−09 | KCD119 | 3.68E+05 | 3.16E−04 | 237.05 | 8.57E−10 |
| KCD003 | 6.64E+05 | 7.00E−04 | 154.22 | 1.05E−09 | KCD008 | 3.40E+05 | 1.49E−03 | 291.8 | 4.38E−09 |
| KCD013 | 4.49E+05 | 3.29E−03 | 117.5 | 7.32E−09 | KCD018 | 1.78E+05 | 7.24E−03 | 109 | 4.08E−08 |
| KCD030 | 2.16E+05 | 9.02E−04 | 76 | 4.17E−09 | KCD039 | 1.46E+05 | 7.69E−03 | 96.59 | 5.25E−08 |
| KCD045 | 0.00E+00*** | 0.00E+00*** | 0.00E+00*** | 0.00E+00*** | KCD052 | 2.09E+05 | 6.43E−04 | 89.82 | 3.07E−09 |
| KCD060 | 0.00E+00*** | 0.00E+00*** | 0.00E+00*** | 0.00E+00*** | KCD065 | 1.97E+05 | 6.45E−04 | 287 | 3.28E−09 |
| KCD073 | 0.00E+00*** | 0.00E+00*** | 0.00E+00*** | 0.00E+00*** | KCD102 | 3.15E+05 | 1.12E−03 | 338.4 | 3.56E−09 |
| KCD109 | 0.00E+00*** | 0.00E+00*** | 0.00E+00*** | 0.00E+00*** | KCD114 | 2.31E+05 | 1.86E−03 | 156.55 | 8.06E−09 |
| KCD121 | 5.52E+05 | 9.95E−04 | 178.49 | 1.80E−09 | KCD125 | 3.06E+05 | 1.15E−03 | 173.9 | 3.75E−09 |
| KCD130 | 0.00E+00*** | 0.00E+00*** | 0.00E+00*** | 0.00E+00*** | KCD135 | 1.65E+05 | 3.49E−03 | 132.92 | 2.12E−08 |
| KCD139 | 3.63E+05 | 1.92E−03 | 96.98 | 5.28E−09 | KCD210 | 2.76E+05 | 9.72E−04 | 122.29 | 3.52E−09 |
| KCD216 | 4.46E+05 | 1.37E−03 | 124.99 | 3.07E−09 | KCD224 | 7.92E+04 | 9.27E−05 | 146.74 | 1.17E−09 |
| KCD232 | 1.51E+05 | 4.20E−04 | 25.82 | 2.79E−09 | Isotype Control | 0.00E+00*** | 0.00E+00*** | 0.00E+00*** | 0.00E+00*** |

*Antibodies with values in grey did not bind CFD under these conditions

*Antibodies with values marked with *** did not bind CFD under these conditions

TABLE 2.2

Binding affinities of 91 recombinantly expressed anti-CFD antibodies to various human and cyno CFD proteins.

| | hCFD-Comptech | rcyCFD-His | rhCFD-His | rhCFD-mut1-His |
|---|---|---|---|---|
| KCD000 | 2.5E−10 | 4.2E−10 | 2.1E−10 | na |
| KCD009 | 5.6E−09 | 9.9E−09 | 4.0E−09 | na |
| KCD019 | 7.2E−09 | 4.7E−08 | 6.1E−08 | 1.8E−07 |
| KCD040 | 1.9E−09 | 1.7E−07 | 1.4E−09 | 7.5E−10 |
| KCD056 | 6.0E−08 | 3.1E−08 | 5.2E−08 | 8.4E−08 |
| KCD066 | 2.9E−09 | 4.0E−09 | 1.9E−09 | 1.2E−09 |
| KCD103 | 4.4E−09 | 6.3E−08 | 3.1E−09 | 2.5E−09 |
| KCD115 | 1.3E−08 | 1.8E−08 | 6.2E−09 | 7.8E−09 |
| KCD126 | 3.4E−10 | 9.3E−10 | 2.9E−10 | 1.8E−10 |
| KCD136 | 4.5E−09 | 2.7E−08 | 3.4E−09 | 1.4E−09 |
| KCD212 | 4.7E−10 | 3.8E−09 | 2.1E−10 | 2.0E−10 |
| KCD225 | 8.7E−09 | 4.6E−08 | 5.0E−09 | 6.2E−09 |
| KCD001 | 2.2E−10 | 6.3E−10 | 2.2E−10 | 1.9E−10 |
| KCD010 | 3.1E−09 | 2.9E−09 | 2.5E−09 | na |
| KCD022 | 5.7E−08 | 5.4E−08 | 8.3E−08 | 1.1E−07 |
| KCD042 | 1.4E−09 | 3.0E−09 | 1.0E−09 | 4.2E−10 |
| KCD057 | 2.7E−09 | 3.1E−09 | 2.7E−09 | 2.5E−09 |
| KCD068 | na | na | na | na |
| KCD104 | 1.6E−09 | 7.2E−08 | 1.2E−09 | 8.2E−10 |
| KCD118 | 7.6E−10 | 1.3E−09 | 5.4E−10 | na |
| KCD128 | 1.4E−08 | 3.3E−09 | 1.4E−08 | 1.3E−08 |
| KCD137 | 5.0E−10 | 5.9E−09 | 5.5E−09 | 4.6E−09 |
| KCD214 | 1.6E−09 | 2.6E−08 | 1.1E−09 | 1.3E−09 |
| KCD229 | 1.2E−09 | 1.6E−09 | 1.2E−09 | 2.4E−09 |
| KCD002 | 1.3E−10 | 4.1E−10 | 1.1E−10 | 8.0E−11 |
| KCD011 | 7.7E−08 | 3.8E−08 | 5.9E−08 | 1.1E−07 |
| KCD023 | 5.3E−09 | 6.0E−09 | 4.1E−09 | na |
| KCD044 | 2.6E−09 | 6.0E−09 | 1.8E−09 | 9.6E−10 |
| KCD058 | 9.9E−09 | 1.1E−08 | 9.4E−09 | 7.6E−09 |
| KCD070 | 3.8E−09 | 4.9E−09 | 3.3E−09 | 7.0E−10 |
| KCD107 | na | na | na | na |
| KCD119 | 3.7E−10 | 7.0E−10 | 2.8E−10 | na |
| KCD129 | 2.9E−09 | 6.0E−09 | 2.1E−09 | 2.7E−09 |
| KCD138 | na | 1.1E−08 | na | na |
| KCD215 | na | na | na | na |
| KCD230 | 2.5E−09 | 2.7E−09 | 1.6E−09 | 8.8E−10 |
| KCD003 | 1.1E−09 | 1.8E−09 | 8.1E−10 | na |
| KCD013 | 7.3E−09 | 9.3E−08 | 1.1E−08 | 1.9E−08 |
| KCD030 | 4.2E−09 | na | 3.8E−09 | 1.3E−09 |
| KCD045 | na | na | na | na |
| KCD060 | na | na | na | na |
| KCD073 | na | na | na | na |
| KCD109 | na | na | na | na |
| KCD121 | 1.8E−09 | 2.9E−09 | 1.3E−09 | na |
| KCD130 | na | na | na | na |
| KCD139 | 5.3E−09 | 3.8E−09 | 3.3E−09 | 3.5E−09 |
| KCD216 | 3.1E−09 | 1.3E−08 | 2.0E−09 | 1.9E−09 |
| KCD232 | 2.8E−09 | 5.5E−09 | 2.4E−09 | 4.4E−09 |
| KCD004 | 3.5E−10 | 9.2E−10 | 2.4E−10 | 1.4E−10 |
| KCD014 | 2.2E−08 | na | 2.0E−08 | na |
| KCD033 | 1.1E−08 | 9.3E−08 | 1.9E−08 | 2.8E−08 |
| KCD047 | 4.4E−09 | 1.6E−07 | 3.4E−09 | 2.9E−09 |
| KCD062 | 2.4E−08 | 1.9E−08 | 3.2E−08 | 6.2E−08 |
| KCD075 | 3.7E−09 | 3.2E−09 | 2.5E−09 | 3.4E−09 |
| KCD110 | 3.7E−09 | 5.3E−09 | 2.0E−09 | 4.1E−09 |
| KCD122 | 1.4E−09 | 1.9E−09 | 9.5E−10 | na |
| KCD131 | 1.4E−10 | 9.9E−10 | 4.7E−11 | 4.5E−11 |
| KCD205 | 3.0E−09 | 3.3E−09 | 1.9E−09 | 1.8E−09 |
| KCD219 | 4.3E−09 | 1.2E−08 | 3.0E−09 | 3.6E−09 |
| KCD48-2 | 2.0E−09 | 2.1E−08 | 1.4E−09 | 8.6E−10 |
| KCD005 | 1.4E−09 | 2.3E−09 | 1.2E−09 | na |
| KCD015 | 6.2E−09 | 2.5E−07 | 4.5E−09 | 3.7E−09 |
| KCD036 | 2.6E−08 | 6.4E−08 | 2.9E−08 | 8.0E−08 |
| KCD048 | 1.9E−09 | 2.1E−08 | na | 8.3E−10 |
| KCD063 | 3.3E−08 | 2.4E−08 | na | na |
| KCD077 | 1.7E−08 | 1.4E−08 | na | 1.3E−08 |
| KCD111 | 6.6E−09 | 7.2E−09 | 4.2E−09 | 7.8E−09 |
| KCD123 | 2.8E−09 | 2.9E−09 | 1.3E−09 | na |
| KCD132 | 2.6E−09 | 8.0E−09 | 1.6E−09 | 1.4E−09 |
| KCD207 | 7.8E−10 | 1.4E−09 | 3.2E−10 | 3.1E−11 |
| KCD220 | 5.4E−11 | 2.8E−10 | 7.4E−11 | 2.9E−11 |
| OG1931 | 5.0E−10 | 6.4E−10 | 2.9E−10 | na |
| KCD006 | 6.3E−09 | 1.5E−07 | 5.8E−09 | 1.1E−08 |
| KCD017 | 7.8E−09 | 1.1E−08 | 1.3E−08 | 1.0E−08 |

TABLE 2.2-continued

Binding affinities of 91 recombinantly expressed anti-CFD antibodies to various human and cyno CFD proteins.

| | hCFD-Comptech | rcyCFD-His | rhCFD-His | rhCFD-mut1-His |
|---|---|---|---|---|
| KCD038 | 3.7E−08 | 4.5E−08 | 4.8E−08 | 8.4E−08 |
| KCD050 | 2.0E−09 | 8.2E−09 | 3.1E−09 | 1.9E−09 |
| KCD064 | 2.0E−08 | 1.5E−08 | 2.0E−08 | 3.7E−08 |
| KCD101 | 3.8E−09 | 2.4E−07 | 2.7E−09 | 2.8E−09 |
| KCD112 | 8.0E−09 | 9.1E−09 | 4.3E−09 | 7.1E−09 |
| KCD124 | 4.3E−09 | 5.2E−09 | 3.3E−09 | na |
| KCD133 | 1.2E−08 | 8.4E−08 | 1.4E−08 | 1.3E−08 |
| KCD208 | 2.5E−09 | 5.2E−08 | 1.9E−09 | 1.8E−09 |
| KCD221 | na | na | na | na |
| KCD119 | 8.6E−10 | 1.1E−09 | 5.6E−10 | na |
| KCD008 | 4.4E−09 | 6.6E−08 | 3.2E−09 | 5.7E−09 |
| KCD018 | 4.1E−08 | 5.2E−08 | 4.1E−08 | 9.9E−08 |
| KCD039 | 5.3E−08 | 3.9E−08 | 4.3E−08 | 7.0E−08 |
| KCD052 | 3.1E−09 | 1.0E−08 | 3.7E−09 | 2.5E−09 |
| KCD065 | 3.3E−09 | 2.5E−08 | 1.7E−08 | 2.5E−08 |
| KCD102 | 3.6E−09 | 2.3E−07 | 2.5E−09 | 2.5E−09 |
| KCD114 | 8.1E−09 | 8.4E−09 | 3.8E−09 | 8.4E−09 |
| KCD125 | 3.8E−09 | 4.1E−09 | 2.5E−09 | 2.7E−09 |
| KCD135 | 2.1E−08 | 1.8E−08 | 1.3E−08 | 1.5E−08 |
| KCD210 | 3.5E−09 | 3.6E−09 | 2.9E−09 | 2.9E−09 |
| KCD224 | 1.2E−09 | 1.0E−07 | 5.4E−10 | 1.1E−09 |
| Isotype Control | na | 3.9E−08 | na | na |

Example 3—Epitope Binning of Anti-CFD Antibodies Using Competition Binding Assay (Classical Binning)

Epitope binning of the 91 newly identified and recombinantly expressed anti-CFD antibodies together with a known anti-CFD antibody OG1931 were done by Wasatch Microfluidics using the MX96 SPR machine. In this classical binning assay, a competition cycle for each mAb was configured such that each ligand is immobilized on the surface and loaded with the target during the first phase, followed by injection of one of the competing species to test whether is binds or is blocked by the surface species.

Since the target CFD is monomeric, the classical binning configuration was used where the antibodies are amine-coupled to a 96-cell array. Each mAb was binned by testing its ability to block and sandwich with every other mAb in the array in a pair-wise, competition format. For each cycle, the target (serum purified CFD, rhCFD, or rcyCFD) was injected over the array and immediately followed by one of the sandwiching species. The array surface was regenerated between each cycle.

Example 4—Group Network Based on Binding Characteristics

Anti-CFD antibodies were grouped in discreet bins (Table 4.1) depending on their blocking/sandwiching behavior for binding to serum CFD, rhCFD, and rcyCFD, using the Scrubber software (BioLogic Software, LLC) and the Binning Tool (Wasatch Microfluidics Inc.).

TABLE 4.1

| Binning result using Washatch 96 × 96 antibody competition binding to CFD. | | | | | | | | | | |
|---|---|---|---|---|---|---|---|---|---|---|
| Group 1 | Group 2 | Group 3 | Group 4 | Group 5 | Group 6 | Group 7 | Group 8 | Group 9 | Group 10 | Group 11 |
| KCD023 | KCD036 | KCD017 | KCD112 | KCD225 | KCD220 | KCD230 | KCD210 | KCD224 | KCD062 | KCD038 |
| KCD010 | KCD212 | KCD050 | KCD115 | KCD030 | KCD004 | KCD135 | | KCD047 | KCD056 | KCD039 |
| KCD119 | KCD073 | KCD052 | KCD114 | KCD001 | KCD077 | | | KCD104 | KCD058 | |
| KCD122 | KCD207 | KCD065 | | KCD219 | KCD126 | | | KCD040 | KCD063 | |
| KCD119 | KCD107 | KCD019 | | KCD216 | KCD139 | | | KCD214 | KCD011 | |
| KCD003 | KCD068 | KCD128 | | KCD132 | KCD205 | | | KCD48-2 | KCD064 | |
| KCD121 | KCD033 | KCD137 | | KCD111 | KCD125 | | | KCD015 | KCD057 | |
| KCD123 | KCD133 | KCD022 | | KCD131 | KCD075 | | | KCD103 | | |
| OG1931 | KCD129 | | | KCD002 | KCD060 | | | KCD102 | | |
| KCD118 | KCD229 | | | KCD110 | KCD066 | | | KCD136 | | |
| KCD124 | KCD109 | | | | KCD018 | | | KCD101 | | |
| KCD005 | | | | | | | | KCD006 | | |
| KCD000 | | | | | | | | KCD008 | | |
| KCD009 | | | | | | | | KCD013 | | |
| | | | | | | | | KCD048 | | |
| | | | | | | | | KCD042 | | |
| | | | | | | | | KCD044 | | |
| | | | | | | | | KCD208 | | |

Example 5. Identification and Characterization of Antagonistic Anti-CFD Antibodies Amongst 91 antibody synthesized and expressed in 293 cells, 29 blocked alternative pathway dependent hemolysis of rabbit red blood cells (RBC) by human plasma. Table 0.1A shows the variable domain sequences of these 29 antibodies. All 29 blocking antibodies blocked CFD binding to C3bB. These 29 antibodies were grouped into 6 phenotypic bins based on their effect on CFD enzymatic activity using a small synthetic peptide substrate, and if they can sandwich with the anti-CFD positive control antibody OG1931 (tables 5.3-5.9).

Hemolysis assay: Hemolysis assay—For the hemolysis assay, rabbit red blood cells ("RBCs", CompTech #B301) are diluted or re-suspended and washed with $GVB^0$ (without $Ca^{2+}$ and $Mg^{2+}$, CompTech #B101) 3 times, then re-suspended in ice-cold GVB++ buffer (GVB/2 mM MgEGTA) at 4.33e8/mL and kept at 4° C. when ready to be used.

Proteolysis assay—Anti-CFD antibodies (AFDs) were evaluated for their ability to affect the enzymatic activity of human CFD for the synthetic substrate Z-L-Lys-SBzl hydrochloride. For the proteolysis assay, human CFD is diluted to 200 uM in assay buffer (50 mM Tris, 220 mM NaCl, pH 7.5). Substrate (Z-L-Lys-SBzl hydrochloride, Sigma, C3647, 100 mM stock in DMSO) is diluted to 4 mM in assay buffer with 4 mM 5,5'Dithio-bis-(2-nitrobenzoic acid) (DTNB, Sigma, Catalog #D-8130, 100 mM stock in DMSO)2. 50 μL of the diluted CFD is loaded into a 96 well clear plate, and 50 uls of AFD is added. The reaction is started by adding 100 μL of substrate/DTNB mixture to wells. A substrate blank containing 100 μL assay buffer and 100 μL substrate mixture without any CFD is included. Using a plate reader (SpectraMax Plus or equivalent), samples are read in kinetic mode for 45 minutes at an absorbance of 405 nm. To calculate specific activity the following formula is used: Specific Activity (pmol/min/μg)=Adjusted Vmax*(OD/min)×well volume (L)×$10^{12}$ pmol/mol. ext. coeff($M^{-1}cm^{-1}$)×path corr.*(cm)×amount of enzyme (μg). *Adjusted for substrate blank, Using the extinction coefficient 13,260 $M^{-1}cm^{-1}$, *Using the path correction 0.320 cm.

Binding characterization ELISA (enzyme-linked immunosorbent assay) assays were used to characterize binding of anti-CFD antibodies ("AFDs") to CFD or a mutant of CFD (CFD mutant 1). CFD mutant 1 was generated that does not bind its substrate C3bB, but retains CFD enzymatic activity. CFD mutant 1 has the mutations R157A and R207A (positions based on linear positions in mature protein; using the canonical sequence based on chymotrypsin, the mutations are positions R177A and R227A. Katschke et al. 2012, Supplemental Materials FIG. S6).

Competition assay—To determine whether anti-CFD antibodies (AFDs) block binding of CFD to Factor B (FB), a competition assay was used. Purified human C3b (CompTech) was immobilized onto a CM5 biosensor chip (GE). Recombinant C3b was diluted to 40 ug/ml in acetate buffer (pH 4.5) and immobilized via amine coupling to the CM5 chip by following the immobilization wizard software (Biacore™ T200) with a 7 minute contact time. C3b was immobilized at 14000 resonance units (RU) on a Biacore T200 (GE Healthcare). HBS buffer (no EDTA) with 2 mM $MgCl_2$ was used as running buffer to assess binding of (a) FB, (b) CFD, or (c) FB+CFD to immobilized C3b in the presence and absence of AFDs. 3 M $MgCl_2$ was used as a regeneration buffer to remove all bound proteins after processing each sample.

A confirmed AFD non-blocker, antibody KCD004, was used as a control for maximal binding of a FB/CFD/AFD complex to C3b, while FB alone was used to set to lower limit of binding to C3b, such as would be the case with a full AFD-blocking antibody.

The anti-CFD antibodies were sorted into six different bins based on binding specificity, ability to inhibit complement-activated hemolysis, and effect on enzymatic activity of human CFD for the synthetic substrate Z-L-Lys-SBzl hydrochloride.

Table 5.3 summarizes the six bins and their characteristics, Tables 5.4 through 5.9 provides examples of anti-CFD antibodies belonging to each bin.

TABLE 5.3

| 29 Blocking Antibodies Belong to 6 Phenotype Bins | | | | | |
|---|---|---|---|---|---|
| | Rabbit RBC Hemolysis | CFD Enzymatic activity | CFD Binding to C3bB | Sandwich with OG1931 | Group Network Groups |
| Bin 1 (OG1931) | Inhibit | increase | inhibit | No | Group 1 |
| Bin 2 | Inhibit | inhibit | inhibit | No | Group 1 |
| Bin 3 | Inhibit | no effect | inhibit | No | Group 1 |
| Bin 4 | Inhibit | increase | inhibit | Yes | Group 9 |
| Bin 5 | Inhibit | inhibit | inhibit | Yes | Group 9 |
| Bin 6 | Inhibit | no effect | inhibit | Yes | Group 9, 5 |

TABLE 5.4

| Bin 1 | | | | | | | |
|---|---|---|---|---|---|---|---|
| Antibody | Rabbit RBC Hemolysis | CFD Enzymatic activity (% of Neg Ctrl) | kD (M) | Mut1 Binding (% wt) | Sandwich with OG1931 | Competition Binding | Mouse # |
| Bin 1 | Inhibit | Increase | | No | No | | |
| OG1931 | +++ | 211.08 | 7.52E−12 | 7.01 | No | Bin A | N/A |

TABLE 5.5

| Bin 2 | | | | | | | |
|---|---|---|---|---|---|---|---|
| Antibody | Rabbit RBC Hemolysis | CFD Enzymatic activity (% of Neg Ctrl) | kD (M) | Mut1 Binding (% wt) | Sandwich with OG1931 | Competition Binding | Mouse # |
| Bin 2 | Inhibit | Inhibit | | No | No | | |
| KCD010 | +++ | 49.38 | 1.46E−09 | 3.77 | No | Bin A | Balb/c #2 |
| KCD003 | +++ | 19.62 | 3.18E−10 | 1.53 | No | Bin A | C57BL#1 or #2 |
| KCD005 | +++ | 49.23 | 7.26E−10 | 1.79 | No | Bin A | C57BL #1 or #2 |
| KCD118 | +++ | 13.96526 | 8.83E−11 | 0.762389 | No | Bin A | C57BL#2 |
| KCD119 | +++ | 15.69617 | 3.58E−11 | 13.58885 | No | Bin A | C57BL#2 |
| KCD121 | +++ | 16.67982 | 2.93E−10 | 0.602107 | No | Bin A | C57BL#2 |
| KCD122 | +++ | 17.31039 | 1.62E−10 | 2.247191 | No | Bin A | C57BL#2 |
| KCD123 | +++ | 18.74613 | 2.77E−10 | 2.910053 | No | Bin A | C57BL#2 |
| KCD124 | +++ | 19.69798 | 7.80E−10 | −0.6435 | No | Bin A | C57BL#2 |

TABLE 5.6

| Bin 3 | | | | | | | |
|---|---|---|---|---|---|---|---|
| Antibody | Rabbit RBC Hemolysis | CFD Enzymatic activity (% of Neg Ctrl) | kD (M) | Mut1 Binding (% wt) | Sandwich with OG1931 | Competition Binding | Mouse # |
| Bin 3 | Inhibit | No Effect | | No | No | | |
| KCD009 | +++ | 148.39 | 3.47E−09 | 5.15 | No | Bin A | Balb/C #2 |
| KCD023 | +++ | 71.84 | 1.77E−06 | 7.64 | No | Bin A | Balb/C #2 |

TABLE 5.7

| Antibody | Rabbit RBC Hemolysis | CFD Enzymatic activity (% of Neg Ctrl) | kD (M) | Mut1 Binding (% wt) | Sandwich with OG1931 | Competition Binding | Mouse # |
|---|---|---|---|---|---|---|---|
| Bin 4 | | | | | | | |
| Bin 4 | Inhibit | Increase | | Yes | Yes | | |
| KCD048 | +++ | 333.2908 | 9.97E−10 | 62.32239 | Yes | Bin B | Balb/C #2 |
| KCD070 | +++ | 169.2659 | 1.77E−09 | 84.61538 | Yes | N/A | Balb/C #2 |

TABLE 5.8

| Antibody | Rabbit RBC Hemolysis | CFD Enzymatic activity (% of Neg Ctrl) | kD (M) | Mut1 Binding (% wt) | Sandwich with OG1931 | Competition Binding | Mouse # |
|---|---|---|---|---|---|---|---|
| Bin 5 | | | | | | | |
| Bin 5 | Inhibit | Inhibit | | Yes | Yes | | |
| KCD042 | +++ | 6.797026 | 1.09E−09 | 65.55184 | Yes | Bin B | Balbc #2 |
| KCD040 | +++ | 13.6563 | 7.91E−08 | 62.1775 | Yes | Bin B | Balbc #2 |
| KCD044 | +++ | 8.801277 | 1.02E−09 | 62.54489 | Yes | Bin B | Balbc #2 |
| KCD047 | +++ | 47.29286 | 6.62E−09 | 58.8909 | Yes | Bin B | Balbc #2 |
| KCD208 | +++ | 0 | 4.51E−10 | 56.70651 | Yes | Bin B | Swiss webster #2 |
| KCD214 | +++ | 12.77884 | 2.45E−10 | 44.29379 | Yes | Bin B | Swiss webster #2 |
| KCD224 | +++ | 36.31433 | 1.56E−11 | 121.4383 | Yes | Bin B | Swiss webster #2 |
| KCD136 | +++ | 11.81753 | 5.87E−10 | 78.3358 | Yes | Bin B | C57BL#2 |

TABLE 5.9

| Antibody | Rabbit RBC Hemolysis | CFD Enzymatic activity (% of Neg Ctrl) | kD (M) | Mut1 Binding (% wt) | Sandwich with OG1931 | Competition Binding | Mouse # |
|---|---|---|---|---|---|---|---|
| Bin 6 | | | | | | | |
| Bin 6 | Inhibit | No effect | | Yes | Yes | | |
| KCD002 | +++ | 143.72 | 3.07E−11 | 71.24 | Yes | Bin D | C57BL#1 or #2 |
| KCD101 | +++ | 93.15411 | 1.45E−09 | 65.79151 | Yes | Bin B | C57BL#2 |
| KCD102 | +++ | 92.27025 | 6.98E−09 | 64.26183 | Yes | Bin B | C57BL#2 |
| KCD103 | +++ | 126.4488 | 1.48E−09 | 65.2 | Yes | Bin B | C57BL#2 |
| KCD104 | +++ | 92.28768 | 1.32E−09 | 68.27279 | Yes | Bin B | C57BL#2 |
| KCD131 | +++ | 65.91077 | 3.42E−11 | 80.71025 | Yes | Bin D | C57BL#2 |
| KCD220 | +++ | 88.10648 | 6.39E−11 | 74.10941 | Yes | Bin G | Swiss Webster #2 |

Example 6

Figure 3A:
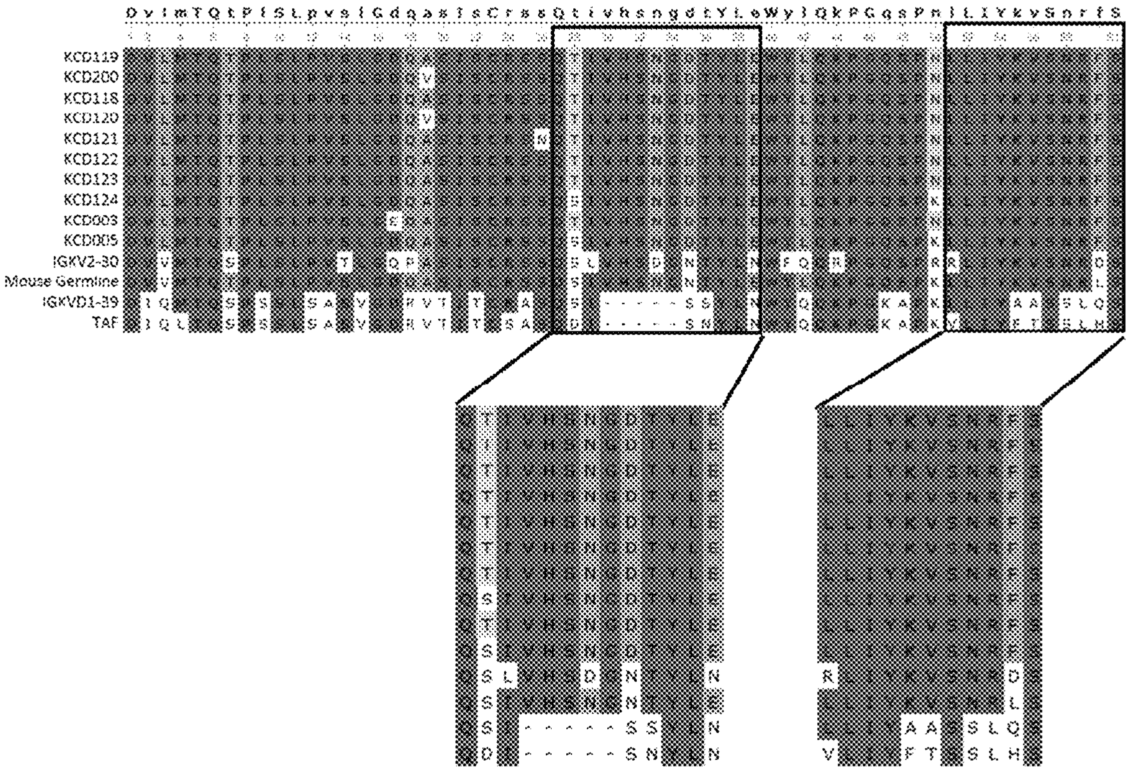
FIG. 3A shows KCD119 Family light chain alignment with human frameworks.
Figure 3B:
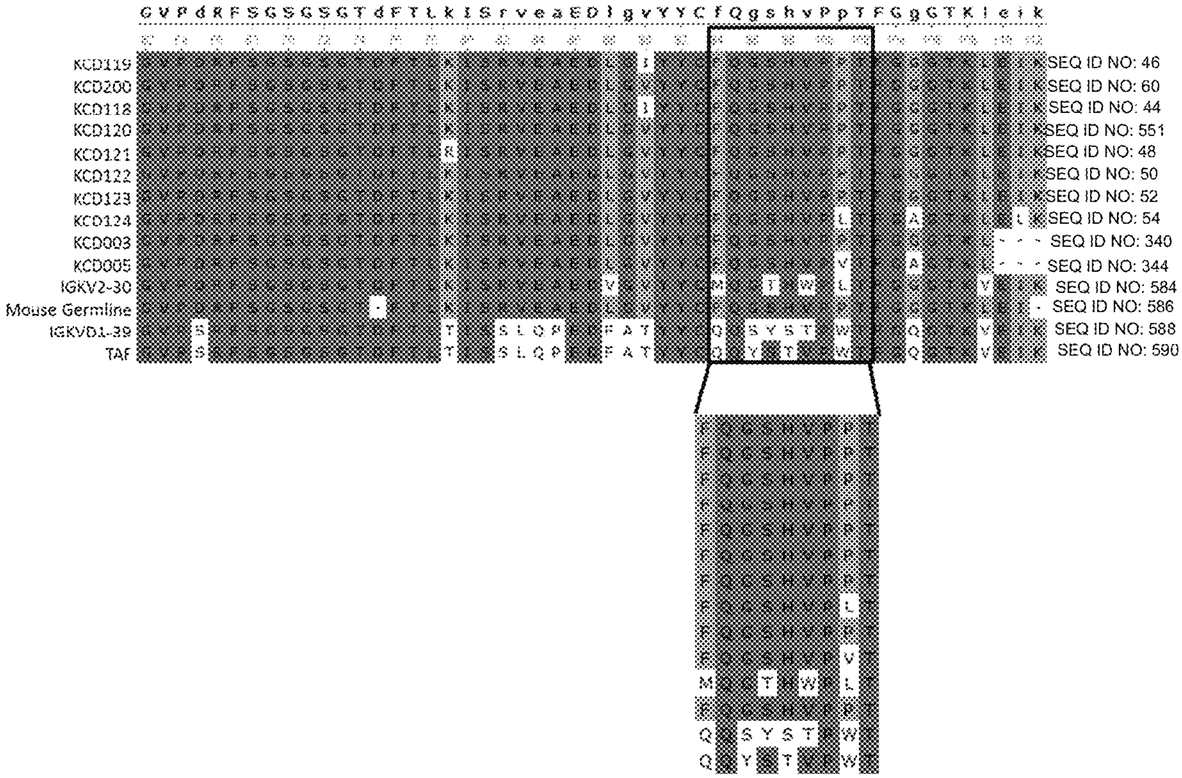
FIG. 3B shows KCD119 Family light chain alignment with human frameworks.
Figure 4A:
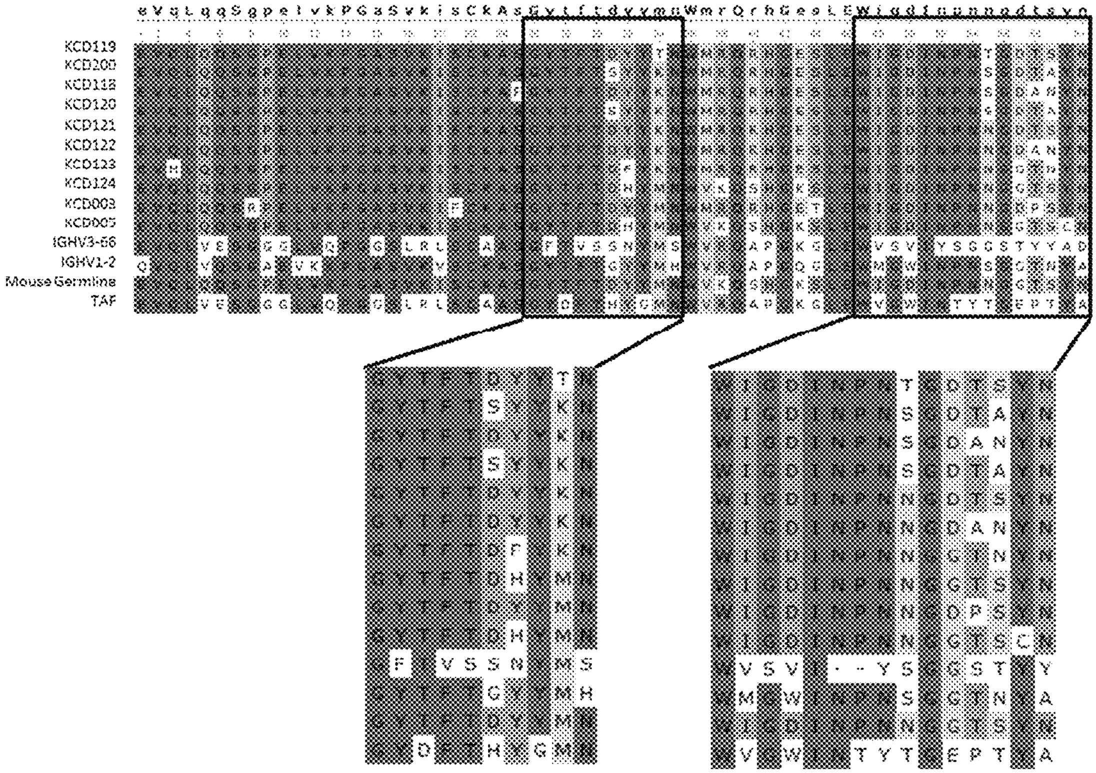
FIG. 4A shows KCD119 Family heavy chain alignment with human frameworks.
Figure 4B:
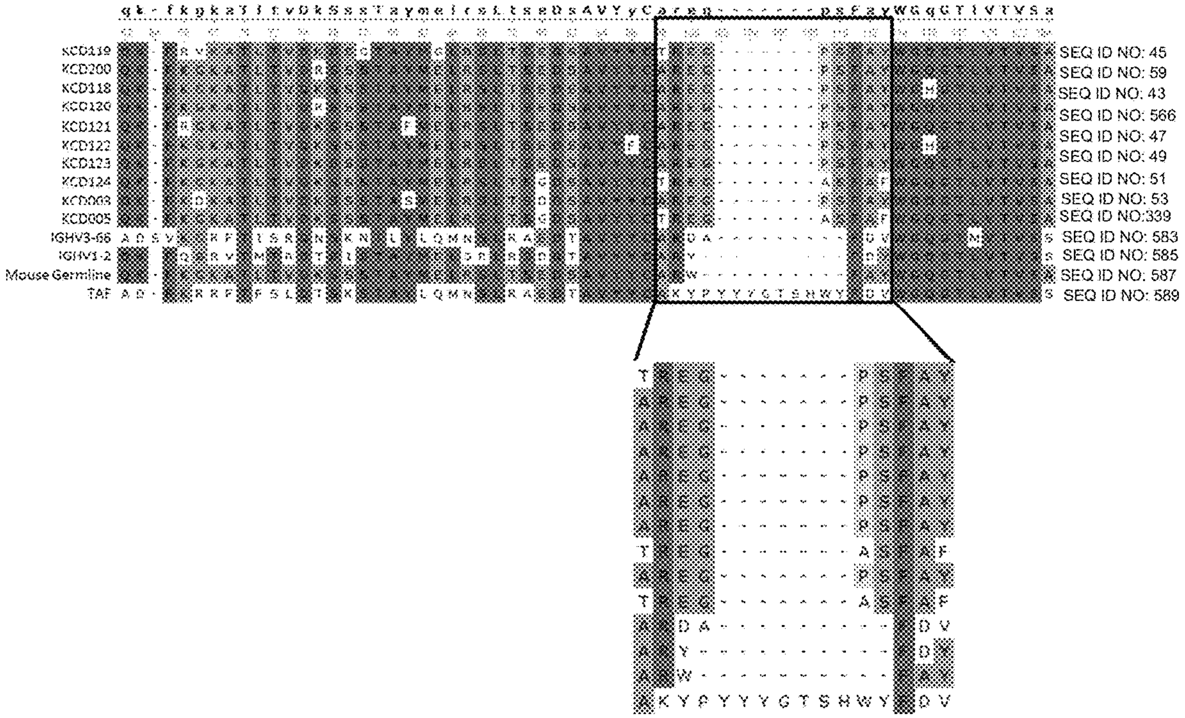
FIG. 4B shows KCD119 Family heavy chain alignment with human frameworks.

FIG. 3A and FIG. 31B show light chain alignment of a representative bin 2 antibody KCD119, and other antibodies obtained during screening that show high sequence identity to KCD119 (KCD119 family), along with representative human frameworks that KCD19 was grafted on. FIG. 4A and FIG. 4B show KCD119 Family heavy chain alignment.

Example 7—Humanization of KCD119

Binding kinetics were determined by measuring serum purified complement factor D binding to full-length IgG captured on protein A chip or Fab captured on CM5 chip coated with anti-Fab (Biacore Human Fab Capture Kit) according to manufacturer's instructions.

Figure 5A:
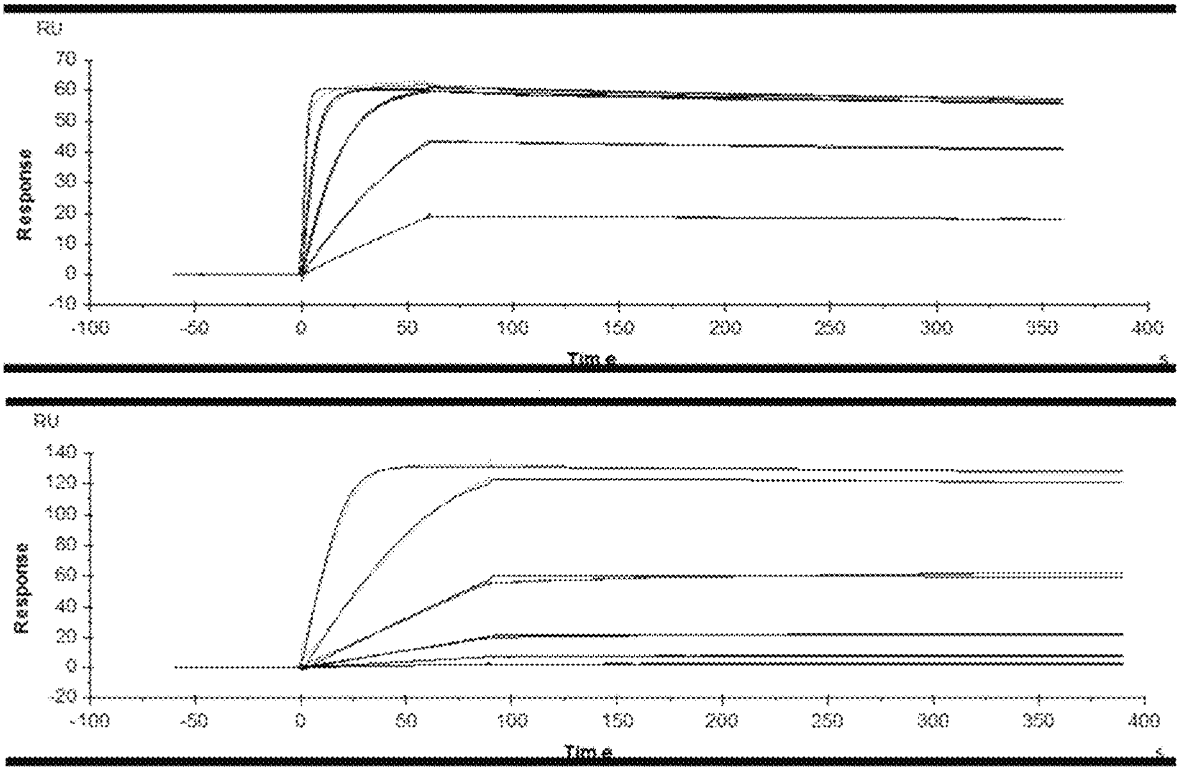
FIG. 5A shows binding affinity of KCD119-mouse monoclonal antibody to purified human CFD measured on Biacore T2000. Top panel shows binding and disassociation curve of full IgG (capture on Protein A chip). Bottom panel shows binding and disassociation curve of Fab (capture on CM5 chip immobilized with anti-human Fab capture kit).
Figure 5B:
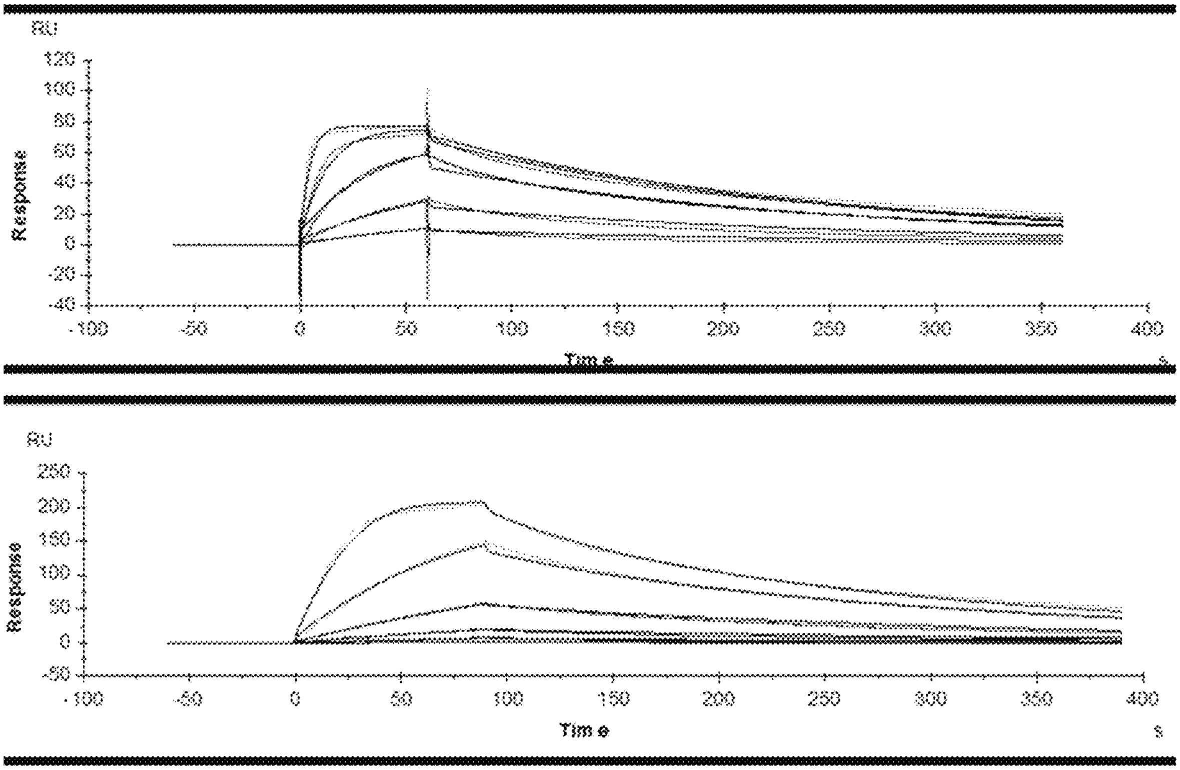
FIG. 5B shows binding affinity of KCD119-3-66 (KCD119 CDRs grafted onto human germlines IGHV3-66 and IGKVD1-39) binding affinity to purified human CFD measured on Biacore T2000 Top panel shows binding and disassociation curve of full IgG (capture on Protein A chip). Bottom panel shows binding and disassociation curve of Fab (capture on CM5 chip immobilized with anti-human Fab capture kit).
Figure 5C:
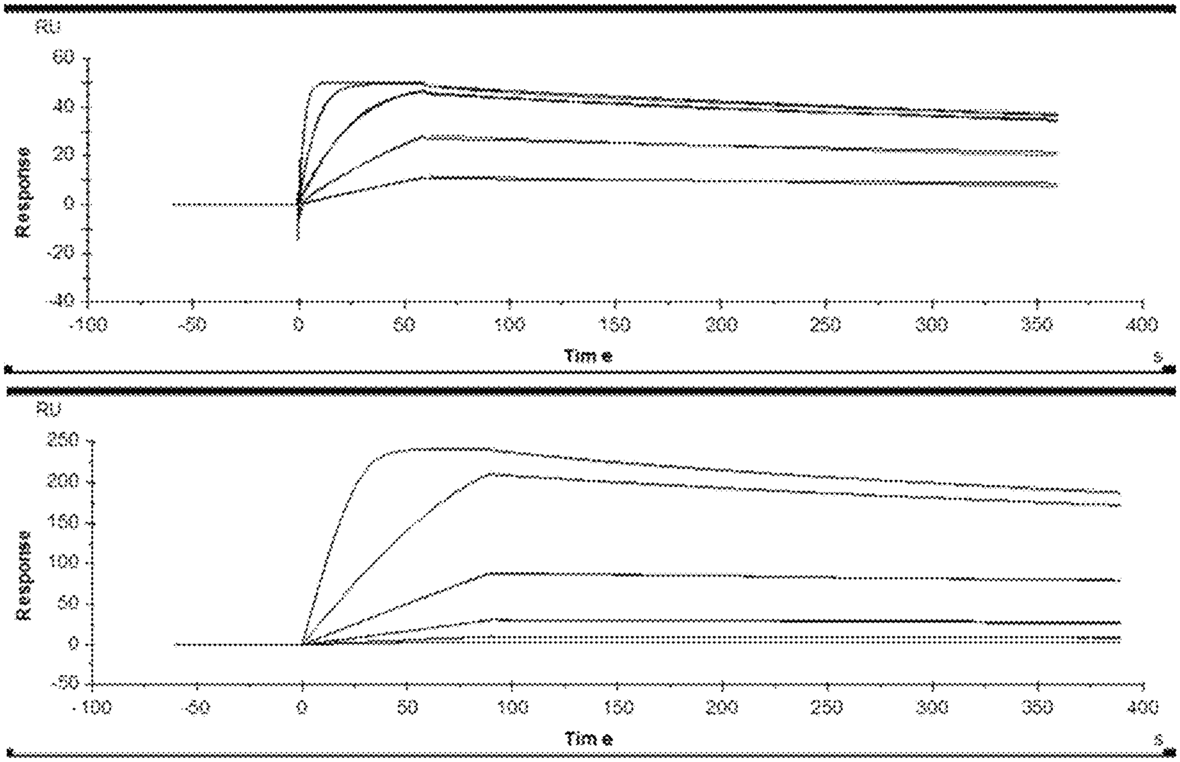
FIG. 5C shows binding affinity of KCD119-TAF to purified human CFD measured on Biacore 2000. Top panel shows binding and disassociation curve of full IgG (capture on Protein A chip). Bottom panel shows binding and disassociation curve of Fab (capture on CM5 chip immobilized with anti-human Fab capture kit).
Figure 6A:
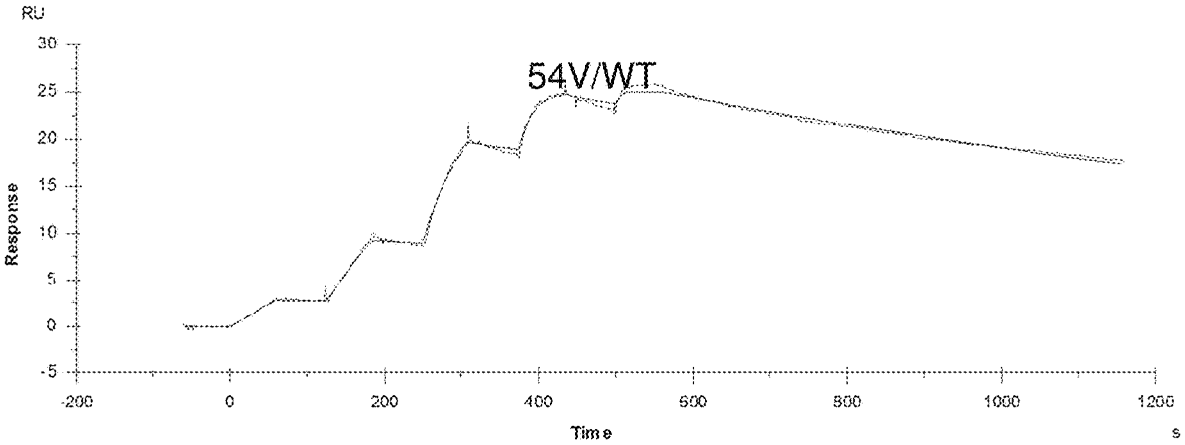
FIG. 6A shows Factor D binding kinetics data for an embodiment of a combination of both heavy and light chain mutations that corresponded with positive changes in affinity.
Figure 6B:
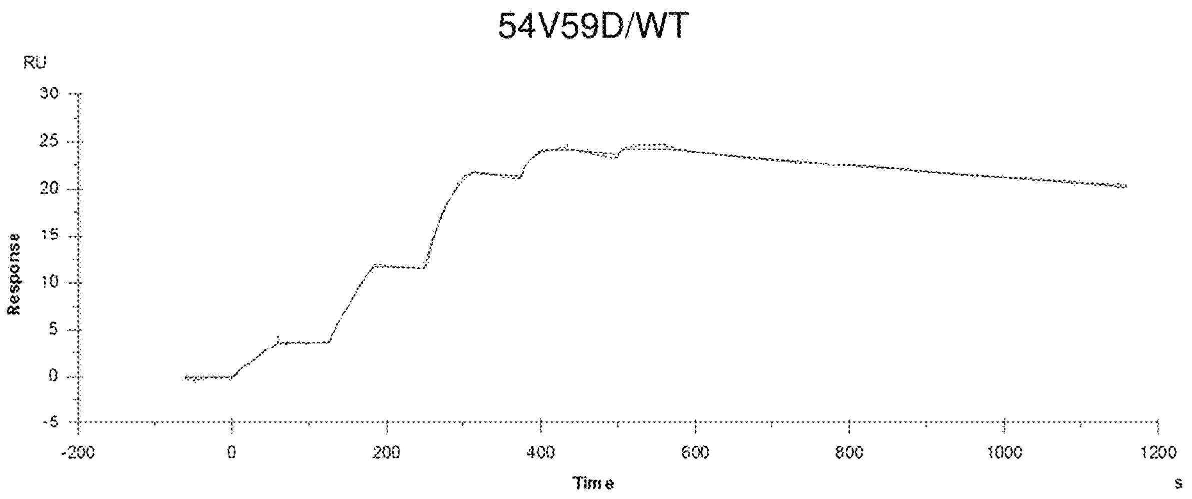
FIG. 6B shows Factor D binding kinetics data for an embodiment of a combination of both heavy and light chain mutations that corresponded with positive changes in affinity.
Figure 6C:
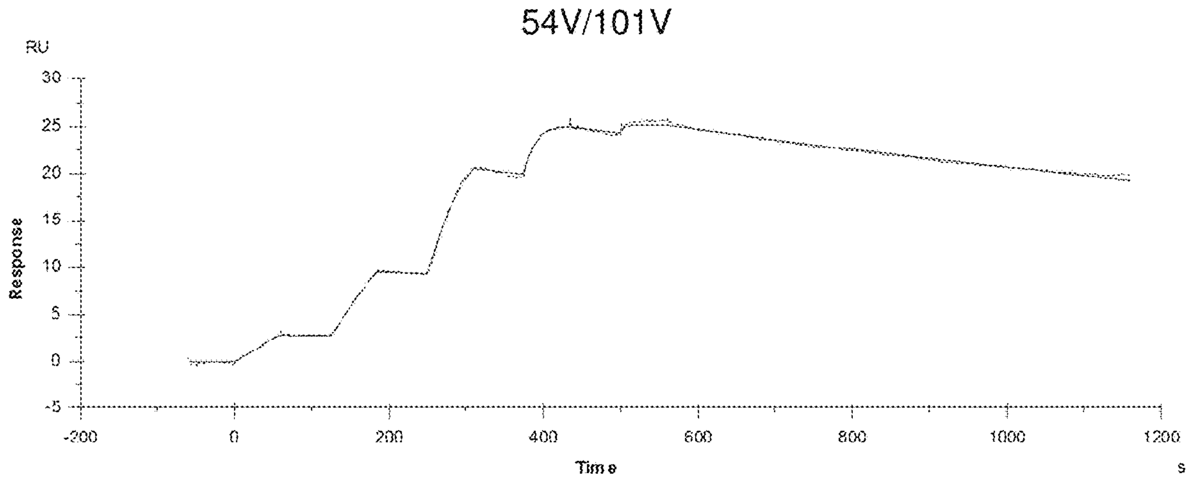
FIG. 6C shows Factor D binding kinetics data for an embodiment of a combination of both heavy and light chain mutations that corresponded with positive changes in affinity.
Figure 6D:
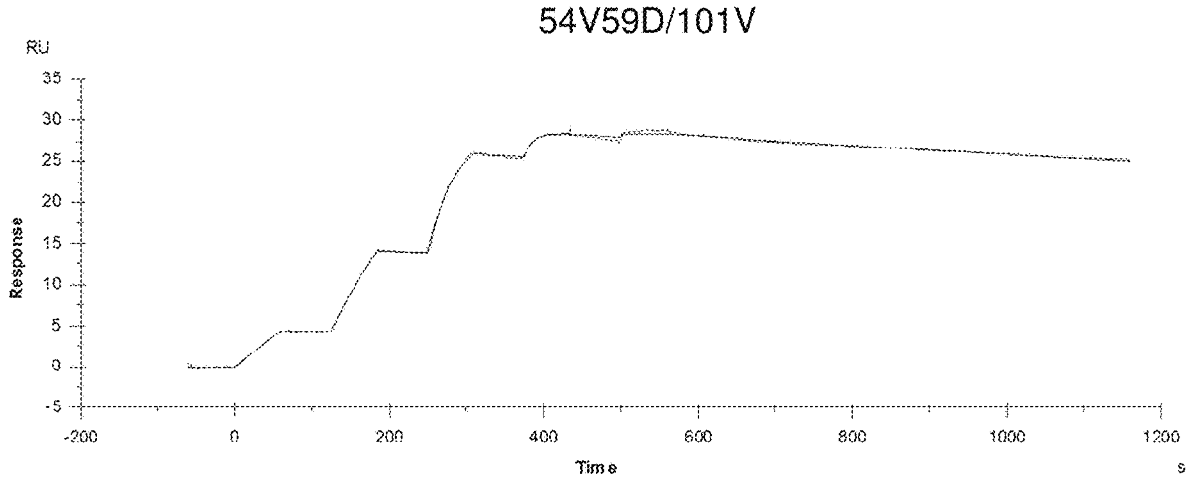
FIG. 6D shows Factor D binding kinetics data for an embodiment of a combination of both heavy and light chain mutations that corresponded with positive changes in affinity.

KCD119 CDR1, CDR2, and CDR3 for both the heavy and light chains were grafted into human variable domain frameworks IGHV 3-66 and IGK1-39, or “TAF” (IGHV 3-66 and IGK1-39 with some framework mutations), or IGHV1-2 and IGKv2-30. KCD119 CDRs with the original mouse framework (FIG. 5A) has a kD for human Complement Factor D of 40 pM, while KCD1119 CDRs grafted into the TAF framework has kD of 230 pM (FIG. 5C), and KCD119 CDRs grafted into IGHV 3-66/IGK1-39framework has a kD of 2.60 nM (FIG. 5B). KCD119 CDRs grafted into IGHV 1-2/IGKV2-30 framework did not express sufficient antibody. The affinities for Fab were roughly equivalent to the full IgG for each framework.

KCD119 TAF (FIG. 5C) has the highest binding affinity to human CFD post grafting and is therefore chosen as the template to further affinity mature.

Example 8—Screening Results for Light Chain CDRs for Affinity Maturation of TAF KCD119 Molecule To increase the binding affinity of the humanized molecule TAF KCD119, all three CDRs in both light and heavy chain were subjected to mutagenesis to identify favorable point mutations in the CDRs.

Each residue in the light chain CDRs was mutated following manufacturer's instructions for the NEB site directed mutagenesis kit and using a mixture of mutagenic primers encoding 16 amino acids (excluding parent, C, M, and N, with a few exceptions as noted in the table). Mutants were selected by sequencing, and plasmids encoding unique heavy and light chain antibody sequences were identified and co-transfected into Expi293™ cells. After 5 days, the supernatants from the cells containing secreted antibody were diluted 1:10 in HBS-EP plus running buffer and captured on a protein A chip on a Biacore™ T200 system (GE). 45 nM, 15 nM, 5 nM, and 1.7 nM serum purified human CFD was then flowed over the captured antibody to determine affinity by single cycle kinetics using BIAevaluation software (GE).

Affinity Fold Changes Caused by Light Chain CDR Mutations was assessed. Affinity results were from Biacore testing of un-purified supernatant from Expi293 cells transfected with mutagenized KCD119 plasmid DNA. Mutant residues may have been screened on a background of other mutations.

Data are presented in Table 8.1 for CDR1, Table 8.2 for CDR2 and Table 8.3 for CDR3. Increase in fold change (>1.0) indicates loss of affinity, while decrease in fold change (<1.0) indicates increased affinity. Boxes are marked with * when the aa substitution has similar or better affinity. Boxes are marked with *** when aa substitution has worse affinity. "XX" indicates no sufficient antibody expression.

TABLE 8.1

| Affinity Fold Changes Caused by Light Chain CDR Mutations in CDR1 | | | | | | | | | | | | |
|---|---|---|---|---|---|---|---|---|---|---|---|---|
| | 28T | 29I | 30V | 31H | 32S | 33N | 34G | 35D | 36T | 37Y | 38L | 39E |
| A | | 0.3* | 1.8* | | 0.5* | 12.5*** | 13.7*** | 6.2*** | 3.6*** | | 11.4*** | 9.6*** |
| C | | | | | | | | | | | | |
| D | 0.3* | | 0.7* | 7.9*** | 0.4* | 17.9*** | 6.9*** | | 21.9*** | 550.0*** | | 733.6*** |
| E | | 78.9*** | 0.3* | 9.0*** | | 18.7*** | 1.6* | 0.5* | | 145.5*** | 7.2*** | |
| F | | 16.6*** | 0.5* | | 0.8* | 16.6*** | 2.0* | | 11.9*** | 4.3*** | 3.5*** | |
| G | 0.1* | 53.6*** | 2.3*** | 46.7*** | 0.5* | 2.7*** | | 4.8*** | 18.8*** | 2022.7*** | | xx*** |
| H | 0.9* | | | | | | 4.8*** | | 4.3*** | | 10.9*** | 8.8*** |
| I | 0.9* | | 0.6* | | 0.9* | 61.3*** | 62.8*** | | 3.8*** | 37.4*** | 1.2* | |
| K | | 133.6*** | 0.9* | 83.4*** | | 183.6*** | 19.0*** | | | | 50.6*** | xx*** |
| L | | 0.0 | 1.7* | 13.8*** | | 22.7*** | 3.2*** | | 6.9*** | 4.1*** | | |
| M | | | | | | 22.2*** | 18.8*** | | | | | |
| N | 0.4* | | | | | | | | | | | |
| P | | | | 33.7*** | | 47.6*** | 16.3*** | | 27.2*** | | 117.4*** | xx*** |
| Q | 0.9* | | 0.3* | 18.4*** | | 32.1*** | | | | | 11.5*** | 3.9*** |
| R | 1.3* | 47.4*** | 1.1* | 124.6*** | 0.7* | 83.4*** | 5.8*** | 52.6*** | 10.3*** | 252.3*** | 252.3*** | |
| S | 0.0 | XX*** | 0.5* | 8.5*** | | 13.2*** | 1.9* | 408.3*** | 2.0* | 571.2*** | 34.3*** | 9.6*** |
| T | | 2.9*** | | 12.0*** | 0.9* | 4.1*** | 8.6*** | | | | 10.7*** | xx*** |
| V | 0.2* | 0.2* | | 10.7*** | 0.7* | 21.3*** | 24.2*** | 12.9*** | 1.1* | 271.2*** | | xx*** |
| W | 0.2* | | 1.5* | | 0.3* | 8.5*** | 3.3*** | 14.3*** | 11.2*** | 704.5*** | | |
| Y | | | 0.3* | | | 11.1*** | 4.9*** | | 7.5*** | | | |

TABLE 8.2

| Affinity Fold Changes Caused by Light Chain CDR Mutations in CDR2 | | | | | | | | | |
|---|---|---|---|---|---|---|---|---|---|
| 50N | 51L | 52L | 53I | 54Y | 55K | 56V | 57S | 58N | 60F |
| | 54.2*** | | 3.2*** | | 7.9*** | 1.2* | 0.8* | | |
| 0.9* | 38.3*** | 12.0*** | 70.7*** | 1.3* | 137.0*** | 18.0*** | 10.9*** | 2.7*** | 2.8*** |
| 0.6* | 25.2*** | 19.8*** | 11.7*** | 1.1* | 16.9*** | 6.5*** | | 0.9* | 1.5* |
| | | | 3.3*** | 0.5* | | 14.6*** | 1.2* | | |
| | 69.5*** | 15.1*** | 13.5*** | 0.4* | 7.6*** | 6.8*** | 1.1* | 1.1* | 0.8* |
| | | 20.8*** | 5.6*** | | 13.1*** | 13.3*** | | 0.2* | |
| 0.0 | 1.9* | | | 2.8*** | | 1.2* | | 1.9* | 0.3* |
| | | 6.2*** | 7.6*** | | | | 0.6* | | |
| | | | | 1.9* | 6.6*** | 5.5*** | 1.0* | 1.9* | 1.2* |
| | 48.6*** | 16.1*** | 40.4*** | 32.9*** | 14.3*** | 67.4*** | | | |
| | 28.2*** | 17.1*** | 7.7*** | | 2.9*** | 3.8*** | 1.0* | 0.8* | |
| 0.8* | 623.5*** | 18.0*** | 36.9*** | 0.1* | 3.7*** | 2.8*** | 0.7* | | 1.5* |
| 0.8* | 176.5*** | 14.5*** | 5.9*** | 0.2* | 9.2*** | 3.3*** | | 0.8* | 2.1*** |
| 4.3*** | | 13.3*** | 1.9* | 0.4* | 10.9*** | 6.4*** | 1.0* | 1.6* | 8.7*** |
| 0.5* | 7.1*** | 10.2*** | 2.6*** | 1.1* | 11.2*** | | 15.8*** | 1.8* | 2.2*** |
| | 32.4*** | 18.0*** | | 2.3*** | | 34.9*** | | 2.8*** | 0.4* |
| 0.7* | 43.1*** | | | | 10.4*** | 13.0*** | 1.4* | | |

TABLE 8.3

| Affinity Fold Changes Caused by Light Chain CDR Mutations in CDR3 | | | | | | | |
|---|---|---|---|---|---|---|---|
| 94F | 95Q | 96G | 97S | 98H | 99V | 100P | 101P |
| 33.5*** | 38.0*** | 3.3*** | 7.3*** | 0.8* | 2.8*** | 8.4*** | 3.6*** |
| | | 134.2*** | 143.3*** | | 2.7*** | | 2.7*** |
| | 12.4*** | 352.9*** | 288.1*** | 0.7* | 9.2*** | | 23.8*** |
| | 127.7*** | 75.3*** | 126.8*** | 0.7* | 3.6*** | | |
| 6.5*** | 118.4*** | | 5.9*** | 1.1* | 8.4*** | 12.6*** | 3.1*** |
| | 125.8*** | 53.9*** | 286.2*** | | | | 37.7*** |
| 8.7*** | | 21.4*** | | X*** | 2.9*** | | 4.8*** |
| | 1189.0*** | | | X*** | 8.8*** | | 129.9*** |
| 5.3*** | 701.5*** | 98.1*** | 110.8*** | 1.4* | 4.9*** | 8.3*** | 4.3*** |
| 1.0* | | 224.9*** | | | 2.7 | | |
| 137.1*** | | | 42.0*** | 1.2* | 1.4* | | |
| 9.2*** | 206.8*** | | 146.7*** | 56.7*** | 6.7*** | | |
| | | | | 0.7* | 2.0* | | 15.8*** |
| 295.6*** | 562.4*** | 20.6*** | 221.2*** | X*** | 6.6*** | 9.7*** | 332.7*** |
| 153.4*** | 28.8*** | 78.6*** | | | 2.2*** | 14.8*** | 8.4*** |
| 12.4*** | 58.8*** | 286.2*** | | 1.2* | | | 15.3*** |
| 6.9*** | 54.2*** | 64.5*** | 32.0*** | 0.7* | | 8.8*** | 1.6* |
| | 248.9*** | | 250.9*** | 0.7* | 1.1* | 10.7*** | 13.8*** |
| 19.2*** | 219.9*** | 260.2*** | 136.4*** | 0.7* | 4.9*** | | |

Example 9—Screening Results for Heavy Chain CDR1 and CDR2 of TAF KCD119 Molecule Heavy chain CDR1 and CDR2 were mutagenized and screened similarly as the light chain CDRs.

Affinity Fold Changes Caused by Heavy Chain CDR Mutations was assessed. Affinity results were from Biacore testing of un-purified supernatant from Expi293 cells transfected with mutagenized KCD119 plasmid DNA. Mutant residues may have been screened on a background of other mutations. H3 was screened in *E. coli* first to determine tolerant residues (Example 10; Table 9.1).

Data are presented in Table 9.1 for CDR1 and Table 9.2 for CDR2. Increase in fold change (>1.0) indicates loss of affinity, while decrease in fold change (<1.0) indicates increased affinity. Boxes are marked with * when the aa substitution has similar or better affinity. Boxes are marked with *** when aa substitution has worse affinity. "XX" indicates no sufficient antibody expression.

TABLE 9.1

| Affinity Fold Changes Caused by Heavy Chain CDR Mutations in CDR1 | | | | | | |
|---|---|---|---|---|---|---|
| | 28T | 29F | 31D | 32Y | 33Y | 34M |
| A | 1.2* | 19.2*** | 0.6* | 17.0*** | 51.6*** | 9.0*** |
| C | | | | | | |
| D | 1.8* | 48.8*** | | 266.1*** | 111.8*** | 4.5*** |
| E | 1.1* | 140.1*** | 37.7*** | 108.7*** | | 2.8*** |
| F | 0.6* | 4.0*** | 0.3* | 0.7* | 3.7*** | 14.0*** |
| G | 2.9*** | 100.0*** | 0.6* | 542.6*** | 7.5*** | 8.0*** |
| H | 0.8* | 12.5*** | | | | 1.3* |
| I | 0.6* | 4.1*** | | 246.1*** | 267.1*** | 0.7* |
| K | 0.8* | | | 647.0*** | | 4.2*** |
| L | 2.2*** | | | | 29.4*** | |
| M | | | | | | |
| N | | | | | | |
| P | 1.1* | | 35.2*** | 34.3*** | 0.9* | |
| Q | XX*** | | | 24.4*** | 301.4*** | 4.9*** |
| R | 0.9* | 50.2*** | 3.5*** | 11.7*** | 36.0*** | |
| S | 0.5* | 34.6*** | 0.2* | 42.4*** | 8.4*** | 11.8*** |
| T | 2.3*** | 18.2*** | 7.5*** | 93.0*** | 2.8*** | |
| V | | 1.2* | 1.0* | | 219.0*** | 5.7*** |
| W | 0.0* | | | | 491.3*** | |
| Y | 0.8* | 4.1*** | 0.6* | | 1.6* | 9.6*** |

TABLE 9.2

| Affinity Fold Changes Caused by Heavy Chain CDR Mutations in CDR2 | | | | | | | | | | | |
|---|---|---|---|---|---|---|---|---|---|---|---|
| 49G | 50D | 51I | 52N | 53P | 54N | 55T | 56G | 57D | 58T | 59S | 61N |
| 5.5*** | 2.4*** | | 1.1* | | 1.3* | 6.1*** | 0.8* | 1.1* | 0.5* | 0.7* | 1.2* |
| | | | | | | | | | | 0.7* | 2.0* |
| 25.0*** | | 14.7*** | | 35.4*** | 1.7* | 8.1*** | 2.3*** | | 0.7* | 0.4* | 1.7* |
| 23.5*** | 6.0*** | 5.1*** | | | 3.4*** | 5.4*** | | 1.0* | 0.7* | 0.8* | 1.5* |
| 14.9*** | | 2.8*** | 16.3*** | 19.5*** | 2.5*** | 4.5*** | | 1.3* | 1.4* | 0.6* | |
| | 30.9*** | 3.9*** | 1.1* | | 1.5* | 2.6*** | | 1.2* | 0.7* | 0.7* | 1.2* |
| 26.1*** | | | | | 0.5* | | | 1.1* | 0.7* | | |
| 14.0*** | | | | 64.5*** | 0.2* | 0.9* | | | 2.1*** | | 2.2*** |
| 17.6*** | 1295.7*** | | 37269.8*** | | 3.3*** | 1.5* | | 1.0* | 0.5* | 5.0*** | 0.8* |
| 24.8*** | 26.4*** | 0.4* | 55254.6*** | 43.6*** | 1.5* | 0.4* | | 1.9* | 1.0* | 1.4* | 0.9* |
| | 11.7*** | | | | XX*** | | | 1.2* | | 0.8* | 1.4* |
| | | | | | | | | 1.8* | 0.6* | 0.8* | |
| 11.3*** | 18.5*** | | | | | 7.3*** | | | 0.9* | | |
| 19.2*** | 41.3*** | | 44745.4*** | | XX*** | 1.0* | | 1.0* | 0.6* | 1.3* | 1.2* |
| 18.0*** | 297.4*** | 14.0*** | | 6.7*** | 1.8* | 1.1* | | 1.2* | 0.5* | 42.1*** | 0.8* |

TABLE 9.2-continued

| Affinity Fold Changes Caused by Heavy Chain CDR Mutations in CDR2 | | | | | | | | | | | |
|---|---|---|---|---|---|---|---|---|---|---|---|
| 49G | 50D | 51I | 52N | 53P | 54N | 55T | 56G | 57D | 58T | 59S | 61N |
| 9.0*** | 11.3*** | 2.2*** | 6.4*** | 21.9*** | 3.3*** | 1.2* | 2.5*** | 1.4* | 0.5* | 0.6* | 1.0* |
| 30.9*** | | 2.3*** | | 1.8* | 0.3* | | | 1.2* | 0.5* | 1.2* | 1.5* |
| | 172.2*** | 1.4* | 71.5*** | 30.9*** | 0.5* | 1.0* | 0.5* | 1.1* | 0.5* | 1.0* | 1.7* |
| 16.2*** | 5.6*** | | 11.6*** | | 0.7* | | | | 0.7* | 1.1* | 2.5*** |
| 16.1*** | | 4.0*** | 1571.0*** | | 0.3* | 6.1*** | | 1.4* | 0.7* | 1.0* | 1.1* |

Example 10—Screen Result for Heavy Chain CDR3 of TAF KCD119 Molecule

Heavy Chain CDR3 was screened in *E. coli* before looking at expression and binding in the Expi293 system (Table 10.1). Fab fragment of KCD119 was mutagenized using degenerate oligos at each residue independently across heavy chain CDR3. Site directed mutagenesis of heavy chain KCD119 TAF Fab (cloned into pCDisplay-4 with the KCD119 TAF light chain dually expressed) using NEB Q5 Site Directed mutagenesis kit and primers RDJ63&66 (residue 1). 95 colonies were picked into a 96-well plate, reserving WT for well A1. 1.5 ml cultures were grown overnight at 30 degrees (LB+50 ug/ml Amp, 100 glucose). Cultures were diluted back to 0.2OD (600 nm) and allowed to grow for 1.5 hours. IPTG was added to 0.5 mM final concentration to induce expression for 5 hours. Cultures were spun down for 15 minutes and resuspended in 400 uls of 20% sucrose, 100 mM Hepes to osmotically stress the cells. After a 15 minute incubation at RT, cells were spun for 10 minutes. The pellet was resuspended in 200 uls of 4 mM MgCl2 and incubated on ice for 20 minutes. Samples were spun down and 180 uls of the resulting supernatant was removed (periplasmic fraction). 20 uls of 10×HBS-EP buffer and filtered through a 2 um filter plate before running on Biacore T200. Plates were screened on Biacore T200 for binding to CFD by capturing CFD on a CM5 chip coated with KCD004. Lysates were flowed over captured CFD for 1.5 minutes, and allowed to dissociate for 2 minutes. Any hits with off-rates comparable or better than WT KCD119 were sequenced and cloned into pCDNA3.3 by PCR amplifying the variable region with primers RDJ121 (gatcgaattcgGAGGTGCAGCTGGTGGAA) (SEQ ID NO: 511) (the underlined section is a restriction site) and RDJ122 (gatcGGAGGACACTGTCACCAG) (SEQ ID NO: 512). Resulting PCR fragments were cloned into a pCDNA3.3 vector between an IL2-SS and huGI Fc domain. Transfected positive clones with KCD119 TAF LC into Hek293 cells and check for binding to CFD on Biacore T200 using Protein A chip and single cycle kinetics.

The results are shown in Table 10.1. Boxes are marked with * when the aa substitution has similar or better affinity. Boxes are marked with *** when aa substitution has worse affinity. Positive hits were sequenced and cloned into mammalian expression vector. Mutations with "XX" or numerical values were tested in Expi293 cells for expression and Factor D binding. XX indicates no sufficient antibody expression.

TABLE 10.1

| Affinity Fold Changes Caused by Heavy Chain CDR Mutations in CDR3 | | | | | | | | | |
|---|---|---|---|---|---|---|---|---|---|
| | 97T | 98R | 99E | 100G | 101P | 102S | 103F | 104A | 105Y |
| A | 15.0* | *** | *** | *** | *** | 1.6* | *** | *** | 4.4* |
| C | *** | *** | *** | *** | *** | 10.0* | *** | *** | *** |
| D | 6.0* | *** | *** | *** | *** | *** | *** | *** | *** |
| E | XX* | *** | *** | *** | *** | *** | *** | *** | *** |
| F | *** | *** | 23.3* | *** | *** | *** | *** | 9.6* | 3.8* |
| G | *** | *** | *** | *** | *** | 20.9* | *** | *** | *** |
| H | *** | *** | *** | *** | *** | *** | *** | *** | 1.5* |
| I | *** | *** | *** | *** | XX* | *** | *** | 18.0* | *** |
| K | *** | *** | *** | *** | *** | *** | *** | *** | *** |
| L | *** | *** | 18.6* | *** | 5.0* | *** | *** | *** | 2.7* |
| M | *** | *** | XX* | *** | *** | *** | *** | *** | *** |
| N | *** | *** | *** | *** | *** | 15.0* | *** | *** | *** |
| P | *** | *** | *** | *** | *** | *** | *** | *** | *** |
| Q | 5.0* | *** | *** | *** | *** | *** | *** | *** | *** |
| R | *** | *** | *** | XX* | *** | *** | *** | 2.5* | *** |
| S | 208.0* | *** | *** | *** | *** | *** | *** | *** | *** |
| T | *** | *** | *** | *** | *** | *** | *** | 19.8* | *** |
| V | *** | *** | *** | *** | *** | *** | *** | *** | 3.8* |
| W | *** | *** | *** | *** | *** | XX* | *** | *** | *** |
| Y | *** | *** | *** | *** | *** | *** | *** | *** | 1.9* |

Example 11—Identifying Additive or Synergistic Mutation Combos of TAF KCD119

Mutations that corresponded with positive changes in affinity were combined for both heavy and light chains, and various heavy and light chain pairings were tested for expression and Factor D binding kinetics.

313 unique heavy chain mutants and 451 unique light chain mutants, for a total of 764 mutants were designed and engineered within the 6 CDRs of KCD119. The tolerability of each residue within each of the 6 CDRs was assessed for various amino acid substitutions while determining functional pairings between various heavy and light chain mutants. A total of 865 mutant combinations were tested. The 865 pairings were designed in an iterative process, where light chain mutants that increased affinity were combined with heavy chain mutants that increased affinity until single digit pM affinity was achieved.

During the combination screening, each antibody containing a unique light and heavy chain combo was transfected and the resulting conditioned media was used for initial screening on Biacore. Combos that are additive were purified from Expi293 supernatants following a standard protocol. Antibodies were diluted to 0.5 ug/ml in HIBS-EP+ buffer and captured on a protein A chip for 25 seconds to reach approximately 70 resonance units. 45 nM, 15 nM, 5 nM, 1.67 nM, and 0.56 nM serum purified Complement Factor D (diluted in HIBS-EP+ buffer) was flowed over the captured antibodies for 60 seconds in a single cycle kinetics method, and dissociated for 30 minutes at both 25 and 37 degrees. Binding kinetic information was obtained by the BIAevaluation software (GE). Representative data are presented in FIG. 6A-FIG. 6D, and Table 11.1 and Table 11.2.

TABLE 11.1

Identifying Additive or Synergistic Mutation Combinations

| Heavy Chain | Light Chain | ka (1/Ms) | kd (1/s) | KD (M) |
|---|---|---|---|---|
| KCD119 TAF | KCD119 TAF | 4.46E6 | 1.03E−3 | 2.30E−10 |
| 54V | KCD119 TAF | 4.09E6 | 6.27E−4 | 1.53E−10 |
| 54V | 101V | 4.88E6 | 4.63E−4 | 9.49E−11 |
| 54V59D | KCD119 TAF | 5.85E6 | 3.07E−4 | 5.26E−11 |
| 54V59D | 101V | 6.64E6 | 2.13E−4 | 3.21E−11 |

TABLE 11.2

Affinity results of mutant combinations

| | | 25 Degrees | | | | 37 Degrees | | | |
|---|---|---|---|---|---|---|---|---|---|
| Heavy Chain | Light Chain | ka (1/Ms) | kd (1/s) | KD (M) | Rmax (RU) | ka (1/Ms) | kd (1/s) | KD (M) | Rmax (RU) |
| 28Q31S54V59D | 101V | 7.15E+06 | 1.64E−04 | 2.30E−11 | 17.3 | 1.35E+07 | 1.03E−03 | 7.57E−11 | 21.2 |
| 28S31S54V59D | 101V | 7.64E+06 | 1.66E−04 | 2.17E−11 | 17.3 | 1.26E+07 | 9.18E−04 | 7.27E−11 | 21.7 |
| 28V31S54V59D | 101V | 7.91E+06 | 4.76E−05 | 6.01E−12 | 16 | 1.66E+07 | 8.50E−04 | 5.10E−11 | 19.8 |
| 28H31S54V59D | 101V | 6.65E+06 | 1.67E−04 | 2.51E−11 | 18.9 | 1.72E+07 | 4.43E−04 | 2.57E−11 | 24.8 |
| 28I31S54V59D | 101V | 7.59E+06 | 1.34E−04 | 1.77E−11 | 17.5 | 2.00E+07 | 3.90E−04 | 1.95E−11 | 24 |
| 28K31S54V59D | 101V | 7.30E+06 | 1.63E−04 | 2.24E−11 | 16.6 | | | | |
| 54V56V | 101V | 5.44E+06 | 3.51E−04 | 6.45E−11 | 19.4 | 9.69E+06 | 1.04E−03 | 1.07E−10 | 22.5 |
| 54V59D | 101V | 6.94E+06 | 2.58E−04 | 3.71E−11 | 19.6 | | | | |
| 31S48V54V59D | 101V | 5.98E+06 | 1.01E−04 | 1.69E−11 | 15.9 | | | | |
| 31S54V59D | 101V | 6.95E+06 | 1.31E−04 | 1.88E−11 | 18.2 | | | | |
| 54I59D | 101V | 7.43E+06 | 1.52E−04 | 2.04E−11 | 18.7 | | | | |
| 54V59D | 32W60W101V | 7.88E+06 | 4.79E−05 | 6.07E−12 | 13.6 | | | | |
| 48V54V59D | 32W60W101V | 5.96E+06 | 9.50E−05 | 1.59E−11 | 16.4 | 1.31E+07 | 2.78E−04 | 2.12E−11 | 18.6 |
| 31S54V59D | 32W60W101V | 5.58E+06 | 8.84E−05 | 1.58E−11 | 16.3 | 1.29E+07 | 2.93E−04 | 2.27E−11 | 18.3 |
| 54I59D | 32W60W101V | 7.57E+06 | 3.50E−05 | 4.62E−12 | 14 | 1.50E+07 | 1.97E−04 | 1.31E−11 | 16.8 |
| 54V59D | 32W50I101V | 6.64E+06 | 1.05E−04 | 1.58E−11 | 16.7 | 1.37E+07 | 3.05E−04 | 2.23E−11 | 18.9 |
| 54V59D | 32D50I101V | 8.11E+06 | 1.60E−04 | 1.97E−11 | 17.3 | 1.50E+07 | 4.10E−04 | 2.74E−11 | 20.2 |
| 54V59D | 32D60W101V | 1.25E+07 | 1.28E−04 | 1.02E−11 | 14 | 8.93E+06 | 3.71E−04 | 4.15E−11 | 16.9 |
| 54V59D | 34D60W101V | 8.80E+06 | 1.87E−04 | 2.13E−11 | 15.8 | 1.56E+07 | 8.30E−04 | 5.31E−11 | 18.7 |
| 54V59D | 34D50V101V | 7.26E+06 | 1.87E−04 | 2.57E−11 | 17.8 | 1.34E+07 | 7.90E−04 | 5.91E−11 | 20.8 |
| 54V | 101V | 7.14E+06 | 4.91E−04 | 6.88E−11 | 16.6 | 1.11E+07 | 1.58E−03 | 1.42E−10 | 20.4 |
| OG1931 | OG1931 | 3.83E+07 | 1.64E−04 | 4.27E−12 | 13.3 | 2.65E+07 | 4.35E−04 | 1.64E−11 | 15 |
| 54I59D | 50I60W101V | 5.53E+06 | 6.67E−05 | 1.21E−11 | 15.6 | 1.04E+07 | 3.29E−04 | 3.18E−11 | 18 |
| 54I59D | 32W60W101V | 4.91E+06 | 8.32E−05 | 1.69E−11 | 14 | 6.86E+06 | 6.67E−05 | 9.72E−12 | 17.2 |
| 54I59D | 54R101V (SEQ ID NO: 184) | 1.10E+07 | 7.04E−05 | 6.42E−12 | 15.1 | 2.64E+07 | 1.87E−04 | 7.10E−12 | 17.1 |
| 54I59D | 54G101V | 1.15E+07 | 9.56E−05 | 8.33E−12 | 14.8 | 2.78E+07 | 2.15E−04 | 7.74E−12 | 17.1 |
| 54I59D | 101V | 5.78E+06 | 1.54E−04 | 2.67E−11 | 13.5 | 9.19E+06 | 4.37E−04 | 4.75E−11 | 16.4 |
| 31S54I59D | 50I60W101V | 5.14E+06 | 3.98E−05 | 7.74E−12 | 13.6 | 9.26E+06 | 2.56E−04 | 2.76E−11 | 16.7 |
| 31S54I59D | 32W60W101V | 3.83E+06 | 6.30E−05 | 1.65E−11 | 13.5 | 6.55E+06 | 2.25E−04 | 3.43E−11 | 14.4 |
| 31S54I59D | 54R101V (SEQ ID NO: 184) | 1.02E+07 | 7.94E−05 | 7.79E−12 | 13.8 | 3.48E+07 | 2.10E−04 | 6.05E−12 | 15.4 |
| 31S54I59D | 54G101V | 1.20E+07 | 8.25E−05 | 6.89E−12 | 13.2 | 2.38E+07 | 2.22E−04 | 9.31E−12 | 15.2 |
| 31S54V59D | 101V | 5.71E+06 | 1.01E−04 | 1.76E−11 | 15.4 | 9.08E+06 | 3.73E−04 | 4.11E−11 | 17.6 |
| 31S34I54I59D | 32W60W101V | 3.31E+06 | 5.69E−05 | 1.72E−11 | 13.2 | 6.67E+06 | 2.08E−04 | 3.12E−11 | 15.1 |
| 31S54I59D84T | 32W60W101V | 3.83E+06 | 6.01E−05 | 1.57E−11 | 12.9 | 7.79E+06 | 2.24E−04 | 2.88E−11 | 14.3 |
| 31S54I59D845 | 32W60W101V | 3.83E+06 | 7.76E−05 | 2.03E−11 | 11.1 | 8.90E+06 | 2.09E−04 | 2.35E−11 | 12.4 |
| 54I59D84T | 32W60W101V | 4.99E+06 | 8.43E−05 | 1.69E−11 | 11.2 | 1.41E+07 | 3.65E−04 | 2.58E−11 | 12.7 |
| 54V59D | 54R101V (SEQ ID NO: 184) | 1.19E+07 | 1.41E−04 | 1.19E−11 | 11.7 | 2.40E+07 | 3.70E−04 | 1.54E−11 | 13.3 |
| OG1931 | | 2.24E+07 | 6.83E−05 | 3.05E−12 | 14 | 1.41E+08 | 4.72E−04 | 3.34E−12 | 15.5 |
| 54I59D | 101V | 6.32E+06 | 5.74E−05 | 9.08E−12 | 25 | 1.21E+07 | 2.22E−04 | 1.84E−11 | 29.7 |
| 54I59D | 32W60W101V | 5.83E+06 | 6.85E−05 | 1.18E−11 | 20.9 | 1.17E+07 | 5.83E−05 | 5.01E−12 | 25.4 |
| 54I59D | 4G101V 5 | 5.91E+06 | 9.41E−08 | 1.59E−14 | 21 | 1.36E+07 | 4.08E−07 | 2.99E−14 | 25.3 |
| 31S54V59D | 54R101V (SEQ ID NO: 184) | 1.39E+07 | 5.48E−05 | 3.94E−12 | 22.3 | 3.33E+07 | 2.42E−04 | 7.25E−12 | 25.3 |
| 31S54I59D | 54R101V (SEQ ID NO: 184) | 1.40E+07 | 5.12E−05 | 3.66E−12 | 23.2 | 3.09E+07 | 2.14E−04 | 6.91E−12 | 26.7 |
| 54I59D | 54R101V (SEQ ID NO: 184) | 2.02E+07 | 5.95E−05 | 2.94E−12 | 21.3 | 4.74E+07 | 2.57E−04 | 5.43E−12 | 24.6 |
| 31S34I54I59D | 54R101V (SEQ ID NO: 184) | 1.39E+07 | 1.06E−04 | 7.60E−12 | 23.2 | 2.69E+07 | 1.57E−04 | 5.83E−12 | 26.6 |
| 31554159D845 | 54R101V (SEQ ID NO: 184) | 1.49E+07 | 9.14E−05 | 6.13E−12 | 22.2 | 2.84E+07 | 1.74E−04 | 6.13E−12 | 25.9 |

TABLE 11.2-continued

Affinity results of mutant combinations

| | | 25 Degrees | | | | 37 Degrees | | | |
|---|---|---|---|---|---|---|---|---|---|
| Heavy Chain | Light Chain | ka (1/Ms) | kd (1/s) | KD (M) | Rmax (RU) | ka (1/Ms) | kd (1/s) | KD (M) | Rmax (RU) |
| 54I59D | 32W33G60W101V | 7.78E+06 | 4.00E−04 | 5.14E−11 | 17.1 | 1.14E+07 | 1.20E−03 | 1.05E−10 | 20.9 |
| 54I59D | 32W33G60W101V | 6.14E+06 | 3.28E−04 | 5.34E−11 | 21.2 | 1.51E+07 | 1.48E−03 | 9.79E−11 | 23 |
| 54I59D | 32W33G60W101V | 4.53E+06 | 3.52E−04 | 7.78E−11 | 20.7 | 8.69E+06 | 1.17E−03 | 1.35E−10 | 23.3 |
| 54I59D | 32W545101V | 7.69E+06 | 7.29E−05 | 9.48E−12 | 18.7 | 1.41E+07 | 1.55E−04 | 1.10E−11 | 21.4 |
| 54I59D | 54560W101V | 7.19E+06 | 7.08E−05 | 9.85E−12 | 19.5 | 1.24E+07 | 1.48E−04 | 1.19E−11 | 23.4 |
| 54I59D | 32W54560W101V | 6.25E+06 | 5.37E−05 | 8.58E−12 | 14.4 | 1.10E+07 | 1.36E−04 | 1.24E−11 | 17.2 |
| 54I59D | 54G60W101 | 6.83E+06 | 8.54E−05 | 1.25E−11 | 17.5 | 1.19E+07 | 1.18E−04 | 9.89E−12 | 19.5 |
| 54I59D | 54R101V (SEQ ID NO: 184) | 1.71E+07 | 9.80E−05 | 5.72E−12 | 20.7 | 3.09E+07 | 2.05E−04 | 6.63E−12 | 23.7 |
| 34I54I59D | 54R101V (SEQ ID NO: 184) | 1.80E+07 | 1.01E−04 | 5.62E−12 | 15.9 | 3.27E+07 | 2.64E−04 | 8.08E−12 | 18.4 |
| 31S34I54I59D | 54R101V (SEQ ID NO: 184) | 1.32E+07 | 7.84E−05 | 5.96E−12 | 18.7 | 2.46E+07 | 2.37E−04 | 9.61E−12 | 20.6 |
| 31S54I59D | 54R101V (SEQ ID NO: 184) | 1.44E+07 | 1.20E−04 | 8.36E−12 | 18 | 2.78E+07 | 2.27E−04 | 8.17E−12 | 19.9 |
| 34I54I59D | 32W60W101V | 6.45E+06 | 1.36E−04 | 2.11E−11 | 13.3 | 1.29E+07 | 2.79E−04 | 2.17E−11 | 15.1 |
| 54I59D | 54R101V (SEQ ID NO: 184) | 1.82E+07 | 9.50E−05 | 5.23E−12 | 18.5 | 3.78E+07 | 3.00E−04 | 7.92E−12 | 20.8 |
| OG1931 | | 3.48E+07 | 1.15E−04 | 3.29E−12 | 18.6 | 2.17E+08 | 8.96E−04 | 4.13E−12 | 20.6 |
| OG1931 | OG1931 | 3.11E+07 | 1.36E−05 | 4.37E−13 | 18.1 | 2.94E+08 | 9.10E−04 | 3.10E−12 | 21 |
| 31S34I54I59D84S | 54R101V (SEQ ID NO: 184) | 1.66E+07 | 1.69E−08 | 1.02E−15 | 21 | 3.50E+07 | 1.37E−04 | 3.92E−12 | 24.4 |
| 34I54I59D84S (SEQ ID NO: 183) | 54R101V (SEQ ID NO: 184) | 2.06E+07 | 9.02E−05 | 4.37E−12 | 18.2 | 4.00E+07 | 2.02E−04 | 5.04E−12 | 21.1 |
| 31S34I54I59D845 | 54G101V | 4.42E+06 | 1.81E−10 | 4.10E−17 | 19.8 | 1.21E+07 | 7.36E−05 | 6.11E−12 | 22.3 |
| 34I54I59D845 (SEQ ID NO: 183) | 54G101V | 7.59E+06 | 5.18E−05 | 6.83E−12 | 19.5 | 1.45E+07 | 1.12E−04 | 7.74E−12 | 24.1 |
| KCD119 TAF | KCD119TAF | 1.38E+07 | 1.55E−03 | 1.13E−10 | 20.5 | 1.26E+07 | 6.28E−03 | 4.99E−10 | 26.1 |

*kD values <1E−12 are outside of the limits of the Biacore T200.

Heavy and light chain sequence of high-affinity anti-CFD antibodies and their representative variants are shown in Table 11.3.

TABLE 11.3

Amino acid sequences of final heavy and light chain candidates and their variants (KCD119 Variant Sequences; a CDR embodiment is underlined.)

| | |
|---|---|
| **Heavy Chain** | |
| KCD119 TAF | EVQLVESGGGLVQPGGSLRLSCAASGYTFTDYYMN WVRQAPGKGLEWIGDINPNTGDTSYNADFKRRFTF SLDTSKSTAYLQMNSLRAEDTAVYYCTREGPSFAY WGQGTLVTVSS (SEQ ID NO: 513) |
| 54V | EVQLVESGGGLVQPGGSLRLSCAASGYTFTDYYMN WVRQAPGKGLEWIGDINPVTGDTSYNADFKRRFTF SLDTSKSTAYLQMNSLRAEDTAVYYCTREGPSFAY WGQGTLVTVSS (SEQ ID NO: 514) |
| 54I | EVQLVESGGGLVQPGGSLRLSCAASGYTFTDYYMN WVRQAPGKGLEWIGDINPITGDTSYNADFKRRFTF SLDTSKSTAYLQMNSLRAEDTAVYYCTREGPSFAY WGQGTLVTVSS (SEQ ID NO: 515) |
| 54V59D | EVQLVESGGGLVQPGGSLRLSCAASGYTFTDYYMN WVRQAPGKGLEWIGDINPVTGDTDYNADFKRRFTF SLDTSKSTAYLQMNSLRAEDTAVYYCTREGPSFAY WGQGTLVTVSS (SEQ ID NO: 516) |
| 54I59D | EVQLVESGGGLVQPGGSLRLSCAASGYTFTDYYMN WVRQAPGKGLEWIGDINPITGDTDYNADFKRRFTF SLDTSKSTAYLQMNSLRAEDTAVYYCTREGPSFAY WGQGTLVTVSS (SEQ ID NO: 517) |

TABLE 11.3-continued

Amino acid sequences of final heavy and light chain candidates and their variants (KCD119 Variant Sequences; a CDR embodiment is underlined.)

| | |
|---|---|
| 34I54I59D | EVQLVESGGGLVQPGGSLRLSCAASGYTFTDYYIN WVRQAPGKGLEWIGDINPITGDTDYNADFKRRFTF SLDTSKSTAYLQMNSLRAEDTAVYYCTREGPSFAY WGQGTLVTVSS (SEQ ID NO: 518) |
| 31S34I54I59D | EVQLVESGGGLVQPGGSLRLSCAASGYTFTSYYIN WVRQAPGKGLEWIGDINPITGDTDYNADFKRRFTF SLDTSKSTAYLQMNSLRAEDTAVYYCTREGPSFAY WGQGTLVTVSS (SEQ ID NO: 519) |
| 34I54I59D84S | EVQLVESGGGLVQPGGSLRLSCAASGYTFTDYYIN WVRQAPGKGLEWIGDINPITGDTDYNADFKRRFTF SLDTSKSTAYLQMSSLRAEDTAVYYCTREGPSFAY WGQGTLVTVSS (SEQ ID NO: 520) |
| 31S34I54I59D84S | EVQLVESGGGLVQPGGSLRLSCAASGYTFTSYYIN WVRQAPGKGLEWIGDINPITGDTDYNADFKRRFTF SLDTSKSTAYLQMSSLRAEDTAVYYCTREGPSFAY WGQGTLVTVSS (SEQ ID NO: 521) |
| **Light Chain** | |
| KCD119 TAF | DIQLTQSPSSLSASVGDRVTITCRSSQTIVHSNGD TYLEWYQQKPGKAPNLLIYKVSNRFSGVPSRFSGS GSGTDFTLTISSLQPEDFATYYCFQGSHVPPTFGQ GTKVEIK (SEQ ID NO: 522) |
| 54R | DIQLTQSPSSLSASVGDRVTITCRSSQTIVHSNGD TYLEWYQQKPGKAPNLLIRKVSNRFSGVPSRFSGS GSGTDFTLTISSLQPEDFATYYCFQGSHVPPTFGQ GTKVEIK (SEQ ID NO: 523) |

TABLE 11.3-continued

| Amino acid sequences of final heavy and light chain candidates and their variants (KCD119 Variant Sequences; a CDR embodiment is underlined.) | |
|---|---|
| 101V | DIQLTQSPSSLSASVGDRVTITCRSSQTIVHSNGD<br>TYLEWYQQKPGKAPNLLIYKVSNRFSGVPSRFSGS<br>GSGTDFTLTISSLQPEDFATYYCFQGSHVPVTFGQ<br>GTKVEIK (SEQ ID NO: 524) |
| 54R101V | DIQLTQSPSSLSASVGDRVTITCRSSQTIVHSNGD<br>TYLEWYQQKPGKAPNLLIRKVSNRFSGVPSRFSGS<br>GSGTDFTLTISSLQPEDFATYYCFQGSHVPVTFGQ<br>GTKVEIK (SEQ ID NO: 525) |
| 54G101V | DIQLTQSPSSLSASVGDRVTITCRSSQTIVHSNGD<br>TYLEWYQQKPGKAPNLLIGKVSNRFSGVPSRFSGS<br>GSGTDFTLTISSLQPEDFATYYCFQGSHVPVTFGQ<br>GTKVEIK (SEQ ID NO: 526) |

TABLE 11.4

| Heavy and light chain nucleotide sequences of high-affinity anti-CFD antibodies and their variants | |
|---|---|
| | Heavy Chain |
| KC<br>D119<br>Taf | GAGGTGCAGCTGGTGGAATCTGGCGGCGGACTGGTGCAGCCTGGCGGCTCCCTGAGACTGTCTTGC<br>GCCGCCTCCGGCTACACCTTCACCGACTACTACATGAACTGGGTGCGACAGGCCCCTGGCAAGGGC<br>CTGGAATGGATCGGCGACATCAACCCCAACACCGGCGACACCAGCTACAACGCCGACTTCAAGCGG<br>CGGTTCACCTTCTCCCTGGACACCTCCAAGTCCACCGCCTACCTGCAGATGAACTCCCTGCGGGCCG<br>AGGACACCGCCGTGTACTACTGTACCAGAGAGGGCCCCTCCTTCGCCTACTGGGGCCAGGGCACAC<br>TGGTGACAGTGTCCTCC (SEQ ID NO: 527) |
| 54V | GAGGTGCAGCTGGTGGAATCTGGCGGCGGACTGGTGCAGCCTGGCGGCTCCCTGAGACTGTCTTGC<br>GCCGCCTCCGGCTACACCTTCACCGACTACTACATGAACTGGGTGCGACAGGCCCCTGGCAAGGGC<br>CTGGAATGGATCGGCGACATCAACCCCGTCACCGGCGACACCAGCTACAACGCCGACTTCAAGCGG<br>CGGTTCACCTTCTCCCTGGACACCTCCAAGTCCACCGCCTACCTGCAGATGAACTCCCTGCGGGCCG<br>AGGACACCGCCGTGTACTACTGTACCAGAGAGGGCCCCTCCTTCGCCTACTGGGGCCAGGGCACAC<br>TGGTGACAGTGTCCTCC (SEQ ID NO: 528) |
| 54I | GAGGTGCAGCTGGTGGAATCTGGCGGCGGACTGGTGCAGCCTGGCGGCTCCCTGAGACTGTCTTGC<br>GCCGCCTCCGGCTACACCTTCACCGACTACTACATGAACTGGGTGCGACAGGCCCCTGGCAAGGGC<br>CTGGAATGGATCGGCGACATCAACCCCATCACCGGCGACACCAGCTACAACGCCGACTTCAAGCGG<br>CGGTTCACCTTCTCCCTGGACACCTCCAAGTCCACCGCCTACCTGCAGATGAACTCCCTGCGGGCCG<br>AGGACACCGCCGTGTACTACTGTACCAGAGAGGGCCCCTCCTTCGCCTACTGGGGCCAGGGCACAC<br>TGGTGACAGTGTCCTCC (SEQ ID NO: 529) |
| 54V<br>59D | GAGGTGCAGCTGGTGGAATCTGGCGGCGGACTGGTGCAGCCTGGCGGCTCCCTGAGACTGTCTTGC<br>GCCGCCTCCGGCTACACCTTCACCGACTACTACATGAACTGGGTGCGACAGGCCCCTGGCAAGGGC<br>CTGGAATGGATCGGCGACATCAACCCCGTCACCGGCGACACCGACTACAACGCCGACTTCAAGCGG<br>CGGTTCACCTTCTCCCTGGACACCTCCAAGTCCACCGCCTACCTGCAGATGAACTCCCTGCGGGCCG<br>AGGACACCGCCGTGTACTACTGTACCAGAGAGGGCCCCTCCTTCGCCTACTGGGGCCAGGGCACAC<br>TGGTGACAGTGTCCTCC (SEQ ID NO: 530) |
| 54I<br>59D | GAGGTGCAGCTGGTGGAATCTGGCGGCGGACTGGTGCAGCCTGGCGGCTCCCTGAGACTGTCTTGC<br>GCCGCCTCCGGCTACACCTTCACCGACTACTACATGAACTGGGTGCGACAGGCCCCTGGCAAGGGC<br>CTGGAATGGATCGGCGACATCAACCCCATCACCGGCGACACCGACTACAACGCCGACTTCAAGCGG<br>CGGTTCACCTTCTCCCTGGACACCTCCAAGTCCACCGCCTACCTGCAGATGAACTCCCTGCGGGCCG<br>AGGACACCGCCGTGTACTACTGTACCAGAGAGGGCCCCTCCTTCGCCTACTGGGGCCAGGGCACAC<br>TGGTGACAGTGTCCTCC (SEQ ID NO: 531) |
| 34I<br>54I<br>59D | GAGGTGCAGCTGGTGGAATCTGGCGGCGGACTGGTGCAGCCTGGCGGCTCCCTGAGACTGTCTTGC<br>GCCGCCTCCGGCTACACCTTCACCGACTACTACATCAACTGGGTGCGACAGGCCCCTGGCAAGGGC<br>CTGGAATGGATCGGCGACATCAACCCCATCACCGGCGACACCGACTACAACGCCGACTTCAAGCGG<br>CGGTTCACCTTCTCCCTGGACACCTCCAAGTCCACCGCCTACCTGCAGATGAACTCCCTGCGGGCCG<br>AGGACACCGCCGTGTACTACTGTACCAGAGAGGGCCCCTCCTTCGCCTACTGGGGCCAGGGCACAC<br>TGGTGACAGTGTCCTCC (SEQ ID NO: 532) |
| 31S<br>34I<br>54I<br>59D | GAGGTGCAGCTGGTGGAATCTGGCGGCGGACTGGTGCAGCCTGGCGGCTCCCTGAGACTGTCTTGC<br>GCCGCCTCCGGCTACACCTTCACCAGCTACTACATCAACTGGGTGCGACAGGCCCCTGGCAAGGGC<br>CTGGAATGGATCGGCGACATCAACCCCATCACCGGCGACACCGACTACAACGCCGACTTCAAGCGG<br>CGGTTCACCTTCTCCCTGGACACCTCCAAGTCCACCGCCTACCTGCAGATGAACTCCCTGCGGGCCG<br>AGGACACCGCCGTGTACTACTGTACCAGAGAGGGCCCCTCCTTCGCCTACTGGGGCCAGGGCACAC<br>TGGTGACAGTGTCCTCC (SEQ ID NO: 533) |
| 34I<br>54I<br>59D<br>84S | GAGGTGCAGCTGGTGGAATCTGGCGGCGGACTGGTGCAGCCTGGCGGCTCCCTGAGACTGTCTTGC<br>GCCGCCTCCGGCTACACCTTCACCGACTACTACATCAACTGGGTGCGACAGGCCCCTGGCAAGGGC<br>CTGGAATGGATCGGCGACATCAACCCCATCACCGGCGACACCGACTACAACGCCGACTTCAAGCGG<br>CGGTTCACCTTCTCCCTGGACACCTCCAAGTCCACCGCCTACCTGCAGATGAGCTCCCTGCGGGCCG<br>AGGACACCGCCGTGTACTACTGTACCAGAGAGGGCCCCTCCTTCGCCTACTGGGGCCAGGGCACAC<br>TGGTGACAGTGTCCTCC (SEQ ID NO: 534) |

TABLE 11.4-continued

| Heavy and light chain nucleotide sequences of high-affinity anti-CFD antibodies and their variants | |
|---|---|
| 31S | GAGGTGCAGCTGGTGGAATCTGGCGGCGGACTGGTGCAGCCTGGCGGCTCCCTGAGACTGTCTTGC |
| 34I | GCCGCCTCCGGCTACACCTTCACCAGCTACTACATCAACTGGGTGCGACAGGCCCCTGGCAAGGGC |
| 54I | CTGGAATGGATCGGCGACATCAACCCCATCACCGGCGACACCGACTACAACGCCGACTTCAAGCGG |
| 59D | CGGTTCACCTTCTCCCTGGACACCTCCAAGTCCACCGCCTACCTGCAGATGAGCTCCCTGCGGGCCG |
| 84S | AGGACACCGCCGTGTACTACTGTACCAGAGAGGGCCCCTCCTTCGCCTACTGGGGCCAGGGCACAC |
| | TGGTGACAGTGTCCTCC (SEQ ID NO: 535) |
| Light Chain | |
| KC | GACATCCAGCTGACCCAGAGCCCCTCCAGCCTGTCCGCCTCTGTGGGCGACAGAGTGACCATCACCT |
| D119 | GTCGGTCCTCCCAGACCATCGTGCACTCCAACGGCGACACCTACCTGGAATGGTATCAGCAGAAGCC |
| Taf | CGGCAAGGCCCCTAACCTGCTGATCTACAAGGTGTCCAACCGGTTCTCCGGCGTGCCCTCCAGATTC |
| | TCCGGCTCCGGCTCTGGCACCGACTTCACCCTGACCATCTCCAGCCTGCAGCCCGAGGACTTCGCCA |
| | CCTACTACTGTTTTCAAGGCTCCCACGTGCCACCCACCTTCGGCCAGGGCACCAAGGTGGAAATCAA |
| | G (SEQ ID NO: 536) |
| 54R | GACATCCAGCTGACCCAGAGCCCCTCCAGCCTGTCCGCCTCTGTGGGCGACAGAGTGACCATCACCT |
| | GTCGGTCCTCCCAGACCATCGTGCACTCCAACGGCGACACCTACCTGGAATGGTATCAGCAGAAGCC |
| | CGGCAAGGCCCCTAACCTGCTGATCCGCAAGGTGTCCAACCGGTTCTCCGGCGTGCCCTCCAGATTC |
| | TCCGGCTCCGGCTCTGGCACCGACTTCACCCTGACCATCTCCAGCCTGCAGCCCGAGGACTTCGCCA |
| | CCTACTACTGTTTTCAAGGCTCCCACGTGCCACCCACCTTCGGCCAGGGCACCAAGGTGGAAATCAA |
| | G (SEQ ID NO: 537) |
| 101V | GACATCCAGCTGACCCAGAGCCCCTCCAGCCTGTCCGCCTCTGTGGGCGACAGAGTGACCATCACCT |
| | GTCGGTCCTCCCAGACCATCGTGCACTCCAACGGCGACACCTACCTGGAATGGTATCAGCAGAAGCC |
| | CGGCAAGGCCCCTAACCTGCTGATCTACAAGGTGTCCAACCGGTTCTCCGGCGTGCCCTCCAGATTC |
| | TCCGGCTCCGGCTCTGGCACCGACTTCACCCTGACCATCTCCAGCCTGCAGCCCGAGGACTTCGCCA |
| | CCTACTACTGTTTTCAAGGCTCCCACGTGCCAGTCACCTTCGGCCAGGGCACCAAGGTGGAAATCAA |
| | G (SEQ ID NO: 538) |
| 54R | GACATCCAGCTGACCCAGAGCCCCTCCAGCCTGTCCGCCTCTGTGGGCGACAGAGTGACCATCACCT |
| 101V | GTCGGTCCTCCCAGACCATCGTGCACTCCAACGGCGACACCTACCTGGAATGGTATCAGCAGAAGCC |
| | CGGCAAGGCCCCTAACCTGCTGATCCGCAAGGTGTCCAACCGGTTCTCCGGCGTGCCCTCCAGATTC |
| | TCCGGCTCCGGCTCTGGCACCGACTTCACCCTGACCATCTCCAGCCTGCAGCCCGAGGACTTCGCCA |
| | CCTACTACTGTTTTCAAGGCTCCCACGTGCCAGTCACCTTCGGCCAGGGCACCAAGGTGGAAATCAA |
| | G (SEQ ID NO: 539) |
| 54G | GACATCCAGCTGACCCAGAGCCCCTCCAGCCTGTCCGCCTCTGTGGGCGACAGAGTGACCATCACCT |
| 101V | GTCGGTCCTCCCAGACCATCGTGCACTCCAACGGCGACACCTACCTGGAATGGTATCAGCAGAAGCC |
| | CGGCAAGGCCCCTAACCTGCTGATCGGAAAGGTGTCCAACCGGTTCTCCGGCGTGCCCTCCAGATTC |
| | TCCGGCTCCGGCTCTGGCACCGACTTCACCCTGACCATCTCCAGCCTGCAGCCCGAGGACTTCGCCA |
| | CCTACTACTGTTTTCAAGGCTCCCACGTGCCAGTCACCTTCGGCCAGGGCACCAAGGTGGAAATCAA |
| | G (SEQ ID NO: 540) |

Example 12—Removal of Sequence Liability for Manufacturability

Sequence in heavy chain TAF KCD119 CDR2 contain potential deamidation site 'NPNT'. Mutagenesis of NPNT reveal N54V or N54I enhanced affinity. Resulting molecule (54V/wt) was tested in Mass Spec under oxidation or temperature/high pH stress to look for additional glycosylation, oxidation and deamidation sites.

No N- or O-glycosylation sites were found in CDRs by mass spectrometry analysis (Example 13.2).

One Methionine oxidation was found in Heavy chain CDR1 (M34) by mass spectrometry analysis (Example 13.3).

One deamidation site in heavy chain FW3 that was increasingly deamidated in a high temperature/high pH stressed sample (2 weeks at 40 degree pH9) in 54V/wt was identified by mass spectrometry analysis (Example 13.4).

Example 13.1—Glycosylation Sites 54 v/wt sample was deglycosylated to remove N-linked glycans with only PNGase F (New England BioLabs, P/N P0705L). The sample was denatured with 8 M urea in 100 mM Tris (pH 8.0), buffer exchanged, deglycosylated at 37° C. overnight (16 hours), buffer exchanged, reduced with 25 mM DTT, and alkylated with 50 mM IAA. The sample was then digested in tandem with first endoproteinase Lys-C (2 hours) and then trypsin overnight (16 hours).

54 v/wt sample was deglycosylated to remove N-linked and O-linked glycans using the deglycosylase mix (New England BioLabs, P/N P6039). The sample was denatured with 8 M urea in 100 mM Tris (pH 8.0), buffer exchanged, deglycosylated at 37° C. overnight (16 hours), buffer exchanged, reduced with 25 mM DTT and alkylated with 50 mM IAA. The sample was digested in tandem by first adding the endoproteinase Lys-C for 2 hours at 37° C. and then adding trypsin before allowing the digestion to proceed overnight (16 hours) at 37° C.

The glycosylated sample was denatured with 8 M urea in 100 mM Tris (pH 8.0), reduced with 25 mM DTT and alkylated with 50 mM IAA. The sample was digested in tandem by first adding the endoproteinase Lys-C for 2 hours at 37° C. and then adding trypsin before allowing the digestion to proceed overnight (16 hours) at 37° C.

Peptide sequence coverage from Mass Spec analysis was compared amongst glycosylated and deglycosylated samples. No additional N- or O-glycosylation sites were found in CDRs.

Example 13.2—Oxidation Sites

Two 54 v/wt samples were stressed in a light chamber at 765 W/m2 over a 24 hour period. One sample was removed and frozen (−20° C.) at 8 hours. The remaining material was removed after 24 hours. The stressed samples were treated with the deglycosylase mix to remove N-linked and O-linked glycans as described in the previous slide.

Peptide sequence coverage from Mass Spec analysis was compared amongst UV stressed and non-stressed samples. One Methionine oxidation was found in Heavy chain CDR1 (M34).

For removal of M34 oxidation site, substitutions at residue 34 were screened. Looked for residues to improve or have no effect on affinity, and found that M34I did not affect affinity of 54 v/wt. M34I was then engineered into the high affinity variants 31S54I59D/54R101V or 54I59D/54R101V to determine its effects on binding affinity at 25 and 37 degrees (Table 13.2.1 and Table 13.2.2).

TABLE 13.2.1

| Screening substitutions for removal of M34 oxidation site at 25 C. | | | | |
|---|---|---|---|---|
| Heavy Chain | Light Chain | ka (1/Ms) | kd (1/s) | KD (M) |
| 31S54I59D | 54R101V (SEQ ID NO: 184) | 1.44E+07 | 1.20E−04 | 8.36E−12 |
| 54I59D | 54R101V (SEQ ID NO: 184) | 1.71E+07 | 9.80E−05 | 5.72E−12 |
| 34I54I59D | 54R101V (SEQ ID NO: 184) | 1.80E+07 | 1.01E−04 | 5.62E−12 |
| 31S34I54I59D | 54R101V (SEQ ID NO: 184) | 1.32E+07 | 7.84E−05 | 5.96E−12 |

TABLE 13.2.2

| Screening substitutions for removal of M34 oxidation site at 37 C. | | | | |
|---|---|---|---|---|
| Heavy Chain | Light Chain | ka (1/Ms) | kd (1/s) | KD (M) |
| 31S54I59D | 54R101V (SEQ ID NO: 184) | 2.78E+07 | 2.27E−04 | 8.17E−12 |
| 54I59D | 54R101V (SEQ ID NO: 184) | 3.09E+07 | 2.05E−04 | 6.63E−12 |
| 34I54I59D | 54R101V (SEQ ID NO: 184) | 3.27E+07 | 2.64E−04 | 8.08E−12 |
| 31S34I54I59D | 54R101V (SEQ ID NO: 184) | 2.46E+07 | 2.37E−04 | 9.61E−12 |

Example 13.3—Deamidation Sites 54 v/wt samples were adjusted to pH9 and incubated at 40 degrees for 2 weeks. The stressed samples were treated with the deglycosylase mix to remove N-linked and 0-linked glycans. Deamidation of residue 84N in HFW3 was found to be significantly increased in the 54 v/wt sample that was incubated at 40 degree and pH9 for 2 weeks as compared to a sample that did not go through the temperature and pH stress (22.5% vs. 7.5%).

For removal of 84N Deamidation site, 84N was substituted with S or T (the second and third commonly occurring amino acids at 84 position with 25% and 7% frequency, respectively). 84S did not affect affinity (Table 13.3.1 and Table 13.3.2).

TABLE 13.3.1

| Screening substitutions for removal of 84N deamidation site at 25 C. | | | | |
|---|---|---|---|---|
| Heavy Chain | Light Chain | ka (1/Ms) | kd (1/s) | KD (M) |
| 31S54I59D | 54R101V (SEQ ID NO: 184) | 1.40E+07 | 5.12E−05 | 3.66E−12 |
| 31S54I59D84S | 54R101V (SEQ ID NO: 184) | 1.49E+07 | 9.14E−05 | 6.13E−12 |

TABLE 13.3.2

| Screening substitutions for removal of 84N deamidation site at 37 C. | | | | |
|---|---|---|---|---|
| Heavy Chain | Light Chain | ka (1/Ms) | kd (1/s) | KD (M) |
| 31S54I59D | 54R101V (SEQ ID NO: 184) | 3.09E+07 | 2.14E−04 | 6.91E−12 |
| 31S54I59D84S | 54R101V (SEQ ID NO: 184) | 2.84E+07 | 1.74E−04 | 6.13E−12 |

Example 14—Polyreactivity

Figure 7A:
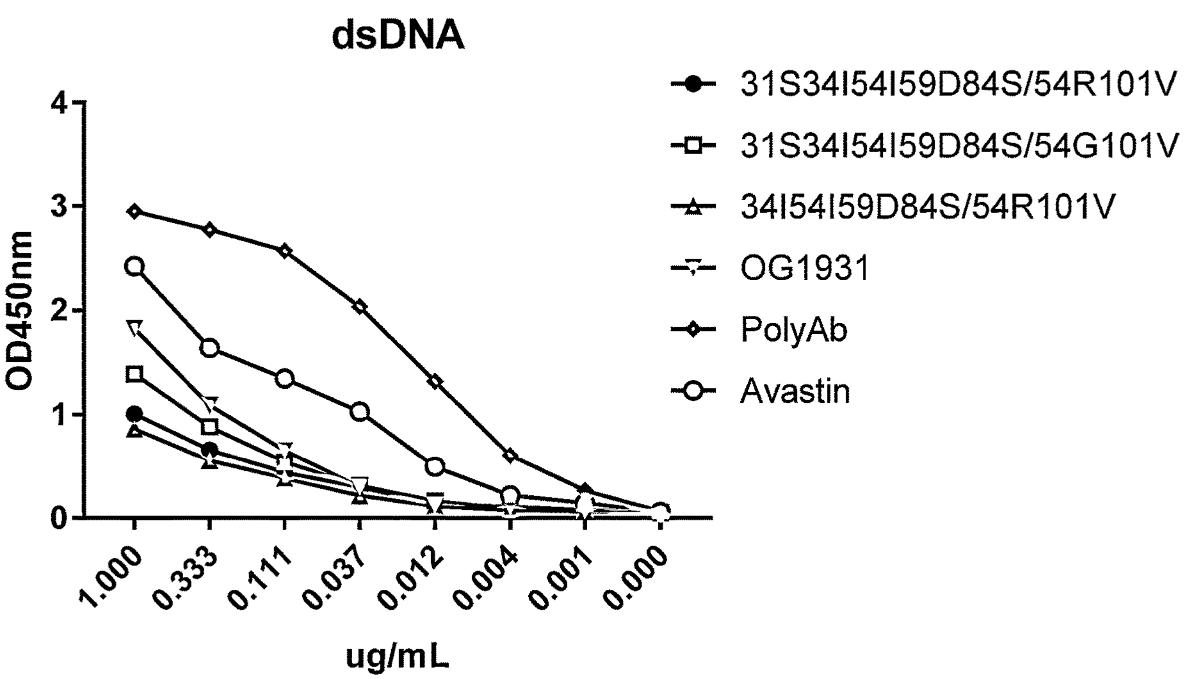
FIG. 7A shows polyreactivity profile of a panel of antibodies tested by ELISA against dsDNA antigen.
Figure 7B:
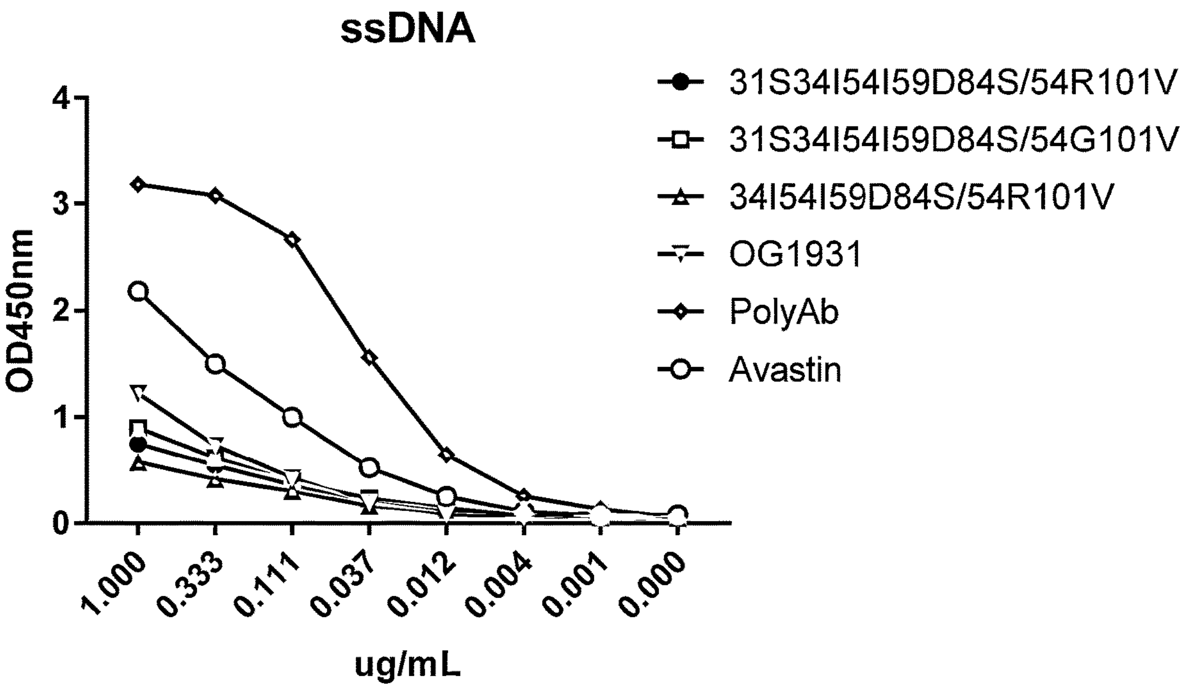
FIG. 7B shows polyreactivity profile of a panel of antibodies tested by ELISA against ssDNA antigen.
Figure 7C:
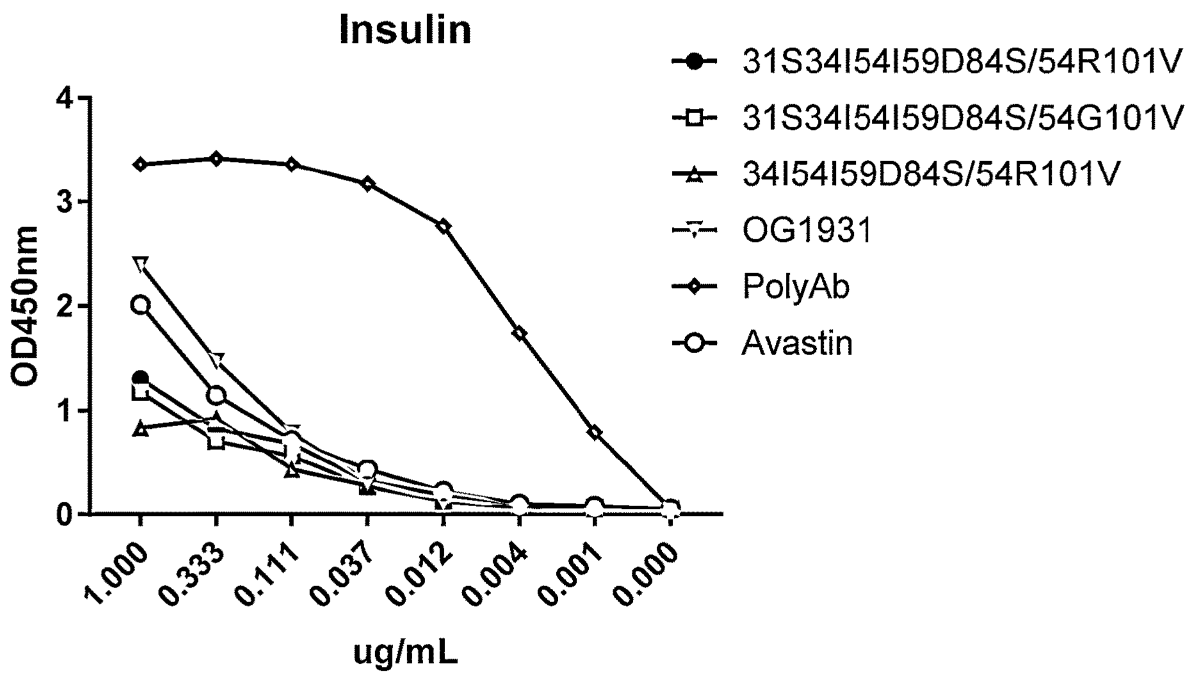
FIG. 7C shows polyreactivity profile of a panel of antibodies tested by ELISA against insulin antigen.
Figure 7D:
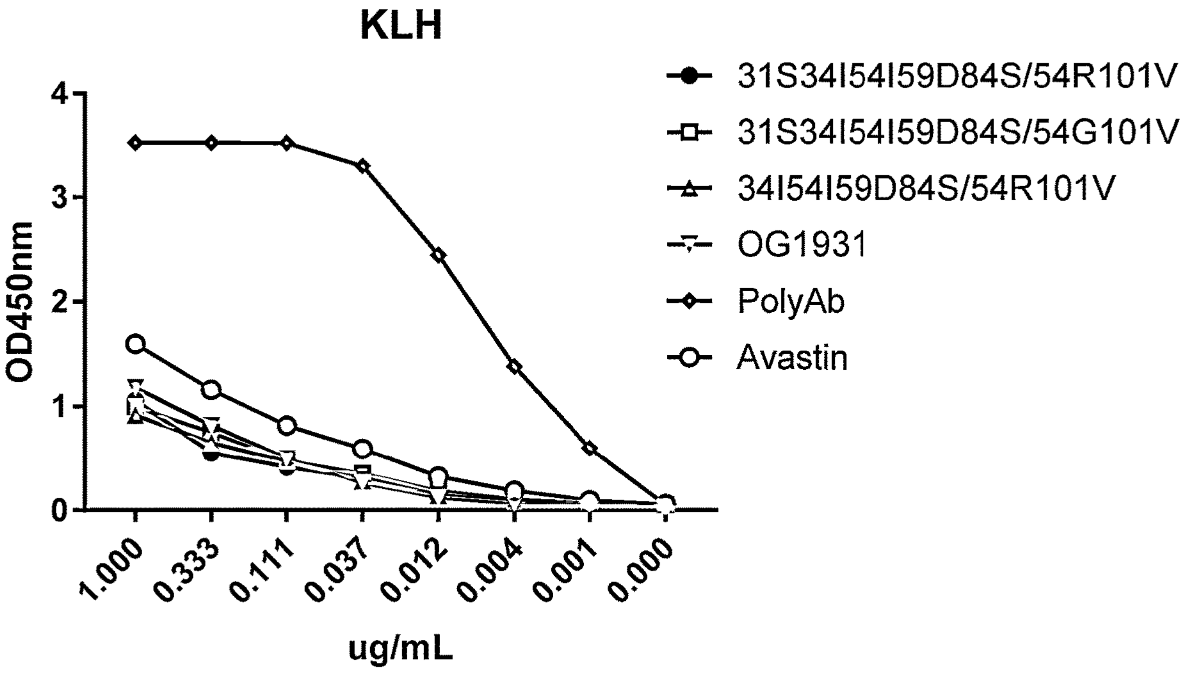
FIG. 7D shows polyreactivity profile of a panel of antibodies tested by ELISA against KLH antigen.
Figure 7E:
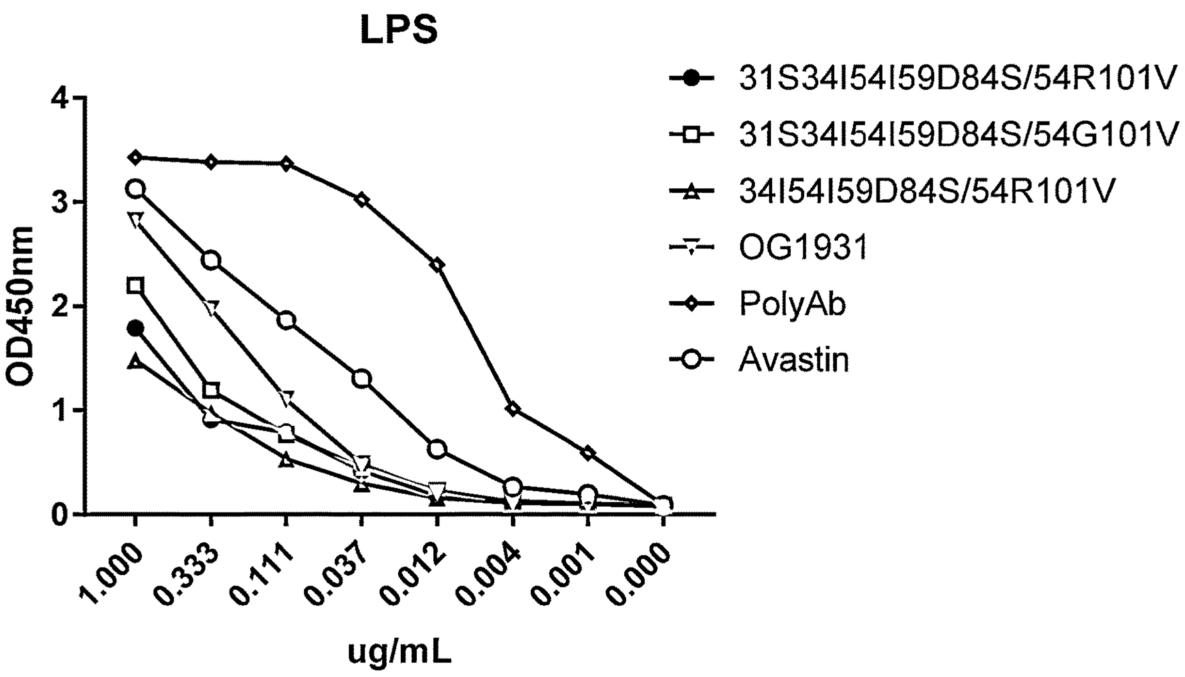
FIG. 7E shows polyreactivity profile of a panel of antibodies tested by ELISA against LPS antigen.
Figure 7F:
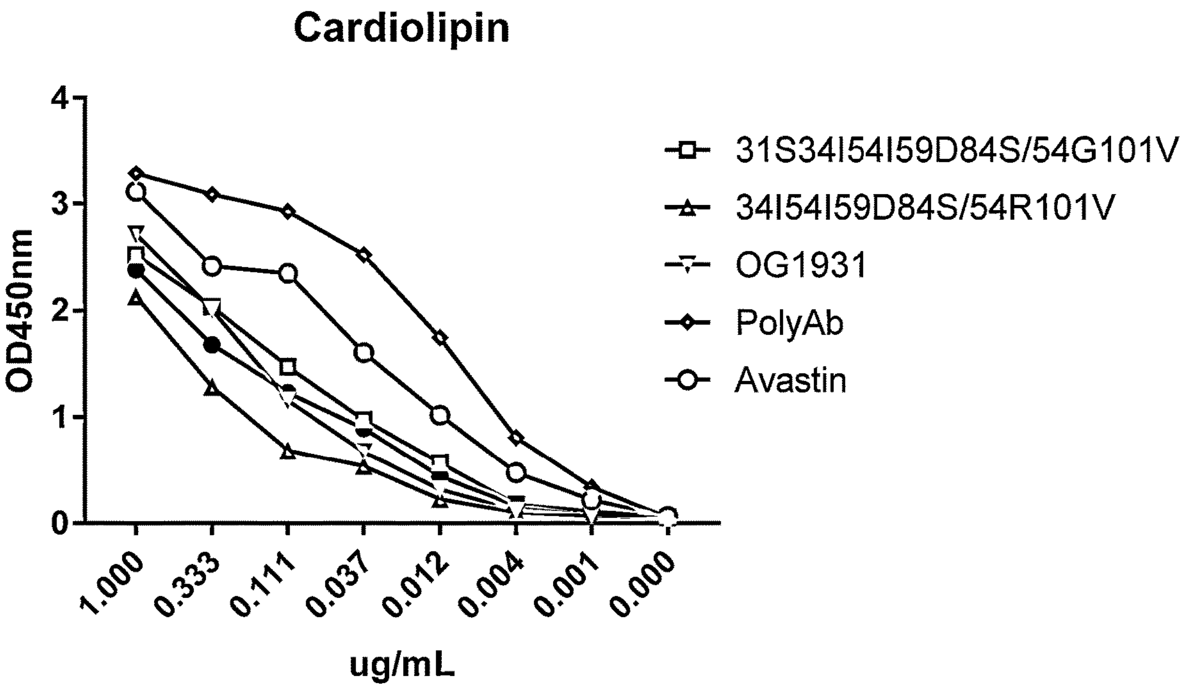
FIG. 7F shows polyreactivity profile of a panel of antibodies tested by ELISA against cardiolipin antigen.

The polyreactivity profile of a panel of high-affinity humanized anti-CFD antibodies were tested by ELISA. Briefly, various antigens (dsDNA (FIG. 7A), ssDNA (FIG. 7B), insulin (FIG. 7C), KLH (FIG. 7D), LPS (FIG. 7E) and cardiolipin (FIG. 7F)) were coated overnight at room temperature at 5 ug/mL; except for insulin at 2.5 ug/mL. Plates were washed in water then blocked in ELISA buffer (1 mM EDTA, 0.05% Tween 20) for 2 hours at room temperature. Antibody panel was titrated 1:3 from a top concentration of 1 ug/mL in 1×PBS and incubated for 2 hours at room temperature, followed by 3 washes in water and incubation with an HRP conjugated anti-human Fc antibody in ELISA buffer for 1 hour at room temperature. Lastly, plates were washed in water, incubated in ELISA buffer for 5 min at room temperature followed by a final wash in water prior to TMB development.

Example 15—Manufacturability

Representative high affinity anti-CFD antibodies and their variants have excellent expression in Mammalian Cells Table as determined by antibody expression levels in the supernatant of transiently transfected HEK293 and CHO cells. Data are presented in Table 15.1.

TABLE 15.1

| Antibody expression levels in the supernatant of transiently transfected HEK293 and CHO cells | | | |
|---|---|---|---|
| Heavy | Light | Expi293 Expression (3 ml) (mg/L) | CHO Expression (1 L) (mg/L) |
| OG1931 | OG1931 | 140 | 13.6 |
| 31S34I54I59D84S | 54R101V (SEQ ID NO: 184) | 124 | 228.3 |

TABLE 15.1-continued

Antibody expression levels in the supernatant of transiently transfected HEK293 and CHO cells

| Heavy | Light | Expi293 Expression (3 ml) (mg/L) | CHO Expression (1 L) (mg/L) |
|---|---|---|---|
| 34I54I59D84S (SEQ ID NO: 183) | 54R101V (SEQ ID NO: 184) | 86 | 206.1 |
| 31S34I54I59D84S | 54G101V | 35 | 248.7 |
| 34I54I59D84S (SEQ ID NO: 183) | 54G101V | 123 | NA |
| KCD119 TAF | KCD119TAF | 84 | |

Example 16

One embodiment of the antibody included the point mutations of 34I54I59D84S (heavy, SEQ ID NO: 183 or 520)/54R101V (light, SEQ ID NO: 184 or 525), also called OG1965.

Example 17.1—FB Cleavage Assay for Anti-CFD Antibodies

Figure 8:
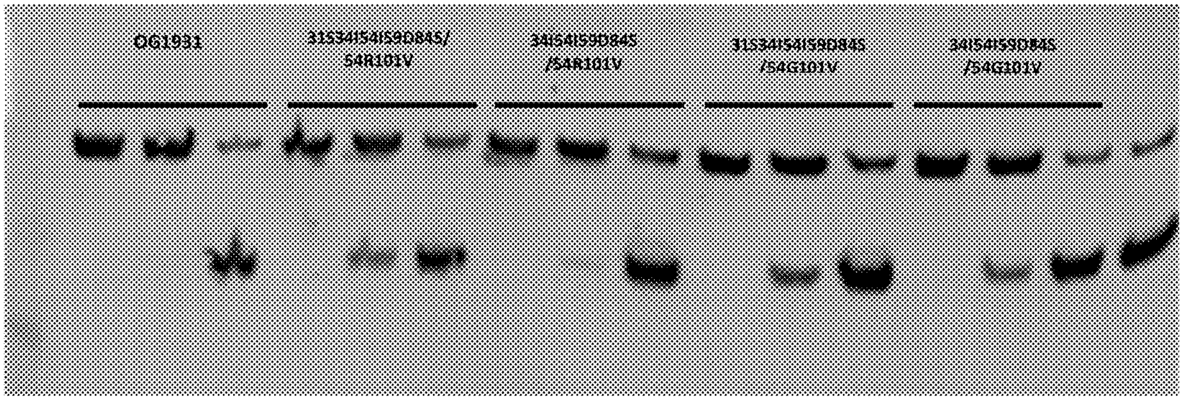
FIG. 8 shows an image of a Western blot of an FB cleavage assay for anti-CFD antibodies.
Figure 9:
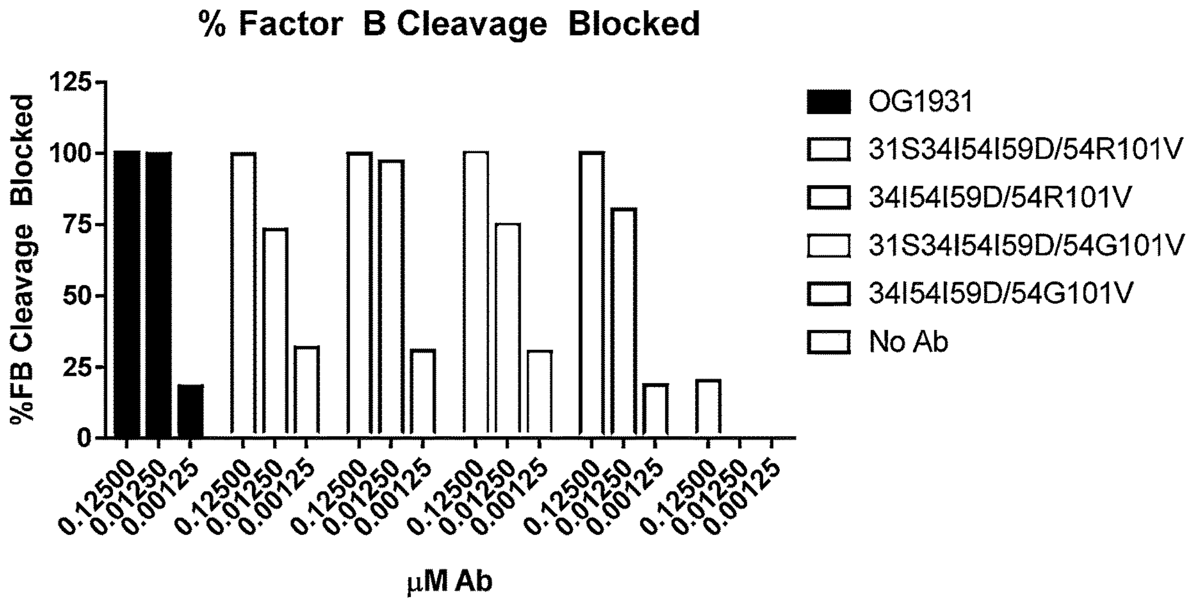
FIG. 9 shows a graph of the % of FB cleavage blocked in the FB cleavage assay for anti-CFD antibodies.

Factor B Cleavage Assay—To determine whether anti-CFD antibodies (AFDs) block factor B (FB) cleavage, a FB cleavage assay was used. For the assay, 0.15 uM CFD (serum purified; CompTech cat. no. A136) was mixed with varying concentrations of AFDs (0.5 uM down to 0.005 uM) in a final volume of 10 uls. The complexes were incubated at room temperature for 45 minutes. 0.5 uM of Factor B (FB; serum purified; A135 CompTech) and 0.5 uM C3b (serum purified; CompTech cat. no. A114) were combined and incubated for 15 minutes at room temperature in a final volume of 10 uls for each sample. 10 uls of FB/C3b complex was added to 10 uls of CFD/AFD so that the final concentrations of FB/C3b were 0.25 uM and CFD was 0.0375 uM in a final volume of 20 uls. The proteins were then incubated at 37° C. for 45 minutes. Following incubation, sample buffer with reducing agent was added to samples and run on a 4-12% Bis-Tris gel before being transferred to a nitrocellulose membrane for western blot analysis. Membranes were blocked for 1 hour in Odyssey® Blocking Buffer (LI-COR®) and then incubated with 1:1000 dilution of anti-Factor B antibody (Rabbit monoclonal antibody; EPR9288 (B) Abcam) overnight. The blot was washed 3 times with PBS with 0.5% Tween®, and incubated with 1:10000 dilution of goat anti-Rabbit 800 secondary antibody (LI-COR®). The blot was then washed 3 times with PBS, once with water, and imaged on a LI-COR® Odyssey® Fc scanner. Factor B cleavage was quantified using Image Studio® Western Blot analysis software. The blocking ability of each antibody was calculated by taking the percentage of cleaved Factor B of the total Factor B (cleaved and uncleaved) for each sample. Data are presented in FIG. 8 and FIG. 9.

These data indicate that the anti-CFD antibodies potently and effectively blocked CFD mediated cleavage of C3bB in a dose-dependent manner.

Example 17.2—FB Cleavage Assay for 34I54I59D84S/54R101V

Figure 10:
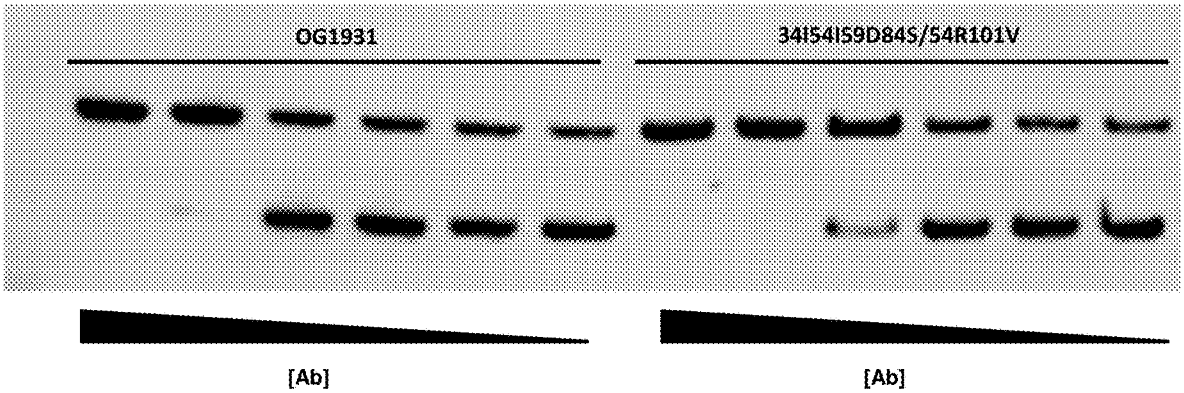
FIG. 10 shows an image of a Western blot of an FB cleavage assay for anti-CFD antibodies.
Figure 11:
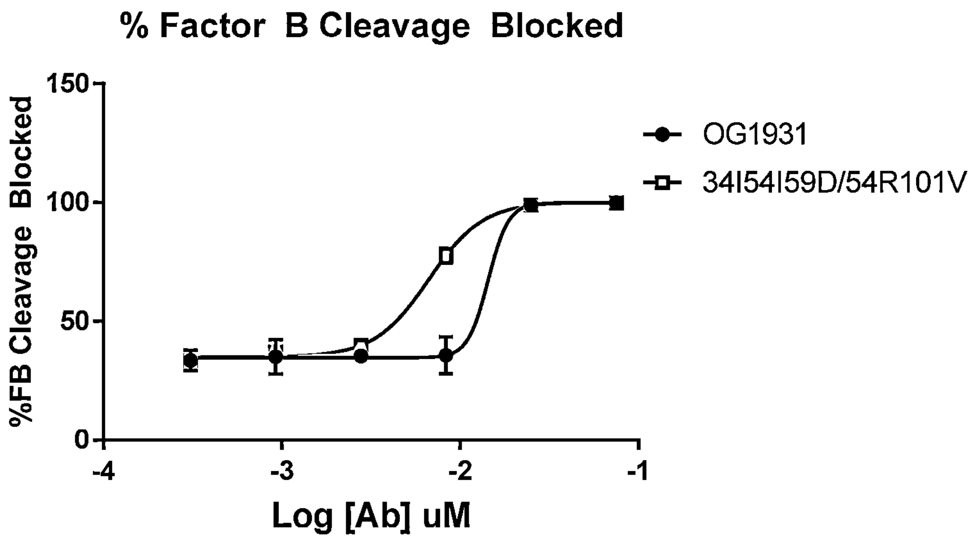
FIG. 11 shows a graph of the % of FB cleavage blocked in an FB cleavage assay for anti-CFD antibodies.

To determine whether anti-CFD antibodies (AFDs) block factor B (FB) cleavage, an FB cleavage assay was used. For the assay, 0.15 uM CFD (serum purified; CompTech cat. no. A136) was mixed with varying concentrations of AFDs (1:3 dilutions from 0.075 uM down to 0.00031 uM) in a final volume of 10 uls. The complexes were incubated at room temperature for 30 minutes. 0.5 uM of Factor B (FB; serum purified; A135 CompTech) and 0.5 uM C3b (serum purified; CompTech cat. no. A114) were combined and incubated for 45 minutes at room temperature in a final volume of 10 uls for each sample. 10 uls of FB/C3b complex was added to 10 uls of CFD/AFD so that the final concentrations of FB/C3b were 0.25 uM and CFD was 0.0375 uM in a final volume of 20 uls. The proteins were then incubated at 37° C. for 45 minutes. Following incubation, sample buffer with reducing agent was added to samples and run on a 4-12% Bis-Tris gel before being transferred to a nitrocellulose membrane for western blot analysis. Membranes were blocked for 1 hour in Odyssey® Blocking Buffer (LI-COR®) and then incubated with 1:1000 dilution of anti-Factor B antibody (Rabbit monoclonal antibody; EPR9288(B) Abcam) overnight. The blot was washed 3 times with PBS with 0.5% Tween®, and incubated with 1:10000 dilution of goat anti-Rabbit 800 secondary antibody (LI-COR®). The blot was then washed 3 times with PBS, once with water, and imaged on a LI-COR® Odyssey® Fc scanner. Factor B cleavage was quantified using Image Studio® Western Blot analysis software. The blocking ability of each antibody was calculated by taking the percentage of cleaved Factor B of the total Factor B (cleaved and uncleaved) for each sample. 34I54I59D84S (SEQ ID NO: 183 or 520)/54R101V (SEQ ID NO: 184 or 525) antibody was comparable or slightly better at blocking CFD mediated cleavage of CFB than OG1931. Data are presented in FIG. 10 and FIG. 11.

Under these conditions, Factor B cleavage was blocked completely by 34I54I59D84S/54R101V in a dose dependent manner with an EC50 of 7 nM.

Example 18—Binding Affinities of Humanized Anti-CFD Antibodies

Figure 18:
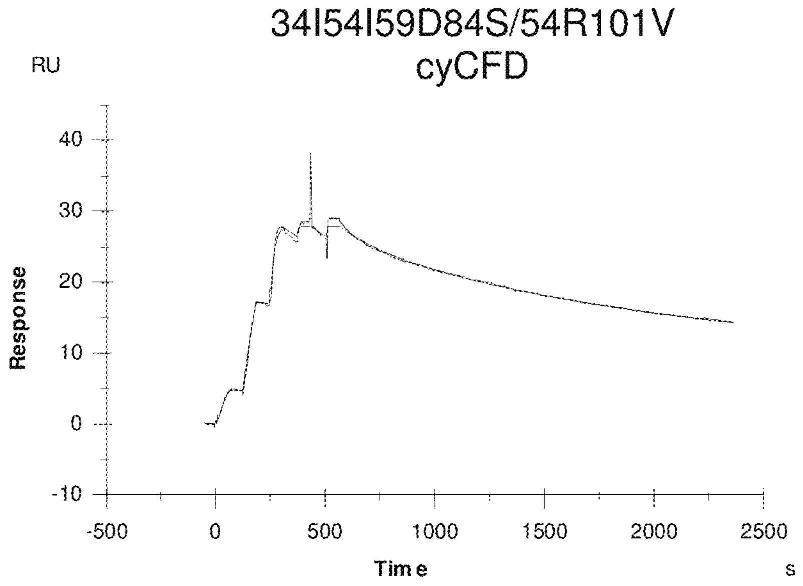
FIG. 18 shows binding affinity of 34I54I59D84S/54R101V to Cynomolgus CFD.

Antibodies were purified from Expi293 supernatants following a standard protocol. Antibodies were diluted to 0.5 ug/ml in HBS-EP+ buffer and captured on a protein A chip for 25 seconds to reach approximately 70 resonance units. 45 nM, 15 nM, 5 nM, 1.67 nM, and 0.56 nM serum purified Complement Factor D (diluted in HBS-EP+ buffer) or recombinant cynomologus Complement Factor D (cyCFD) was flowed over the captured antibodies for 60 seconds in a single cycle kinetics method, and dissociated for 30 minutes. Binding kinetic information was obtained by the BIAevaluation software (GE). Representative data are presented in FIG. 18 and Table 18.1 and Table 18.2. In some embodiments, the construct 34I54I59D84S as the heavy and 54R101V as the light is especially advantageous.

Figure 19:
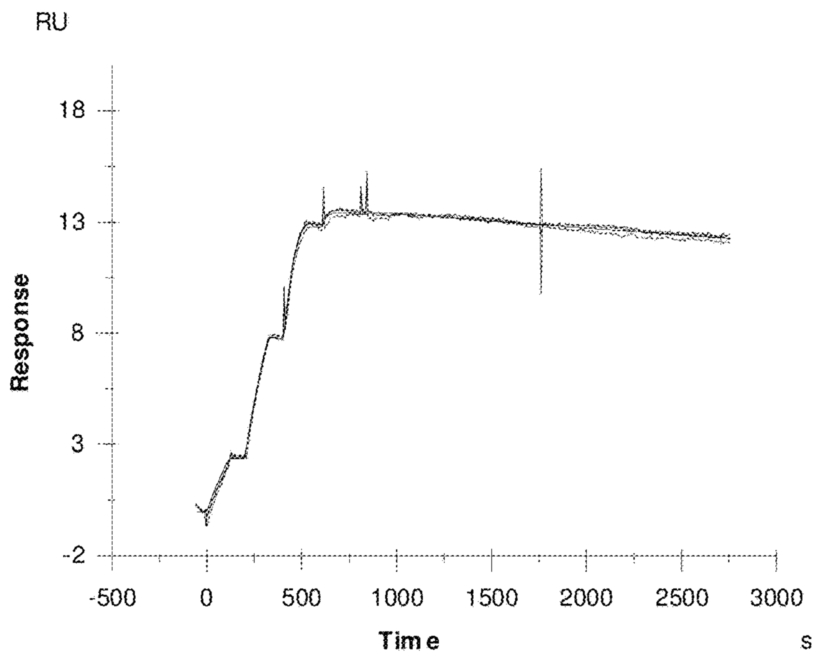
FIG. 19 shows binding affinities of 34I54I59D84S/54R101V to purified human CFD at 25 degree and 37 degree Celsius.
Figure 19:
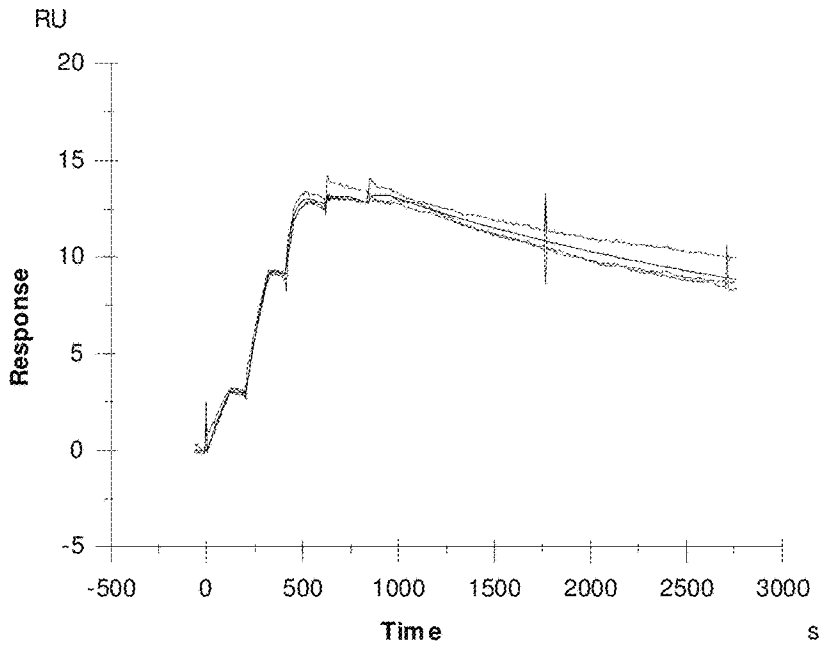

To better determine CFD binding kinetics by SPR of final candidate OG1965, a semi-covalent immobilization technique was employed. OG1965 was biotinylated using Thermo EZ-Link Maleimide-PEG2-Biotin kit at a 10:1 ratio. Approximately 1-2 biotin molecules were conjugated to each antibody molecule. 10,000 RUs of neutravidin (Thermo) was directly immobilized to a CM5 chip on a Biacore T200 following the standard amine coupling immobilization method. 50 RUs of OG1965 was captured on flow cell 2, and single cycle kinetics for binding to serum purified human CFD (15 nM, 5 nM, 1.67 nM, 0.56 nM, 0.19 nM) was performed at both 25 and 37 degrees. Data are shown in FIG. 19 and Table 18.3.

TABLE 18.1

| Binding kinetics data for Final Candidates to serum purified human Complement Factor D | | | | | | | |
|---|---|---|---|---|---|---|---|
| | | 25 Degrees | | | 37 Degrees | | |
| Heavy | Light | ka (1/Ms) | kd (1/s) | KD (M) | ka (1/Ms) | kd (Vs) | KD (M) |
| OG1931 | OG1931 | 3.11E+07 | 1.36E−05 | 4.37E−13 | 2.94E+08 | 9.10E−04 | 3.10E−12 |
| 3I534I54I59D84S | 54R101V | 1.66E+07 | 1.69E−08 | 1.02E−15 | 3.50E+07 | 1.37E−04 | 3.92E−12 |
| 34I54I59D84S | 54R101V | 2.06E+07 | 9.02E−05 | 4.37E−12 | 4.00E+07 | 2.02E−04 | 5.04E−12 |
| 3I534I54I59D84S | 54G101V | 4.42E+06 | 1.81E−10 | 4.10E−17 | 1.21E+07 | 7.36E−05 | 6.11E−12 |
| 34I54I59D84S | 54G101V | 7.59E+06 | 5.18E−05 | 6.83E−12 | 1.45E+07 | 1.12E−04 | 7.74E−12 |
| D19 TAF | D19TAF | 1.38E+07 | 1.55E−03 | 1.13E−10 | 1.26E+07 | 6.28E−03 | 4.99E−10 |

TABLE 18.2

| Binding kinetics data for OG1965 to cyno CFD (cyCFD) at 37 degrees | | | | |
|---|---|---|---|---|
| Ligand | Sample | ka (1/Ms) | kd (1/s) | KD (M) |
| OG1965 | cyCFD | 3.49E+07 | 9.78E−04 | 2.80E−11 |

TABLE 18.3

| Binding kinetics data for semi-covalently immobilized OG1965 at 25 and 37 degrees | | | |
|---|---|---|---|
| | Ka (1/Ms) | Kd (1/s) | KD (M) |
| 25° | 1.40E+07 | 5.08E−05 | 3.64E−12 |
| 37° | 2.55E+07 | 2.41E−04 | 9.56E−12 |

Example 19.1—Enzymatic Assay of Anti-CFD Antibodies

Proteolysis assay—Anti-CFD antibodies (AFDs) were evaluated for their ability to affect the enzymatic activity of human CFD for the synthetic substrate Z-L-Lys-SBzl hydrochloride. For the proteolysis assay, human CFD is diluted to 200 uM in assay buffer (50 mM Tris, 220 mM NaCl, pH 7.5). Substrate (Z-L-Lys-SBzl hydrochloride, Sigma, C3647, 100 mM stock in DMSO) is diluted to 4 mM in assay buffer with 4 mM 5,5'Dithio-bis-(2-nitrobenzoic acid) (DTNB, Sigma, Catalog #D-8130, 100 mM stock in DMSO). 50 μLs of the diluted CFD is loaded into a 96 well clear plate, and 50 uls of AFD is added. The reaction is started by adding 100 μL of substrate/DTNB mixture to wells. A substrate blank containing 50 μL assay buffer and 50 μL substrate mixture without any CFD is included. Using a plate reader (SpectraMax Plus or equivalent), samples are read in kinetic mode for 45 minutes at an absorbance of 405 nm. To calculate specific activity the following formula is used: Specific Activity (pmol/min/μg)=Adjusted Vmax*(OD/min)×well volume (L)×$10^{12}$ pmol/mol. ext. coeff($M^{-1}cm^{-1}$)×path corr.*(cm)×amount of enzyme (μg). *Adjusted for substrate blank, Using the extinction coefficient 13,260 $M^{-1}cm^{-1}$, *Using the path correction 0.320 cm. Data are presented in FIG. 12 and Table 19.1.1.

Figure 12:
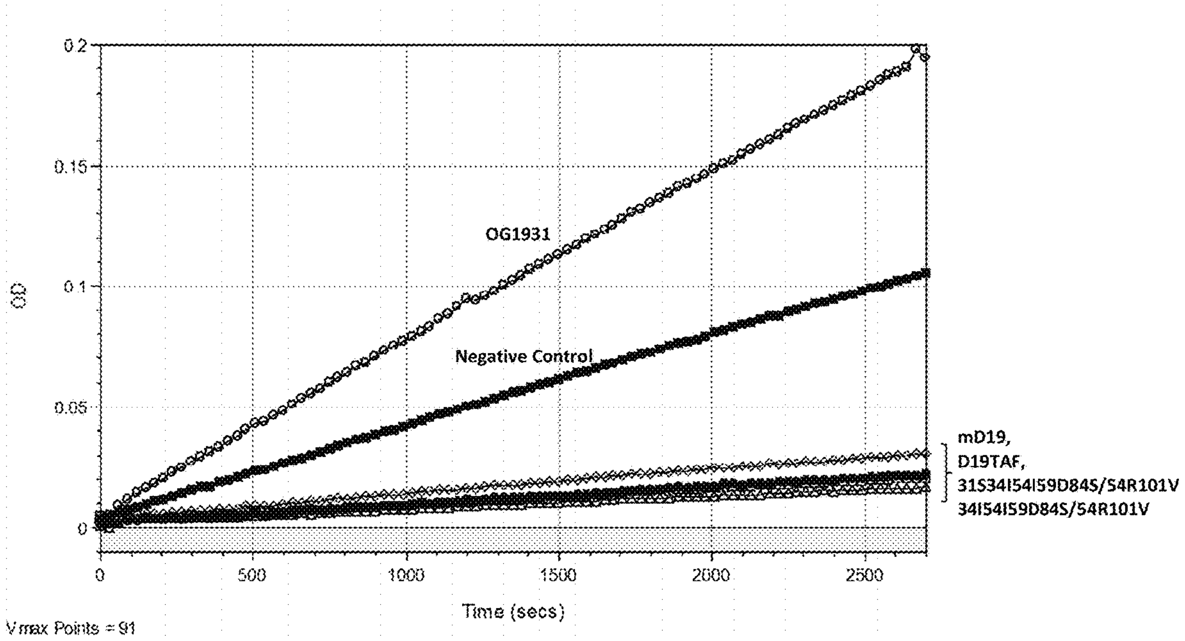
FIG. 12 shows effect of anti-CFD antibodies on the enzyme activity of human CFD for the synthetic substrate Z-L-Lys-SBzl hydrochloride.

FIG. 12 shows that KCD119 variants block enzymatic activity of human Complement Factor D (serum purified), while a control antibody (OG1931) enhances enzymatic activity relative to no antibody control or negative antibody (OG1321) control.

TABLE 19.1.1

| Enzymatic Assay of anti-CFD antibodies | | |
|---|---|---|
| | Vmax (OD/sec) | % no ab control |
| OG1931 | 4.231 | 203.06 |
| KCD119TAF | 0.408 | 19.58 |
| Mouse KCD119 | 0.318 | 15.26 |
| 31S34I54V59D84S/54R101V (SEQ ID NO: 184) | 0.596 | 28.60 |
| 34I54V59D84S/54R101V (SEQ ID NO: 184) | 0.486 | 23.32 |
| OG1321 | 2.335 | 112.06 |
| No Ab | 2.063 | 100.00 |

Example 19.2—Effect of Anti-CFD Antibodies on Alternative Compliment Dependent Hemolysis Assay To assess the ability of anti-CFD antibodies to inhibit alternative complement pathway, a hemolysis assay was used.

Hemolysis assay—For the hemolysis assay, rabbit red blood cells ("RBCs", CompTech #B301) are diluted or re-suspended and washed with $GVB^0$ (without $Ca^{2+}$ and $Mg^{2+}$, CompTech #B101) 3 times, then re-suspended in ice-cold GVB++ buffer (GVB/2 mM MgEGTA) at 4.33e8/mL and kept at 4° C. when ready to be used.

Normal human serum (NHS) were incubated with anti-CFD antibody (AFD) at room temperature for ten minutes in well of a round-bottom plate. Add the prepared RBCs to the wells with NHS/AFD on the incubation plate; incubate at room temperature for 35 minutes, mixing every 10 minutes. Stop the reaction with $GVB^0$/10 mM EDTA CompTech #B104).

Figure 13:
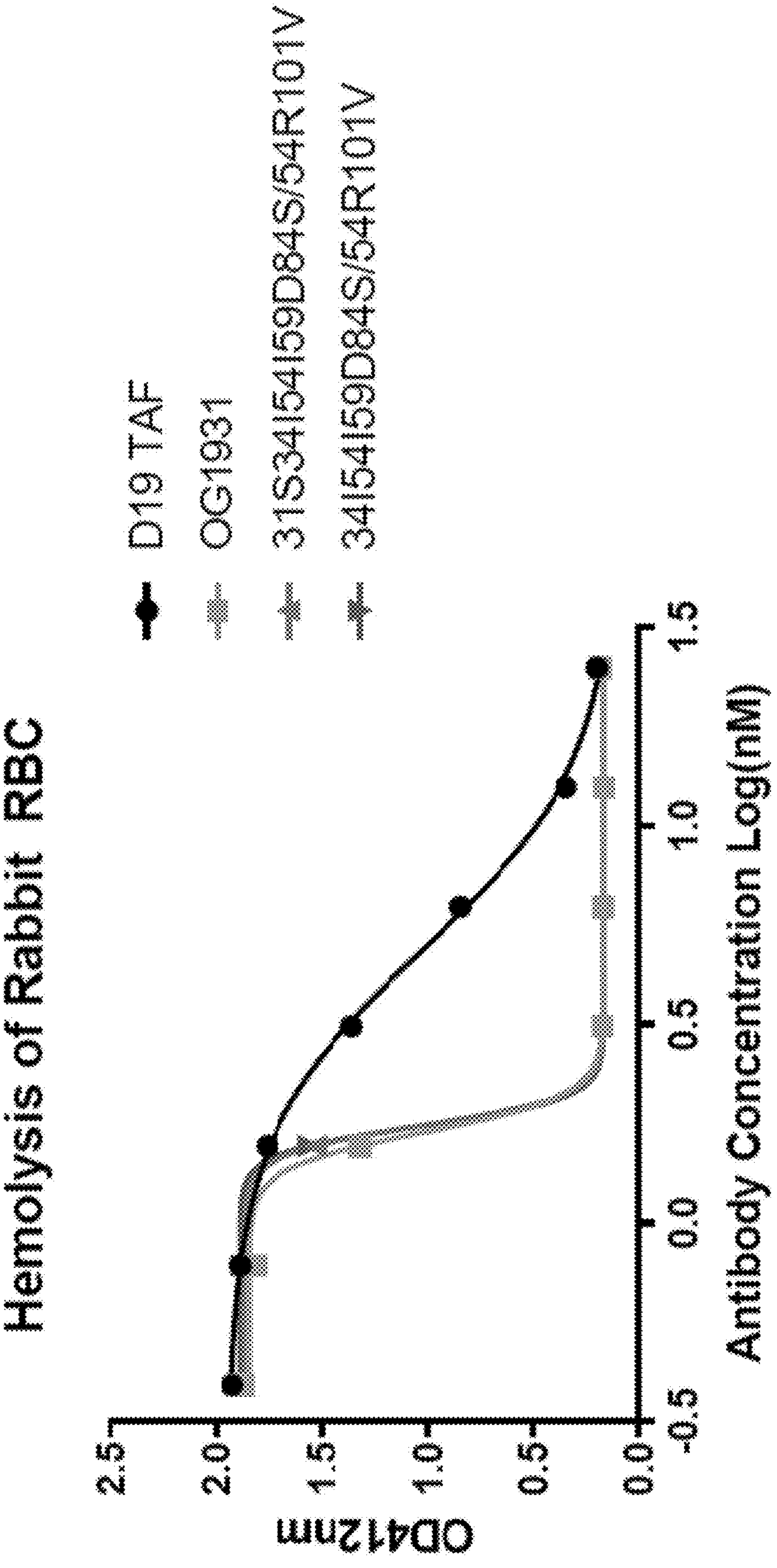
FIG. 13 shows the effect of anti-CFD antibodies on complement-mediated hemolysis of rabbit RBCs.

To measure lysis, supernatant is collected by centrifuging the plate at 1,500 rpm for 5 min, no break or low break. Supernatants are transferred to wells on a flat-bottom 96-well plate (200 uL per well). The plates are read using a SpectraMax Plus™, 25° C. at OD412 nm. In the analysis 100% of lysis: RBCs/NHS without AFD; Inhibition: RBCs/NHS/AFD. Percentage of inhibition is calculated as follows: 100×(OD RBCs/NHS)−(OD RBCs/NHS/AFD). Data are presented in FIG. 13

Figure 14:
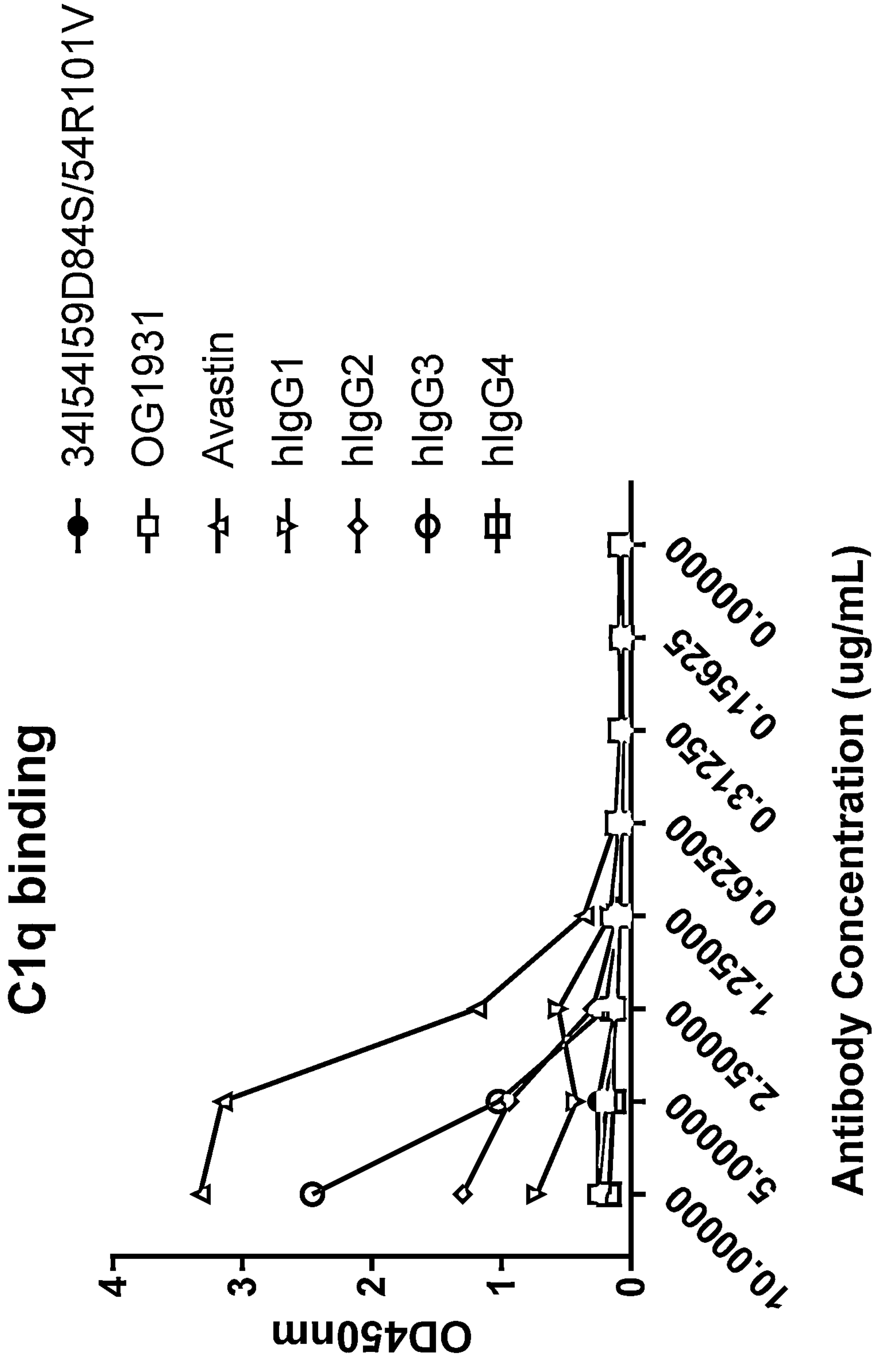
FIG. 14 shows results of binding of anti-CFD antibodies and controls to C1q.

Example 19.3—34I54I59D84S/54R101V has Diminished Effector Functions and does not Bind to Complement C1q Complement engagement liabilities was assessed by C1q ELISA binding. Briefly, antibody panel was titrated 1:2 from a top concentration of 10 ug/mL in 1×PBS for overnight coating at 4C. Plates were then blocked After a 2 hour blocking step in 1% BSA, purified human C1q was then applied at 5 ug/mL in 1% BSA for 2 hours at room temperature followed by detection with HRP-conjugated anti-human C1q antibody and TMB development. Data are shown in FIG. 14.

Figure 15A:
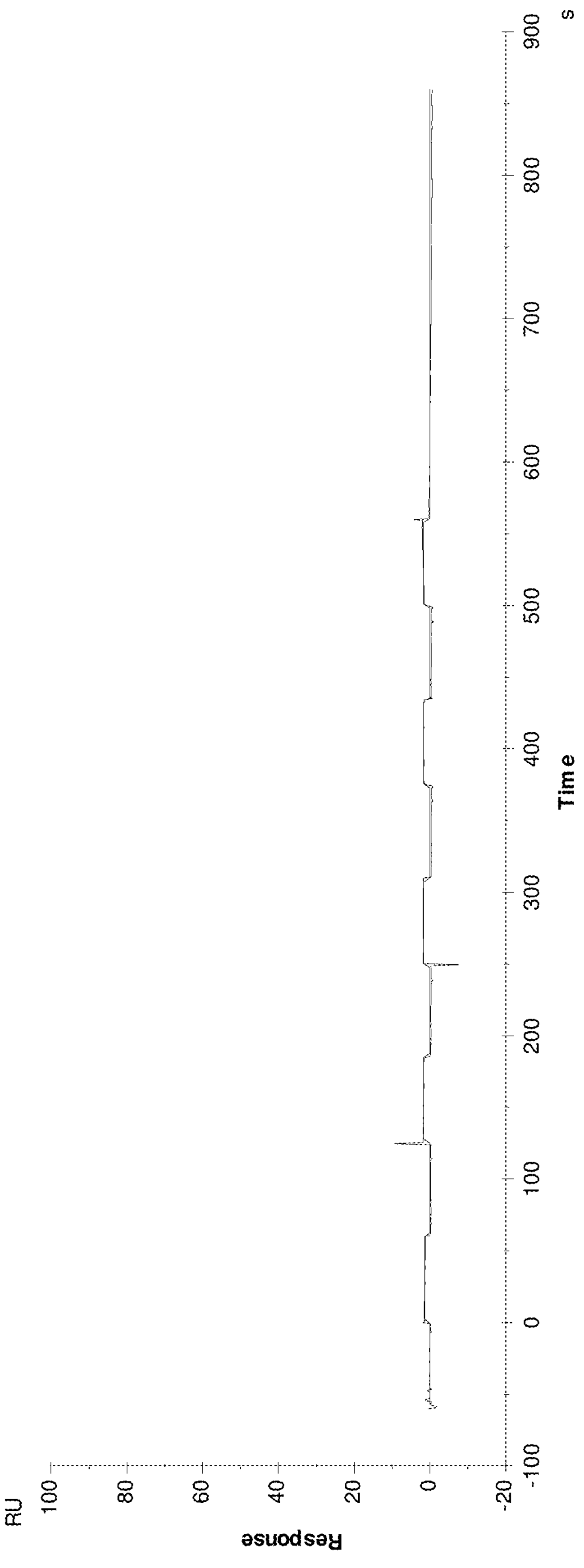
FIG. 15A shows binding kinetics of 34I54I59D84S/54R101V to FcγRI.
Figure 15B:
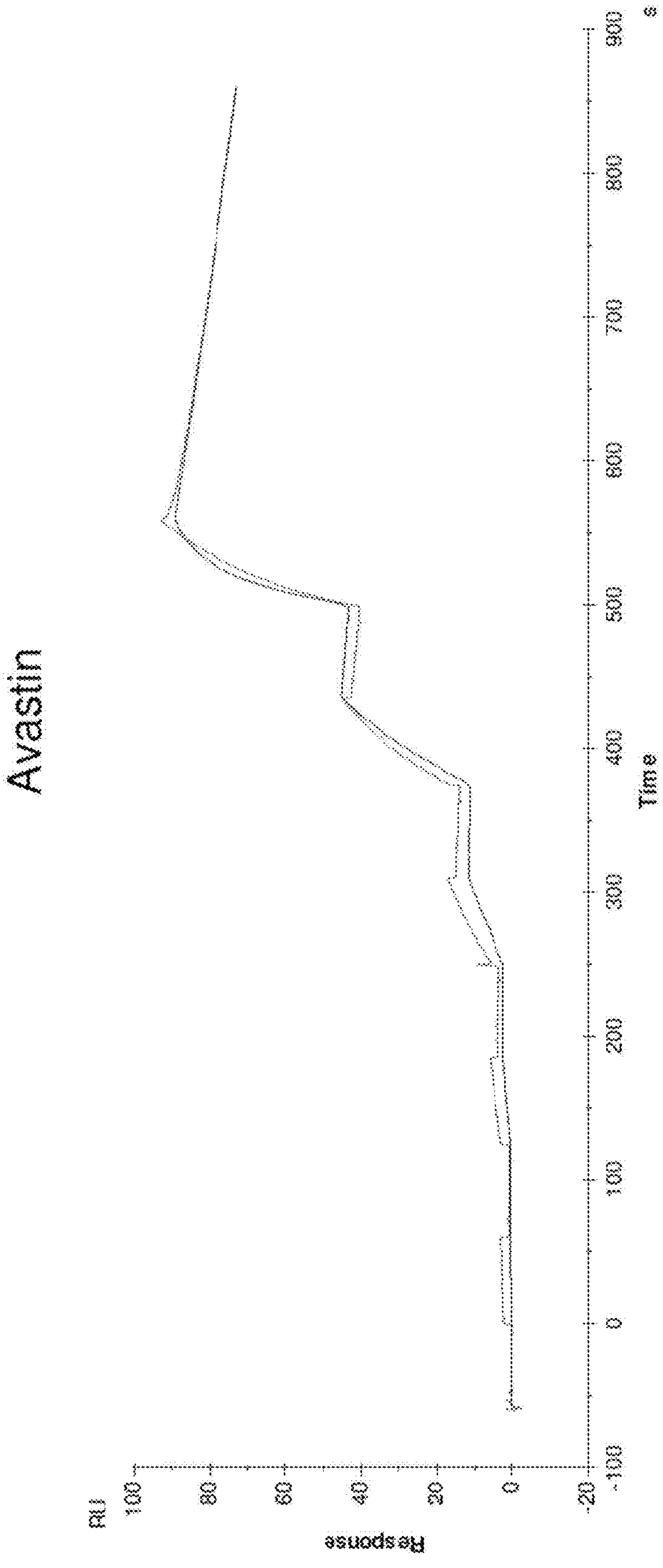
FIG. 15B shows binding kinetics of Avastin to FcγRI.
Figure 16A:
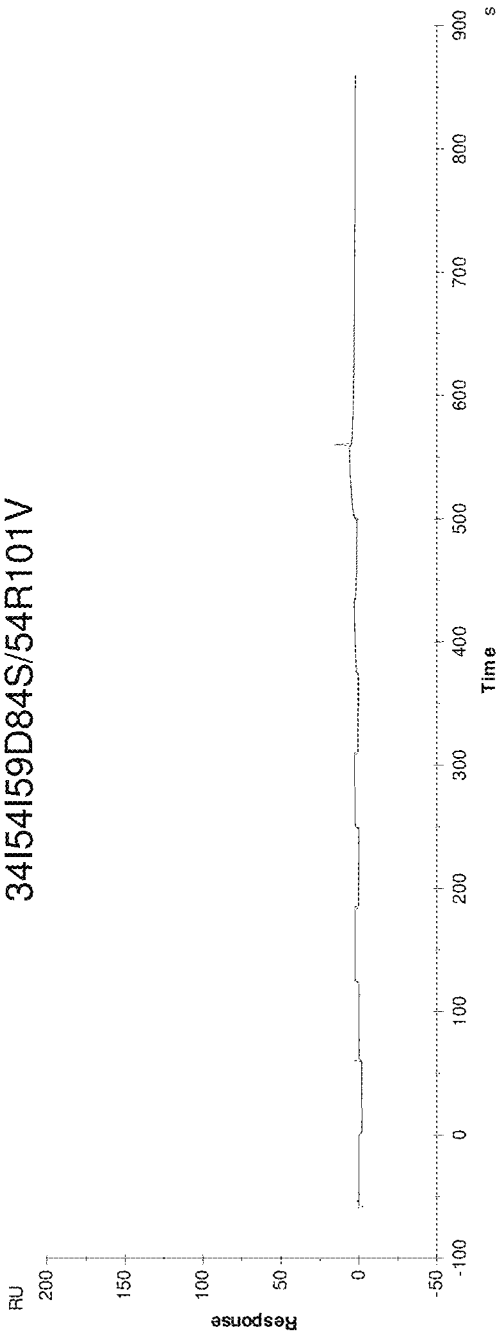
FIG. 16A shows binding kinetics of 34I54I59D84S/54R101V to FcγRIIIa.
Figure 16B:
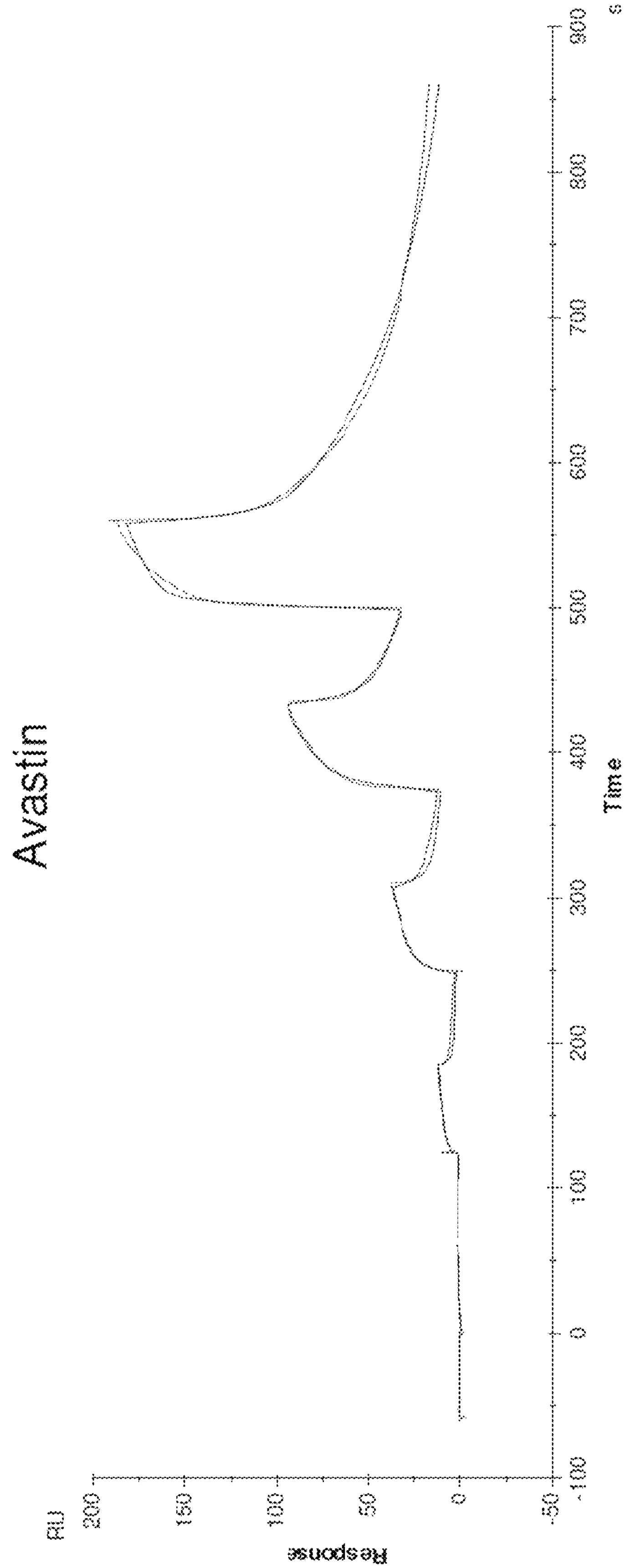
FIG. 16B shows binding kinetics of Avastin to FcγRIIIa.

Example 19.4—34I54I59D84S/54R101V has Diminished Effector Functions and does not Bind to FcγRI, FcγRIIIa, FcγRIIa, and FcγRIIIb For Fc receptor Binding Kinetics on Biacore, all binding kinetics were performed at 25° C. using a BIAcore T200. Briefly, an anti-his antibody was immobilized on a CM5 chip. Histidine-tagged FcγRI (FIG. 15A and FIG. 15B) and FcγRIIIa (FIG. 16A and FIG. 16B) at a concentration of 0.5 μg/mL prepared in HBS-EP buffer (0.01M HEPES pH7.4, 0.15M NaCl, 3 mM EDTA, 0.005% Tween-20) were injected independently for 60-s using a flow rate of 5 μL/min in the active flow cell only. Antibody candidate and Avastin, used as a positive control, were then injected over the reference and active flow cell using 60-s injections at 30 μL/mL, applying single-cycle kinetics method. Antibody concentration in the range of 0.48 to 300 nM were used for FcγRI and 7.8 nM to 2000 nM for FcγRIIIa. Following each run, flow cells were regenerated with a 60 s injection of 10 mM glycine pH 1.7 using a flow-rate of 50p/mL. Data was double referenced, using subtraction of both reference flow cell and blank cycles. Analysis was performed using BIA evaluation software.

Figure 16C:
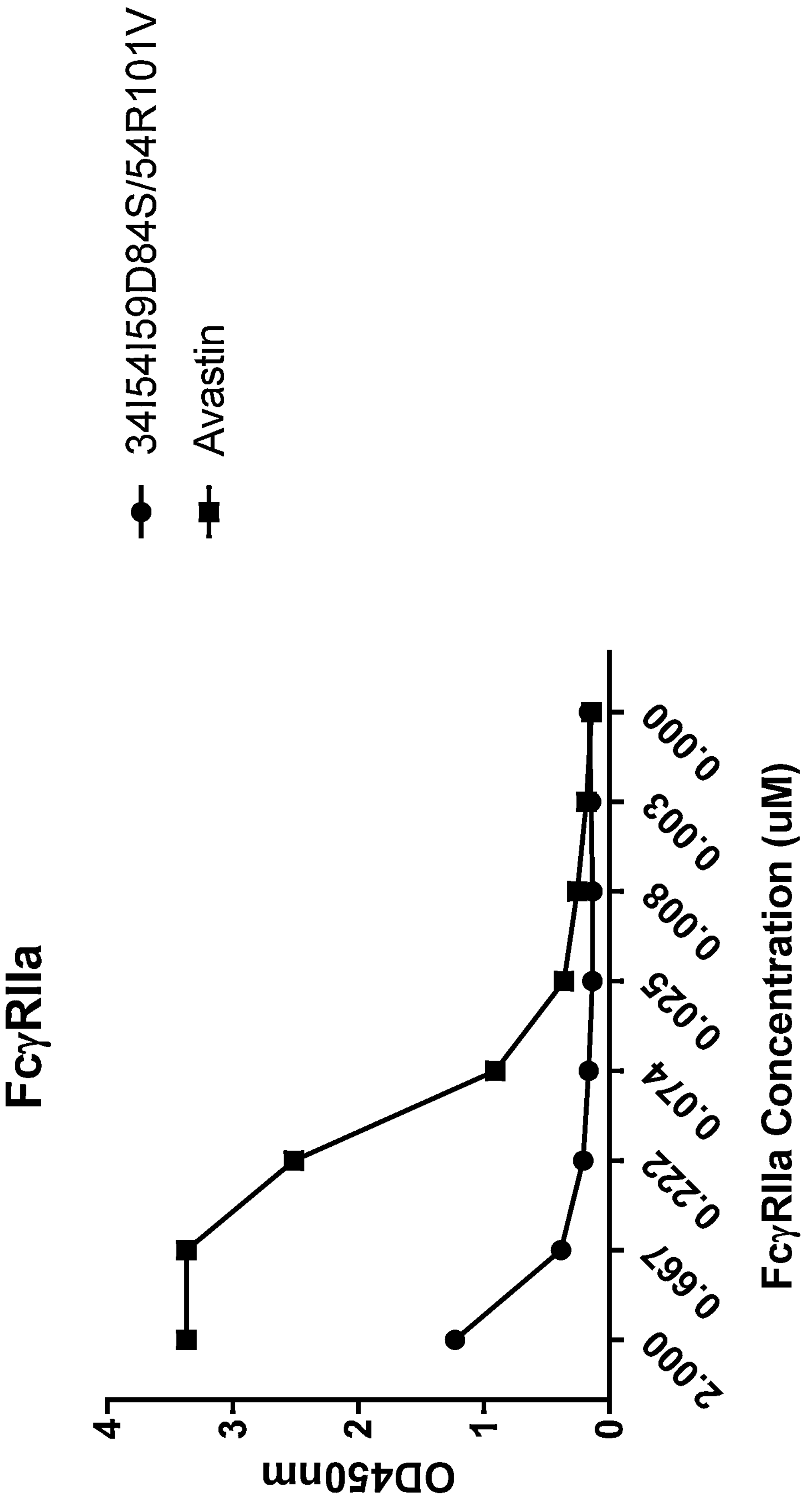
FIG. 16C shows binding of 34I54I59D84S/54R101V and Avastin to FcγRIIa.
Figure 16D:
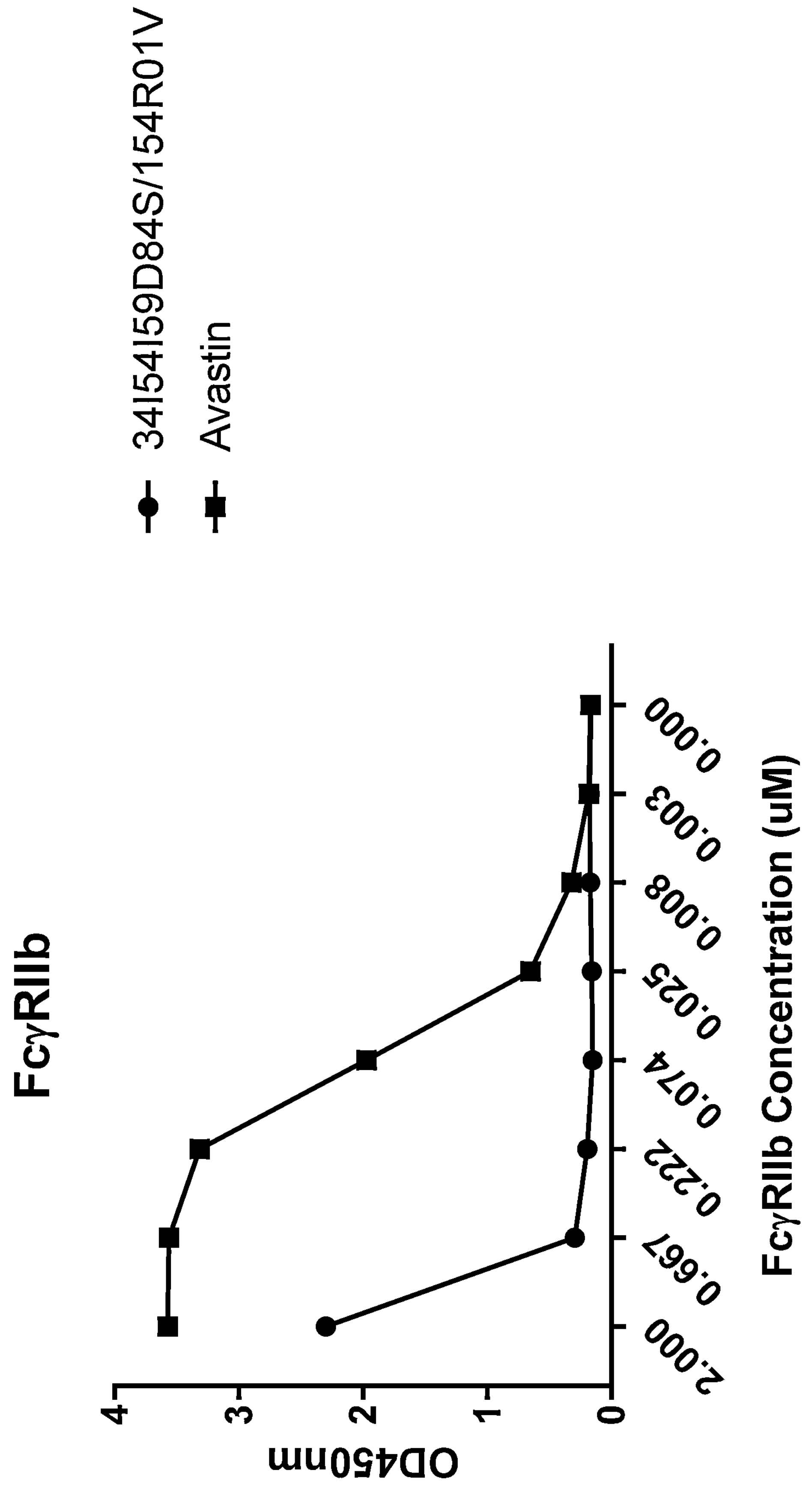
FIG. 16D shows binding of 34I54I59D84S/54R101V and Avastin to FcγRIIb.
Figure 16E:
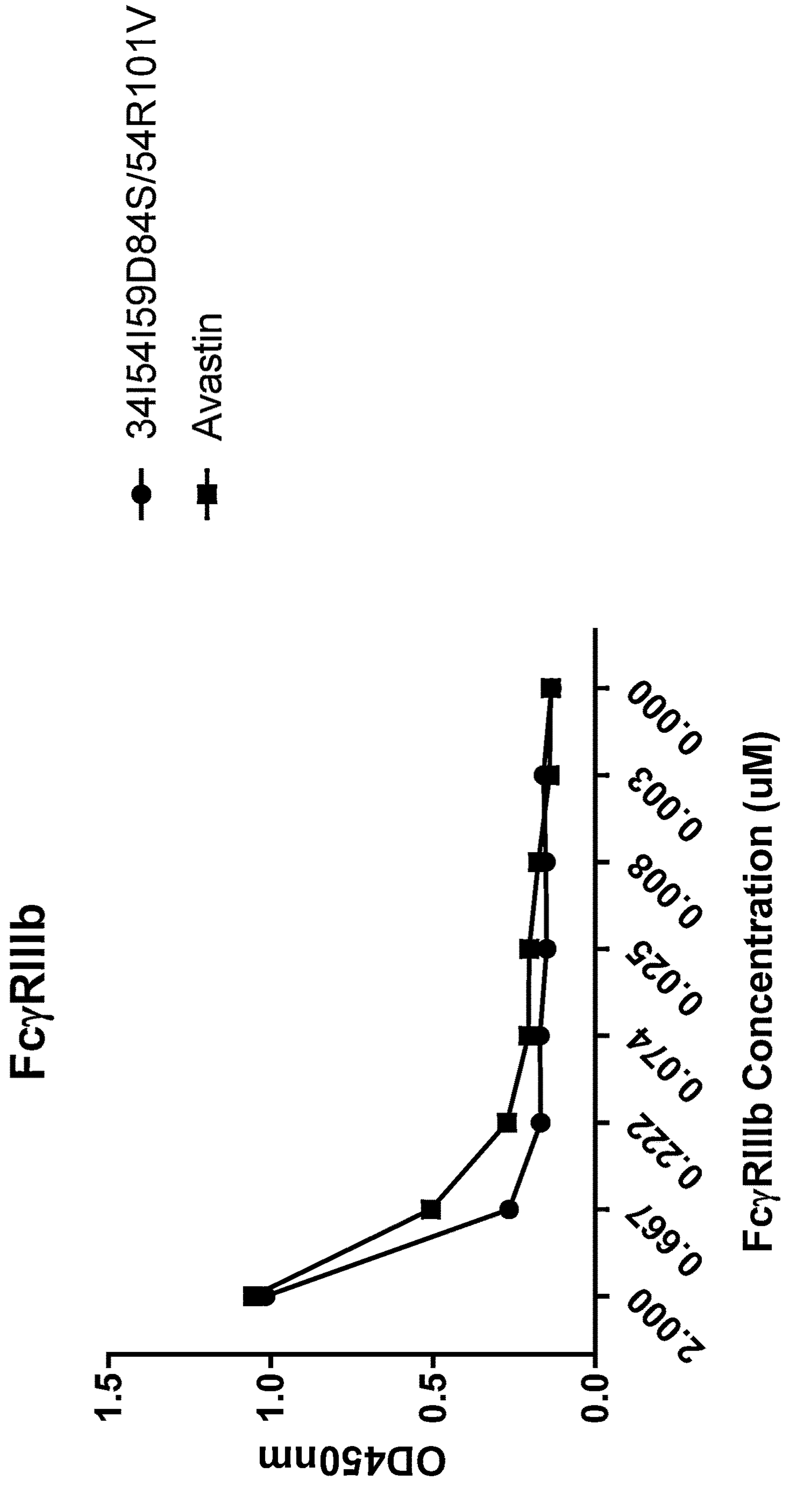
FIG. 16E shows binding of 34I54I59D84S/54R101V and Avastin to FcγRIIIb.

The binding to FcγRIIa (FIG. 16C), FcγIIb (FIG. 16D) and FcγIIIb (FIG. 16E) was assessed by ELISA. Briefly, the final candidate antibody along with Avastin, used as positive control, were coated at 2 uM in 1×PBS on Nunc MaxiSorp plates overnight at 4° C., followed by a 2 hour blocking step with 1% BSA in 1×PBS at room temperature. Recombinant His-tagged Fcγ receptors (R&D Systems) were titrated 1:3 from a top concentration of 2 uM in 1% BSA and incubated for 1 hour at 37° C. Following a series of washes, the plate was incubated with an HRP-conjugated anti-His antibody at 1:1000 for 1 hour at room temperature. Lastly, after a final wash, the plate was developed in TMB.

This antibody showed no significant binding to either FcγRIIa and FcγIIb compared to positive control avastin. Binding to FcγIIIb was minimal for both antibodies tested, in this assay format.

Example 20—Route 1 Synthesis of OG1802

A first route for the synthesis of OG1802 is as follows. First, TFA/amine salt initiator (Compound L) having the structure shown in FIG. 2A was synthesized as follows.

First, Compound K, having the structure shown in FIG. 2B was synthesized as follows. Into a 200 mL round bottom flask under nitrogen was placed Compound J (OG1563) (1.9 g, 2.67 mmol, 3.3 equiv)

COMPOUND J

Figure 2L:
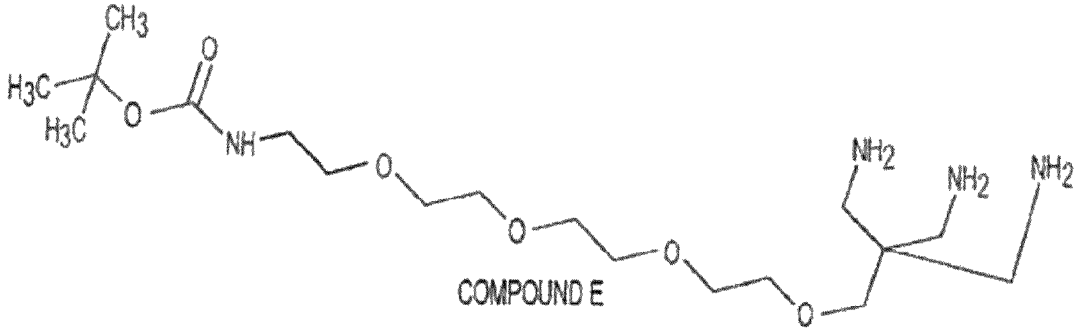
FIG. 2L shows Compound E.

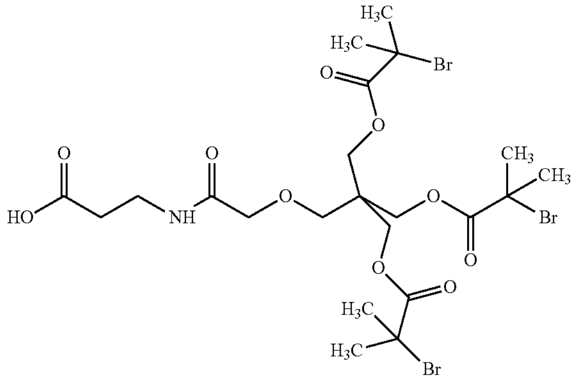

and Compound E (0.525 g, 0.81 mmol, 1.0 equiv) (see FIG. 2L) followed by dimethylformamide (10 mL) then diisopropylethylamine (2.5 mL, 14.6 mmol, 18 equiv). The flask was cooled to 0° C. using an ice bath. To this was added propylphosphonic anhydride solution (50 wt. % in ethyl acetate, 2.5 mL, 4.04 mmol, 5 equiv) over ~6 minutes.

The reaction was warmed to room temperature and stirred for 15 minutes. The reaction was quenched by adding water (20 mL), saturated aqueous sodium bicarbonate (20 mL) and ethyl acetate (100 mL). The organic layer was separated and the aqueous layer extracted with ethyl acetate (75 mL). The combined organic layers were washed with saturated aqueous sodium bicarbonate (30 mL), 0.5 M aqueous citric acid (40 mL), water (25 mL), and saturated aqueous sodium chloride (40 mL), then dried (sodium sulfate), filtered and concentrated under vacuum. The residue which was used without further purification resulted in 2.0 g (0.80 mmol, 99%) of Compound K.

1H NMR (400 MHz DMSO-d6): δ=1.36 (s, 9H, OCCH3), 1.90 (s, 54H, CC(CH3)2Br), 2.31 (t, J=7.2 Hz, 6H, CCH2CH2NH), 2.98 (d, J=5.6 Hz, 6H, CCH2NH), 3.04 (q, J=6.0 Hz, 2H, OCH2CH2NH), 3.18 (s, 2H, OCH2C), 3.3-3.37 (m, 8H, CH2), 3.47-3.55 (m, 12H, CH2), 3.58 (s, 6H, OCH2C), 3.87 (s, 6H, O═CCH2O), 4.27 (s, 18H, CCH2OC═O), 6.74 (br t, 1H, CH2NHC═O), 7.69 (t, J=6.8 Hz, 3H, CH2NHC═O), 7.84 (t, J=6.0 Hz, 3H, CH2NHC═O).

LC-MS (ES, m/z): [(M+2H-boc)/2]+ Calcd for (C84H136Br9N7O33+2H-Boc)/2=1196.6; Found 1196.6.

Next Compound L (FIG. 2A) was synthesized as follows: into a 100 mL round bottom under nitrogen was added Compound K (2.0 g, 0.8 mmol), dichloromethane (10 mL) followed by trifluoroacetic acid (5 mL). The reaction was stirred at room temperature for 30 minutes. The reaction was concentrated under a vacuum. The reaction was diluted using dichloromethane (10 mL) and concentrated under a vacuum. The residue was dissolved using acetonitrile (10 mL), filtered through a syringe filter (Acrodisc CR25, PN 4225T) and loaded onto a preparatory HPLC column and eluted with 60% acetonitrile in water (with 0.1% trifluoroacetic acid) up to 98% acetonitrile (with 0.1% trifluoroacetic acid). The tubes containing product were pooled, concentrated under vacuum, frozen and placed on a lyophilizer. This resulted in 990 mgs (0.4 mmol, 50% over 2 steps) Compound L as a white powder.

1H NMR (400 MHz DMSO-d6): δ=1.90 (s, 54H, CC(CH3)2Br), 2.31 (t, J=7.2 Hz, 6H, CCH2CH2NH), 2.97-3.0 (m, 8H, CCH2NH and OCH2CH2NH), 3.17 (s, 2H, OCH2C), 3.3 (q, 6H, CH2CH2NHC═O), 3.4-3.59 (m, 20H, CH2), 3.87 (s, 6H, O═CCH2O), 4.27 (s, 18H, CCH2OC═O), 7.69-7.84 (m, 9H, both CH2NHC═O and NH3+).

LC-MS (ES, m/z): [(M+2H)/2]+ Calcd for (C84H136Br9N7O33+2H)/2=1196.6; Found 1197.4.

Next, Compound L (FIG. 2A) was used as an initiator to synthesize MPC polymer. Initiator is typically prepared as a stock solution in DMF of about 100 mg/mL. The initiator and the ligand (2,2'-bipyridyl) were introduced into a Schlenk tube. The resultant solution was cooled to −78° C. using a dry ice/acetone mixture, and was degassed under vacuum for 10 min. The tube was refilled under Argon and the catalyst (CuBr unless otherwise indicated), kept under Argon, was introduced into the Schlenck tube (the Molar ratio of atom bromine on the initiator/catalyst (CuBr)/ligand was kept at 1/1/2). The solution became dark brown immediately. The Schlenk tube was sealed and immediately purged by applying a short cycle vacuum/Argon. A solution of HEMA-PC was prepared by mixing a defined quantity of monomer, prepared in a glovebox kept under nitrogen, with 200 proof degassed ethanol. The monomer solution was added drop wise into the Schlenk tube (via cannula) (and homogenized by light stirring). The temperature was maintained at −78° C. A thorough vacuum was applied to the reaction mixture for at least 10 to 15 min. until bubbling from the solution ceased. The tube was then refilled with Argon and warmed to room temperature. The solution was stirred, and as the polymerization proceeded, the solution became viscous. After 3 to 8 hours or just left overnight, the reaction was quenched by direct exposure to air in order to oxidize Cu (I) to Cu (II), the mixture became blue-green in color, and was passed through a silica column in order to remove the copper catalyst. The collected solution was concentrated by rotary evaporation and the resulting mixture was either precipitated with tetrahydrofuran or dialyzed against water followed by freeze drying to yield a free-flowing white powder. Table 20.1 below sets forth polymer data for polymer employing compound L as an initiator.

TABLE 20.1

| Theor. MW (kDa) | Polymer ID No. | Initiator | Mn (kDa) | Mp (kDa) | PDI |
|---|---|---|---|---|---|
| 500 | 130 | L | 490 | 530 | 1.1 |
| 750 | 150 | L | 645 | 750 | 1.1 |

Next, the maleimide Mal-PEG4-PFP ester was snapped on (as set forth in FIG. 2C) to the 750 kDa polymer referred to above to provide OG1802. Into a 20 mL vial was placed Polymer R3707 (750 kDa polymer made using L as initiator, 515 mg) and dissolved using ethanol (4.0 mL) after stirring for 40 minutes. To this was added a 1% solution of 4-methylmorpholine in acetonitrile (22 uL). In a separate vial was dissolved Mal-PEG4-PFP (1.97 mg) in acetonitrile (1.0 mL) and this solution was added to the polymer solution over ~2 minute at room temperature and the resulting solution was stirred for overnight. The reaction was diluted with 0.1% aqueous trifluoroacetic acid (2 mL) (pH ~5) followed by water (~12 mL), filtered through a syringe filter (Acrodisc Supor, PN 4612) and placed evenly into 3 Amicon centrifuge membrane dialysis tubes (30,000 mwco). The tubes were diluted and mixed with water (~5 mL each), placed into centrifuge (rpm 3200) for 25 minutes. The filtrate is removed for analysis while the retentate is diluted and mixed with water (~10 mL/tube). The centrifuge procedure repeated 5 more times, after which the retentate is removed and placed into a vial. The Amicon membrane tubes were rinsed with water (2×~2 mL each tube) and this combined with the retentate. The retentate solution was filtered through a syringe filter (Acrodisc Supor, PN 4612), frozen and placed on a lyophilizer. This resulted in 485 mgs as a white powder.

Example 21—Synthesis of Initiator OG1786

OG1786 is the nine-arm initiator for polymer synthesis used as a precursor in the synthesis of OG1802. Each arm is terminated with a 2-bromoisobutyrate which is capable of initiating polymerization under ATRP. OG1786 is a salt of trifluoro acetic acid (TFA) as shown in FIG. 2D. OG1786 is prepared as follows. First, OG1550 is reacted with TFA (trifluoro acetic acid) to produce OG1546 as depicted in FIG. 2E.

In a 1 L round bottom flask equipped with a magnetic stir bar and an addition funnel was added OG1550 (14.8 g), methyl tert-butyl ether (MTBE) (350 ml) and water (30 ml). The mixture was stirred to dissolve the OG1550, then cooled in an ice bath. To this mixture was added a solution of trifluoroacetic acid (4.9 ml) in water (90 ml) dropwise over 90 minutes. After addition is complete the mixture was stirred an additional 15 minutes then removed from the ice bath and allowed to warm to room temperature. The mixture was stirred (after removal from the ice bath) for a further 4-5 hours, until tlc showed ~5% starting material remaining, and the pH of the aqueous was between 3 and 4 (pH paper).

The mixture was partitioned. The MTBE layer was washed with water (30 ml). Combine aqueous layers then the aqueous extracted with MTBE (150 ml). This second MTBE phase was washed with water (30 ml). The combined aqueous layers were washed with a third portion of MTBE (100 ml). The third MBTE phase was washed with water (25 ml). The aqueous layers were again combined (~250 ml, pH ~4, by pH paper).

The product was collected by lyophilization. 11.5 g white solid was obtained. This material is extremely hygroscopic, so best handled under nitrogen. The product was confirmed by LCMS.

The prepared OG1546 was then reacted with OG1563 to yield OG1784 (as depicted in FIG. 2F).

In a 250 ml flask under nitrogen equipped with a stir bar was added OG1546 (hygroscopic, 9.0 g), followed by N,N-dimethylformamide (110 ml). The mixture was stirred at room temperature until all OG1546 dissolved (about 15 minutes), then OG1563 (29.9 g) was added, and the mixture stirred a further 3 minutes until the OG1563 had also been dissolved. The resulting solution was cooled in an ice bath, and N,N-diisopropylethylamine (37.6 ml) was added over 3 minutes, followed by propylphosphonic anhydride (T3P), 50% in ethyl acetate (34.5 ml) dropwise over 5 minutes (T3P addition is exothermic). After T3P addition was complete, the flask was removed from the cooling bath and allowed to reach room temperature. Samples were then taken at 5 minute intervals for LCMS analysis. The reaction showed very light yellow/tan color.

After 20 minutes the reaction was cooled again in an ice bath and 5 ml water added. The mixture was then removed from the cooling bath and a further 50 ml water portion added, followed by 50 ml 0.5 M citric acid then isopropylacetate (300 ml). The mixture was partitioned. The aqueous phase (~300 ml) was extracted with additional isopropyl acetate (150 ml). The aqueous phase was AQ1 for HPLC test. The combined organics were washed with aqueous citric acid (115 ml, 65 mM, which was the mixture of 15 ml of 0.5 M citric acid plus 100 ml water), and the aqueous phase was AQ2 (pH~3). The organic phase was washed with water/saturated sodium chloride (100 ml/25 ml), and the aqueous phase was AQ3 (pH~3). The organic phase was finally washed with saturated sodium chloride (100 ml), and the aqueous phase was AQ4. None of the AQ fractions contained any significant product (data not provided). The organic phase confirmed the product via LCMS. The product was dried over sodium sulfate (80 g), filtered and rinsed with isopropyl acetate (75 ml), and concentrated on a rotary evaporator to a tan oil (33.2 g). The crude was stored overnight under nitrogen.

The next day the crude was allowed to come to room temperature, then dissolved in acetonitrile/water (46 ml/12 ml) and filtered using an HPLC filter disk (Cole-Parmer PTFE 0.2 µm, product number 02915-20). The filtrate was split into three equal portions and purified in three runs.

The filtrate was loaded onto a RediSep Rf Gold C18 column (275 g, SN 69-2203-339, Lot #24126-611Y) equilibrated with 50% acetonitrile/water. The material was eluted at 100 ml/min using the following gradient (solvent A: water, solvent B: acetonitrile). All the relevant fractions were checked by HPLC. The fractions adjudged to be pure enough were pooled (from all three runs) and concentrated (bath temperature kept at about 20° C.) on rotovap, then partitioned between dichloromethane (100 ml) and water (5 ml)/saturated sodium chloride (25 ml). The aqueous was extracted twice more with dichloromethane (2×30 ml). The combined organics were dried over sodium sulfate (35 g), filtered, rinsed with DCM (30 ml), and concentrated. The product and purity were confirmed by LCMS methods. The isolated yield and the purity of the R5172 and R5228 lots are shown in Table 21.1.

TABLE 21.1

| | OG1784 lot | |
|---|---|---|
| | R5172 | R5228 |
| OG1546 used | 5.3 g | 9.0 g |
| OG1563 used | 17.6 g | 29.9 g |
| Isolated yield | 53% | 58% |
| Purity (a/a 210 nm) | 99.3% | 100.0% |

Next OG1405 was prepared from OG1784 as depicted in FIG. 2G. In a 500 ml round bottom flask equipped with a magnetic stir bar was added OG1784 (20.9 g), followed by dichloromethane (50 ml) then trifluoroacetic acid (20 ml). The mixture was stirred at room temperature and HPLC analysis showed complete deprotection in 23 minutes. The mixture was concentrated on a rotary evaporator, redissolved in dichloromethane (25 ml) and re-concentrated, then redissolved in acetonitrile (25 ml) and re-concentrated. The product was confirmed by LCMS. The material from above (OG1405, 34.5 g, assume 21.0 g as quantitative yield) was used as a crude oil in the next step. No purification is needed.

Next, OG1405 was reacted with OG1402 to prepare OG1785 as set forth in FIG. 2H. In a 500 ml flask under nitrogen equipped with a stir bar was placed OG1402 (5.5 g), followed by acetonitrile (70 ml), then N,N-diisopropylethylamine (26.3 ml) and T3P solution (see above) (7.9 ml). The solution was stirred at room temperature for 30 minutes, then cooled in an ice water bath and a solution of OG1405 (crude oil from above, 34.5 g) in acetonitrile (70 ml) added. The mixture was warmed to room temperature. After 20 minutes the reaction was cooled in an ice water bath and quenched with water (5 ml). The mixture was then concentrated under vacuum using a rotary evaporator to half volume. Samples were taken for LCMS.

More water (50 ml), followed by 0.5 M citric acid (75 ml) and isopropyl acetate (175 ml) was added. The mixture was partitioned in 5 minutes. The aqueous was extracted with additional isopropyl acetate (50 mL). The combined organics were washed with aqueous citric acid (0.13 M, 30 ml, consist of 10 ml of 0.5 M citric acid and 20 ml water). The organics were then washed with the mixture of saturated sodium chloride (25 ml) and water (25 ml), then finally washed with the saturated sodium chloride (25 ml). They were then dried over sodium sulfate (124 g), filtered and rinsed with isopropyl acetate (30 ml), and concentrated under rotary evaporator to a tan oil (27.3 g). Samples were taken for LCMS analysis.

The oil was dissolved in acetonitrile/water (3:1, 15 ml/5 ml), filtered through an HPLC filter disk (Cole-Parmer PTFE membrane 0.2 µm, product number 02915-20) and split into three equal portions, each of which were individually purified as follows.

Portions were loaded onto Redi-Sep Gold C18 column (275 g, SN—69-2203-339, Lot 241234-611W) equilibrated at 50% solvent B (acetonitrile)/50% solvent A (water). The material was then purified by reverse phase HPLC with a solvent A: water/solvent B: acetonitrile gradient. Appropriate fractions were pooled and partitioned between dichloromethane (150 ml) and water (5 ml)/saturated sodium chloride (25 ml). The aqueous was extracted twice with dichloromethane (2×50 ml). Combined organics were dried over sodium sulfate (60 g), filtered and rinsed with dichloromethane (40 ml) and concentrated. Structure and purity were confirmed by various analytics including LCMS: OG1785 was isolated as a foamy solid (R5329, 19.0 g, 83% yield, 95.1% purity (a/a 210 nm), stored under nitrogen at 4° C.

Next, the tert-butyloxycarbonyl protecting group on OG1785 was removed using trifluoroacetic acid (TFA) to produce OG1786 as depicted in FIG. 2I.

Example 22—Synthesis of Polymer OG1801

Polymer OG1801 is made first from the initiator OG1786. OG1801 has an amine functionality, which is more stable (than maleimide) during polymer synthesis. To synthesize polymer OG1801, a modified version of ATRP is used wherein the copper species (Cu(I)) is generated in situ by adding metallic copper to Cu (II). Starting materials and reagents needed in the reaction are calculated based on batch input of the monomer (HEMA-PC) OG47, as well as the targeted molecular weight (MW).

Weighed 50 g monomer OG47 in glove box and added 200 mL of degassed EtOH to dissolve the monomer at room temperature; sampled for monomer concentration test. Weighed Cu (II), Bpy, Cu(0) in a 500 mL flask; purged with Argon, while adding monomer solution to the flask; sealed the flask with stopper and vacuumed for 25 min until no bubbles. The reaction changed color gradually from light green to dark green, then to light brown; weighed ~200 mg of initiator OG1786 in glove box, and dissolved in ~2000 uL of DMF under room temperature to make 100 mg/mL stock solution; sampled for initiator concentration and purity test; added the initiator solution to the flask under Argon. The reaction solution became dark brown and started thickening over time; sealed the system and let the reaction occur over 2 days.

OG1801 was then prepared for addition of the maleimide and catalyst (copper) was removed as follows: A prepacked RediSep® Rf normal phase silica column is used to remove the catalyst. The size of the column is chosen based on the copper amount in the reaction mixture. For instance, a 330 g column (Cat. #69-2203-330, Column size 330 g, CV=443 mL) was used for a 50 g batch of OG1801. Teflon tubing is used for all the connection as EtOH is the elute solvent.

After copper removal, all the fractions were transferred to a round bottom flask in batches, and evaporated the EtOH by rotary evaporator at 45-50° C. at reduced pressure to dryness. In this step, EtOH volume collected from condensation was monitored to make sure EtOH removal was >90%. The polymer was dissolved in 250 mL of WFI and filtered using a 0.2 um filter. It resulted in a clear to light yellow polymer solution at ~150 mg/mL. The solution could be stored at 2-8° C. up to 3 month before use.

Example 23—Synthesis of Polymer OG1802

Starting materials and reagents needed in the reaction are calculated based on batch input of OG1801. The linker is 3-maleimidopropionic acid, NHS ester. Added 30 ml of 0.5 M sodium phosphate (in WFI, pH 8) to 50 g polymer solution (~150 mg/mL). Let stir for 1 min; pH was 8.0 by pH paper. Weighed 204.8 mg of linker and dissolved in DMF 4.1 mL to make 50 mg/mL stock sln. Added linker solution dropwise 815 uL per minute to the polymer sln with strong stirring. Took 5 min to added 4095 uL of linker solution. Reacted at room temperature for 30 min. Quenched reaction with 20 mL of 5% acetic acid to achieve a final pH of 5. Filtered the solution using 1 L vacuum filter (0.2 um).

OG1802 (shown in FIG. 2J) is then purified as follows: Milipore cross flow cassettes are used for polymer purification in aqueous system. Started with concentrating the polymer solution to 250 mL (~200 mg/mL). Added the fresh WFI from reservoir, and adjusted the flow rate of the fresh WFI feed to the same as the permeate (~2 mL/min). The UF/DF was set up at 2-8° C. overnight. Typically 2.5 L of WFI was used (10× volume ratio to the polymer solution). A sample of retente was collected for purity test. The targeted purity was >98%. Filtered the polymer solution by 0.2 μM 1 L filter bottle. The polymer solution could be stored at 2-8° C. for up to 3 month before conjugation.

Example 24—Alternative Phosphorylcholine Polymers

A HEA-PC polymer was synthesized as described below. HEA-PC (2-(acryloyloxy)ethyl-2-(trimethylammonium) ethyl phosphate), which is an acrylate as opposed to the methacrylate HEMA-PC described above, has the following structure:

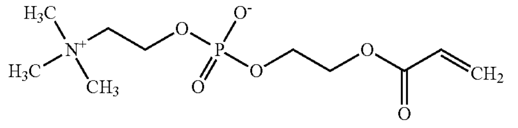

HEA-PC

HEA-PC was polymerized to the initiator shown in Example 20 as compound L.

TABLE 24.1

| Reactant | Name | Amount | MW |
|---|---|---|---|
| Initiator | Compound L (see above) | 1.65 mg | 2505.5 |
| Monomer | HEA-PC | 0.461 g | 281.24 |
| Catalyst | Cu (I) Bromide | 1.2 mg | 143.45 |
| Ligand | Tris [2-(dimethylamino)ethyl]amine (Me6TREN) | 2.73 mg | 230.39 |
| Solvent A | N,N-Dimethylformamide (DMF) | 21.85 μl | 73.09 |
| Solvent B | Water | 0.7 ml | 18.02 |
| Solvent C | Methanol | 0.7 ml | 32.04 |

Prepared a stock solution of initiator at 200 mg/mL by dissolving 2.2 mg of initiator in 11 μl of dry DMF and a 200 mg/ml solution of ligand by dissolving 4.6 mg of Me6TREN in 23 μL of dry DMF. Dispense 8.25 μl of the stock solution of initiator and 13.6 μl of the ligand into a tube. Degas at −78° C. for 5 min then refill with Argon and add 1.2 mg of CuBr. Degas and refill with Argon. Add a stock solution of HEA-PC in methanol (weigh out 0.461 g of HEA-PC and dissolve it in 0.5 mL of methanol) to the solution inside the reactor at −78° C. Rinse the vial with 200 μl of methanol and add it inside the reactor at −78° C. and then 0.5 mL of distilled water then another 200 μl of water. Degas thoroughly until no bubbling is seen and all heterogeneity disappears (solid particulates dissolve or disappear). Refill with 4 psi of Argon and let the reaction to proceed at RT for an hour. The reaction was already viscous. The reaction was allowed to proceed for about one hour. A solution of bipyrindine in methanol (5 mg in 0.5 uL) was added. Another 2-3 ml of methanol was added and the catalyst was allowed to oxidize overnight at 4° C. Conversion determined by 1H NMR was estimated to be 94%.

The next day the polymer was dialyzed and subjected to SEC/MALS analysis using Shodex SB806M_HQ column (7.8×300 mm) in 1×PBS pH 7.4 at 1 ml/min, giving a PDI of 1.157, Mn of 723.5 kDa, Mp of 820.4 kDa and Mw of 837.2 kDa (before dialysis PDI is 1.12, Mn=695 kDa, Mp=778 kDa). Next a maleimide functionality was added to the polymer so that it could be conjugate to a protein.

Next, the maleimide Mal-PEG4-PFP (see Example 20 above) ester was snapped on to the HEA-PC polymer as shown in Example 20. The resulting maleimide functionalized TEA-PC polymer can then be conjugated to sulfhydryl groups as discussed herein for HEMA-PC polymers.

An acrylamide PC polymer was also made using the monomer 2-(acrylamyl)ethyl-2-(trimethylammonium)ethyl phosphate (Am-PC), having the following structure:

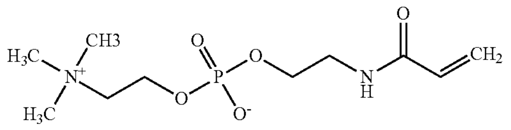

Am-PC

The Am-PC was used for polymerization employing a 3 arm initiator (a TFA salt) having the structure:

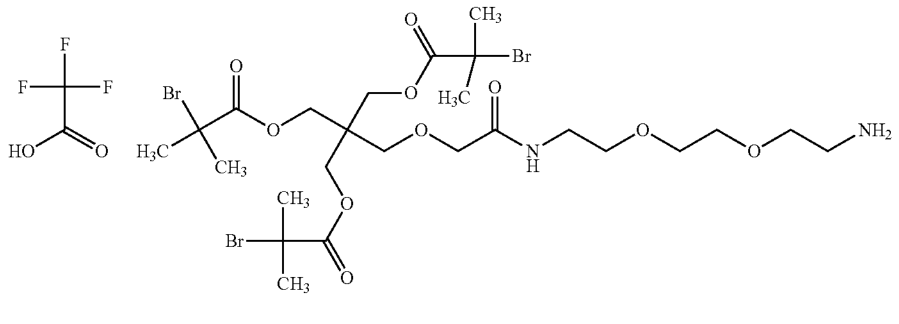 [SMILES: O=C(O)C(F)(F)F ; CC(C)(Br)C(=O)OCC(COCC(=O)NCCOCCOCCN)(COC(=O)C(C)(C)Br)COC(=O)C(C)(C)Br]

The synthesis of the Am-PC polymer was conducted as follows:

TABLE 24.2

| Reactant | Name/Identity | Amount | MW |
|---|---|---|---|
| Initiator | 3-arm initiator (see above) | 2.2 mg | 885.35 |
| Monomer | Am-PC | 0.5 g | 280.26 |
| Catalyst (I) | Copper (I) Bromide | 1 mg | 143.45 |
| Catalyst (II) | Copper (II) Bromide | 0.2 mg | 223.35 |
| Ligand | Tris[2-(dimethylamino)ethyl]amine (Me6TREN) | 3.94 mg | 230.39 |
| Solvent A | N,N-Dimethylformamide (DMF) | 31.7 μl | 73.09 |
| Solvent B | Water | 1 ml | 18.02 |
| Solvent C | Methanol | 1 ml | 32.04 |

A stock solution of ligand at 200 mg/mL was prepared by dissolving 9 mg of Me6TREN in 45 uL of dry DMF. Add 19.7 uL of the stock solution to a reaction vessel. Prepare a stock solution of initiator at 200 mg/mL by dissolving 6.5 mg of material in 32.5 uL of DMF. Add 11 uL of the initiator stock solution to the ligand from above. Degas for 5 min. Add 1 mg of CuBr. Prepared a stock solution of $CuBr_2$ at 200 mg/mL by dissolving 4 mg $CuBr_2$ in 20 μL of DMF. Add 0.5 g of monomer (AmPC) to 1 mL of methanol (slow dissolution/viscous solution), followed by 1 uL of the stock solution of $CuBr_2$. Add the monomer solution dropwise to the reaction mixture above. Rinse with 1 mL of water. Degas the reaction mixture thoroughly (freeze-thaw). Let the reaction proceed for 24 hours.

Afterwards the Am-PC polymer may be dialyzed. The molecular weight of the above polymer was determined by SEC/MALS: Mn is 215 kDa, Mp: 250 kDa, PDI is 1.17. Conversion was estimated by 1H NMR to be 94%. A maleimide functionality can be added to the Am-PC polymer as discussed above for HEMA-PC and HEA-PC. Maleimide functionalized Am-PC polymer can be conjugated to a protein as described above.

Example 25—Reverse Ellman's Assay for Calculating Free Maleimide in a Compound After addition of the maleimide functionality to polymer OG1801 to form OG1802 (see above), an Ellman's assay was used to determine the amount of functional maleimide expressed as percent function (i.e. conjugatable) in a sample. Thiol converted Ellman's reagent (DTNB) to TNB—then to TNB2—in water at neutral and alkaline pH, which gave off a yellow color (measured at 412 nm). A standard curve was established with cysteine. Since the maleimide reacts with thiol, this assay actually measured the thiol (cysteine) left. The inhibition was calculated as the molarity ratios of (original thiol−thiol left after maleimide polymer addition)/(original thiol) and is expressed as a percentage where the higher the percent the higher the maleimide functionalization.

Reagents Employed in Assay: A standard curve was prepared using the cysteine from 62.5 μM to 2 μM. Polymer stock solutions were prepared by dissolving the powder in 1×PBS pH7.4 (reaction buffer) and mixing thoroughly. An equal molar of polymer and cysteine solutions were mixed and allowed to react at 27° C. for 30 minutes. The 150 μM of DTNB solution was added into the cysteine standards and polymer/cysteine reactions and the color was developed at 27° C. for 5 minutes. OD at 412 nm was read on the Spectramax plate reader and percent inhibition was calculated with the Softmax Pro software and the cysteine standard curve.

Example 26—Purification and Decapping of OG1965

The OG1965 heavy and light chains may be cloned into expression plasmids and transfected into CHO cells. Cells can be grown up in appropriate media and harvested. OG1965 may be purified using Protein A affinity column capture and elution. The OG1965 cysteine at position 443 (L443C (EU numbering), or position 442C of seq ID 183) residue is typically "capped" or oxidized by chemicals in the cell culture media and is not available for conjugation. In this regard, purified OG1965 may be subjected to a decapping (i.e. reducing) procedure to remove the cap and enable the free (i.e. those not involved in Cys-Cys disulfide bonds) cysteine residue to be conjugated to the maleimide functionality of a polymer. Decapping may be done by mixing purified OG1965 protein with a 30× molar excess for 1 hour at ambient temperature of the reducing agent TCEP (3,3',3"-Phosphanetriyltripropanoic acid). The reduction reaction with TCEP may be monitored by SDS-PAGE. Following reduction, the OG1965 protein may be buffer exchanged using a Pellicon XL Ultrafiltration Cassette with 20 mM Tris pH7.5, 100 mM NaCl, 0.5 mM TCEP buffer to remove the cap. The TCEP reagent may then be removed in the same buffer exchange setup with 20 mM Tris pH7.5, 100 mM NaCl. Reduced OG1965 may then be allowed to reoxidized using 15× molar excess of the oxidation agent DHAA (DeHydroxy Ascorbic Acid) for 1 hr at ambient temperature which again is monitored by SDS-PAGE assay. The DHAA reagent may then be removed in the same buffer exchange setup with 20 mM Tris pH7.5, 100 mM NaCl.

Example 27—Excipient Screening Experiment for Prevention of OG1802 Polymer Induced IgG1 Precipitation Conjugation reaction process setup was further developed with human IgG1 antibody (OG1898) to improve the conjugation efficiency which either SDS-PAGE or ion exchanger analysis was used for quantitative measurement.

Conditions tested included (1) varying polymer molar excess ratio from 3 to 20; (2) preadjusting the reaction solution pH to more acidic (e.g. pH 5.0) or basic (e.g. pH 8.5) from the standard neutral pH range (e.g. pH 6.5-7.5); (3) adding excipients, such as 0.1-1% polysorbate20 or tween20, 0.1-1% Sodium Dodecyl Sulfate (SDS), 6-10% trehalose or sucrose, 0.03-1 mM glutamic acid, 0.03-1 mM aspartic acid, 1-100 mM lysine or arginine, 1-100 mM urea, guanidine hydrochloride analog, 1-100 mM arginine, 0.03-1 mM PEG8000, or 20% ethanol.

Protein is known to carry net surface charge that helps protein solubility in aqueous solution. The amino acids are referred to as hydrophilic amino acids which include arginine, lysine, aspartic acid, and glutamic acid. At neutral pH 7 the side chains of these amino acids carry charges—positive for arginine and lysine, negative for aspartic acid, and glutamic acid. Altering the solution pH could modulate the intrinsic protein solubility which is therefore in some of the troubleshoot experiments mentioned above such as (2) this approach is applied. In theory, proteins solubility in aqueous solution differs depending on the level of hydrophobic or hydrophilic properties of the surface. Proteins with surfaces that have greater hydrophobic properties will readily precipitate. The addition of ions (e.g. NaCl or other salt) creates an electron shielding effect that nullifies some activity between water particles and the protein, reducing solubility as the proteins bind with each other and begin to aggregate. In the current situation, it is hypothesized that the biopolymer directly or indirectly modulates the protein surface charge and/or exposed surfaces in a manner that promotes the intermolecular hydrophobic interactions which results in protein precipitation.

Excipients that can modulate protein solubility include the following categories (i) detergents including neutral detergent (e.g. 0.1-1% polysorbate20 or tween20) or charged detergent (e.g. 0.1-1% Sodium Dodecyl Sulfate (SDS)) (ii) sugars (e.g. 6% Trehalose or 6% sucrose) (iii) negatively charged amino acids (e.g. 0.03-1 mM glutamic acid or 0.03-1 mM aspartic acid) or positively charged amino acids (e.g. 1-100 mM lysine or arginine) (iv) chaotropic agents or denaturants (e.g. 1-100 mM urea, guanidine hydrochloride analog or 1-100 mM arginine) (v) polyethylene glycol (e.g. 0.03-1 mM PEG8000); and (vi) organic solvent (e.g. 20% ethanol).

Other options that can be tested in regard to excipients include OG1898_R5782_5xR7473 (as a control), 5 mg/mL_R5782_5xR7473_pH4, 5 mg/mL_R5782_5xR7473_pH9, 5 mg/mL_R5782_5xR7473_1% Tween20, 5 mg/mL_R5782_5xR7473_0.1% Tween20, 5 mg/mL_R5782_5xR7473_1% SDS, 5 mg/mL_R5782_5xR7473_0.1% SDS, 5 mg/mL_R5782_5xR7473_6% Sucrose, 5 mg/mL_R5782_5xR7473_6% Trehalose, 5 mg/mL_R5782_5xR7473_0.03 mM Aspartic acid, 5 mg/mL_R5782_5xR7473_1 mM Aspartic acid, 5 mg/mL_R5782_5xR7473_0.03 mM Glutamic acid, 5 mg/mL_R5782_5xR7473_1 mM Glutamic acid, 5 mg/mL_R5782_5xR7473_1 mM Arginine, 5 mg/mL_R5782_5xR7473_100 mM Arginine, 5 mg/mL_R5782_5xR7473_1 mM Urea, 5 mg/mL_R5782_5xR7473_100 mM Urea, 5 mg/mL_R5782_5xR7473_0.03 mM PEG8000, 5 mg/mL_R5782_5xR7473_1 mM PEG8000, 5 mg/mL_R5782_5xR7473_20% EtOH, 5 mg/mL_R5782_5xR7473_1 mM Lysine, 5 mg/mL_R5782_5xR7473_100 mM Lysine. Reaction buffers include 20 mM Tris pH 7.4, 100 mM NaCl, sodium acetate. sodium carbonate.

In a further design of experiment (DOE) study, various excipients from each category mentioned above are selected based on their compatibility to the pharmaceutical manufacturing for human injectable use. In addition, extreme acidic pH at 4 and basic pH at 9 are also included in such evaluation. A standard IgG1 protein sample is selected for such evaluation which does not contain an engineered cysteine to minimize any potential interference of such unpaired cysteine residue.

Example 28—Conjugation of OG1965 to MPC Polymer

Decapped OG1965 may be conjugated to polymer OG1802 to yield OG1970 bioconjugate. An excess of OG1802 is used (3-20 fold molar excess). Conjugation can be monitored by cation-exchanger HPLC chromatography and driven to near completion. OG1970 conjugate may be purified via cation exchanger chromatography and buffer exchanged into the formulation buffer by ultrafiltration/diafiltration (UF/DF). OG1970 conjugate may be purified chromatographically as described above.

Example 29—Binding Kinetics of OG1965 and OG1970

To determine and directly compare binding kinetics of OG1965 and OG1970, they were subjected to biacore analysis as above by capturing the antibodies on a Protein A chip. 0.5 ug/ml of OG1965 was flowed at a rate of 10 uls/min over a protein A chip for 25 seconds. To accommodate the polymer, 5 ug/ml of OG1970 was flowed at a rate of 10 uls/ml for 3 minutes. Roughly equivalent levels of antibody were captured under these conditions. Serum purified human complement factor D was flowed over the captured antibodies at 15 nM, 5 nM, 1.67 nM, 0.56 nM, 18.7 nM. These analyses were performed in triplicate at 25 degrees. Both antibodies bound with single digit pM affinity.

Furthermore, the Kinetic Exclusion Assay (KinExA®) was used to measure the equilibrium binding affinity and kinetics between OG1965 or OG1970 and CFD in solution. The rate of association, $k_{on}$, was experimentally determined, while the rate of dissociation, $k_{off}$, was calculated based on the following equation: $k_{off}=K_d \times k_{on}$. Azlactone beads coated with OG1931 were used to capture a portion of free Complement Factor D from an equilibrated sample of OG1965 or OG1970. Captured Complement Factor D was detected with KCD004 (SEQ ID NOs: 341 & 342) conjugated with an AlexaFluor 647 fluorophore to make KCD004-A647. The fluorescent signal was converted to a voltage signal that was directly proportional to the amount of free Complement Factor D in the equilibrated sample. The Azlactone-OG1931 column was used as the capture reagent for kinetic experiments and for equilibrium experiments. The amount of free Complement Factor D in the sample was measured pre-equilibrium, yielding data points that monitor the decrease in free Complement Factor D as the sample moved toward equilibrium. The KinExA Pro software performed a least squares analysis on the measured data to fit optimal solutions for the $K_d$ and the activity of the CBP to a curve representative of a 1:1 reversible bi-molecular interaction. The results from this assay showed that OG1965 and OG1970 bound with similar, single digit pM affinity at 37 degrees, and there is no significant difference in Kd, activity, or on-rates, indicating the biopolymer does not affect antibody interactions with CFD.

Figure 20:
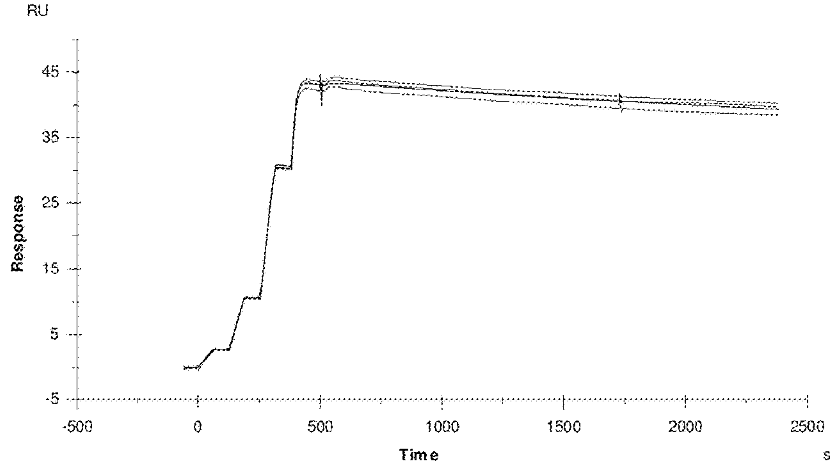
FIG. 20 shows the binding affinity of OG1965 and its bio-conjugate (OG1970) to purified human CFD.
Figure 20:
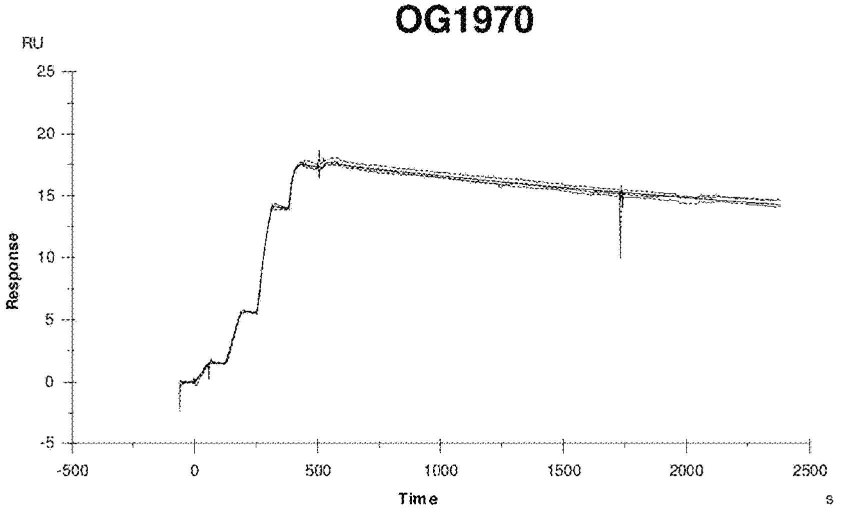
Figure 21:
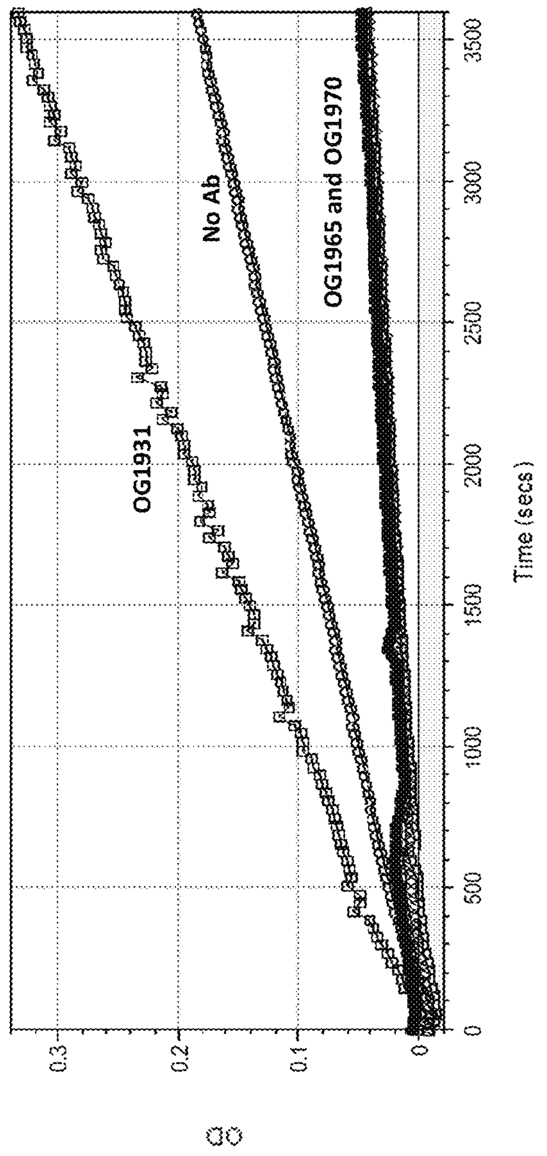

Both the KinExA data and Biacore data are shown in FIG. 20 and table 29.1.

TABLE 29.1

| Binding kinetics of OG1965 and OG1970 | | | | |
|---|---|---|---|---|
| Molecule | Platform (° C.) | $K_{on}$ (M) | $K_{off}$ (M) | $K_D$ (pM) |
| OG1965 | Biacore (25°) | $2.52 \times 10^7$ | $6.30 \times 10^{-5}$ | 2.50 |
| | KinExA (37°) | $3.06 \times 10^7$ | $1.79 \times 10^{-4}$ | 5.86 |
| OG1970 | Biacore (25°) | $2.16 \times 10^7$ | $1.33 \times 10^{-4}$ | 6.14 |
| | KinExA (37°) | $3.67 \times 10^7$ | $2.96 \times 10^{-4}$ | 8.07 |

Example 30—Enzymatic Assay of OG1965 and OG1970

To compare OG1970 functional behavior to OG1965, both molecules were subjected to the CFD enzymatic assay. OG1965 and OG1970 both effectively block enzymatic activity of CFD relative to no antibody control.

Figure 21:
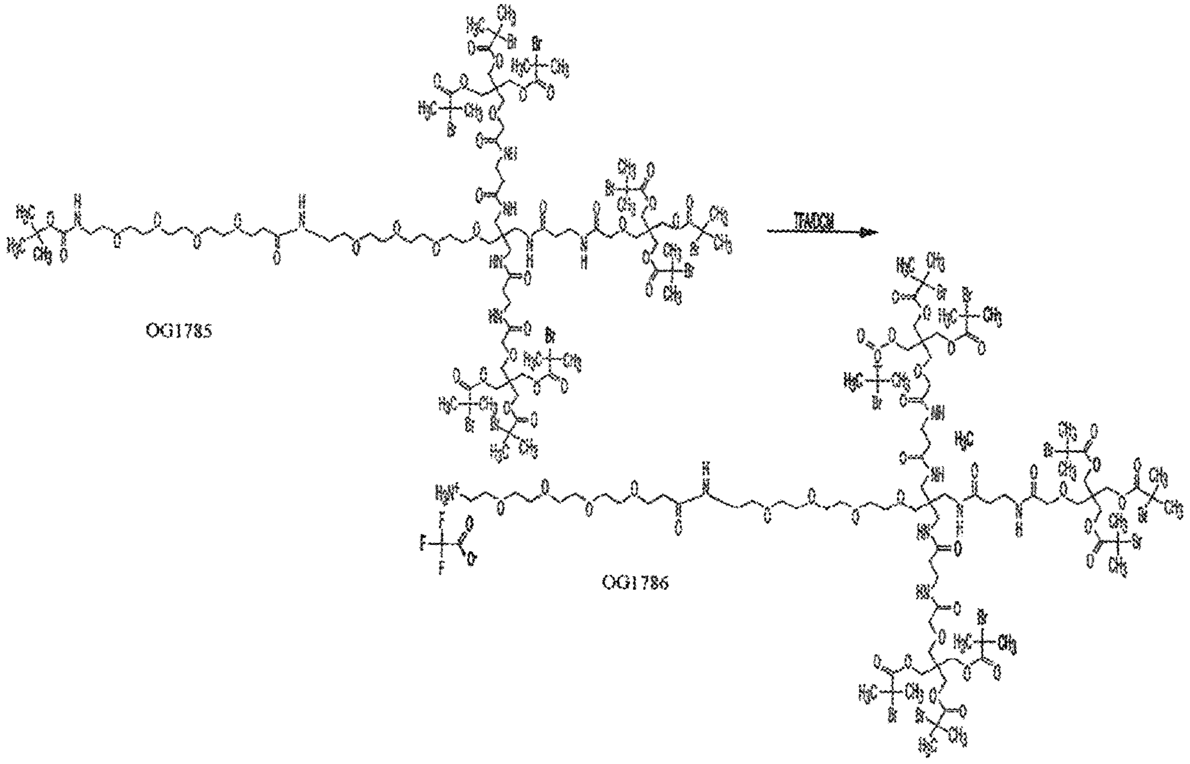
FIG. 21 shows effect of OG1965 and OG1970 on the enzymatic activity of human CFD to cleave a peptide substrate.

Proteolysis assay—Anti-CFD antibodies (AFDs) were evaluated for their ability to affect the enzymatic activity of human CFD for the synthetic substrate Z-L-Lys-SBzl hydrochloride. For the proteolysis assay, human CFD is diluted to 200 uM in assay buffer (50 mM Tris, 220 mM NaCl, pH 7.5). Substrate (Z-L-Lys-SBzl hydrochloride, Sigma, C3647, 100 mM stock in DMSO) is diluted to 4 mM in assay buffer with 4 mM 5,5'Dithio-bis-(2-nitrobenzoic acid) (DTNB, Sigma, Catalog #D-8130, 100 mM stock in DMSO). 50 μLs of the diluted CFD is loaded into a 96 well clear plate, and 50 uls of AFD is added. The reaction is started by adding 100 μLs of substrate/DTNB mixture to wells. A substrate blank containing 100 μLs assay buffer and 100 μLs substrate mixture without any CFD is included. Using a plate reader (SpectraMax Plus or equivalent), samples are read in kinetic mode for 45 minutes at an absorbance of 405 nm. To calculate specific activity the following formula is used: Specific Activity (pmol/min/μg)=Adjusted Vmax*(OD/min)×well volume (L)×$10^{12}$ pmol/mol. ext. coeff($M^{-1}cm^{-1}$)×path corr.*(cm)×amount of enzyme (μg). *Adjusted for substrate blank, Using the extinction coefficient 13,260 $M^{-1}$ $cm^{-1}$, *Using the path correction 0.320 cm. Data are shown in FIG. 21 and Table 30.1.

TABLE 30.1

| Enzymatic assay comparing OG1970 vs. OG1965 | | |
|---|---|---|
| | Vmax (milliOD/min) | % control |
| OG1931 | 5.5885 | 179.8527 |
| OG1965 | 0.81 | 26.06794078 |
| OG1970 | 0.655 | 21.07963112 |

Figure 22A:
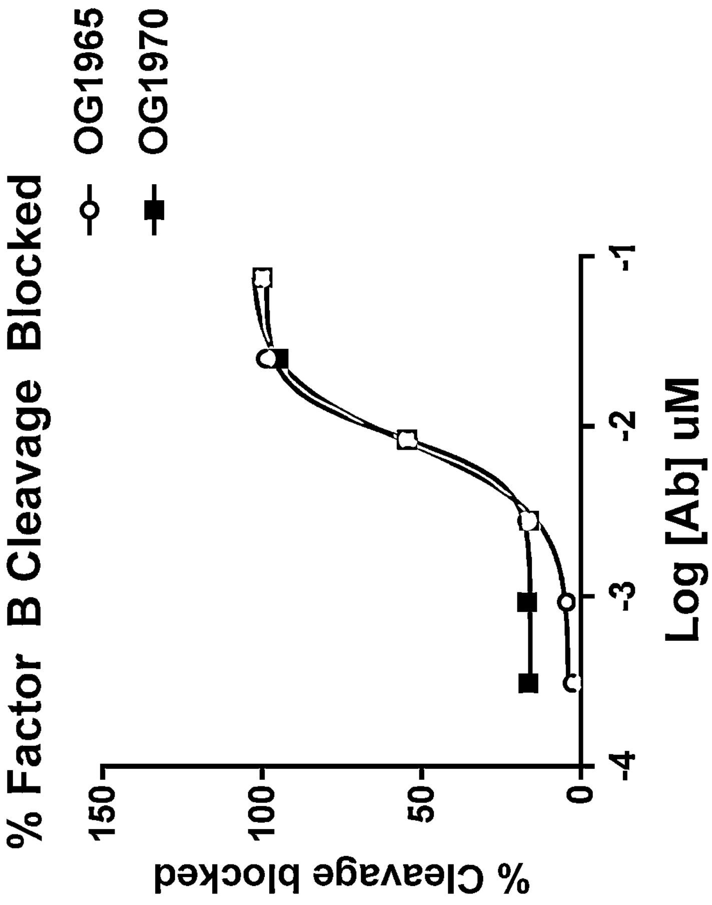
FIGS. 22A and 22B display the results (graph and gel) for the FB cleavage assay for OG1965 and OG1970.
Figure 22B:
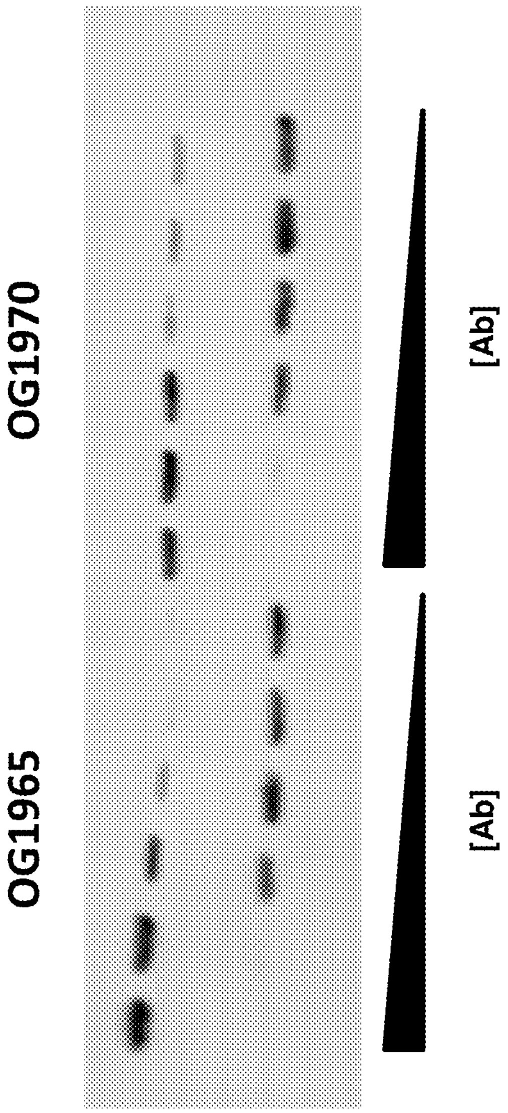

Example 31—FB Cleavage Assays for Assessing OG1965 and OG1970 Inhibition of CFD Factor D mediated cleavage of Factor B was performed exactly as in Example 17.2, only using AFD molecules OG1965 and OG1970. Under these conditions, the conjugated antibody and unconjugated antibodies perform roughly the same. Data are shown in FIGS. 22A and 22B.

Figure 22C:
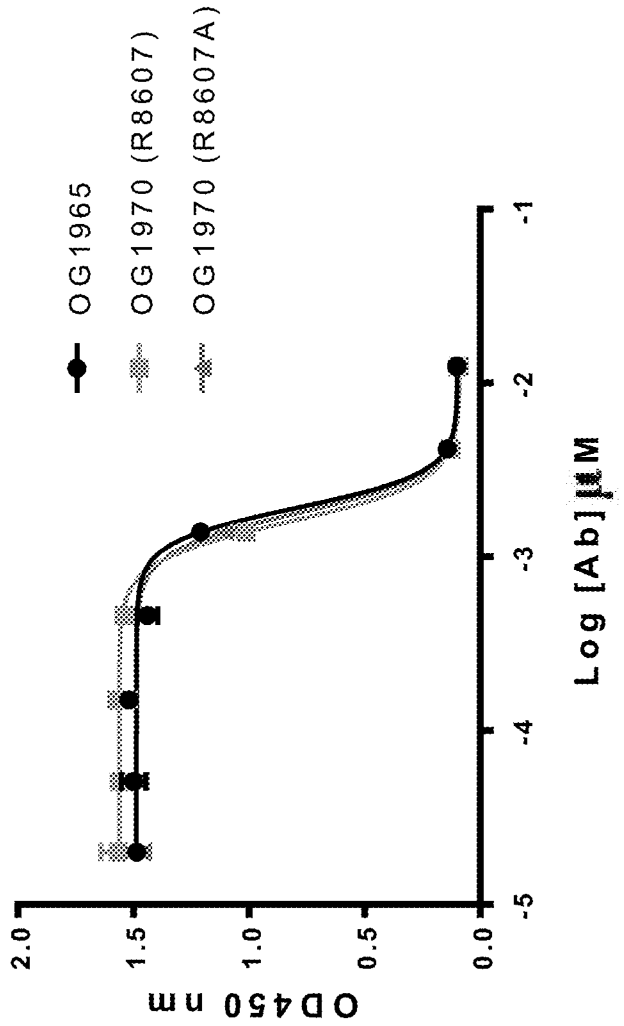
FIG. 22C displays FB cleavage assay using ELISA based method for OG 1965 and OG1970.

Furthermore, a FB cleavage assay using an ELISA based method was performed. All proteins and complexes were prepared using complex buffer (20 mM Hepes, 7.5, 2 mM MgCl2, 150 mM NaCl). In a 96 well plate, 25 nM Factor D (FD; serum purified; A136 Comptech) was mixed with increasing concentrations of anti-Factor D antibodies (aFD; 0.4 nM up to 0.1 uM in 1:3 dilution series) in a final volume of 55 uls. The complexes were incubated at room temperature for 45-60 minutes. 200 nM of Factor B (FB; serum purified; A135 CompTech) and 200 nM C3b (serum purified; A114 Comptech) were combined (final concentrations 100 nM each) and incubated for 45-60 minutes at room temperature in a final volume of 55 uls for each sample. 55 microliteres of FB/C3b complex was added to 55 microliteres of FD/aFD in the 96 well plate so that the final concentrations of FB/C3b were 50 nM and FD was 6.25 nM in a final volume of 110 microliteres. The complexes were then incubated at 37 degrees for 45 minutes. Following incubation, duplicates of 50 microliteres for each sample were added to a MicroVue Bb Plus ELISA kit strips (Quidel; A027). The ELISA was followed according to the manufacturer's protocol to detect Factor Bb that was released by CFD mediated cleavage of C3bB. As shown in FIG. 22C, OG1965 and OG1970 effectively block cleavage of C3bB (EC50 1.9 nM vs. 1.6 nM/1.8 nM respectively).

Example 32—Hemolysis Assay for OG1965 and OG1970

To assess the ability of anti-CFD antibodies to inhibit alternative complement pathway, a hemolysis assay was used.

Hemolysis assay—For the hemolysis assay, rabbit red blood cells ("RBCs", CompTech #B301) were diluted or re-suspended and washed with $GVB^0$ (without $Ca^{2+}$ and $Mg^{2+}$, CompTech #B101) 3 times, then re-suspended in ice-cold GVB++ buffer (GVB/2 mM MgEGTA) at 4.33e8/mL and kept at 4° C. when ready to be used.

Normal human serum (NHS) were incubated with anti-CFD antibody (AFD) at 37 degrees for 60 minutes in well of a round-bottom plate. The prepared RBCs were added to the wells with NHS/AFD on the incubation plate; incubated at room temperature for 35 minutes, and mixed every 10 minutes. The reaction was stopped with $GVB^0$/10 mM EDTA CompTech #B104).

Figure 23:
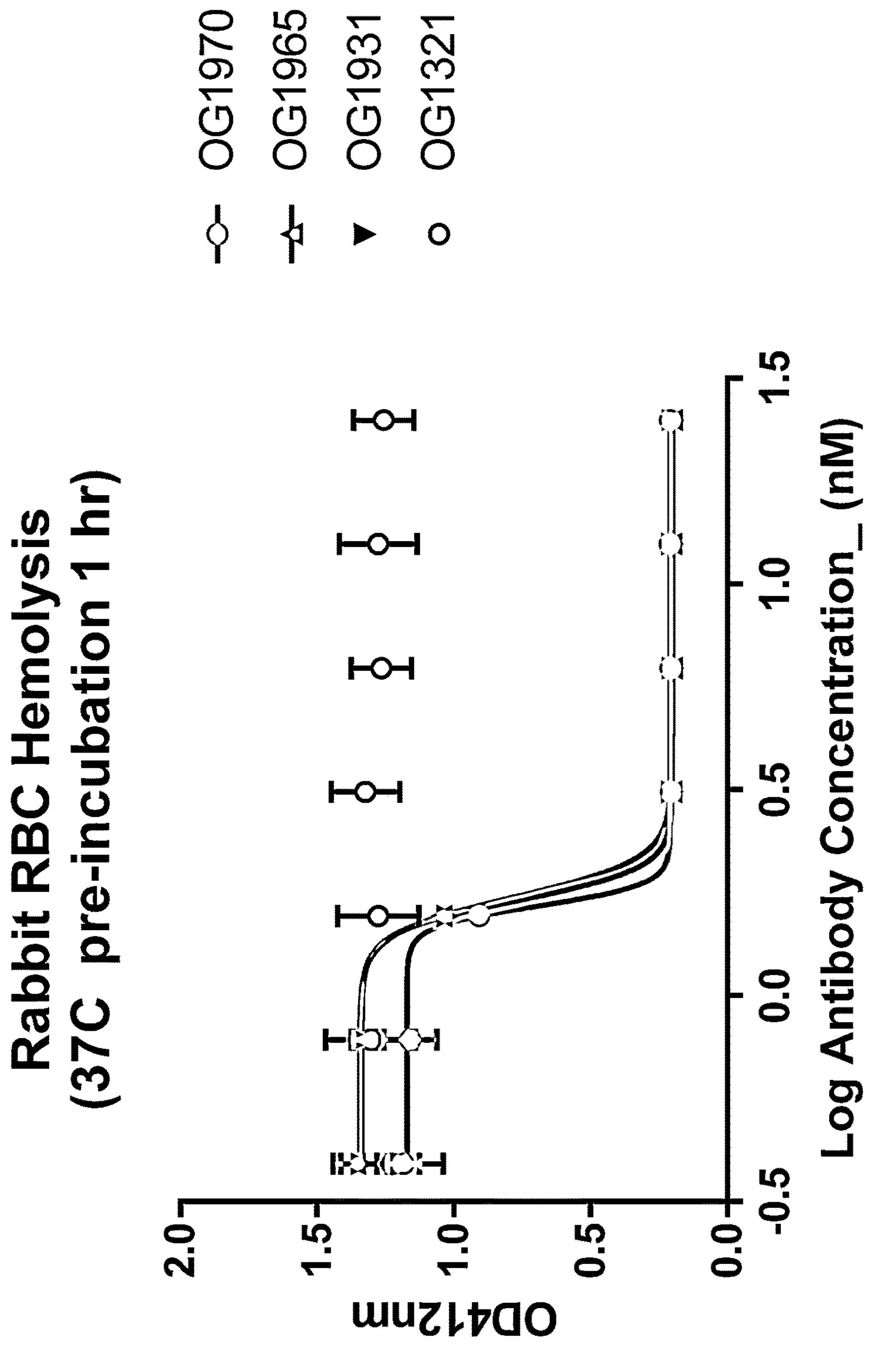
FIG. 23 displays the results of a hemolysis assay for OG1965 and OG1970 and controls.

To measure lysis, supernatant was collected by centrifuging the plate at 1,500 rpm for 5 min, no break or low break. Supernatants were transferred to wells on a flat-bottom 96-well plate (200 uL per well). The plates are read using a SpectraMax Plus™, 25° C. at OD412 nm. In the analysis 100% of lysis: RBCs/NHS without AFD; Inhibition: RBCs/NHS/AFD. Percentage of inhibition was calculated as follows: 100×(OD RBCs/NHS)−(OD RBCs/NHS/AFD). Data are presented in FIG. 23 and Table 32.1. OG1965 and OG1970 both potently inhibit alternative complement pathway-dependent hemolysis of rabbit RBC.

TABLE 32.1

| EC50 of OG1931 and OG1965 in hemolysis assay | |
|---|---|
| | EC50 (nM) |
| OG1931 | 1.704 |
| OG1965 | 1.741 |
| OG1970 | 1.654 |

Example 33

Dry AMD

A patient presents with symptoms and signs of Dry AMD such as and not limited to difficulty reading in dim light confirmed by low luminance visual acuity testing or blurred regions in the visual field confirmed by microperimetry. Following one or more sessions of intraocular treatment with an antibody comprising SEQ ID NO:s 183 and 184, (which can be, in the alternative, conjugated so as to form OG1970), one will observe a decrease in the rate of progression and possible reversal of the symptoms and signs of the disorder. The antibody or bioconjugate can be administered alone or, in the alternative, in combination with another agent.

In some embodiments, the antibody or bioconjugate can be administered via intravitreal injection, at 2.5, 5, or 10 mg/eye, once every 1, 2, 3, 4, or 6 months. The antibody or bioconjugate can also be administered suprachoroidly, with potentially up to 100 mg/eye, once every 1, 2, 3, 4, 6, or 12 month.

Example 34

Wet AMD

A patient presents with Wet AMD in an eye and advanced Dry AMD in the other eye. They are considered a high risk patient to develop Wet AMD in the other eye. One or more sessions with intraocular treatment with an antibody comprising SEQ ID NO:s 183 and 184, (which can be, in the alternative, conjugated so as to form OG1970), will prevent (including delay) the conversion of Dry to Wet AMD. The antibody or bioconjugate can be administered alone or, in the alternative, in combination with another agent.

In some embodiments, the antibody or bioconjugate can be administered via intravitreal injection, at 2.5, 5, or 10 mg/eye, once every 1, 2, 3, 4, or 6 months. The antibody or bioconjugate can also be administered suprachoroidly, with potentially up to 100 mg/eye, once every 1, 2, 3, 4, 6, or 12 month.

Example 35

Diabetic Retinopathy

A patient present with symptoms Diabetic Retinopathy such as and not limited to difficulty in reading confirmed by near vision visual acuity. Ocular exam, OCT and Fluorescein Angiography reveals Diabetic Macular Edema and generalized Diabetic Retinopathy. Following one or more sessions of treatment with an antibody comprising SEQ ID NO:s 183 and 184, (which can be, in the alternative, conjugated so as to form OG1970) the symptoms will resolve, OCT reveals reduction in the macular edema or resolution and the diabetic retinopathy did not progress, regressed, or resolved. The antibody or bioconjugate can be administered alone or, in the alternative, in combination with another agent.

In some embodiments, the antibody or bioconjugate can be administered via intravitreal injection, at 2.5, 5, or 10 mg/eye, once every 1, 2, 3, 4, or 6 months. The antibody or bioconjugate can also be administered suprachoroidly, with potentially up to 100 mg/eye, once every 1, 2, 3, 4, 6, or 12 month.

Example 36

Paroxysmal Nocturnal Hemoglobinuria (PNH)

Hemolysis can cause one or more of the following symptoms in a patient with PNH: severe anemia, disabling fatigue, recurrent pain, shortness of breath, pulmonary hypertension, intermittent episodes of dark colored urine (hemoglobinuria), kidney disease, impaired quality of life and blood clots. Following one or more sessions of treatment with an antibody comprising SEQ ID NO:s 183 and 184, (which can be, in the alternative, conjugated so as to form OG1970) hemolysis is reduced and hemoglobin levels increase and stabilize. The antibody or bioconjugate can be administered alone or, in the alternative, in combination with another agent.

In some embodiments, the antibody or bioconjugate can be administered via intravenous or subcutaneous injections, at 0.1 to 30 mg/kg, once every 2 weeks, 1, 2, 3, or 4 months.

Example 37

RE: Expression, Purification, Crystallization and Structure Determination of OG1965-CFD Methods CFD and OG1965 Fab expression and purification: Human mature CFD peptide with N-terminal His tag was expressed in Expi293 cells (Thermo Scientific) and purified from media using Ni-NTA resin (30 mM Tris pH 8.0, 200 mM Nacl and 250 mM imidazole) followed by size exclusion chromatography (30 mM HEPES pH 7.5 and 200 mM NaCl). OG1965 was expressed in CHO-S1 cells and purified using mAbSelect (GE Healthcare Life Sciences) by following manufacture's instruction.

Purified OG1965 was digested with crystalline papain (50:1 OG1965:crystalline papain ratio) in 10 mM DTT, 25 mM HEPES pH 7.5, 200 mM NaCl. The reaction was incubated for 4 hours at 37° C. Approximately 30 mg of mAb were digested and the resulting Fab fragments were alkylated with iodoacetamide and purified using a protein A resin. The presence of Fab chains at the flow through was confirmed by SDS-PAGE, while the absence of Fc chain was confirmed by ESI-MS.

CFD-Fab complex formation and purification. A mixture containing CFD and Fab proteins was prepared at an equimolar concentration, incubated at room temperature for one hour and later injected in a size exclusion (Superdex-200) column pre-equilibrated with 25 mM HEPES pH 7.5, 100 mM NaCl, and 3% (v/v) glycerol. Peak fractions containing Fab and CFD were identified by SDS-PAGE, pooled, concentrated to 10 mg/ml and carried out to crystallization experiments.

CFD-Fab complex crystallization. Conditions for CFD-Fab complex crystallization were screened by the sitting drop vapor diffusion method with in-house and commercial crystallization screens at 4° C. and room temperature (RT). Protein crystals were obtained in three different conditions: A—0.1 M Bicine pH 9.0 and 20% PEG 6000 at RT; B—0.1 M Tris pH 8.0, 30% Peg 1000, and 0.1 M Sodium Malonate at RT; C—0.1 M Mes pH 6.0 and 20% PEG 6000 at 4° C. Crystals grown at room temperatures are thin plates and were seeded to get diffraction quality crystals. Meanwhile, crystal at 4° C. appeared after a week and present tetragonal morphology.

X-ray data collection. Crystals were flash-cooled by direct immersion in liquid nitrogen using mother liquor supplemented with 20% (v/v) ethylene glycol. X-ray intensity data were collected at the SER-CAT beam line of the Advanced Photon Source (APS) using Rayonix 300 high-speed detector. Crystals grown at room temperature (pH 9.0) diffracted to 2.7 Å, and belong to the triclinic space group $P_1$ with four complex molecules in the asymmetric unit. Whereas crystals grown at 4° C. (pH 6.0) diffracted to 2.4 Å, and belong to the tetragonal space group $P4_1$ 22 with two complex molecules in the asymmetric unit. Data were indexed, integrated and scaled using the program HKL2000.

Structure determination and refinement. The crystal structure of the complex was determined by molecular replacement with Phaser using the CFD (PDB: 1DSU) and Fab (PDB: 3HR5) monomers as the initial search models. The model was refined by rigid-body refinement followed by restrained refinement using REFMAC. All crystallographic calculations were performed with the CCP4 suite of programs. Model building of the complex in the electron density was done using the graphics program COOT. Most of the model was fitted well in the electron density especially at the antigen-antibody interface. After an iterative model building and refinement, relatively high R and freeR (R/freeR=0.27/0.32) were noticed due to the disorder of the constant domains (Cl and Ch1) in one of the four complex molecules. This disorder, as found in a number of Fab structures, is due to the flexible elbow angle between the variable and constant domains.

For the structure of the complex at pH 6.0, previously refined models of the CFD and Fab complex at pH 9 were used as search models to solve the structure. The structure at pH 6 presents better refinement statistics (R/freeR=0.22/0.28) and was selected for further validation using the Ramachandran plot and the program PROCHECK. The structural coordinates can be found in CTKDK001A.txt, filed herewith and incorporated by reference in its entirety.

Example 38

Structural Analysis of OG1965

Figure 24A:
FIG. 24A shows OG1965 binding to CFD. Fab heavy and light chains are shown in surface representation, CFD is shown in ribbon. Figure was prepared using software PyMOL (Open-Source PyMOL 0.99rc6).
Figure 24B:
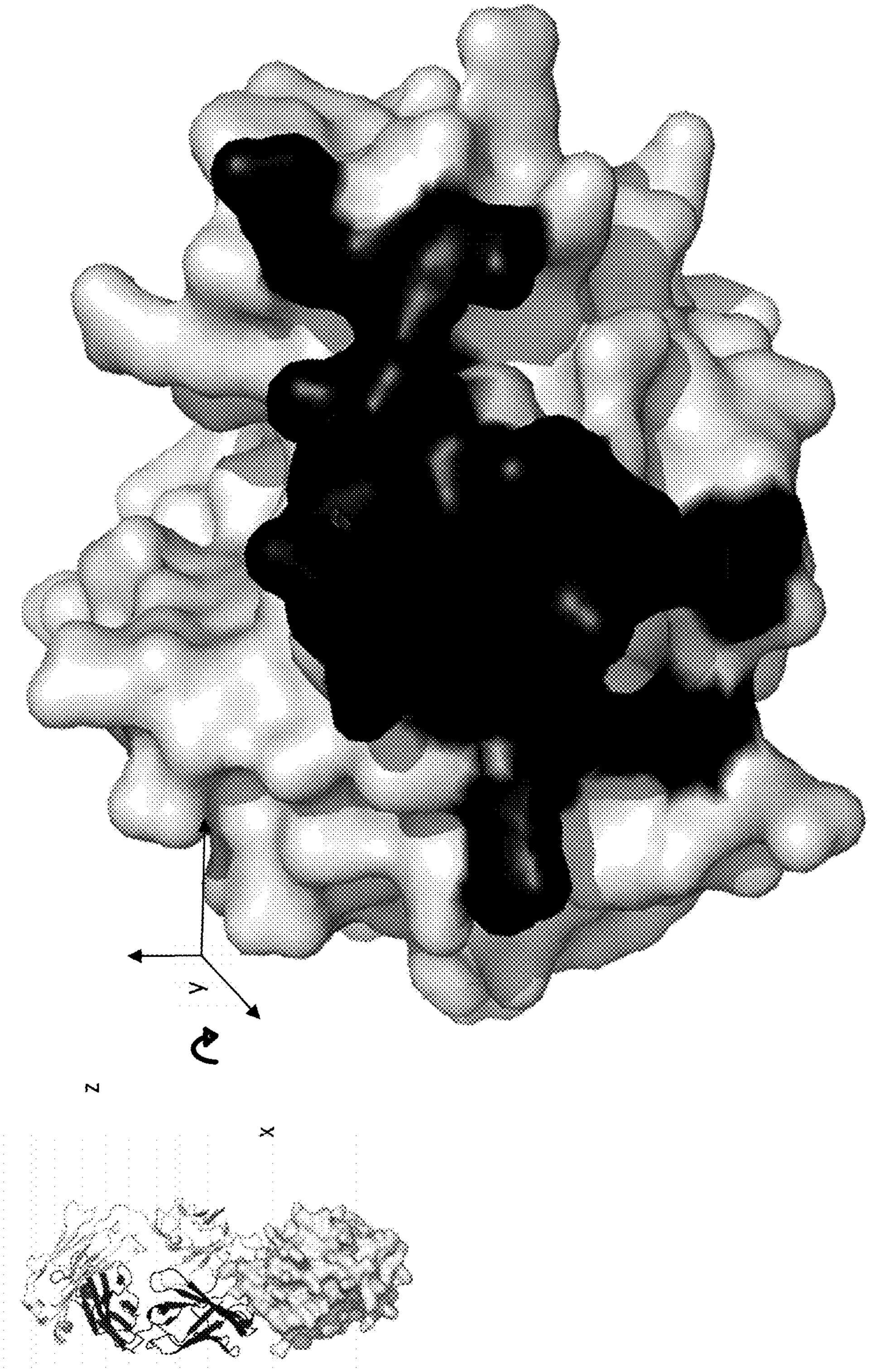
FIG. 24B shows the OG1965 binding region at the CFD domain. The figure displays CFD in surface representation, OG1965 heavy and light chains are presented in black and white ribbons, respectively. Buried surface residues between Fab and CFD are highlighted in black over CFD surface representation. Figure was prepared using software PyMOL (Open-Source PyMOL 0.99rc6).
Figure 25:
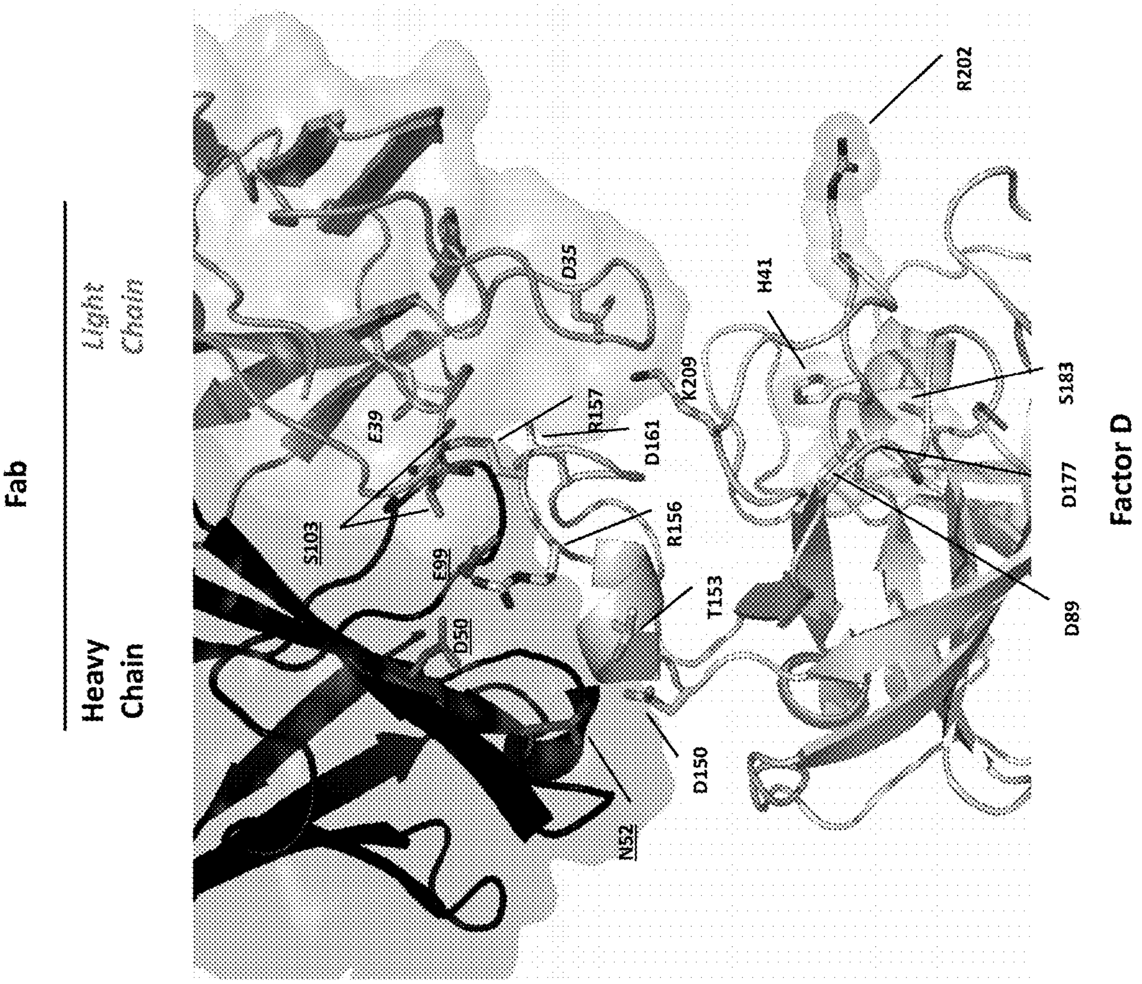
FIG. 25 shows residues (stick representation) at the CFD: Fab interface that are within a distance shorter than 3 Å. CFD is presented in ribbon, Fab heavy (underlined residues) and light chains (italicized residues) are presented in dark and light ribbons overlapped by transparent surface representations. Residues at the CFD active site (H41, D89, S183), self-inhibitory loop (R202) and S1 pocket (D177) are shown in sticks and highlighted by spheres. Figure was prepared using software PyMOL (Open-Source PyMOL 0.99rc6).
Figure 26A:
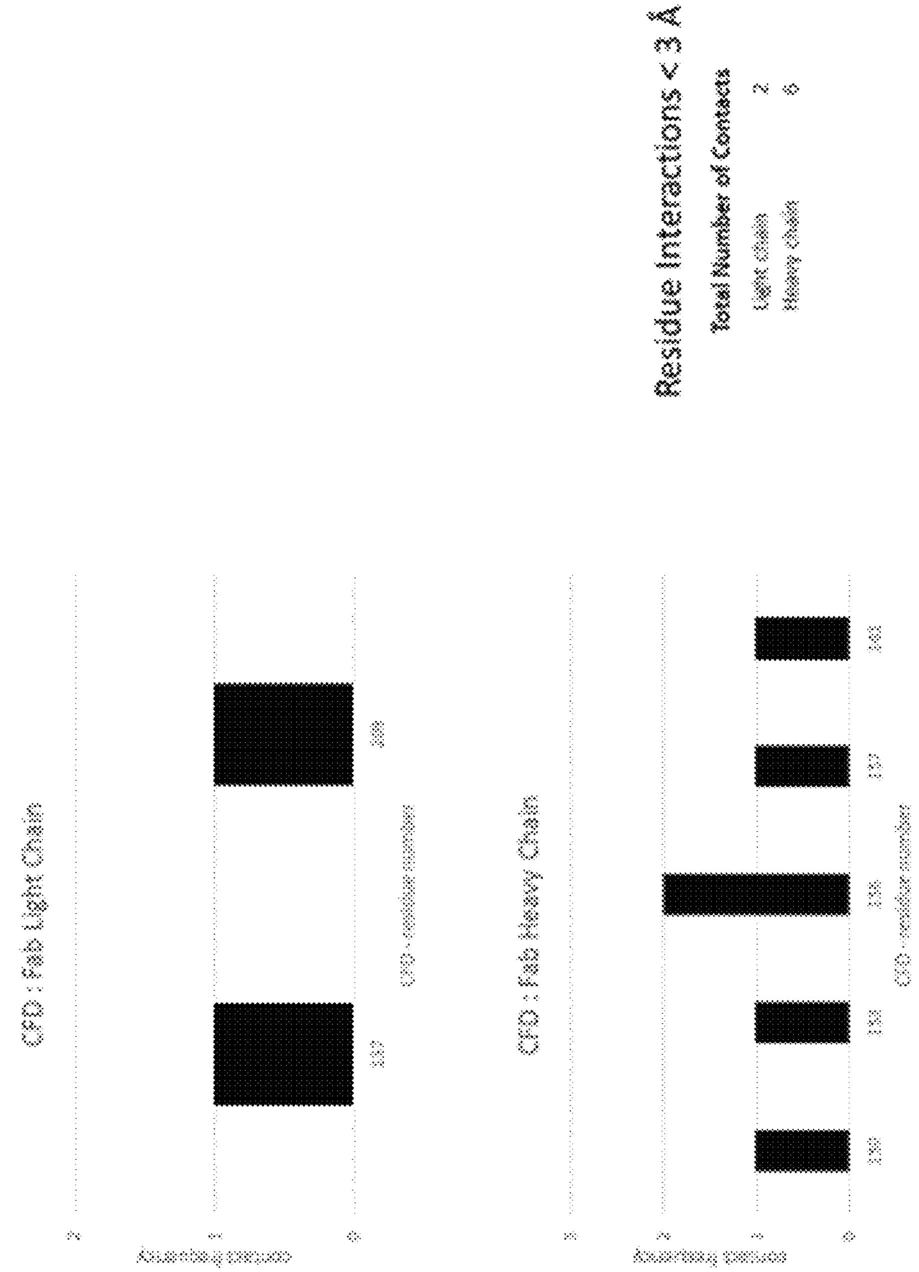
FIGS. 26A-26C show CFD and Fab residue contacts frequency. Top and bottom panels display the number of interactions between CFD and Fab light/heavy chains, respectively. Residue interactions were identified using an in-house Python-based algorithm developed to measure distances between inter-chain atoms. Contacts below 3 Å were selected and counted on a residue basis in FIG. 26A. Contacts below 5 Å were selected and counted on a residue basis in FIG. 26B. Contacts below 6 Å were selected and counted on a residue basis in FIG. 26C.
Figure 26B:
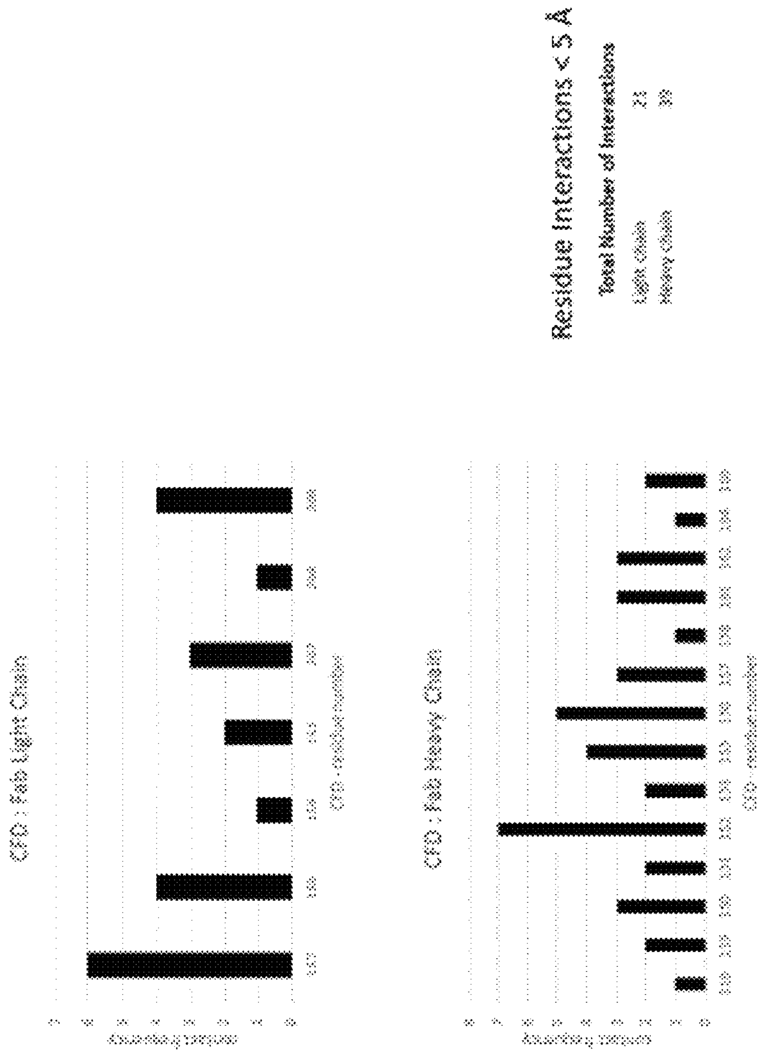
Figure 26C:

CFD-Fab interface residue analysis. Residues at the interface between CFD and Fab (heavy and light chains) were identified using an in-house modified version of the PyMOL script InterfaceResidues available online at world wide web //pymolwiki “dot” org/index “dot” php/InterfaceResidues. This script calculates the accessible surface area (ASA) of residues in two situations: i) at the complex as a whole and ii) at the isolated chains. Then, it calculates the difference between ASA in both situations, residues with differences above a user-defined cutoff value (defined as 1 in this study) are identified as interface residues. This analysis was performed on chains A—CFD, H—Fab Heavy chain, L—Fab Light chain of OG1965. The antibody as bound to CFD is depicted in FIG. 24A. The atomic coordinates are in the accompanying text file, filed herewith (CTKDK001A.txt). Interface residues were mapped on the CFD surface representation as illustrated in FIG. 24B.

Interatomic contact distances at the CFD-Fab complex. Distances between inter-chain atoms were determined using an in-house Python-based algorithm following the equation described below:

$$\text{distance}=\{(x_1-x_0)^2+(y_1-y_0)^2+(z_1-z_0)^2\}^{0.5}$$, given two points in three dimensions are defined by $(x_0,y_0,z_0)$ and $(x_1,y_1,z_1)$.

Distance shorter than a user defined cutoff value (3, 5 and 6 angstroms in this study) were selected. To remove residue contact redundancy, only the shortest interatomic distance was chosen within a pair of residues. Those contacts were later grouped into clusters based on CFD residue numeration and counted. This analysis was performed on chains A—CFD, H—Fab Heavy chain, L—Fab Light chain of OG1965. Interface residues were mapped on the CFD surface representation as illustrated in FIGS. 25 and 26A-26C and Tables 38.1-38.3.

TABLE 38.1

List of residue contacts between CFD and Fab chains below 3 Å

| CFD | Heavy chain | Light chain |
|---|---|---|
| D150 | N52 | |
| T153 | N52 | |
| R156 | D50, E99 | |
| R157 | E99 | E39 |
| D161 | S103 | |
| K209 | | D35 |

TABLE 38.2

List of residue contacts between CFD and Fab chains below 5 Å

| CFD | Heavy chain | Light chain |
|---|---|---|
| D116 | D31 | |
| P119 | T55, I54 | |
| D150 | I54, N52, T55 | |
| R151 | I54, D31 | |
| A152 | T30, D31, Y32, I54, Y33, N52, P53 | |
| T153 | Y33, N52 | |
| N155 | D31, E99, G100, Y32 | |
| R156 | E99, Y33, D50, D59, N35 | |
| R157 | E99, S103, F104 | Y37, E39, G96, F94, Y41, V101 |
| T158 | E99 | Y37, N33, H31, G96 |
| H159 | | Y37 |
| D161 | G100, P101, S103 | R54, K55 |
| G162 | G100, P101, Y32 | |
| I164 | Y32 | |
| E166 | D31, T28 | |
| R207 | | N33, G34, S32 |
| K208 | | N33 |
| K209 | | N33, D35, Y37, K55 |

TABLE 38.3

List of residue contacts between CFD and Fab chains below 6 Å

| CFD | Heavy chain | Light chain |
|---|---|---|
| D116 | D31, I54 | |
| P119 | I54, T55 | |
| D150 | I54, T55, N52, Y33, T30 | |
| R151 | T30, D31, I54, Y32 | |
| A152 | T30, D31, Y32, Y33, N52, I54, P53, E99 | |
| T153 | D31, Y33, N52, I54, T55 | |
| N155 | D31, Y32, E99, G100, P101, Y33 | |
| R156 | Y33, E99, G100, D50, N35, D59, W47 | |
| R157 | E99, G100, S103, F104, N35, P101 | Y37, E39, D35, K55, G96, F94, Q95, S97, V101, Y41 |
| T158 | E99 | N33, Y37, H31, G96, D35, S97 |
| H159 | | N33, Y37, D35 |
| H160 | G100 | |
| D161 | G100, P101, S103, E99 | R54, K55, E39, Y37 |
| G162 | Y32, E99, G100, P101, R98 | |
| A163 | Y32, G100 | |
| I164 | Y32, D31 | |
| T165 | Y32, D31 | |
| E166 | D31, T28 | |

TABLE 38.3-continued

| List of residue contacts between CFD and Fab chains below 6 Å | | |
|---|---|---|
| CFD | Heavy chain | Light chain |
| N206 | | S32, N33 |
| R207 | | N33, S32, G34 |
| K208 | | N33 |
| K209 | | N33, D35, Y37, K55 |

Example 39—CFB Binding Inhibition Assay

To determine whether anti-CFD antibodies inhibit CFD from binding to C3bB, a SPR approach was implemented to assess complex assembly. 200 RUs of C3b (Complement Technologie) in Acetate pH 5.0 buffer was amine coupled to a CM5 Series S sensor chip by following the immobilization wizard on Biacore instrument software. $CFD_{S183A}$ is a catalytically dead mutant of CFD that still binds to CFB without cleaving it. For complex assembly, 100 nM of recombinant human $CFD_{S183A}$ was complexed with 100 nM CFB by incubating the mixture in HBS+ with 2 mM MgCl2. The resulting complex was then incubated in the presence or absence of 100 nM OG1965, OG1970, or OG2063 (positive control; also named KCD004 (SEQ ID NOs: 341 and 342)).

Using HIBS+ with 2 mM MgCl2 running buffer, 100 nM CFB (Complement Technologies) was injected for 60 seconds followed by CFB: $CFD_{S183A}$ complex or CFB: $CFD_{S183A}$:AFD mixtures for 60 seconds at 30 uls/min using the dual injection function. The complexes were allowed to dissociate for 5 minutes, and the surface was regenerated with 3M MgCl2 for 60 seconds at 50 uls/min. Sensorgrams were evaluated using Biacore T200 Evaluation Software (GE Life Sciences).

Figure 27:
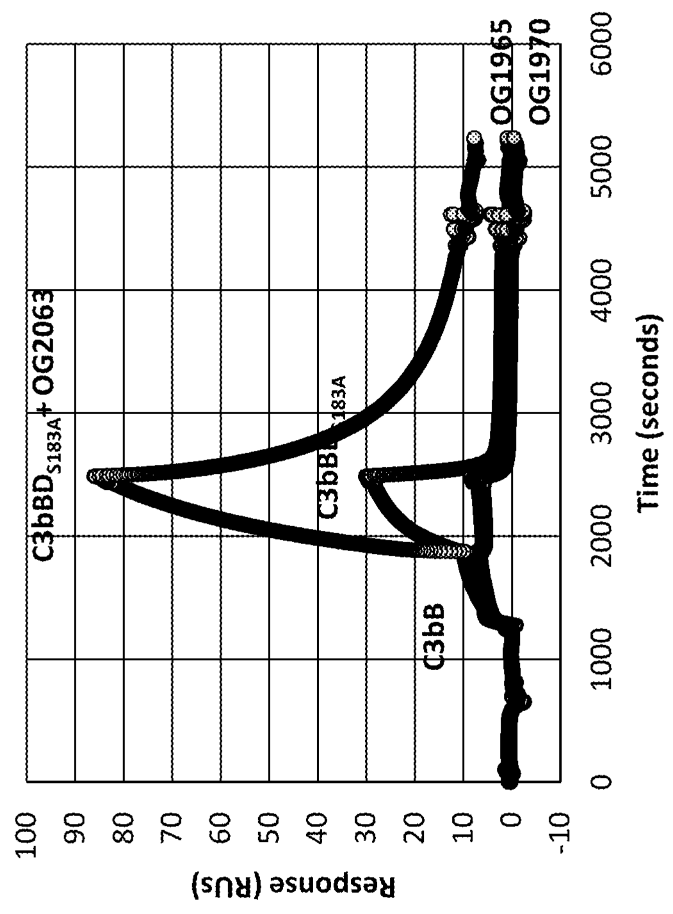
FIG. 27 illustrates a biacore complex assembly assay showing that both OG1965 and OG1970 inhibit CFD from binding to C3bB. KCD004 is used as a positive control.

As shown in FIG. 27, CFB and CFB:$CFD_{S183A}$ bound to C3b with correlative increases in resonance units following injection. In the presence of OG2063, a non-blocking anti-CFD antibody, the response of KCD004:$CFD_{S183A}$ was significantly higher than what was observed for $CFD_{S183A}$ alone, which is indicative of C3bBD-mAb complex formation. OG1965/$CFD_{S183A}$ and OG1970/$CFD_{S183A}$ do not show any change in binding, supporting the position that $CFD_{S183A}$ does not effectively bind to C3bB when it is bound to OG1965 or OG1970. KCD004 is referenced elsewhere as SEQ ID NO: 341 and 342.

Example 40—Complement Activation on ARPE19 Cells

The retinal pigment epithelial cell line, ARPE19, (ATCC) was cultured on trans-well filters (Millipore) in DMEM with pyruvate until cells were pigmented (12-16 weeks). Anti-CFD molecules preincubated for 1 hour with 10% normal human serum (NHS) were added to ARPE19 cells at 37 degrees for 1 hour to induce complement activation. Supernatants were harvested and cells were fixed with 4% PFA.

Figure 28A:
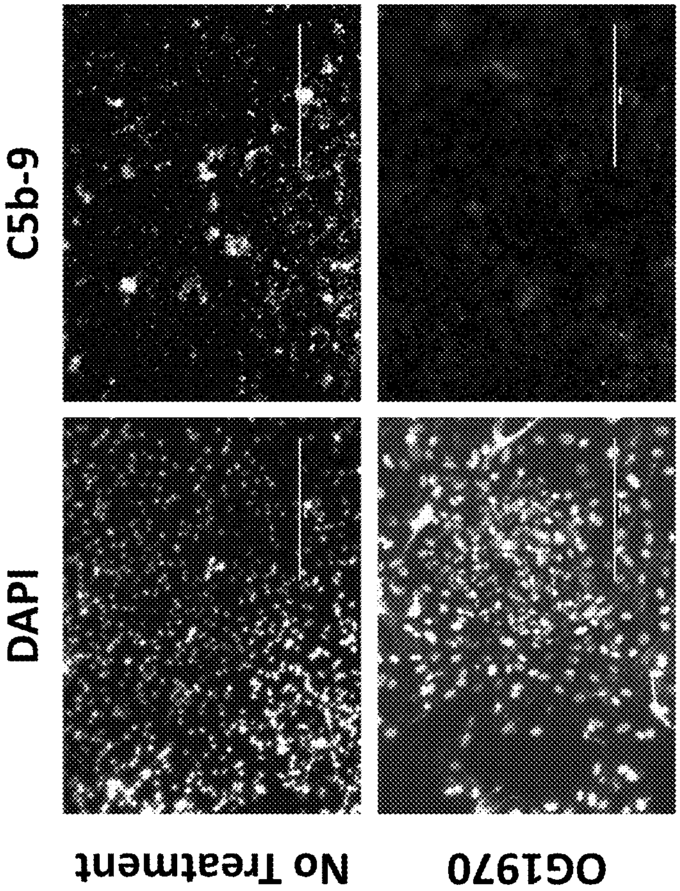
FIG. 28A and FIG. 28B utilize immunofluorescence and ELISA to observe CFB cleavage as well as formation of the terminal complement complex, C5b-9, on ARPE19 cells.

Immunofluorescence: Fixed cells were incubated with αC5b-9 (Abcam), Donkey α-mouse-488 (Rockland Immunochemicals), and imaged on an EVOS fluorescence microscope (Life Technologies). Scale bar=400 μm. The results are shown in FIG. 28A and provide evidence that OG1970 effectively inhibited formation of the terminal complement complex C5b-9 on ARPE19 cells relative to cells subjected to serum alone.

Figure 28B:
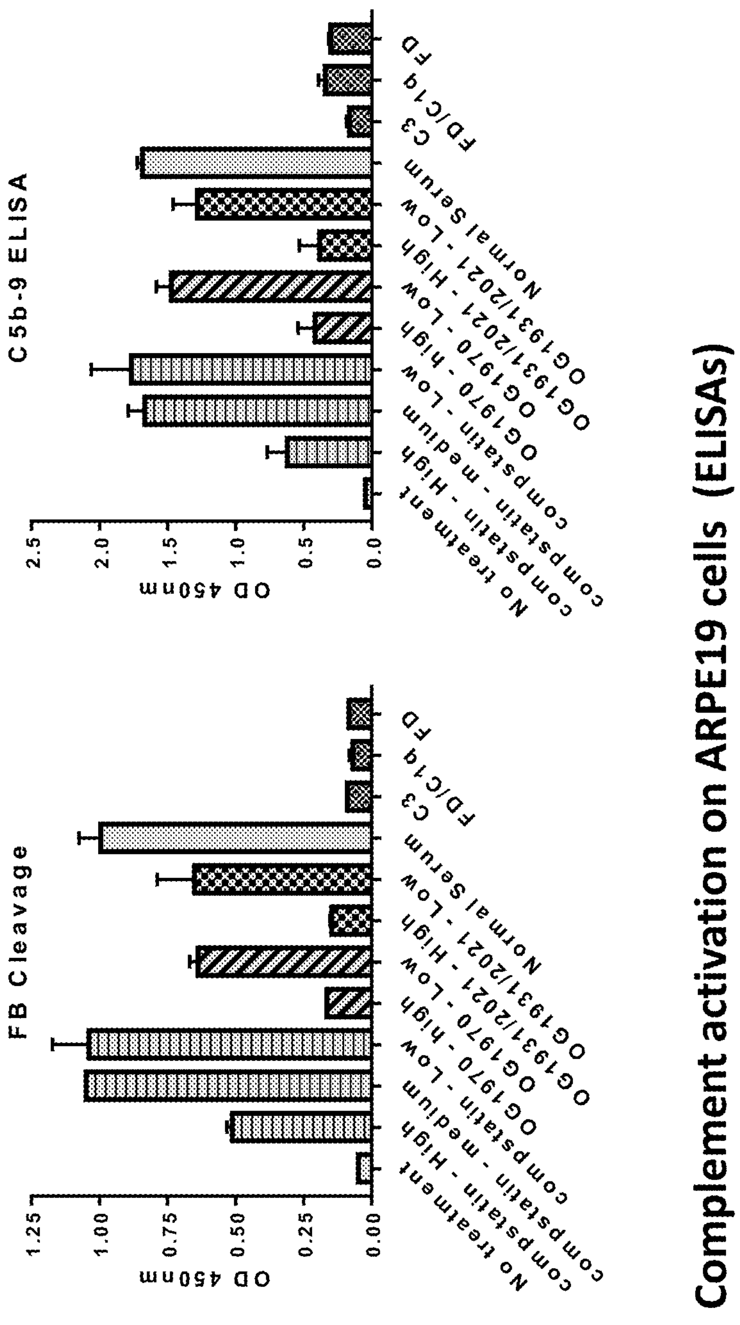

Bb and Cb5-9 complex ELISAs: Harvested supernatants were diluted 4-fold in Quidel diluent buffer before being added to MicroVue Bb Plus or MicroVue C5b-9 ELISA kit strips (Quidel). Manufacturer's instructions were followed and relative Bb or C5b-9 levels were measured at OD450 nm on a SpectraMax Plus. The results are shown in FIG. 28B as the average of replicates with standard deviation.

The results indicated that OG1970 inhibited C5b-9 complex formation as effectively as OG1931 and the classical pathway inhibitor Compstatin. OG1970 inhibition of CFB cleavage to Bb was superior to that of compstatin and comparable to OG1931 at both high and low doses tested. Additionally, OG1970 treated cells had similar levels of both Bb and C5b-9 as cells treated with C3 depleted sera (classical and alternative pathways), FD/C1q depleted sera (classical and alternative pathways), and FD depleted sera (alternative pathway), indicating that inhibition of CFD was sufficient for inhibiting the complement pathways under these conditions.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

What is claimed is:

1. A conjugate comprising:

an isolated antagonistic antibody that binds to complement factor D (CFD), the antibody comprising:

a CDR$_H$1 that is the CDR$_H$1 in SEQ ID NO: 520;

a CDR$_H$2 that is the CDR$_H$2 in SEQ ID NO: 520;

a CDR$_H$3 that is the CDR$_H$3 in SEQ ID NO: 520;

a CDR$_L$1 that is the CDR$_L$1 in SEQ ID NO: 525;

a CDR$_L$2 that is the CDR$_L$2 in SEQ ID NO: 525;

a CDR$_L$3 that is the CDR$_L$3 in SEQ ID NO: 525;

at least one of the following mutations (EU numbering): L234A, L235A, and G237A; and at least one of the following mutations (EU numbering): Q347C or L443C; and a polymer, wherein the polymer is covalently attached to the antibody.

2. A conjugate comprising:

(a) an isolated antagonist antibody that specifically binds to complement factor D (CFD), wherein the antibody comprises:

a heavy chain variable region (VH) comprising:

a VH complementarity determining region 1 (CDR$_H$1) that is the CDR$_H$1 in SEQ ID NO: 520;

a CDR$_H$2 that is the CDR$_H$2 in SEQ ID NO: 520;

a CDR$_H$3 that is the CDRH3 in SEQ ID NO: 520; and a light chain variable region (VL) comprising:

a VL complementarity determining region 1 (CDRL1) comprising H31, N33, G34 or E34 or F34 or S34, D35 or E35, T36 or S36 or V36, Y37, L38 or I38, and E39 (EU numbering);

a CDR$_L$2 comprising L51 or H51, 153 or V53, and K55 (EU numbering); and a $CDR_L3$ comprising F94 or L94, Q95, G96, S97, V99 or N99 or Q99 or W99, P100, and P101 or V101 (EU numbering); and (b) a phosphorylcholine containing polymer, wherein the polymer is covalently bonded to the antibody.

3. The conjugate of claim 2, wherein the conjugate is capable of blocking at least 80% of an interaction between CFD and C3bB.

4. The conjugate of claim 2, wherein the polymer is covalently bonded to the antibody at a non-native cysteine outside a variable region of the antibody.

5. The conjugate of claim 2, wherein the polymer is formed by 2 (methacryloyloxy)ethyl (2-(trimethylammonio) ethyl) phosphate (MPC) monomers.

6. The conjugate of claim 2, wherein the polymer has a peak molecular weight between 300,000 and 1,750,000 Daltons as measured by size exclusion chromatography-multi angle light scattering (hereinafter "SEC-MALS").

7. The conjugate of claim 2, wherein the polymer has 2 or more arms.

8. The conjugate of claim 2, wherein the polymer is covalently bonded to a sulfhydryl group from a cysteine residue on the heavy chain.

9. The conjugate of claim 8, wherein the polymer is covalently bonded to a sulfhydryl group from a cysteine residue at position 347 or 443 (EU numbering).

10. The conjugate of claim 2, wherein the conjugate has a molecular weight between about 350,000 and 1,900,000 Daltons.

11. The conjugate of claim 2, wherein the polymer has 9 arms; and the polymer has a molecular weight of between about 600,000 to about 900,000 Da.

12. The conjugate of claim 2, which has the following structure:

Formula (17)

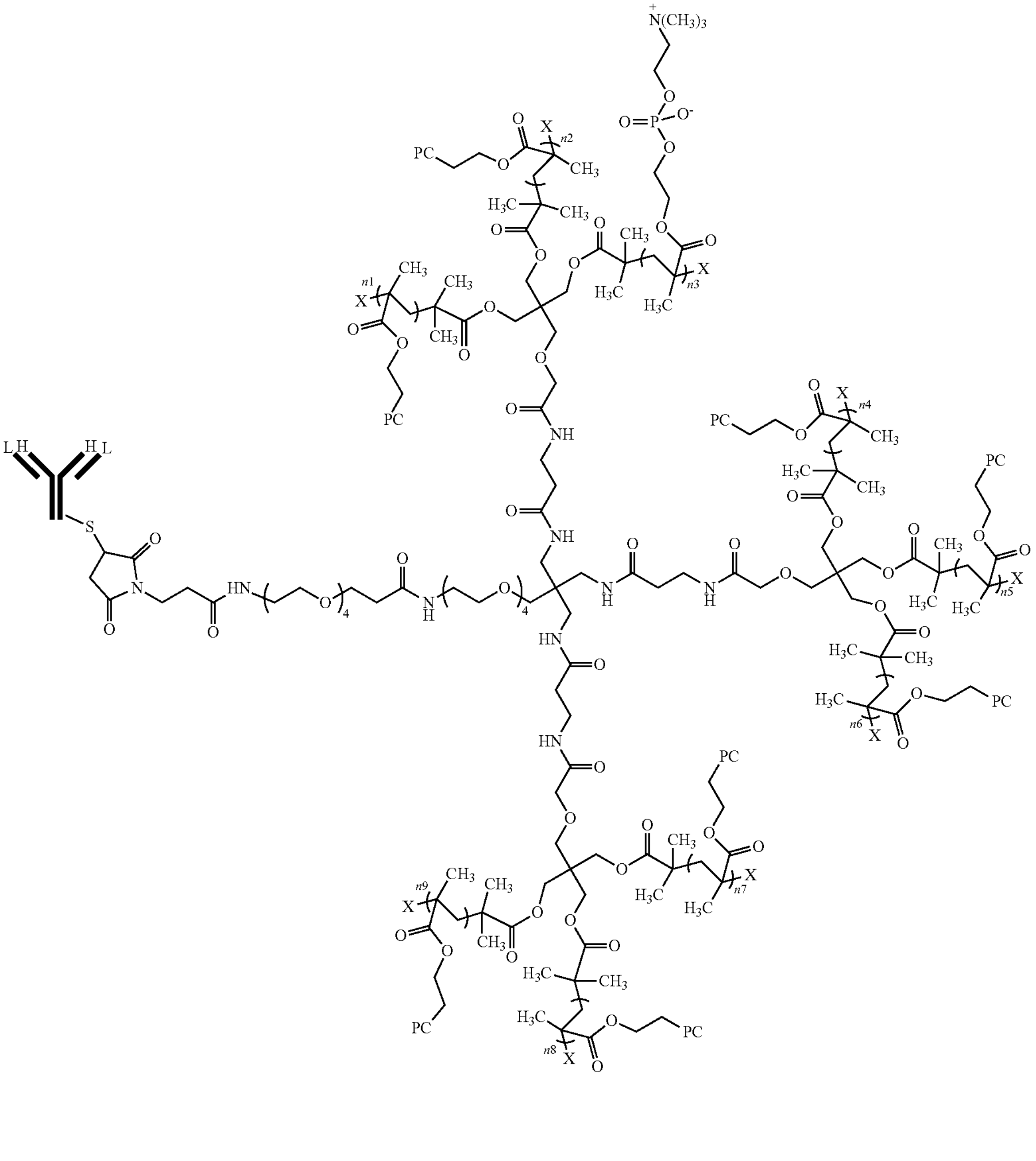

wherein:

each heavy chain of the antibody is denoted by the letter H, and each light chain of the antibody is denoted by the letter L, the polymer is bonded to the antibody through the sulfhydryl of C443 (EU numbering), which bond is depicted on one of the heavy chains, PC is

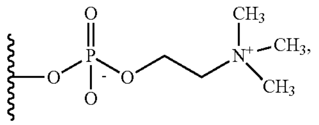 [SMILES: *OP(=O)(O)OCC[N+](C)(C)C]

wherein the curvy line indicates the point of attachment to the rest of the polymer, X is:

a) OR, wherein R is: methyl; ethyl; propyl; or isopropyl;

b) H; or c) any halogen, and n1, n2, n3, n4, n5, n6, n7, n8 and n9 are the same or different such that the sum of n1, n2, n3, n4, n5, n6, n7, n8 and n9 is 2500 plus or minus 15%.

13. A pharmaceutical composition comprising a conjugate of claim 2, and a pharmaceutically acceptable carrier.

14. The conjugate of claim 2, wherein (a) when bound, the antibody is within 3 Å of residue 209 of SEQ ID NO: 1 of CFD, or (b) when bound, the antibody is within 3 Å of residue 156 of SEQ ID NO: 1 of CFD, or (c) the antibody binds to one or more of residues 156 or 209 of SEQ ID NO: 1 of CFD, or (d) when bound to CFD, the antibody is not within 6 angstroms of at least one of 117, 118, and 156 of SEQ ID NO: 1.

15. The conjugate of claim 2, wherein the isolated antagonist antibody (a) specifically binds to complement factor D (CFD) and directly inhibits a proteolytic activity of CFD, or (b) specifically binds to complement factor D (CFD), inhibits a proteolytic activity of CFD, and inhibits CFD binding to C3bB complex, or (c) specifically binds to complement factor D (CFD), wherein the antibody does not bind a human CFD mutant comprising mutations R157A and R207A, or (d) binds an epitope on human CFD, wherein the epitope excludes positions R157 and R207.

16. The conjugate of claim 2, wherein the light chain variable region of the antibody comprises three complementarity determining regions (CDRs) comprising the amino acid sequences shown in SEQ ID NO: 525.

17. The conjugate of claim 2, wherein the heavy chain variable region (VH) of the antibody comprises three CDRs comprising the amino acid sequences shown in SEQ ID NO: 541, SEQ ID NO: 542, and SEQ ID NO: 543, and the light chain variable region (VL) of the antibody comprises three CDRs comprising the amino acid sequences shown in SEQ ID NO: 544, SEQ ID NO: 545, and SEQ ID NO: 546.

18. The conjugate of claim 17, wherein the VH comprises the amino acid sequences shown in SEQ ID NO: 520, and the VL comprises three CDRs comprising the amino acid sequences shown in SEQ ID NO: 544, SEQ ID NO: 545 and SEQ ID NO: 546.

19. The conjugate of claim 18, wherein the VL comprises the amino acid sequence shown in SEQ ID NO: 525.

20. The conjugate of claim 2, wherein the antibody comprises a heavy chain comprising the amino acid sequence shown in SEQ ID NO: 183, with or without the C-terminal lysine, and a light chain comprising the amino acid sequence shown in SEQ ID NO: 184.

21. The conjugate of claim 12, wherein X is Br.

22. A conjugate comprising:

an isolated antagonist antibody that specifically binds to complement factor D (CFD), the antibody comprising:

a heavy chain variable region (VH) comprising 3 CDRs of the CDRs in SEQ ID NO: 339; and a light chain variable region (VH) comprising 3 CDRs of the CDRs in SEQ ID NO: 340; or a VH comprising 3 CDRs of the CDRs in SEQ ID NO: 343; and a VL comprising 3 CDRs of the CDRs in SEQ ID NO: 344; or a VH comprising 3 CDRs of the CDRs in SEQ ID NO: 435; and a VL comprising 3 CDRs of the CDRs in SEQ ID NO: 436; or a VH comprising 3 CDRs of the CDRs in SEQ ID NO: 437; and a VL comprising 3 CDRs of the CDRs in SEQ ID NO: 438; or a VH comprising 3 CDRs of the CDRs in SEQ ID NO: 441; and a VL comprising 3 CDRs of the CDRs in SEQ ID NO: 442; or a VH comprising 3 CDRs of the CDRs in SEQ ID NO: 443; and a VL comprising 3 CDRs of the CDRs in SEQ ID NO: 444; or a VH comprising 3 CDRs of the CDRs in SEQ ID NO: 445; and a VL comprising 3 CDRs of the CDRs in SEQ ID NO: 446; or a VH comprising 3 CDRs of the CDRs in SEQ ID NO: 447; and a VL comprising 3 CDRs of the CDRs in SEQ ID NO: 448; or a VH comprising 3 CDRs of the CDRs in SEQ ID NO: 351; and a VL comprising 3 CDRs of the CDRs in SEQ ID NO: 352; or a VH comprising 3 CDRs of the CDRs in SEQ ID NO: 373; and a VL comprising 3 CDRs of the CDRs in SEQ ID NO: 374; or a VH comprising 3 CDRs of the CDRs in SEQ ID NO: 387; and a VL comprising 3 CDRs of the CDRs in SEQ ID NO: 388; or a VH comprising 3 CDRs of the CDRs in SEQ ID NO: 385; and a VL comprising 3 CDRs of the CDRs in SEQ ID NO: 386; or a VH comprising 3 CDRs of the CDRs in SEQ ID NO: 389; and a VL comprising 3 CDRs of the CDRs in SEQ ID NO: 390; or a VH comprising 3 CDRs of the CDRs in SEQ ID NO: 391; and a VL comprising 3 CDRs of the CDRs in SEQ ID NO: 392; or a VH comprising 3 CDRs of the CDRs in SEQ ID NO: 509; and a VL comprising 3 CDRs of the CDRs in SEQ ID NO: 510; or a VH comprising 3 CDRs of the CDRs in SEQ ID NO: 485; and a VL comprising 3 CDRs of the CDRs in SEQ ID NO: 486; or a VH comprising 3 CDRs of the CDRs in SEQ ID NO: 495; and a VL comprising 3 CDRs of the CDRs in SEQ ID NO: 496; or a VH comprising 3 CDRs of the CDRs in SEQ ID NO: 471; and a VL comprising 3 CDRs of the CDRs in SEQ ID NO: 472; or a VH comprising 3 CDRs of the CDRs in SEQ ID NO: 337; and a VL comprising 3 CDRs of the CDRs in SEQ ID NO: 338; or a VH comprising 3 CDRs of the CDRs in SEQ ID NO: 423; and a VL comprising 3 CDRs of the CDRs in SEQ ID NO: 424; or a VH comprising 3 CDRs of the CDRs in SEQ ID NO: 439; and a VL comprising 3 CDRs of the CDRs in SEQ ID NO: 440; or a VH comprising 3 CDRs of the CDRs in SEQ ID NO: 459; and a VL comprising 3 CDRs of the CDRs in SEQ ID NO: 460; or a VH comprising 3 CDRs of the CDRs in SEQ ID NO: 477; and a VL comprising 3 CDRs of the CDRs in SEQ ID NO: 478; or a VH comprising 3 CDRs of the CDRs in SEQ ID NO: 461; and a VL comprising 3 CDRs of the CDRs in SEQ ID NO: 462; or a VH comprising 3 CDRs of the CDRs in SEQ ID NO: 493; and a VL comprising 3 CDRs of the CDRs in SEQ ID NO: 494; and a phosphorylcholine containing polymer, wherein the polymer is covalently bonded to the antibody.

* * * * *